(12) United States Patent
Charles et al.

(10) Patent No.: US 11,166,706 B2
(45) Date of Patent: Nov. 9, 2021

(54) SURGICAL VISUALIZATION SYSTEMS

(71) Applicant: CAMPLEX, INC., Germantown, TN (US)

(72) Inventors: Steven T. Charles, Memphis, TN (US); John Tesar, Tucson, AZ (US)

(73) Assignee: CamPlex, Inc., Germantown, TN (US)

( * ) Notice: Subject to any disclaimer, the term of this patent is extended or adjusted under 35 U.S.C. 154(b) by 0 days.

(21) Appl. No.: 16/357,081

(22) Filed: Mar. 18, 2019

(65) Prior Publication Data
US 2019/0380566 A1   Dec. 19, 2019

Related U.S. Application Data

(63) Continuation of application No. 14/411,068, filed as application No. PCT/US2013/047972 on Jun. 26, (Continued)

(51) Int. Cl.
*A61B 17/02*   (2006.01)
*A61B 90/00*   (2016.01)
(Continued)

(52) U.S. Cl.
CPC .......... *A61B 17/02* (2013.01); *A61B 1/0005* (2013.01); *A61B 1/00009* (2013.01); (Continued)

(58) Field of Classification Search
CPC .......... A61B 1/0005; A61B 1/00179; A61B 1/00195; A61B 1/247; A61B 90/50; A61B 2090/37
See application file for complete search history.

(56) References Cited

U.S. PATENT DOCUMENTS

| 497,064 A | 5/1893 | Van Meter |
|---|---|---|
| 2,826,114 A | 3/1958 | Bryan |
| (Continued) | | |

FOREIGN PATENT DOCUMENTS

| CN | 2336380 Y | 9/1999 |
|---|---|---|
| CN | 101518438 | 9/2009 |
| (Continued) | | |

OTHER PUBLICATIONS

US 10,945,590 B2, 03/2021, Tesar et al. (withdrawn)
(Continued)

*Primary Examiner* — Nicholas W Woodall
(74) *Attorney, Agent, or Firm* — Knobbe, Martens, Olson & Bear, LLP

(57) ABSTRACT

A surgical device includes a plurality of cameras integrated therein. The view of each of the plurality of cameras can be integrated together. A surgical tool that includes an integrated camera may be used in conjunction with the surgical device. The image produced by the camera integrated with the surgical tool may be associated with the images generated by the plurality of cameras integrated in the surgical device. The position and orientation of the cameras and/or the surgical tool can be tracked, and the surgical tool can be rendered as at least partially transparent. A surgical device may be powered by a hydraulic system, thereby reducing electromagnetic interference with tracking devices.

10 Claims, 102 Drawing Sheets

Related U.S. Application Data 2013, now Pat. No. 10,231,607, which is a continuation of application No. 13/802,362, filed on Mar. 13, 2013, now Pat. No. 9,492,065, and a continuation of application No. 13/802,162, filed on Mar. 13, 2013, now Pat. No. 9,615,728, and a continuation of application No. 13/802,485, filed on Mar. 13, 2013, now Pat. No. 9,216,068, and a continuation of application No. 13/802,635, filed on Mar. 13, 2013, now Pat. No. 10,022,041, and a continuation of application No. 13/802,509, filed on Mar. 13, 2013, now Pat. No. 8,882,662, and a continuation of application No. 13/802,582, filed on Mar. 13, 2013, now Pat. No. 9,629,523, and a continuation of application No. 13/802,577, filed on Mar. 13, 2013, now Pat. No. 9,936,863.

(60) Provisional application No. 61/665,243, filed on Jun. 27, 2012, provisional application No. 61/670,550, filed on Jul. 11, 2012, provisional application No. 61/703,727, filed on Sep. 20, 2012, provisional application No. 61/753,398, filed on Jan. 16, 2013.

(51) Int. Cl.
| | | |
|---|---|---|
| *A61B 17/16* | (2006.01) | |
| *A61B 1/24* | (2006.01) | |
| *A61B 34/20* | (2016.01) | |
| *A61B 90/30* | (2016.01) | |
| *A61B 50/13* | (2016.01) | |
| *A61B 50/15* | (2016.01) | |
| *A61B 90/20* | (2016.01) | |
| *A61B 1/04* | (2006.01) | |
| *A61B 1/32* | (2006.01) | |
| *A61B 17/00* | (2006.01) | |
| *A61B 1/00* | (2006.01) | |
| *A61B 1/045* | (2006.01) | |
| *A61B 1/05* | (2006.01) | |
| *A61B 17/3211* | (2006.01) | |
| *A61B 5/00* | (2006.01) | |

(52) U.S. Cl.
CPC ...... *A61B 1/00039* (2013.01); *A61B 1/00149* (2013.01); *A61B 1/00193* (2013.01); *A61B 1/04* (2013.01); *A61B 1/045* (2013.01); *A61B 1/051* (2013.01); *A61B 1/24* (2013.01); *A61B 1/32* (2013.01); *A61B 17/00* (2013.01); *A61B 17/025* (2013.01); *A61B 17/0206* (2013.01); *A61B 17/0218* (2013.01); *A61B 17/0293* (2013.01); *A61B 17/16* (2013.01); *A61B 17/1604* (2013.01); *A61B 17/1628* (2013.01); *A61B 17/1644* (2013.01); *A61B 17/3211* (2013.01); *A61B 34/20* (2016.02); *A61B 50/13* (2016.02); *A61B 50/15* (2016.02); *A61B 90/20* (2016.02); *A61B 90/30* (2016.02); *A61B 90/361* (2016.02); *A61B 90/37* (2016.02); *A61B 5/0077* (2013.01); *A61B 5/7425* (2013.01); *A61B 5/7475* (2013.01); *A61B 2017/00207* (2013.01); *A61B 2017/0256* (2013.01); *A61B 2090/371* (2016.02); *A61B 2576/00* (2013.01)

(56) References Cited

U.S. PATENT DOCUMENTS

| | | |
|---|---|---|
| 3,050,870 A | 8/1962 | Heilig |
| 3,108,781 A | 10/1963 | Saffir |
| 3,128,988 A | 4/1964 | Mandroian |
| 3,141,650 A | 7/1964 | Saffir |
| 3,405,990 A | 10/1968 | Nothnagle et al. |
| 3,409,346 A | 11/1968 | Stapsy |
| 3,664,330 A | 5/1972 | Deutsch |
| 4,056,310 A | 11/1977 | Shimizu et al. |
| 4,063,557 A | 12/1977 | Wuchinich et al. |
| 4,087,198 A | 5/1978 | Theis, Jr. |
| 4,167,302 A | 9/1979 | Karasawa |
| 4,176,453 A | 12/1979 | Abbott |
| 4,223,676 A | 9/1980 | Wuchinich et al. |
| 4,226,228 A | 10/1980 | Shin et al. |
| 4,344,746 A | 8/1982 | Leonard |
| 4,354,734 A | 10/1982 | Nkahashi |
| 4,395,731 A * | 7/1983 | Schoolman ............ G02B 7/002 348/53 |
| 4,562,832 A | 1/1986 | Wilder et al. |
| 4,651,201 A | 3/1987 | Schoolman |
| 4,655,557 A | 4/1987 | Takahashi |
| 4,665,391 A | 5/1987 | Spani |
| 4,684,224 A | 8/1987 | Yamashita et al. |
| 4,703,314 A | 10/1987 | Spani |
| 4,718,406 A * | 1/1988 | Bregman ............ A61B 1/0005 600/113 |
| 4,750,488 A | 6/1988 | Wuchinich et al. |
| 4,750,902 A | 6/1988 | Wuchinich et al. |
| 4,779,968 A | 10/1988 | Sander |
| 4,783,156 A | 11/1988 | Yokota |
| 4,786,155 A | 11/1988 | Fantone et al. |
| 4,813,927 A | 3/1989 | Morris et al. |
| 4,873,572 A | 10/1989 | Miyazaki et al. |
| 4,900,301 A | 2/1990 | Morris et al. |
| 4,905,670 A | 3/1990 | Adair |
| 4,920,336 A | 4/1990 | Meijer |
| 4,922,902 A | 5/1990 | Wuchinich et al. |
| 4,986,622 A | 1/1991 | Martinez |
| 4,989,452 A | 2/1991 | Toon et al. |
| 5,016,098 A | 5/1991 | Cooper et al. |
| 5,032,111 A | 7/1991 | Morris et al. |
| 5,047,009 A | 9/1991 | Morris et al. |
| 5,098,426 A | 3/1992 | Sklar et al. |
| 5,143,054 A | 9/1992 | Adair |
| 5,151,821 A | 9/1992 | Marks |
| 5,176,677 A | 1/1993 | Wuchinich et al. |
| 5,201,325 A | 4/1993 | McEwen et al. |
| 5,221,282 A | 6/1993 | Wuchinich |
| 5,251,613 A | 10/1993 | Adair |
| 5,327,283 A | 7/1994 | Zobel |
| 5,354,314 A | 10/1994 | Hardy et al. |
| 5,417,210 A | 5/1995 | Funda et al. |
| 5,441,059 A | 8/1995 | Dannan |
| 5,464,008 A | 11/1995 | Kim |
| 5,523,810 A | 6/1996 | Volk |
| 5,537,164 A | 7/1996 | Smith |
| 5,553,995 A | 9/1996 | Martinez |
| 5,575,789 A | 11/1996 | Bell et al. |
| 5,584,796 A | 12/1996 | Cohen |
| 5,593,402 A | 1/1997 | Patrick |
| 5,601,549 A | 2/1997 | Miyagi |
| 5,625,493 A | 4/1997 | Matsumura et al. |
| 5,634,790 A | 6/1997 | Pathmanabhan et al. |
| 5,667,481 A | 9/1997 | Villalta et al. |
| 5,697,891 A | 12/1997 | Hori |
| 5,712,995 A | 1/1998 | Cohn |
| 5,716,326 A | 2/1998 | Dannan |
| 5,743,731 A | 4/1998 | Lares et al. |
| 5,743,846 A | 4/1998 | Takahashi et al. |
| 5,747,824 A | 5/1998 | Jung et al. |
| 5,751,341 A | 5/1998 | Chaleki |
| 5,797,403 A | 8/1998 | DiLorenzo |
| 5,803,733 A | 9/1998 | Trott et al. |
| 5,822,036 A | 10/1998 | Massie et al. |
| 5,825,534 A | 10/1998 | Strahle |
| 5,835,266 A | 11/1998 | Kitajima |
| 5,841,510 A | 11/1998 | Roggy |
| 5,861,983 A | 1/1999 | Twisselman |
| 5,889,611 A | 3/1999 | Zonneveld |
| 5,897,491 A | 4/1999 | Kastenbauer et al. |
| 5,909,380 A | 6/1999 | Dubois |

(56) References Cited

U.S. PATENT DOCUMENTS

| | | |
|---|---|---|
| 5,913,818 A | 6/1999 | Co et al. |
| 5,928,139 A | 7/1999 | Koros et al. |
| 5,949,388 A | 9/1999 | Atsumi |
| 5,982,532 A | 11/1999 | Mittelstadt et al. |
| 6,016,607 A | 1/2000 | Morimoto et al. |
| 6,023,638 A | 2/2000 | Swanson |
| 6,088,154 A | 7/2000 | Morita |
| 6,139,493 A | 10/2000 | Koros et al. |
| 6,152,736 A | 11/2000 | Schmidinger |
| 6,152,871 A | 11/2000 | Foley et al. |
| 6,176,825 B1 | 1/2001 | Chin et al. |
| 6,217,188 B1 | 4/2001 | Wainwright et al. |
| 6,246,898 B1 | 6/2001 | Vesely et al. |
| 6,293,911 B1 | 9/2001 | Imaizumi et al. |
| 6,317,260 B1 | 11/2001 | Ito |
| 6,319,223 B1 | 11/2001 | Wortrich et al. |
| 6,340,363 B1 | 1/2002 | Bolger et al. |
| 6,350,235 B1 | 2/2002 | Cohen et al. |
| 6,354,992 B1 | 3/2002 | Kato |
| 6,398,721 B1 | 6/2002 | Nakamura |
| 6,405,072 B1 | 6/2002 | Cosman |
| 6,434,329 B1 | 8/2002 | Dube et al. |
| 6,443,594 B1 | 9/2002 | Marshall et al. |
| 6,450,706 B1 | 9/2002 | Chapman |
| 6,450,950 B2 | 9/2002 | Irion |
| 6,491,661 B1 | 12/2002 | Boukhny et al. |
| 6,508,759 B1 | 1/2003 | Taylor et al. |
| 6,517,207 B2 | 2/2003 | Chapman |
| 6,525,310 B2 | 2/2003 | Dunfield |
| 6,525,878 B1 | 2/2003 | Takahashi |
| 6,527,704 B1 | 3/2003 | Chang et al. |
| 6,538,665 B2 | 3/2003 | Crow et al. |
| 6,549,341 B2 | 4/2003 | Nomura et al. |
| 6,561,999 B1 | 5/2003 | Nazarifar et al. |
| 6,582,358 B2 | 6/2003 | Akui et al. |
| 6,587,711 B1 * | 7/2003 | Alfano ............... A61B 5/0068 600/410 |
| 6,589,168 B2 | 7/2003 | Thompson |
| 6,618,207 B2 | 9/2003 | Lei |
| 6,626,445 B2 | 9/2003 | Murphy et al. |
| 6,633,328 B1 | 10/2003 | Byrd et al. |
| 6,635,010 B1 | 10/2003 | Lederer |
| 6,636,254 B1 | 10/2003 | Onishi et al. |
| 6,661,571 B1 | 12/2003 | Shioda et al. |
| 6,668,841 B1 | 12/2003 | Chou |
| 6,698,886 B2 | 3/2004 | Pollack et al. |
| 6,720,988 B1 | 4/2004 | Gere et al. |
| 6,757,021 B1 | 6/2004 | Nguyen-Nhu |
| 6,805,127 B1 | 10/2004 | Karasic |
| 6,817,975 B1 | 11/2004 | Farr et al. |
| 6,824,525 B2 | 11/2004 | Nazarifar et al. |
| 6,847,336 B1 | 1/2005 | Lemelson et al. |
| 6,869,398 B2 | 3/2005 | Obenchain et al. |
| 6,873,867 B2 | 3/2005 | Vilsmeier |
| 6,892,597 B2 | 5/2005 | Tews |
| 6,903,883 B2 | 6/2005 | Amanai |
| 6,908,451 B2 | 6/2005 | Brody et al. |
| 6,985,765 B2 | 1/2006 | Morita |
| 6,996,460 B1 | 2/2006 | Krahnstoever et al. |
| 7,034,983 B2 | 4/2006 | Desimone et al. |
| 7,050,225 B2 | 5/2006 | Nakamura |
| 7,050,245 B2 | 5/2006 | Tesar et al. |
| 7,054,076 B2 | 5/2006 | Tesar et al. |
| 7,116,437 B2 | 10/2006 | Weinstein et al. |
| 7,125,119 B2 | 10/2006 | Farberov |
| 7,150,713 B2 | 12/2006 | Shener et al. |
| 7,150,714 B2 | 12/2006 | Myles |
| 7,154,527 B1 | 12/2006 | Goldstein et al. |
| 7,155,316 B2 | 12/2006 | Sutherland |
| 7,163,543 B2 | 1/2007 | Smedley et al. |
| 7,226,451 B2 | 6/2007 | Shluzas et al. |
| 7,244,240 B2 | 7/2007 | Nazarifar et al. |
| 7,278,092 B2 | 10/2007 | Krzanowski |
| 7,298,393 B2 | 11/2007 | Morita |
| 7,306,559 B2 | 12/2007 | Williams |
| 7,307,799 B2 | 12/2007 | Minefuji |
| 7,326,183 B2 | 2/2008 | Nazarifar et al. |
| 7,471,301 B2 | 12/2008 | Lefevre |
| 7,480,872 B1 | 1/2009 | Ubillos |
| 7,494,463 B2 | 2/2009 | Nehls |
| 7,518,791 B2 | 4/2009 | Sander |
| 7,537,565 B2 | 5/2009 | Bass |
| 7,538,939 B2 | 5/2009 | Zimmerman et al. |
| 7,559,887 B2 | 7/2009 | Dannan |
| 7,621,868 B2 | 11/2009 | Breidenthal et al. |
| 7,633,676 B2 | 12/2009 | Brunner et al. |
| 7,644,889 B2 | 1/2010 | Johnson |
| 7,651,465 B1 | 1/2010 | Sperling et al. |
| 7,713,237 B2 | 5/2010 | Nazarifar et al. |
| 7,764,370 B2 | 7/2010 | Williams et al. |
| 7,766,480 B1 | 8/2010 | Graham et al. |
| 7,777,941 B2 | 8/2010 | Zimmer |
| 7,785,253 B1 | 8/2010 | Arambula |
| 7,786,457 B2 | 8/2010 | Gao |
| 7,806,865 B1 | 10/2010 | Wilson |
| 7,844,320 B2 | 11/2010 | Shahidi |
| 7,872,746 B2 | 1/2011 | Gao et al. |
| 7,874,982 B2 | 1/2011 | Selover et al. |
| 7,896,839 B2 | 3/2011 | Nazarifar et al. |
| 7,907,336 B2 | 3/2011 | Abele et al. |
| 7,927,272 B2 | 4/2011 | Bayer et al. |
| 7,932,925 B2 | 4/2011 | Inbar et al. |
| 7,956,341 B2 | 6/2011 | Gao |
| 8,009,141 B1 | 8/2011 | Chi et al. |
| 8,012,089 B2 | 9/2011 | Bayat |
| 8,018,523 B2 | 9/2011 | Choi |
| 8,018,579 B1 | 9/2011 | Krah |
| 8,027,710 B1 | 9/2011 | Dannan |
| 8,038,612 B2 | 10/2011 | Paz |
| 8,070,290 B2 | 12/2011 | Gille et al. |
| 8,088,066 B2 | 1/2012 | Grey et al. |
| 8,136,779 B2 | 3/2012 | Wilson et al. |
| 8,149,270 B1 | 4/2012 | Yaron et al. |
| 8,159,743 B2 | 4/2012 | Abele et al. |
| 8,169,468 B2 | 5/2012 | Scott et al. |
| 8,187,167 B2 | 5/2012 | Kim |
| 8,187,180 B2 | 5/2012 | Pacey |
| 8,194,121 B2 | 6/2012 | Blumzvig et al. |
| 8,221,304 B2 | 7/2012 | Shioda et al. |
| 8,229,548 B2 | 7/2012 | Frangioni |
| 8,294,733 B2 | 10/2012 | Eino |
| 8,295,693 B2 | 10/2012 | McDowall |
| 8,351,434 B1 * | 1/2013 | Fukuda ............... H04L 1/1854 370/278 |
| 8,358,330 B2 | 1/2013 | Riederer |
| 8,405,733 B2 | 3/2013 | Saijo |
| 8,408,772 B2 | 4/2013 | Li |
| 8,409,088 B2 | 4/2013 | Grey et al. |
| 8,419,633 B2 | 4/2013 | Koshikawa et al. |
| 8,419,634 B2 | 4/2013 | Nearman et al. |
| 8,430,840 B2 | 4/2013 | Nazarifar et al. |
| 8,439,830 B2 | 5/2013 | McKinley et al. |
| 8,460,184 B2 | 6/2013 | Nearman et al. |
| 8,464,177 B2 | 6/2013 | Ben-Yoseph et al. |
| 8,482,606 B2 | 7/2013 | Razzaque |
| 8,498,695 B2 | 7/2013 | Westwick et al. |
| 8,521,331 B2 | 8/2013 | Itkowitz |
| 8,702,592 B2 | 4/2014 | Langlois et al. |
| 8,702,602 B2 | 4/2014 | Berci et al. |
| 8,734,328 B2 | 5/2014 | McDowall |
| 8,786,946 B2 | 7/2014 | Nakamura |
| 8,827,899 B2 | 9/2014 | Farr et al. |
| 8,827,902 B2 | 9/2014 | Dietze, Jr. et al. |
| 8,836,723 B2 | 9/2014 | Tsao et al. |
| 8,858,425 B2 | 10/2014 | Farr et al. |
| 8,876,711 B2 | 11/2014 | Lin et al. |
| 8,878,924 B2 | 11/2014 | Farr |
| 8,882,662 B2 | 11/2014 | Charles |
| 8,976,238 B2 | 3/2015 | Ernsperger et al. |
| 8,979,301 B2 | 3/2015 | Moore |
| 9,033,870 B2 | 5/2015 | Farr et al. |
| 9,216,068 B2 | 12/2015 | Tesar |
| 9,492,065 B2 | 11/2016 | Tesar et al. |
| 9,615,728 B2 | 4/2017 | Charles et al. |

(56) References Cited

U.S. PATENT DOCUMENTS

| | | | |
|---|---|---|---|
| 9,629,523 B2 | 4/2017 | Tesar et al. |
| 9,642,606 B2 | 5/2017 | Charles et al. |
| 9,681,796 B2 | 6/2017 | Tesar et al. |
| 9,723,976 B2 | 8/2017 | Tesar |
| 9,782,159 B2 | 10/2017 | Tesar |
| 9,936,863 B2 | 4/2018 | Tesar |
| 10,022,041 B2 | 7/2018 | Charles et al. |
| 10,028,651 B2 | 7/2018 | Tesar |
| 10,231,607 B2 | 3/2019 | Charles et al. |
| 10,555,728 B2 | 2/2020 | Charles et al. |
| 10,568,499 B2 | 2/2020 | Tesar |
| 10,702,353 B2 | 7/2020 | Tesar |
| 10,881,286 B2 | 1/2021 | Tesar et al. |
| 10,918,455 B2 | 2/2021 | Tesar |
| 10,925,472 B2 | 2/2021 | Tesar |
| 10,925,589 B2 | 2/2021 | Tesar et al. |
| 10,932,766 B2 | 3/2021 | Tesar et al. |
| 10,966,798 B2 | 4/2021 | Tesar et al. |
| 2001/0045506 A1 | 11/2001 | Masuyama |
| 2001/0055062 A1 | 12/2001 | Shioda et al. |
| 2002/0013514 A1 | 1/2002 | Brau |
| 2002/0038075 A1 | 3/2002 | Tsai |
| 2002/0049367 A1 | 4/2002 | Irion et al. |
| 2002/0065461 A1 | 5/2002 | Cosman |
| 2002/0082498 A1* | 6/2002 | Wendt .................. H04N 13/246 600/411 |
| 2003/0055410 A1 | 3/2003 | Evans et al. |
| 2003/0059097 A1 | 3/2003 | Abovitz et al. |
| 2003/0078494 A1 | 4/2003 | Panescu et al. |
| 2003/0088179 A1 | 5/2003 | Seeley et al. |
| 2003/0102819 A1 | 6/2003 | Min et al. |
| 2003/0103191 A1 | 6/2003 | Staurenghi et al. |
| 2003/0142204 A1 | 7/2003 | Rus et al. |
| 2003/0147254 A1 | 8/2003 | Yoneda et al. |
| 2004/0017607 A1 | 1/2004 | Hauger et al. |
| 2004/0027652 A1 | 2/2004 | Erdogan et al. |
| 2004/0036962 A1 | 2/2004 | Brunner et al. |
| 2004/0070822 A1 | 4/2004 | Shioda et al. |
| 2004/0087833 A1 | 5/2004 | Bauer et al. |
| 2004/0111183 A1 | 6/2004 | Sutherland |
| 2004/0196553 A1 | 10/2004 | Banju et al. |
| 2004/0230191 A1 | 11/2004 | Frey et al. |
| 2005/0018280 A1 | 1/2005 | Richardson |
| 2005/0019722 A1 | 1/2005 | Schmid et al. |
| 2005/0026104 A1 | 2/2005 | Takahashi |
| 2005/0031192 A1 | 2/2005 | Sieckmann |
| 2005/0033117 A1 | 2/2005 | Ozaki et al. |
| 2005/0052527 A1 | 3/2005 | Remy et al. |
| 2005/0063047 A1 | 3/2005 | Obrebski et al. |
| 2005/0064936 A1 | 3/2005 | Pryor |
| 2005/0065435 A1 | 3/2005 | Rauch et al. |
| 2005/0095554 A1 | 5/2005 | Wilkinson |
| 2005/0107808 A1 | 5/2005 | Evans et al. |
| 2005/0171551 A1 | 8/2005 | Sukovich et al. |
| 2005/0215866 A1 | 9/2005 | Kim |
| 2005/0228231 A1 | 10/2005 | MacKinnon et al. |
| 2005/0228232 A1 | 10/2005 | Gillinov et al. |
| 2005/0279355 A1 | 12/2005 | Loubser |
| 2006/0004261 A1 | 1/2006 | Douglas |
| 2006/0020213 A1 | 1/2006 | Whitman et al. |
| 2006/0025656 A1 | 2/2006 | Buckner et al. |
| 2006/0069315 A1 | 3/2006 | Miles et al. |
| 2006/0069316 A1 | 3/2006 | Dorfman et al. |
| 2006/0085969 A1 | 4/2006 | Bennett et al. |
| 2006/0092178 A1 | 5/2006 | Tanguya, Jr. et al. |
| 2006/0114411 A1 | 6/2006 | Wei et al. |
| 2006/0129140 A1 | 6/2006 | Todd et al. |
| 2006/0152516 A1 | 7/2006 | Plummer |
| 2006/0235279 A1 | 10/2006 | Hawkes et al. |
| 2006/0236264 A1 | 10/2006 | Cain et al. |
| 2006/0241499 A1 | 10/2006 | Irion et al. |
| 2006/0276693 A1 | 12/2006 | Pacey |
| 2006/0293557 A1 | 12/2006 | Chuanggui et al. |
| 2007/0010716 A1 | 1/2007 | Malandain |
| 2007/0019916 A1 | 1/2007 | Takami |
| 2007/0030344 A1 | 2/2007 | Miyamoto et al. |
| 2007/0038080 A1 | 2/2007 | Salisbury, Jr. et al. |
| 2007/0086205 A1 | 4/2007 | Krupa et al. |
| 2007/0129608 A1 | 6/2007 | Sandhu |
| 2007/0129719 A1 | 6/2007 | Kendale et al. |
| 2007/0153541 A1 | 7/2007 | Bennett et al. |
| 2007/0173853 A1 | 7/2007 | MacMillan |
| 2007/0238932 A1 | 10/2007 | Jones et al. |
| 2007/0282171 A1 | 12/2007 | Karpowicz et al. |
| 2008/0015417 A1 | 1/2008 | Hawkes et al. |
| 2008/0058606 A1 | 3/2008 | Miles et al. |
| 2008/0081947 A1 | 4/2008 | Irion et al. |
| 2008/0091066 A1 | 4/2008 | Sholev |
| 2008/0094583 A1 | 4/2008 | Williams et al. |
| 2008/0096165 A1 | 4/2008 | Virnicchi et al. |
| 2008/0097467 A1 | 4/2008 | Gruber et al. |
| 2008/0123183 A1* | 5/2008 | Awdeh .................. G02B 21/368 359/368 |
| 2008/0151041 A1 | 6/2008 | Shafer et al. |
| 2008/0183038 A1 | 7/2008 | Tilson et al. |
| 2008/0195128 A1 | 8/2008 | Orbay et al. |
| 2008/0221394 A1 | 9/2008 | Melkent et al. |
| 2008/0221591 A1 | 9/2008 | Farritor et al. |
| 2008/0266840 A1 | 10/2008 | Nordmeyer et al. |
| 2008/0269564 A1 | 10/2008 | Gelnett |
| 2008/0269730 A1 | 10/2008 | Dotson |
| 2008/0278571 A1 | 11/2008 | Mora |
| 2008/0300465 A1 | 12/2008 | Feigenwinter et al. |
| 2008/0303899 A1 | 12/2008 | Berci |
| 2008/0310181 A1 | 12/2008 | Gurevich et al. |
| 2008/0319266 A1 | 12/2008 | Poll et al. |
| 2009/0030436 A1 | 1/2009 | Charles |
| 2009/0034286 A1 | 2/2009 | Krupa et al. |
| 2009/0040783 A1 | 2/2009 | Krupa et al. |
| 2009/0052059 A1 | 2/2009 | Lin |
| 2009/0105543 A1 | 4/2009 | Miller et al. |
| 2009/0137893 A1 | 5/2009 | Seibel et al. |
| 2009/0137989 A1 | 5/2009 | Kataoka |
| 2009/0149716 A1 | 6/2009 | Diao et al. |
| 2009/0156902 A1 | 6/2009 | Dewey et al. |
| 2009/0185392 A1 | 7/2009 | Krupa et al. |
| 2009/0190209 A1* | 7/2009 | Nakamura .......... G02B 21/361 359/375 |
| 2009/0190371 A1 | 7/2009 | Root et al. |
| 2009/0209826 A1 | 8/2009 | Sanders et al. |
| 2009/0225159 A1 | 9/2009 | Schneider et al. |
| 2009/0238442 A1 | 9/2009 | Upham et al. |
| 2009/0244259 A1 | 10/2009 | Kojima et al. |
| 2009/0245600 A1 | 10/2009 | Hoffman et al. |
| 2009/0248036 A1 | 10/2009 | Hoffman et al. |
| 2009/0258638 A1 | 10/2009 | Lee |
| 2009/0304582 A1 | 12/2009 | Rousso et al. |
| 2009/0318756 A1 | 12/2009 | Fisher et al. |
| 2009/0326322 A1 | 12/2009 | Diolaiti |
| 2009/0326331 A1 | 12/2009 | Rosen |
| 2010/0013910 A1 | 1/2010 | Farr |
| 2010/0013971 A1 | 1/2010 | Amano |
| 2010/0063508 A1 | 3/2010 | Borja et al. |
| 2010/0081919 A1 | 4/2010 | Hyde et al. |
| 2010/0107118 A1 | 4/2010 | Pearce |
| 2010/0128350 A1 | 5/2010 | Findlay et al. |
| 2010/0161129 A1 | 6/2010 | Costa et al. |
| 2010/0168520 A1 | 7/2010 | Poll et al. |
| 2010/0182340 A1 | 7/2010 | Bachelder et al. |
| 2010/0198014 A1 | 8/2010 | Poll et al. |
| 2010/0198241 A1 | 8/2010 | Gerrah et al. |
| 2010/0208046 A1 | 8/2010 | Takahashi |
| 2010/0245557 A1* | 9/2010 | Luley, III ............. G02B 21/367 348/79 |
| 2010/0249496 A1 | 9/2010 | Cardenas et al. |
| 2010/0286473 A1 | 11/2010 | Roberts |
| 2010/0305409 A1 | 12/2010 | Chang |
| 2010/0312069 A1 | 12/2010 | Sutherland et al. |
| 2010/0318099 A1 | 12/2010 | Itkowitz et al. |
| 2010/0331855 A1 | 12/2010 | Zhao et al. |
| 2011/0034781 A1 | 2/2011 | Loftus |
| 2011/0038040 A1 | 2/2011 | Abele et al. |
| 2011/0042452 A1 | 2/2011 | Cormack |
| 2011/0046439 A1 | 2/2011 | Pamnani et al. |

(56) References Cited

U.S. PATENT DOCUMENTS

| | | |
|---|---|---|
| 2011/0063734 A1 | 3/2011 | Sakaki |
| 2011/0065999 A1 | 3/2011 | Manzanares |
| 2011/0071359 A1 | 3/2011 | Bonadio et al. |
| 2011/0080536 A1 | 4/2011 | Nakamura et al. |
| 2011/0115882 A1 | 5/2011 | Shahinian et al. |
| 2011/0115891 A1 | 5/2011 | Trusty |
| 2011/0144436 A1 | 6/2011 | Nearman et al. |
| 2011/0178395 A1 | 7/2011 | Miesner et al. |
| 2011/0184243 A1 | 7/2011 | Wright et al. |
| 2011/0190588 A1 | 8/2011 | McKay |
| 2011/0234841 A1 | 9/2011 | Akeley et al. |
| 2011/0249323 A1 | 10/2011 | Tesar et al. |
| 2011/0257478 A1 | 10/2011 | Kleiner et al. |
| 2011/0257488 A1 | 10/2011 | Koyama et al. |
| 2011/0263938 A1 | 10/2011 | Levy |
| 2011/0264078 A1 | 10/2011 | Lipow et al. |
| 2011/0288560 A1 | 11/2011 | Shohat et al. |
| 2011/0298704 A1 | 12/2011 | Krah |
| 2011/0301421 A1 | 12/2011 | Michaeli et al. |
| 2011/0316994 A1 | 12/2011 | Lemchen |
| 2012/0029280 A1 | 2/2012 | Kucklick |
| 2012/0035423 A1 | 2/2012 | Sebastian et al. |
| 2012/0035638 A1 | 2/2012 | Mathaneswaran et al. |
| 2012/0040305 A1 | 2/2012 | Karazivan et al. |
| 2012/0041272 A1 | 2/2012 | Dietze, Jr. et al. |
| 2012/0041534 A1 | 2/2012 | Clerc et al. |
| 2012/0059222 A1 | 3/2012 | Yoshida |
| 2012/0065468 A1 | 3/2012 | Levy et al. |
| 2012/0087006 A1 | 4/2012 | Signaigo |
| 2012/0088974 A1 | 4/2012 | Maurice |
| 2012/0089093 A1 | 4/2012 | Trusty |
| 2012/0097567 A1 | 4/2012 | Zhao et al. |
| 2012/0108900 A1 | 5/2012 | Viola et al. |
| 2012/0116173 A1 | 5/2012 | Viola |
| 2012/0127573 A1 | 5/2012 | Robinson et al. |
| 2012/0130399 A1 | 5/2012 | Moll et al. |
| 2012/0134028 A1 | 5/2012 | Maruyama |
| 2012/0157775 A1 | 6/2012 | Yamaguchi |
| 2012/0157787 A1 | 6/2012 | Weinstein et al. |
| 2012/0157788 A1 | 6/2012 | Serowski et al. |
| 2012/0158015 A1 | 6/2012 | Fowler et al. |
| 2012/0190925 A1 | 7/2012 | Luiken |
| 2012/0197084 A1 | 8/2012 | Drach et al. |
| 2012/0230668 A1 | 9/2012 | Vogt |
| 2012/0232352 A1 | 9/2012 | Lin et al. |
| 2012/0245432 A1 | 9/2012 | Karpowicz et al. |
| 2012/0265023 A1 | 10/2012 | Berci et al. |
| 2012/0320102 A1 | 12/2012 | Jorgensen |
| 2012/0330129 A1 | 12/2012 | Awdeh |
| 2013/0012770 A1 | 1/2013 | Su |
| 2013/0027516 A1 | 1/2013 | Hart et al. |
| 2013/0041226 A1 | 2/2013 | McDowall |
| 2013/0041368 A1 | 2/2013 | Cunningham et al. |
| 2013/0060095 A1 | 3/2013 | Bouquet |
| 2013/0066304 A1 | 3/2013 | Belson et al. |
| 2013/0072917 A1 | 3/2013 | Kaschke et al. |
| 2013/0076863 A1* | 3/2013 | Rappel ............... G02B 21/22 |
| | | 348/46 |
| 2013/0077048 A1 | 3/2013 | Mirlay |
| 2013/0085337 A1 | 4/2013 | Hess et al. |
| 2013/0159015 A1 | 6/2013 | O'Con |
| 2013/0197313 A1 | 8/2013 | Wan |
| 2013/0245383 A1 | 9/2013 | Friedrich et al. |
| 2013/0298208 A1 | 11/2013 | Ayed |
| 2013/0331730 A1 | 12/2013 | Fenech et al. |
| 2014/0005485 A1 | 1/2014 | Tesar et al. |
| 2014/0005486 A1 | 1/2014 | Charles et al. |
| 2014/0005487 A1 | 1/2014 | Tesar |
| 2014/0005488 A1 | 1/2014 | Charles et al. |
| 2014/0005489 A1 | 1/2014 | Charles |
| 2014/0005555 A1 | 1/2014 | Tesar |
| 2014/0081659 A1 | 3/2014 | Nawana et al. |
| 2014/0168785 A1 | 6/2014 | Belgum |
| 2014/0168799 A1 | 6/2014 | Hurbert et al. |
| 2014/0179998 A1 | 6/2014 | Pacey et al. |
| 2014/0187859 A1 | 7/2014 | Leeuw et al. |
| 2014/0198190 A1 | 7/2014 | Okumu |
| 2014/0247482 A1 | 9/2014 | Doi et al. |
| 2014/0275801 A1 | 9/2014 | Menchaca et al. |
| 2014/0276008 A1 | 9/2014 | Steinbach et al. |
| 2014/0285403 A1 | 9/2014 | Kobayashi |
| 2014/0316209 A1 | 10/2014 | Overes et al. |
| 2014/0327742 A1 | 11/2014 | Kiening et al. |
| 2014/0347395 A1 | 11/2014 | Tsao et al. |
| 2014/0362228 A1 | 12/2014 | McCloskey et al. |
| 2014/0378843 A1 | 12/2014 | Valdes et al. |
| 2015/0018622 A1 | 1/2015 | Tesar |
| 2015/0025324 A1 | 1/2015 | Wan |
| 2015/0080982 A1 | 3/2015 | Van Funderburk |
| 2015/0085095 A1 | 3/2015 | Tesar |
| 2015/0087918 A1 | 3/2015 | Vasan |
| 2015/0094533 A1 | 4/2015 | Kleiner et al. |
| 2015/0112148 A1 | 4/2015 | Bouquet |
| 2015/0141755 A1 | 5/2015 | Tesar |
| 2015/0297311 A1 | 10/2015 | Tesar |
| 2015/0300816 A1 | 10/2015 | Yang et al. |
| 2015/0317830 A1 | 11/2015 | Kihara et al. |
| 2016/0018598 A1 | 1/2016 | Hansson |
| 2016/0089026 A1 | 3/2016 | Heerren |
| 2016/0139039 A1 | 5/2016 | Ikehara et al. |
| 2016/0220324 A1 | 8/2016 | Tesar |
| 2017/0020627 A1 | 1/2017 | Tesar |
| 2017/0143442 A1 | 5/2017 | Tesar |
| 2017/0258550 A1 | 9/2017 | Vazales |
| 2018/0055348 A1 | 3/2018 | Tesar et al. |
| 2018/0055502 A1 | 3/2018 | Charles et al. |
| 2018/0064316 A1 | 3/2018 | Charles et al. |
| 2018/0064317 A1 | 3/2018 | Tesar |
| 2018/0070804 A1 | 3/2018 | Tesar |
| 2018/0256145 A1 | 9/2018 | Tesar |
| 2018/0318033 A1 | 11/2018 | Tesar |
| 2018/0353059 A1 | 12/2018 | Tesar |
| 2018/0368656 A1 | 12/2018 | Austin et al. |
| 2019/0046021 A1 | 2/2019 | Charles et al. |
| 2019/0053700 A1 | 2/2019 | Tesar |
| 2020/0318810 A1 | 10/2020 | Tesar |
| 2021/0000461 A1 | 1/2021 | Charles et al. |
| 2021/0015355 A1 | 1/2021 | Tesar |
| 2021/0169606 A1 | 6/2021 | Tesar |

FOREIGN PATENT DOCUMENTS

| | | |
|---|---|---|
| CN | 102495463 | 6/2012 |
| CN | 202920720 | 5/2013 |
| DE | 103 41 125 | 4/2005 |
| DE | 10 2010 030 285 | 12/2011 |
| DE | 10 2010 044 502 | 3/2012 |
| EP | 0 293 228 | 11/1988 |
| EP | 0 233 940 | 11/1993 |
| EP | 0 466 705 | 6/1996 |
| EP | 1 175 106 | 1/2002 |
| EP | 1 333 305 | 8/2003 |
| EP | 2 641 561 | 9/2013 |
| JP | 49-009378 | 3/1974 |
| JP | 03-018891 | 1/1991 |
| JP | 06-315487 | 11/1994 |
| JP | 07-194602 | 8/1995 |
| JP | 07-261094 | 10/1995 |
| JP | 08-131399 | 5/1996 |
| JP | 2001-087212 | 4/2001 |
| JP | 2001-117049 | 4/2001 |
| JP | 2001-161638 | 6/2001 |
| JP | 2001-161640 | 6/2001 |
| JP | 2002-011022 | 1/2002 |
| JP | 3402797 | 5/2003 |
| JP | 2003-322803 | 11/2003 |
| JP | 2004-024835 | 1/2004 |
| JP | 3549253 | 8/2004 |
| JP | 2004-305525 | 11/2004 |
| JP | 2007-068876 | 3/2007 |
| JP | 2009-288296 | 12/2009 |
| JP | 4503748 | 7/2010 |
| JP | 2010-206495 | 9/2010 |
| JP | 2011-509729 | 3/2011 |

(56) References Cited

FOREIGN PATENT DOCUMENTS

| JP | 2011-118741 | 6/2011 |
|---|---|---|
| WO | WO 87/001276 | 3/1987 |
| WO | WO 91/012034 | 8/1991 |
| WO | WO 99/017661 | 4/1999 |
| WO | WO 00/078372 | 12/2000 |
| WO | WO 01/072209 | 10/2001 |
| WO | WO 2007/047782 | 4/2007 |
| WO | WO 2008/073243 | 6/2008 |
| WO | WO 2009/051013 | 4/2009 |
| WO | WO 2010/079817 | 7/2010 |
| WO | WO 2010/114843 | 10/2010 |
| WO | WO 2010/123578 | 10/2010 |
| WO | WO 2011/069469 | 6/2011 |
| WO | WO 2012/047962 | 4/2012 |
| WO | WO 2012/078989 | 6/2012 |
| WO | WO 2013/049679 | 4/2013 |
| WO | WO 2013/109966 | 7/2013 |
| WO | WO 2013/116489 | 8/2013 |
| WO | WO 2014/004717 | 1/2014 |
| WO | WO 2014/060412 | 4/2014 |
| WO | WO 2014/189969 | 11/2014 |
| WO | WO 2015/042460 | 3/2015 |
| WO | WO 2015/042483 | 3/2015 |
| WO | WO 2015/100310 | 7/2015 |
| WO | WO 2016/090336 | 6/2016 |
| WO | WO 2016/154589 | 9/2016 |
| WO | WO 2017/091704 | 6/2017 |
| WO | WO 2018/208691 | 11/2018 |
| WO | WO 2018/217951 | 11/2018 |

OTHER PUBLICATIONS

Official Communication in European Application No. 13808996.6, dated May 13, 2019.
Final Office Action in U.S. Appl. No. 15/483,995, dated Nov. 29, 2018.
Amendment in U.S. Appl. No. 15/483,995, dated May 28, 2019.
Office Action in U.S. Appl. No. 15/483,995, dated Jun. 13, 2019.
Final Office Action in U.S. Appl. No. 15/645,589, dated Nov. 28, 2018.
Amendment in U.S. Appl. No. 15/645,589, dated May 28, 2019.
Office Action in U.S. Appl. No. 15/645,589, dated Jun. 13, 2019.
Preliminary Amendment filed in U.S. Appl. No. 16/036,665, dated Nov. 1, 2018.
Final Office Action in U.S. Appl. No. 15/626,516, dated Jan. 15, 2019.
Response in U.S. Appl. No. 15/626,516, dated Jul. 15, 2019.
Restriction Requirement in U.S. Appl. No. 15/495,484, dated May 14, 2019.
Amendment in U.S. Appl. No. 15/589,058, dated Feb. 26, 2019.
Office Action in U.S. Appl. No. 15/589,058, dated Mar. 5, 2019.
Amendment in U.S. Appl. No. 15/589,058, dated Sep. 5, 2019.
Preliminary Amendment in U.S. Appl. No. 16/042,318, dated Nov. 8, 2018.
Office Action in U.S. Appl. No. 16/042,318, dated May 8, 2019.
Office Action in U.S. Appl. No. 14/491,935, dated May 13, 2019.
Official Communication in European Application No. 14846410.0, dated Mar. 20, 2019.
Final Office Action in U.S. Appl. No. 14/581,779, dated Jan. 4, 2019.
Amendment in U.S. Appl. No. 14/581,779, dated Jul. 2, 2019.
Office Action in U.S. Appl. No. 14/581,779, dated Aug. 5, 2019.
Official Communication in Japanese Application No. 2016-542194, dated Nov. 6, 2018.
Decision of Rejection in Japanese Application No. 2016-542194, dated May 14, 2019.
Office Action in U.S. Appl. No. 14/960,276, dated Nov. 2, 2018.
Amendment in U.S. Appl. No. 14/960,276, dated May 2, 2019.
Final Office Action in U.S. Appl. No. 14/960,276, dated Jun. 7, 2019.
Final Office Action in U.S. Appl. No. 15/081,653, dated Nov. 16, 2018.
Final Amendment in U.S. Appl. No. 15/081,653, dated May 15, 2019.
Office Action in U.S. Appl. No. 15/081,653, dated Jul. 12, 2019.
Extended European Search Report in European Application No. 16769809.1, dated Nov. 23, 2018.
Amendment in U.S. Appl. No. 15/360,565, dated Feb. 8, 2019.
Office Action in U.S. Appl. No. 15/360,565, dated May 22, 2019.
Extended European Search Report in European Application No. 16869253.1, dated May 29, 2019.
Office Action in U.S. Appl. No. 15/973,433, dated Jun. 28, 2019.
Aesculap Inc.; Aesculap Neurosurgery Pneumatic Kerrison; http://www.aesculap.com/assets/base/doc/doc796-pneumatic_kerrison_brochure.pdf; 2008; in 12.
Aliaga, Daniel G.; "Image Morphing and Warping"; Department of Computer Science; Purdue University; Spring 2010; in 61 pages.
"ARRI Medical Shows SeeFront 3D Display with HD 3D Surgical Microscope"; dated Jun. 9, 2013; downloaded from http://www.seefront.com/news-events/article/arri-medical-shows-seefront-3d-display-with-hd-3d-surgical-microscope/ in 2 pages.
"ARRISCOPE: A New Era in Surgical Microscopy"; Arriscope Brochure published May 20, 2014 in 4 pages.
AustriaMicroSystems; "AS5050: Smallest Magnetic Rotary Encoder for µA Low Power Applications"; www.austriamicrosystems.com printed Nov. 2012 in 2 pages.
Bayonet Lock Video; 00:16 in length; Date Unknown; Received Oct. 15, 2014 [Screenshots captured at 00:00, 00:02, 00:05, 00:08, and 00:16].
BellowsTech; "Actuators"; www.bellowstech.com/metal-bellows/actuators/ printed Jul. 17, 2012 in 4 pages.
"Carl Zeiss Unveils $99 VR One Virtual Reality Headset"; www.electronista.com/articles/14/10/10/zeiss.vr.one.able.to.accept.variety.of.smartphones.using.custom.travs printed Oct. 13, 2014 in 2 pages.
Designboom; "Bright LED"; http://www.design.boom.com/project/fiber-optics-light-glove/; Sep. 28, 2007.
Fei-Fei, Li; Lecture 10: Multi-View Geometry; Stanford Vision Lab; Oct. 24, 2011; in 89 pages.
"Fuse$^{TM}$". Full Spectrum Endoscopy$^{TM}$; http://www.endochoice.com/Fuse printed Oct. 7, 2013 in 3 pages.
Hardesty, Larry; "3-D Cameras for Cellphones: Clever math could enable a high-quality 3-D camera so simple, cheap and power-efficient that it could be incorporated into handheld devices"; MIT News Office; http://web.mit.edu/newsoffice/2011/lidar-3d-camera-cellphones-0105.html; Jan. 5, 2012; in 4 pages.
Hartley et al.; "Multiple View Geometry in Computer Vision: Chapter 9—Epipolar Geometry and the Fundamental Matrix" ; http://www.robots.ox.ac.uk/—vgg/hzbook/hzbook/hzbook2/HZepipolar.pdf; Mar. 2004; 2nd Edition; Ch. 9; pp. 239-261.
Heidelberg Engineering; "MultiColor: Scanning Laser Imaging"; http://www.heidelbergengineering.com/us/products/spectralis-models/imaging-modes/multicolor/; Copyright © 2013; printed Apr. 5, 2013.
Kramer, Jennifer; "The Right Filter Set Gets the Most out of a Microscope"; Biophotonics International; Jan./Feb. 1999; vol. 6; pp. 54-58.
Krishna, Golden; "Watch: What Good is a Screen?"; http:www.cooper.com/author/golden_krishna as printed Jul. 9, 2014 in 62 pages.
Lang et al.; "ZEISS Microscopes for Microsurgery"; Springer-Verlag; Berlin, Heidelberg; 1981.
Leica Microsystems; "Images TrueVision Integrated 3D"; http://www.leica-microsystems.com/products/surgical-microscopes/neurosurgery-spine/details/product/truevision-integrated-3d/gallery/; Nov. 26, 2014; in 3 pages.
Leica Microsystems; "Leica Microsystems' Ophthalmic Surgical Microscopes with TrueVision 3D Technology Available Globally" ; http://www.leica-microsystems.com/products/surgical-microscopes/neurosurgery-spine/details/product/truevision-integrated-3d/news/; Sep. 18, 2014; in 5 pages.
Lutze et al.; "Microsystems Technology for Use in a Minimally Invasive Endoscope Assisted Neurosurgical Operating System—MINOP II"; 2005; http://web.archive.org/web/20151120215151/

(56) References Cited

OTHER PUBLICATIONS http://www.meditec.hia.rwth-aachen.de/fileadmin/content/meditec/bilder/forschung/aktuelle_projekte/robotische/Exoscope_Aesculap.pdf; Nov. 20, 2015 in 4 pages.
Male Bayonet Video; 00:04 in length; Date Unknown; Received Oct. 10, 2014 [Screenshots captured at 00:00, 00:01, 00:02, 00:03, and 00:04].
MediTec; "Minop II—Robotical Microscope Platform"; http://web.archive.org/web/20151120213932/http://www.meditec.hia.rwth-aachen.de/en/research/former-projects/minop-ii/; Nov. 20, 2015 in 3 pages.
Melexis; "MLX75031 Optical Gesture and Proximity Sensing IC"; http://melexis.com/optical-sensors/optical-sensing.mlx75031-815.aspx?sta printed Mar. 15, 2013 in 1 page.
MMR Technologies; "Micro Miniature Refrigerators"; http://www.mmr-tech.com/mmr_overview.php; Copyright © 2011; printed Feb. 11, 2013.
Moog; "Surgical Handpieces: Therapeutic Ultrasonic Devices"; http://www.moog.com/products/surgical-hpieces/ printed Sep. 25, 2013 in 1 page.
Morita; "TwinPower Turbine® High Speed Handpieces Standard, 45°, and Ultra Series Head Designs"; J. Morita Mfg. Corp., http://www.morita.com/usa/root/img/pool/pdf/product_brochures/twinpower_brochure_1-264_0512_web.pdf; May 2012; in 20 pages.
"Narrow Band Imaging"; http://web.archive.org/web/20150701233623/https://en.wikipedia.org/Narrow_band_imaging printed July. 1, 2015 in 1 page.
Olympus; "Olympus Introduces the World's First and Only Monopolar, Disposable Tonsil Adenoid Debrider (DTAD)"; http://www.olympusamerica.com/corporate/corp_presscenter_headline.asp?pressNo=926; Sep. 11, 2012; in 2 pages.
OmniVision; "OV2722 full HD (1080p) product brief: 1/6-Inch Native 1080p HD CameraChip Sensor for Ultra-Compact Applications"; http://web.archive.org/web/20120730043057/http://www.ovt.com/download_document.php?type=sensor&sensorid=119; May 2012 in 2 pages.
Orthofix; "ProView Map System Retractors"; www.us.orthofix.com/products/proviewretractors/asp?cid=39; Copyright © 2010; printed Apr. 1, 2013.
OrtusTech; "Sample Shipment Start: World's Smallest Size Full-HD Color TFT LCD"; http://ortustech.co/jp/english/notice/20120427.html printed May 22, 2012 in 2 pages.
"Portion"; Definition; American Heritage® Dictionary of the English Language; Fifth Edition; 2016; Retrieved Apr. 12, 2018 from https://www.thefreedictionary.com/portion in 1 page.
Purcher, Jack; "Apple Wins a Patent for an Oculus Rift-Like Display System"; http://www.patentlyapple.com/patently-apple/2014/09/apple-wins-a-patent-for-an-oculus-rift-like-display-system.html; Sep. 9, 2014.
Rustum, Dr. Abu; "ICG Mapping Endometrial Cancer"; Pinpoint Endometrium Ca Lenfedenektomi MSKCC May 2013; Memorial Sloan Kettering Cancer Center; May 2013; Published to YouTube.com Sep. 1, 2013; in 2 pages; http://web.archive.org/web/20150402210857/https://www.youtube.com/watch?v=DhChvaUCe4I.
Saab, Mark; "Applications of High-Pressure Balloons in the Medical Device Industry"; http://www.ventionmedical.com/documents/medicalballoonpaper.pdf; Copyright © 1999; in 19 pages.
Savage, Lynn; "Sound and Light, Signifying Improved Imaging"; www.photonics.com/Article.aspx?AID=45039; Nov. 1, 2010; in 6 pages.
Sun et al.; "Neurotoxin-Directed Synthesis and in Vitro Evaluation of Au Nanoclusters"; RSC Advances, 2015; vol. 5, No. 38; pp. 29647-29652.
Timm, Karl Walter; "Real-Time View Morphing of Video Streams"; University of Illinois; Chicago, Illinois; 2003; in 168 pages.
TrueVision Microscopes; http://truevisionmicroscopes.com/image/productsnew/081a-f.jpg; printed Nov. 26, 2014 in 1 page.
TrueVision; "About TrueVision"; http://web.archive.org/web/20071208125103/http://www.truevisionsys.com/about.html; as viewed Dec. 8, 2007 in 2 pages.
TrueVision; "Leica Microsystems and TrueVision® 3D Surgical create the first 3D digital hybrid microscope"; Press Release; Oct. 5, 2012; in 2 pages.
TrueVision; "TrueVision Technology"; http://web.archive.org/web/20071208125125/http://www.truevisionsys.com/technology.html; as viewed Dec. 8, 2007 in 2 pages.
Whitney et al.; "Pop-up book MEMS"; Journal of Micromechanics and Microengineering; Oct. 14, 2011; vol. 21; No. 115021; in 7 pages.
Wikipedia; "Zoom Lens"; http://en.wikipedia.org/wiki/Optical_Zoom; printed Oct. 7, 2014 in 3 pages.
Zeiss; "Informed for Medical Professionals, Focus: Fluorescence"; Carl Zeiss; 2nd Issue; Oct. 2006; 30-801-LBW-GFH-X-2006; Printed in Germany; in 32 pages.
Zeiss; "Ophthalmic Surgery in Its Highest Form, OPMI® VISU 210"; Carl Zeiss, 2005, 30-097/III-e/USA Printed in Germany AW-TS-V/2005 Uoo; in 19 pages.
Zeiss; "SteREO Discovery. V12, Expanding the Boundaries"; Carl Zeiss, Sep. 2004; 46-0008 e09.2004, in 6 pages.
Zeiss; "Stereomicroscopes: Stemi SV 6, Sv 11, SV 11 Apo"; The Profile; 1999; in 30 pages.
Zeiss; "Time for a Change: OPMI® pico for ENT"; Carl Zeiss, 2005, 30-451/lll-e Printed in Germany LBW-TS-V/2005 Uoo, in 8 pages.
Zhang, Michael; "LIFX: A WiFi-Enabled LED Bulb that May Revolutionize Photographic Lighting"; http://www.petapixel.com/2012/09/22/lifx-a-wifi-enabled-led-bulb-that-may-revolutionize-photographic-lighting/ printed Sep. 28, 2012 in 9 pages.
Zhang, Sarah; "The Obscure Neuroscience Problem That's Plaguing VR"; http://web.archive.org/web/20150812172934/http://www.wired.com/2015/08/obscure-neuroscience-problem-thats-plaguing-vr/; Aug. 11, 2015 in 5 pages.
Official Communication in European Application No. 13808996.6, dated Jan. 4, 2016.
Official Communication in European Application No. 13808996.6, dated Apr. 14, 2016.
Official Communication in European Application No. 13808996.6, dated Feb. 21, 2017.
Official Communication in European Application No. 13808996.6, dated Jun. 6, 2017.
Official Communication in European Application No. 13808996.6, dated Jun. 15, 2018.
Official Communication in Japanese Application No. 2015-520471, dated May 9, 2017.
Official Communication in Japanese Application No. 2015-520471, dated Nov. 21, 2017.
Notice of Decision or Rejection in Japanese Application No. 2015-520471, dated Jul. 24, 2018.
International Search Report and Written Opinion in PCT Application No. PCT/US2013/047972, dated Jan. 3, 2014.
International Preliminary Report on Patentability in PCT Application No. PCT/US2013/047972, dated Jan. 8, 2015.
Preliminary Amendment in U.S. Appl. No. 15/483,995, dated Nov. 21, 2017.
Office Action in U.S. Appl. No. 15/483,995, dated Mar. 9, 2018.
Amendment in U.S. Appl. No. 15/483,995, dated Sep. 7, 2018.
Office Action in U.S. Appl. No. 15/645,589, dated Feb. 9, 2018.
Amendment in U.S. Appl. No. 15/645,589, dated Aug. 7, 2018.
Office Action in U.S. Appl. No. 15/626,516, dated Mar. 14, 2018.
Amendment in U.S. Appl. No. 15/626,516, dated Sep. 13, 2018.
Amendment in U.S. Appl. No. 15/589,058, dated Nov. 15, 2017.
Office Action in U.S. Appl. No. 15/589,058, dated Dec. 8, 2017.
Amendment in U.S. Appl. No. 15/589,058, dated Jun. 7, 2018.
Final Office Action in U.S. Appl. No. 15/589,058, dated Aug. 27, 2018.
Official Communication in European Application No. 14800423.7, dated Feb. 8, 2017.
International Search Report and Written Opinion in PCT Application No. PCT/US2014/038839, dated Oct. 17, 2014.

(56) References Cited

OTHER PUBLICATIONS

International Preliminary Report on Patentability in PCT Application No. PCT/US2014/038839, dated Dec. 3, 2015.
Preliminary Amendment in U.S. Appl. No. 14/491,935, dated Feb. 5, 2015.
Restriction Requirement in U.S. Appl. No. 14/491,935, dated Sep. 8, 2017.
Restriction Requirement and Election of Species Response in U.S. Appl. No. 14/491,935, dated Jan. 8, 2018.
Partial Supplementary European Search Report in European Application No. 14845427.5, dated May 4, 2017.
Extended European Search Report in European Application No. 14845427.5, dated Aug. 8, 2017.
Extended European Search Report in European Application No. 14846410.0, dated Jun. 23, 2017.
Official Communication in European Application No. 14846410.0, dated Jul. 18, 2018.
Official Communication in Japanese Application No. 2016-544032, dated Jun. 26, 2018.
International Search Report and Written Opinion in PCT Application No. PCT/US2014/056643, dated Dec. 11, 2014.
International Preliminary Report on Patentability and Written Opinion in PCT Application No. PCT/US2014/056643, dated Mar. 31, 2016.
Invitation to Pay Additional Fees in PCT Application No. PCT/US2014/056681, dated Jan. 14, 2015.
International Search Report and Written Opinion in PCT Application No. PCT/US2014/056681, dated Mar. 20, 2015.
International Preliminary Report on Patentability and Written Opinion in PCT Application No. PCT/US2014/056681, dated Mar. 31, 2016.
Preliminary Amendment in U.S. Appl. No. 14/581,779, dated Jul. 6, 2015.
Restriction Requirement in U.S. Appl. No. 14/581,779, dated Oct. 31, 2017.
Restriction Requirement and Election of Species Response in U.S. Appl. No. 14/581,779, dated Jan. 2, 2018.
Office Action in U.S. Appl. No. 14/581,779, dated Apr. 24, 2018.
Amendment in U.S. Appl. No. 14/581,779, dated Sep. 24, 2018.
Extended European Search Report in European Application No. 14873324.9, dated Aug. 25, 2017.
Invitation to Pay Additional Fees in PCT Application No. PCT/US2014/072121, dated Mar. 2, 2015.
International Search Report and Written Opinion in PCT Application No. PCT/US2014/072121, dated May 1, 2015.
International Preliminary Report on Patentability and Written Opinion in PCT Application No. PCT/US2014/072121, dated Jul. 7, 2016.
Preliminary Amendment in U.S. Appl. No. 14/960,276, dated Apr. 18, 2016.
Office Action in U.S. Appl. No. 14/960,276, dated Jul. 28, 2017.
Amendment in U.S. Appl. No. 14/960,276, dated Jan. 26, 2018.
Office Action in U.S. Appl. No. 14/960,276, dated Mar. 8, 2018.
Amendment in US Patent Application No. 14/960,276, dated Sep. 7, 2018.
Extended European Search Report in European Application No. 15865454.1, dated Jun. 27, 2018.
International Search Report and Written Opinion in PCT Application No. PCT/US2015/064133, dated Feb. 9, 2016.
International Preliminary Report on Patentability and Written Opinion in PCT Application No. PCT/US2015/064133, dated Jun. 15, 2017.
Preliminary Amendment in U.S. Appl. No. 15/081,653, dated Oct. 11, 2016.
Office Action in U.S. Appl. No. 15/081,653, dated Mar. 28, 2018.
Amendment in U.S. Appl. No. 15/081,653, dated Sep. 27, 2018.
International Search Report and Written Opinion in PCT Application No. PCT/US2016/024330, dated Jul. 1, 2016.
International Preliminary Report on Patentability and Written Opinion in PCT Application No. PCT/US2016/024330, dated Oct. 5, 2017.
Preliminary Amendment in U.S. Appl. No. 15/360,565, dated Feb. 6, 2017.
Office Action in U.S. Appl. No. 15/360,565, dated Aug. 10, 2018.
Invitation to Pay Additional Fees in PCT Application No. PCT/US2016/063549, dated Feb. 2, 2017.
International Search Report and Written Opinion in PCT Application No. PCT/US2016/063549, dated Apr. 14, 2017.
International Preliminary Report on Patentability and Written Opinion in PCT Application No. PCT/US2016/063549, dated Jun. 7, 2018.
International Search Report and Written Opinion in PCT Application No. PCT/US2018/031442, dated Sep. 14, 2018.
International Search Report and Written Opinion in PCT Application No. PCT/US2018/034227, dated Jul. 30, 2018.
Burle Industries, Technical Memorandum 100—Fiber Optics: Theory and Applications, archived Feb. 21, 2007, in 20 pages https://web.archive.org/web/20070221125354/http://www.burle.com/cgi-bin/byteserver.pl/pdf/100r.pdf.
Decision to Refuse received in European Application No. 13808996.6, dated Oct. 19, 2020.
Official Communication in Japanese Application No. 2018-218745, dated Feb. 25, 2020.
Official Communication in Japanese Application No. 2018-218745, dated Dec. 15, 2020.
Amendment in U.S. Appl. No. 15/483,995, dated Dec. 12, 2019.
Final Office Action in U.S. Appl. No. 15/483,995, dated Feb. 20, 2020.
Amendment in U.S. Appl. No. 15/483,995, dated Aug. 19, 2020.
Office Action in U.S. Appl. No. 15/483,995, dated Sep. 4, 2020.
Amendment in U.S. Appl. No. 15/483,995, dated Mar. 4, 2021.
Final Office Action in U.S. Appl. No. 15/483,995, dated Apr. 1, 2021.
Amendment in U.S. Appl. No. 15/645,589, dated Dec. 12, 2019.
Office Action in U.S. Appl. No. 15/645,589, dated Dec. 26, 2019.
Amendment in U.S. Appl. No. 15/645,589, dated Jun. 26, 2020.
Notice of Allowance in U.S. Appl. No. 15/645,589, dated Jul. 14, 2020.
Notice of Allowance in U.S. Appl. No. 15/645,589, dated Nov. 18, 2020.
Preliminary Amendment filed in U.S. Appl. No. 16/036,665, dated Sep. 5, 2019.
Office Action in U.S. Appl. No. 16/036,665, dated Sep. 26, 2019.
Amendment filed in U.S. Appl. No. 16/036,665, dated Mar. 26, 2020.
Office Action in U.S. Appl. No. 16/036,665, dated Jul. 13, 2020.
Amendment filed in U.S. Appl. No. 16/036,665, dated Jan. 13, 2021.
Office Action in U.S. Appl. No. 16/036,665, dated Mar. 3, 2021.
Amendment in U.S. Appl. No. 16/786,054, dated Sep. 25, 2020.
Office Action in U.S. Appl. No. 16/786,054, dated Apr. 23, 2021.
Restriction Requirement in U.S. Appl. No. 15/948,842, dated Jan. 22, 2020.
Response to Restriction Requirement in U.S. Appl. No. 15/948,842, dated Jul. 21, 2020.
Office Action in U.S. Appl. No. 15/948,842, dated Aug. 24, 2020.
Amendment in U.S. Appl. No. 15/948,842, dated Feb. 23, 2021.
Office Action in U.S. Appl. No. 15/948,842, dated Mar. 12, 2021.
Amendment in U.S. Appl. No. 16/799,168, dated Oct. 9, 2020.
Notice of Allowance in U.S. Appl. No. 16/799,168, dated Nov. 4, 2020.
Notice of Allowance in U.S. Appl. No. 16/799,168, dated Jun. 11, 2021.
Amendment in U.S. Appl. No. 14/581,779, dated Feb. 4, 2020.
Final Office Action in U.S. Appl. No. 14/581,779, dated Apr. 29, 2020.
Amendment in U.S. Appl. No. 14/581,779, dated Oct. 29, 2020.
Office Action in U.S. Appl. No. 14/581,779, dated Nov. 23, 2020.
Amendment in U.S. Appl. No. 14/581,779, dated May 21, 2021.
Final Office Action in U.S. Appl. No. 14/581,779, dated Jun. 7, 2021.

(56) References Cited

OTHER PUBLICATIONS

Official Communication in Japanese Application No. 2019-165048, dated Oct. 27, 2020.
Preliminary Amendment in U.S. Appl. No. 16/920,582, dated Feb. 12, 2021.
Amendment in U.S. Appl. No. 15/081,653, dated Jan. 10, 2020.
Final Office Action in U.S. Appl. No. 15/081,653, dated Jan. 31, 2020.
Amendment in U.S. Appl. No. 15/081,653, dated Jul. 30, 2020.
Office Action in U.S. Appl. No. 15/081,653, dated Sep. 17, 2020.
Amendment in U.S. Appl. No. 15/081,653, dated Mar. 16, 2021.
Notice of Allowance in U.S. Appl. No. 15/081,653, dated Jun. 3, 2021.
Official Communication in European Application No. 16869253.1, dated Jan. 21, 2021.
International Preliminary Report on Patentability and Written Opinion in PCT Application No. PCT/US2018/031442, dated Nov. 21, 2019.
International Preliminary Report on Patentability and Written Opinion in PCT/US2018/034227, dated Dec. 5, 2019.
Amendment in U.S. Appl. No. 16/677,441, dated Jun. 26, 2020.
Restriction Requirement in U.S. Appl. No. 16/677,441, dated Dec. 8, 2020.

\* cited by examiner

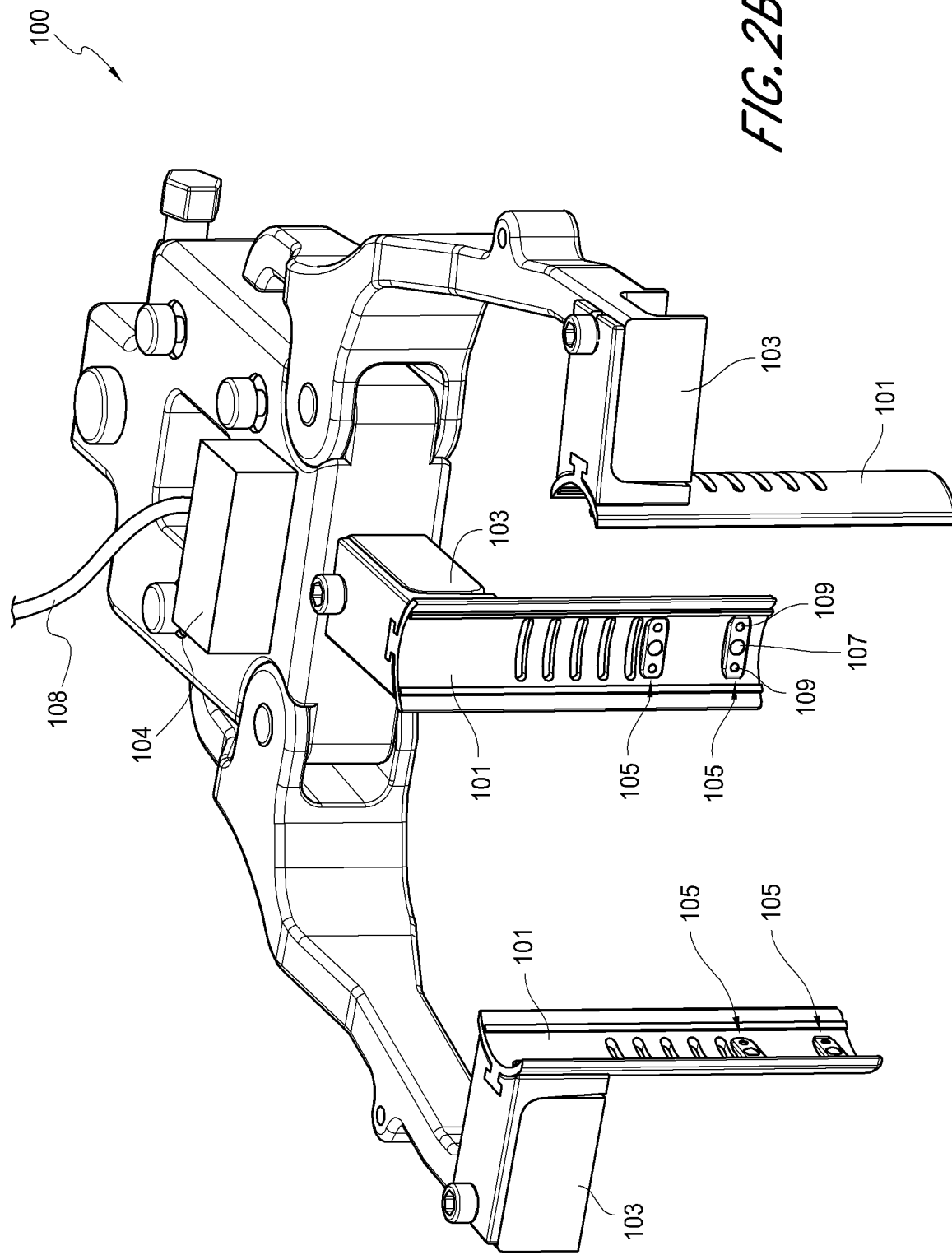

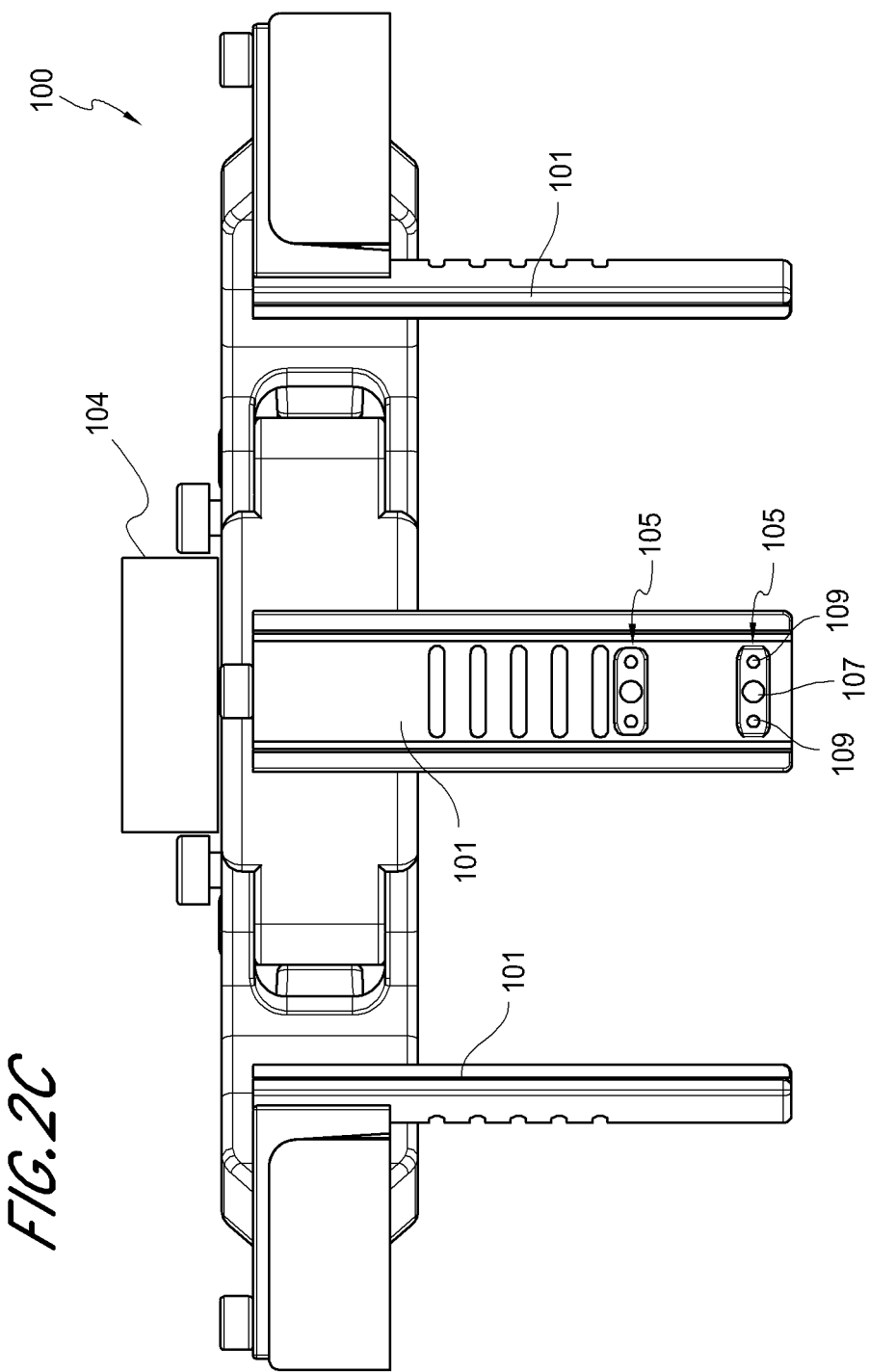

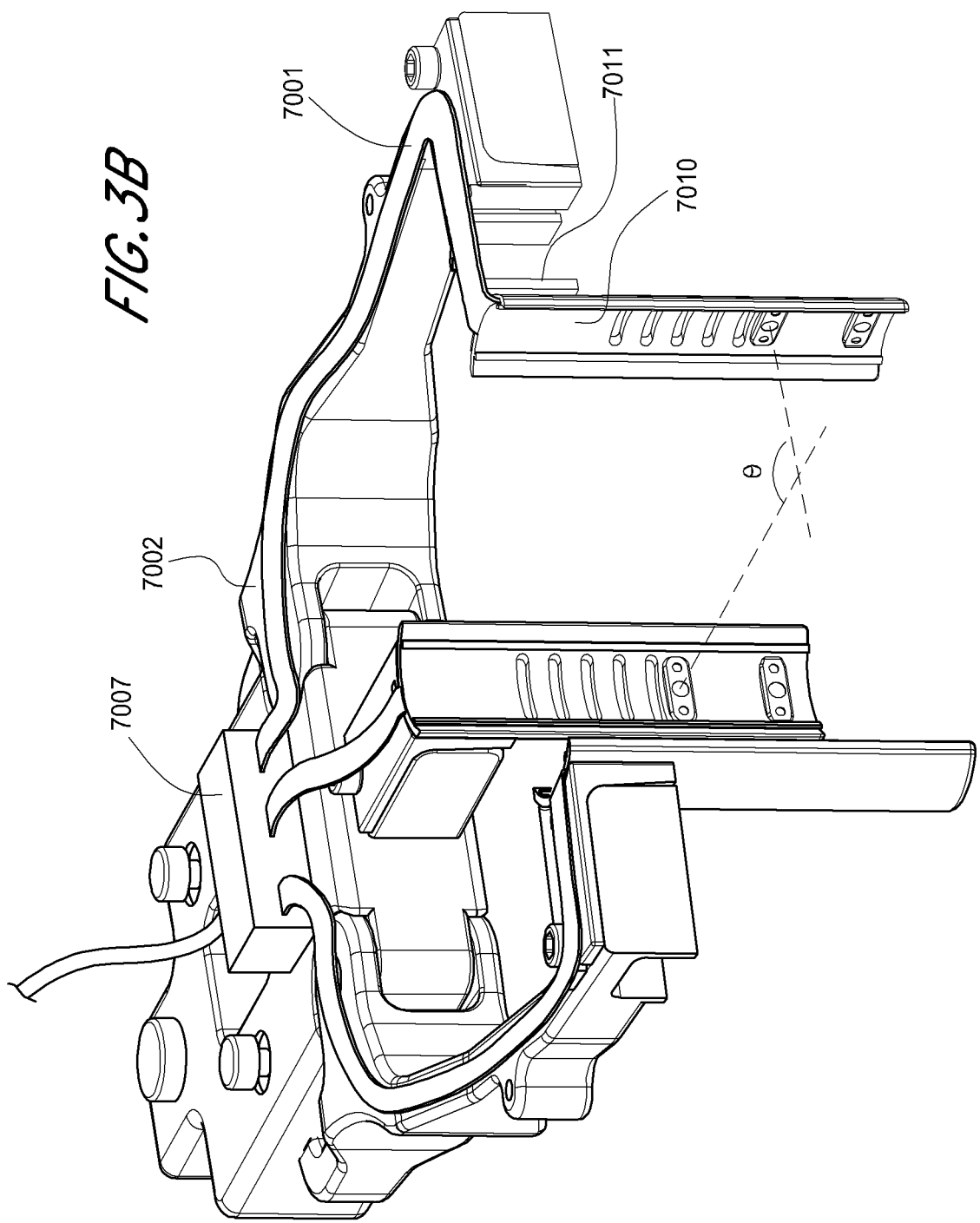

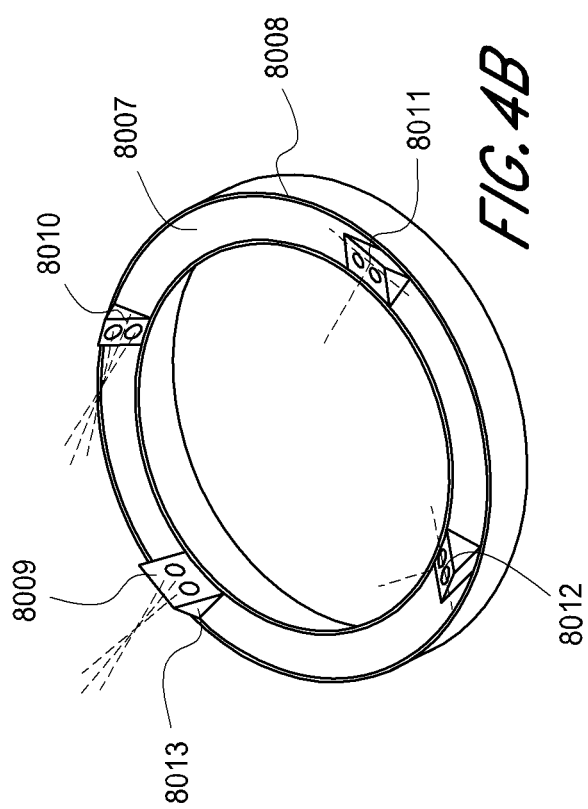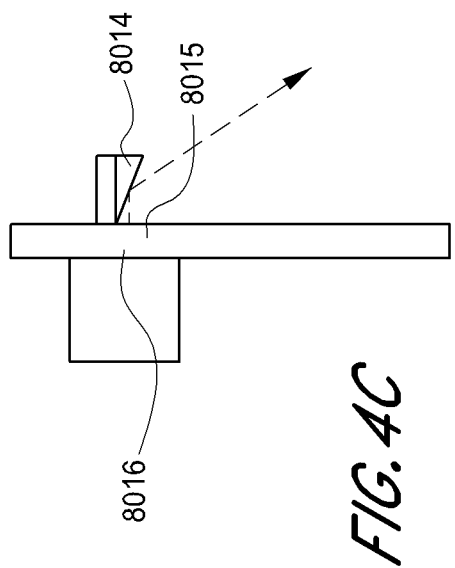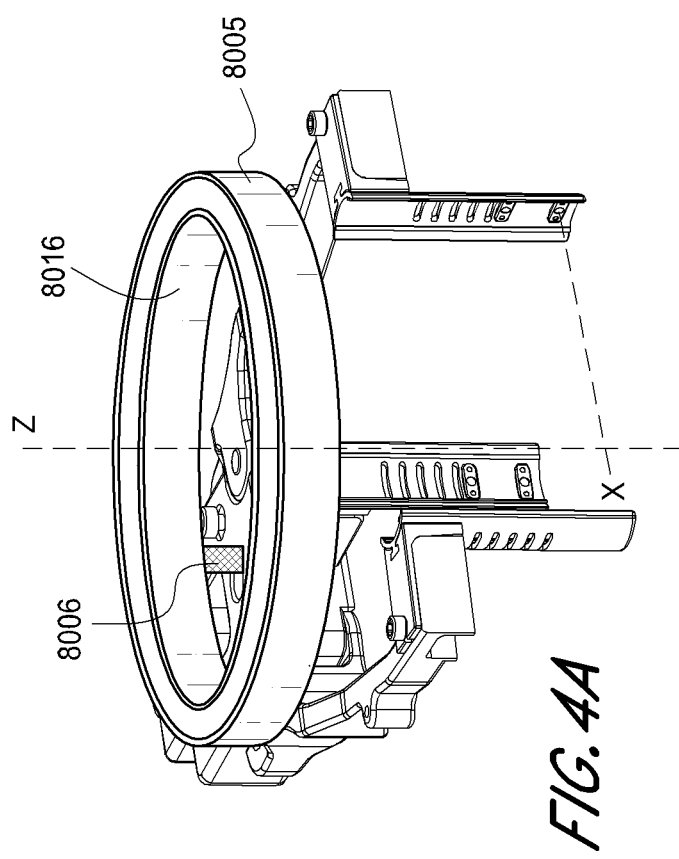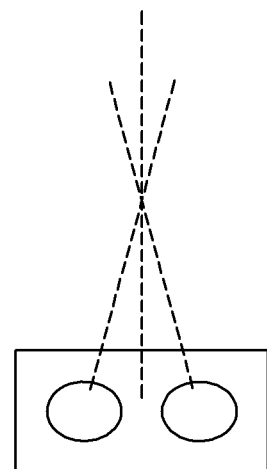

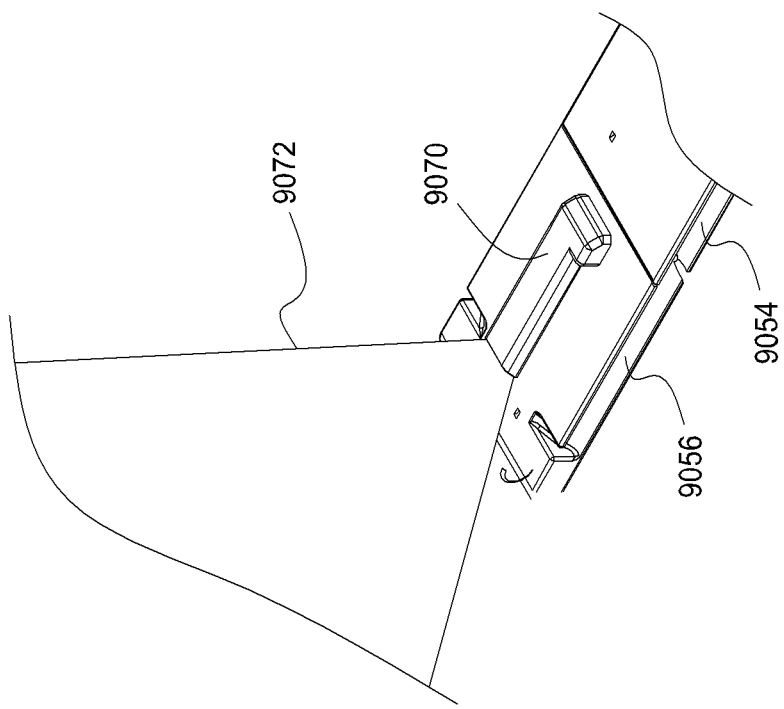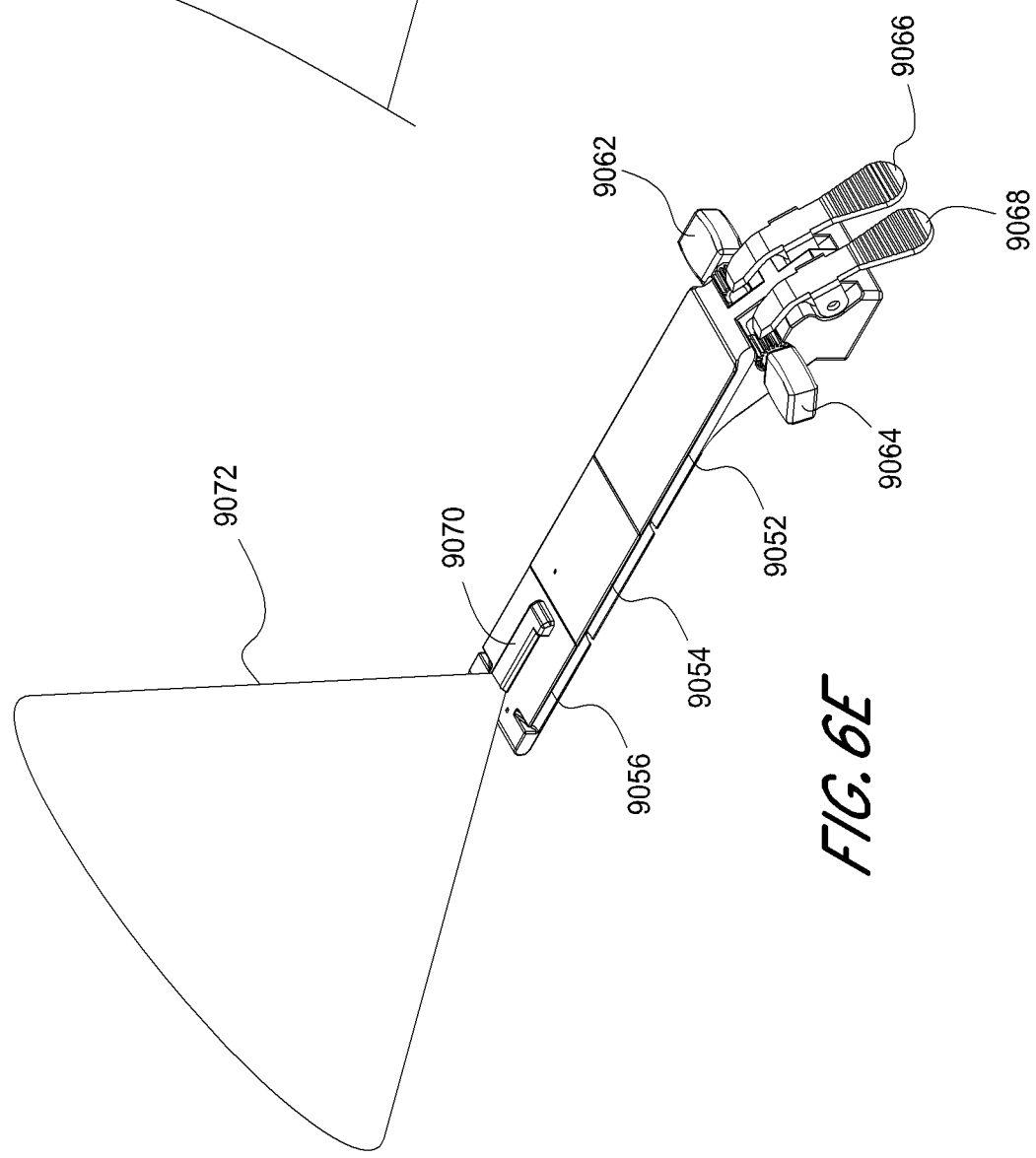

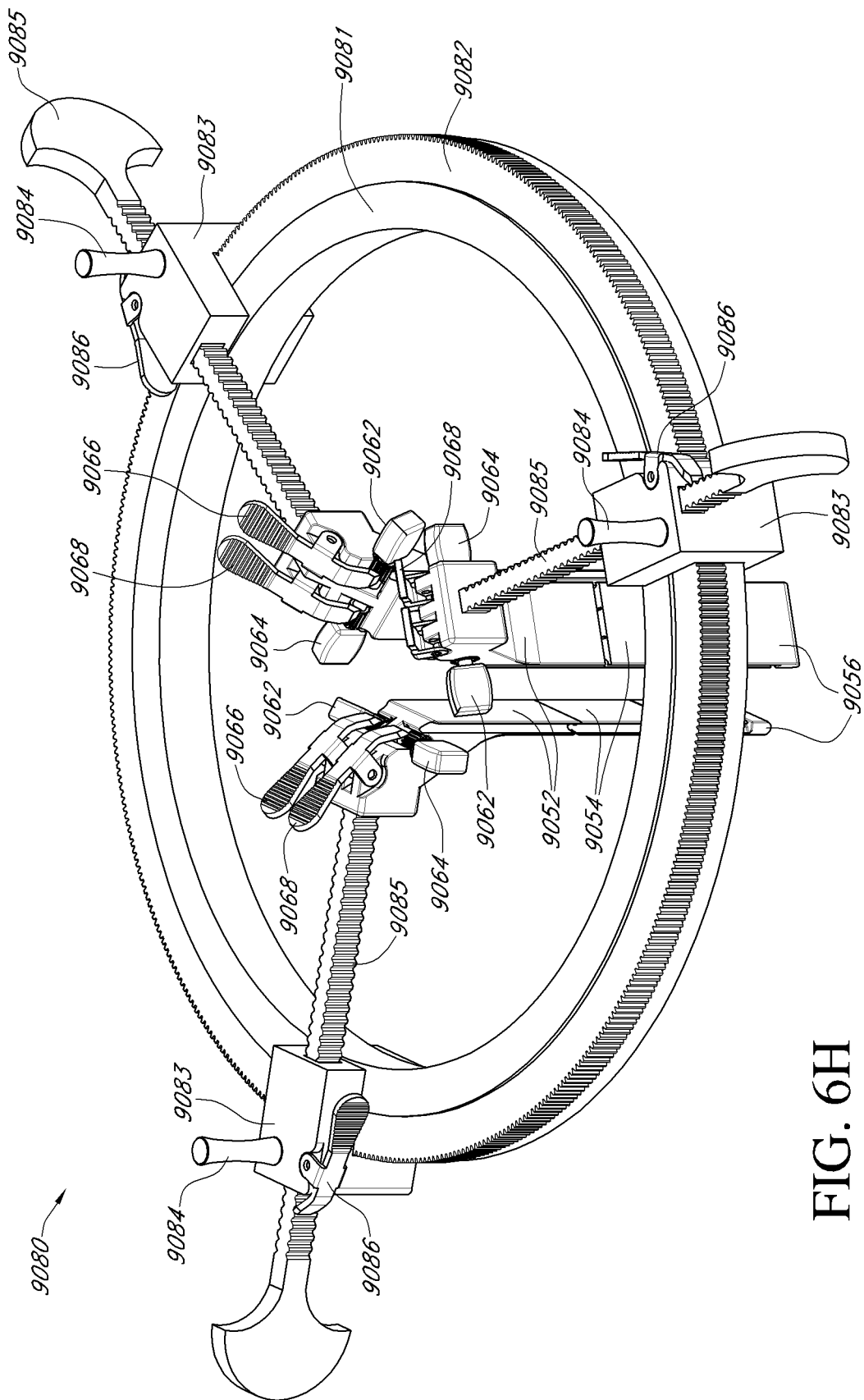

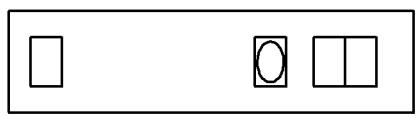
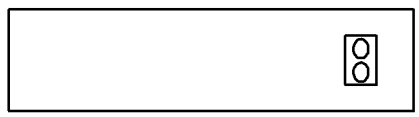
FIG. 7
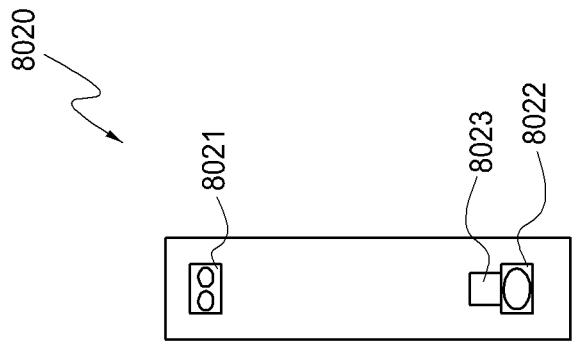
FIG. 8

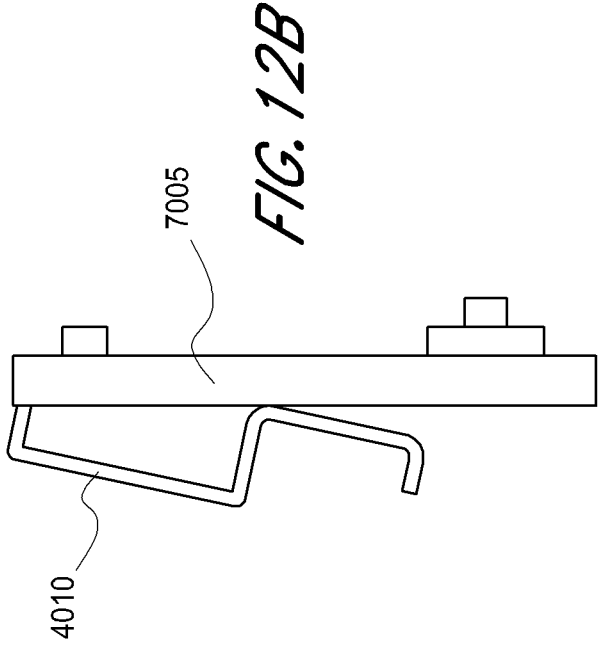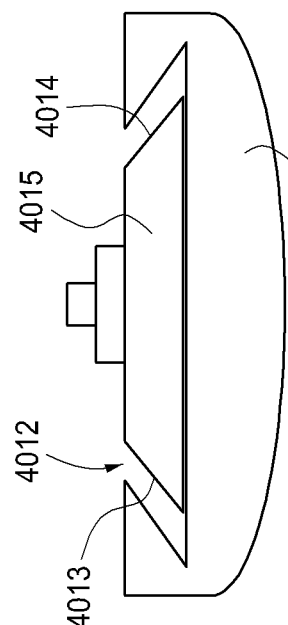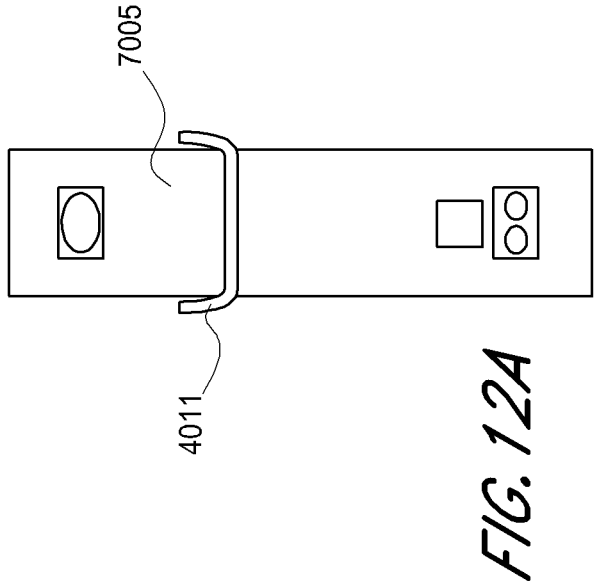

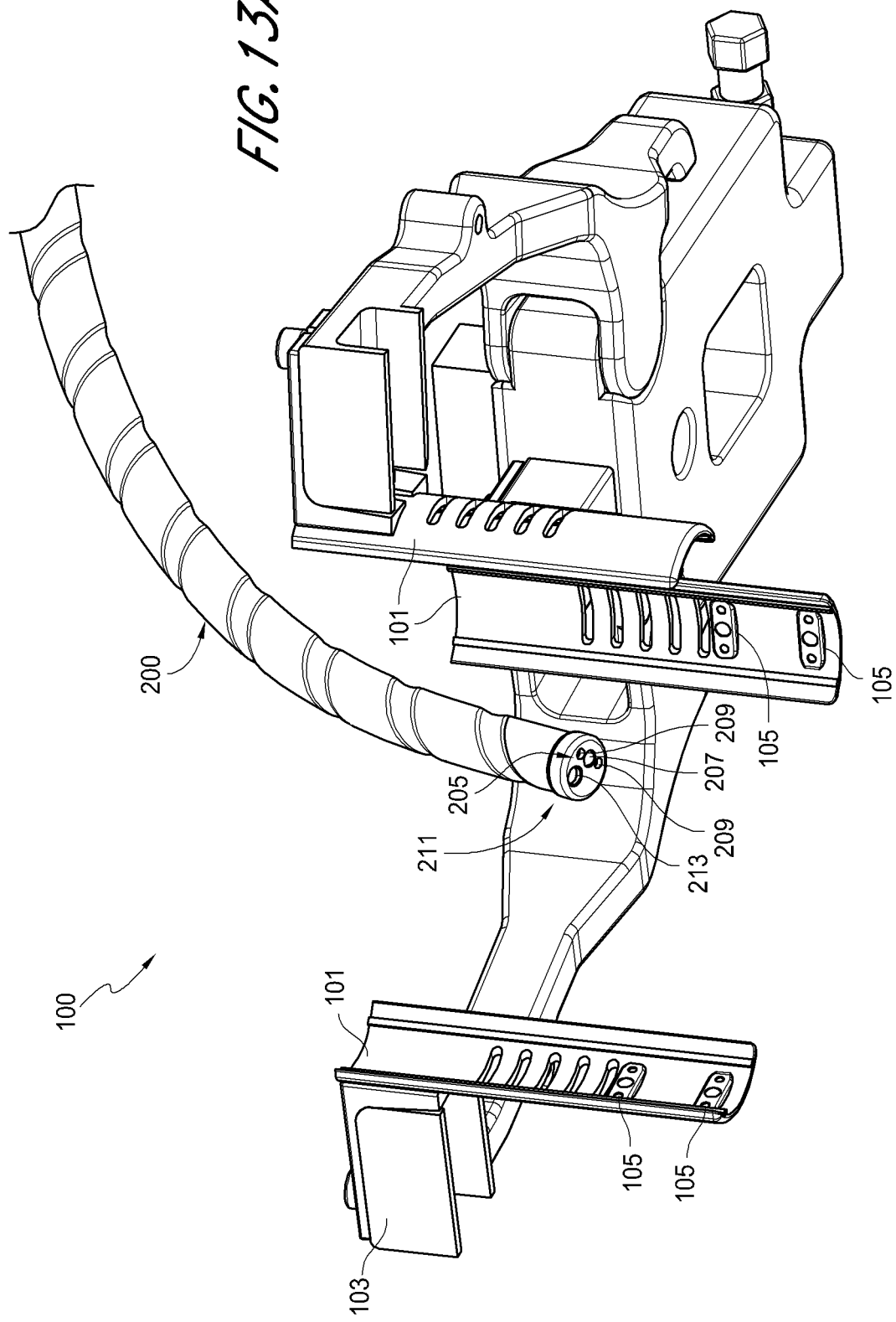

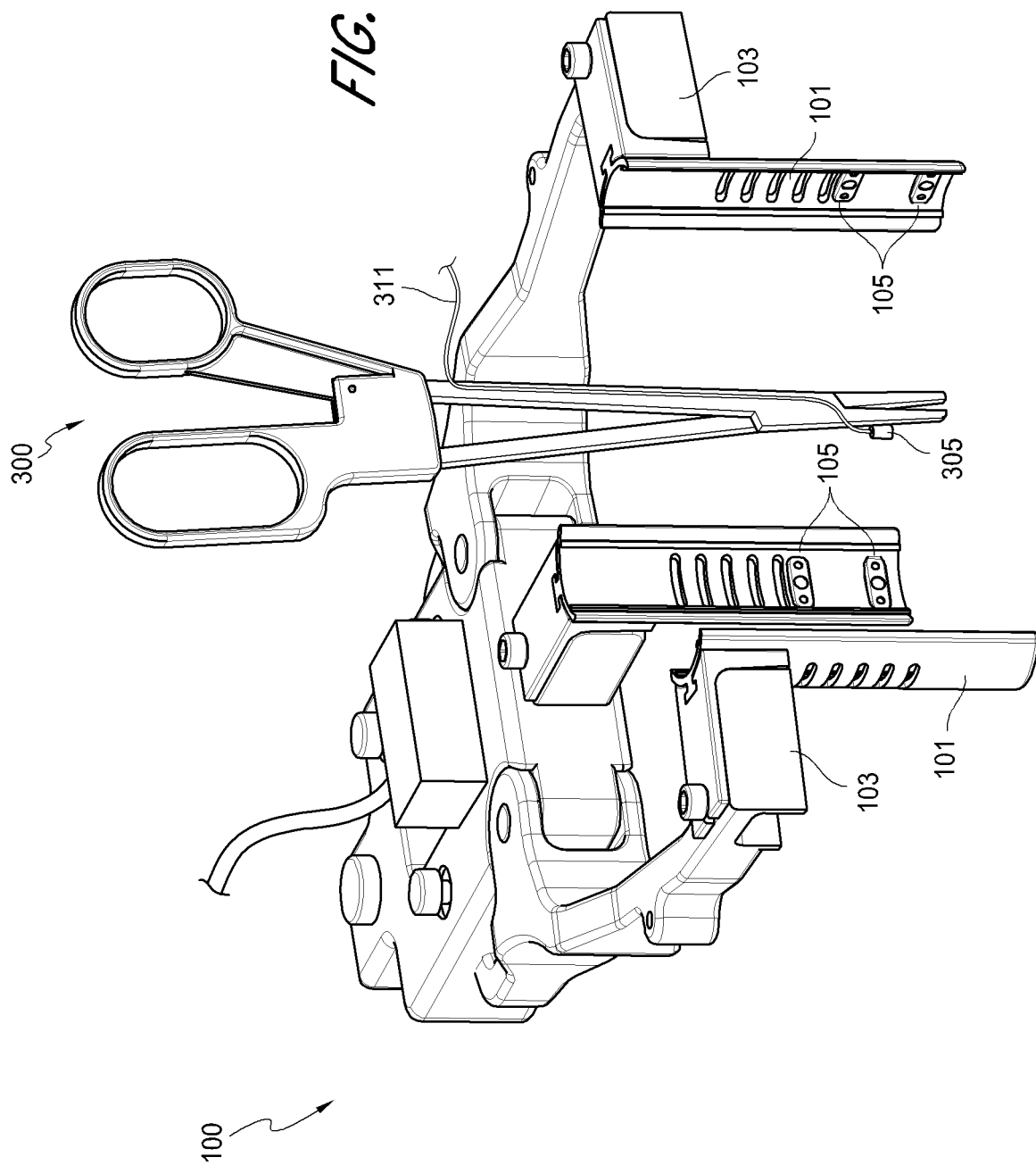

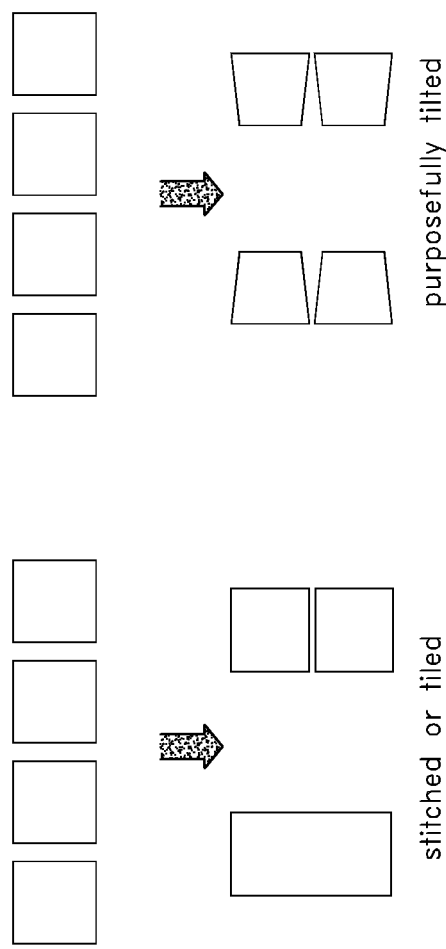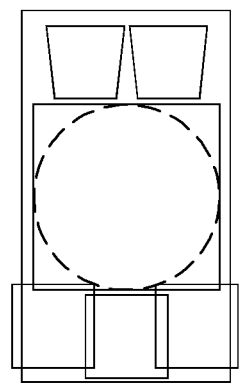
FIG. 16
Distal and proximal cameras viewed in display
central stereo from proximal camera or   tool in wide field

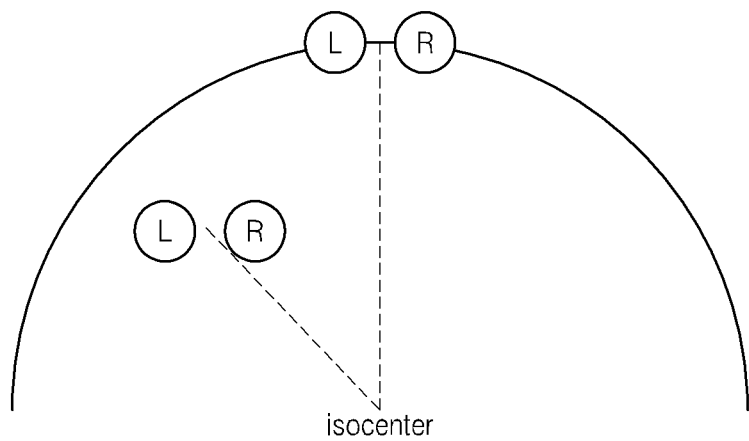
The display provides a horizon consistent with an ergonomically advantageous viewing position for the user. The isocenter is defined as the postion bewtween the two eyes parallel to the display's horizon.
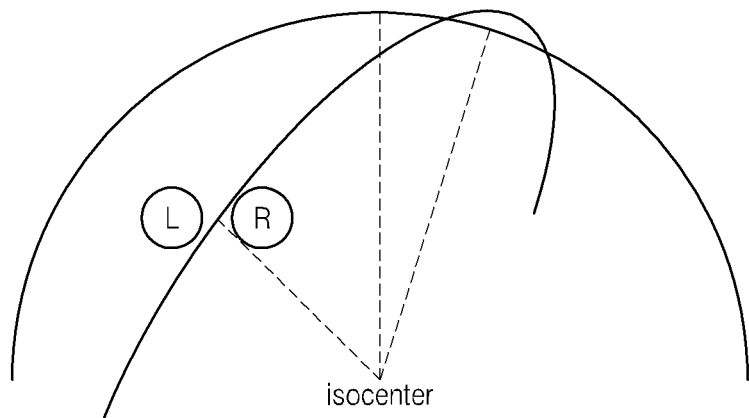
FIG. 21-D2

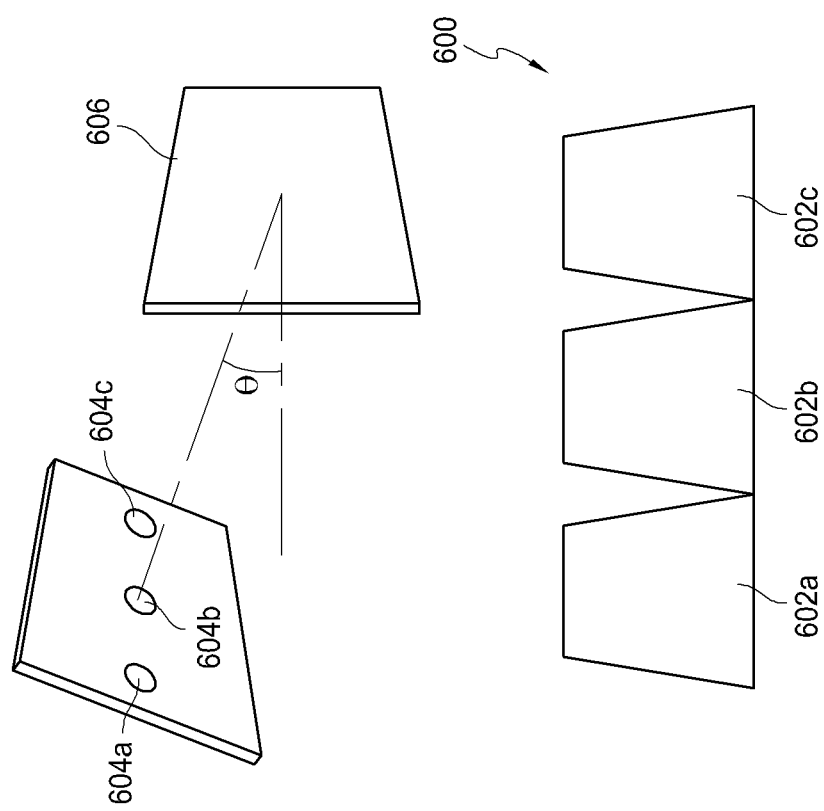
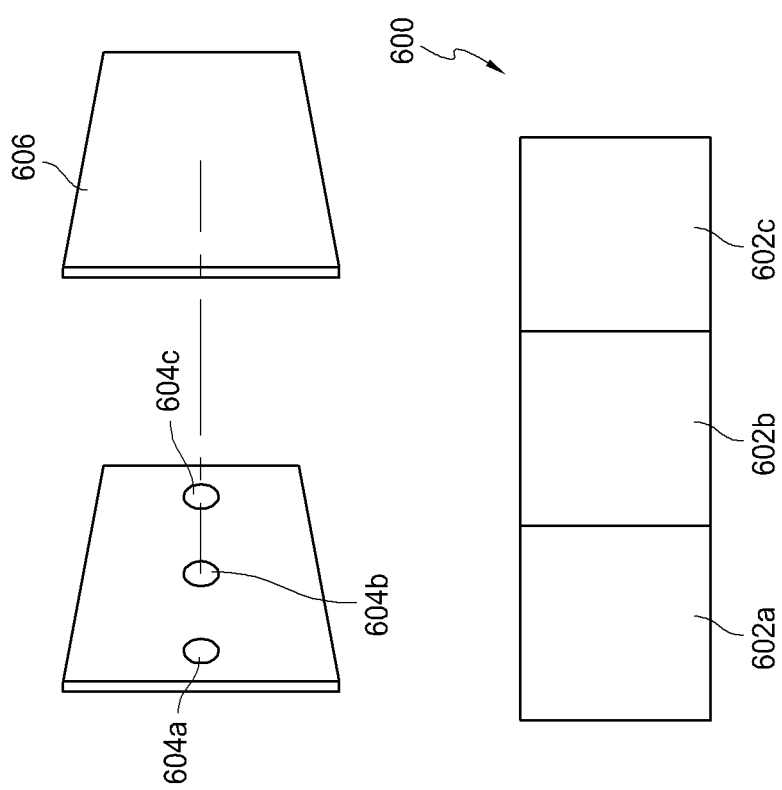
FIG. 22A
FIG. 22B

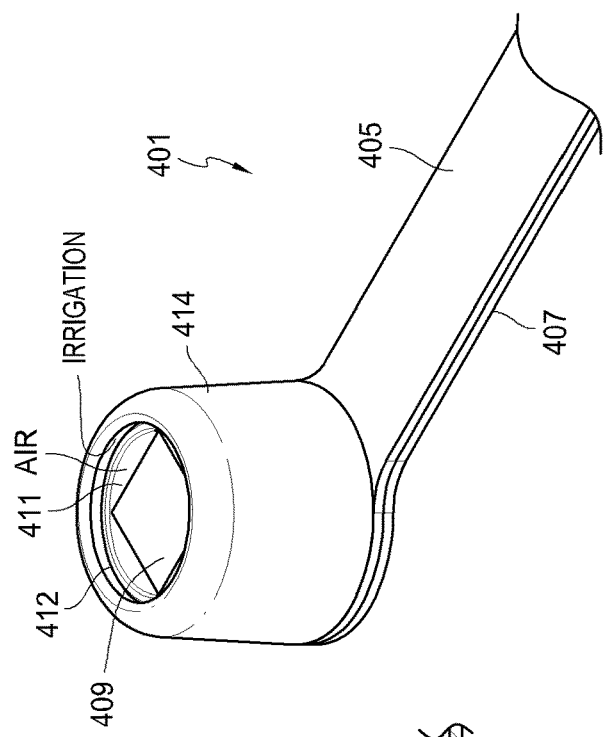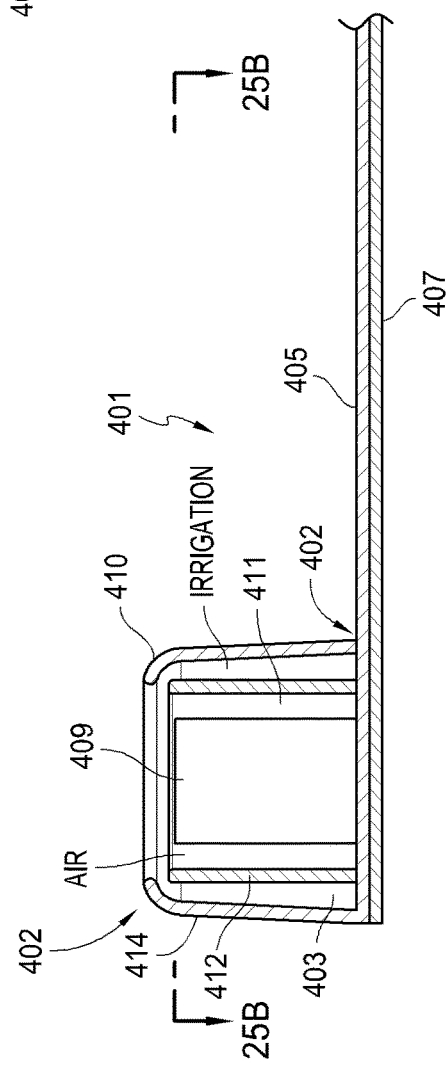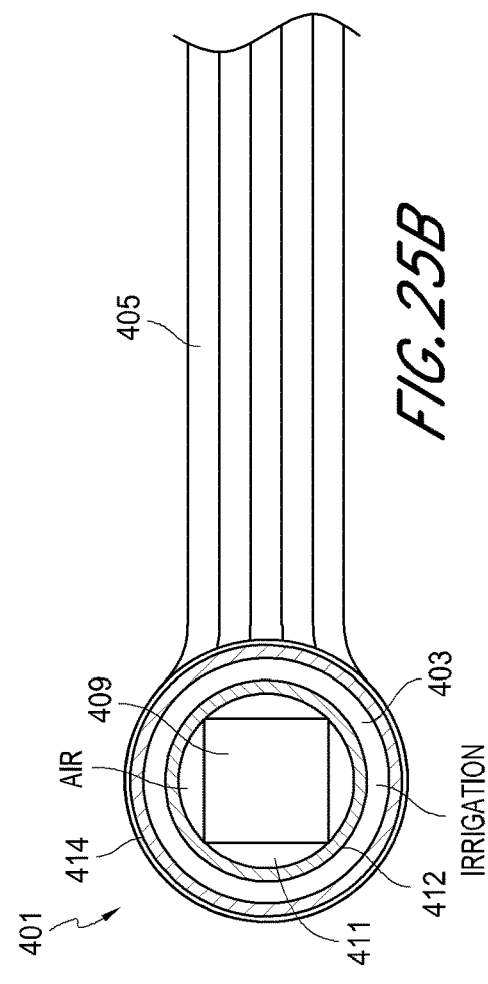

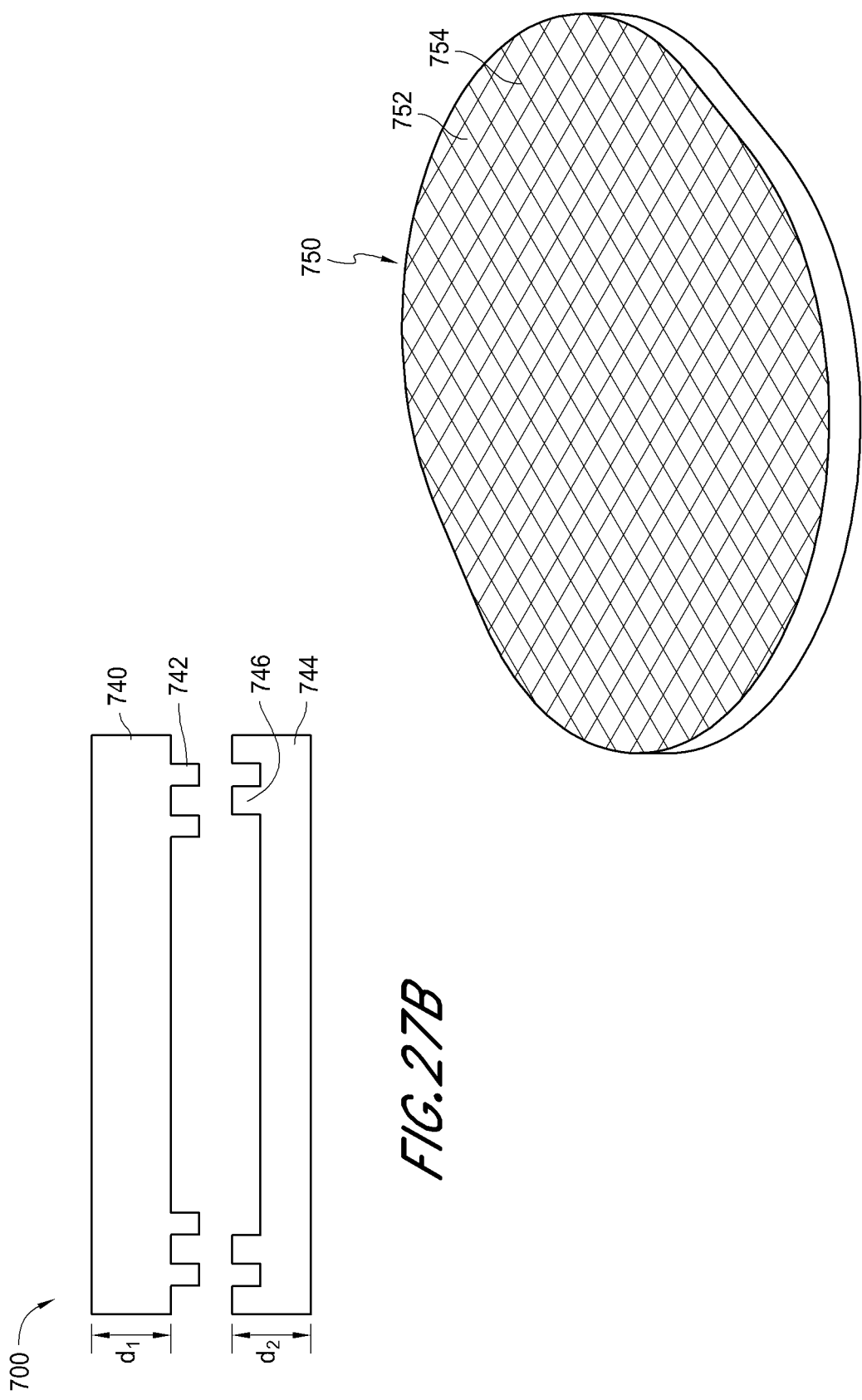

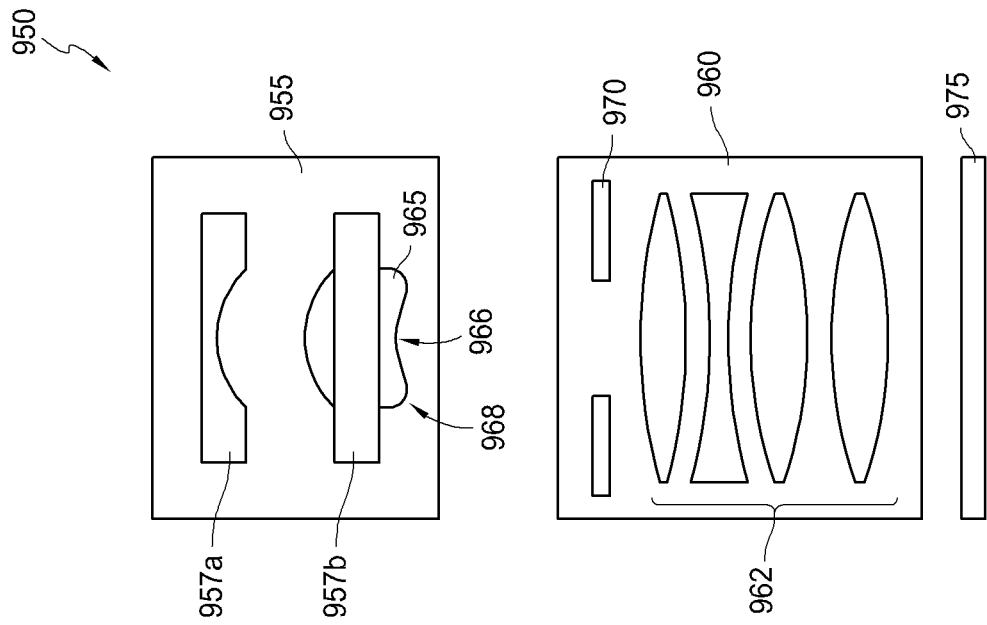
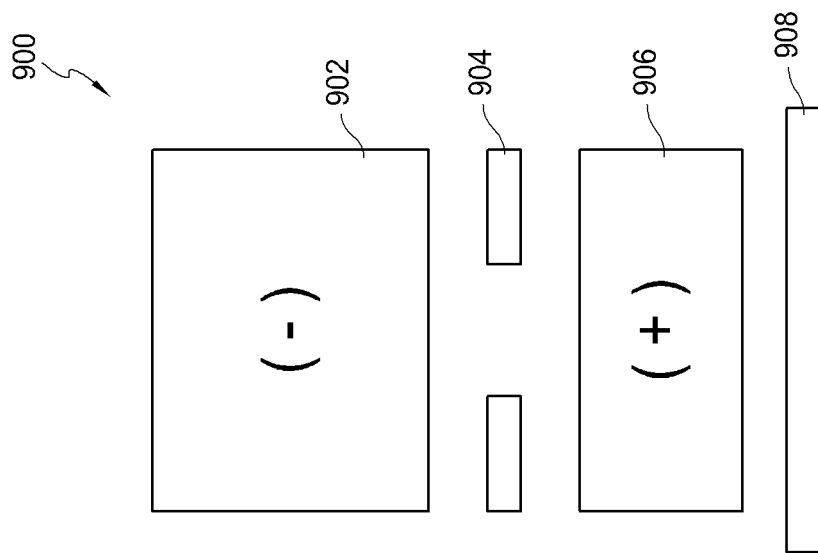
FIG. 29B
FIG. 29A

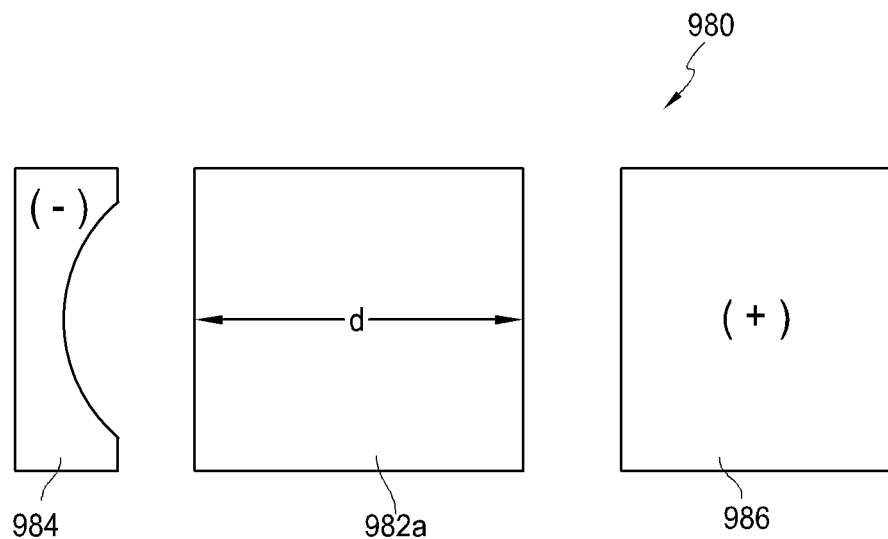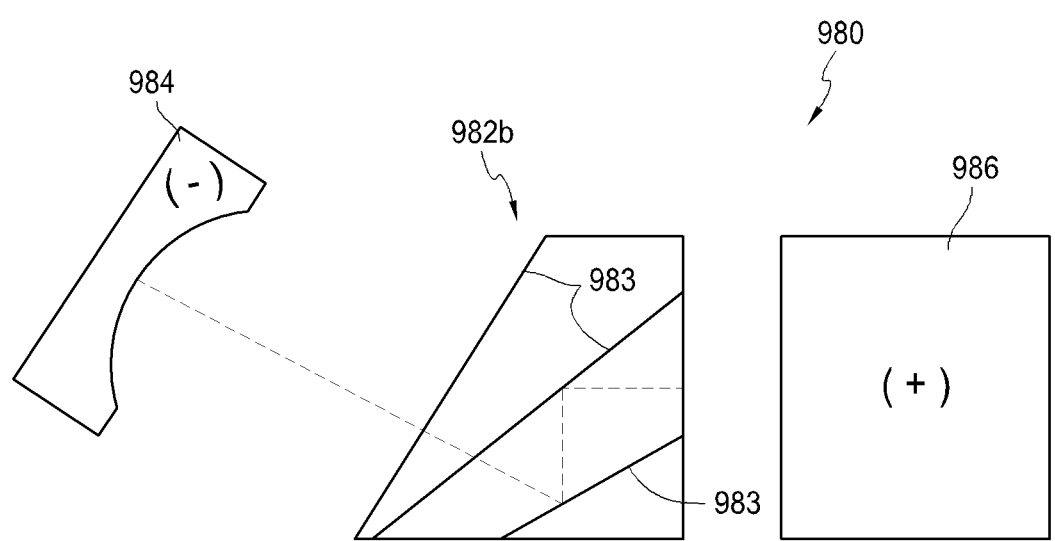
FIG.29C

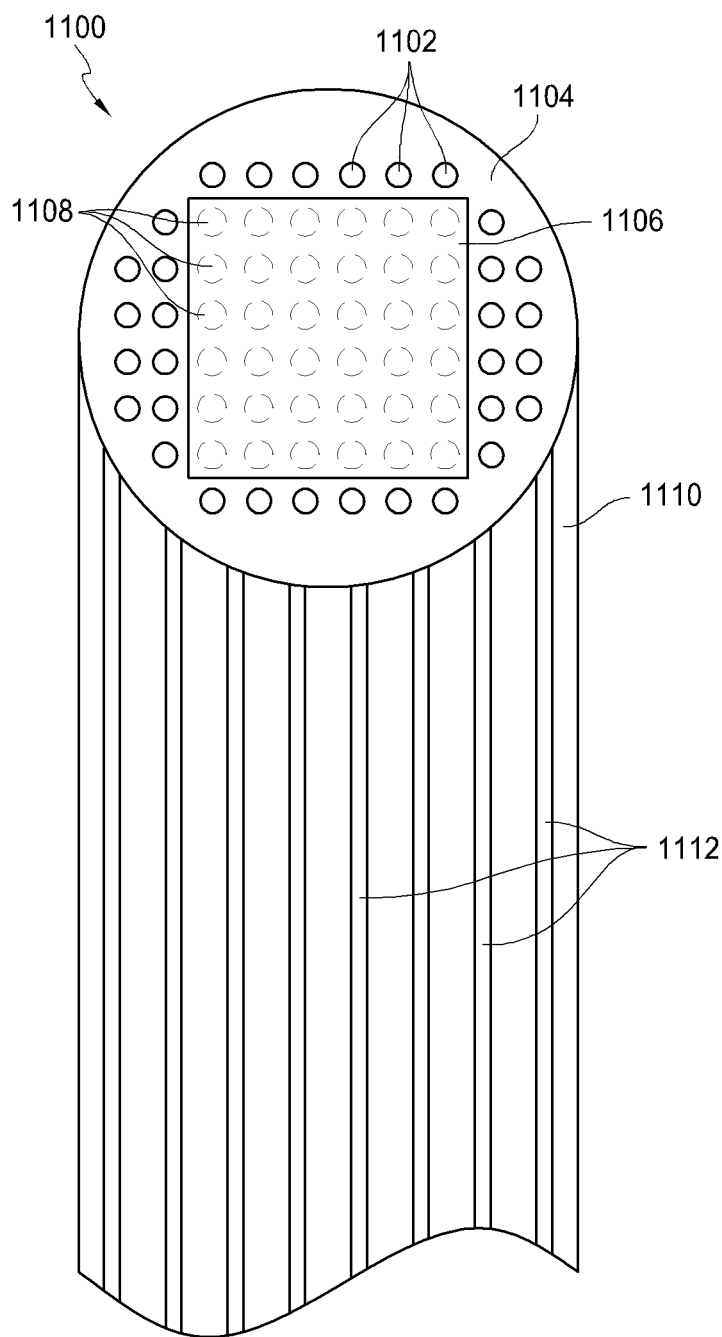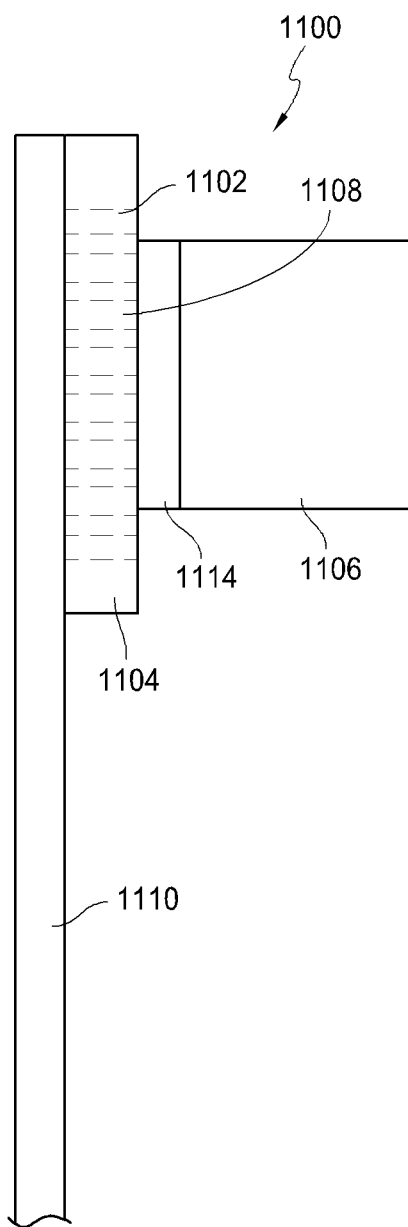
FIG.31A
FIG.31B

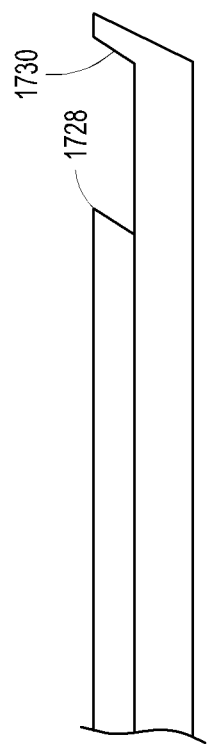
FIG. 47D
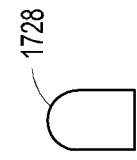
FIG. 47G
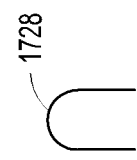
FIG. 47F
FIG. 47E

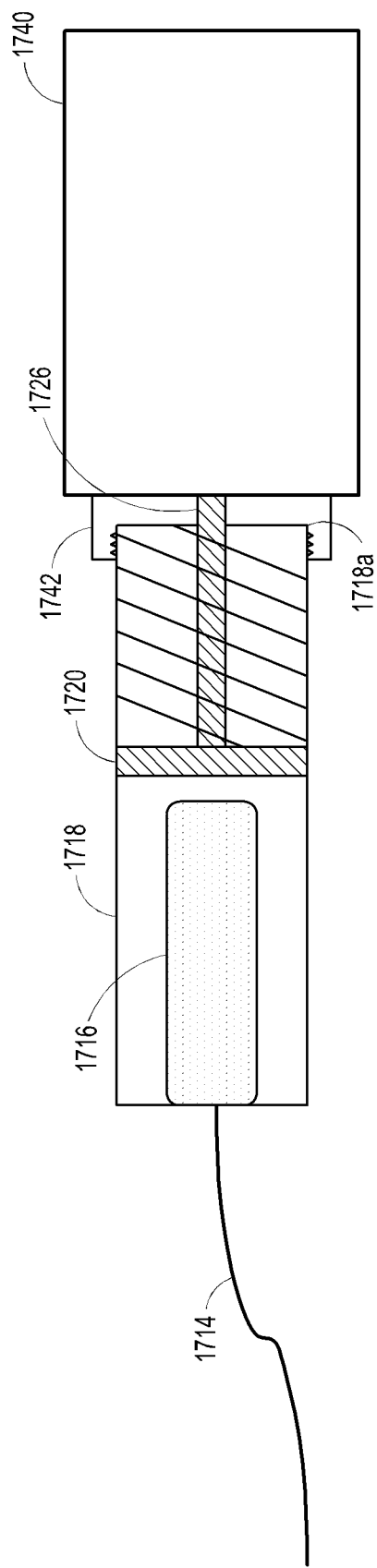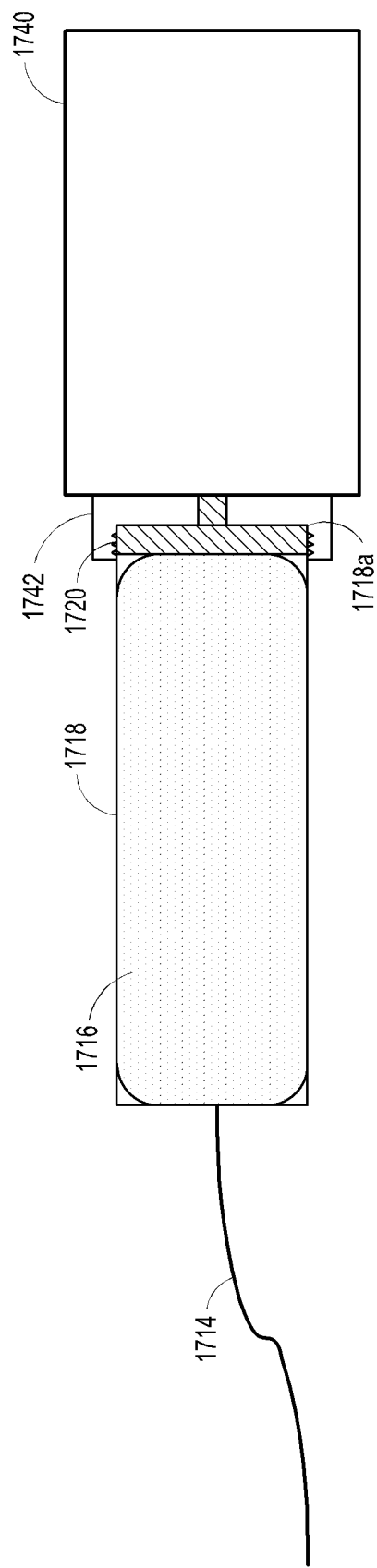

SURGICAL VISUALIZATION SYSTEMS

CROSS-REFERENCE TO RELATED APPLICATIONS

This application is a continuation of U.S. application Ser. No. 14/411,068, filed Dec. 23, 2014, which is a national stage application under 35 U.S.C. § 371 of International Application No. PCT/US2013/047972, filed Jun. 26, 2013, which is a continuation of U.S. application Ser. No. 13/802,362, filed Mar. 13, 2013, U.S. application Ser. No. 13/802,162, filed Mar. 13, 2013, U.S. application Ser. No. 13/802,485, filed Mar. 13, 2013, U.S. application Ser. No. 13/802,635, filed Mar. 13, 2013, U.S. application Ser. No. 13/802,509, filed Mar. 13, 2013, U.S. application Ser. No. 13/802,582, filed Mar. 13, 2013, and U.S. application Ser. No. 13/802,577, filed Mar. 13, 2013. PCT/US2013/047972 also claims the benefit of priority under 35 U.S.C. § 119(e) to U.S. Provisional Application No. 61/665,243, filed Jun. 27, 2012, U.S. Provisional Application No. 61/670,550, filed Jul. 11, 2012, U.S. Provisional Application No. 61/703,727, filed Sep. 20, 2012, and U.S. Provisional Application No. 61/753,398, filed Jan. 16, 2013. Each of these applications is hereby incorporated by reference in its entirety.

BACKGROUND

Field

Embodiments of the present disclosure relate to surgical devices and visualization systems for use during surgery.

Description of Related Art

Some surgical operations involve the use of large incisions. These open surgical procedures provide ready access for surgical instruments and the hand or hands of the surgeon, allowing the user to visually observe and work in the surgical site, either directly or through an operating microscope or with the aide of loupes. Open surgery is associated with significant drawbacks, however, as the relatively large incisions result in pain, scarring, and the risk of infection as well as extended recovery time. To reduce these deleterious effects, techniques have been developed to provide for minimally invasive surgery. Minimally invasive surgical techniques, such as endoscopy, laparoscopy, arthroscopy, pharyngo-laryngoscopy, as well as small incision procedures utilizing an operating microscope for visualization, utilize a significantly smaller incision than typical open surgical procedures. Specialized tools may then be used to access the surgical site through the small incision. However, because of the small access opening, the surgeon's view and workspace of the surgical site is limited. In some cases, visualization devices such as endoscopes, laparoscopes, and the like can be inserted percutaneously through the incision to allow the user to view the surgical site. Alternatively operating microscopes may be used to view the surgical site through a small incision held open by one or a number of surgical retractors.

The visual information available to a user through laparoscopic, endoscopic, or operating microscope contain trade-offs in approach. Accordingly, there is a need for improved visualization systems, for use in minimally invasive surgery.

SUMMARY OF THE INVENTION

The systems, methods and devices of the disclosure each have several innovative aspects, no single one of which is solely responsible for the desirable attributes disclosed herein.

In accordance with one aspect, a medical apparatus comprises a surgical retractor configured to hold open an incision and thereby provide a pathway for access of surgical tools to a surgical site; and a plurality of cameras disposed on the surgical retractor, the cameras inwardly facing toward the pathway. In some embodiments, the surgical retractor can comprise a plurality of retractor blades and the cameras are disposed on the retractor blades. In some embodiments, the surgical retractor comprises a tube and the cameras can be disposed on an inside surface of the tube. In some embodiments, the surgical retractor can comprise: a proximal camera at a proximal location; and a distal camera at a distal location; wherein the distal location is configured to be disposed closer to the surgical site than the proximal location. In some embodiments, the medical apparatus can further comprise a plurality of proximal cameras at the proximal location and a plurality of distal cameras at the distal location. In some embodiments, the plurality of proximal cameras can comprise at least 3 cameras. In some embodiments, the plurality of distal cameras can comprise at least 3 cameras. In some embodiments, the surgical retractor can be configured for use in spine surgery. In some embodiments, the surgical retractor can be configured for use in head or neck surgery. In some embodiments, the surgical retractor can be configured for use in neurosurgery. In some embodiments, the plurality of cameras can comprise at least 8 cameras.

In accordance with another aspect, a method comprises: inserting a retractor into an opening in a body; holding open edges of the opening with the retractor, thereby providing a pathway for access of surgical tools to a surgical site; and inserting a surgical tool at least partially through pathway and to the surgical site, wherein the retractor comprises a plurality of cameras disposed on the surgical retractor, the cameras inwardly facing toward the pathway. In some embodiments, the surgical tool can comprise a scalpel, a rongeur, a Kerrison, a laser, or a drill. In some embodiments, the surgical site is a portion of a spine of the body. In some embodiments, the surgical site is in a head or in a neck of the body. In some embodiments, the surgical site is in a brain of the body. In some embodiments, the opening is a mouth of the body. In some embodiments, the retractor comprises a plurality of retractor blades and the cameras are disposed on the retractor blades. In some embodiments, the retractor comprises a tube and the cameras are disposed on an inside surface of the tube. In some embodiments, the method further comprises removing bone at the surgical site with the surgical tool.

In accordance with another aspect, a surgical visualization system comprises: a retractor; a plurality of cameras disposed on the retractor, said cameras producing respective images; and an image processing module configured to display said respective images, wherein said surgical visualization system is configured to track the location of said cameras. In some embodiments, said cameras are associated with tracking devices to track the relative location of the different cameras. In some embodiments, said tracking devices comprise electromagnetic (EM) tracking devices. In some embodiments, the cameras are disposed on movable blades of the retractor. In some embodiments, the surgical visualization system tracks the location of the plurality of cameras by tracking the position of the retractor blades. In some embodiments, the retractor blades comprise a plurality of segments connected by at least one hinge. In some embodiments, the retractor blades are malleable. In some embodiments, the cameras are removably coupled to the retractor. In some embodiments, the cameras are associated with tracking devices to track the relative locations of the different cameras, and the tracking devices are removably coupled to the retractor.

In accordance with another aspect, a method comprises: inserting a retractor into an opening in a body, the retractor comprising a plurality of cameras disposed thereon; and electronically tracking the locations of said cameras. In some embodiments, the method further comprises obtaining respective images from each of the plurality of cameras, and processing said respective images for simultaneous viewing. In some embodiments, said processing comprises using the tracked locations of said cameras. In some embodiments, said electronically tracking comprises electromagnetic (EM) tracking. In some embodiments, said electronically tracking comprises tracking the position of a first camera relative to the position of a second camera. In some embodiments, said cameras are disposed on blades of the retractor, and said electronically tracking comprises tracking position of the blades. In some embodiments, said blades are movable with respect to one another. In some embodiments, said blades are malleable or articulated. In some embodiments, said electronically tracking comprises tracking the degree to which said blades are bent or articulated.

In accordance with another aspect, a medical apparatus comprises: a surgical retractor configured to provide access to a surgical site; a plurality of cameras disposed on the retractor; a plurality of tracking devices configured to track the locations of at least some of the plurality of cameras. In some embodiments, the plurality of cameras comprises at least a first camera and a second camera each have tracking devices associated therewith to track the relative positions of the first and second camera with respect to each other. In some embodiments, the retractor comprises at least a first retractor blade and a second retractor blade each having at least one camera thereon, and each of said first and second retractor blades have tracking devices thereon to track the relative positions of the first and second retractor blades with respect to each other. In some embodiments, said tracking devices comprise electromagnetic (EM) tracking devices.

In accordance with another aspect, a medical apparatus comprises: a surgical retractor configured to hold open an incision and thereby provide a pathway for access of surgical tools to a surgical site; and at least one camera (e.g., a plurality of cameras) disposed on the surgical retractor. In some embodiments said at least one camera is inwardly facing toward said pathway. In some embodiments, said surgical retractor comprises at least one retractor blades and said camera is disposed on said retractor blade. In some embodiments, said surgical retractor comprises a tube and said at least one camera is disposed on an inside surface of said tube. In some embodiments, said surgical retractor comprises at least one proximal camera and at least one distal camera. In some embodiments, the camera is fastened to the surgical retractor using a clip-on fastener. In some embodiments, said clip-on fastener comprises a clip, a snap, a screw, a bolt, a nut, magnet. In some embodiments, the medical apparatus further comprises an electrical bus and electrical connector configured to connect said camera to said electrical bus. In some embodiments, said electrical bus is fastened to said surgical retractor using a clip-on fastener.

In some embodiments, the camera is integrated into the surgical retractor. In some embodiments, one or more cameras (e.g., a plurality of cameras on a retractor, or at least one camera on a retractor and at least one camera located elsewhere such as on a surgical tool) produce respective images, and the apparatus further comprises an image processing module. In some embodiments, the image processing module is configured to display at least a portion of said respective images as stitched together. In some embodiments, the image processing module is configured to display at least a portion of said respective images as tiled. In some embodiments, the image processing module is configured to display said respective tiled images as arranged with a first central image and a plurality of surrounding images, said first central image from a different camera than said plurality of surrounding images. In some embodiments, said first central image and a plurality of surrounding images correspond to a first central view and a plurality peripheral views. In some embodiments, said first central image has larger zoom magnification than said plurality peripheral views. In some embodiments, said first central image comprises at least a portion of said respective images stitched together. In some embodiments, said first central image comprises a stereo image. In some embodiments, said plurality of surrounding images comprises at least a portion of said respective images tiled together. In some embodiments, said plurality of surrounding images comprises at least a portion of said respective images stitched together. In some embodiments, the image processing module is configured to display said respective images as arranged with a main view and a plurality of images superimposed on said main view, said main view from a different camera than said plurality of superimposed images. In some embodiments, said first main view covers a larger field-of-view than any of said other superimposed images. In some embodiments, said first main view comprises a first background view. In some embodiments, the apparatus further comprises a picture-in-picture in said main view, said picture-in-picture having a larger zoom magnification than said main view. In some embodiments the picture-in-picture image may comprise a stereo image. In some embodiments the main view image may comprise a wide field-of-view image. In some embodiments the main view may comprise a plurality of image, for example, stitched or tiled together. In some embodiments, said picture-in-picture comprises plurality of said images stitched together. In some embodiments, the image processing module is further configured to display a first central image disposed centrally with respect to said main view and said plurality of superimposed images. In some embodiments, said first central images has a larger zoom magnification than said main view. In some embodiments, said main view comprises at least a portion of at least a plurality of said respective images stitched together. In some embodiments, said main view comprises at least a portion of at least a plurality of said respective images tiled together. In some embodiments, said plurality of superimposed images comprises at least a portion of at least a plurality of said respective images tiled together. In some embodiments, said plurality of superimposed images comprises at least a portion of said respective images stitched together. In some embodiments, said respective images are arranged with a first main view and an image superimposed on said main view, said main view from a different camera than said superimposed image, said first main view comprising a larger field-of-view than said superimposed image. In some embodiments, said first main view covers a larger field of view than any of said other superimposed images. In some embodiments, said first main view comprises a first background view. In some embodiments, said superimposed image comprises a picture-in-picture image. In some embodiments, said image processing module is configured to receive selection of views from a user via an interface. In some embodiments, a main view having a wide field-of-view is provided with a plurality of narrow field-of-views tiled images superimposed thereon. In some embodiments a picture-in-picture (PIP) image is superimposed on the main view and as well. The PIP image may be more centrally located than the tiled images, and may, for example, be surrounded by the tiled images. In some embodiments, the PIP image may comprise a stereo image. In some embodiments, the PIP image may comprise an image from a camera mounted on a tool. In some embodiments, the PIP image may comprise an image from a proximal camera, for example, located at a proximal end of the retractor. In some embodiments, said image processing module is configured such that a user can select a plurality of views and the image processor at least partially locates the views based on the location of said cameras with respect to each other. In some embodiments, said image processing module is configured such that a user can specify a mode and the image processor provides a collection of views associated with that mode without the user independently specifying the images or sensors.

In some embodiments the cameras are electrically connected via wiring that is external to the retractor, for example, attached thereon. In some embodiments, the wiring is integrate with the retractor, for example, embedded therein. In some embodiments, an aggregator is included to receive wiring segments from separate cameras. In some embodiments, light sources are included with said cameras to provide illumination for viewing the surgical site. In some embodiments, for example the light sources are included on the retractor. In some embodiments, the light source is affixed to or supported on a support structure affixed to or disposed on the retractor. In some embodiments, cooling is provided for the light sources to manage temperature. In some embodiments, the cameras are configured to be cleaned while on the retractor, for example, while in the surgical site. In some embodiments, for example, hydraulic cleaning is provided. For example, a liquid wash and an air dry may be provided. One or more fluid lines may provide liquid wash to remove material from the camera that would otherwise block or interfere with the view of the camera. In some embodiments one or more fluid lines may provide air such as pulse air to dry the camera, for example, after liquid washing. In some embodiments, drying is facilitated by the venture effect, which causes pressure differentials the produce air flow.

In various embodiments, the camera(s) and/or other features can be included without the retractor, and may, for example, be configured for use with a retractor or other surgical device such as a surgical tool. Additionally, the camera(s) and/or other features may be configured for use and/or used with medical devices other than retractors. Moreover, any combination of the various features of any of the embodiments disclosed herein may be combined with any other features from other embodiments.

In accordance with another aspect, a method comprises: inserting a retractor into an opening in a body; holding open edges of the opening with the retractor, thereby providing a pathway for access of surgical tools to a surgical site; and inserting a surgical tool at least partially through pathway and to the surgical site, wherein said retractor comprises at least one camera (e.g. a plurality of cameras) disposed on the surgical retractor. In some embodiments said camera is inwardly facing toward said pathway. In some embodiments, the surgical tool comprises a scalpel, a rongeur, a Kerrison, a laser, or a drill. In some embodiments, the plurality of cameras comprises at least 8 cameras. In some embodiments, the surgical site is an area of the spine of the body. In some embodiments, the surgical site is an area of a head or neck of the body. In some embodiments, the retractor comprises a retractor blade and said camera is disposed on said retractor blade. In some embodiments, the retractor comprises a tube and said camera is disposed on an inside surface of the tube. In some embodiments, the surgical retractor comprises at least one proximal camera and at least one distal camera. In some embodiments, the method further comprises obtaining respective images produced by the at least one camera (e.g., a plurality of cameras on a retractor, or at least one camera on a retractor and at least one camera located elsewhere such as on a surgical tool). In some embodiments, the method further comprises displaying said respective images simultaneously. In some embodiments, the respective images are displayed as stitched together. In some embodiments, the respective images are displayed as tiled.

In accordance with another aspect, a medical apparatus comprises: a surgical retractor configured to hold open an incision formed in a body and thereby provide a pathway for access for surgical tools to a surgical site in said body, said retractor including proximal and distal locations, said distal location configured to be disposed further within said body than said proximal location; and a plurality of cameras disposed on the surgical retractor, including at least one proximal camera at said proximal location and at least one distal camera at said distal location. In some embodiments, said surgical retractor comprises a plurality of retractor blades and said cameras are disposed on at least one proximal and at least one distal location of said retractor blades. In some embodiments, said surgical retractor comprises a tube and said cameras are disposed on at least one proximal and at least one distal location on inside surface of said tube. In some embodiments, said cameras are fastened to the surgical retractor using a clip-on fastener. In some embodiments, said clip-on fastener comprises a clip, a snap, a screw, a bolt, a nut, or a magnet. In some embodiments, the medical apparatus further comprises an electrical bus and electrical connector configured to connect said cameras to said electrical bus. In some embodiments, said cameras are integrated into the surgical retractor. In some embodiments, the proximal camera and the distal camera produce respective images, and the apparatus further comprises an image processing module configured to display respective images for simultaneous viewing. In some embodiments, the proximal camera is oriented along a first optical axis, and the distal camera is oriented along a second optical axis, and the first and second optical axes are substantially parallel. In some embodiments, the proximal camera is oriented along a first optical axis, and wherein the distal camera is oriented along a second optical axis, and wherein the first and second optical axes intersect at a first point. In some embodiments, the first point is within the pathway for access for surgical tools to the surgical site. In some embodiments, the proximal camera is oriented along a first optical axis, wherein the first optical axis is substantially orthogonal to a plane of a surface of the retractor at the proximal location. In some embodiments, the distal camera is oriented along a second optical axis, wherein the second optical axis is substantially orthogonal to a plane of a surface of the retractor at the distal location. In some embodiments, the proximal camera provides a first field-of-view and the distal camera provides a second field of view, the second field of view being smaller than the first field-of-view. In some embodiments, the first and second fields of view at least partially overlap. In some embodiments, the first field of view is between about 80 and 100 degrees. In some embodiments, the second field of view is between about 50 and 70 degrees. In some embodiments, the retractor is configured such that when holding open the incision formed in the body and thereby providing a pathway for access for surgical tools to the surgical site in said body, the first and second fields of view each encompass at least a portion of the surgical site. In some embodiments, said cameras produce respective images, and wherein the apparatus further comprises an image processing module configured to display respective images for simultaneous viewing. In some embodiments, the image processing module is configured to display at least a portion of said respective images as stitched together. In some embodiments, the image processing module is configured to display at least a portion of said respective images as tiled.

In accordance with another aspect, a surgical visualization system comprises: a surgical retractor having proximal and distal locations, said distal location configured to be disposed further within a body than said proximal location; a proximal camera disposed at said proximal location; and a distal camera disposed at said distal location. In some embodiments, said surgical retractor comprises a plurality of retractor blades and said cameras are disposed on at least one proximal and at least one distal location of said retractor blades. In some embodiments, said surgical retractor comprises a tube and said cameras are disposed on at least one proximal and at least one distal location on inside surface of said tube.

In accordance with another aspect, a method comprises: inserting a retractor into an opening in a body; holding open edges of the opening with the retractor, thereby providing a pathway for access of surgical tools to a surgical site; and inserting a surgical tool at least partially through pathway, wherein said retractor comprises a proximal camera and a distal camera, said cameras inwardly facing toward said pathway. In some embodiments, the surgical tool comprises a scalpel, a rongeur, a Kerrison, a laser, or a drill. In some embodiments, the retractor comprises a plurality of proximal cameras and a plurality of distal cameras. In some embodiments, the surgical site is an area of the spine of the body. In some embodiments, the surgical site is an area of a head or neck of the body.

In accordance with another aspect, a surgical visualization system comprises: a retractor having at least one, for example, a plurality of cameras disposed thereon; a surgical tool having at least one camera disposed thereon; and an image processing module configured to display respective images from said plurality of cameras on said retractor and said camera on said surgical tool for simultaneous viewing. In some embodiments, the surgical tool is movable with respect to the retractor. In some embodiments, at least one of the plurality of cameras substantially faces another one of the plurality of cameras. In some embodiments, the image processing module is configured to display said respective images for simultaneous viewing as a composite first image. In some embodiments, the image processing module is configured to integrate a second image obtained from the at least one camera on the surgical tool with the composite first image. In some embodiments, the composite first image is produced by tiling or stitching the respective images from the plurality of cameras on the retractor. In some embodiments, the image processing module is configured to display the second image as a picture-in-picture over the composite first image. In some embodiments, the image processing module is configured to stitch the second image with the composite first image to produce a composite third image. In some embodiments, the plurality of cameras are attached to a surface of blades of the retractor. In some embodiments, the plurality of cameras are integrated within blades of the retractor. In some embodiments, the plurality of cameras comprises at least 1, 2, 3, 4, 5, 6, 7, or 8 cameras. In some embodiments, the surgical tool comprises a scalpel, a rongeur, a Kerrison, a laser, scissors, forceps, or a drill.

In accordance with another aspect, a surgical visualization system comprises: a retractor having at least one camera, for example, a plurality of cameras disposed thereon; a camera configured to be associated with a surgical tool; and an image processing module configured to display respective images from said plurality of cameras on said retractor and images from said camera associated with said surgical tool for simultaneous viewing. In some embodiments, at least one of the plurality of cameras disposed on the retractor substantially faces another one of the plurality of cameras disposed on the retractor. In some embodiments, the image processing module is configured to display images from one camera on the retractor, and images from one camera on the tool. In some embodiments, the image processing module is configured to display respective images from a plurality of cameras on said retractor for simultaneous viewing as a composite first image. In some embodiments, the image processing module is configured to integrate a second image obtained from the camera configured to be associated with the surgical tool with the composite first image.

As disclosed elsewhere herein, in various embodiments, the camera(s) and/or other features can be included without the retractor, and may, for example, be configured for use with a retractor or other surgical device such as a surgical tool. Additionally, the camera(s) and/or other features may be configured for use and/or used with medical devices other than retractors. Moreover, any combination of the various features of any of the embodiments disclosed herein may be combined with any other features from other embodiments.

In accordance with another aspect, a method comprises: receiving from a plurality of cameras disposed on a retractor a first plurality of image data; receiving from a camera disposed on a surgical tool a second plurality of image data; processing the first plurality of image data to produce a first image; and processing the second plurality of image data to produce a second image. In some embodiments, producing the first image comprises stitching or tiling separate images obtained from the plurality of cameras. In some embodiments, the method further comprises integrating the second image with the first image. In some embodiments, integrating comprises disposing the second image as a picture-in-picture over the first image. In some embodiments, integrating comprises stitching the second image with the first image to produce a composite third image.

In accordance with another aspect, a surgical visualization kit comprises: a plurality of cameras configured to be disposed on a retractor, said cameras configured to produce respective images; an image processing module configured to display said respective images; and a camera configured to be disposed on a surgical tool. In some embodiments, the image processing module is configured to display said respective images for simultaneous viewing as a composite first image. In some embodiments, displaying said composite first image is produced by stitching or tiling the respective images produced by the plurality of cameras. In some embodiments, the image processing module is further configured to display a second image obtained from the camera configured to be disposed on the surgical tool. In some embodiments, the image processing module is configured to display the second image as a picture-in-picture over the first image. In some embodiments, the image processing module is configured to stitch the second image with the first image to produce a composite third image. In some embodiments said tool is included as part of said kit. In various embodiments, said tool comprises scalpel, a rongeur, a Kerrison, a laser, scissors, forceps, or a drill although other tools may be used. In some embodiments said tool is included in said kit and said kit only includes one camera for said retractor.

In accordance with another aspect, a method comprises: inserting a retractor into an opening in a body, the retractor comprising at least one, for example, a plurality of cameras disposed thereon; inserting a surgical tool at least partially into a working space of the retractor, the surgical tool comprising at least one camera disposed thereon. In some embodiments, at least some of the plurality of cameras are disposed on a blade of the retractor and substantially face the working space. In some embodiments, the plurality of cameras comprises at least 1, 2, 3, 4, 5, 6, 7, or 8 cameras.

In accordance with another aspect, a medical apparatus comprises: a surgical retractor configured to hold open an opening in a body and thereby provide a pathway for access of surgical tools to a surgical site, wherein the retractor comprises a rotatable platform; and at least one, for example, a plurality of cameras disposed on the rotatable platform. In some embodiments, said retractor comprises retractor blades configured to hold open the opening. In some embodiments, said rotatable platform is movable with respect to the retractor blades. In some embodiments, said retractor blades move with rotation of said rotatable platform. In some embodiments, said retractor comprises a proximal end and a distal end, said distal end configured to be disposed further within said body, and wherein said rotatable platform is arranged proximal to the retractor blades. In some embodiments, the apparatus further comprises a second plurality of cameras disposed on the retractor blades. In some embodiments, said cameras are configured to produce respective images, the apparatus further comprising an image processing module configured to display respective images simultaneously. In some embodiments, rotation of said rotatable platform produces rotation of the simultaneous display of the respective images. In some embodiments, the image processing module is configured to display at least a portion of said respective images as stitched together. In some embodiments, the image processing module is configured to display at least a portion of said respective images as tiled. In some embodiments, the plurality of cameras comprises a first camera and a second camera, wherein the first camera has a first field of view, and the second camera has a second field of view. In some embodiments, the retractor is configured such the first field of view encompasses the surgical site. In some embodiments, the retractor is configured such the first and second fields of view each encompass the surgical site. In some embodiments, the retractor is configured such the first and second fields of view at least partially overlap. In some embodiments, at least one of the plurality of cameras substantially faces the pathway for access of surgical tools.

In accordance with another aspect, a surgical visualization system comprises: a surgical retractor having proximal and distal locations, said distal location configured to be disposed further within a body than said proximal location, said retractor comprising a rotatable platform; and at least one, for example, a plurality of cameras disposed on the rotatable platform. In some embodiments, said retractor comprises retractor blades configured to hold open the opening, wherein the retractor blades are distal to the rotatable platform. In some embodiments, said rotatable platform is rotatable with respect to the retractor blades. In some embodiments, said retractor comprises a tube configured to hold open the opening, wherein the tube is distal to the rotatable platform. In some embodiments, said rotatable platform is rotatable with respect to the tube. In some embodiments, the retractor defines a pathway for access of surgical tools to a surgical site, and wherein at least one of the cameras substantially faces the surgical site.

In accordance with another aspect, a method comprises: inserting a retractor at least partially into an opening in a body, the retractor comprising a rotatable platform having a plurality of cameras thereon; holding open edges of the opening with the retractor, thereby providing a pathway for access of surgical tools to a surgical site; and rotating the rotatable platform, thereby altering the orientation of the plurality of cameras with respect to the opening. In some embodiments, the rotatable platform is disposed outside the opening of the body. In some embodiments, the surgical site is an area of the spine of the body. In some embodiments, the surgical site is an area of a head or neck of the body. In some embodiments, the opening is a mouth of the body. In some embodiments, the plurality of cameras comprises at least 8 cameras. In some embodiments, the retractor comprises a plurality of retractor blades, and wherein upon insertion of the retractor at least partially into the opening, said retractor blades are closer to said surgical site than said rotatable platform. In some embodiments, the retractor comprises a tube, and upon insertion of the retractor at least partially into the opening, said tube is closer to said surgical site than said rotatable platform.

In accordance with another aspect, a medical apparatus comprises: a surgical device; at least one camera disposed on the surgical device; and a hydraulic system configured to deliver fluid pulses to the at least one camera. In some embodiments, the surgical device is a retractor. In some embodiments, the fluid comprises water. In some embodiments, the fluid comprises pharmaceuticals, fluorescent dyes, or saline. In some embodiments, the fluid pulses are configured to remove obstructions from the at least one camera. In some embodiments, the apparatus further comprises a plurality of cameras, wherein the hydraulic system is configured to deliver fluid pulses to each of the plurality of cameras. In some embodiments, the hydraulic system comprises a plurality of microfluidic channels coupled to a fluid source. In some embodiments, the microfluidic channels comprise a flex cable configured to be positioned over an electronic cable. In some embodiments, the microfluidic channels are disposable. In some embodiments, the distal end of the flex cable comprises an outer housing secured over the camera. In some embodiments, the shape of the outer housing is configured to direct fluid from the flex cable over a surface of the camera. In some embodiments, hydraulic system comprises a disposable diaphragm pump. In some embodiments, the hydraulic system comprises at least one of: a rolling edge diaphragm, Bourdon tube, or a bellow. In some embodiments, the at least one camera comprises a lens including a stop behind a plano window, and wherein the hydraulic system is configured to deliver a fluid pulse over the plano window. In some embodiments, the hydraulic system is further configured to deliver pulses of pressurized air to the camera. In some embodiments, the pulses of pressurized air are configured to dry the camera following the fluid pulses. In some embodiments, the hydraulic system is controlled by a proportional foot pedal. In some embodiments, the hydraulic system is further configured to provide egress of gases and/or liquids.

In accordance with another aspect, a surgical visualization system comprises: a surgical retractor having a plurality of cameras disposed thereon; a surgical tool having at least one camera disposed thereon; and an image processing module configured to receive signals from said cameras on said retractor and said surgical tool for display of respective images from said cameras, wherein said image processing module is configured to track the locations of said plurality of cameras and of said surgical tool. In some embodiments, said surgical tool is movable with respect to said surgical retractor. In some embodiments, said surgical tool is associated with a tracking device to track the location of the surgical tool. In some embodiments, said tracking device comprises an EM tracking device. In some embodiments, said cameras disposed on the surgical retractor are associated with tracking devices to track the location of the cameras. In some embodiments, said tracking devices comprise EM tracking devices. In some embodiments, the image processing module is configured to track the location of said surgical tool with optical tracking. In some embodiments, the system further comprises an overhead camera, wherein the surgical tool includes identifying markers visible to the overhead camera, and wherein the image processing module is configured to track the location of the surgical tool by tracking the identifying markers on the surgical tool. In some embodiments, the image processing module is configured to display said respective images simultaneously. In some embodiments, the image processing module is configured to adjust the display of said respective images depending upon the tracked location of said surgical tool. In some embodiments, the image processing module is configured to display respective images obtained from the cameras disposed on said retractor for simultaneous viewing as a composite first image. In some embodiments, the image processing module is configured to display an image obtained from the camera disposed on said surgical tool simultaneously with the composite first image. In some embodiments, the image processing module is configured to display the image obtained from the camera disposed on said surgical tool as a picture-in-picture over the composite first image. In some embodiments, the image processing module is configured to stitch the image obtained from the camera disposed on said surgical tool with the first composite image to produce a second composite image. In some embodiments, the plurality of cameras are attached to a surface of blades of the retractor. In some embodiments, the plurality of cameras face inwardly towards a pathway defined by the blades of the retractor. In some embodiments, the blades of the retractor are malleable or articulated. In some embodiments, the blades of the retractor are movable with respect to one another.

In accordance with another aspect, a method comprises: inserting a retractor into an opening in a body, the retractor comprising a plurality of cameras disposed thereon, wherein the retractor defines a pathway for access of surgical tools to a surgical site within the body; inserting a surgical tool into the pathway; electronically tracking the locations of said cameras and the location of said surgical tool. In some embodiments, the surgical tool comprises a camera disposed thereon. In some embodiments, the method further comprises obtaining respective images from each of the cameras, and processing said respective images for simultaneous viewing. In some embodiments, said processing comprises using the tracked locations of said cameras. In some embodiments, said electronically tracking comprises EM tracking. In some embodiments, said plurality of cameras are disposed on blades of the retractor, and wherein said electronically tracking comprises tracking position of the blades. In some embodiments, said blades are malleable or articulated. In some embodiments, said electronically tracking comprises tracking the degree to which said blades are bent or articulated.

In accordance with another aspect, a medical apparatus can comprise a surgical device, a hydraulic system providing hydraulic power to said surgical device, the hydraulic system comprising, a hydraulic fluid source, and a cassette assembly having a plurality of external fluid ports, one or more hydraulic pressure chambers, and a plurality of valves positioned on one or more fluid paths fluidly connecting the external fluid ports to the one or more hydraulic pressure chambers, the hydraulic fluid source being in fluid communication with the one or more hydraulic pressure chambers via one or more of the external fluid ports, and an electromagnetic tracking device. In some embodiments, the electromagnetic tracking device can be configured to track said surgical device. In some embodiments, electromagnetic tracking device can be configured to track camera modules on a retractor. In some embodiments, one or more of the plurality of valves can be a diaphragm valve. In some embodiments, wherein one or more of the plurality of valves can be a proportional valve. In some embodiments, one or more of the plurality of valves can be an elastomeric valve. In some embodiments, the cassette assembly can comprise disposable components. In some embodiments, the entire cassette assembly can be disposable. In some embodiments, the hydraulic system can further comprise a hydraulic turbine operably connected to the surgical device to actuate the surgical device. In some embodiments, the apparatus can further comprise one or more washing nozzles in fluid communication with one or more of the hydraulic pressure chambers or the hydraulic fluid source, the one or more washing nozzles configured to direct hydraulic fluid toward one or more light sources.

In accordance with another aspect, a medical apparatus can comprise a surgical device, a hydraulic system providing hydraulic power to said surgical device, the hydraulic system comprising, a hydraulic fluid source, and a cassette assembly having a plurality of external fluid ports, one or more hydraulic pressure chambers, and a plurality of valves positioned on one or more fluid paths fluidly connecting the external fluid ports to the one or more hydraulic pressure chambers, the hydraulic fluid source being in fluid communication with the one or more hydraulic pressure chambers via one or more of the external fluid ports, and one or more cameras for providing a view of an area in the body. In some embodiments, the apparatus can further comprise an electromagnetic tracking device. In some embodiments, said electromagnetic tracking device can be configured to track camera modules on a retractor. In some embodiments, said camera can be on said surgical device. In some embodiments, said camera can be on a retractor in said area in the body. In some embodiments, one or more of the plurality of valves can be a diaphragm valve. In some embodiments, one or more of the plurality of valves can be a proportional valve. In some embodiments, one or more of the plurality of valves can be an elastomeric valve. In some embodiments, the cassette assembly can comprise disposable components. In some embodiments, the entire cassette assembly can be disposable. In some embodiments, the hydraulic system can further comprise a hydraulic turbine operably connected to the surgical device to actuate the surgical device.

In accordance with another aspect, a method of tracking a surgical device can comprise providing a surgical device, operably connecting the surgical device to a hydraulic system, the hydraulic system can comprise: a hydraulic fluid source, and a cassette assembly having a plurality of external fluid ports, one or more hydraulic pressure chambers, and a plurality of valves positioned on one or more fluid paths fluidly connecting the external fluid ports to the one or more hydraulic pressure chambers, the hydraulic fluid source being in fluid communication with and providing hydraulic fluid to the one or more hydraulic pressure chambers via one or more of the external fluid ports; pressurizing the hydraulic fluid; tracking the surgical device using one or more of a camera and an electromagnetic tracking device. In some embodiments, the method of tracking a surgical device can further comprise operably connecting a hydraulic turbine of the surgical device to the hydraulic system.

In accordance with another aspect, a medical apparatus comprises: a retractor stage comprising a ring defining an aperture, the ring substantially aligned with a first plane substantially orthogonal to a first axis; a plurality of blades coupled to said stage and positioned within said aperture, each of the blades extending away from the first plane, wherein each of the blades is configured to be: rotationally moved with respect to said ring; radially moved inward and outward with respect to said ring; and tilted with respect to said first axis. In some embodiments, each of the blades is configured to be tilted by flexing. In some embodiments, each of the blades is jointed, and each of the blades is configured to be titled by bending at a joint. In some embodiments, each of the blades is coupled to said stage by a stem extending between a proximal end of the blade and the stage. In some embodiments, the stem is coupled to the stage by a clamp. In some embodiments, the clamp is configured to be moved rotationally around the ring, thereby rotationally moving the stem and retractor blade. In some embodiments, the stem is configured to be slidably moved through the clamp, thereby moving the stem and the retractor blade radially inward or outward with respect to said ring. In some embodiments, the apparatus further comprises a plurality of cameras disposed on the retractor blades.

In accordance with another aspect, an articulated retractor blade comprises: a proximal segment; a middle segment coupled at a first joint to a distal end of the proximal segment; a distal segment coupled at a second joint to a distal end of the middle segment; a first actuator configured to cause rotation of the middle segment about the first joint; and a second actuator configured to cause rotation of the distal segment about the second joint. In some embodiments, the first actuator comprises a first internal cable extending through the proximal segment, across the first joint, and into the middle segment. In some embodiments, proximal movement of the first internal cable causes the middle segment to rotate about the first joint. In some embodiments, the articulated retractor blade further comprises a retention mechanism configured to releasably retain the position of the first internal cable. In some embodiments, the retention mechanism comprises a pinion key coupled to a ratchet. In some embodiments, the second actuator comprises a second internal cable extending through the proximal segment, across the first joint, and into the middle segment, across the second joint, and into the distal segment. In some embodiments, proximal movement of the second internal cable causes the distal segment to rotate about the second joint. In some embodiments, the articulated retractor blade comprises a retention mechanism configured to releasably retain the position of the first internal cable. In some embodiments, the retention mechanism comprises a pinion key coupled to a ratchet. In some embodiments, the articulated retractor blade comprises at least one camera disposed on a surface of the middle segment.

In accordance with another aspect, a method comprises: positioning a retractor stage over an opening in a body, wherein the retractor stage comprises a ring defining an aperture, the ring substantially aligned with a first plane substantially orthogonal to a first axis; arranging at least one blade coupled to said stage and positioned within said central aperture, the blade away from said plane and into the opening; positioning the at least one blade rotationally and radially with respect to said ring such that a surface of the blade abuts an edge of the opening; and tilting the at least one blade with respect to the first axis; and inserting a surgical tool at least partially through the aperture and into the opening in the body. In some embodiments, the method further comprises: arranging a plurality of blades coupled to said stage and positioned within said central aperture, each of the blades extending away from said plane and into the opening; positioning each of the blades rotationally and radially with respect to said ring such that a surface of each blade abuts an edge of the opening; and tilting each of the blades with respect to the first axis. In some embodiments, tilting the at least one blade comprises flexing the blade. In some embodiments, the at least one blade is jointed, and wherein tilting the at least one blade comprises bending the blade at a joint. In some embodiments, the at least one blade comprises: a proximal segment; a middle segment coupled at a first joint to a distal end of the proximal segment; a distal segment coupled at a second joint to a distal end of the middle segment; a first actuator configured to cause rotation of the middle segment about the first joint; and a second actuator configured to cause rotation of the distal segment about the second joint. In some embodiments, the at least one blade comprises at least one camera disposed therein. In some embodiments, the method further comprises obtaining an image from the camera and displaying said image.

In accordance with another aspect, a retractor comprises: a main body; a first blade comprising clip-on fastener for removable attaching said first blade to said main body, a second blade comprising clip-on fastener for removable attaching said second blade to said main body, at least one camera connected to at least said first blade. In some embodiments, at least one of said first and second blades are flexible. In some embodiments, said first and second blades have different dimensions. In some embodiments, said first and second blades have different stiffness.

In accordance with another aspect, a retractor comprises: a main body; a first blade comprising clip-on fastener for removable attaching said first blade to said main body, a second blade comprising clip-on fastener for removable attaching said second blade to said main body, wherein at least one of said first and second blades have different dimensions, stiffness, or both. In some embodiments, at least one of said first and second blades are flexible.

In accordance with another aspect, a surgical visualization system comprises: a retractor; and a plurality of cameras disposed on the retractor, said cameras producing respective images, wherein the cameras are fastened to the retractor using a clip-on fastener. In some embodiments, said clip-on fastener comprises a clip, a snap, a screw, a bolt, a nut, or magnet.

In various embodiments, said different blades have different components, e.g., optical components, included therewith. For example, different blades may have cameras, light sources, or combinations thereof. Different camera types that may be included on different blades include stereo, monocular, distal, proximal, cameras with different lines of sights, cameras with different field-of-views and combinations thereof. Different blades may be equipped with channels that output liquid or air. Any of these features may be combined on different blades. The blades may be interchangeable and interchanged to provide the desired functionality. A kit may include a variety of such blades, some with different components or arrangement of components thereon or integrated therewith.

In accordance with another aspect, a clip-on camera system for clipping on a retractor comprises: a plurality of camera modules comprising a plurality of support platforms and at least one camera disposed on the support platforms; a fastened configured to clip-on the support platform onto the retractor; electrical signal lines from the camera; an electrical connector electrically connected to the electrical sensor; and a central bus box or aggregator for receiving the plurality of electrical lines and connectors. In some embodiments, said clip-on fastener comprises a clip, a snap, a screw, a bolt, a nut, or magnet. In some embodiments, said electrical signal lines are between about 1 to 4 inches long.

In various embodiments, the different support platforms have different components, e.g., optical components, included therewith. For example, different support platforms may have cameras, light sources, or combinations thereof. Different camera types that may be included on different support platforms include stereo, monocular, distal, proximal, cameras with different lines of sights, cameras with different field-of-views and combinations thereof. Different support platforms may be equipped with channels that output liquid or air. Any of these features may be combined on different support platforms. The support platforms may be interchangeable and interchanged to provide the desired functionality. A kit may include a variety of such support platforms, some with different components or arrangement of components thereon or integrated therewith.

In accordance with another aspect, a surgical visualization system comprises: a retractor configured to provide access to a surgical site; a plurality of cameras configured to acquire video images of the surgical site, at least one of the plurality of cameras being disposed on the retractor and configured to acquire video images within an opening to which the retractor provides access; and an image processing system in communication with the plurality of cameras, the image processing system comprising at least one physical processor, wherein the image processing system is configured to: receive the video images acquired by the plurality of cameras; receive input from a user indicating a selection of at least two of the plurality of cameras, said selection being less than all of said cameras in said plurality of cameras; provide output video images based on the video images acquired by the selected cameras, the output video images being provided for simultaneous viewing; and resize or arrange the simultaneously viewable output video images from the selected cameras to present them on a display according to received input. In some embodiments, the image processing system is configured to increase a size of a first one of the simultaneously viewable output video images in relation to a second one of the simultaneously viewable output video images based at least partly on received input. In some embodiments the image processing system is configured to arrange a first one of the simultaneously viewable output video images in a more central location in relation to a second one of the simultaneously viewable output video based at least partly on received input. In some embodiments at least one of the simultaneously viewable output video images are represented by a reduced-size real-time video stream that is configured to be presented on a graphical user interface for selection by a user, wherein the graphical user interface includes a representation of a position of the retractor and the plurality of cameras. In some embodiments at least one of the simultaneously viewable output video images is represented by a reduced-size real-time video stream that is configured to be presented on a display for selection by a user, the reduced-size real-time video stream comprising video from the respective camera. In some embodiments the image processing system is (a) configured to display video images that are from a camera that is not selected and that are not displayed on the display after receiving input from the user indicating a selection thereof, (b) is configured to display video images that are from the camera that is not selected and that are displayed as a reduced-size real-time video stream more prominently after receiving input from the user indicating a selection thereof, or (c) configured as set forth in both (a) and (b). In some embodiments the image processing system is configured to the output video images in a tiled format. In some embodiments the tiled output images comprise at least three images. In some embodiments the tiled output images comprise at least four images. In some embodiments the image processor is configured to rotate the tiled output images around a single, common axis. In some embodiments the output video images from at least two of the plurality of cameras are discontinuous. In some embodiments, the system further comprises a second display, wherein the cameras that are not selected by the user can be displayed on the second display. In some embodiments the plurality of selected cameras comprise at least first and second cameras that are disposed on the retractor in positions opposite one another. In some embodiments the image processing system is further configured rotate video images from said first selected camera 180° with respect to video images from said second selected camera.

In accordance with another aspect, a surgical visualization system comprises: a retractor configured to provide access to a surgical site; a plurality of cameras configured to acquire video images of the surgical site, at least one of the plurality of cameras being disposed on the retractor and configured to acquire video images of said surgical site; and an image processing system in communication with the plurality of cameras, the image processing system comprising at least one physical processor, wherein the image processing system is configured to: receive the video images acquired by the plurality of cameras; receive input indicating a selection of video images from a camera; and providing output video images based on video images acquired with the selected camera, wherein the image processing system is configured to present output video images from a first camera, and wherein the image processing system is further configured to swap the presentation of the output video images of the first camera with video images from a second camera in response to a request to resize the output video images from the second camera to be larger than a threshold size. In some embodiments, the image processing system is configured to recognize enlargement by the user of a reduced-size real-time video stream beyond the threshold value as the request to resize the output video images from the second camera. In some embodiments, the image processing system is configured to convert the first image to a reduced-size real-time video stream as part of swapping the presentation of the video images from the second camera with the video images of the first camera. In some embodiments, in response to selection by a user, the image processing system is configured to present output video images from a third camera positioned over output video images from the second camera, wherein the output images from the third camera are less than the threshold value. In some embodiments, in response to selection by a user after the presentation of the output video images of the first camera is swapped with video images from a second camera, the image processing system is configured to present output video images from the first camera positioned over output video images from the second camera, wherein the output images from the first camera are less than the threshold value. In some embodiments, the system further comprises a display in communication with said image processing system, said display configured to display said video images from said first and second cameras, wherein said threshold value is at least 70% and less than 85% of the size of the display. In some embodiments, said threshold value is at least 85% of the size of the display. In some embodiments, the system further comprises a second display, wherein the cameras that are not selected by the user can be displayed on the second display. In some embodiments, the second display presents a graphical user interface for configuration of the output video images on the display.

In accordance with another aspect, a surgical visualization system can comprise: a retractor configured to provide an opening in a surgical site; a plurality of cameras configured to acquire video images of the surgical site, at least one of the plurality of cameras being disposed on the retractor and configured to acquire video images within the opening provided by the retractor; and an image processing system in communication with the plurality of cameras, the image processing system comprising at least one physical processor, wherein the image processing system is configured to: receive the video images acquired by the plurality of cameras; provide representations of each of the plurality of cameras by a camera icon on a display, each camera icon presenting a real-time representation of the video images acquired by the camera associated with the camera icon; receive input indicating a selection of a camera based on a selection of the associated camera icon; and providing output video images based on video images acquired with the selected camera, the output video images initially arranged in a manner consistent with a physical arrangement of the selected camera. In some embodiments, the image processing system can be further configured to: receive input indicating a size with which to present output video images acquired with a designated camera, a relative position to present the output video images acquired with the designated camera, or both; and provide the output images of the designated camera according to the received input. In some embodiments, in response to selection by a user, the image processing system can be configured to present output video images from a first camera positioned over output video images from a second, wherein the output images from the second camera is larger than the output imagery from the first camera. In some embodiments, a the image processing system can be further configured to swap the presentation of the output video images of the first and second cameras in response to a request to resize the first output video images to be larger than a first threshold size or a request to resize the second output video images to be smaller than a second threshold size. In some embodiments, the image processor can be further configured to rotate the output video images of the first and second cameras around a single, common axis.

In accordance with another aspect, a surgical visualization system comprises: a retractor; a plurality of cameras, at least one of said cameras being disposed on said retractor; and an image processing module in communication with said cameras, said image processing module configured to arranged a plurality of video images for simultaneous viewing on a display in a tiled format, said tiled video images being superimposed over a larger video image from one of said cameras. In some embodiments, said larger video image comprises a wider field-of-view image and said tiled video images comprise narrower field-of-view images. In some embodiments, said wide field-of-view image has a field at least 1.3 times larger than one of said tiled video images. In some embodiments, said wide field-of-view image has a field at least 1.5 times larger than one of said tiled video images. In some embodiments, said wide field-of-view image has a field at least 1.75 times larger than one of said tiled video images. In some embodiments, said wide field-of-view image has a field at least 2.0 times larger than one of said tiled video images. In some embodiments, at least two of said cameras are disposed on said retractor. In some embodiments, at least one of said cameras is disposed on said retractor. In some embodiments, at least one of said cameras is disposed on a surgical tool.

In accordance with another aspect, a surgical visualization system comprises: a retractor; at least one camera disposed on said retractor; and an image processing module in communication with said camera, said image processing module configured to provide a main video image on a display, said image processing module further configured to receive a video image from a camera disposed on a surgical tool and superimpose said video image from said surgical tool camera on said main video image, wherein said main video image is larger than said video image from said surgical tool camera. In some embodiments, said main video image comprises a relatively wide field-of-view image in comparison to said video image from said camera on said surgical tool which comprise a relatively narrow field-of-view image. In some embodiments, said main field-of-view image has a field at least 1.5 times larger than said video images from said camera on said surgical tool. In some embodiments, said main field-of-view image has a field at least 1.75 times larger than said video images from said camera on said surgical tool. In some embodiments, said main field-of-view image has a field at least 2.0 times larger than said video images from said camera on said surgical tool. In some embodiments, said main field-of-view image has a field at least 2.3 times larger than said video images from said camera on said surgical tool. In some embodiments, at least two of said cameras are disposed on said retractor. In some embodiments, at least one of said cameras is disposed on a surgical tool.

In accordance with another aspect, some embodiments provide for a surgical visualization system that includes a retractor configured to provide an opening in a surgical site. The surgical visualization system includes a plurality of cameras configured to acquire video images of the surgical site, at least one of the plurality of cameras being disposed on the retractor and configured to acquire video images within the opening provided by the retractor. The surgical visualization system includes an image processing system in communication with the plurality of cameras, the image processing system comprising at least one physical processor. The image processing system is configured to receive the video images acquired by the plurality of cameras; receive input from a user indicating a selection of at least two of the plurality of cameras; provide output video images based on the video images acquired by the selected cameras, the output video images being provided for simultaneous viewing; and resize or arrange the simultaneously viewable output video images from the selected cameras to present them more prominently on a display in comparison to output video images based on the video images acquired by any of the plurality of cameras which is not selected. In some aspects, the image processing system is configured to increase a size of the simultaneously viewable output video images in relation to the output video images from the non-selected cameras. The image processing system can also be configured to arrange the simultaneously viewable output video images in a more central location in relation to the output video images from the non-selected cameras. In some implementations, the simultaneously viewable output video images include icons that are configured to be presented on a display for selection by a user. The icons can include images from the respective cameras.

In some embodiments, the image processing system is configured to arrange the output video images from the selected cameras in a manner consistent with a physical arrangement of the selected cameras. The physical arrangement of the selected cameras can include a location of the selected cameras, a field-of-view of the selected cameras, or both. In some aspects, the image processing system is configured to output video images in a tiled format. The tiled output images can be arranged in a geometrical arrangement consistent with locations of the plurality of cameras with respect to each other, with orientations of the plurality of cameras with respect to each other, or both. The tiled output images can include in some aspects at least four images. In some implementations, the image processor is configured to rotate the tiled output images around a single, common axis. In some aspects, the output video images from at least two of the plurality of cameras are discontinuous.

In some embodiments, at least two of the plurality of cameras can be disposed on the retractor positioned opposite one another. The image processing system can be further configured to output video images from the at least two cameras disposed on the retractor that are rotated 180 degrees with respect to one another. The image processing system can be further configured to arrange the output video images from the selected cameras in a manner consistent with a location of the at least two cameras disposed on the retractor, a field-of-view of the at least two cameras disposed on the retractor, or both.

In accordance with another aspect, some embodiments provide for a surgical visualization system that includes a retractor configured to provide an opening in a surgical site. The surgical visualization system includes a plurality of cameras configured to acquire video images of the surgical site, at least one of the plurality of cameras being disposed on the retractor and configured to acquire video images within the opening provided by the retractor. The surgical visualization system includes an image processing system in communication with the plurality of cameras, the image processing system comprising at least one physical processor. The image processing system is configured to receive the video images acquired by the plurality of cameras; to provide representations of each of the plurality of cameras by a camera icon on a display, each camera icon presenting a real-time representation of the video images acquired by the camera associated with the camera icon; to receive input indicating a selection of a camera based on a selection of the associated camera icon; and to provide output video images based on video images acquired with the selected camera, the output video images initially arranged in a manner consistent with a physical arrangement of the selected camera. In a further aspect, the image processing system is configured to receive input indicating a size with which to present output video images acquired with a designated camera, a relative position to present the output video images acquired with the designated camera, or both; and to providing the output images of the designated camera according to the received input. In some implementations, in response to selection by a user, the image processing system is configured to present output video images from a first camera positioned over output video images from a second, wherein the output images from the second camera is larger than the output imagery from the first camera. The image processing system can be further configured to swap the presentation of the output video images of the first and second cameras in response to a request to resize the first output video images to be larger than a first threshold size or a request to resize the second output video images to be smaller than a second threshold size. In some aspects, the image processor is configured to rotate the output video images of the first and second cameras around a single, common axis.

In accordance with another aspect, a surgical visualization system can comprise: a retractor configured to provide an opening in a surgical site; a plurality of cameras configured to acquire video images of the surgical site, at least one of the plurality of cameras being disposed on the retractor and configured to acquire video images within the opening provided by the retractor; and an image processing system in communication with the plurality of cameras, the image processing system comprising at least one physical processor, wherein the image processing system is configured to: receive the video images acquired by the plurality of cameras; receive input from a user indicating a selection of at least two of the plurality of cameras; provide output video images based on the video images acquired by the selected cameras, the output video images being provided for simultaneous viewing; and resize or arrange the simultaneously viewable output video images from the selected cameras to present them more prominently on a display in comparison to output video images based on the video images acquired by any of the plurality of cameras which is not selected. In some embodiments, the image processing system is configured to arrange the output video images from the selected cameras in a manner consistent with a physical arrangement of the selected cameras. According to some variants, the physical arrangement of the selected cameras comprises a location of the selected cameras, a field-of-view of the selected cameras, or both. The image processing system can be configured to increase a size of the simultaneously viewable output video images in relation to the output video images from the non-selected cameras. In some embodiments, the image processing system is configured to arrange the simultaneously viewable output video images in a more central location in relation to the output video images from the non-selected cameras. The simultaneously viewable output video images can comprise icons that are configured to be presented on a display for selection by a user. In some embodiments, the icons comprise images from the respective cameras.

In accordance with another aspect, a surgical visualization system can comprise: a retractor configured to provide an opening in a surgical site; a plurality of cameras, each camera having a field of view and configured to acquire video images of a portion of the surgical site corresponding to the field of view, at least one of the plurality of cameras being disposed on the retractor and configured to acquire video images within the opening provided by the retractor; and an image processing system in communication with the plurality of cameras, the image processing system comprising at least one physical processor, wherein the image processing system is configured to: receive the video images acquired by the plurality of cameras; for each of the plurality of cameras, provide output video images based on the acquired video images, the output video images being provided for simultaneous viewing; and arrange each of the output video images from the plurality of cameras in a manner consistent with their respective fields of view. The image processing system can be configured to the output video images in a tiled format. In some embodiments, the tiled output images are arranged in a geometrical arrangement consistent with locations of the plurality of cameras with respect to each other, with orientations of the plurality of cameras with respect to each other, or both. The tiled output images can comprise at least four images. In some embodiments, the image processor is configured to rotate the tiled output images around a single, common axis. The output video images from at least two of the plurality of cameras can be discontinuous.

According to some variants, the plurality of cameras are each represented by an icon that is configured to be presented on a display for selection by a user. The icons can be configured to present a real-time representation of the video images acquired by the respective camera. In some embodiments, the image processing system is configured to receive input from a user indicating a size with which to present output video images acquired with the selected camera, a relative position to present the output video images acquired with the selected camera, or both. Some embodiments can be configured such that, in response to selection by a user, the image processing system is configured to present output video imagery from a first camera positioned over output video imagery from a second, wherein the output imagery from the second camera is larger than the output imagery from the first camera. The image processing system can be configured to swap the presentation of the output video imagery of the first and second cameras in response to a request to resize the first video output to be larger than a first threshold size or a request to resize the second video output to be smaller than a second threshold size. In some embodiments, at least two of the plurality of cameras are disposed on the retractor positioned opposite one another. In some embodiments, the image processing system is configured to output video images from the at least two cameras disposed on the retractor that are rotated 180 degrees with respect to one another.

In accordance with another aspect, a medical apparatus comprises: a retractor configured to provide access to a surgical site; a plurality of cameras configured to acquire video images of the surgical site, at least one of the plurality of cameras being disposed on the retractor and configured to acquire video images within the opening provided by the retractor; a binocular viewing assembly comprising a housing and a plurality of oculars, the plurality of oculars configured to provide views of at least one display disposed in the housing; a viewing articulating arm, the binocular viewing assembly disposed on the viewing articulating arm, the viewing articulating arm configured to adjust a position of the binocular viewing assembly; a support, the viewing articulating arm attached to the support such that the viewing articulating arm can move relative to the support; and an image processing system in communication with the plurality of cameras and the at least one display, the image processing system comprising at least one physical processor, wherein the image processing system is configured to: receive video images acquired by the plurality of cameras, provide output video images based on the received video images, and present the output video images on the at least one display so that the output video images are viewable through the plurality of oculars, wherein the binocular viewing assembly does not provide a view of the surgical site through the oculars via an optical pathway that passes through the housing. In some embodiments, the image processing system is configured to provide 3-D viewing of camera images through the binoculars. In some embodiments, the apparatus further comprises an auxiliary camera disposed on the binocular viewing assembly, the camera having a field of view that can be configured to include the surgical site, wherein the camera is configured to provide a surgical microscope view of the surgical site. In some embodiments, the auxiliary camera disposed on the binocular viewing assembly comprises an optical assembly providing an adjustable working distance of between about 15 cm and about 45 cm. In some embodiments, the optical assembly has a variable magnification of between about −0.5× and about 10×. In some embodiments, the medical apparatus further comprises a second articulating arm; and an auxiliary camera disposed on the second articulated arm, the auxiliary camera having a field of view that can be configured to include the surgical site wherein the camera is configured to provide a surgical microscope view of the surgical site, wherein the image processing system is configured to display the surgical microscope view on the at least one display. In some embodiments, the auxiliary camera disposed on the camera platform comprises an optical assembly providing an adjustable working distance of between about 15 cm and about 45 cm. In some embodiments, the optical assembly has a variable magnification of between about −0.5× and about 10×.

In accordance with another aspect, a medical apparatus comprises: a retractor configured to provide access to a surgical site; a plurality of cameras configured to acquire video images of the surgical site, at least one of the plurality of cameras being disposed on the retractor and configured to acquire video images within the opening provided by the retractor; an auxiliary camera having a field of view that can be configured to include the surgical site, wherein the auxiliary camera is configured to provide a surgical microscope view of the surgical site; a binocular viewing assembly comprising a housing and a plurality of oculars, the plurality of oculars configured to provide views of at least one display disposed in the housing; a viewing articulating arm, the binocular viewing assembly disposed on the viewing articulating arm, the viewing articulating arm configured to adjust a position of the binocular viewing assembly; a support, the viewing articulating arm attached to the support such that the viewing articulating arm can move relative to the support; and an image processing system in communication with the plurality of cameras, the auxiliary camera, and the at least one display, the image processing system comprising at least one physical processor, wherein the image processing system is configured to: receive video images acquired by the plurality of cameras, receive video images acquired by the auxiliary camera, provide output video images based on the received video images, present the output video images on the at least one display so that the output video images are viewable through the plurality of oculars, and switch between displaying the output video images comprising at least one output video image from the auxiliary camera and at least one output video image from the at least one camera disposed on the retractor, wherein the binocular viewing assembly does not provide a view of the surgical site through the oculars via an optical pathway that passes through the housing. In some embodiments, the auxiliary camera comprises a 3-D camera and the displays are configured to provide 3-D viewing of images from the 3-D cameras. In some embodiments, the auxiliary camera comprises an optical assembly having an adjustable working distance of between about 15 cm and about 45 cm. In some embodiments, the optical assembly has a variable magnification of between about −0.5× and about 10×. In some embodiments, the auxiliary camera is configured to provide views of the surgical site from a distance further than the cameras disposed on the retractor.

In accordance with another aspect, a medical apparatus comprises a retractor configured to provide access to a surgical site; a plurality of cameras configured to acquire video images of the surgical site, at least one of the plurality of cameras being disposed on the retractor and configured to acquire video images within the opening provided by the retractor; a viewing assembly comprising a housing and at least one display within the housing, the at least one display being configured to provide images from the plurality of cameras; at least one virtual display input device configured to acquire input from a user of the medical apparatus; and an image processing system in communication with the plurality of cameras, the at least one virtual display camera, and the at least one display, the image processing system comprising at least one physical processor, wherein the image processing system is configured to: receive video images acquired by the plurality of cameras, provide output video images based on the received video images, detect the input from the user, interpret the input from the user, and provide a virtual touchscreen wherein interaction with the virtual touchscreen is provided through the detected and interpreted user input. In some embodiments, the user input is associated with features of a graphical user interface displayed on the at least one display. In some embodiments, the graphical user interface includes reduced-size video image feeds provided by the image processing module. In some embodiments, the viewing assembly comprises a pair of oculars, and optical paths from the oculars to the at least one display. In some embodiments, the at least one virtual display input device is disposed on the viewing assembly. In some embodiments, the apparatus further comprises virtual display sensors configured to provide information related to the user input to the image processing system, the information being provided in addition to the data acquired with the virtual display input device. In some embodiments, the apparatus further comprises at least one auxiliary camera configured such that images from the at least one auxiliary camera can be viewed on at least one of the displays, said auxiliary camera configured to provide a surgical microscope view. In some embodiments, the at least one virtual display input device comprises a camera. In some embodiments, the at least one virtual display input device comprises at least 3 cameras.

In accordance with another aspect, a medical apparatus comprises: a retractor configured to provide an opening in a surgical site; a plurality of cameras configured to acquire video images of the surgical site, at least one of the plurality of cameras being disposed on the retractor and configured to acquire video images within the opening provided by the retractor; a binocular viewing assembly comprising a housing and a plurality of oculars, the plurality of oculars configured to provide views of at least one display disposed in the housing; a viewing articulating arm, the binocular viewing assembly disposed on the viewing articulating arm, the viewing articulating arm configured to adjust a position of the binocular viewing assembly; a support stand, the viewing articulating arm attached to the support stand such that the viewing articulating arm can move relative to the support stand; and an image processing system in communication with the plurality of cameras and the at least one display, the image processing system comprising at least one physical processor, wherein the image processing system is configured to: receive video images acquired by the plurality of cameras, provide output video images based on the received video images, and present the output video images on the at least one display so that the output video images are viewable through the plurality of oculars, wherein the binocular viewing assembly does not provide a view of the surgical site through the oculars via an optical pathway that passes through the housing. In some embodiments, the image processing system is configured to provide 3-D viewing of camera images through the binoculars using at least two displays. In some embodiments, the apparatus further comprises a camera disposed on the binocular viewing assembly, the camera having a field of view that can be configured to include the surgical site, wherein the camera is configured to provide a surgical microscope view of the surgical site. In some embodiments, the camera disposed on the binocular viewing assembly comprises an optical assembly providing an adjustable working distance of between about 15 cm and about 45 cm. In some embodiments, the microscope objective microscope objective has a variable magnification of between about 1× and 6×. In some embodiments, the apparatus further comprises: a second articulating arm attached to the support stand; a camera platform attached to the second articulating arm such; and a camera disposed on the camera platform, the camera having a field of view that can be configured to include the surgical site wherein the camera is configured to provide a surgical microscope view of the surgical site, wherein the second articulating arm is adjustable independent of the viewing articulating arm, and wherein the image processing system is configured to display the surgical microscope view on the at least one display. In some embodiments, the camera disposed on the camera platform comprises an optical assembly providing an adjustable working distance of between about 15 cm and about 45 cm. In some embodiments, the microscope objective microscope objective has a variable magnification of between about 1× and 6×.

In accordance with another aspect, a medical apparatus comprises: a retractor configured to provide an opening in a surgical site; a plurality of cameras configured to acquire video images of the surgical site, at least one of the plurality of cameras being disposed on the retractor and configured to acquire video images within the opening provided by the retractor; a surgical microscope camera having a field of view that can be configured to include the surgical site, wherein the surgical microscope camera is configured to provide a surgical microscope view of the surgical site; a binocular viewing assembly comprising a housing and a plurality of oculars, the plurality of oculars configured to provide views of at least one display disposed in the housing; a viewing articulating arm, the binocular viewing assembly disposed on the viewing articulating arm, the viewing articulating arm configured to adjust a position of the binocular viewing assembly; a support stand, the viewing articulating arm attached to the support stand such that the viewing articulating arm can move relative to the support stand; and an image processing system in communication with the plurality of cameras, the surgical microscope camera, and the at least one display, the image processing system comprising at least one physical processor, wherein the image processing system is configured to: receive video images acquired by the plurality of cameras, receive video images acquired by the surgical microscope camera, provide output video images based on the received video images, and present the output video images on the at least one display so that the output video images are viewable through the plurality of oculars, the output video images comprising at least one output video image from the surgical microscope camera being presented with at least one output video image from the at least one camera disposed on the retractor, wherein the binocular viewing assembly does not provide a view of the surgical site through the oculars via an optical pathway that passes through the housing. In some embodiments, the surgical microscope camera comprises a pair of 3-D cameras and the displays are configured to provide 3-D viewing of images from the pair of 3-D cameras. In some embodiments, the surgical microscope camera comprises a microscope objective having an adjustable working distance of between about 15 cm and about 45 cm. In some embodiments, the microscope objective microscope objective has a variable magnification of between about 1× and 6×. In some embodiments, the surgical microscope camera is configured to provide views of the surgical site from a distance further than the at least one of the plurality of cameras disposed on the retractor.

In accordance with another aspect, a medical apparatus comprises: a retractor configured to provide an opening in a surgical site; a plurality of cameras configured to acquire video images of the surgical site, at least one of the plurality of cameras being disposed on the retractor and configured to acquire video images within the opening provided by the retractor; a viewing assembly comprising a housing and at least one display attached to the housing, the at least one display being configured to provide images from the plurality of cameras; at least one virtual display camera configured such that images from the at least one virtual display camera can be viewed on at least one of the displays, the at least one virtual display camera providing views of gestures by a viewer of the display; and an image processing system in communication with the plurality of cameras, the at least one virtual display camera, and the at least one display, the image processing system comprising at least one physical processor, wherein the image processing system is configured to: receive video images acquired by the plurality of cameras, provide output video images based on the received video images, and provide a virtual touchscreen by detecting the gestures made by the viewer imaged by the virtual image camera. In some embodiments, the gestures are associated with imaged features displayed on the at least one display. In some embodiments, the image features comprise icons provided by the image processing module. In some embodiments, the viewing assembly comprises a housing, a pair of oculars, and optical paths from the oculars to the at least one display, the at least one display disposed in the housing. In some embodiments, the at least one virtual display camera is disposed on the viewing assembly. In some embodiments, the at least one viewing assembly is disposed on an articulating arm. In some embodiments, the apparatus further comprises at least one surgical microscope camera configured such that images from the at least one surgical microscope camera can be viewed on at least one of the displays.

In accordance with another aspect, a surgical system can comprise: one or more surgical tools that can be configured to be powered by hydraulic fluid; a hydraulic pressure system fluidly connected to the one or more surgical tools, the hydraulic pressure system can be configured to pressurize the hydraulic fluid, the hydraulic pressure system can comprise a first hydraulic pressure source having a first hydraulic fluid chamber in selective fluid communication with the one or more surgical tools, the first hydraulic pressure source having a compression stroke in which the first hydraulic pressure source increases the pressure of the hydraulic fluid within the first hydraulic fluid chamber and an expansion stroke in which the first hydraulic pressure source decreases the pressure of the hydraulic fluid within the first hydraulic fluid chamber; a second hydraulic pressure source having a second hydraulic fluid chamber in selective fluid communication with the one or more surgical tools, the second hydraulic pressure source having a compression stroke in which the second hydraulic pressure source increases the pressure of the hydraulic fluid within the second hydraulic fluid chamber and an expansion stroke in which the second hydraulic pressure source decreases the pressure of the hydraulic fluid within the second hydraulic fluid chamber, wherein the second hydraulic pressure source can be configured to operate its compression stroke when the first hydraulic pressure source operates its expansion stroke and wherein the second hydraulic pressure source can be configured to operates its expansion stroke when the first hydraulic pressure source operates its compression stroke; and one or more valves positioned in a fluid path between the one or more surgical tools and one or more of the first hydraulic pressure source and the second hydraulic pressure source, the one or more valves can be configured to selectively close and open fluid communication between the one or more surgical tools and one or more of the first hydraulic pressure source and the second hydraulic pressure source; and one or more hydraulic fluid sources in selective fluid communication with one or more of the first hydraulic pressure source and the second hydraulic pressure source. In some embodiments, a surgical system can further comprise a first pneumatic pressure source, the first pneumatic pressure source can comprise: a pneumatic fluid chamber; a piston positioned within the fluid chamber; and an actuator operably connected to the piston, the actuator can be configured to move the piston in a compression stroke and an expansion stroke; wherein the pneumatic fluid chamber can be in selective fluid communication with one or more of the first hydraulic fluid chamber and the second hydraulic fluid chamber. In some embodiments, the surgical system can include a pneumatic pump in selective fluid communication with the pneumatic fluid chamber. In some embodiments, the surgical system can further comprise a hydraulic turbine that can be configured to actuate one or more of the one or more surgical tools, the hydraulic turbine in selective fluid communication with the hydraulic pressure system. In some embodiments, the hydraulic turbine can be powered by pressurized hydraulic fluid from the hydraulic pressure system. In some embodiments, at least a portion of the pressurized hydraulic fluid used to power the hydraulic turbine can be returned to the hydraulic pressure system after powering the hydraulic turbine. In some embodiments, the surgical system can further comprise one or more surgical tools configured to be powered by pneumatic fluid. In some embodiments, the surgical system can further comprise a pneumatic assembly that can be configured to selectively power one or more of the one or more surgical tools that can be configured to be powered by pneumatic fluid, the pneumatic assembly in selective fluid communication with a pneumatic pump. In some embodiments, the surgical device can be a drill.

In accordance with another aspect, a surgical system can comprise: one or more surgical tools that can be configured to be powered by hydraulic fluid; a hydraulic pressure system fluidly connected to the one or more surgical tools, the hydraulic pressure system can be configured to pressurize the hydraulic fluid, the hydraulic pressure system comprising: a cassette assembly that can have: a cassette housing; a first hydraulic fluid chamber positioned at least partially within the cassette housing and in selective fluid communication with one or more of the one or more surgical tools; a plurality of fluid ports positioned on the cassette housing; and one or more valves located in or on the cassette housing; a first hydraulic pressure source fluidly coupled with the first hydraulic fluid chamber, the first hydraulic pressure source having a compression stroke in which the first hydraulic pressure source increases the pressure of the hydraulic fluid within the first hydraulic fluid chamber and an expansion stroke in which the first hydraulic pressure source decreases the pressure of the hydraulic fluid within the first hydraulic fluid chamber; one or more valves positioned in a fluid path between the one or more surgical tools and the first hydraulic fluid chamber, the one or more valves configured to selectively close and open fluid communication between the one or more surgical tools and the first hydraulic fluid chamber; and one or more hydraulic fluid sources in selective fluid communication with one or more of the first hydraulic pressure source and the second hydraulic pressure source. In some embodiments, the cassette assembly can further comprise: a second hydraulic fluid chamber positioned at least partially within the cassette housing and in selective fluid communication with one or more of the one or more surgical tools; and a second hydraulic pressure source fluidly coupled to the second hydraulic fluid chamber, the second hydraulic pressure source can have a compression stroke in which the second hydraulic pressure source increases the pressure of the hydraulic fluid within the second hydraulic fluid chamber and an expansion stroke in which the second hydraulic pressure source decreases the pressure of the hydraulic fluid within the second hydraulic fluid chamber, wherein the second hydraulic pressure source can be configured to operate its compression stroke when the first hydraulic pressure source operates its expansion stroke and wherein the second hydraulic pressure source can be configured to operates its expansion stroke when the first hydraulic pressure source operates its compression stroke. In some embodiments, the surgical system can further comprise one or more valves positioned in a fluid path between the one or more surgical tools and the second hydraulic fluid chamber, the one or more valves can be configured to selectively close and open fluid communication between the one or more surgical tools and the second hydraulic fluid chamber. In some embodiments, the cassette assembly can be disposable. In some embodiments, the surgical tool can be disposable. In some embodiments, the surgical system can further comprise one or more washing nozzles in fluid communication with one or more of the first hydraulic fluid chambers or the second hydraulic fluid chamber or the hydraulic fluid source, the one or more washing nozzles can be configured to direct hydraulic fluid toward one or more light sources.

In accordance with another aspect, a medical apparatus can comprise: a surgical drill; and a hydraulic motor providing hydraulic power to said drill. In some embodiments, the surgical drill can be configured to mill. In some embodiments, said hydraulic motor can comprise a turbine connect to a saline supply.

In accordance with another aspect, a hydraulic actuation system can comprise: a user interface; a drive system in communication with the user interface; a chamber; an inflatable element at least partially in the chamber, the inflatable element inflatable upon the user interface sending a signal to the drive system causing fluid to flow into the inflatable element; and a piston configured to be linearly displaced by the inflatable element upon inflation of the inflatable element. In some embodiments, the inflatable element can comprise a balloon.

In accordance with another aspect, a medical apparatus can comprise: a surgical tool; and a hydraulic system providing hydraulic power to said surgical tool, wherein said hydraulic system can comprise (a) a pump with disposable components and (b) disposable lines. In some embodiments, the hydraulic system can comprise a disposable spindle valve body. In some embodiments, the hydraulic system can comprise disposable Kerrison balloons. In some embodiments, the surgical tool can comprise a disposable drill. In some embodiments, the surgical tool can be disposable and non-autoclavable. In some embodiments, the hydraulic system can comprise a disposable and non-autoclavable slave pump actuator. In some embodiments, the hydraulic system can comprise a disposable and non-autoclavable slave turbine. In some embodiments, the hydraulic system can comprise a disposable and non-autoclavable valve.

In accordance with another aspect, a method of cleaning a hydraulic system for coupling to a surgical tool, the method can comprise: flushing fluid through at least part of the hydraulic system; flushing air through said part of the hydraulic system; and sterilization of said part of said hydraulic system. In some embodiments, said flushing fluid can be followed by flushing air. In some embodiments, said flushing air can be followed by sterilization. In some embodiments, said flushing fluid can be followed by sterilization. In some embodiments, said flushing fluid can be followed by flushing air and said flushing air can be followed by sterilization.

In accordance with another aspect, a medical apparatus can comprise: a surgical device; a hydraulic system providing hydraulic power to said surgical device; and manifold configured to selectively direct hydraulic fluid to different applications. In some embodiments, said manifold can be disposable. In some embodiments, said manifold can comprise valves. In some embodiments, said manifold can comprise pumps.

In accordance with another aspect, a surgical tool can comprise: a drill; a hydraulic impeller assembly can comprise: a turbine housing defining a blade cavity, a flow director positioned at least partially within the turbine housing, an impeller having a plurality of impeller blades, the impeller positioned at least partially within the blade cavity, an output shaft rotatably connected to the impeller, the output shaft configured to transfer a torque from the impeller to the drill, and one or more ports in a wall of the blade cavity providing fluid communication between an interior of the blade cavity and an exterior of the blade cavity; a hydraulic pressure source; a return fluid line configured to connect to facilitate fluid communication between the one or more ports and the hydraulic pressure source; and a vacuum source configured to extract fluid through the one or more ports from the blade cavity. In some embodiments, the vacuum source can be a pump. In some embodiments, the vacuum source a bypass channel can be configured to direct high velocity fluid past the blade cavity, wherein a pressure differential between the high velocity fluid in the bypass channel and a low velocity fluid in the blade cavity draws low velocity fluid through the one or more ports from the blade cavity to the bypass channel.

In accordance with another aspect, a medical device system can comprise: a surgical tool; a hydraulic fluid source; a disposable cassette comprising: a housing; one or more hydraulic fluid chambers housed at least partially housed within an interior of the housing; a plurality of fluid ports positioned on the housing and configured to facilitate fluid communication between an exterior of the fluid housing and the interior of the housing; a plurality of proportional valves positioned on the housing; and a plurality of fluid channels configured to facilitate fluid communication between the plurality of ports, the one or more hydraulic fluid chambers, and the plurality of proportional valves; a tool fluid line fluidly connecting one of the plurality of fluid ports to the surgical tool; and a fluid source line fluidly connecting the hydraulic fluid source to one of the plurality of fluid ports. In some embodiments, one or more of the plurality of proportional valves can comprise a valve cavity in the housing and a flexible pad sealingly disposed over the valve cavity. In some embodiments, one or more of the plurality of proportional valves can be actuated by a linear electromagnetic actuators. In some embodiments, the surgical tool can be controlled by one or more of the plurality of proportional valves. In some embodiments, the hydraulic fluid source can be an IV bag. In some embodiments, the hydraulic fluid can be saline. In some embodiments, the hydraulic fluid can be a physiologically compatible fluid. In some embodiments, the hydraulic fluid can be a physiological saline. In some embodiments, the medical device system can further comprise one or more optical components. In some embodiments, the medical device system can further comprise one or more nozzles in fluid communication with one or more of the plurality of ports, the one or more nozzles configured to direct a high velocity, low volume flow of hydraulic fluid to the one or optical components.

In accordance with another aspect, a surgical visualization system comprises a binocular viewing assembly comprising a housing and a pair of eyepieces, said eyepieces configured to provide a view of at least one display disposed in the housing; an optical assembly disposed on the binocular viewing assembly, the optical assembly configured to provide a surgical microscope view of a surgical site, the optical assembly comprising at least one auxiliary camera; an articulating arm, the binocular viewing assembly disposed on the articulating arm, the articulating arm configured to adjust a position of the binocular viewing assembly and the optical assembly; and an image processing system in communication with the optical assembly and the display, the image processing system comprising at least one physical processor, wherein the image processing system is configured to: receive video images acquired by the auxiliary camera, provide output video images based on the received video images, and present the output video images on the display so that the output video images are viewable through the eyepiece, wherein the optical assembly is configured to provide a working distance that is adjustable between about 15 cm and about 45 cm. In some embodiments, the optical assembly is mounted to an isocenter positioning system. In some embodiments, the isocenter positioning system comprises elements configured to allow the optical assembly to be adjusted in three-dimensions such that a field of view of the auxiliary camera always includes a common point. In some embodiments, the isocenter positioning system comprises an isocenter track attached to the binocular viewing assembly, the isocenter track configured to allow the auxiliary camera to be moved to a plurality of locations along the isocenter track and to position the auxiliary camera such that at said plurality of locations said auxiliary camera said remains a fixed distance away from a common point. In some embodiments, said auxiliary camera comprises a Greenough configuration. In some embodiments, said auxiliary camera comprises a pair of optical paths oriented at an angle with respect to each other that converge at said common point established by said isocenter positioning system. In some embodiments, the system further comprises a virtual touch camera configured to image a hand of a user, wherein the image processing system is configured to identify hand gestures based at least partly on the acquired images of the hand of the user to allow the user to interact with a graphical user interface provided on the display. In some embodiments, said hand gestures include gesturing with an optical tool held in said hand. In some embodiments, the system further comprises a virtual touch sensor attached to the binocular viewing assembly, said image processing system being configured to use information from the virtual touch sensor in conjunction with image data from the virtual touch camera to identify gestures to allow the user to interact with a graphical user interface provided on the display. In some embodiments, said binocular viewing assembly is configured not to provide a surgical microscope view via an optical path from said eyepiece through an aperture in said housing. In some embodiments, said auxiliary includes a turning mirror or turning prism configured to reduce the thickness profile of said optical assembly. In some embodiments, said auxiliary camera comprises a pair of optical paths that do not share a common objective lens. In some embodiments, the system further comprises a virtual touch input device configured to receive user input, wherein the image processing system is configured to identify commands based at least partly on the acquired input from the user to allow the user to interact with a graphical user interface provided on the display through a representation of the user's hand.

In accordance with another aspect, a surgical visualization system comprises: a surgical visualization system comprising: a binocular viewing assembly comprising a housing and a plurality of oculars, the plurality of oculars configured to provide display views of at least one display disposed in the housing, the two display views corresponding respectively to a left-eye view and a right-eye view; an optical assembly disposed on the binocular viewing assembly, the optical assembly comprising a left-eye camera and a right-eye camera configured to provide a stereoscopic surgical microscope view of a surgical site; an articulating arm, the binocular viewing assembly disposed on the articulating arm, the articulating arm configured to adjust a position of the binocular viewing assembly and the optical assembly; and an image processing system in communication with the optical assembly and the at least one display, the image processing system comprising at least one physical processor, wherein the image processing system is configured to: receive video images acquired by the left-eye camera and the right-eye camera, provide output video images based on the received video images, and present the left-eye output video images via the left-eye display view and the right-eye output video images via the right-eye display view so that the output video images are viewable through the plurality of oculars, wherein the optical assembly provides a convergence angle, the convergence angle being an angle between a left-eye optical path and a right-eye optical path at the surgical site. In some embodiments, the optical assembly is configured to provide a substantially constant convergence angle with changing working distance. In some embodiments, the left-eye camera comprises: a left-eye turning prism configured to direct light from the surgical site along a left-eye lens path; a left-eye lens assembly configured to receive the directed light from the left-eye turning prism and to create a left-eye image; a left-eye image sensor configured to capture the left-eye image and generate a left-eye video image. In some embodiments, the right-eye camera comprises: a right-eye turning prism configured to direct light from the surgical site along a right-eye lens path; a right-eye lens assembly configured to receive the directed light from the right-eye turning prism and to create a right-eye image; a right-eye image sensor configured to capture the right-eye image and generate a right-eye video image. In some embodiments, the left-eye camera and the right-eye camera are configured to acquire video images of the surgical site at a convergence point and wherein a distance from the binocular viewing assembly to the convergence point comprises a working distance. In some embodiments, the optical assembly is configured to provide an adjustable working distance between about 15 cm and about 45 cm. In some embodiments, the left-eye camera comprises a left-eye turning prism and the right-eye camera comprises a right-eye turning prism, the left-eye turning prism and the right-eye turning prism being configured to change their relative orientations thereby changing the convergence angle to provide the adjustable working distance. In some embodiments, the optical assembly is configured to provide a substantially constant convergence angle with changing working distance. In some embodiments, the left-eye camera and the right-eye camera are configured to adjust their relative orientation and position to provide the substantially constant convergence angle. In some embodiments, the left-eye camera comprises a left-eye prism assembly and the right-eye camera comprises a right-eye prism assembly, the left-eye prism assembly and the right-eye prism assembly being configured to adjust their relative orientation and position to provide the substantially constant convergence angle, wherein other elements of the left-eye camera and the other elements of the right-eye camera remain substantially stationary. In some embodiments, the optical assembly is configured to provide a sufficiently narrow convergence angle to provide stereoscopic imagery through an insertion tube. In some embodiments, the insertion tube has a width between about 25 mm and about 50 mm. In some embodiments, the sufficiently narrow convergence angle is also substantially constant with changes in working distance.

In accordance with another aspect, a surgical visualization system can comprise: a binocular viewing assembly comprising a housing and an eyepiece, the eyepiece configured to provide a view of a display disposed in the housing; an optical assembly disposed on the binocular viewing assembly, the optical assembly configured to provide a surgical microscope view of a surgical site, the optical assembly comprising a surgical microscope camera; an articulating arm, the binocular viewing assembly disposed on the articulating arm, the articulating arm configured to adjust a position of the binocular viewing assembly and the optical assembly; and an image processing system in communication with the optical assembly and the display, the image processing system comprising at least one physical processor, wherein the image processing system is configured to: receive video images acquired by the surgical microscope camera, provide output video images based on the received video images, and present the output video images on the display so that the output video images are viewable through the eyepiece, wherein the optical assembly is configured to provide a working distance that is adjustable between about 15 cm and about 45 cm. In some embodiments, the optical assembly can be mounted to an isocenter positioning system. In some embodiments, the isocenter positioning system can comprise elements configured to allow the optical assembly to be adjusted in three-dimensions such that a field of view of the surgical microscope camera always includes a common point. In some embodiments, the isocenter positioning system can comprise an isocenter track attached to the binocular viewing assembly, the isocenter track configured to allow the surgical microscope camera to be moved to any location along the isocenter track, wherein the isocenter track orients the surgical microscope camera such that a field of view of the surgical microscope camera includes a common point at any location along the track. In some embodiments, the surgical visualization can further comprise a virtual touch camera attached to the binocular viewing assembly, the virtual touch camera configured to image a hand of a user to allow the user to interact with a graphical user interface provided on the display. In some embodiments, the surgical microscope camera can also be the virtual touch camera. In some embodiments, the surgical visualization can further comprise a: a retractor configured to provide an opening in a surgical site; and a plurality of cameras configured to acquire video images of the surgical site, at least one of the plurality of cameras being disposed on the retractor and configured to acquire video images within the opening provided by the retractor, wherein the image processing system is further configured to: receive video images acquired by the plurality of cameras disposed on the retractor; provide output images based on the received video images from the plurality of cameras; and present the output images from the surgical microscope camera, the output images from the plurality of cameras disposed on the retractor, or a combination of output images from the surgical microscope camera and at least one of the plurality of cameras disposed on the retractor. In some embodiments, the image processor system can be further configured to receive input indicating which output video images to display.

In accordance with another aspect, a surgical visualization system can comprise: a binocular viewing assembly comprising a housing and a plurality of oculars, the plurality of oculars configured to provide views of two displays disposed in the housing, the two displays corresponding respectively to a left-eye display and a right-eye display; an optical assembly disposed on the binocular viewing assembly, the optical assembly comprising a left-eye camera and a right-eye camera configured to provide a stereoscopic surgical microscope view of a surgical site; an articulating arm, the binocular viewing assembly disposed on the articulating arm, the articulating arm configured to adjust a position of the binocular viewing assembly and the optical assembly; and an image processing system in communication with the optical assembly and the two displays, the image processing system comprising at least one physical processor, wherein the image processing system is configured to: receive video images acquired by the left-eye camera and the right-eye camera, provide output video images based on the received video images, and present the left-eye output video images on the left-eye display and the right-eye output video images on the right-eye display so that the output video images are viewable through the plurality of oculars, wherein the optical assembly provides a convergence angle, the convergence angle being an angle between a left-eye optical path and a right-eye optical path at the surgical site. In some embodiments, the left-eye camera can comprise: a left-eye turning prism configured to direct light from the surgical site along a left-eye lens path; a left-eye lens assembly configured to receive the directed light from the left-eye turning prism and to create a left-eye image; a left-eye image sensor configured to capture the left-eye image and generate a left-eye video image. In some embodiments, the right-eye camera can comprise: a right-eye turning prism configured to direct light from the surgical site along a right-eye lens path; a right-eye lens assembly configured to receive the directed light from the right-eye turning prism and to create a right-eye image; a right-eye image sensor configured to capture the right-eye image and generate a right-eye video image. In some embodiments, the left-eye camera and the right-eye camera can be configured to acquire video images of the surgical site at a convergence point. In some embodiments, a distance from the binocular viewing assembly to the convergence point can comprise a working distance. In some embodiments, the optical assembly can be configured to provide an adjustable working distance between about 15 cm and about 45 cm. In some embodiments, the left-eye camera can comprise a left-eye turning prism and the right-eye camera comprises a right-eye turning prism, the left-eye turning prism and the right-eye turning prism being configured to change their relative orientations thereby changing the convergence angle to provide the adjustable working distance. In some embodiments, the optical assembly can be configured to provide a substantially constant convergence angle with changing working distance. In some embodiments, the left-eye camera and the right-eye camera can be configured to adjust their relative orientation and position to provide the substantially constant convergence angle. In some embodiments, the left-eye camera comprises a left-eye prism assembly and the right-eye camera comprises a right-eye prism assembly, the left-eye prism assembly and the right-eye prism assembly can be configured to adjust their relative orientation and position to provide the substantially constant convergence angle, wherein other elements of the left-eye camera and the other elements of the right-eye camera remain substantially stationary. In some embodiments, the optical assembly can be configured to provide a sufficiently narrow convergence angle to provide stereoscopic imagery through an insertion tube. In some embodiments, the sufficiently narrow convergence angle can be also substantially constant with changes in working distance.

In accordance with another aspect, a medical apparatus can comprise: a surgical retractor; at least one video camera comprising imaging optics and an optical sensor, said at least one camera disposed on said surgical retractor, wherein said imaging optics comprises wafer-scale optics. In some embodiments, the medical apparatus can further comprise a stop forward said imaging optics. In some embodiments, said sensor is proximal said imaging optics with said imaging optics between said stop and said sensor, and wherein said stop is the most distal optical element of said camera. In some embodiments, said stop can be just prior to said wafer optics. In some embodiments, the medical apparatus can further comprise a cover plate, said stop disposed between said cover plate and said wafer-scale optics, said cover plate comprising sapphire. In some embodiments, the medical apparatus can further comprise a stop within said imaging optics. In some embodiments, said stop can be disposed within said wafer-scale optics. In some embodiments, the medical apparatus can further comprise a movable optical element within said imaging optics. In some embodiments, said movable optical element can be within said wafer-scale optics. In some embodiments, said wafer-scale optics can include a movable optical element configured to be moved to adjust said imaging optics. In some embodiments, the medical apparatus can further comprise an actuator configured to move said a movable optical element to adjust said imaging optics. In some embodiments, said imaging optics can comprise non-wafer-scale lens elements. In some embodiments, said imaging optics can comprise a negative power non-wafer-scale lens element. In some embodiments, said negative power non-wafer-scale lens element can be disposed forward any wafer-scale optics such that said wafer-scale optics is disposed in an optical path between said negative power non-wafer-scale lens element and said optical sensor. In some embodiments, said imaging optics can comprise a negative lens group, a stop, and a positive lens group arranged in an optical path forward of said optical sensor such that said stop and said positive group are disposed between said negative lens group and said optical sensor. In some embodiments, said stop can be between said negative lens group and said positive lens group. In some embodiments, said imaging optics can provide a field of view of at least 70° and up to 125. In some embodiments, said imaging optics can comprise non-wafer-scale optics, a stop, and wafer-scale optics. In some embodiments, said non-wafer scale optics can comprise negative optical power and said wafer-scale optics comprise positive optical power. In some embodiments, said imaging optics can comprise a stack of non-wafer-scale optics lenses having negative power, a stop, and positive lens group. In some embodiments, said imaging optics can comprise a front stop, a positive lens, a negative lens, and a plurality of lenses having positive power disposed in an optical path such that the negative lens is between the positive lens and the plurality of lenses having positive power. In some embodiments, said imaging optics can provide a field of view between about 50°-70°. In some embodiments, said imaging optics can comprise a front stop and four wafer-scale optics lenses. In some embodiments, said imaging optics can comprise no more than four wafer-scale optics lenses. In some embodiments, said imaging optics can provide a field of view between about 50°-70°. In some embodiments, said wafer-scale optics can comprise a stack of wafer scale optics elements having air gaps therebetween, wherein said air gaps are in fluid communication with each other. In some embodiments, said wafer scale optics can comprise fiducials on plates that provide stress to counteract bowing. In some embodiments, said fiducials can be interlocking. In some embodiments, said imaging optics can be configured to be disposed laterally with respect to said optical sensor to provide camera pointing.

In accordance with another aspect, the medical apparatus can further comprise actuators to move said imaging optics laterally with respect to said optical sensor to provide camera pointing. In another aspect, the medical apparatus can further comprise actuators to move said optical sensor laterally with respect to said imaging optics to provide camera pointing.

In accordance with another aspect, a medical apparatus can comprise: at least one video camera comprising imaging optics and an optical sensor; and a platform configured to be disposed on a surgical retractor, said at least one video camera disposed on said platform, wherein said imaging optics comprises wafer-scale optics.

In accordance with another aspect, an apparatus comprising two or more support structures, the two or more support structures comprising at least one light guide and at least one camera, the two or more support structures further comprises at least one fluidic channel, wherein the two or more support structures are configured to be supported by a surgical device. In some embodiments, said surgical device comprises a surgical retractor. In some embodiments, said surgical device comprises a tubular retractor. In some embodiments, said at least one fluid channel comprises an air line. In some embodiments, said at least one fluid channel comprises a saline line. In some embodiments, said at least one fluid channel comprises an aspiration channel, wherein said aspiration channel configured to remove blood, saline or other liquid. In some embodiments, said at least one fluid channel comprises a first end and a second end, said first end configured to be connected to a fluid source, said second end configured to deliver water, saline, or air. In some embodiments, said at least one light guide comprises a plurality of light guides. In some embodiments, said at least one camera comprises a plurality of cameras.

In accordance with another aspect, a camera module comprises: a support structure, the support structure comprising one or more cameras disposed thereon; the support structure comprising a length, a width, and a thickness; the length being greater than the width and the thickness; the support structure has a distal end and a proximal end; the proximal end configured to be connected to electrical lines; and the camera module configured to be supported by a surgical device. In some embodiments, the camera module further comprise a window disposed over the camera, wherein the window is configured to allow the camera to view a surgical area. In some embodiments, the support structure comprises a distal end and a proximal end, the proximal end configured to provide electrical contacts, wherein the electrical contacts comprise a male connector. In some embodiments, the support structure comprises a flexible cable. In some embodiments, the camera module is configured to be inserted into a surgical device. In some embodiments, the camera module and surgical device comprise a dovetail attachment for inserting the camera module into the surgical device. In some embodiments, the surgical device comprises a retractor.

In accordance with another aspect, a device comprising: a flexible flat cable, the flexible flat cable comprising at least one camera disposed on the flexible flat cable, and the flexible flat cable comprising a first end configured to attach to a surgical device and a second end configured to connect to an electrical connector. In some embodiments, the surgical device comprises a retractor. In some embodiments, the device further comprises an aggregator configured to receive the electrical connector. In some embodiments, the device further comprises an electrical circuit configured to receive said electrical connector.

In accordance with another aspect, a device comprising: a flexible flat cable, the flexible flat cable comprising at least one camera disposed on the flexible flat cable, the flexible flat cable comprises at least one microfluidic channel, and the flexible flat cable comprising a first end configured to attach to a surgical device and a second end configured to connect to an electrical connector. In some embodiments, the surgical device comprises a retractor. In some embodiments, the device further comprising an aggregator configured to receive the electrical connector.

In accordance with another aspect, a device comprising: a flexible flat cable, the flexible flat cable comprising at least one camera disposed on the flexible flat cable, and the flexible flat cable comprising a distal end configured to be coupled to a surgical device, wherein the distal end comprises at least one cutout, the at least one cutout forms two or more extensions. In some embodiments, the surgical device comprises a retractor. In some embodiments, the device further comprises a retractor blade, wherein the two or more extensions are configured to be attached to the different retractor blades. In some embodiments, the device further comprises a retractor blade, wherein one of the two or more extensions are attached different retractor blades.

In accordance with another aspect, a device comprising a flexible flat cable, the flexible flat cable comprising at least one camera disposed on the flexible flat cable, the flexible flat cable comprising a first end configured to attach to a surgical device and a second end configured to connect to an electrical connector, and at least one via configured to pass from the flexible flat cable to the camera, wherein the at least one via is configured to permit fluid flow. In some embodiments, the device further comprises: a sensor layer comprising a two-dimensional detector array; a via layer comprising a layer having a plurality of vias therein; and a flex layer comprising said flexible flat cable.

In accordance with another aspect, a device comprising: a flexible flat cable; the flexible flat cable comprising at least one camera disposed on the flexible flat cable; the flexible flat cable comprising at least one microfluidic channel; the flexible flat cable comprising at least one electronic line; and the flexible flat cable comprising a first end configured to attach to a surgical device and a second end configured to connect to an electrical connector. In some embodiments, the surgical device comprises a retractor. In some embodiments, the second end comprises a male connector, wherein the male connector can be sterilized.

In accordance with another aspect, a system comprising: an aggregator; a flexible flat cable; the flexible flat cable comprising at least one camera, the at least one camera disposed on the flexible flat cable, the flexible flat cable comprising a first end configured to attach to a surgical device and a second end configured to be received by the aggregator; the second end comprising a male connector, wherein the male connector can be sterilized; the aggregator comprising a female connector configured to connect to the male connector; and the aggregator configured to be disposable. In some embodiments, the device further comprises at least one sensor module disposed on the flexible flat cable, wherein the at least one sensor module can be sterilized.

In accordance with another aspect, a device comprising: a flexible flat cable; the flexible flat cable comprising at least one camera; and the flexible flat cable comprising a first end configured to attach to a surgical device and a second end configured to connect to an electronic component; wherein the device can be sterilized.

In accordance with another aspect, a device comprising: a flexible flat cable; the flexible flat cable comprising at least one camera; and the flexible flat cable comprising a first end configured to attach to a surgical device and a second end configured to connect to an electronic component; wherein the device can be disposable.

In accordance with another aspect, a system comprising: a flexible flat cable; the flexible flat cable comprising a first end configured to attach to a surgical device and a second end configured to be received by an aggregator; the flexible flat cable comprising at least one camera, the at least one camera disposed on the first end of the flexible flat cable; and the second end comprising a male connector configured to connect the flexible flat cable to the aggregator, wherein the male connector can be sterilized.

In accordance with another aspect, an apparatus for imaging features within a surgical site, said apparatus comprising: a camera configured to be disposed on a surgical device within a surgical site; a movable membrane disposed with respect to said camera to remove material attenuating light from said surgical site entering said camera; and an actuator connected to said movable membrane to move said movable membrane with respect to said camera so as to remove said material. In some embodiments, said movable membrane comprises elastomeric material. In some embodiments, said movable membrane comprises silicone rubber surface. In some embodiments, said movable membrane comprises a rotary ring. In some embodiments, said movable membrane comprises a ring. In some embodiments, said ring include aperture therein.

In accordance with another aspect, an apparatus comprising: a camera, the camera disposed on a surgical device; a least one fluidic channel disposed on a support structure; and the least one fluidic channel comprising a distal end and a proximal end, the distal end configured to release fluid directed onto said camera. In some embodiments, the support structure further comprises a flexible cable. In some embodiments, the fluid comprises a liquid to clean the camera. In some embodiments, the liquid is released from the fluidic channel in a high-pressure fluid pulse. In some embodiments, the fluid comprises air to dry the camera. In some embodiments, the air is released from the at least one fluidic channel in a high-pressure fluid pulse. In some embodiments, the fluid is released from the at least one fluidic channel to create a Venturi effect. In some embodiments, an apparatus further comprising a heater disposed near the camera, the heater configured to heat the camera thereby reducing condensation.

In accordance with another aspect, an apparatus comprising: an electrical support structure configured to provide electrical lines; and a camera is disposed on the electrical support structure; and a sheath covering the camera. In some embodiments, the electrical support structure further comprises a flexible cable. In some embodiments, the sheath provides an irrigation channel. In some embodiments, the sheath provides an air spray channel. In some embodiments, the sheath further comprises an outer casing disposed over the camera. In some embodiments, the sheath further comprises a space between the camera and the outer casing of the sheath, wherein the space is configured to allow air to flow to reduce condensation.

In accordance with one aspect, a graphical user interface system can comprise a plurality of cameras configured to acquire video images of a surgical site, at least one of the plurality of cameras configured to be disposed on a surgical site; and an image processing system in communication with the plurality of cameras, the image processing system comprising at least one physical processor. In some embodiments, the image processing system can be configured to: display a graphic representative of the surgical device on a graphical user interface display; and display a graphic representative of the plurality of cameras on the display, wherein the display of the graphic representative of the surgical device and the display of the graphic representative of the plurality of cameras are based at least in part on a location and/or orientation of the plurality of cameras with respect to the surgical device. In some embodiments, at least one of the plurality of cameras can be disposed within the surgical site. In some embodiments, the image processing system can be configured to receive tracking information associated with the location and/or orientation of at least one of the plurality of cameras. In some embodiments, the graphic of the surgical device and/or the graphic of the plurality of cameras are based at least in part on the tracking information. In some embodiments, the graphic of the plurality of cameras can comprise a schematic field of view associated with at least one of the plurality of cameras. In some embodiments, the graphic of the plurality of cameras can comprise a cone indicating the field of view associated with at least one of the plurality of cameras.

In accordance with another aspect, a graphical user interface system can comprise a plurality of cameras configured to acquire video images of a surgical site, at least one of the plurality of cameras configured to be disposed on a surgical device; and an image processing system in communication with the plurality of cameras, the image processing system comprising at least one physical processor. In some embodiments, the image processing system can be configured to: receive user input associated with the plurality of cameras; display a graphic representative of the plurality of cameras on a graphical user interface display; and display a graphic representative of the surgical device on the display. In some embodiments, at least one of the plurality of cameras can be disposed within the surgical site. In some embodiments, the graphic of the plurality of cameras can be based at least in part on the user input associated with the plurality of cameras. In some embodiments, the image processing system can be configured to: receive video images acquired by at least one of the plurality of cameras; and display at least one reduced-size real-time video stream of the acquired video images on the graphical user interface display.

In accordance with another aspect, the image processing system can be configured to: receive user input indicating a selection of the plurality of cameras; and output an indication of the selection of the plurality of cameras for operation, based at least in part on the user input indicating the selection. In some embodiments, the image processing system can be configured to: receive video images acquired by the selection of the plurality of cameras; and display at least one reduced-size real-time video stream of the acquired video images on the graphical user interface display, based at least in part on the user input indicating the selection. In some embodiments, the image processing system can be configured to: receive user input indicating a display parameter of the at least one real-time video stream; and change the display parameter of the at least one real-time video stream, based at least in part on the user input indicating the display parameter. In some embodiments, the display parameter can comprise size, position, or a combination thereof. In some embodiments, the selection can comprise one of the plurality of cameras. In some embodiments, the image processing system can be configured to: receive video images acquired by the selection of one of the plurality of cameras; and display a background comprising a real-time video stream of the acquired video images on the graphical user interface display.

In accordance with another aspect, the selection of the plurality of cameras can comprise one of the plurality of cameras; and the imaging processing system can be configured to present a main view for display on a surgical visualization system display, based at least in part on the selection. In some embodiments, the selection of the plurality of cameras can comprise at least two of the plurality of cameras. In some embodiments, the imaging processing system can be configured to present video images for display on a surgical visualization display, based at least in part on the selection of two of the plurality of cameras. In some embodiments, video images can be displayed in a tiled format.

In accordance with another aspect, the image processing system can be configured to: receive user input indicating a desired position and/or orientation of the selection of the plurality of cameras; and change the position and/or orientation of the selection of the plurality of cameras, based at least in part on the user input indicating the desired position and/or orientation. In some embodiments, the image processing system can be configured to: change the graphic of the plurality of cameras, based at least in part on the user input indicating the desired position and/or orientation. In some embodiments, the graphical user interface can further comprise light sources associated with the plurality of cameras. In some embodiments, the image processing system can be configured to: receive user input indicating a parameter of the light sources; and change the parameter of the light sources, based at least in part on the user input indicating the parameter of the light sources.

In accordance with another aspect, an image processing system can be configured to: receive user input indicating an orientation configuration; and change an orientation of the plurality of cameras, based at least in part on the user input indicating the orientation configuration. In some embodiments, the image processing system can be configured to change the graphic of the plurality of cameras, based at least in part on the user input indicating the orientation configuration. In some embodiments, the image processing system can be configured to display a menu for orienting the at least one of the plurality of cameras. In some embodiments, the user input indicating the orientation information can be received via the menu. In some embodiments, the orientation configuration can be based at least in part on gravity, a patient, the display, or a table.

In accordance with another aspect, a processing system can be configured to receive user input associated with an external source. In some embodiments, the image processing system can be configured to display imagery associated with the external source on the graphical user interface display, based at least in part on the user input associated with the external source.

In some embodiments, the external source can comprise an imaging modality, and the imagery can comprise computed tomography (CT), magnetic resonance (MR), C-arm, O-arm, ultrasound, or a combination thereof. In some embodiments, the image processing system can be configured to: receive user input indicating a display parameter of the imagery; and change the display parameter of the imagery, based at least in part on the user input indicating the display parameter. In some embodiments, the display parameter can comprise size, position, or a combination thereof.

In accordance with another aspect, the image processing system can be configured to: receive user input indicating a selection of a tool; receive user input indicating a parameter of a tool; and change the parameter of the tool, based at least in part on the user input indicating the selection of the tool and/or the user input indicating the parameter of the tool. In some embodiments, the image processing system can be configured to: receive user input indicating a selection of a fluidics control function; receive user input indicating a parameter of the fluidics control function; and change the parameter of the fluidics control function, based at least in part on the user input indicating the selection of the fluidics control function and/or the user input indicating the parameter of the fluidics control function. In some embodiments, the tool can be a drill, a Kerrison, a power aneurysm clip applier, power forceps, bipolar forceps, or power scissors. In some embodiments, the fluidics control function can be optics washing, optics drying, or light source cooling. In some embodiments, the parameter of the tool can be power on, power off, power control, fluid pressure, or an air pressure. In some embodiments, the parameter of the fluidics control function can be power on, power off, power control, standby mode, auto mode, frequency, fluid pressure, or air pressure. In some embodiments, the user input indicating the selection of the tool and/or the selection of the fluidics control function can be a tactile input. In some embodiments, the imaging processing system can be configured to display a submenu comprising a mode and a parameter.

In accordance with another aspect, a graphical user interface system can comprise: at least one camera configured to acquire video images of a surgical site, the at least one of the camera configured to be disposed on a surgical device; and an image processing system in communication with at least one camera, the image processing system comprising at least one physical processor. In some embodiments, the image processing system can be configured to: receive video images acquired by at least one camera; and display a video stream of the acquired video images on the graphical user interface display. In some embodiments, at least one camera can be configured to rotate when the surgical device moves, such that the video stream remains rotationally constant when the surgical device moves. In some embodiments, the image processing system can be configured to: receive video images acquired by at least one camera; and display a video stream of the acquired video images on the graphical user interface display, wherein at least one camera is configured to follow movement of the surgical device.

In accordance with another aspect, the graphical user interface system can be coupled to a surgical visualization system. In some embodiments, the display of the graphical user interface system can be a surgical visualization system display.

In accordance with another aspect, a graphical user interface system can comprise: a plurality of cameras configured to acquire video images of a surgical site, at least one of the plurality of cameras configured to be disposed on a surgical device; and an image processing system in communication with the plurality of cameras, the image processing system comprising at least one physical processor. In some embodiments, the image processing system can be configured to: receive video images acquired by the plurality of cameras; and display a plurality of reduced-size real-time video streams of the acquired video images on the graphical user interface display. In some embodiments, at least one of the plurality of cameras can be disposed within the surgical site.

In accordance with another aspect, a graphical user interface system can comprise: at least one camera configured to acquire video images of a surgical site, the at least one camera configured to be disposed on a surgical device; and an image processing system in communication with the at least one camera, the image processing system comprising at least one physical processor. In some embodiments, the image processing system can be configured to: receive user input indicating a parameter of the at least one camera with movement of the surgical device; and change the parameter of the at least one camera with movement of the surgical device. In some embodiments, the image processing system can be configured to display a graphic representative of at least one camera. In some embodiments, the image processing system can be configured to receive tracking information association with the location and/or orientation of at least one camera. In some embodiments, the graphic representative of at least one camera can be displayed based at least in part on the tracking information. In some embodiments, the parameter of at least one camera can be changed based at least in part on the tracking information. In some embodiments, the surgical device can be a retractor.

In accordance with another aspect, a surgical visualization system includes a retractor configured to hold open an incision and thereby provide a pathway for access of surgical tools to a surgical site. The surgical visualization system also includes a plurality of cameras disposed on the retractor. The retractor, in use, includes a top position, a bottom position opposite the top position, and a first and second lateral position opposite one another and between said top position and said bottom position. The plurality of cameras includes at least one stereo pair of cameras. The at least one stereo pair of cameras is oriented in a horizontal manner when disposed at said top position or said bottom position and in a vertical manner when disposed at said first lateral position or said second lateral position. In some embodiments, the top position corresponds to a 12 o'clock position on the retractor, the bottom position corresponds to a 6 o'clock position on the retractor, and the first and second lateral positions correspond respectively to 3 o'clock and 9 o'clock positions on the retractor. In some embodiments, being oriented in a horizontal manner includes horizontally orienting a line intersecting each optical axis of the at least one stereo pair of cameras. In some embodiments, being oriented in a vertical manner comprises vertically orienting a line intersecting each optical axis of the at least one stereo pair of cameras.

In accordance with another aspect, a surgical visualization system includes a retractor configured to hold open an incision and thereby provide a pathway for access of surgical tools to a surgical site. The surgical visualization system includes a plurality of cameras disposed on the retractor. The plurality of cameras includes at least one stereo pair of cameras and at least one monocular camera.

In accordance with another aspect, a surgical visualization system includes a retractor configured to hold open an incision and thereby provide a pathway for access of surgical tools to a surgical site. The surgical visualization system also includes a plurality of cameras disposed on the retractor. The retractor, in use, includes a top position, a bottom position opposite the top position, and a first and second lateral position opposite one another and between said top position and said bottom position. The plurality of cameras includes at least two stereo pairs of cameras, a first stereo pair disposed at the first lateral position of said retractor and a second stereo pair disposed at the second lateral position of said retractor. The plurality of cameras includes a monocular camera disposed at the top position or the bottom position of said retractor. In some embodiments, the top position corresponds to a 12 o'clock position on the retractor, the bottom position corresponds to a 6 o'clock position on the retractor, and the first and second lateral positions correspond respectively to 3 o'clock and 9 o'clock positions on the retractor. In some embodiments, said first stereo pair of cameras and said second stereo pair of cameras are disposed vertically on said retractor. In some embodiments, the monocular camera has an aspect ratio with a horizontal dimension being larger than a vertical dimension, the monocular camera being oriented such that the horizontal dimension is parallel to a line connecting the first lateral position and the second lateral position. In some embodiments, the aspect ratio of the monocular camera is about 16:9. In some embodiments, the surgical visualization system further includes a surgical tool camera being disposed on a surgical tool such that the surgical tool camera moves with the surgical tool through the pathway.

In accordance with another aspect, the surgical visualization system includes a retractor configured to hold open an incision and thereby provide a pathway for access of surgical tools to a surgical site, said retractor having a longitudinal axis extending through the pathway to the surgical site. The surgical visualization system also includes a plurality of cameras disposed on the retractor. The retractor, in use, includes a top position, a bottom position opposite the top position, and a first and second lateral position opposite one another and between said top position and said bottom position. The plurality of cameras includes at least two monocular cameras, each monocular camera having an aspect ratio with a horizontal dimension larger than a vertical dimension. A first monocular camera is disposed at the top position and oriented such that the vertical dimension is aligned with the longitudinal axis of the retractor. A second monocular camera is disposed at the bottom position and oriented such that the vertical dimension is aligned with the longitudinal axis of the retractor. In some embodiments, the top position corresponds to a 12 o'clock position on the retractor, the bottom position corresponds to a 6 o'clock position on the retractor, and the first and second lateral positions correspond respectively to 3 o'clock and 9 o'clock positions on the retractor. In some embodiments, the aspect ratio is about 16:9.

In accordance with another aspect, the surgical visualization system includes a retractor configured to hold open an incision and thereby provide a pathway for access of surgical tools to a surgical site, said retractor having a longitudinal axis extending through the pathway to the surgical site. The surgical visualization system also includes a plurality of cameras disposed on the retractor. The retractor, in use, includes a top position, a bottom position opposite the top position, and a first and second lateral position opposite one another and between said top position and said bottom position. The plurality of cameras includes at least two stereo pairs of cameras, a first stereo pair disposed at the top position of said retractor and a second stereo pair disposed at the bottom position of said retractor. In some embodiments, the top position corresponds to a 12 o'clock position on the retractor, the bottom position corresponds to a 6 o'clock position on the retractor, and the first and second lateral positions correspond respectively to 3 o'clock and 9 o'clock positions on the retractor. In some embodiments, said plurality of cameras further includes at least two monocular cameras, a first monocular camera disposed at the first lateral position of said retractor and a second monocular camera disposed at the second lateral position of said retractor. In some embodiments, the first monocular camera has an aspect ratio with a horizontal dimension greater than a vertical dimension, the first monocular camera being oriented such that the horizontal dimension is parallel to the longitudinal axis of the retractor. In some embodiments, the aspect ratio is about 16:9. In some embodiments, said first stereo pair of cameras and said second stereo pair of cameras are oriented such that a line intersecting each optical axis of each stereo pair of cameras is perpendicular to the longitudinal axis of the retractor.

In accordance with another aspect, a surgical visualization system includes a binocular viewing assembly comprising a pair of oculars, said pair of oculars configured to provide a view of a display disposed in the binocular viewing assembly. The surgical visualization system also includes an optical assembly disposed on the binocular viewing assembly, the optical assembly configured to provide a surgical microscope view of a surgical site, the optical assembly comprising a stereo pair of cameras. The surgical visualization system is configured such that an ocular line is parallel to a camera line, said ocular line being a line that intersects each optical axis of the pair of oculars and said camera line being a line that intersects each optical axis of the stereo pair of cameras. In some embodiments, said ocular line is orthogonal to each optical axis of said pair of oculars. In some embodiments, said camera line is orthogonal to each optical axis of said stereo pair of cameras. In some embodiments, said ocular line intersects each optical axis of said pair of oculars at approximately a same distance along each optical axis. In some embodiments, said camera line intersects each optical axis of said stereo pair of cameras at approximately a same distance along each optical axis. In some embodiments, said surgical visualization system is configured to maintain said ocular line parallel to said camera line when an orientation of said pair of oculars changes. In some embodiments, said surgical visualization system is configured to provide an audible or visual indicator when said ocular line and said camera line are not parallel. In some embodiments, said display comprises a stereo display configured to provide stereo imagery visible through said pair of oculars. In some embodiments, said surgical visualization system includes a second stereo pair of cameras. In some embodiments, said surgical visualization system is configured such that said ocular line is parallel to a second camera line, said second camera line being a line that intersects each optical axis of said second stereo pair of cameras. In some embodiments, said second camera line is orthogonal to each optical axis of said pair of oculars.

In accordance with another aspect, a surgical visualization system includes a binocular viewing assembly comprising a pair of oculars, said pair of oculars configured to provide a view of a display disposed in the binocular viewing assembly. The surgical visualization system also includes an optical assembly disposed on the binocular viewing assembly, the optical assembly configured to provide a surgical microscope view of a surgical site, the optical assembly comprising a stereo pair of cameras. In the surgical visualization system, a z-axis is defined as a line parallel to a gravity vector and a horizon plane is defined as a plane perpendicular to the z-axis. The surgical visualization system is configured such that a projected ocular line is parallel to a projected camera line where said projected ocular line is a geometrical projection onto the horizon plane of an ocular line, said ocular line being a line that intersects each optical axis of the pair of oculars. Said projected camera line, which is parallel to said projected ocular line, is a geometrical projection onto the horizon plane of a camera line, said camera line being a line that intersects each optical axis of the stereo pair of cameras. In some embodiments, said surgical visualization system is configured to maintain said projected ocular line parallel to said projected camera line when an orientation of the pair of oculars changes. In some embodiments, said surgical visualization system is configured to rotate the stereo pair of cameras along an x-axis or a y-axis, said x-axis and said y-axis parallel to said z-axis. In some embodiments, said surgical visualization system is configured to rotate the pair of oculars along an x-axis or a y-axis, said x-axis and said y-axis parallel to said z-axis. In some embodiments, said display is configured to display video acquired with the stereo pair of cameras such that a gravity vector of the acquired video is aligned with the z-axis when displayed. In some embodiments, said surgical visualization system is configured to provide an audible or visual indicator when said projected ocular line and said projected camera line are not parallel.

In accordance with another aspect, a surgical visualization system includes a binocular viewing assembly comprising a pair of oculars, said pair of oculars configured to provide a view of a display disposed in the binocular viewing assembly. The surgical visualization system also includes an optical assembly disposed on the binocular viewing assembly, the optical assembly configured to provide a surgical microscope view of a surgical site. The optical assembly includes an optical sensor having an input face for receiving light, said optical sensor producing an electrical signal based on said received light. The optical assembly also includes a plurality of lenses in an optical path between said optical sensor and said surgical site, said plurality of lenses having an optical axis substantially parallel to a bottom portion of the binocular viewing assembly. The optical assembly also includes redirection optics located in said optical path, said redirection optics configured to redirect light from said surgical site to the plurality of lenses. In some embodiments, said redirection optics comprises a prism. In some embodiments, said redirection optics comprises at least one reflective surface. In some embodiments, said redirection optics redirects light from said surgical site to said plurality of lenses at an angle of about 90 degrees.

In accordance with another aspect, a system for supporting a display, said system comprising: a housing having a front side and a rear side and left and right sides; a support rearward said rear side of said housing; an arm secured to said support, said arm configured to extend from said rear side of said housing along the left side of said housing or the right side of the housing; and a display mount connected to said arm, said display mount configured to dispose a display forward said housing. In some embodiments, said support is secured to said housing. In some embodiments, said support comprises a vertical support extending in the vertical direction. In some embodiments, said vertical support comprises a pole. In some embodiments, the system further comprises connector configured to connect said arm to said vertical support. In some embodiments, said connector is configured to provide vertical adjustment of said arm along said vertical support. In some embodiments, said connector is configured to permit rotation of said arm about said vertical support. In some embodiments, said connector comprises a ring and said ring is disposed on said vertical support to rotate said arm about said vertical support. In some embodiments, said connector is configured to provide rotation of said arm about a horizontal axis such that said arm can be flipped from a first position where said arm extends from said rear side of said housing along said left side of said housing to a second position where said arm extends from said rear side of said housing along said right side of said housing. In some embodiments, said display mount is configured to rotate with respect to said arm. In some embodiments, said display mount is configured to rotate from 0 to 180 degrees. In some embodiments, said display mount is configured to rotate about the same horizontal axis about which said arm rotates to flip from said left side to said right side of said housing. In some embodiments, said connector comprises a pivot attachment, wherein said pivot attachment is disposed on said arm to rotate said arm about the horizontal axis.

In accordance with another aspect, a medical apparatus comprising: a plurality of cameras configured to be disposed on a surgical retractor, said plurality of cameras comprising at least first and second cameras having respective first and second field-of-views; a plurality of light source providing illumination for said cameras, said plurality of light sources comprising at least first and second light sources; and electronics configured to switch said first and second light sources, wherein said electronics is configured to lower the intensity of said second light source when an image was being captured by said first camera. In some embodiments, said electronics is configured to lower the intensity of said first light source when an image was being captured by said second camera. In some embodiments, said electronics is configured to switch said second light source of when said first camera is capturing an image. In some embodiments, the medical apparatus further comprises a surgical retractor, said plurality of cameras disposed on the surgical retractor. In some embodiments, said surgical retractor comprises a plurality of retractor blades and said cameras are disposed on said retractor blades. In some embodiments, said surgical retractor comprises a tube and said cameras are disposed on an at least one inside surface of said tube. In some embodiments, said second light source was in the first field-of-view of the first camera. In some embodiments, said first light source is in the first field-of-view of the second camera and said electronics are configured to lower the intensity of said first light source when an image is being captured by said second camera. In some embodiments, said a surgical retractor is configured to provide a pathway for access of surgical tools to a surgical site, and said cameras are face inwardly facing toward said pathway. In some embodiments, said cameras face inwardly toward each other. In some embodiments, said plurality of cameras and light sources are disposed on a plurality of imaging modules configured to be attached to a surgical retractor.

In accordance with another aspect, medical imaging equipment comprising: a plurality of cameras configured to be disposed on a surgical retractor, said plurality of cameras each having a respective field-of-view; and a color balancing target having substantially similar color characteristics in the field-of-views of said cameras so as to provide color balancing for said cameras.

In some embodiments, said color balancing target is white and said color balancing comprises white balancing. In some embodiments, the medical imaging equipment further comprising a station where said plurality of cameras can be disposed while color balancing, said color balancing target included with said station. In some embodiments, said station is configured to support said plurality of cameras such that said cameras face inwardly toward each other and said color balancing target. In some embodiments, the medical imaging equipment further comprises a surgical retractor, said plurality of cameras disposed on the surgical retractor. In some embodiments, said a surgical retractor is configured to provide a pathway for access of surgical tools to a surgical site, and said cameras are face inwardly facing toward said pathway. In some embodiments, said color balancing target is disposed in said pathway. In some embodiments, said cameras face inwardly toward each other and said color balancing target. In some embodiments, said cameras face inwardly toward each other and said color balancing target.

In accordance with another aspect, a medical apparatus comprising: a station for supporting a plurality of cameras configured to be disposed on a surgical retractor, said plurality of cameras comprising at least first and second cameras having respective first and second field-of-views; and a white balancing target associated with said station, said white balancing target having substantially similar color characteristics in the first and second field-of-views of said first and second cameras so as to provide white balancing for said first and second cameras.

In accordance with another aspect, a medical imaging device comprising: at least one camera; a platform configured to be disposed on a surgical retractor, said at least one camera supported on said platform; an electronic identification device on said platform, said electronic identification device configured to communicate with a receiver associated with a retractor based surgical visualization system, said electronic identification device configured to provide information relating to said camera. In some embodiments, said platform is configured to attached to a retractor blade or a surface of a tubular retractor. In some embodiments, said electronic identification device comprises an RFID tag. In some embodiments, said electronic identification device comprises a memory with an electrical connector for providing connection to a connector in communication with said receiver. In some embodiments, said information includes at least one of camera field of view and camera resolution.

In accordance with another aspect, medical apparatus comprising: a surgical retractor; a flexible platform supporting at least one camera supported on said platform; actuators configured to move said platform, wherein said actuators are configured to move in response to remote control while the retractor is within a human body.

In accordance with another aspect, a surgical visualization device comprises: a surgical retractor configured to provide access to a surgical site; a plurality of cameras configured to acquire video images of the surgical site; and at least one of the plurality of cameras being disposed on the retractor and configured to acquire video images of said surgical site, wherein the at least one of the plurality of cameras is configured to be moved with respect to the retractor, thereby adjusting the position and/or orientation of the plurality of cameras. In some embodiments, the plurality of cameras are configured to be tilted to adjust the camera orientation. In some embodiments, at least one of the plurality of cameras is disposed on an adjustment platform. In some embodiments, the plurality of cameras comprises an electrical actuator configured to provide movement. In some embodiments, the plurality of cameras is configured to utilize manual actuation to provide movement. In some embodiments, the manual actuation comprises a hand manipulation. In some embodiments, the device further comprises a fluid line. In some embodiments, the device further comprises an air line. In some embodiments, the plurality of cameras point inward on the surgical retractor. In some embodiments, the plurality of cameras are configured to removably attach to the surgical retractor.

In accordance with one aspect, medical imaging equipment can comprise: medical imaging equipment comprising: a retractor; a plurality of cameras disposed on the surgical retractor, said plurality of cameras comprising at least first and second cameras having respective first and second field-of-views; and a first marking on said second camera in the first field-of-view of said first camera, said marker assisting in the identifying the first camera. In some embodiments, the medical imaging equipment can comprise a second marking on said first camera in the second field-of-view of said second camera, said marker assisting in the identifying the second camera. In some embodiments, the first and second markings can be different. In some embodiments, the first and second markings can have different colors.

In accordance with another aspect, medical imaging equipment can comprise: a plurality of members for attaching to a retractor; a plurality of cameras on said plurality of members, said plurality of cameras comprising at least first and second cameras having respective first and second fields-of-view; and a first marking on said second camera in the first field-of-view of said first camera, said marker assisting in the identifying the first camera. In some embodiments, the medical imaging equipment can comprise a second marking on said first camera in the second field-of-view of said second camera, said marker assisting in identifying the second camera. In some embodiments, the first and second marking can be different. In some embodiments, the first and second marking can have different colors. In some embodiments, said plurality of members can be configured to attach to a plurality of retractor blades.

In accordance with another aspect, a medical imaging device can comprise: at least one camera; at least one platform for disposing on a surgical retractor, said at least one camera supported on said platform, said platform comprising an elongate member supporting electrical lines therethrough, wherein said platform is rollable such that said plate form can be rolled up for storage and at least partially unrolled for deployment on a surgical retractor. In some embodiments, said platform can be configured to attach to a plurality of retractor blades. In some embodiments, said platform can be configured to be disposed on an at least one inside surface of a tubular retractor. In some embodiments, said platform can have proximal and distal ends and said at least one camera can be disposed at said distal end. In some embodiments, said distal end can be wider than said proximal end. In some embodiments, said at least one camera can include a plurality of cameras at said distal end. In some embodiments, said platform can be separated into multiple extensions at said distal end. In some embodiments, separate cameras can be disposed on at least two separate of said extensions. In some embodiments, said platform can comprise flex cable. In some embodiments, said platform can comprise microfluidic line, and said platform can comprise flex cable. In some said at least one platform can comprise a plurality of rollable platforms having cameras thereon, said platforms aggregated at a common aggregator.

In accordance with another aspect, a medical device can comprise an operative portion and a handle portion connected to the operative portion. In some embodiments, the medical device further comprises an alignment feature connected to the handle and/or to the operative portion. The medical device can include a camera. In some embodiments, the alignment feature is configured to indicate to a user of the medical device the alignment of the camera relative to the user. In some embodiments, the alignment feature is a tactile feature. For example, the alignment feature can be a faceted ring, a nub, a dimple, a protrusion, a roughened portion and/or any combination of tactile features including, but not limited to the features listed above. In some embodiments, the alignment feature is a visual feature. For example, the alignment feature can be a light (e.g., an LED), a coloration feature, or some other visual feature configured to indicate to the user the alignment of the camera. In some embodiments, an operative portion of the medical device is a drill, a Kerrison, forceps, scissors, or any other medical and/or surgical device. In some embodiments, the medical device includes a coupler. In some such embodiments, the operative portion is connected to the handle via the coupler. In some embodiments, the camera is mounted on the handle of the medical device. In some embodiments, the camera is mounted on the body portion of the medical device, on the coupler, and/or on the operative portion of the medical device. In some embodiments, the alignment feature is positioned on the medical device on a side of the medical device opposite the camera. In some embodiments, the camera is fixedly connected with the alignment feature. In some embodiments, the camera and the alignment features are rotatably connected to the handle portion to permit rotation of the operative portion of the medical device independent from rotation of the camera and the alignment feature. In some such embodiments, the user can maintain the position of the camera while rotating the handle portion.

In accordance with another aspect, a Kerrison can comprise a moveable cutting surface and a fixed cutting surface operably coupled with the moveable cutting surface. In some embodiments, the Kerrison include an actuator mechanism configured to move the moveable cutting surface with respect to the fixed cutting surface. In some embodiments, the moveable cutting surface has a D-shape or a U-shape. In some embodiments, the fixed cutting surface has a D-shape of a U-shape. In some embodiments, the moveable cutting surface is moved by a hydraulic pressure source.

In accordance with another aspect, a medical device can comprise a hydraulic fluid source fluidly connected with a first inflatable element. In some embodiments, the medical device includes a second inflatable element selectively fluidly connected to the first inflatable element. In some embodiments, the medical device can include an actuating element. The actuating element can be configured to move in response to force from the second inflatable element (e.g., in response to expansion and compression of the second inflatable element). In some embodiments, compression of the first inflatable element causes expansion of the second inflatable element. In some embodiments, expansion and contraction of the second inflatable element moves the actuating element. In some embodiments, the medical device further comprises a user interface the user interface configured to selectively compress the first inflatable element in response to user input via the user interface. In some embodiments, the user input device is (a foot pedal, a knob, a button, a switch, a lever). In some embodiments, the medical device further comprises a drive system configured to selectively compress the first inflatable element in response to user input via the user interface. In some embodiments, the medical device further comprises a third inflatable element selectively fluidly connected to the first inflatable element and a second actuating element configured to move in response to force from the second inflatable element. In some embodiments, the medical device further comprises a surgical tool configured to operate in response to movement of the actuating element. In some embodiments, the medical device comprises a tactile feedback mechanism to provide tactile feedback from the surgical tool to the user input device. In some such embodiments, the surgical tool is a Kerrison, forceps, micro-forceps, scissors, bipolar forceps, clip appliers, and/or other similar or dissimilar medical/surgical tools. In some embodiments, the medical device further comprises a biasing member configured to exert a biasing force upon the actuating member to bias the actuating member to a first position, the actuating element configured to transition to a second position in response to force from the second inflatable element sufficient to overcome the biasing force. In some embodiments, the medical device further comprises a manifold in fluid communication with the first inflatable element and a third inflatable element in selective fluid communication with the first inflatable element via the manifold.

In accordance with another aspect, a surgical system can comprise a hydraulic pressure system including a first hydraulic pressure source and a second hydraulic pressure source configured to power a hydraulic surgical tool. The surgical system can include one or more valves configured to direct fluid flow through the surgical system. In some embodiments, a pneumatic pressure source pressurizes the hydraulic pressure system. In some embodiments, one or more surgical tools are powered at least in part by a pneumatic pressure source. The surgical tool can be powered by a hydraulic turbine. In some embodiments, the pneumatic pressure source can be a hospital pneumatic system.

In accordance with another aspect, a surgical system can comprise a hydraulic pressure system including a first hydraulic pressure source and a second hydraulic pressure source. In some embodiments, the first hydraulic pressure source and/or the second hydraulic pressure source are configured to pressurize hydraulic fluid in the surgical system. In some embodiments, the first hydraulic pressure source and/or the second hydraulic pressure source have a compression stroke in which the first hydraulic pressure source and/or the second hydraulic pressure source increase the pressure of the hydraulic fluid within the first hydraulic pressure source and/or the second hydraulic pressure source. In some embodiments, the first hydraulic pressure source and/or the second hydraulic pressure source have an expansion stroke in which the first hydraulic pressure source and/or the second hydraulic pressure source decrease the pressure of the hydraulic fluid within the first hydraulic pressure source and/or the second hydraulic pressure source. In some embodiments, the second hydraulic pressure source is configured to operate its compression stroke when the first hydraulic pressure source operates its expansion stroke. In some embodiments, the second hydraulic pressure source is configured to operates its expansion stroke when the first hydraulic pressure source operates its compression stroke. In some embodiments, the surgical system includes a surgical tool. In some embodiments, one or more valves are positioned in a fluid path between the one or more surgical tools and one or more of the first hydraulic pressure source and the second hydraulic pressure source. In some embodiments, the one or more valves are configured to selectively close and open fluid communication between the one or more surgical tools and one or more of the first hydraulic pressure source and the second hydraulic pressure source. In some embodiments, the surgical system can comprise one or more hydraulic fluid sources in selective fluid communication with one or more of the first hydraulic pressure source and the second hydraulic pressure source.

In some embodiments, the surgical system can comprise a first pneumatic pressure source. In some embodiments, the first pneumatic pressure source comprises a pneumatic fluid chamber. In some embodiments, the first pneumatic pressure source comprises a piston positioned within the fluid chamber. In some embodiments, the first pneumatic pressure source comprises an actuator operably connected to the piston. In some such embodiments, the actuator is configured to move the piston in a compression stroke and an expansion stroke. In some embodiments, the pneumatic fluid chamber is in selective fluid communication with one or more of the first hydraulic fluid chamber and the second hydraulic fluid chamber.

In some embodiments, the surgical system can comprise a pneumatic pump. The pneumatic pump can be in selective fluid communication with the pneumatic fluid chamber. In some embodiments, the surgical system comprises a hydraulic turbine configured to actuate one or more surgical tools. In some embodiments, the hydraulic turbine is in selective fluid communication with the hydraulic pressure system. In some embodiments, the hydraulic turbine is powered by pressurized hydraulic fluid from the hydraulic pressure system. In some embodiments, at least a portion of the pressurized hydraulic fluid used to power the hydraulic turbine is returned to the hydraulic pressure system after powering the hydraulic turbine. In some embodiments, the surgical system comprises one or more surgical tools configured to be powered by pneumatic fluid. In some embodiments, the surgical system comprises a pneumatic assembly configured to selectively power one or more of the one or more surgical tools configured to be powered by pneumatic fluid. In some embodiments, the pneumatic assembly is in selective fluid communication with a pneumatic pump. In some embodiments, the surgical tool is a drill, a Kerrison, forceps, scissors, or another surgical instrument/tool. In some embodiments, the surgical system includes a hospital pneumatic pressure source. In some embodiments, the hospital pneumatic pressure source pressurizes the hydraulic fluid in the hydraulic pressure system.

In accordance with another aspect, a surgical system can comprise a cassette assembly with one or more valves. The one or more valves can be elastomeric and/or proportional. In some embodiments, actuators are used to operate the one or more valves. The cassette assembly can include a plurality of inlets, outlets, channels, and/or connecting conduits. In some embodiments, the cassette assembly includes one or more fluid chambers. The fluid chambers can house bellows or other pressurizing components.

In accordance with another aspect, a surgical system can comprise a cassette assembly. In some embodiments, the cassette assembly comprises a cassette housing. In some embodiments, the cassette assembly comprises a first hydraulic fluid chamber. The first hydraulic fluid chamber can be positioned at least partially within the cassette housing. In some embodiments, the cassette assembly comprises a plurality of fluid ports positioned on the cassette housing. In some embodiments, the cassette assembly comprises a plurality of fluid channels connecting the ports, the fluid chambers and other features of the cassette to each other. In some embodiments, the cassette assembly comprises one or more valves located in or on the cassette housing. In some embodiments, the surgical system includes a first hydraulic pressure source fluidly coupled with the first hydraulic fluid chamber. In some embodiments, the first hydraulic pressure source has a compression stroke in which the first hydraulic pressure source increases the pressure of the hydraulic fluid within the first hydraulic fluid chamber and an expansion stroke in which the first hydraulic pressure source decreases the pressure of the hydraulic fluid within the first hydraulic fluid chamber. In some embodiments, the surgical system includes one or more valves. The one or more valves can be proportional. In some embodiments, the one or more valves include elastomeric portions configured to receive deforming force from one or more actuators. In some embodiments, the one or more actuators are linear actuators. In some embodiments, the surgical system includes a surgical tool. The surgical tool can be configured to be powered by hydraulic fluid. In some embodiments, the first hydraulic fluid chamber is in selective fluid communication with one or more of the one or more surgical tools. In some embodiments, the one or more valves are positioned in a fluid path between the one or more surgical tools and the first hydraulic fluid chamber. In some embodiments, the one or more valves are configured to selectively and/or proportionally close and open fluid communication between the one or more surgical tools and the first hydraulic fluid chamber. In some embodiments, the surgical system includes one or more hydraulic fluid sources in selective fluid communication with one or more of the first hydraulic pressure source and the second hydraulic pressure source.

According to some variants, the cassette assembly further includes a second hydraulic fluid chamber positioned at least partially within the cassette housing and in selective fluid communication with one or more of the one or more surgical tools. In some embodiments, the cassette assembly includes a second hydraulic pressure source fluidly coupled to the second hydraulic fluid chamber. In some embodiments, the second hydraulic pressure source can have a compression stroke in which the second hydraulic pressure source increases the pressure of the hydraulic fluid within the second hydraulic fluid chamber and an expansion stroke in which the second hydraulic pressure source decreases the pressure of the hydraulic fluid within the second hydraulic fluid chamber. In some embodiments, the second hydraulic pressure source is configured to operate its compression stroke when the first hydraulic pressure source operates its expansion stroke. In some embodiments, the second hydraulic pressure source is configured to operates its expansion stroke when the first hydraulic pressure source operates its compression stroke. The surgical system can include one or more valves positioned in a fluid path between the one or more surgical tools and the second hydraulic fluid chamber. In some embodiments, the one or more valves are configured to selectively close and open fluid communication between the one or more surgical tools and the second hydraulic fluid chamber.

In some embodiments, the cassette assembly or portions thereof are disposable. In some embodiments, the surgical tool or portions thereof are disposable. In some embodiments, the surgical system includes one or more washing nozzles in fluid communication with one or more of the first hydraulic fluid chambers or the second hydraulic fluid chamber or the hydraulic fluid source. The one or more washing nozzles can be configured to direct hydraulic fluid toward one or more light sources. In some embodiments, the cassette assembly can be configured to connect with a plurality of surgical tools. In some embodiments, the cassette assembly includes bellows. The bellows can be positioned within the first hydraulic fluid chamber and/or within the second hydraulic fluid chamber.

In accordance with another aspect, a medical device system can include a cassette assembly. In some embodiments, the cassette assembly is disposable. In some embodiments, the cassette assembly includes a housing. The cassette assembly can include one or more hydraulic fluid chambers. In some embodiments, the one or more hydraulic fluid chambers are housed at least partially within an interior of the housing. The cassette assembly can include a plurality of fluid ports. In some embodiments, the fluid ports are positioned on the housing. The fluid ports can be configured to facilitate fluid communication between an exterior of the fluid housing and an interior of the fluid housing. In some embodiments, the cassette assembly includes a plurality of proportional valves positioned on the housing. In some embodiments, the cassette assembly includes a plurality of fluid channels configured to facilitate fluid communication between the plurality of ports, the one or more hydraulic fluid chambers, and the plurality of proportional valves. The medical device system can include a surgical tool. The surgical tool can be configured to be powered by a hydraulic fluid source. In some embodiments, the medical device system includes a tool fluid line fluidly connecting one or more fluid ports to the surgical tool. In some embodiments, the hydraulic fluid source is connected to one or more of the fluid ports via one or more fluid source lines.

According to some variants, one or more of the plurality of proportional valves comprises a valve cavity in the housing and a flexible pad sealingly disposed over the valve cavity. In some embodiments, one or more of the plurality of proportional valves is actuated by a linear electromagnetic actuators. In some embodiments, the surgical tool is controlled by one or more of the plurality of proportional valves. In some embodiments, the hydraulic fluid source is an IV bag. In some embodiments, the hydraulic fluid is saline, a physiologically compatible fluid, and/or a physiological saline. In some embodiments, the medical device system includes one or more optical components. In some embodiments, the medical device system includes one or more nozzles in fluid communication with one or more of the plurality of ports. The nozzles can be configured to direct a high velocity, low volume flow of hydraulic fluid to the one or optical components.

In accordance with another aspect, a medical device system can include a hydraulic impeller configured to receive pressurized hydraulic fluid from a hydraulic system and configured to operate a rotary surgical tool. The hydraulic impeller can include a mechanism for scavenging fluid from the hydraulic impeller back to the hydraulic system and/or to components of the hydraulic system. The In accordance with another aspect, a medical device system can include a hydraulic impeller. In some embodiments, hydraulic impeller includes a turbine housing. The turbine housing can define a blade cavity. In some embodiments, the hydraulic impeller includes a flow director. The flow director can be configured to fit at least partially within the turbine housing. In some embodiments, the hydraulic impeller includes an impeller. The impeller can have a plurality of impeller blades. In some embodiments, the impeller can be positioned at least partially within the blade cavity. The flow director can include one or more openings to direct fluid to the impeller blades. In some embodiments, the openings in the flow director are nozzled. In some embodiments, the openings in the flow director can direct the fluid at a steep angle with respect to the impeller blades (e.g., an angle close to perpendicular). In some embodiments, the impeller is configured to direct fluid toward a radially-outward portion of the blade cavity after the fluid impacts the impeller blades. The hydraulic impeller can include an output shaft. The output shaft can be configured to operably connect with a surgical tool. In some embodiments, the output shaft transfers a torque from the hydraulic turbine to the surgical tool. The hydraulic impeller can include one or more ports in a wall of the blade cavity. The one or more ports can be configured to provide fluid communication between an interior of the blade cavity and an exterior of the blade cavity. In some embodiments, the medical device system includes a hydraulic pressure source. The medical device system can include a return fluid line. The return fluid line can be configured to fluidly connect the one or more ports to the hydraulic pressure source. In some embodiments, the hydraulic impeller includes a vacuum source. In some embodiments, the vacuum source is a pump (e.g., a peristaltic pump or other fluid pump). In some embodiments, the vacuum source is a bypass channel of the hydraulic impeller. The bypass channel can be configured to direct high velocity fluid past the blade cavity. In some such embodiments, a pressure differential between the high velocity fluid in the bypass channel and a low velocity fluid in the blade cavity draws low velocity fluid through the one or more ports from the blade cavity to the bypass channel. In some embodiments, the bypass channel can direct fluid from the blade cavity back to the hydraulic pressure source or to some component thereof. In some embodiments, the hydraulic impeller can include a hydrostatic bearing.

In accordance with another aspect, a medical device system can include a surgical device. In some embodiments, the medical device system can further include a camera. The camera can be mounted on the surgical device or on some other component of the medical device system. In some embodiments, the medical device system includes a tracking system. The tracking system can be, for example, an electromagnetic tracking system. The tracking system can be configured to track to the location of the surgical device. In some embodiments, the medical device system can further include a hydraulic system configured to drive the surgical device. In some embodiments, the surgical device is controlled by a foot pedal. In some embodiments, the medical device system includes a tactile feedback mechanism configured to provide tactile feedback from the surgical device to a user of the system.

In accordance with another aspect, a medical device system can include a hydraulic pressure source. The hydraulic pressure source can be in fluid communication with a valve. The valve can be configured to selectively facilitate fluid communication between the hydraulic pressure source and a tool and/or between the hydraulic pressure source and a manifold. In some embodiments, fluid can be directed from a manifold to the hydraulic pressure source. In some embodiments, fluid can be directed from the tool to the hydraulic pressure source and/or to the manifold. In some embodiments, the medical device system includes a pump (e.g., a peristaltic pump) configured to pump fluid to the hydraulic pressure source from the manifold and/or from the tool. In some embodiments, the manifold is configured to direct fluid to a second tool, to one or more optical components (e.g., to cameras), and/or to one or more light sources (e.g., LEDs or other light emitters).

In accordance with another aspect, a medical device system can include a fluid source. The fluid source can be selectively fluidly connected to a surgical tool. In some embodiments, the fluid source is selectively fluidly connected to a manifold. The manifold can be configured to direct fluid to a second tool, to one or more optical components, and/or to one or more light sources. In some embodiments, the medical device system includes a bellows configured to pressurize fluid. Fluid from the bellows can be directed to the surgical tool and/or to the manifold. In some embodiments, the medical device system includes a valve to selectively direct fluid from the bellows to the surgical tool and/or to the manifold. In some embodiments, fluid from the surgical tool can be directed to the manifold. The medical device system can include a pump (e.g., a peristaltic pump) configured to pressurize fluid. In some embodiments, the pump pressurizes fluid directed to the manifold. In some embodiments, the medical device system includes a second valve configured to selectively direct fluid from the fluid source to the pump and/or to the bellows. The medical device system can include a check valve positioned on a fluid line between the second valve and the bellows. In some embodiments, the check valve is configured to inhibit fluid flow from the bellows to the second valve and to permit fluid flow from the second valve to the bellows.

In accordance with another aspect, an imaging module for disposing on a surgical device, said imaging module configured to provide images of a surgical site within a field-of-view of said imaging module, comprises: an optical sensor comprising a two-dimensional detector array having a planar imaging surface configured to output an electrical signal when light is incident on said imaging surface; a plurality of lenses configured to focus light from said surgical site onto said optical sensor to form images of said surgical site on said optical sensor, said plurality of lenses and optical sensor defining an optical path; first redirection optics in said optical path between said plurality of lenses and said optical sensor, said first redirection optics configured to redirect light from said plurality of lenses to said optical sensor such that said optical sensor can be oriented so as to reduce obstruction to said surgical site by said optical sensor; and second redirection optics configured to redirect said field-of-view at a view angle different than would be provided by said plurality of lenses without said redirection optics. In some embodiments, a group of said plurality of lenses extend longitudinally in a direction substantially parallel to a plane defined by said planar imaging surface of said two-dimensional detector array. In some embodiments, said plane is parallel to a surface of said surgical device on which said imaging module is disposed. In some embodiments, a group of said plurality of lenses have an optical axis substantially parallel to a plane defined by said planar imaging surface of said two-dimensional detector array. In some embodiments, said plane is parallel to a surface of said surgical device on which said imaging module is disposed. In some embodiments, said view angle is non-parallel to a surface of said surgical device on which said imaging module is disposed. In some embodiments, said view angle is non-parallel to a central axis into said surgical site defined by said surgical device. In some embodiments, said view angle is non-parallel to an optical axis of a group of said plurality of lenses. In some embodiments, said second redirection optics includes at least one reflective surface. In some embodiments, said second redirection optics includes at least two reflective surfaces. In some embodiments, said second redirection optics comprises a prism. In some embodiments, said second redirection optics comprises a plurality of prism sections that are adjoined to provide at least two surfaces that totally internally reflect light thereby altering said view angle. In some embodiments, said second redirection optics redirects light using multiple reflections. In some embodiments, said second redirection optics includes at least one reflective surface. In some embodiments, said first redirection optics comprises a prism. In some embodiments, said first redirection optics comprises a prism that redirects light from a group of said plurality of lenses to said optical sensor at an angle of 90 degrees, said group being between said first redirection optics and said second redirection optics. In some embodiments, said first redirection optics comprises a non-powered optical element. In some embodiments, said second redirection optics comprises a non-powered optical element. In some embodiments, at least one of said plurality of lenses is negative, said second redirection optics being disposed between said negative lens and other lenses in said plurality of lenses. In some embodiments, a group of said plurality of lenses has positive power, said group being between said first redirection optics and said second redirection optics. In some embodiments, said group comprises multiple positive lenses and at least one negative lens. In some embodiments, the imaging module further comprises an auto focus mechanism disposed in said optical path between said optical sensor and said first redirection optics. In some embodiments, said plurality of lenses has an optical axis substantially along the length of a flex cable. In some embodiments, said surgical device comprises a retractor. In some embodiments, said surgical device comprises a surgical tool such as Kerrison, forceps, or a drill.

In accordance with another aspect, a medical device comprises: a surgical retractor configured to hold open an incision and thereby provide a pathway for access of surgical tools into a surgical site; and at least one video camera disposed on said surgical retractor, said video camera comprising a sensor and a plurality of lenses, said at least one video camera having a line-of-sight, said at least one video camera further comprising redirection optics that alters the line-of-sight provided by the video camera. In some embodiments, said redirection optics comprises a reflector with one or more reflective surfaces. In some embodiments, said redirection optics redirects said line-of-sight using multiple reflections. In some embodiments, said redirection optics does not have optical power. In some embodiments, said redirection optics comprises a prism. In some embodiments, said redirection optics comprises a plurality of prism sections that are adjoined to provide at least two surfaces that totally internally reflect light. In some embodiments, the surgical retractor comprises a plurality of retractor blades, each of said plurality of retractor blades comprising at least one video camera and redirection optics. In some embodiments, said surgical retractor is a cylindrical retractor and video cameras are disposed inside said retractor. In some embodiments, the medical apparatus comprises: a proximal video camera at a proximal location; and a distal video camera at a distal location; wherein the distal location is configured to be disposed deeper into the surgical site than the proximal location. In some embodiments, the medical apparatus further comprises a plurality of proximal video cameras at the proximal location and a plurality of distal video cameras at the distal location. In some embodiments, the surgical retractor is comprises a spinal retractor. In some embodiments, the surgical retractor is configured for use in head or neck surgery. In some embodiments, the surgical retractor is configured for use in neurosurgery.

In accordance with another aspect, an apparatus for providing images of a surgical site within a surgical cavity comprises: a segment of said flexible flat cable extending into said surgical cavity; an optical sensor electrically connected to said flexible flat cable, said optical sensor having a input face for receiving light, said optical sensor producing an electrical signal based on said received light; a plurality of lenses in an optical path between said optical sensor and said surgical site, said plurality of lenses having an optical axis more parallel than normal to said input face of said optical sensor; and redirection optics located in said optical path, said redirection optics redirecting light to said optical sensor. In some embodiments, said optical sensor is disposed on a flat portion of said flexible flat cable such that said input face of said optical sensor is parallel to said flat portion of said flexible flat cable. In some embodiments, said redirection optics comprises a prism. In some embodiments, said redirection optics comprises a plurality of prism sections that are adjoined to provide at least two surfaces that totally internally reflect. In some embodiments, the surgical device comprises a surgical retractor. In some embodiments, the surgical device comprises a surgical tool such as Kerrison, forceps, or a drill. In some embodiments, the flexible cable is removably attached to the surgical device. In some embodiments, the imaging module comprises a plurality of segments of flexible cable extending into the surgical cavity, said plurality of segments including optical sensors electrically connected thereto, said optical sensor having respective redirection optics to redirect light thereinto.

In accordance with another aspect, a surgical device comprises: at least one camera disposed on said surgical device, said at least one camera having a field of view within a surgical site; and at least one light source disposed on said surgical device, said at least one light source is configured to output a beam having substantially the same size as said field-of-view. In some embodiments, at least one light source and said at least one camera are in such proximity to each other that said camera field-of-view matches said field illuminated by said light source. In some embodiments, said light source comprises a light source that emits visible light. In some embodiments, said at least one light source comprises light emitting diodes (LEDs). In some embodiments, said surgical device comprises a surgical retractor. In some embodiments, said surgical device comprises a surgical tool such as Kerrison, forceps, or a drill. In some embodiments, said beam is in the shape of a cone.

In accordance with another aspect, a method for orienting and/or positioning a camera disposed on a surgical device, said camera having a field-of-view, comprises: using a light source to illuminate an area, said light source configured to output a beam having substantially the same size as said field-of-view of said camera, said at least one light source positioned in proximity of said at least one camera such that said camera field-of-view matches the area illuminated by said light source; using a light source to illuminate an area, said light source configured to output a beam having substantially the same size as said field-of-view of said camera, said at least one light source positioned in proximity of said at least one camera such that said camera field-of-view matches the area illuminated by said light source; moving the camera together with the light source; and viewing the beam from the light source, wherein said beam from the light source is used to guide the movement of said camera to obtain the desired field-of-view for the camera. In some embodiments, the surgical device comprises a surgical retractor.

In various embodiments, hydraulic systems comprise a saline hydraulic system. Saline hydraulic fluid may be employed. Accordingly, in various embodiments, for example, the hydraulic pressure system comprises a saline hydraulic pressure system, hydraulic fluid sources comprise saline hydraulic fluid sources, and hydraulic fluid chambers comprise saline hydraulic fluid chambers, etc.

As disclosed elsewhere herein, in various embodiments, the camera(s) and/or other features can be included without the retractor, and may, for example, be configured for use with a retractor or other surgical device such as a surgical tool. Additionally, the camera(s) and/or other features may be configured for use and/or used with medical devices other than retractors. Described herein are various exemplary embodiments containing different combinations of features. Any of the various features of the embodiments disclosed herein may be combined with any other feature(s) from any of the other embodiments disclosed herein to form other embodiments. Moreover, one or more features of any embodiment disclosed herein may be omitted to form other embodiments. Various features that are described in the context of a single embodiment can be implemented in multiple embodiments separately or in any suitable subcombination.

BRIEF DESCRIPTION OF THE DRAWINGS

FIGS. 2A-C show an embodiment of a surgical retractor device having an integrated imaging assembly.

FIG. 3B shows an embodiment of an imaging assembly containing electrical lines and cameras integrated with the retractor blades.

FIG. 4A shows an embodiment of a rotatable stage attached to a retractor frame.

FIG. 4B shows a bottom view of a rotatable stage.

FIG. 4C shows a side view of an embodiment of a camera and prism mounted on the inside surface of the rotatable stage.

FIG. 4D shows an enlarged view of a stereo camera pair.

FIGS. 6E-G show an embodiment of a rigid articulating retractor blade in an unflexed position.

FIG. 6H shows an embodiment of a retractor.

FIG. 7 shows embodiments of the distal end of clip-on flexible cable that is attached to a retractor blade.

FIG. 8 shows a front surface of a retractor blade or of a flexible cable that can be attached to a retractor blade.

FIG. 12A shows an embodiment of a clip-on fastener for fastening the flexible cable to the retractor blade surface.

FIG. 12B shows an embodiment of a hairpin attachment fastener for fastening the flexible cable to the retractor blade surface.

FIG. 12C shows a top view of an embodiment with a dovetail attachment fastener for fastening the flexible cable to the retractor blade surface.

FIG. 13A shows the surgical retractor of FIGS. 2A-C with a laser device positioned through the opening.

FIG. 13B shows the surgical retractor of FIGS. 2A-C with a needle holder positioned through the opening.

FIG. 16 shows the example output for display of FIG. 15 with additional imagery from distal cameras displayed as well.

FIGS. 21D and 21D-2 illustrates an example surgical viewing system that includes an isocenter positioning system attached to the viewing platform.

FIGS. 22A and 22B show examples of displaying a composite image by stitching and tiling images from cameras.

FIGS. 25A-C show an irrigation assembly for cleansing an optical sensor.

FIG. 27B shows substrates configured to be interlocked to form wafer-scale optics.

FIG. 27C shows a wafer to be diced to provide a plurality of substrates for forming the wafer-scale optics.

FIG. 29A shows an embodiment of a wide field-of-view optical assembly with a buried stop for use with a surgical device.

FIG. 29B shows an example embodiment of an optical assembly comprising an afocal module coupled to an optical imaging module for use with a surgical device.

FIG. 29C shows an imaging module comprising interchangeable optical elements configured to change imaging properties of the imaging module.

FIGS. 31A and 31B respectively show top and side views of some embodiments of an imaging module comprising an imaging stack, sensor layer, via layer, and flex layer.

FIG. 47D is a schematic illustration of another embodiment of a hydraulically actuated surgical device.

FIG. 47E is a schematic illustration of an embodiment of a cutting tip of the surgical device embodiment of FIG. 47D.

FIG. 47F is a schematic illustration of another embodiment of a cutting tip of the surgical device embodiment of FIG. 47D.

FIG. 47G is a schematic illustration of another embodiment of a cutting tip of the surgical device embodiment of FIG. 47D.

FIG. 51A is a schematic illustration of another embodiment of a hydraulically actuated surgical device in a first position.

FIG. 51B is a schematic illustration of another embodiment of a hydraulically actuated surgical device in a second position.

DETAILED DESCRIPTION

Figure 1:
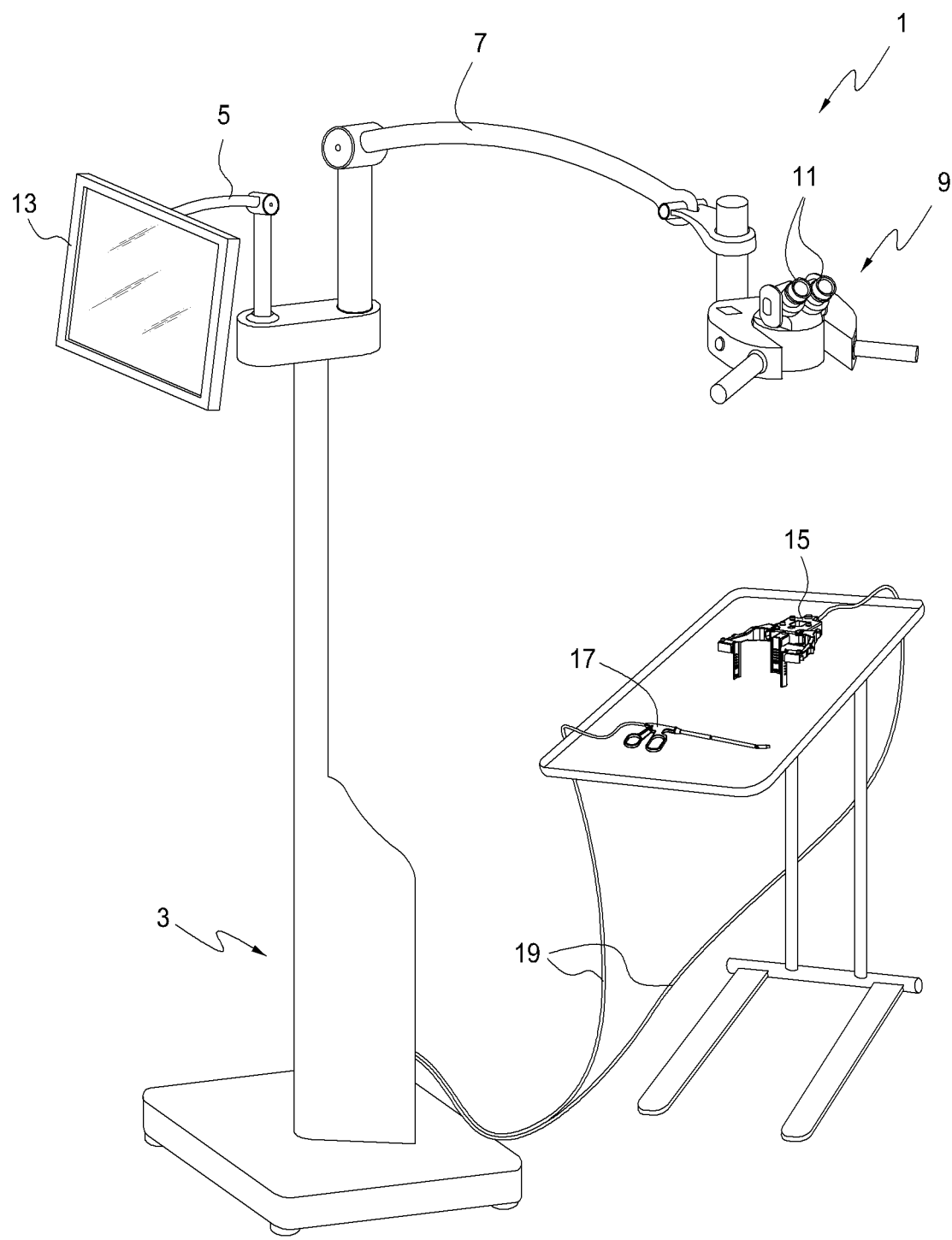
FIG. 1 shows an embodiment of a surgical visualization.

The following description is directed to certain embodiments for the purposes of describing the innovative aspects of this disclosure. However, a person having ordinary skill in the art will readily recognize that the teachings herein can be applied in a multitude of different ways. The described embodiments may be implemented in any device or system that can be configured to provide visualization of a surgical site. Thus, the teachings are not intended to be limited to the embodiments depicted solely in the figures. and described herein, but instead have wide applicability as will be readily apparent to one having ordinary skill in the art.

Surgical Field Visualization

In order to provide for improved visualization of the surgical site, a surgical device can be provided with multiple cameras integrated therein. For example, the surgical device can be a retractor, and a plurality of cameras may be mounted on or within the retractor. In other embodiments, the surgical device can be a platform having cameras mounted thereon, but may be separate from any retractor used during the surgery. Each of the cameras may capture a distinct view of the surgical site. In some embodiments imagery from the plurality of cameras may be integrated together, for example, "stitched" together to form composite mosaic imagery that may be displayed disposed over background imagery, or arranged in an array of tiled images shown individually disposed over background imagery for particular emphasis of a surgical work area. Tiled, individual, or composite imagery can provide the user with a view of the area of the body on which surgery is being performed. The user can select the imagery to be displayed and the manner in which it is displayed for enhanced utility during surgery. As used herein, the term imagery and images includes video and/or images captured from one or more cameras. Images from video are often referred to as video images or simply images. The term images may also refer to still images or snap shots. Video feed or video stream may also be used to describe the video images such as video images from a camera.

Such cameras can be of particular use when disposed on surgical devices, such as retractors, which are at least partly disposed within the opening through which the surgery is being performed, so as to provide the user with a perspective of being within or just about within the body. Retractors, for example, may be used to hold open a region in the body where surgery is to be performed. This region is formed by making an incision to provide access to the region or surgical site. Accordingly, various embodiments described herein pertain to non-percutaneous procedures, for example, non-laparoscopic. Additionally, various embodiments described herein pertain to non-endoscopic procedures. Additionally, various embodiments employ open surgery and cut-down as opposed to percutaneous procedures. Likewise various embodiments employ larger incisions than would be made for arthroscopy, laparoscopy etc. Various embodiments described herein pertain to minimally invasive surgery (MIS) for spine surgery, all of neurosurgery and trans-oral approaches to various cancers such as tongue, tonsils, oral and nasal pharynx and anterior skull base (brain). The region may have an area of, for example, from 400 to 2500 mm$^2$, 1 to 20 cm$^2$ or 1 to 10 cm$^2$ so as to permit the surgeon ready access to the surgical site such that the surgeon can manipulate tools to perform surgery. For example, trans-oral surgeries can retract the mandible, maxilla, and each cheek to provide an approximately 45 by 45 mm working space. A minimally invasive spine surgery can use a tubular retractor having a circular working space with a diameter of approximately 25 mm. The retractor contains blades, fingers, or at least one barrier such as e.g., a tube that holds tissue back to maintain open the surgical site. Multiple cameras located on the retractor at locations within the surgical field or in very close proximity thereto, e.g., within 75 mm of the surgical opening, can provide a useful viewpoint for the surgeon. The cameras may for example be located on the blades, fingers, tubular barrier, or other portion of the retractor close to the surgical field or within the patient and the surgical field. The cameras may include pairs of cameras arranged and/or oriented to provide stereo and thus 3D imaging or single CMOS camera chips with dual optics to provide stereo. The cameras may be located at various locations in relation to surgical devices, for example, the cameras can be located proximally and distally along or near a retractor, wherein the location of the cameras can be configured to facilitate both the progression of surgery and an enhanced view or view selection of an area of interest.

In various embodiments, the retractor maintains a central open region that permits the surgeon central access to the surgical field through the opening provided by the retractor and cameras and/or stereo camera pairs disposed on the retractor provide views surrounding the surgical field. Accordingly, the retractor may comprise a plurality of blades or fingers or other members disposed about an open central region. In some embodiments, the retractor comprises a hollow tube that forms a barrier against the tissue surrounding the surgical site. The hollow tube has a central open region that permits central access to the surgical field through the tube. Accordingly, in various embodiments, the retractor is designed to provide the central open region unobstructed by the retractor to permit tools and other surgical devices to have ready access to the surgical site and the central portion of the surgical site.

In various embodiments, cameras and/or stereo camera pairs are mounted on the retractor and directed inward toward this central surgical site to provide a view thereof. Accordingly, in various embodiments the cameras and/or stereo camera pairs surround the central portion or are disposed about a portion, for example, ¼, ⅓, ½, ⅔, ¾ or more of the surgical site. The cameras and/or stereo camera pairs may for example be disposed at 3 or 4 or more points, for example up to 6, 8, 10, or more points about the surgical side. For example, the cameras and/or stereo camera pairs may be disposed at positions at 3 o'clock, 6 o'clock, and 9 o'clock, or 3 o'clock, 6 o'clock, 9 o'clock, and 12 o'clock as viewed from above the surgical site. In other embodiments, the cameras and/or stereo camera pairs may be disposed at 2 o'clock, 6 o'clock, and 10 o'clock, or 2 o'clock and 10 o'clock as viewed from above the surgical site. These cameras and/or stereo camera pairs may generally face toward the open central region and thus in some embodiments, at least one camera and/or stereo camera pair has a field-of-view in which another camera and/or stereo camera pair is visible in that field-of-view. Or one or more cameras and/or stereo camera pairs may have a portion of the retractor in their field-of-view in some embodiments.

Accordingly, the cameras and/or stereo camera pairs on a retractor or a plurality of retractors may point in different directions or otherwise provide different vantage points. The direction of each camera and/or stereo camera pair may be characterized by its field of view and/or optical axis. The optical axis may extend outwardly along the center of the camera's and/or stereo camera pair's field of view. In some embodiments, the optical axes of two or more cameras and/or stereo camera pairs may be non-parallel and thus not point in exactly the same directions. In some embodiments, the optical axes of the cameras and/or stereo camera pairs on the retractor may be at an angle greater than 10, 20, 30, 40, 50, 60, 70, 80 degree's with respect to each other and may be substantially orthogonal but less than 20, 30, 40, 50, 60, 70, 80, 90, 100 degrees in some embodiments. In some embodiments, the optical axes of the cameras and/or stereo camera pairs on the retractor may be at a larger angle such as greater than 90, 100, 110, 120, 130, 140, 150, 160, or 170, degree's with respect to each other but less than 100, 110, 120, 130, 140, 150, 160, 170 or 180 degrees in some embodiments. In some embodiments, the optical axes of two cameras and/or stereo camera pairs may be anti-parallel and in various examples may at least be directed in opposite directions. In certain embodiments, these camera and/or stereo camera pairs may be directed at least toward a common central area and may potentially have field-of-views that at least partially overlap. In some embodiments, the centerlines of the field-of-views of two cameras or stereo camera pairs may converge at a point or small central area (e.g., less than 500 mm$^2$ or less than 100 mm$^2$) within the surgical site.

In some embodiments, the projected angle (as seen from directly above the surgical site) between the optical axes of two cameras and/or stereo camera pairs on the retractor may be 0 degrees, however, in various embodiments it may be at least 5, 15, 30, 45, 60, 75, or 90 degrees but less than 100 degrees such as between 5 and 15, 15 and 30, 30 and 45, 45 and 60, 60 and 75, 75 and 90 degrees with respect to one another with the cameras and/or stereo camera pairs facing inward toward the surgical site. More than two cameras and/or stereo camera pairs on the retractor may be oriented such that optical axes of the more than two cameras and/or stereo camera pairs (as seen from directly above the surgical site) is at least 5, 15, 30, 45, 60, 75, or 90 degrees such as between 5 and 15, 15 and 30, 30 and 45, 45 and 60, 60 and 75, 75 and 90 degrees with respect to one another.

In some embodiments, the projected angle (as seen from directly above the surgical site) between the optical axes of two cameras and/or stereo camera pairs on the retractor may be at least 95, 105, 115, 125, 135, 145, 155, 165, or 175 degrees but less than 180 degrees such as between 95 and 105, 105 and 115, 115 and 125, 125 and 135, 135 and 145, 145 and 155, or 165 and 175 degrees with respect to one another with the cameras or stereo camera pairs facing inward toward the surgical site. More than two cameras and/or stereo camera pairs on the retractor may be oriented such that optical axes of the more than two cameras or stereo camera pairs (as seen from directly above the surgical site) is at least 95, 105, 115, 125, 135, 145, 155, 165, or 175 degrees but less than 180 degrees such as between 95 and 105, 105 and 115, 115 and 125, 125 and 135, 135 and 145, 145 and 155, 155 and 165, 165 and 175, or 175 and 180 degrees with respect to one another.

The cameras and/or stereo camera pairs may be configured to be oriented in such directions. For example, as discussed herein, the cameras may be disposed on platforms that removably attach to the retractor blades in a manner in which the position and/or orientation of the cameras can be altered. For such cameras and/or stereo camera pairs, for example, at least two or more such cameras and/or stereo camera pairs may be configured to be at least 5, 15, 30, 45, 60, 75, or 90 degrees but less than 100 degrees or 95, 115, 130, 145, 160, 175, degrees but less than 180 degrees with respect to one another. The cameras and/or stereo camera pairs can be arranged in many directions to provide a substantially increased range of views of the surgical site for the user. Accordingly, the effective field of view provided by the plurality of cameras and/or stereo camera pairs can be substantially increased. Likewise, although each separate camera and/or stereo camera pair may have a small field-of-view, stitching or tiling images from the different cameras and/or stereo camera pairs together may provide a larger field of view. This wide field-of-view within the surgical site provides enhanced situational awareness for the surgeon. Embodiments described herein can be implemented with virtually any retractor system. For example, suitable retractor systems include the ProView MAP system, DePuy SPOTLIGHTR Access System, Metrx X-Tube Retraction System.

In various embodiments, the use of cameras integrated within a retractor can be applied to neurological, spinal, head and neck, oral, and ENT (ear, nose, and throat) surgeries. Additionally, as described in more detail below, a separate camera can be integrated with a surgical tool, such as but not limited to a drill, forceps, scissors, Kerrison, bipolar cautery (RF), confocal imager, or laser delivery system.

The cameras may be, for example, Omnivision OV2722 1080P, ⅙ inch. Other configurations are possible. For example, the cameras may include wafer-level optics, conventional optics, molded optics, and combinations thereof. In various embodiments, the camera may include imaging optics comprising a negative distal lens group having one or more lenses that produce a total optical power for that group that is negative and a positive proximal lens group having one or more lenses that produce a total optical power for the group that is positive. In certain embodiments, the camera can include an afocal assembly while in other embodiments the imaging optics are not afocal. In various embodiments, an aperture stop for the imaging optics is between lens elements. For example, the aperture stop may be between the negative lens group and the positive lens group. These lenses may comprise wafer scale optics. In some embodiments, the camera can include wafer-scale optics in combination with non-wafer-scale optics. In some embodiments, the wafer scale optical imaging optics comprises layers comprising, e.g., lens elements, separated by spacers that provide air gaps between the layers. The air gaps between the layers may be in communication with each other and/or an air or gas reservoir or reservoirs to reduce the risk of condensation on optical surfaces.

The cameras may comprise, for example, CCD or CMOS sensor arrays or other types of detector arrays. A frame grabber may be configured to capture data from the cameras. For example, the frame grabber may be a Matrox Solios eA/XA, 4 input analog frame grabber board. Image processing of the captured images may be undertaken. Such image processing can be performed by, for example, the Matrox Supersight E2 with Matrox Supersight SHB-5520 with two Intel Six Core Xeon E5645 2.4 GHz processors with DDR3-1333 SDRAM. This system can be designed to support eight or more camera inputs using two Matrox Solios eA/XA, 4 input, analog frame grabber boards. More or less cameras may be employed. In some implementations, a field programmable gate array ("FPGA") can be used to capture and/or process imagery received from the cameras. For example, the image processing can be performed by Xilinx series 7 FPGA boards. Other hardware devices can be used as well, including ASIC, DSP, computer processors, a graphics board, and the like. The hardware devices can be standalone devices or they can be expansion cards integrated into a computing system through a local computer bus, e.g., a PCI card or PCIe card.

A plurality of illumination sources may be provided to enhance the visualization provided by the cameras. For example, in some embodiments, each camera can have two LEDs associated with it. The LEDs may be positioned on opposite sides of the camera, and may be positioned to illuminate the field of view of the camera. The electronic connections for the cameras and/or LEDs can be provided using coaxial cables or flex cables. Flex cables are stronger and more heat resistant than coaxial in comparable sizes. The use of flex cables can allow for a lower profile system, since the aspect ratio of width and thickness is significantly higher than conventional coaxial or endoscopic approaches. In some embodiments, the illumination element, such as an LED may be directly soldered onto the flex cable. In various embodiments, both the illumination element and the camera may be permanently affixed to the flex cable by soldering. In some cases an assembly of flex cables can be utilized consisting of a flex cable for CMOS sensor or sensors, a flex cable for one or more LED's, and an EM sensor cable or assembly. Such a combined assembly can be sandwiched as layers in a protective jacket of silicone or epoxy resin or Teflon tubing and be attached, affixed, or be oriented with the axis of the retractor blade. Such an assembly may terminate in an edge connector typically of a male type.

In some embodiments, the cameras can be disposed on one or more surgical devices or tools, such as a retractor. The cameras can be positioned and oriented such that one camera is within a field of view of another camera. Similarly, cameras can be positioned and oriented such that other portions of the surgical device can be within a field of view of the camera. Labels, fiducials or color markings can be included on the surgical devices, tools, and/or cameras. The labels or color markings can be configured to be within a field of view of another camera. For example, for a retractor having three blades, each with a camera, each blade may also include a corresponding label or color marking. The blades may be labeled, 1, 2, and 3 (or be marked with red, green, or blue) respectively. Likewise, the view from the camera on blade number 1 (red) would show the blade with the number 2 (green) marking or both the blade with the number 2 (green) and number 3 (blue) markings. The markings should also be visible. Such markings can give the user quick identification of which camera generated the image (e.g., the camera on blade number 1 (red) in this example). The labels or markings thus provide increased or enhanced situational awareness to a user or operator by assisting in understanding the position and/or orientation of a camera associated with respect to a surgical tool or device. In some embodiments, the markings, fiducials or labels can be used in image processing such as in stitching or tiling processes to form a composite image.

In certain embodiments, there are an odd number of cameras and/or stereo camera pair provided with the retractor. In some embodiments, the cameras and/or stereo camera pair can be configured to point approximately normal to a retractor axis, and having an odd number of cameras and/or stereo camera pair views can provide for a central camera view providing image data for a central portion of a targeted area and symmetry in the numbers of optical modules views on either side of the central camera view providing image information about peripheral regions. In some embodiments, these sensor module views may be stereoscope views. In such embodiments, an additional camera and/or stereo camera pair can be used to provide a view of a targeted feature, such as a view from a surgical tool (e.g., a cutting tool) and the corresponding area of interest (e.g., area of tissue being cut). In some embodiments, this image of the target features can be displayed in a central portion of a display. The remaining cameras and/or stereo camera pair on the retractor can provide other visual information, such as tool entrance or egress, background or peripheral visual information.

In some embodiments, an electrical connector can be included in each blade of a retractor. In some embodiments, each camera module's connector may be provided at the distal end of an additional run of cabling that attaches to a manifold. Such cabling can be color-coded and/or marked so as to identify or indicate stereoscopic view, field of view differences, etc. The cabling may be plugged into site-specific plugs, which may be unique to the camera type, on a manifold that can, for example, be positioned on the retractor frame near the patient or on a console. In some embodiments, EEPROM tags associated with the different sensors may be used to identify and provide information related to the sensor. In various embodiments, the termination of the cabling is male to facilitate sterilization.

FIG. 1 shows one embodiment of a surgical visualization system. As illustrated, the system 1 includes a base 3 from which two articulating arms 5 and 7 extend. The first articulating arm 5 has mounted to its distal end a viewing platform 9. The viewing platform may include two oculars 11 and be configured similarly to a standard surgical microscope viewing platform. In some embodiments, however, unlike a conventional surgical microscope or a head mounted display the viewing platform 9 is not a direct view device where the surgeon or other user sees directly through the platform, e.g., an aperture in the platform. As discussed in more detail below, the viewing platform 9 may include displays which received signals from cameras which the surgeon or user employs to view the surgical site. In some embodiments, cameras can be mounted to the viewing platform 9 and the cameras can be configured to provide imagery of the surgical site. Accordingly, the cameras can be used to provide imagery similar to a conventional surgical microscope. For example, the cameras on the viewing platform can be configured to provide a virtual working distance, or a distance from the viewing platform to the patient, that can vary using zooming. The virtual working distance can vary, where the working distance can be at least about 150 mm and/or less than or equal to about 450 mm, at least about 200 mm and/or less than or equal to about 400 mm, or at least about 250 mm and/or less than or equal to about 350 mm. The working distance can be selected and/or changed by the surgeon. In some embodiments, the cameras mounted on the viewing platform 9 can be used to provide gesture recognition to allow a surgeon to virtually interact with imagery provided by the display using the surgeon's hands, a surgical tool, or both, as described in greater detail herein. The second articulating arm 5 has mounted to its distal end an input and display device 13. In some embodiments, the input and display device comprises a touchscreen display having various menu and control options available to a user. In some embodiments, the touchscreen can be configured to receive multi-touch input from ten fingers simultaneously, allowing for a user to interact with virtual objects on the display. For example, an operator may use the input device 13 to adjust various aspects of the displayed image. In various embodiments, the surgeon display incorporating a video camera providing a surgical microscope view may be mounted on a free standing articulated arm. The flat panel display touch screen may be positioned on a tilt/rotate device on top of the electronics/fluidics console.

A retractor 15 and surgical tool 17 are both connected to the base 3 by electrical cables 19. In other embodiments, the retractor 15 and surgical tool 17 may be in wireless communication with the base 3, for example via WiFi (IEEE 802.11a/b/g/n), Bluetooth, NFC, WiGig (IEEE 802.11ad), etc. As described in more detail below, one or both of the retractor 15 and surgical tool 17 may include one or more cameras configured to provide imagery, e.g., image and/or video data. In various embodiments, video data can be transmitted to a video switcher, camera control unit (CCU), video processor, or image processing module positioned, for example, within the base 3. The video switching module may then output a display video to the viewing platform 9. The operator may then view the displayed video through the oculars 11 of the viewing platform 9. In some embodiments, the binoculars permit 3D viewing of the displayed video. As discussed in more detail below, the displayed video viewed through the viewing platform 9 may comprise a composite video formed (e.g., stitched or tiled) from two or more of the cameras on the retractor 15 and/or surgical tool 17.

In use, an operator may use the retractor 15 and surgical tool 17 to perform minimally invasive surgery. The operator may view the surgical site by virtue of the displayed imagery in the viewing platform 9. Accordingly, the viewing platform (surgeon display system) 9 may be used in a manner similar to a standard surgical microscope although as discussed above, the viewing platform need not be a direct view device wherein the user sees directly through the platform 9 to the surgical site via an optical path from the ocular through an aperture at the bottom of the viewing platform 9.

Rather in various embodiments, the viewing platform 9 includes a plurality of displays, such as liquid crystal or light emitting diode displays (e.g., LCD, AMLCD, LED, OLED, etc.) that form an image visible to the user by peering into the ocular. Accordingly, one difference, however, is that the viewing platform 9 itself need not necessarily include a microscope objective or a detector or other image-capturing mechanisms. Rather, the image data is acquired via the cameras of the retractor 15 and/or the surgical tool 17. The image data can then be processed by a camera control unit, video processor, video switcher or image processor within the base 3 and displayed imagery may then be viewable by the operator at the viewing platform 9 via the display devices, e.g., liquid crystal or LED displays, contained therein.

Imaging Assembly

Figure 2A:
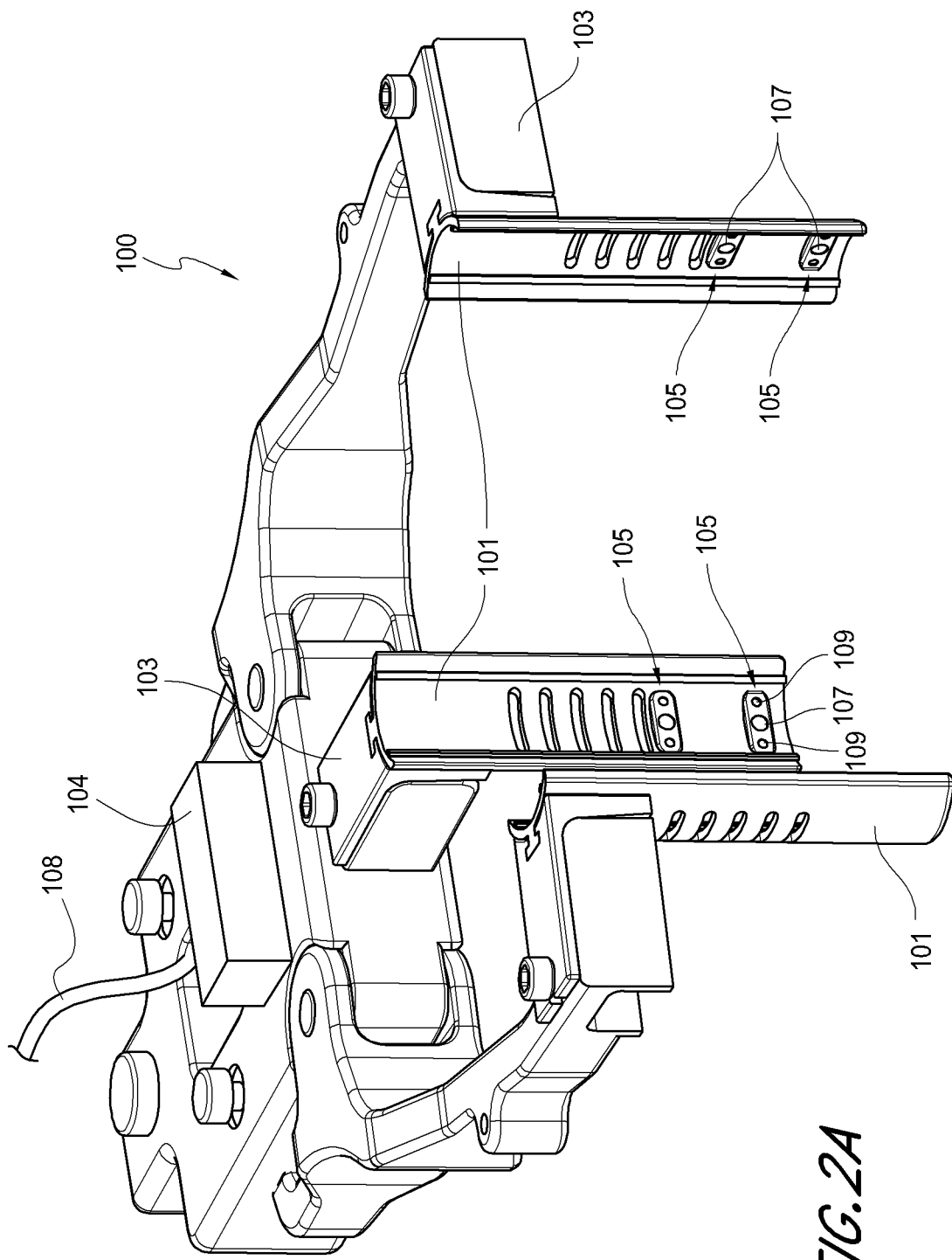

FIGS. 2A-C show one embodiment a surgical retractor device that includes an integrated imaging assembly. In some embodiments, the imaging assembly includes a plurality of integrated cameras. The retractor 100 includes three blades 101, however, more or less may be included depending on the design. Each of the blades may be attached to an articulable arm 103 that allows for the position of the blades to be adjusted during the operation. For example, following a small incision, the three blades 101 can be arranged in a closed position where each are positioned close to one another. In this closed configuration, the three blades can be introduced through the incision, and then expanded to provide for an operating pathway or working space. In other embodiments 4, 5, 6, 7, 8 or more blades, fingers, retractor members, or other barriers may be employed (or fewer members such as two blades, etc., or even a single member such as a single lumen of a tubular retractor may be used). In various embodiments, the surgical area may be at least 400 mm$^2$, for example, have an opening with an areas between 400 and 2100 mm$^2$. The working space may be an area centrally located between retractor blades (or within the lumen of a tubular retractor) that allows for surgical tools or other instruments to pass through. As shown, the retractor does not obstruct the center of the retractor (e.g., array of retractor blades, finger, members, etc., or lumen of a tubular retractor) and the open region formed by the retractor and permits unobstructed access to the center of the surgical site for ready access by the surgeon. Each of the blades 101 includes one or more integrated cameras, or cameras with combined stereo paths to one sensor or camera module 105. In various embodiments the number of camera modules and configurations can vary. In the illustrated embodiment, each camera module 105 includes a camera 107 and one or more, or two illumination sources 109 disposed on opposite sides of the camera 107. In various embodiments, the number of illumination sources per camera module may vary. In some embodiments, the illumination sources may not be disposed directly adjacent any particular camera. In some embodiments, the illumination sources can be omitted, and the camera module can rely on ambient supplementary or overhead light or light directed from a light source located elsewhere. In some embodiments, the orientation of an integrated camera 107 may be substantially fixed with respect to the retractor blade 101 or other surgical tool. In some embodiments, the camera 107 and/or the camera module 105 may be adjustable with respect to the retractor blade 101.

In the illustrated embodiment, the retractor blades 101 are substantially rigid. In various embodiments, the retractor blades may be malleable, and may have a wide range of different structural features such as width, tension, etc. For example, stronger, larger retractor blades may be desired for spinal and trans-oral surgery, while weaker, smaller retractor blades may be desired for neurosurgery. In some embodiments, the retractor can be configured such that different blades can be arranged as desired.

Each of the camera modules 105 are in electrical communication with an aggregator 104. The aggregator 104 is configured to receive input from each of the camera modules 105, and to connect to external components via electrical cable 108. For example, the hub or aggregator 104 may receive image data from each of the camera modules 105 and may transmit the image data to an image processing module (not shown). In the illustrated embodiment, the wiring connecting the camera modules 105 with the aggregator 104 is imbedded within the retractor blades 101 and articulating arms 103 and is not visible. In some embodiments, as described in more detail below, cables connecting the camera modules 105 with the aggregator 104 may be adhered (either permanently or non-permanently, e.g., releasably) to the exterior surface of the retractor 100. In the illustrated embodiment, the hub or aggregator 104 is affixed to an upper surface of the retractor 100. The aggregator may be positioned at any locations relative to the retractor 100, or may be disconnected from the retractor 100 altogether. The aggregator may contain camera interface electronics, tracker interface electronics and SERDES to produce a high speed serial cable supporting all cameras in use. The serial cable extending from the aggregator is preferably male terminated to facilitate sterilization.

Although the illustrated embodiment shows integrated camera modules 105, in various embodiments the camera modules 105 may be removably attached to the retractor blades 101. In some embodiments, the camera modules 105 can be disposed within pre-positioned receptacles on the retractor blades 101 or other surgical device. In some embodiments, the camera modules 105 can be disposed at a plurality or range of locations desired by the user on the retractor blades 101. In various embodiments, the orientation and position of the sensors can be adjusted by the user, e.g., physician, nurse, technician, or other clinician. In some embodiments, for example, the camera may be disposed on a track such that the camera can slide up and down the retractor, e.g., retractor blade. The height of the camera or camera within or above the surgical site may thereby be adjusted as desired. Other arrangements for laterally adjusting the position of the camera may be used. Additionally, in various embodiments, the cameras may be configured to have tip and/or tilt adjustment such that the attitude or orientation of the camera may be adjusted. The line of sight or optical axis of the cameras can thereby be adjusted to, for example, be directed more downward into the surgical site or be directed less into the surgical sight and more level or angled in different lateral directions. The camera modules 105 can include sensors or markers for, e.g., electromagnetic or optical tracking or use encoders accelerometers, gyroscopes, or inertial measurement units (IMUs) or combinations thereof or any other orientation and/or position sensors, as described in more detail below. Tracking can provide location and/or orientation of the cameras. The images obtained by the cameras may be stitched together or tiled using image processing techniques to render a composite mosaic image. Tracking or otherwise knowing the relative locations of the sensor can assist in image processing and display formatting. Tracking position of cameras can support the touch screen user interface, such that a user can select, position and size (zoom) an image array on surgeon display.

In various embodiments, pairs of cameras together provide information for creating a stereo effect or 3-dimensional (3D) image. Pairs of cameras, for example, may be included on each of the blades 101 of the retractor 100. In certain embodiments, images from separate cameras on separate blades 101 can be assembled to provide the stereo and three dimensional effect.

As illustrated, the retractor is configured to hold open tissue so as to produce an open region or cavity centrally located between the blades. Notably, in various embodiments, this open central region is unobstructed by the retractor. In particular, the central portions of the open region would be unobstructed by features of the retractor such that the surgeon would have clear access to the surgical site. The surgeon could thus more freely introduce and utilize his or her tools on locations within the surgical site. Additionally, this may enable the surgeon to use tools with both hands without the need to hold an endoscope.

Also as illustrated, the cameras are disposed on the blades of the retractor such that the cameras face inward toward the surgical site that would be held open by the retractor blades. The cameras in this example would be disposed about the central open region held open by the retractor blades so as to provide views from locations surrounding the surgical site. The camera thus would face objects within the surgical site such as structures on which tools would be used by the surgeon to operate.

In this particular example, the cameras on two of the blades face each other such that the leftmost blade and the cameras thereon would be in the field-of-view of the cameras on the rightmost blade and vice versa. The cameras on the leftmost blade may be anti-parallel to the cameras on the rightmost blade and have optical axes oriented at an angle, θ, of 180° with respect to each other. The cameras on the remaining blade may be directed orthogonally to the other two blades and thus have optical axes directed at an angle, θ, of 90° with respect to each other. Retractors with cameras can be reaffixed to a frame or mounting structure during a procedure and the cameras can reorient themselves with respect to relative position within an array of the cameras through their communication protocol with the aggregator and video switching unit.

In some embodiments, the field-of-views of the different cameras, and hence the images produced by the different cameras, may overlap. Image processing may be employed to yield increased resolution at the regions of overlap. Likewise, the number of sensors used may be increased to provide increased field-of-view and/or resolution. Likewise, cameras with overlapping images can be electronically magnified thereby making their images adjacent rather than overlapping.

Figure 3A:
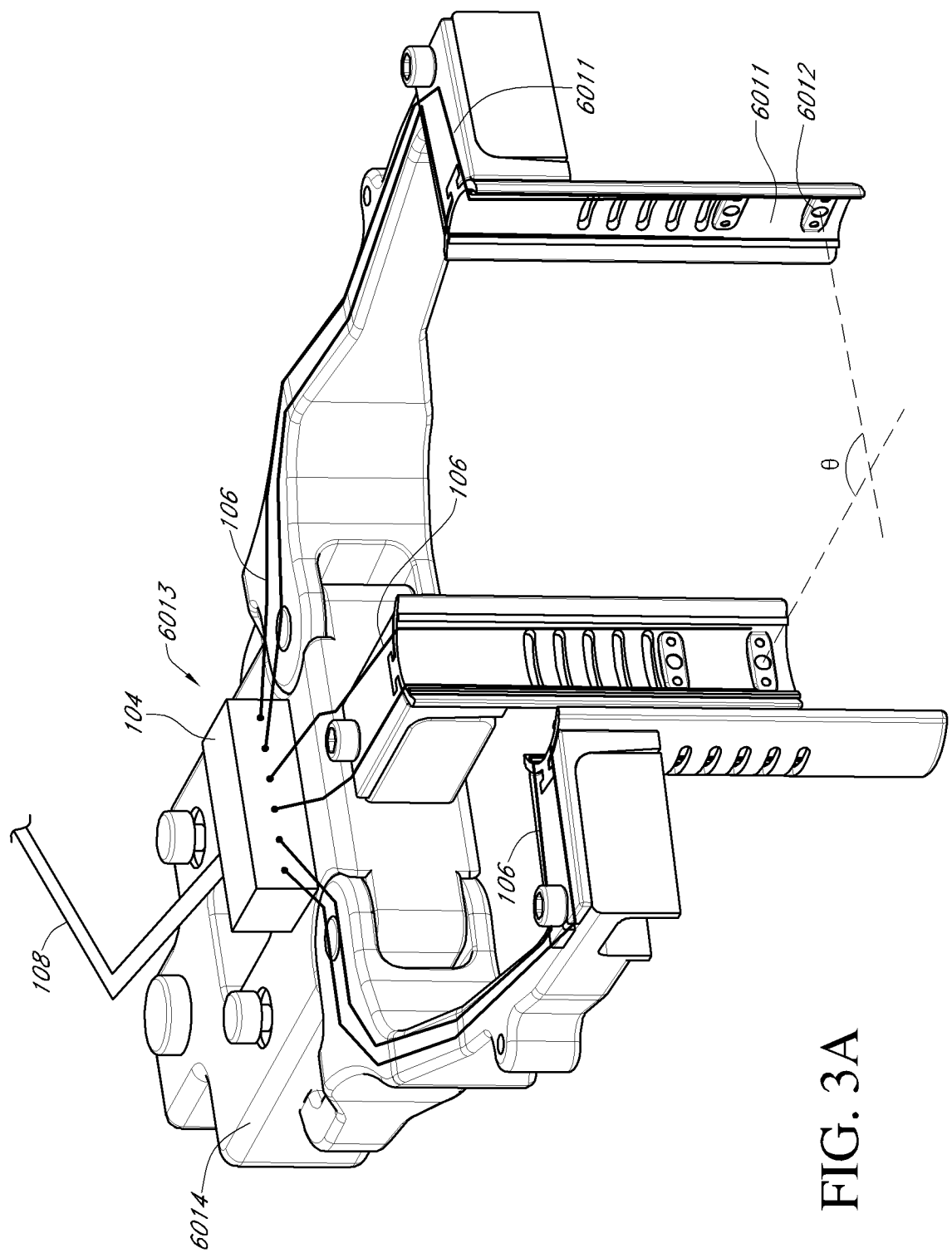
FIG. 3A shows an embodiment of a surgical retractor device having an integrated imaging assembly.

FIG. 3A illustrates another embodiment of a surgical retractor device 6014 having an integrated imaging assembly 6013 shown with a different wiring arrangement than shown in FIG. 2A. In particular, much of the wiring is exposed as opposed to being buried in the retractor. As illustrated, the imaging assembly 6013 comprises a hub or aggregator 104 and one or more imaging subassemblies 6011. The imaging assembly 6013 contains three imaging subassemblies 6011 although more or less may be included. As illustrated, in some embodiments, the imaging subassemblies 6011 can be integrated within the surgical retractor. Also as illustrated, the imaging subassemblies 6011 can contain electrical signal lines 106 and optics and/or sensor elements. In various embodiments, the electrical signal lines 106 can comprise cables or lines that are exposed and visible as opposed to completely imbedded within the retractor. In other embodiments, different portions of the lines may be buried or embedded within the portions of the retractor and thus not exposed. The electrical signal lines 106 can connect at a first end to an aggregator 104 and at a second end to a camera 6012. The camera can contain optics (e.g., imaging lenses) and a sensor element (e.g. a two-dimensional detector array such as a CMOS or CCD 2D-array). The electrical signal lines 106 are combined together within the aggregator 104 to a common bus line. The image processing system cable 108 electrically connects to the aggregator 104, e.g., to the common bus line, at a first end and an image processing unit at a second end (not shown). The imaging subassemblies 6011 can be electrically connected to the aggregator 104 through a male/female connection. In various embodiments, the first end of the electrical signal lines 106 comprises a male connection, while the receiving aggregator 104 connection comprises a female connection. The aggregator 104 (having, for example, female connectors) can be a disposable unit. The imaging subassemblies 6011 (having, for example, male connectors) can be reusable and can be cleaned and/or sterilized. The line 108 can also be terminated by a male connector that plugs into a female connector on the aggregator 104. Similarly, the long cable 108 can be reusable and sterilizable.

FIG. 3B illustrates another embodiment of an imaging assembly in which the electrical lines or cable, for example, flex cable, and cameras are integrated with the retractor blades or connect to a blade having electrical pathways therein or thereon. In certain embodiments, the retractor blades 7010 can contain varying optics, sensors (e.g., 2D detector arrays), and lighting (e.g., light sources such as LEDs, superluminescent diodes, supercontinuum light sources, or xenon lamps). Additionally, in certain embodiments the retractor blades 7010 can have varying widths, lengths, and strengths. As illustrated, the retractor blades 7010 can be removably attached to the retractor frame 7002. In the embodiment shown, the retractor blade includes a protruding rail member that slidably fits into a track on an arm of the retractor. Thus the surgeon is able use different retractor blades with different components, sizes, and strengths thereby permitting the surgeon or user the flexibility to provide the suitable retractor blades or optics for a particular medical procedure.

Figure 3C:
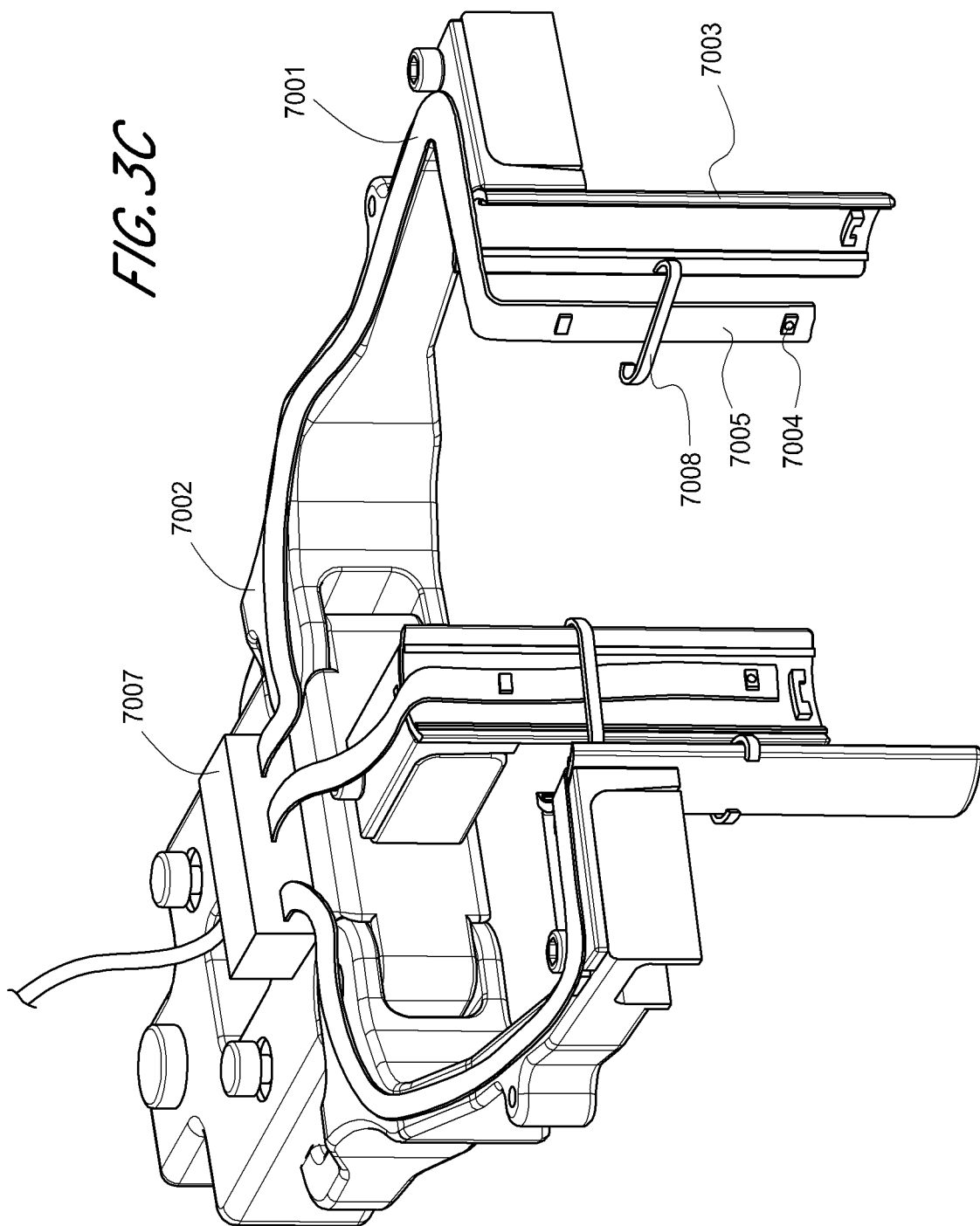
FIG. 3C shows an embodiment of an imaging assembly in which the electrical lines and cameras are integrated into a flexible cable that can be fastened to the retractor frame and retractor blades.

FIG. 3C illustrates an embodiment of an imaging assembly in which the electrical lines and cameras are integrated into a flexible cable that can be readily fastened to the retractor frame and retractor blades. In certain embodiments, the flexible cable 7001 can be affixed to the retractor frame 7002 and the retractor blades 7003 in a manner to be easily affixed and removed. In some embodiments, the flexible cable 7001 can have a distal end 7005. The distal end 7005 of the flexible cable 7001 can contain optics, sensors, or lighting and combinations thereof. In various embodiments, the flexible cable 7001 can contain a camera 7004. In certain embodiments, the flexible cable 7001 and the aggregator 7007 can be clipped on to the retractor blades 7003 and retractor frame 7002, respectively. In one embodiment, the distal end 7005 of the flexible cable 7001 can contain a fastener member 7008 for fastening and unfastening the flexible cable to the retractor frame and/or the retractor blades as shown in FIG. 3C. The fastener member 7008 can include, for example, a clip, a snap, a strap, a screw, a bolt, a nut, or any combination of these as well as any other method that can facilitate convenient attachment. For example, attachment can be accomplished in under one minute possibly less than 20, 10, 5, 3, or 2 seconds per fastener and may be accomplished in more or less than a second or ½ or ¼ second per arm such that attachment can occur, for example, just prior to and in preparation for surgery. In some embodiments, aggregator 7007 can be permanently attached to the retractor frame 7002. In such embodiments, the flexible cables 7001 can connect to the aggregator and be removably fastened to the retractor frame 7002 and/or the retractor blades 7003 with a fastening member 7008. In some embodiments, additional fasteners, not shown, may be located elsewhere, for example, to attach the flex cable 7001 to the retractor arms or other portions of the retractor.

The retractor blades 7003 and the flexible cable 7001 can extend into the interior of the body cavity or surgical field opening when the retractor is in use. For example, the retractor blades can be used to hold open the surgical field. The cameras or sensors (e.g., CMOS or CCD detector arrays) integrated into the retractor blades or integrated into the flexible cable and clipped onto the retractor blades can produce images of the surgical field within the body cavity.

Rotatable Stage or Frame

During surgery it may be desirable to rotate a plurality or array of cameras and/or stereo camera pairs as a group together with respect to the surgical field, patient, or retractor. For example, a surgeon's positioning relative to the surgical field can vary for different procedures and different surgeons or the positioning of the retractor blades may be set at an angle that does not provide for optimal imaging or image processing. Therefore, it may be useful to rotate or otherwise change the positioning of the plurality of cameras and/or stereo camera pairs without changing the retractor blades positioning.

It can be beneficial, for example, that the optics and sensor be in a position to produce an image of the surgical field having vertical and horizontal directions the same or substantially the same as the vertical and horizontal directions that the surgeon associates for the surgical field. If the cameras are not positioned correctly, the image of the surgical field may be rotated on the display such that vertical and horizontal directions on the display do not correspond to vertical and horizontal directions that the surgeon associates with the surgical field as oriented for the surgical procedure. Incorrect positioning or excessive rotation of the surgical field with respect to the vertical and horizontal directions on the display can decouple hand-eye coordination.

Accordingly, various embodiments may include a rotatable support for the array of cameras and/or stereo camera pairs that can rotate or move with respect to the retractor blades. FIG. 4A illustrates an embodiment of a rotatable stage attached to a retractor frame. In some embodiments, the plurality of cameras can be mounted on a rotatable stage 8005 and the rotatable stage can be coupled to the retractor frame. In some embodiments, the rotatable stage 8005 is fixed to the retractor frame through an attachment post 8006. The rotatable ring can have a single or multiple attachment posts 8006 supporting the rotatable stage on the retractor frame. The rotatable stage 8005 can move, for example, rotate, with respect to the retractor blades to permit the image formed by the camera to rotate on the display. Accordingly, the image of the surgical field can be rotated such that the directions on the surgical field that the surgeon or operator associate with vertical and horizontal correspond to the vertical and horizontal directions of the display.

In certain embodiments, the image visible on the display can be rotated using image processing. For example, the surgeon or user can input to the image processor the amount of rotation that is desired. For example, the user can simply rotate the displayed composite image such as a stitched or tiled image as desired. Accordingly, the user can rotate the displayed image until such the directions on the surgical field that the surgeon or operator associates with vertical and horizontal correspond to the vertical and horizontal directions of the display. FIG. 4A shows a plurality of cameras located toward the distal end of the retractor. As illustrated, these cameras are not disposed on a rotating support. In various embodiments, image processing may be employed to rotate the image such as the composite (e.g., stitched or tiled) image formed by these cameras instead of using a rotating support.

When stereo camera pairs are disposed on the retractor about the surgical site, having a rotating support for the plurality of stereo camera pairs may, however, be useful. FIG. 4B, which shows a bottom view of a rotatable stage, illustrates the usefulness of having such a rotating support for certain embodiments having an array of 3D cameras. In the embodiment illustrated in FIG. 4B, four stereo camera pairs are shown disposed about an annular shaped support. The stereo camera pairs in this example are disposed at 3 o'clock, 6 o'clock, 9 o'clock and 12 o'clock. To provide consistent 3D imaging among the cameras, although the cameras at the 6 o'clock and 12 o'clock positions are arranged along a radial of the annular shaped support, the cameras at the 3 o'clock and 9 o'clock positions are arranged along a tangential direction of the annular shaped support. Such an arrangement of the cameras in the various stereo camera pairs provides for consistent 3D imaging as the left and right camera in the stereo camera pairs will be oriented generally along the same direction, e.g., parallel to the x-axis in this example. This direction may be oriented, for example, along the horizontal direction of the surgical field. In various embodiments, each of the stereo cameras may share a common horizon, even if displayed as a stereo circle composed of right and left eye images. If these camera pairs were mounted on fixed retractor blades, in contrast to the rotatable support, and if the retractor were rotated in the surgical field, the direction along which the left and right cameras are aligned may not necessarily be parallel with the direction that the surgeon associates with either horizontal (or vertical). Accordingly, rotation to provide that the left and right cameras are aligned along a line parallel to the direction the surgeon associates with horizontal (or vertical) may be beneficial. Horizontal alignment in particular may be beneficial for ergonomic considerations. While an operating room microscope can be positioned in an oblique position, looking through it, and holding one's head in that position for hours, as is sometimes necessary in neurosurgery can be painful for a surgeon. In embodiments in which the retractor and the display are decoupled, ergonomic viewing is possible even if the surgical access is difficult.

In an alternative arrangement, the stereo camera pairs are not used at the 3 o'clock and 9 o'clock positions and instead monocular cameras are employed. The stereo cameras at the 6 o'clock and 12 o'clock positions as well as the mono cameras at 3 o'clock and 9 o'clock positions need not be mounted on a rotating support. The mono cameras need not rotate but the 6 and 12 o'clock cameras should ideally be configured 'in plane' or their R and L camera views should be parallel with the R and L display views.

Also, in some embodiments stereo proximal camera pairs are mount on a rotating support while distal mono cameras are not mounted on a rotating support in a configuration such as shown in FIG. 4A.

Additionally, in some embodiments, some proximal camera modules include stereo camera pairs and some proximal camera modules include only mono cameras and not stereo camera pairs and a rotating stage need not be used in such a case for the proximal cameras. For example, stereo camera pairs can be positioned at the 6 o'clock and 12 o'clock positions and non-stereo camera at the 3 o'clock and 9 o'clock positions. Accordingly, in various such embodiments, the stereo camera pair(s) together may be positioned halfway between the other non-stereo cameras and/or the non-stereo cameras may be positioned halfway between stereo camera pair(s). Additionally, in various embodiments, stereo camera pairs are on directly opposite sides of the retractor at locations 180° with respect to each other, such as for example at 3 o'clock and 9 o'clock.

However, as shown in FIG. 4A, in some embodiments a rotating support 8005 is employed. The rotatable stage 8005 can include a ring comprising concentric inner and outer rings. In certain embodiments, the inner ring 8007 can move relative to the fixed outer ring 8008. The fixed outer ring 8008 can be attached to the retractor frame at one or multiple points of attachment. The inner ring can be rotatably coupled to fit within or on top of the outer ring. The rotatable stage can support cameras, flexible cables, or other components including but not limited to 3D cameras, LEDs, tracking, cleaning, temperature control, heating or therapeutic delivery systems.

The rotatable stage can include a ring that is rotated by manual movement, motorized movement, or using other actuators. In some embodiments, the rotatable stage ring can contain a bearing surface between the inner ring and outer ring which allows movement of the rotatable ring. The bearing surface can include a plain bearing, a ball bearing, roller bearing, or any other bearing surface. Additionally, in other embodiments the rotatable stage can contain methods of coupling that allow for translational movement between the inner ring and the outer ring so that the rings can move vertically relative to one another. In some embodiments, the ability to rotate the rotatable stage, ring, or alternative platform, allows the stereo image acquisition horizon to remain horizontal. Further, the rotatable stage can include encoders or other tracking devices as for example those described herein to detect movement of the ring and the placement of the cameras.

As illustrated in FIG. 4B, the stereo camera pairs can be directed downward from the rotating ring as well as inward toward an axis of rotation of the ring and a central open region established by the retractor. Despite being downward directed, in some embodiments, the cameras on the rotatable stage are also in different orientations with respect to each other (e.g. rotated differently) as discussed above. An axis of rotation is defined by the line bisecting the optical axis of the left and right cameras of the first stereo camera pair. In some embodiments, the third stereo camera pair 8011 is rotated 180 degrees relative to the first stereo camera pair 8009. In some embodiments, the second stereo camera pair 8010 can be rotated 180 degrees relative to the fourth stereo camera pair 8012. The second stereo camera pair 8010 and the fourth stereo camera pair 8012 can be rotated plus or minus 90 degrees from the first stereo camera pair 8009. The different configurations of the cameras on the rotatable stage can be advantageous to maintain consistency among the camera images of the different stereo cameras on the rotatable stage. A R and L camera view can be rotated 180 degrees but if so the eye views must be reversed electronically, so that upside down R is now L, etc.

In certain embodiments, one or more of the cameras on the rotatable stage can be disposed on the inner surface 8016, as opposed to the bottom surface, of the rotatable stage. A prism or other reflector may be included to redirect the field-of-view from the camera. For example, the camera can be coupled to a prism, similar to the prisms used in the cylindrical retractor shown in FIG. 21 and discussed herein, to allow the camera on the inner surface of the rotatable stage to be directed in a downward direction into the surgical field. FIG. 4C illustrates an embodiment of a side view of the camera and prism mounted on the inside surface of the rotatable stage. The camera 8015 is disposed on the inside surface 8016 of the rotatable stage, which has a prism 8014 attached thereto and in the optical path of the camera. In particular, the prism has a reflective surface that is disposed in the optical path between the front of the camera or stereo cameras pair and the surgical field. This reflective surface may be oriented at an angle with respect to the retractor to direct the optical path at an angle of between 15 to 75 degrees, e.g., 45° with respect to the rotation axis of the ring. The reflective surface of the prism, for example, may be oriented at an angle of 15 to 30 degrees, e.g., about 22.5° with respect to the axis of rotation of the ring so as to redirect light at an angle of between about 15 and 75 degrees, e.g., about 45°. Such a prism may reduce the profile of structures extending into the otherwise open region provided by the retractor so as to maintain a substantially unobstructed opening for the surgeon to access the surgical site. FIG. 4D shows an enlarged view of a stereo camera pair, with intersecting optical axes. In some embodiments a prism having two reflecting surfaces is employed to redirect the optical path.

Retractor Blades

As discussed above, FIG. 3B illustrates an embodiment of an imaging assembly in which the electrical lines and cameras are integrated with detachable retractor blades. In certain embodiments, the retractor blades 7010 can contain varying optics, sensors, and lighting. Additionally, in certain embodiments the retractor blades 7010 can have varying widths, lengths, and strengths. As illustrated, the retractor blades 7010 can be removably attached to the retractor frame 7002 via an attachment system 7011 (e.g., a rail or strip that fits into a track on the retractor arm). The ability to vary the components, sizes, and strengths of the retractor blades allows the surgeon or user the freedom to use various retractor blades or various optics that are appropriate for a particular medical procedure.

Figure 5:
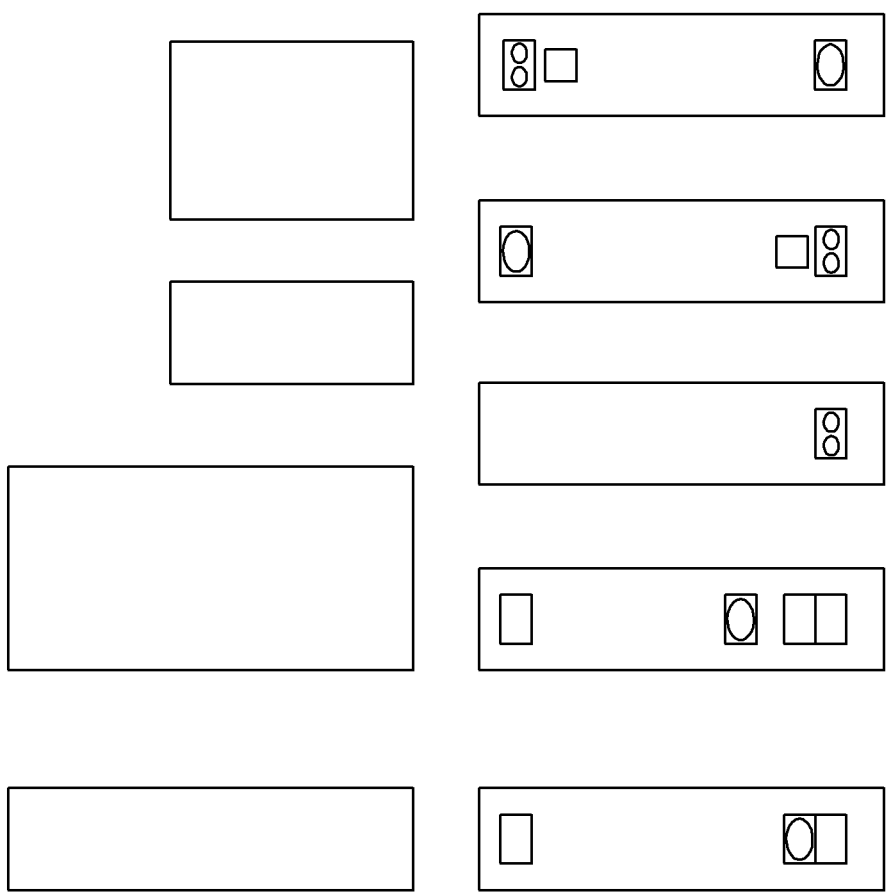
FIG. 5 shows an embodiment comprising a plurality of interchangeable retractor blades for a surgical retractor.

FIG. 5, for example, illustrates an embodiment comprising a plurality of interchangeable retractor blades for a surgical retractor. The interchangeable retractor blades can contain various combinations of cameras, lighting sources, sensors, imaging optics, EM tracker sensors and/or other components such as discussed herein. The retractor blade may also have none of these components and may be employed primarily for mechanical purpose such as to hold back tissue in an incision at the periphery. Accordingly, the retractor blades can be of varying widths and strengths. Thus, although in some embodiments, the retractor blades are permanently attached to the retractor frame or frame (they are typically called frames), in some embodiments, the retractor blades 7010 can be removably attached depending on the desired use or imaging required. Such retractor blades can be interchanged to achieve the desired type of retractor blade depending on the procedure to be performed. For example, the retractor blades for spinal or trans-oral procedures can be larger and stronger because of the higher force requirement, while retractor blades for neurosurgery procedures can be weaker and smaller. A surgeon may also switch out retractor blades during a procedure after commencement thereof. In some embodiments, the retractor blades can have aspiration channels or hold aspirators to remove blood and saline or other liquid. Such aspiration channels can be connected by fluidic lines such as lines in the flex cable to a pump or other vacuum source tubing can also send warmed air towards the cameras to prevent fogging.

Figure 6A:
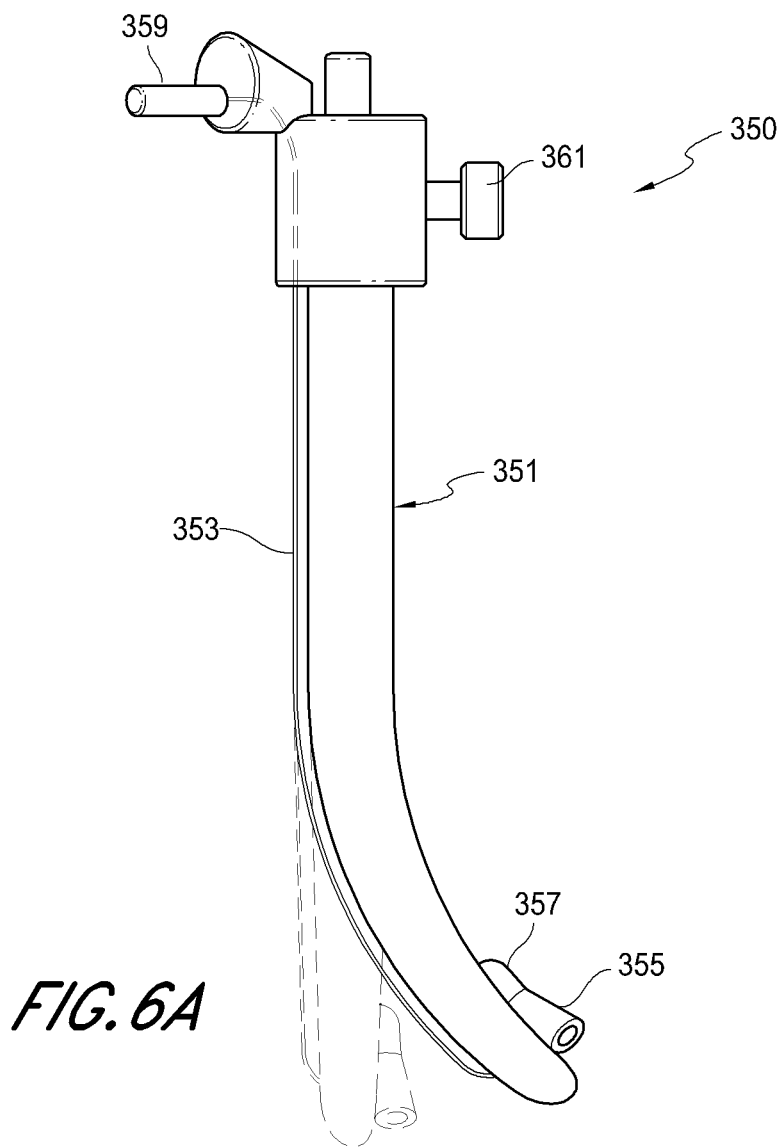
FIG. 6A shows an embodiment of a malleable retractor blade with an integrated optical sensor.
Figure 6B:
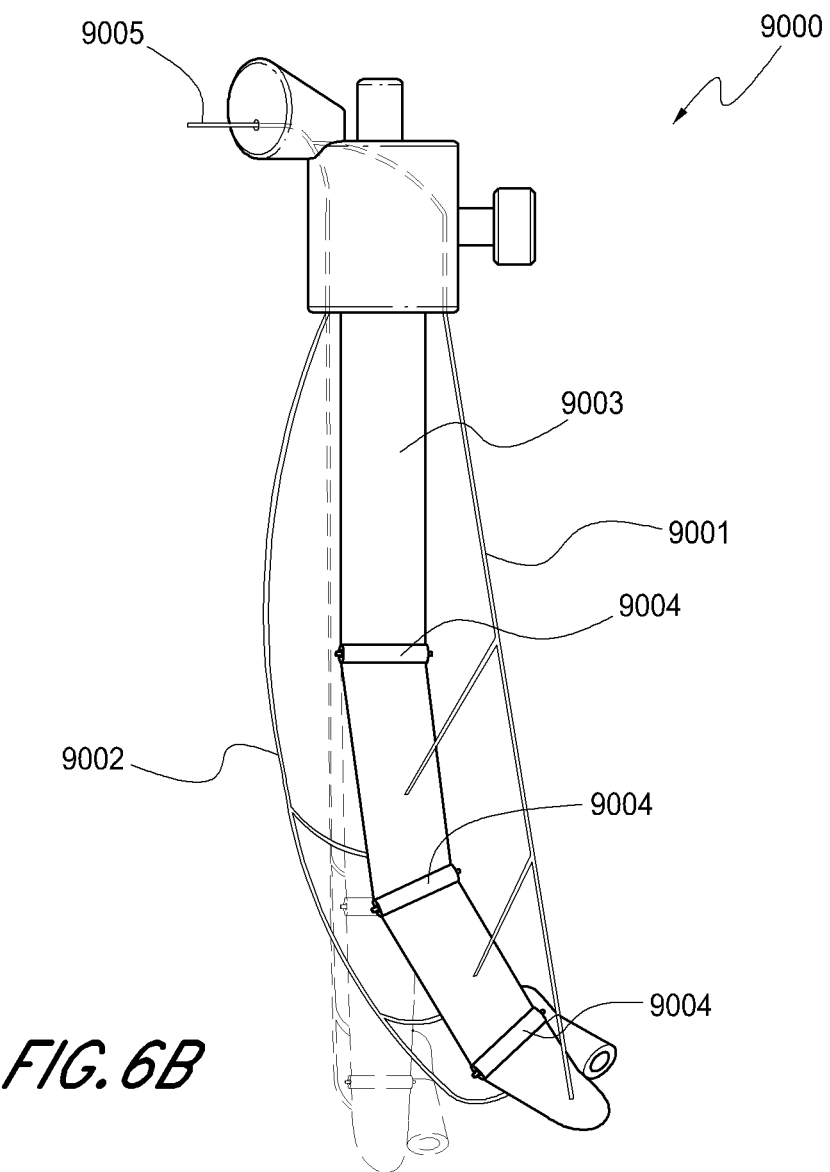
FIG. 6B shows an embodiment of a retractor blade that is flexible and has hinges to enable flexure.
Figure 6C:
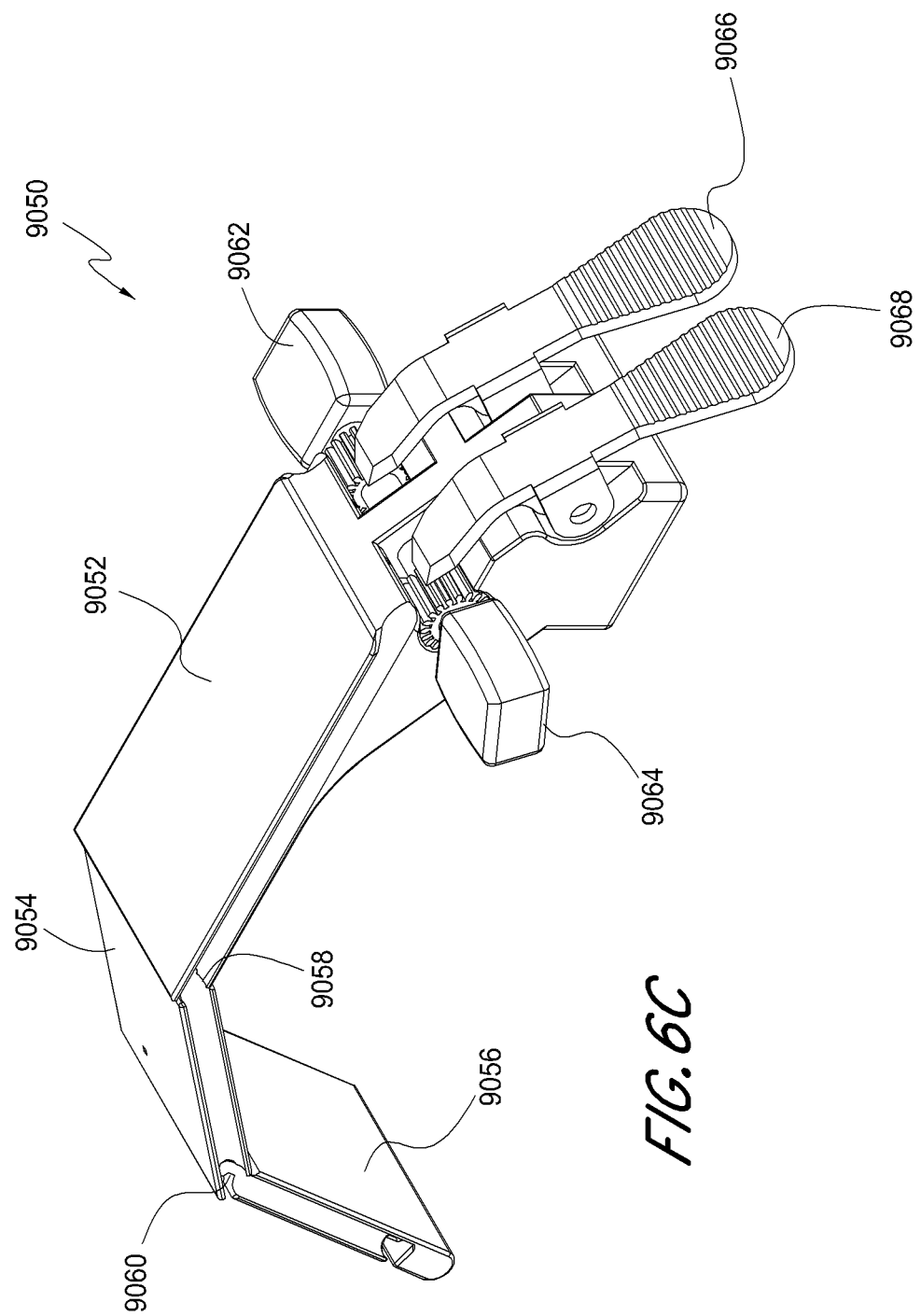
FIGS. 6C-D show an embodiment of a rigid articulating retractor blade in a flexed position.
Figure 6D:
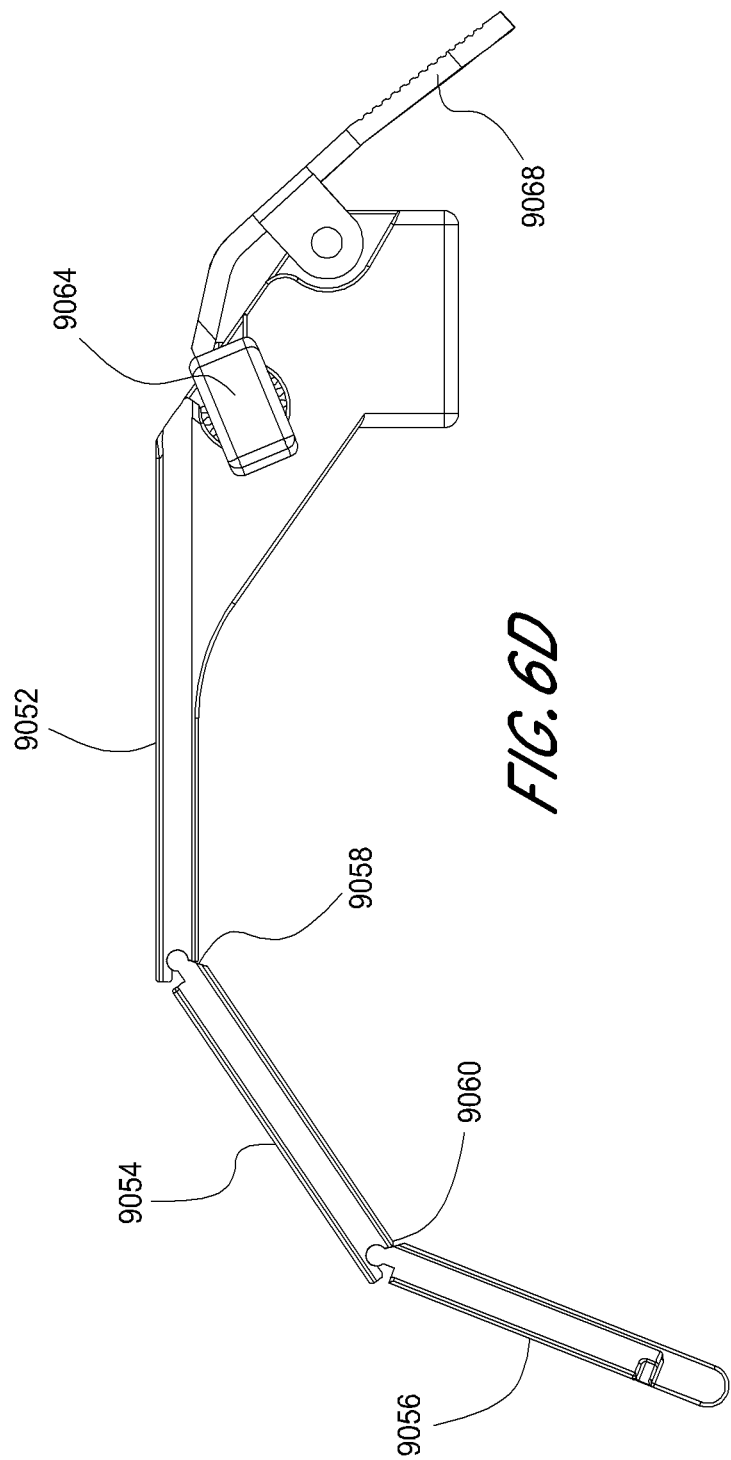
Figure 6G:
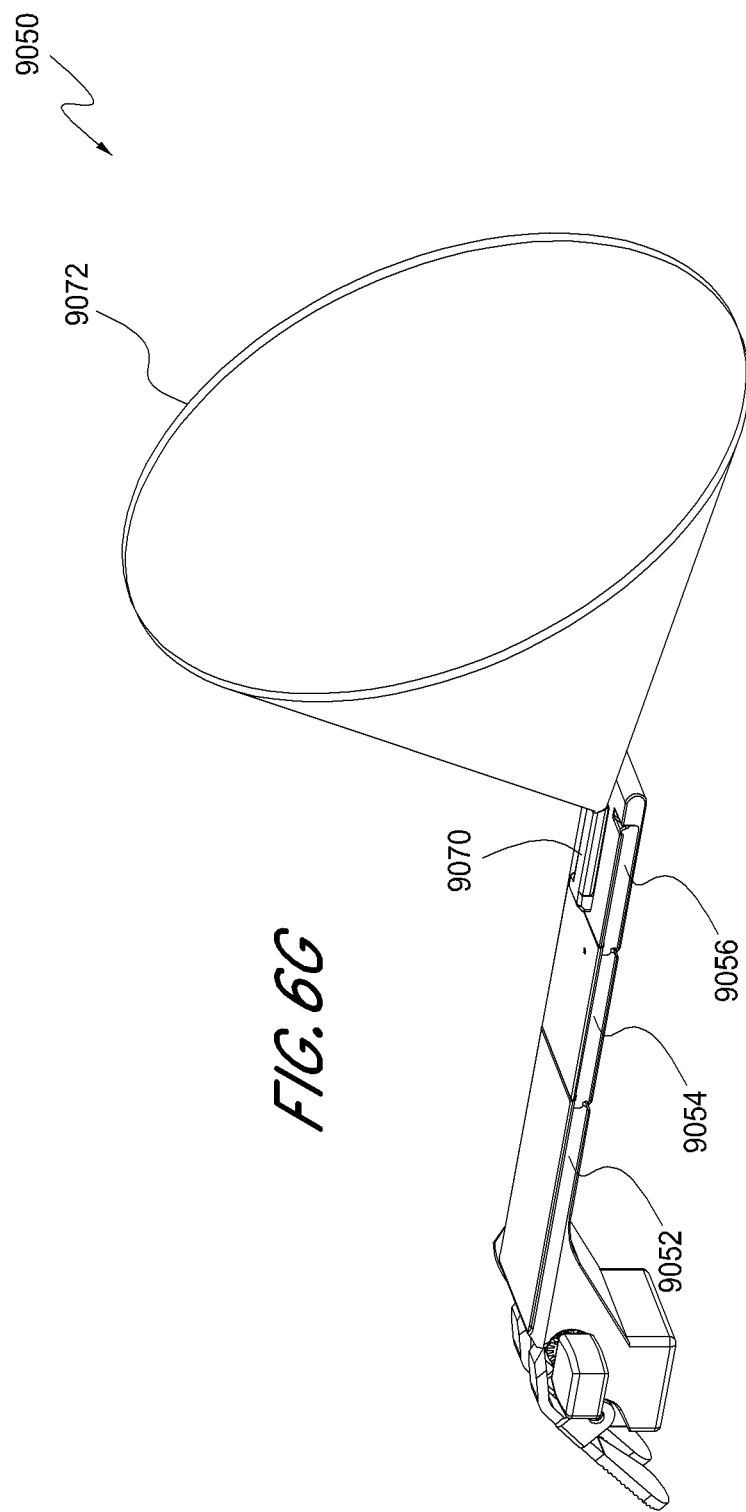

Further, the retractor blades can also be flexible. FIGS. 6A and 6B illustrate example embodiments of retractor blades that are flexible. FIG. 6A illustrates an embodiment of the pre-flexed retractor blade. In some embodiments, the retractor blade can be made of malleable or flexible material that allows for movement of the retractor blade either prior to use or during use, e.g., during a surgical procedure. The retractor blades of the retractor can be made of a flexible or malleable material which allows for the bending or movement to adjust the shape of the retractor blades but still produce the required stiffness for retractor purposes. In some embodiments, the retractor blades can be made of pre-flexed Nitinol retractor blades and may include one or two cables to straighten out the flex. In certain embodiments, the cable(s) is located on the surface away from the patient. The retractor blade can be allowed to bend or move and this movement can be helpful in the imaging of the surgical field and/or assisting in retraction of the tissue in the surgical area. The flexible retractor blades can be fixed to the retractor unit such as described herein for fixed retractor blades. In other embodiments, the flexible retractor blades are clipped onto the retractor unit such as described herein for clip-on retractor blades. In some embodiments, bending or movement of the retractor blade can be controlled remotely, for example by electronic remote control. In some embodiments, the retractor blade may be tilted by at least 10 degrees, 20 degrees, 30 degrees, 40 degrees, or more and less than 90 degrees, less than 80 degrees, less than 70 degrees, less than 60 degrees, or less than 50 degrees via the remote control. In some embodiments, remote control can be provided via a graphic interface.

With continued reference to FIG. 6A, the malleable retractor assembly 350 includes a retractor blade 351 with a push-pull wire 353 attached to the surface of the retractor blade 351. The wire 353 can rest in a low friction cable guide to enable flexure of the blade 351. An integrated camera 355 and electromagnetic tracker sensing coil 357 are disposed within the retractor blade 351. The flexure mechanism can be similar to that used for steerable catheters for interventional procedures. In use, the operator may manipulate the individual retractor blade 351 by use of a small handle 359 that can pull the wire 353 by use of a pulley or other mechanism. For example, the wire 353 can be made of Nitinol, and may be attached to a pulley such that upon rotation of the handle 359, the retractor blade 351 flexes or extends. In some embodiments, the blade 351 always curves outwards away from the surgical site so as to create a working space for the operator. A set screw (cable clamp) 361 can be employed to fix the axial position of the wire 353. The set screw 361 can be loosened as desired to axially move the wire 353, thereby adjusting the flexure of the retractor blade 351. In other embodiments, two or more wires may be employed and used in conjunction to adjust the flexure of the blade. Also, in other embodiments, the flexible retractor blades can comprise front and rear cables or elastic bands as described more fully below.

In various embodiments, the surface of the blade 351 can be coated with PTFE to reduce tissue friction and sticking. In some embodiments, the blade 351 can be coated with a thin layer of elastomeric material or an inflatable balloon to normalize the pressure per area across the entire region of contact with the body. In other embodiments, two wires may be used, one having a distal attachment, the other with a more proximal attachment. For example, the wires may run along the outer curvature of a pre-flexed Nitinol retractor blade. Axially moving one or both wires enables incremental controllable flexure of the blade.

FIG. 6B illustrates an embodiment of a flexible retractor blade with one or more joints. As illustrated, in some embodiments, the flexible retractor blades 9003 can be bent at a joint 9004 or multiple joints within the flexible retractor blade 9003. Front and rear elastic bands 9001, 9002 can be actuated at a proximal end 9005 by one or more motor, piezo, hydraulic actuator, linear actuator, or rotary actuator, or other type of actuator. The flexible retractor blades can have cables or tendon actuation with or without the Nitinol pre-flex retractor blade by the use of, for example, pull-pull cables or lines.

Although FIG. 6B illustrates an embodiment of a flexible retractor blade with front and rear elastic bands 9001, 9002, in certain embodiments, the front and rear elastic bands of a flexible retractor blade 9003 may comprise an extensor and a flexor cable. The flexor and extensor cables can allow for a greater range of motion, bi-directional flexing, and an S-shape with the two joints flexing in opposite directions. In various embodiments, the force of the tissue being retracted causes the retractor blades to return to an unflexed position once tension on the cable or band is released.

FIGS. 6C-6G illustrate an embodiment of a retractor blade having rigid plates or segments connected by discrete joints. In the illustrated embodiment, retractor blade 9050 includes three plates 9052, 9054, and 9056. These plates connect to one another at joints 9058 and 9060. The plates and joints can be manipulated to place the retractor blade in a flexed configuration (as in FIGS. 6C and 6D) or in an unflexed configuration (as in FIGS. 6E-6G). Internal cables (not shown) may extend within the plates 9052, 9054, and 9056, and be attached to pinion keys 9062 and 9064. These pinion keys 9062 and 9064 can be rotated to pull these internal cables. For example, pinion key 9062 may be rotated to pull a first internal cable that extends to the middle plate 9054. Pinion key 9064 may likewise be rotated to pull a second internal cable that extends to the outermost plate 9056. Pulling these respective cables causes the plates to rotate with respect to one another about joints 9058 and 9060. Specifically, rotating pinion key 9062 exerts a pulling force on the first internal cable, which causes the middle plate 9054 to rotate about joint 9058. Similarly, rotating pinion key 9064 exerts a pulling force on the second internal cable, which causes the outermost plate 9056 to rotate about joint 9060. Ratchets 9066 and 9068 operate to restrain the rotary position of the pinion keys 9062 and 9064. Depressing ratchet 9066 releases pinion key 9062, which releases tension on the internal cable, thereby permitting the middle plate 9054 to rotate back to a position substantially parallel to the innermost plate 9052. Similarly, depressing ratchet 9068 releases pinion key 9064, which releases tension on the second internal cable, thereby permitting the outermost plate 9056 to rotate back to a position substantially parallel to the middle plate 9054. As described elsewhere herein, the retractor blade 9050 may include a camera 9070 thereon. In the illustrated embodiment, the camera 9070 is positioned on the upper surface of the outermost plate 9056. Cone 9072 illustrates the field of view of the camera 9070.

In use, retractor blade 9050 may be introduced into an incision, with its upper surface facing a working space, and its lower surface facing the surface of the tissue to be retracted. Articulating the retractor blade 9050 (for example by rotating pinion keys 9062 and 9064) causes the plates 9052, 9054, and 9056 to exert pressure on the tissue, thereby increasing the size of the working area. In some embodiments, articulation of the retractor blade 9050 can be performed electronically, hydraulically, or by other methods. In some embodiments, the articulation can be controlled remotely. Camera 9070 can be positioned with respect to outermost plate 9056 such that its field of view (represented by cone 9072) is directed towards a site of interest within the body. As described elsewhere herein, a plurality of such retractor blades having a plurality of cameras can be used in conjunction to provide for improved visualization of the surgical site. By controlling the position of outermost plate 9056 (for example, by controlling the articulation of retractor blade 9050), the position and orientation of the camera 9070 can be controlled. As noted above, this control may be electronic, hydraulic, or otherwise, and may be performed remotely. In some embodiments, articulation or other movement of the retractor blades can be controlled via a graphic user interface, such as provided by a touchscreen, via voice command, etc. Throughout an operation, the position of the camera 9070 may be controlled (e.g., by manually adjusting the retractor blades, by remote electronic control, or other means) to provide a desired field of view. In some embodiments, bending or movement of the retractor blade can be controlled remotely, for example by electronic remote control. In some embodiments, the retractor blade may be tilted backward or forward by at least 10 degrees, 20 degrees, 30 degrees, 40 degrees, or more and less than 90 degrees, less than 80 degrees, less than 70 degrees, less than 60 degrees, or less than 50 degrees via the remote control. In some embodiments, remote control can be provided via a graphic interface.

In some embodiments, the retractor blades, finger, member, etc. can be hydraulically manipulated to control the movement of the retractor blades. The retractor can have one or more hydraulic members that are hydraulically actuated to displace tissue or apply pressure. The actuator(s) may comprise one or more linear and/or rotary actuators. A linear actuator may comprise bellows, rolling edge diaphragms, piston-cylinders with hydrostatic bearings, other linear actuators or other actuators including those disclosed herein, known in the art, or yet to be devised. A rotary actuator may comprise displacement type hydraulic motors, vane motors, gerotors, Bourdon tubes, or other rotary actuators known in the art. In some embodiments, a force feedback haptic interface could be used to provide tactile feedback to the user. In some embodiments, a dual bellows actuator's hydraulic source could supply substantially constant hydraulic force to the hydraulic members. In some embodiments, linear motors could drive master piston-cylinders with hydrostatic bearings for each axis. Other configurations are possible.

In some embodiments, the hydraulic member can be the retractor blades, fingers, members, etc. In some embodiments, the retractor can have a mechanical extension to move tissue extending from the retractor or the retractor blade. In such embodiments, the hydraulic member can actuate the mechanical extension to move tissue, apply pressure, and/or other functions that might be necessary for the surgical preparation or procedure. In some embodiments, actuation of the retractor blades can be controlled remotely.

In some embodiments, the retractor or retractor blade, finger, member, etc. can contain a positionable tool holder. In certain embodiments, the positionable tool holder can be attached to a retractor blade. In some embodiments, the positionable tool holder can be connected to the retractor base. The positionable tool holder when connected to the retractor base can be out of the field of view of the cameras and does not obstruct the images produced. Additionally, such placement on the retractor unit leaves the surgical field clear and allows the surgeon more room to operate. One example is the inclusion of a large bore suction cannula to remove blood and saline mixture, which is coupled to the positionable tool holder. Another example involves coupling a supplementary light source, such as a fiber optic cable, to the positionable tool holder.

As discussed above, in some embodiments, the flexible retractor blades, finger, member, etc. can vary in sizes and toughness or durability to accommodate certain surgical or medical procedures. For example, the retractor blades for spinal or trans-oral procedures can be larger and stronger because of the higher force requirement, while retractor blades for neurosurgery procedures can be weaker and smaller. Additionally, the configurations for achieving and methods of using the flexible characteristics of the retractor blades can vary such as described herein. Further, the flexible retractor blades can have the various optics, sensors, or other lighting, tracking, or imaging components that can be integrated into the retractor blades such as described herein.

In certain embodiments, the flexible retractor blades can contain cameras and LEDs, cameras only, LEDs only, or any other combination of components herein described. As discussed above, in some embodiments, the flexible retractor blade can contain one or more components that allow for tracking of the location, orientation, or registration of the attached cameras or combinations thereof. The reconfigurable shape of the retractor blade can makes the use of the tracking particularly useful for touch screen user interface. Accordingly, the flexible retractor blades can incorporate various methods of tracking including: EM trackers, optical tracking, inertial measurement units (IMUs), encoders, and other methods including but not limited to those described herein. The flexible retractor blades can, for example, include encoders, inertial measurement units, such as Hall Effect encoders, to detect the change in position of the flexible retractor blades. In some embodiments, the encoder can supply the user with information such as a measurement of degrees of movement of the flexible retractor blade. The encoders can also provide information to track the location of the retractor blade and for example, the camera(s) located thereon.

Further, in some embodiments the flexible retractor blade may be used for mechanical purposes only, such as retraction of tissue, and does not contain any camera, sensors, trackers, or light source components. For example, in some embodiments the flexible nature of the retractor blade can be used to move tissue out of the way. In other embodiments, the flexible nature of the retractor blade can be used to redirect the point-of-view of the camera on the flexible retractor blade. Additionally, in other embodiments, the flexible nature of the retractor blade can be used to both move tissue out of the way and redirect the point-of-view of the camera on the flexible retractor blade. In other embodiments, the flexible retractor blades can have aspiration channels or hold aspirators to remove blood and saline or other liquid. Such aspiration channels can be connected by fluidic lines in the flex cable to a pump or other vacuum source.

Multiple flexible or malleable retractor blades can close on a central, axial bullet-tip rod to be used as a dilator and introducer like MetrX. In some embodiments, a dedicated tool may be used to open and close the blades closed on a central, axial rod.

In some embodiments, the retractor blade as illustrated and described with reference to FIGS. 6C-6G and additional retractor blade embodiments described herein can be assembled onto a retractor blade stage as illustrated in FIG. 6H. The retractor blade stage 9080 can contain a retractor blade stage ring 9081 and a gear ring 9082. In some embodiments, the retractor blade stage ring 9081 can be fixed and shaped to receive the gear ring 9082. In some embodiments, the outer surface of the retractor blade stage ring 9081 can be shaped in an 'L' shape and the gear ring 9082 can sit within the recess of the 'L'. The outer surface of the gear ring 9082 contains teeth and faces the outside of the ring.

In some embodiments, the retractor stage ring 9080 can be used to effect a radial movement of the retractor blades. One or more clamps 9083 can be attached to portions of the retractor blade stage ring 9081 and the gear ring 9082. The clamp 9083 can have a pinion 9084, a stem 9085, and a stem ratchet 9086. The stem 9085 can have an innermost end attached to the proximal end 9052 of the retractor blade 9050. The stem 9085 can have an outermost end that can pass through the clamp 9083. In some embodiments, the stem 9085 can move horizontally through the clamp to effect a radial movement of the retractor blade. The clamp 9083 can have the stem ratchet 9086 to engage teeth of the stem 9085 thereby operating to restrain the radial position of the stem 9085. For example, depressing the stem ratchet 9086 releases the stem 9085 by disengaging the ratchet 9086 from the teeth of the stem, which releases tension on the stem 9085, thereby permitting the stem 9085 to move horizontally through the clamp 9083. The retractor blades can be positioned inside the retractor blade stage 9080 at different distances depending on the positioning of the stem 9085. Additionally, in some embodiments, the retractor stage ring 9081 can be used to effect a radial movement of a plurality of retractor blades.

Additionally, in some embodiments, the retractor stage ring 9081 can be used to effect a rotational movement of a plurality of the retractor blades. In some embodiments, the pinion 9084 can be vertically positioned within the clamp 9083. The pinion 9084 can have a distal end extending into the clamp and a proximal end that protrudes from the top surface of the clamp. The distal end of the pinion 9084 can have teeth that can engage the teeth on the gear ring 9082. When the pinion is rotated, the teeth on the pinion 9084 engage with the teeth on the gear ring 9082 and the resulting torque causes the clamp 9083 to rotate on the retractor blade stage 9080. For example, turning the pinion 9084 causes the clamp 9083 to rotate on the ring 9081, 9082, the stem 9085 that runs through the clamp and connects to the retractor blade rotates with the clamp, and therefore the rotational position of the retractor blade 9050 can be changed by the rotational movement of the clamp 9083 on the ring. Alternatively, in some embodiments, the retractor stage ring 9081 can be used to allow the rotation of each blade individually.

Additionally, in some embodiments, the retractor blade stage 9080 can allow for the flexure of the retractor blades. The retractor blades can be flex-finger retractors as described herein with reference to 6C-6G. Alternatively, the flexure retractor blades can be achieved in retractor blades without joints by a tilting of the retractor blade at an angle with respect to the longitudinal axis of the retractor blade stage. The tilt of the retractor blades can assist in the manipulation of tissue or holding of tissue within the surgical area as well as possibly tilt the camera orientation.

In some embodiments, the retractor blade stage can allow for rotational, radial, and/or flexure movement of the retractor blades to assist in the appropriate positioning of the retractor blades and this movement can be helpful in the imaging of the surgical field and/or assisting in retraction of the tissue in the surgical area. Alternatively, the retractor blade stage can allow for the rotational movement only and no radial or flexure movement can occur. In some embodiments, the retractor blade stage can allow for the rotational movement and radial movement only and no flexure movement can occur. In some embodiments, the retractor blade stage can allow for the rotational movement and flexure movement only and no radial movement can occur. In some embodiments, the retractor blade stage can allow for the radial movement only and no rotational or flexure movement can occur. In some embodiments, the retractor blade stage can allow for the radial movement and flexure movement only and no rotational movement can occur. In some embodiments, the retractor blade stage can allow for the flexure movement only and no rotational or radial movement can occur. In some embodiments, the retractor blade stage can allow for rotational, radial, and flexure movement of the retractor blades. Moreover, the retractor blade stage can incorporate any of or any combination of the features and/or embodiments of the rotatable stage or frame discussed herein. Further, in some embodiments, the retractor blade stage can incorporate various embodiments of retractor blades described elsewhere herein.

FIG. 7 illustrates embodiments of the distal end of the clip-on flexible cable that is attached to a retractor blade. As illustrated, the clip-on flexible cable can contain various combinations of cameras, lighting sources, sensors, tracking, and/or other components such as described herein. In some embodiments, the flexible cable serves as the platform for these devices (e.g. sensors, lighting, optics, imaging components etc.). In other embodiments, the flexible cable or other cable or lines may connect to a separate platform that supports these devices, including rigid or flexible retractor blades or a separate rigid or flexible platform.

The clip-on flexible cable can be interchangeable to provide for different platforms depending on the desired use or imaging required. The clip-on flexible cable can be fastened to the retractor blades with a fastening member which can include, for example, a clip, a snap, a strap, a screw, a bolt, a nut, a magnet, or any combination of these as well as any other method that can facilitate convenient attachment. For example, attachment can be accomplished in under one minute possibly less than 20, 10, 5, 3, or 2 seconds per arm and may be accomplished in more or less than a second or ½ or ¼ second per fastener, which can occur, prior to or during surgery.

As described herein, the retractor blade can be made of malleable or flexible material or contain joints that allow for movement of the retractor blade. In some embodiments, the clip-on flexible cable can be configured to move and bend with the retractor blade allowing for movement of the retractor blade and the attached flexible cable either prior to a surgery or procedure or during surgery or a procedure. Rigid, articulated blades with discrete joints, pulled outward via cables for each DOF to retract tissue, tissue pressure "unretracts" when cables are released, as described above with respect to FIGS. 6C-G.

As evident from the discussion above, the imaging assembly can contain an array of cameras on, adjacent to, or integrated as part of the retractor components. The flexible cable and retractor blade on a given retractor arm can incorporate a single camera or a plurality cameras such as proximal and distal cameras. The cameras can include various sensor arrays and lenses in a variety of configurations. In some embodiments, the cameras provide three dimensional (stereo) views. The cameras can, for example include lenses on a sensor array(s) that mimic the convergence of the eye. The cameras can be tilted to create the convergence necessary. For example, in some embodiments, a stereo view can be formed from two sensors and two lenses. Additionally, the stereo can be a single sensor which can be split with two lenses, which may have converging optical axes that mimic the convergence of a surgeon's eyes. The stereo can be used to provide the surgeon or viewer with a three dimensional view of the operating field. For some views convergence is not required, for many times the focal length in terms of distance the views can be parallel or nearly so.

FIG. 8 illustrates a front surface of an example retractor blade or flexible cable that can be attached to a retractor blade. In certain embodiments, the retractor blades or flexible cables can have a proximal camera 8021 which can be located on a proximal portion of the retractor blade or flexible cable, e.g., closer to the entryway into the surgical site or the main body of the retractor. The proximal cameras 8021 on a proximal portion of a retractor blade can include monocular, e.g., 16:9, and/or stereo views. The proximal camera(s) 8021 on the proximal portion of the retractor blade can contain larger sensor arrays and more resolution. In certain embodiments, the retractor blade can have a distal camera 8022 which can be located on a distal portion of the retractor blade, for example, which will be positioned deeper into the surgical site in comparison to the proximal location. The distal camera(s) 8022 on a distal portion of the retractor blade can provide oblique views and/or side views and may contain smaller sensor arrays and need to provide less resolution than the proximal cameras which may provide a more comprehensive view. The distal camera(s) 8022 on the distal end of the retractor blade can be small cameras for oblique and side views within the body cavity near the middle or tip of the retractor blades. Nonetheless, the smaller distal cameras may be stereo. Distal cameras with oblique views make seeing hidden areas possible when line of sight instruments such as operating room microscopes fail.

In some embodiments, the cameras on the retractor blades or flexible cable can be tilted, for example, upward or downwards or sideways or combinations thereof. The cameras can be tilted to achieve different orientations of the camera. For example, in some embodiments, the cameras can be tilted with the use of hydraulic balloon actuated pistons thereby orienting the camera in different positions relative to the retractor blade. The tilt of the camera can be changed prior to or during a surgical procedure. For example, the cameras can be positioned on a stage and the stage can be tilted with the use of hydraulic balloon actuated pistons thereby orienting the camera in different positions relative to the retractor blade. In some embodiments, the cameras on the retractor blades can be situated on a track that allows the camera to move vertically (and/or laterally) on the retractor blade thereby changing the position of the camera. Such a vertical position can be set prior to surgery or during surgery. The positioning may be performed manually or by using an actuator, such as a motor or other actuator.

In some embodiments, the flexible cable or the retractor blades can contain light sources. The light source can include LEDs and/or multicolor LEDs. A light source such as a single LED or multiple LEDs can be located on, adjacent to, or integrated as part of the retractor blade or flexible cable. The LEDs or other light source can provide illumination of the surgical area as well as possibly color management. The LEDs can provide sufficient brightness for a surgical treatment. In some embodiments, multi-color LEDs can provide color balancing of the image of the surgical area. The intensity of the different colors can be adjusted to provide the desired aggregate color. Through such color management, for example, multi-colored LEDs can be used to control the color temperature of the medical lighting. The color management accomplished with the different color LEDs can allow for precise control of the brightness and color of the light emitted from the LEDs. The control of the color temperature can provide the desired lighting in the surgical field for the surgeons. In the embodiment shown in FIG. 8 the flexible cable or the retractor blades surface contain an LED 8023 at a distal end of the flexible cable or retractor blade for illumination of the surgical area.

As discussed elsewhere herein, the flexible cable or retractor blades can contain a component which allows for tracking of a location and/or orientation, and facilitate registration of the attached cameras. The flexible cable or retractor blades can incorporate various methods of tracking including: EM tracker, optical tracking, inertial measurement units (IMUs), encoders, and other methods as described herein. In some embodiments, the reconfigurable shape of the retractor blade and the flexible cable may increase the usefulness of the tracking for image processing.

As discussed above, platforms other than flex cable can be used.

Flexible Cable

FIG. 3C, described above, however, illustrates an embodiment of a flexible cable 7001 that removably attaches to the retractor blade 7003. In one embodiment, the flexible cable 7001 connects at its proximal end to the aggregator 7007 and has a distal end 7005 that is attached to the front surface of the retractor blade.

The flexible cable 7001 can contain the camera modules, cameras, LEDs, sensors, and/or other components as described herein as well as any signal lines or connectors necessary for their varied operations or use. The flexible cable 7001 can contain the electrical signal lines for the cameras, sensors, or other components. Additionally, in some embodiments, the distal end 7005 of the flexible cable can allow for multiple cameras, sensors, trackers, or LEDs to be positioned in various combinations and varying numbers. In some embodiments, the cameras can be distal relative to the surgeon's hand and tool handle. Additionally, in some embodiments, the cameras or camera modules can also be distal relative to the tool shaft.

The distal end 7005 of the flexible cable can be fastened to the retractor before use through the use of a fastening member which can include, for example, a clip, a snap, a strap, a screw, a bolt, a nut, a magnet, or any combination of these as well as any other method that can facilitate convenient attachment, for example, that can be accomplished in under one minute possibly less than 20, 10, 5, 3, or 2 seconds per arm and may be accomplished in more or less than a second or ½ or ¼ second per fastener, which can occur, for example, prior to surgery. In one embodiment, the distal end 7005 of the flexible cable can be a platform which can be separated from the portion of the flexible cable that connects to the aggregator. The distal end 7005 of the flexible cable can include all functions and components described herein for clip-on flexible cables and retractor blades such as optics, sensors, LEDs, heaters, trackers, and cameras. The distal end 7005 of the flexible cable can be attached to the portion of the flexible cable that connects to the aggregator by a female/male connection port, plug and socket connection, or other hardware interface that allows an electrical signal to pass. In some embodiments, the platform 7005 includes a male connection for ease of cleaning and sterilization.

Figure 9A:
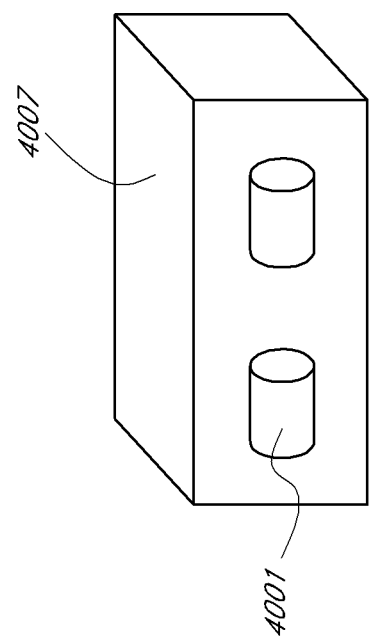
FIGS. 9A and 9B show embodiments of an aggregator, with one or multiple flexible cables in the rolled configuration.
Figure 9B:
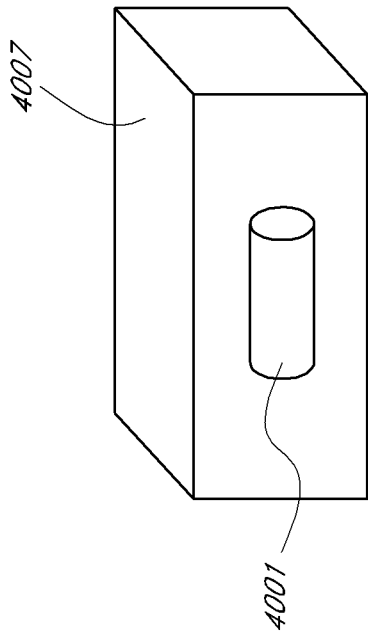
Figure 10A:
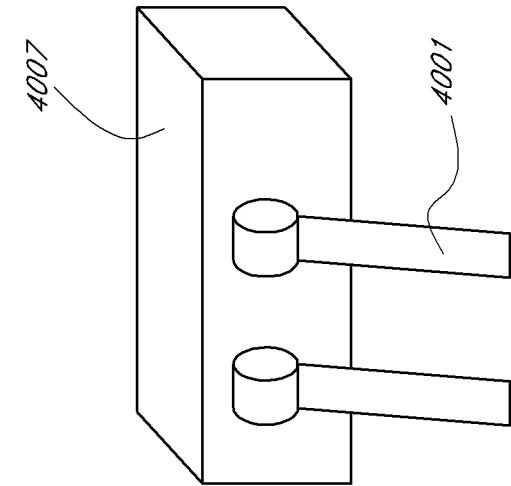
FIGS. 10A and 10B show embodiments of the aggregator, with one or multiple flexible cables in the unrolled configuration.
Figure 10B:
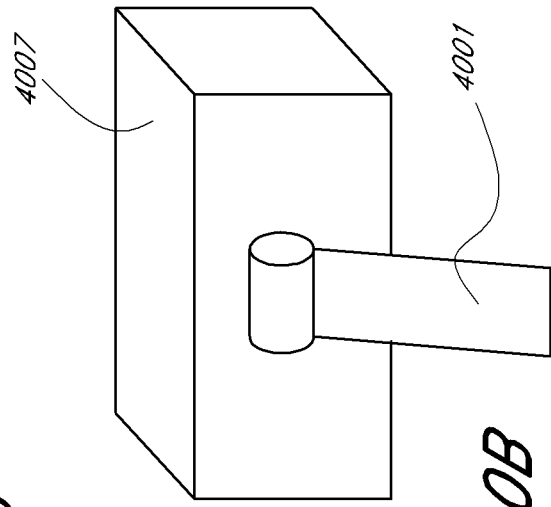

The flexible cable can be made of a material which allows the flexible cable as well as the components on the flexible cable to be rolled or folded into a compact size. FIGS. 9A and 9B illustrate embodiments of an aggregator 4007, with one or multiple flexible cables 4001 in the rolled configuration. FIGS. 10A and 10B illustrate embodiments of the aggregator 4007, with one or multiple flexible cables 4001 in the unrolled configuration. The aggregator 4007 can have one or multiple flexible cables 4001. The flexible cables 4001 can have a single camera or a plurality of cameras, sensors, LEDs, or camera modules as described herein.

Figure 11C:
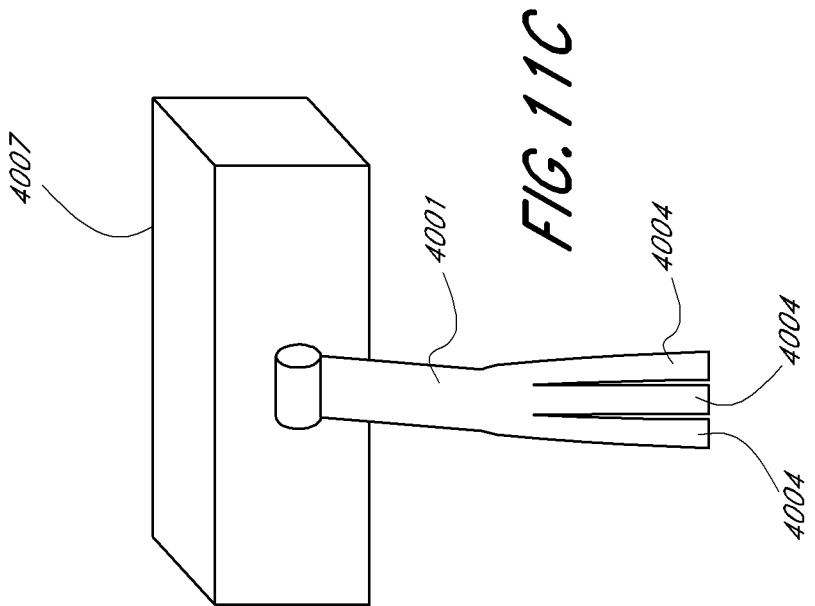
FIG. 11C shows an embodiment of an aggregator, with one flexible cable with cutouts in the unrolled configuration.
Figure 11A:
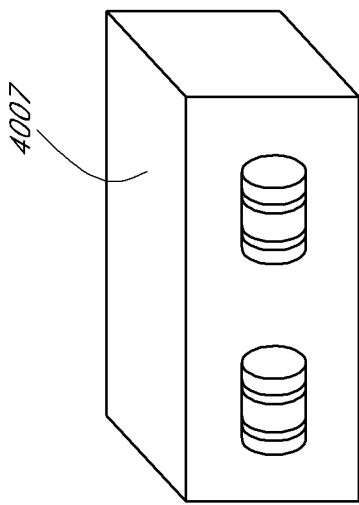
FIG. 11A shows an embodiment of an aggregator, with one or multiple flexible cables with cutouts in the rolled configuration.
Figure 11B:
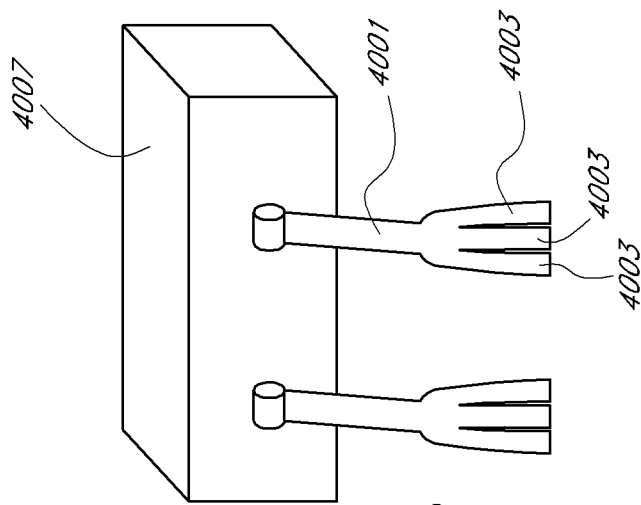
FIG. 11B shows an embodiment of an aggregator, with one or multiple flexible cables with cutouts in the unrolled configuration.

In one embodiment, the flexible cable can be split up at the distal end creating multiple extensions. FIG. 11B illustrates an embodiment of the flexible cable 4001 with cutouts forming multiple extensions 4003. The imaging assembly can have only one flexible cable 4001 with multiple extensions 4004 as shown in FIG. 11C. In various embodiments, the multiple extensions 4003, 4004 can be large enough to fit on a single retractor blade. Accordingly, in some embodiments, the multiple extensions 4003, 4004 together may have a width smaller than the width of the blade although the multiple extensions can be wider. In certain embodiments, the flexible cable in the unrolled configuration can have multiple extensions 4003, 4004 where the extension can have a width such that one extension can be placed on a single retractor blade. Accordingly, in some embodiments, one extension may have a width smaller than the width of the blade. The plurality of extension together however, may be wider than the blade. In various embodiments similar to that shown FIG. 11B the multiple extensions 4003 can be small enough so that all extensions 4003 are placed on the same retractor blade, however, the flexible cable with multiple extensions can have a single camera or stereo camera pair on each extension of the flexible cable. In some embodiments, the flexible cable with multiple extensions can have multiple cameras on each extension of the flexible cable.

In various embodiments, the flexible cable or other platform can be unrolled by hand. In some embodiments, hydraulics or pneumatics may be used to effectuate unrolling. Fluidic lines in the cable may, for example, be connected to a hydraulic or pneumatic pump source which can be applied to cause the cable to unroll and extend.

In various embodiments, the imaging assembly including the aggregator with rolled cables can be provided independent of the retractor unit and clipped-on or otherwise attached to the retractor unit prior to use as described herein. The imaging assembly can be attached at a single attachment point or through multiple attachment points. In various embodiments, for example, the flexible cable clipped on to the retractor frame, arms, and retractor blades. The flexible cables can be attached to the retractor and the retractor blades by a separate attachment mechanism that can be easily attached or removed within seconds. See, for example, FIG. 3C.

FIG. 3B, described above, illustrates an embodiment of the retractor blades with an integrated imaging assembly clipped on to the retractor frame and arms. The retractor blades can be attached to the retractor arms by a separate attachment mechanism that can be easily attached or removed within seconds. In some embodiments, the aggregator is releasably attached via an attachment mechanism to the top surface of the retractor frame. In some embodiments, the imaging assembly can have multiple attachment mechanisms positioned on the aggregator, the flexible cable, the retractor blades or combinations thereof which fasten the imaging assembly to the retractor at various connection points. In certain embodiments, the imaging assembly may have one attachment mechanism and a single connection point on the retractor frame or retractor blades. As discussed above, the attachment mechanisms can include, for example, a clip, a snap, a strap, a screw, a bolt, a nut, a magnet, or any combination of these as well as any other method that can facilitate convenient attachment. For example, fastening can be accomplished in under one minute possibly less than 20, 10, 5, 3, or 2 seconds per fastener and may be accomplished in more or less than a second or ½ or ¼ second per fastener, which can occur, for example, prior to surgery.

A wide variety of fastening systems may be employed. In various embodiments, for example, the distal end 7005 of the flexible cable is fastened to the retractor blade surface or the retractor blades are fastened to the retractor frame through a clip-on mechanism 4011 shown in FIG. 12A which can be secured, for example, prior to surgery.

Figure 21:
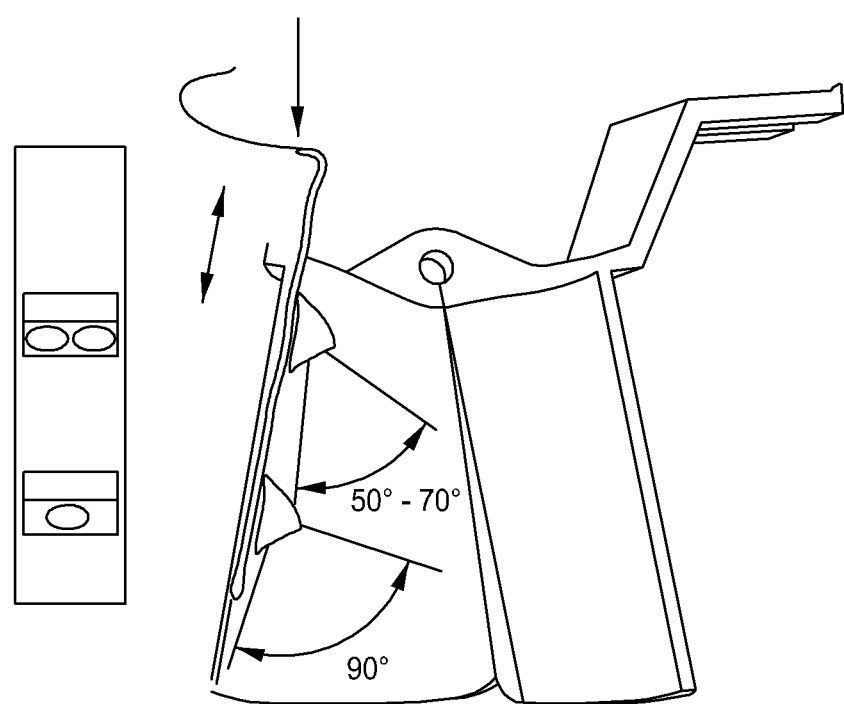
FIG. 21 shows an example configuration of a proximal stereo camera having a first field of view and a second monocular distal camera having a second field of view.

In some embodiments, the clip-on attachment mechanism can also resemble a hairpin attachment 4010 as shown in FIG. 12B. In some embodiments, the hairpin attachment 4010 allows the flexible cable to be releasably and securely attached to the front surface of the retractor blade or the retractor blades to be releasably attached to the retractor frame. Extra fastener components may also be included to reduce risk of inadvertent movement or misalignment. Such clip-on attachment devices may be also used for retractors having different configurations such as for example, cylindrical type retractors such as shown in FIG. 21.

Additionally, in some embodiments, the flexible cable can be attached to the retractor blades or the retractor blades can be attached to the retractor frame via a dovetail attachment. FIG. 12C illustrates an embodiment of a top view of a dovetail attachment mechanism. The retractor blade or retractor frame 4016 may, for example, contain a receiving slot 4012 on the inner surface of the retractor blade or retractor frame opening to the interior of the surgical area. Additionally, the flexible cable or retractor blade 4015 can contain a first and second edge 4013 and 4014 configured to fit within the receiving slot 4012. The insertion of the flexible cable or retractor blade 4015 into the receiving slot 4012 of the retractor blade or retractor frame 4016 provides a secure attachment of the flexible cable to the retractor blades or a secure attachment of the retractor blades to the retractor frame. Further, in some embodiments, the flexible cable can be attached to the retractor blade by insertion into the receiving slot of the retractor blade and also by a clip-on attachment mechanism as described herein. The locations of the receiving slot and edges that are fit therein can be reversed.

In certain embodiments, the aggregator with rolled cables can be permanently attached to the retractor frame. In such embodiments, the flexible cable could be rolled out and clipped on to the retractor blades. In some embodiments, the preattached aggregator and flexible cable can be permanently attached to the retractor unit in the unrolled configuration. In some such embodiments, the flexible cable can be permanently attached to the retractor surface and/or the retractor blade surface.

A variety of options are thus possible. In certain embodiments, the imaging assembly can be a clip-on imaging assembly which can be clipped on to the retractor and/or the retractor blades. In other embodiments, the retractor blades with integrated components can be permanently attached to the retractor frame along with the flexible cable and aggregator. In some embodiments, the retractor blades with integrated components can be permanently attached to the retractor frame but the flexible cable and aggregator can be clipped on to the retractor unit. In such embodiments, the flexible cable would attach to the integrated retractor blades through a hardware interface (e.g., female and male connectors, respectively) that allows the electrical signal to pass. In some embodiments, the retractors can have different shapes. For example, in some embodiments, the retractors have separate arms similar to that shown in FIG. 3A. In some embodiments, the retractor can be a cylindrical retractor such as the retractor shown in FIG. 21.

Surgical Tool with Integrated Camera

In some embodiments, a second surgical device, e.g., surgical tool, may be used in conjunction with a first surgical device. For example, as shown in FIG. 13A, the first surgical device 100 is a retractor with three retractor blades, and the second surgical device 200 can be a surgical laser. The laser 200 also includes an integrated camera module 205 which provides a field of view determined by the position of the distal end 211 of the laser. The laser output aperture 213 is oriented in the same direction as the field of view of the camera module 205 of the surgical laser 200. In some embodiments, the image obtained from the laser 200 may be associated with the composite image generated by the plurality of cameras integrated within the first surgical device 100. For example, in some embodiments, the view obtained by camera module on the laser tool may be superimposed over a portion of the image generated from the plurality of cameras, e.g., in the retractor 100. The superimposed image may be positioned so as to indicate the placement of the view with relation to the view of the surgical field provided by the plurality of cameras mounted in the first surgical device.

In some embodiments, for example as illustrated in FIG. 13B, the second surgical device can be a surgical tool such as a needle holder 300. In various embodiments, the surgical tool can be, for example, drill, Kerrison, a cutting tool, grasping tool, rongeur, scalpel, scissors, forceps, etc. The surgical tool 300 may have a camera module 305 integrated therein or attached thereto, whose field of view is determined by the position of the tool. For example, CMOS sensors and micro-optics can be incorporated into both power and non-power tools. A flex cable 311 extends along the length of the tool 300 and electrically connects to the camera module 305. In various embodiments, the flex cable 311 can provide electrical connection to the camera module, as well as supplying gas and/or fluid for camera cleansing, as described in more detail below. The additional camera included with the surgical tool may have a different magnification than the cameras on the surgical device, may provide increased resolution, and/or reduced obscuration. As described in more detail below, the video stream from the separate camera on the surgical tool can be superimposed over or otherwise displayed with the composite image generated by, e.g., stitching or tiling images from the plurality of cameras integrated with the surgical device 100.

The tool image can provide an extreme close-up view of the tool-tissue interaction, while the wide-field image can provide a stereo image with situational awareness. The enhanced situational awareness is provided by the wide field-of-view deep within the area proximal to the surgical site, and views of anatomy of interest from more perspectives than a single device such as a microscope or endoscope. This perspective may be from within the body if the plurality of sensors on the first surgical device are within the body or at the surgical opening or within a few to 75 millimeters therefrom. In some cases, this perspective may be conveniently provided with surgical devices that are attached to the body such as by retractors.

The CMOS sensors, optics, EM sensor (optional), and tool actuation (if necessary) may be tightly integrated with the second surgical device in order to achieve a sufficiently small package. Power tools can be used, particularly for robotically assisted surgery. Embodiments described herein, however, may be used both in manual and robotic surgery. Electromagnetic tracking sensors, IMUs, and/or one or more cameras may be incorporated into a wide range of tools, including non-powered tools (e.g., pics, knives, curettes, osteotomes, rasps, trocars, dermatomes, retractors, suction cannulas), manually actuated tools (e.g., scissors, forceps (including bipolar cautery/diathermy forceps), clip appliers, rongeurs, and needle holders), and powered tools (e.g., drills, power Kerrison, power bipolar forceps, harmonic scalpels, ultrasonic tissue removers, and lasers). The applicable tools, however, are not limited to these.

As with the first surgical device, pairs of cameras on the second surgical device can provide a stereo or 3D effect.

Power tools can provide an integration of the multiple camera system with master-slave surgical robotic systems, as well as decreasing hand fatigue and increasing precision with manual surgery. A proportional foot pedal control may be used, in which increasing depression of the pedal closes the tool proportionally. In some embodiments, hand actuation may be used instead, for example by use of a control lever or push button. In some embodiments, surgical impedance feedback may be provided. For example, sensed actuation pressure (or current if electrically controlled tool) can correspond to the tissue resistance and can be used to drive current/torque to foot pedal to provide surgical impedance feedback. Other configurations can be used to provide tactile feedback corresponding to mechanical forces experienced by the tools to the surgeon's controls such as the foot pedal.

Tool actuation options include electrodynamic, pneumatic, and hydraulic. Hydraulic actuators advantageously are inexpensive, powerful, and "stiff", meaning that these actuators are less prone to overshoot than their pneumatic and electrodynamic counterparts. Hydraulic actuators may include but are not limited to a rolling edge diaphragm (fluid is only on one side of rolling edge diaphragm), diaphragm with dual actuation (fluid on both sides of diaphragm), as well as a Bourdon tube (axial or helical), or a piston in a cylinder. Master hydraulic actuator options include a brushless DC motor with ball screw linear actuator driving rolling edge diaphragm, and commutated or non-commutated brushless DC motors driving a rolling edge diaphragm. In various embodiments, dual linear actuators can drive dual air cylinders and air over fluid in disposable cassette. Other configurations are possible.

Tracking Tools and Optics

In various embodiments, cameras can be independently adjustable, either rotatable/articulable within the device, or they may be able to be separately mounted prior to or during insertion of the surgical platform. Multiple cameras can each have a position and/or orientation that is tracked, e.g., electronically or optically. Tracking the position and orientation of the sensors can provide the image processor with real-time, low-latency, 6-DOF (six degrees of freedom) information needed to decrease search and registration times for the purpose of stitching a composite image. Tracking can also be employed to assist in tiling or otherwise arranging images such that the position of the image as displayed is consistent with the arrangement of the locations of the cameras or the field-of-views of the cameras in the surgical site. Tracking options include electromagnetic tracking (as, for example, using NDI Aurora or Ascension medSafe). In such systems, 6-DOF sensors may be less than 1 mm in outer diameter. These systems do not require a line-of-sight, as in optical tracking systems. Electromagnetic tracking sensors can be easily integrated within the surgical devices at relatively low cost. In some embodiments, less than 6 degrees of freedom, e.g., 5-DOF tracking can be employed instead of 6-DOF. In some embodiments, for example, IMUs can be used for 5-DOF tracking. In such 5-DOF tracking, the distance to target is not required to be precise so long as the other distances and positions are known. If the distance to target is a few millimeters closer or further away, the difference in magnification can be negligible. In various embodiments, in which the distance to target must be precise, 6-DOF tracking may be required. 6-DOF tracking may improve integration of the tracking with navigation systems and the GUI. The capability of tracking, and thereby knowing the location and orientation of the camera, can provide the opportunity to tell the camera where it needs to be for an array of images to be aligned in a prescribed manner. For example, a plurality of cameras on malleable retractor fingers by definition are not aligned to an equator. Through tracking, the cameras can offload position derived by sensor and image processing to position adjustment, described in more detail below.

Surgical tools can also be tracked. Tracking can provide 6-DOF real-time position and orientation to image process to enable correct positioning of PIP overlay of tool images or alternatively stitching, tiling, and scaling of images into the composite image. EM tracking has significant advantages. Since electromagnetic tracking does not rely on line-of-sight (as opposed to optical tracking), visual obscuration does not interrupt tracking. Particularly in minimally invasive procedures, the presence of various surgical tools within the small incision can provide significant obstacles to optical tracking. The EM tracking may take the form of EM sensor coils, or other techniques. In addition the positions and/or orientations of the cameras and/or the surgical tools can be tracked by using encoders, MEMS IMUs, ultrasonic emitters, optical tracking or other approaches, in some embodiments.

Electromagnetic tracker coils can be positioned within sufficient proximity to the cameras and the tracking device included therewith such that the relative location and/or orientation of the cameras can be determined. Such electromagnetic coils can provide 6-DOF position and orientation information, which may then be transmitted to the image processor. The position and orientation information can be used to reduce the computational load required to stitch or tile the various images into the composite image and/or to render the image in stereo for which a key application is a touch screen user interface. In some embodiments, cameras can be integrated with retractors that include malleable blades, for example retractors designed for neurosurgery. The position of the cameras individually can therefore provide positional information unavailable when detecting only the position of the retractor blade, since the blade itself can be malleable. In some embodiments, the retractor and its blades can be rigid, and accordingly the tracking requirements may be reduced.

In some embodiments, the surgical device and/or any surgical tools can include integrated motion sensors, such as gyroscopes or other MEMS accelerometers. These sensors can measure the physical motion of the cameras due to movement of the device. This motion can be subtracted from the image in order to render a displayed image in which the area of interest is relatively still, despite any movement by the surgical device.

Camera connectors can have EEPROM chips to provide information to the image processor about the camera such as the identity, sensor format (e.g., number of horizontal pixels and vertical pixels, etc.) or other information. In the special case of cameras mounted on a tubular retractor for spine surgery or other retractors with fixed camera position, the fixed positions may be made available to the system.

If an optical navigation/tracking system is used on the retractor, electromagnetic tracking can send tool tracking information to the navigation system to avoid the need for optical recognition features (for example passive reflections of LEDs and/or location of fiducials) on the tool. Electromagnetic trackers can also be positioned on a patient, for example on a bone or anatomic landmarks, as well as being positioned on external fixation systems, for example a cranial fixation system for neurosurgery. The position of the cameras with relation to these external tracked points can be used as input to guide optical navigation systems, for example those provided by Medtronic, Stryker, or BrainLabs.

In the case of malleable retractor blades, the position of the cameras integrated therein are not necessarily fixed with respect to the retractor frame. Accordingly, tracking of the cameras may be useful for enabling an image processor to stitch (register) or tile multiple images together in the proper position and orientation without excessive computational load. A 6-DOF electromagnetic sensor can be attached or integrated within the malleable retractor blade near the camera. In some embodiments, the flex circuits for the camera and sensor coil can be integrated together or may be potted together and use the same cable assembly.

An alternative approach to tracking camera position can be employed in configurations with retractor blades that can flex only in one plane. An example of such a 1-DOF retractor blade is shown in FIG. 6A, as described above. With reference to FIG. 6A, the axial position of the wire 353 can be sensed, for example, by using an optical encoder marking on the wire 353. A moving 6-DOF electromagnetic sensor outside the surgical site also can be attached to the base of the retractor blade 351 at the proximal end, e.g., at the position of attachment to a retractor frame. Information from the 6-DOF sensor along with the sensed axial position of the wire 353 can provide position and orientation information about the camera 355. In other embodiments, two wires may be used, one having a distal attachment, the other with a more proximal attachment. For example, the wires may run along the outer curvature of a pre-flexed Nitinol retractor blade. Axially moving one or both wires, each of which may be sensed, enables incremental controllable flexure of the blade. Encoders may be used again for tracking.

In other embodiments, particularly when the retractor blades are substantially rigid, the position of the blades can be sensed, and the position of the cameras can be inferred from the blade position. For example, the position of the cameras with respect to the retractor blades on which they are mounted can be known in advance. In use, as the retractor blades are moved, the movement can be tracked. For example, encoders may be positioned within joints of the retractor, such that as the retractor blade is rotated at the joint, the degree of rotation is sensed. Similarly movement of an articulating arm to which the retractor blade is attached can be sensed, and this information can be used to derive the position of the cameras.

It is also possible to use optical tracking, where the surgical device includes some kind of identifying markers, and the information is viewed by an overhead camera. The image can then be processed to identify the position and orientation of the surgical tool. The markers, whether shape or color or both, and whether positioned on or within a tool, for example, may provide white balance and intensity information useful for adjusting the sensors or illumination output. In various embodiments, white balancing may be done by inserting the target into the workspace in the field of view of all cameras before surgery. The frame, retractors and assorted cameras could be placed in a holster, whose purpose is multifold, to include but not limited to: authentication, white balance, camera positions with respect to frame, synching camera types to icons in GUI, such as field of view, line of sight, sensor type, stereo pairing, etc.

In various embodiments inertial measurement units may be employed to determine movement and/or orientation of the cameras. Such inertial measurement units may be less expensive than potential alternative tracking options. In certain embodiments, IMUS are used to provide 5-DOF as opposed to 6-DOF.

In some embodiments, the image obtained from the tool may be blurred or otherwise deteriorated due to operation of the tool. For example, a surgical drill with an integrated camera may produce blurred images due to the rotary motion of the drill. Such image motion can be compensated by the image processor. For example, the torque produced by the rotation of the drill can be proportional to the applied current. In view of the applied current, a feed-forward command can be sent to the image processor to compensate for the blur caused by the rotary motion.

In some embodiments, actuation of an electrically powered surgical tool can result in electromagnetic interference with the electromagnetic tracking. In such configurations, optical tracking can be used to supplement electromagnetic tracking as an alternative. Alternatively, a notch filter can be employed to reduce interference from the powered surgical tool with the electromagnetic tracking. The notch filter can be selected such that the stop-band corresponds to the electromagnetic noise produced by the powered surgical tool. The electromagnetic signal used by the trackers may fall outside of the stop-band of the notch filter. Another approach to avoiding deleterious interference with the electromagnetic tracking is for electromagnetic tracking to be suspended during operation of the powered surgical tool. Once operation of the powered surgical tool has ceased, electromagnetic tracking may then re-commence. In various embodiments, a controller can automatically cease electromagnetic tracking when the powered surgical tool is initiated, and similarly can automatically resume electromagnetic tracking when use of the tool ends. Yet another approach involves characterizing the electromagnetic interference caused by a given powered surgical tool, and then using that characterization to subtract out the interference from the electromagnetic tracking signal. For example, in some embodiments, the electromagnetic signatures for a surgical tool may be known in advance, and this signal may be accounted for when electromagnetically tracking the positions of the tool and/or cameras. In other embodiments, the electromagnetic noise caused by the surgical tool may be measured on the fly, and this noise may then be subtracted or otherwise compensated for when calculating the position of the surgical tool and/or cameras.

Surgical System Components

Figure 14:
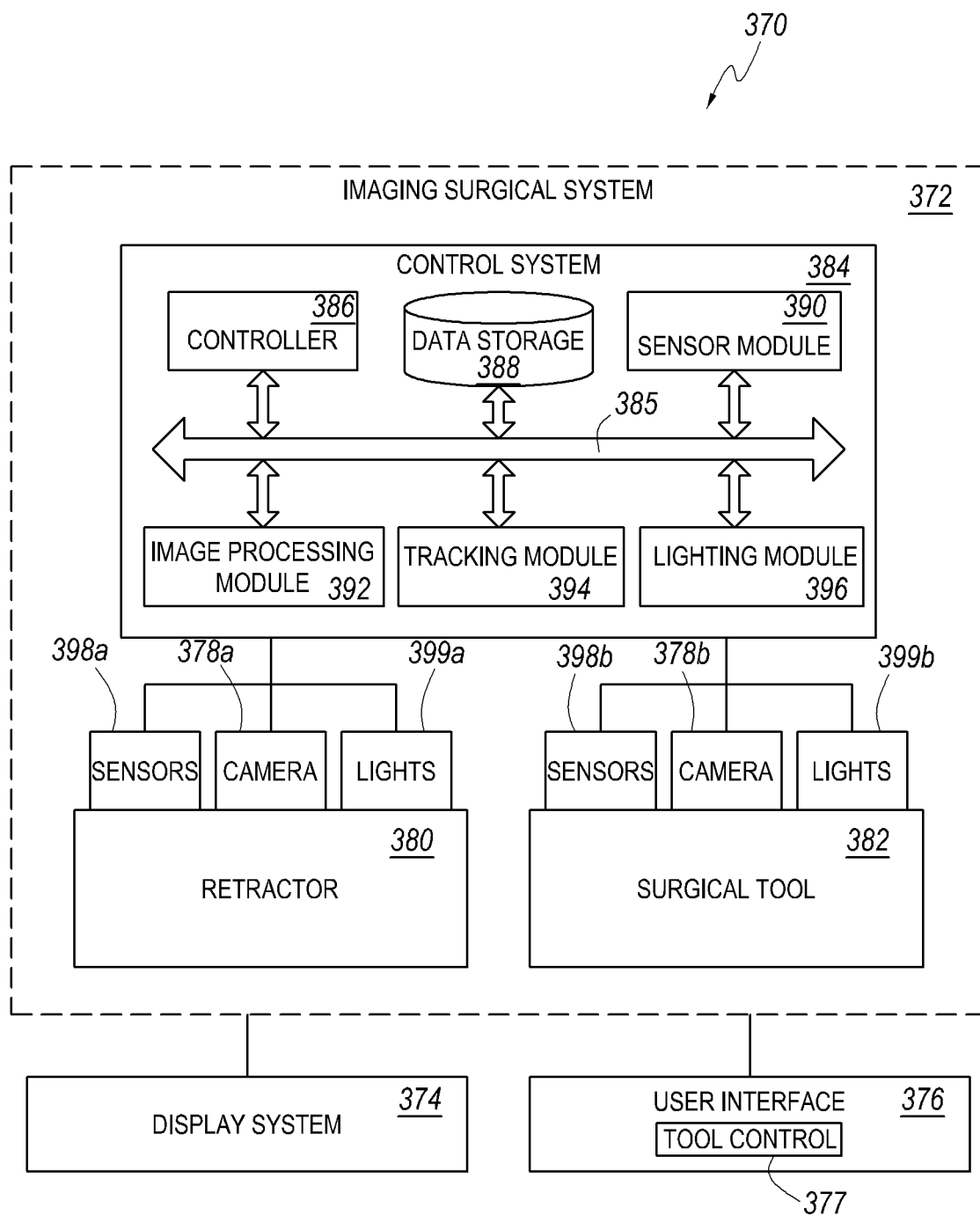
FIG. 14 shows an example surgical system including an imaging surgical system having an image processing system and cameras associated with surgical devices.

FIG. 14 illustrates a block diagram of an example surgical system 370 comprising an imaging surgical system 372, a display system 374, and a user interface 376. The surgical system 370 can be used to visualize a surgical site using multiple cameras 378a and/or 378b associated with a retractor 380, a surgical tool 382, and/or auxiliary cameras. Visual information can be presented to a surgeon using the display system 374 to provide visual feedback to the surgeon to enable the surgeon to control the surgical tool 382 using the user interface 376 and/or the tool control 377. The imaging surgical system 372 can be configured to enhance the situational awareness of the surgeon by displaying imagery (e.g., video and/or still images) of the surgical site where enhancement of the surgeon's situational awareness occurs based at least in part on multiple points of view of the surgical site, an orientation of the imagery on the display, positions of the imagery relative to one another, stereo and/or layered imagery, information about a position of the surgical tool 382, imagery of the surgical site from external sources (e.g., MM, x-ray, CT, or other imaging modality), or any combination of these. The imaging surgical system 372 can be configured to provide imagery of a trajectory of the surgical tool 382, for example, from entry of the surgical tool 382 at a surgical opening to deep within a convoluted surgical site through the use of multiple views provided by multiple cameras 378a.

The imaging surgical system 372 can include a control system 384 configured to receive input from various systems and/or modules, to process information, to store data, to send output to various systems and/or modules, to receive input from a surgeon or other user, or any combination of these. The control system 384 can include a controller 386, data storage 388, a sensor module 390, an image processing module 392, a tracking module 394, and a lighting module 396 which may communicate with one another and/or external systems through communication bus 385.

The control system 384 includes the controller 386 configured to process data and to control communication between the control system 384 and external systems (e.g., the cameras 378a, 378b; the sensors 398a, 398b; the lights 399a, 399b; the display system 374; the user interface 376; the tool control 377; a laptop; a tablet; or any other external system). The controller 386 can be configured to control data communication between control system modules and/or between control system modules and data storage 388. The controller 386 can be implemented in hardware, software, firmware, or any combination of these. For example, the controller 386 can include logical elements configured to receive imagery from the cameras 378a, 378b and perform image processing functions on the imagery according to instructions provided by the image processing module 392. As another example, the controller 386 can include control modules configured to make decisions based on information received from various modules within the control system 384 and/or from external systems. As another example, the controller 386 can include one or more physical processors configured to process information from the user interface 376 or the tool control 377 to send to the surgical tool 382, to the cameras 378a, 378b, the lights 399a, 399b, or to the display system 374. As used herein, the term "processor" refers broadly to any suitable device, logical block, module, circuit, or combination of elements for executing instructions. The controller 386 can include any conventional general purpose single- or multi-chip microprocessor such as an Intel® processor, a MIPS® processor, a Power PC® processor, AMD® processor, ARM® processor, or an ALPHA® processor. The controller 386 can include any conventional special purpose microprocessor such as a digital signal processor. The controller 386 and the various illustrative logical blocks, modules, and circuits described in connection with embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. The controller 386 can be implemented as a combination of computing devices, e.g., a combination of a DSP and a microprocessor, a plurality of microprocessors, one or more FPGAs, one or more microprocessors in conjunction with a DSP core, or any other such configuration. In some embodiments, the controller 386, the sensor module 390, the image processing module 392, the tracking module 394, and the lighting module 396 or any combination thereof can be implemented using one or more FPGAs. In some embodiments, the controller 386 and one or more modules can be implemented using one or more FPGAs with associated components. For example, in certain implementations, an FPGA can be configured to provide image processing capabilities as well as video switching, controlling video sent between components of the system 370, controlling data processing, and/or controlling a flow of data between components of the surgical visualization system 370.

The control system 384 includes data storage 388. Data storage 388 can be coupled to the other components of the control system 384, such as the controller 386, the sensor module 390, the image processing module 392, the tracking module 394, and the lighting module 396. Data storage 388 can refer to electronic circuitry that allows information, typically computer data, to be stored and retrieved. Data storage 388 can refer to external devices or systems, for example, disk drives or solid state drives. Data storage 388 can also refer to fast semiconductor storage (chips), for example, Random Access Memory (RAM) or various forms of Read Only Memory (ROM) such as an EEPROM, which are directly connected to the one or more processors of the control system 384. Other types of memory include bubble memory and core memory. In some embodiments, video output from the image processing module and/or other data from components of the surgical visualization system 370 can be stored on data storage 388. For example, video displayed on the display system 374 can be recorded onto data storage 388. In some embodiments, data storage 388 is a removable data storage system, such as an external USB hard drive, a flash drive, a memory card, or other similar data storage device.

The control system 384 includes sensor module 390 configured to receive and process information from the sensors 398a, 398b associated respectively with the retractor 380 and the surgical tool 382. Sensors can include inertial measurement units (IMUs), gyroscopes, magnetometers, accelerometers, thermal sensors such as thermocouples or thermistors, electromagnetic sensors, photosensors, or other such sensors. In some embodiments, the sensor module 390 receives sensor information and processes it to provide feedback to the surgeon through the user interface 376, the tool control 377, the display system 374, or through some other method such as audible or visual signals. For example, the sensor module 390 can receive accelerometer information from a sensor associated with the surgical tool 382 and the image processing module 392 can use this information to display a position of the surgical tool 382 when outputting imagery to be displayed on the display system 374. In some embodiments, the sensor module 390 receives sensor information and processes it to provide sensor information, for example, to the image processing module 392, the tracking module 394, and/or the lighting module 396. In this way, the control system 384 can use the sensor information to alter operational parameters or control of the surgical system 370 without direct intervention from a user or surgeon. For example, the sensor module 390 can receive temperature information from a thermocouple associated with the surgical tool 382 or camera 378a and the control system 384 can decide to implement a cooling procedure if the temperature exceeds a threshold. In some embodiments, sensor information received by the sensor module 390 is stored in data storage 388 for later use and/or analysis. Other uses of sensors in conjunction with operation of the surgical system 370 are described herein.

In some embodiments, the retractor 380 and/or surgical tool 382 can be configured to provide an encrypted signal to the control system 384, for example, to the sensor module 390 or the image processing module 392. In some embodiments, similar to the encrypted signal, the retractor 380 and/or surgical tool 382 can be configured to provide a header on image data packets to the control system 384, for example, to the sensor module 390 or the image processing module 392. Encryption or the header can be provided by the camera chip or a separate chip electrically connected to the optical sensor in the camera. In some embodiments, the header or the encryption of the signal assists the signal processing system in the recognition of the camera once attached or clipped on to the retractor. The header or encryption may also ensure the proper pairing of imaging assembly and retractor base for the appropriate image processing and imaging system configuration. Additionally, the header or encryption can ensure the proper standard and quality of camera is used and complies with appropriate requirements for the image processing herein described. In various embodiments, decryption can be achieved with, for example, a computer processor or other electronics, possibly the image processing module or other signal processing or computing module. In various embodiments, the header can be used to relay non-image information to the various systems for use in control the system, processing imagery received from cameras, displaying output video or images, and the like.

The control system 384 includes the image processing module 392 configured to receive image data, process the image data, and to output video or image data for display. The image processing module 392 can be configured to receive image data from the cameras 378a and/or 378b and/or from other imaging modalities including MRI, CT, X-ray, and the like. In some embodiments, image data from other imaging modalities can be communicated using, for example, the DICOM3 protocol. The cameras 378a, 378b can include optics, optical sensors such as CCD or CMOS two-dimensional detector arrays, and associated electronics configured to acquire image information of a scene, as described herein with greater detail. The image processing module 392 can be configured to process image data which can include, for example, stitching images, blending images, morphing images, tiling images, performing transformations on the images (e.g., affine transformations, non-linear transformations, etc.), mosaicing images, enhancing resolution of a region using a plurality of images, extracting surgical tool 382 position information, forming stereo images from separate monocular images, or any combination of these or other image processing including but not limited to those described herein.

The image processing module 392 can be configured to output video or images for display on the display system 374, the user interface 376, or both. In some embodiments, the output video or images can include video from a single camera or a composite video where the video is a result of combining imagery from a plurality of cameras. For example, imagery from multiple cameras can be combined to form a single video by stitching the videos to create a video stream having a wider field of view than provided by any of the multiple cameras used in the stitching. As another example, video from multiple cameras can be combined to enhance a resolution of a region of interest such that the resulting video presents a greater number of pixels per unit of area than any individual input video frame. As another example, multiple cameras can provide multiple viewpoints of an object or area and the video from the multiple viewpoints can be morphed to create video from a virtual viewpoint different from any of the viewpoints of the multiple cameras.

In some embodiments, the image processing module 392 outputs video or image data for display where the output includes a plurality of images or video. For example, the image processing module 392 can receive imagery from a plurality of cameras and present these as tiled images or video. In some implementations, the output tiled images or video can be configured to represent information about the input imagery. For example, one or more of the tiled images or video can be presented as a trapezoid or other similar shape to represent an orientation of the camera relative to an object or area being imaged, e.g., to represent that the focal plane of the camera is not parallel to the area or object being imaged. As another example, the output tiled images or video can be positioned to represent their physical arrangement which can include, for example, the relative positions of the cameras providing the imagery and/or the field-of-views of the cameras. In certain implementations, the tiled images or video can be presented with borders around one or more of the images to enhance or help to identify an extent of the corresponding video or images.

Figure 15:
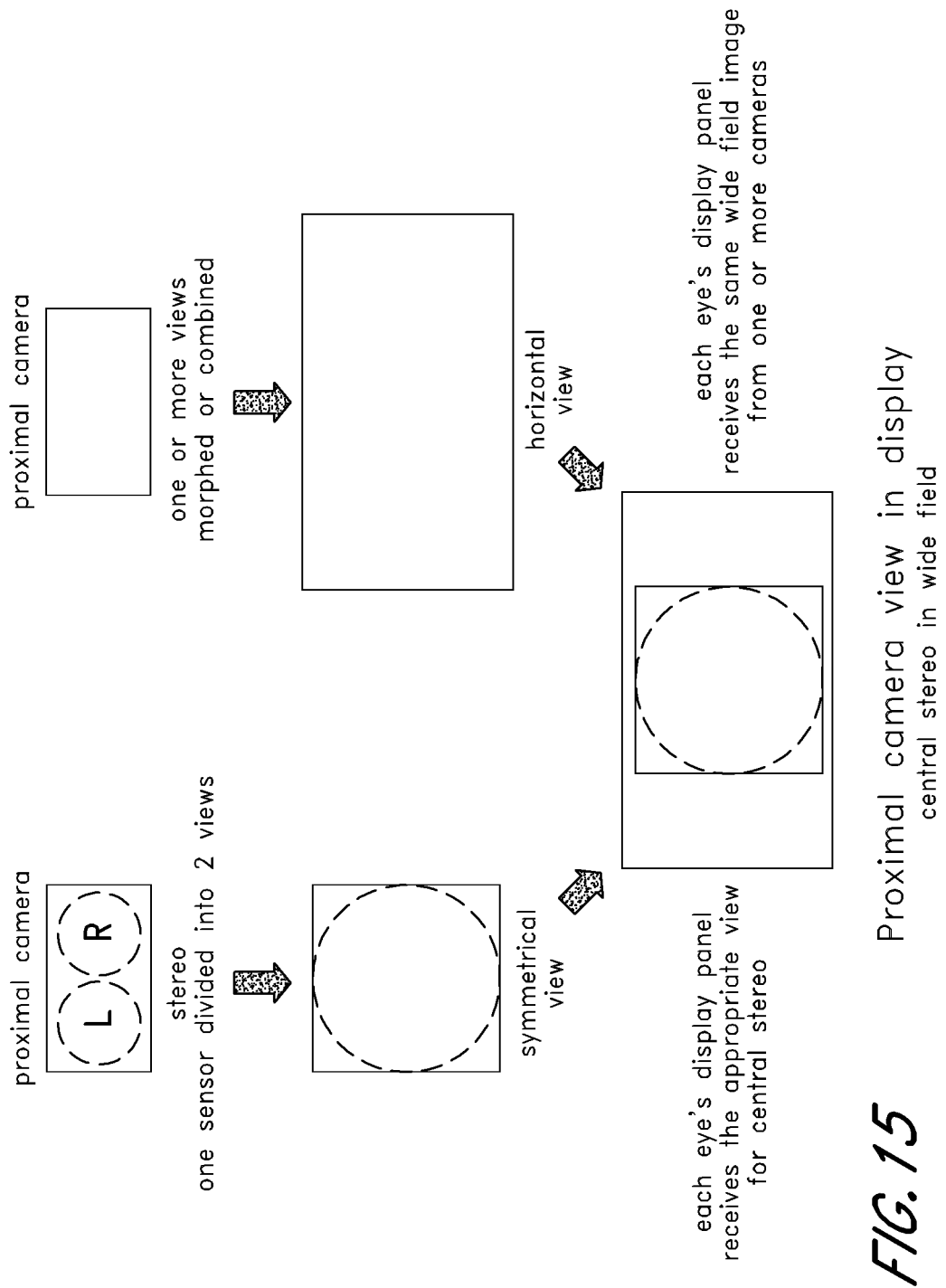
FIG. 15 shows an example output for display of stereo imagery from a proximal stereo camera overlaid with wide field of view imagery from a proximal wide field of view camera.
Figure 17:
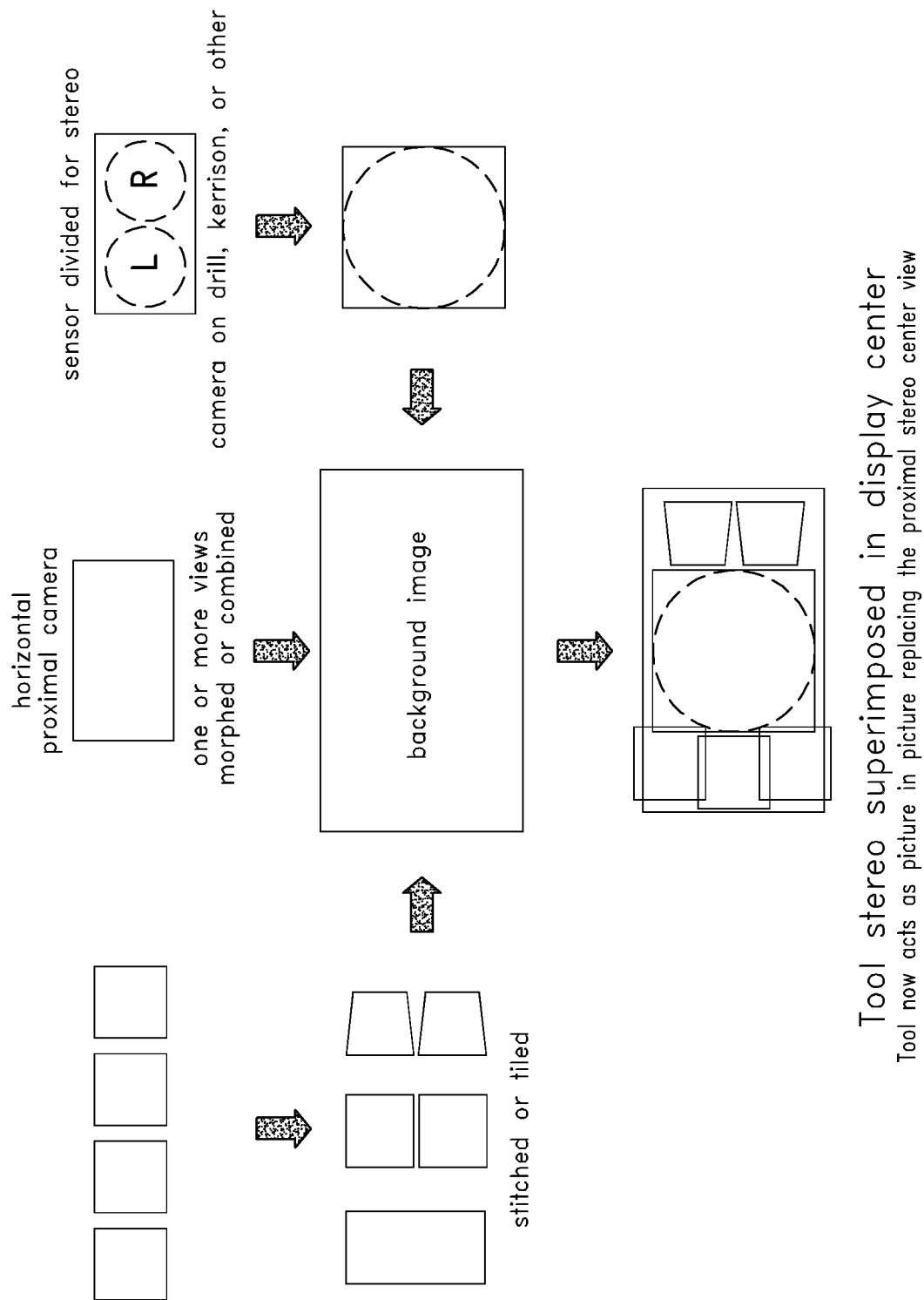
FIG. 17 shows an example display incorporating image data from proximal and distal cameras, as in FIG. 16, along with a picture-in-picture view of imagery acquired by a camera associated with a surgical tool.

In some embodiments, the image processing module 392 outputs a combination of any of individual, tiled, and/or stitched imagery. For example, in certain implementations, the image processing module 392 outputs background imagery having a relatively wide field of view where the background imagery is provided by a single camera or where the background imagery is a result of stitching imagery from a plurality of cameras. In some implementations, overlaid on the background imagery, the image processing module 392 can output video having a narrower field of view than the background imagery. For example, the video with a narrower field of view can be a combination of monocular imagery that form a stereo video, an example of which is illustrated in FIG. 15. As another example, the imagery with a narrower field of view can be imagery provided by a camera 378b on the surgical tool 382, an example of which is illustrated in FIG. 16. In some implementations, overlaid on the background imagery is imagery from a plurality of cameras where the imagery can be tiled and/or stitched, an example of which is illustrated in FIG. 16. In some implementations, the image processing module 392 can output a center image or video that can change between imagery provided by camera(s) 378b on the surgical tool 382 and imagery provided by distal camera(s) 378(a) on the retractor 380. For example, imagery from the surgical tool camera(s) 378a can be presented as a picture-in-picture overlaid on background imagery and/or with stitched or tiled imagery from retractor camera(s) 378a, an example of which is illustrated in FIG. 17. In some embodiments, imagery from three retractor cameras 378a can be displayed as tiled imagery overlaid on background imagery and imagery from the surgical tool camera 378b can be displayed as a picture-in-picture-type display over the background imagery.

In some embodiments, the image processing module 392 is configured to receive imagery from the cameras 378a, 378b and to display the received imagery for simultaneous viewing on the display system 374. In some embodiments, the image processing module 392 is configured to allow a system or user (e.g., a surgeon, an assistant, etc.) to manipulate or interact with the imagery. For example, the image processing module 392 can be configured to provide electronic zoom or magnification according to user input, to system configuration, to camera position, to surgical tool movement or position, or the like. In some embodiments, the image processing module 392 provides feedback to the cameras 378a, 378b to change a focus, a viewing angle, a zoom factor, or the like. Feedback can be provided by the control system 384, external systems, and/or the surgeon or other user through the user interface 376. For example, the surgeon can use the user interface 376 to select images and/or video to view on the display system 374. The control system 384 can receive input from the surgeon, receive imagery from cameras 378a and/or 378b, process the received imagery, and send the processed imagery to the display system 374. Functionality and capabilities of the image processing module 392 and image processing of the imaging surgical system 372 in general is described herein.

The control system 384 includes tracking module 394 configured to provide and track a location of the retractor 380 and/or the surgical tool 382 during use of the surgical system 370. The tracking module 394 can be configured to receive information from the sensors 398a, 398b, the sensor module 390, the image processing module 392, the user interface 376, and/or the tool control 376. The tracking module 394 can process this information to calculate a position of the surgical tool 382. The tracking module 394 can provide this information to the image processing module 392 for display on the display system 374. For example, the image processing module 392 can receive surgical tool 382 position information from the tracking module 394 and display the surgical tool 382 on the display system 374 such that the surgical tool 382 is rendered along with imagery of the surgical site in such a way as to provide situational awareness to the surgeon. Surgical tool 382 rendering is described herein with greater detail. The tracking module 394 can incorporate electromagnetic tracking information, EEPROM, radio-frequency identification ("RFID") information, accelerometer data, gyroscope data, and other such data to calculate a position of the surgical tool 382 and/or other components of the surgical system 370. In some embodiments, the tracking module 394 provides coarse position information of the surgical tool 382 to the image processing module 392 which can be configured to use the coarse position information to calculate fine position information based at least in part on imagery of the surgical tool 382.

The control system 384 includes lighting module 396 configured to control illumination of the surgical site. The lighting module 396 can control the lights and/or other sources of illumination 399a, 399b of the imaging surgical system 372 to provide sufficient illumination of the surgical site for the cameras 378a, 378b to acquire imagery of the site. In some embodiments, the lighting module 396 times or coordinates output of the lights 399a, 399b such that the lights do not directly illuminate one or more cameras 378a, 378*b*, as described herein in greater detail. The lights 399*a*, 399*b* can be LEDs or other such sources of visible, infrared, and/or ultraviolet light, as described herein with greater detail.

The imaging surgical system 372 includes retractor 380 and/or surgical tool 382, both of which are described in greater detail herein. The retractor 380 and/or surgical tool 382 can have sensors 398*a*, 398*b*, cameras 378*a*, 378*b*, lights 399*a*, 399*b*, and/or other elements (e.g., a heater) associated therewith each of which can be controlled using the control system 384, the user interface 376, the tool control 377, or other control mechanism.

The surgical system 370 can include a display system 374 configured to display information to a user or surgeon. The display system 374 is described herein with greater detail. The surgical system 370 can include a user interface 376 configured to receive input and provide feedback to a user. The user interface 376 can include physical elements configured to receive user input such as, for example, a multi-touch screen, buttons, keyboards, pointer device, switches, knobs, and the like. The user interface 376 can include a display configured to provide visual information to the user and to facilitate interaction with the surgical system 370 and control of the system 370. In some embodiments, the user interface 376 can be incorporated into the display system 374 such that it both displays information and receives user input. In some embodiments, the user interface 376 displays the graphical user interface on a separate display that is not a part of the display system 374. In some embodiments, the user interface 376 includes a touch screen interface and/or a gesture recognition system. The user interface 376 can be used to, for example, select imagery to view, zoom-in on imagery, and/or position imagery for display on the display system 374. In some embodiments, the surgical system 370 can receive input in the form of voice commands.

In some embodiments, the display system 374 and the user interface 376 can be combined in a way that allows the surgeon or other user to interact with displayed imagery. In some embodiments, the display system 374 is configured to provide an immersive experience for a user. For example, a virtual display can be used wherein the surgeon viewing displays through binoculars motions with his or her hand in a manner consistent with the imagery seen by the surgeon, and the surgeon's movements are detected. These movements can be mapped to actions that correspond to manipulating output imagery, cameras, surgical tools, or any combination of these. In some implementations, the binocular presentation can allow for three-dimensional information to be displayed to the user and the user can use hand gestures at the point in space where imagery appears to be to initiate a command. In some embodiments, the gesture recognition can be used in conjunction with a surgical tool 382. For example, the surgeon can remove the surgical tool 382 from a surgical field and move the tool 382 in such a way that the gesture recognition system correlates the movement to pointing, flicking, dragging, pointer control, and/or stylus functionality. The display system 374 can include image-based or electromagnetic-based motion sensors to detect the gestures of the surgeon. The tracking system used to track the tool, for example, may be used. Such a display system 374 and user interface 376 can allow for a surgeon to interact with the user interface 376 without potential contamination issues that may arise when using a touch-based user interface.

The user interface 376 can include a graphical user interface configured to facilitate interaction with the surgical system 370. The graphical user interface is described with greater detail below with reference to FIGS. 24 and 24B. In some embodiments, the display system 374 displays the graphical user interface 376. The user interface 376 can include the tool control 377 where the tool control 377 can be integrated into a unitary user interface 376 or the tool control can be a separate element of the user interface 376. The tool control 377 can be configured to receive input from a user to manipulate the surgical tool 382. Examples of the tool control 377 and associated surgical tools include those described herein with reference to FIGS. 34-53.

Video and Image Control and Processing

Surgical visualization systems described herein can include components configured to receive image data, process the image data and other data, and output video and/or images for display. The video and image processing functionality can be provided using any suitable combination of hardware, firmware, and software, such as but not limited to those described herein with reference to FIG. 14. For example, a surgical visualization system can include communication buses and/or interfaces to receive image data and one or more micro-processors, FPGAs, ASICs, or the like or combinations thereof that are configured to process received image data to provide output video for display. For ease of description, video and image processing will be described as being performed by an image processing system which can be any suitable system or component of a surgical visualization system that is configured to receive image data, process image data, and output video or images for display, such as for example the image processing module described herein with reference to FIG. 14. As part of the description, the image processing system is described as receiving and/or outputting imagery, images, and/or video. The processing of images described herein should be understood to be applicable to video. Any description of processing limited to either images or video should not be construed as limiting the disclosure of the functionality solely to images such as still images or video as video can be interpreted as a series of images. Likewise often the term video images or video image, feed or stream or simply images are used in connection with discussion of video.

In some embodiments, the surgical visualization system includes an image processing system configured to output a single image or video stream wherein the single output image is created from a plurality of input images. For example, the image processing system can be configured to receive a plurality of images from cameras associated with a retractor, a surgical tool, another surgical device, or any combination of these. The image processing module can be configured to combine the plurality of images into a single displayed scene. For example, the image processing module can be configured to stitch the images to create a single larger displayed scene by combining images from cameras where the images overlap. In some embodiments, one or more images may be superimposed on or shown forward the stitched image etc. For example, this configuration includes possibly picture-in-picture (PIP) as well as an arrangement of tiled images disposed on the stitched images.

Accordingly, the image processing module can be configured to stitch multiple images together to create a single image. Stitching images can provide a wider field of view or field. Stitching images can reduce or eliminate obscuration of a region of interest in the scene by a surgical tool or other device. Stitching images can reduce or eliminate albedo due at least in part to the multiple cameras in the surgical visualization system which provides the surgeon the ability to "look behind" protruding features, such as an aneurysm. Stitching images can reduce image artifacts such as vignetting caused by a retractor tube or blade. These same benefits may be obtained by other arrangements of a plurality of images from different cameras such as tiling images from different cameras.

The image processing module can be configured to adjust input images when stitching them together to provide a substantially seamless output image. In some embodiments, direct (e.g., pixel-by-pixel) or feature-based image processing can be used to align images where they overlap. Feature-based image processing can include aligning images based on features within the images. This can include image or shape recognition and matching to align the images. In certain implementations, a target structure with alignment features can be included in a field of view of one or more cameras to assist in feature-based alignment methods. Such a target structure may be provided during initial set-up. The target structure can also include white-balancing features, as described in more detail herein. The target structure may be included on the retractor, might be a component added to the retractor during initialization, or may be a feature of a base, pod, station, or other platform in which or on which the retractor is attached, e.g., rests, during an initialization phase. Similarly, pixel-by-pixel alignment processing can be used, for example, in conjunction with position and orientation information to align pixels based on pixel features to stitch the images together. In some embodiments, stitching images can be simplified where the cameras are identical or have identical sensors, where the relative positions and/or orientations of the cameras are known with relative precision (such by using memory devices or tracking systems as describe above), and their distance to the imaged scene is substantially the same. In some implementations, the cameras can be positioned near a non-planar scene, or a scene that is not flat, and non-linear transformations can be used to stitch images. In some implementations, it may be preferable to use centralized cameras, or cameras that provide imagery of a central portion of a scene (where central can be relative to the output image), as reference images in stitching to reduce cumulative errors across an output image when compared to using a peripheral image as a reference.

When stitching images, several techniques can be used to blend overlapping regions of images to provide a substantially visually seamless output image. For example, the image processing system can implement an algorithm to blend image intensities at the seams of stitched images. The algorithm can include blending images using center-weighted averaging (or feathering) wherein pixels near the center of the image are weighted more heavily than pixels near the edge. The algorithm can include using Laplacian pyramid blending and gradient blending to address differences in gain between images at the seams which can result in less blurring than center-weighted averaging. The algorithm can include averaging in the radiance domain appropriate typically where gain differences between images are relatively large. In some embodiments, the image processing system is configured to perform affine transformations on received imagery.

Figure 18:
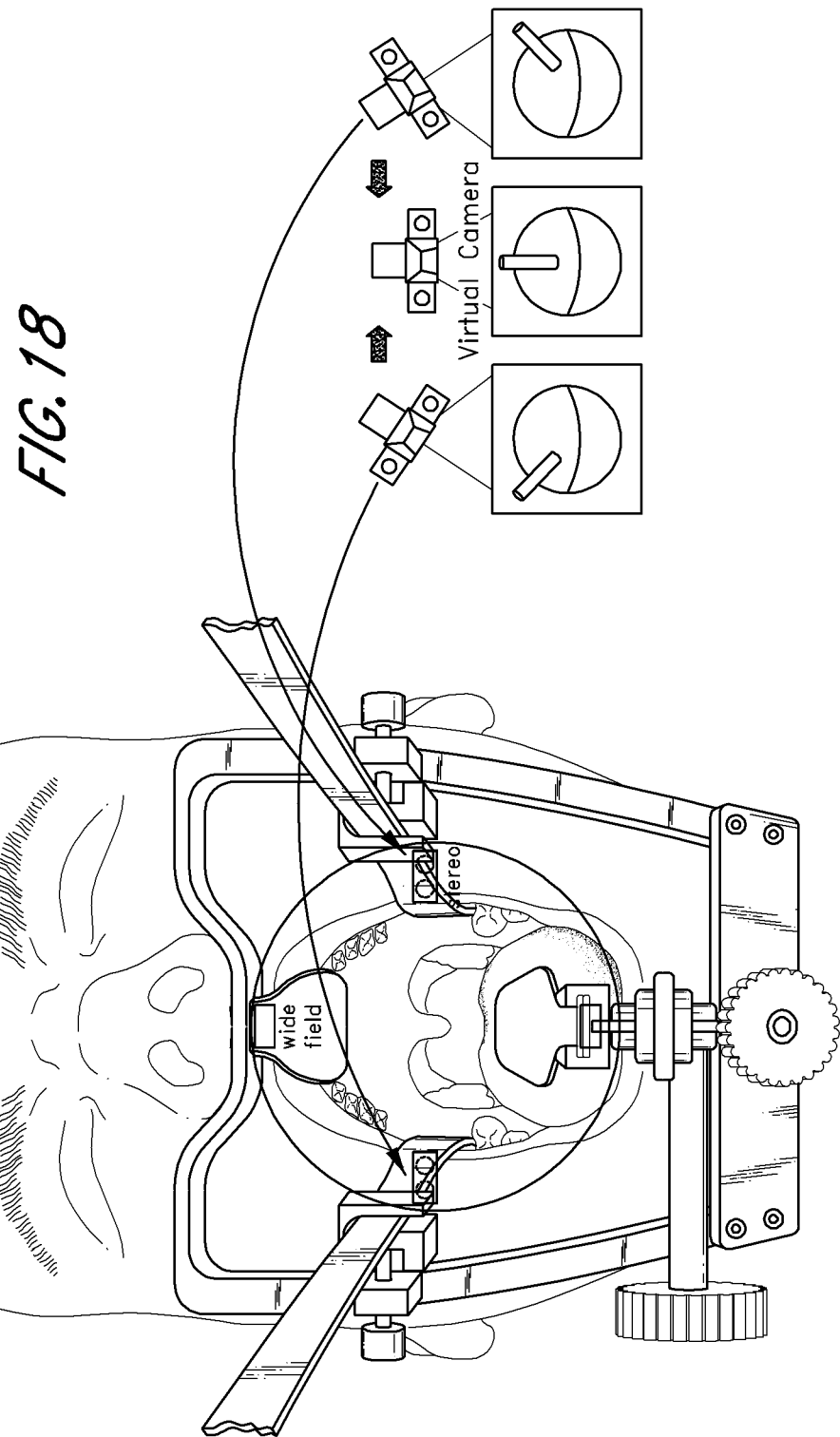
FIG. 18 shows an example of using two or more cameras to create a morphed image to provide a central view of a surgical site.

The image processing system can be configured to morph multiple images from cameras having different viewpoints to create a single image of a scene wherein the single image appears to include a viewpoint that may differ from the viewpoints of the cameras. For example, the image processing system can receive a first image of a region of interest from a first viewpoint and a second image from a second viewpoint of a region of interest and generate intermediate images from viewpoints that lie between the first and second viewpoints. For example, as illustrated in FIG. 18, left and right cameras can be combined to provide a central view from a virtual camera. This approach can be performed for any pair of cameras that image a common region. In some embodiments, more than two cameras are used to reduce or eliminate peripheral ambiguities related to imaging 3-D scenes. This technique can provide, for example, a central view of the surgical site without a central camera, microscope, or endoscope. This technique can be used to simulate camera movement, to provide image data from a viewpoint that is not physically accessible but desirable, to increase image information of a region of interest, or any combination of these. Image morphing can, for example, be accomplished using standard techniques that are known in the art.

The image processing system can be configured to display multiple images as individual images where the multiple images are tiled. The tiled images can be purposely tilted and/or distorted based at least in part on an orientation of the camera providing the images. The tiled images can be presented with borders around each image or groups of images. Tiling images can be differentiated from stitching or morphed images because tiled images are not combined to form a unified image of an area of interest or object of interest. However, in some implementations, images can be stitched or morphed and these stitched or morphed images can be output as tiled images. For example, these morphed or stitched images can be included together with other images in a tiled fashion.

In some embodiments, positions of cameras can be provided to the image processing system to be used when stitching, morphing, or tiling images from the cameras. In certain implementations, the cameras can have relatively fixed positions, such as when the cameras are associated with a tubular spine surgery retractor. The positions of the cameras can be communicated to the image processing system using any tracking systems and/or memory storage devices (e.g., where the positions of the cameras are fixed). For example, EM or optical tracking, one or more inertial measurement units (IMUs), EEPROMs and/or RFID tags, associated with the retractor, surgical tool, and/or with the cameras may be used. In certain implementations, for example, the cameras can have EM trackers, optical trackers, IMUs etc., which communicate their positions and/or orientation during setup to the image processing system. Such information is especially useful if the camera is movable and the camera is reoriented during set up. In some implementations, RFID or EEPROM technology can be used to communicate information about camera field-of-view, resolution, quantity of cameras in use and possibly location and/or orientation. The image processing system can use this tracking information to assist in aligning the images from the various cameras to improve and/or facilitate stitching, morphing, and/or tiling images. In some implementations, the tracking information can provide a coarse position of the cameras and their relative pointing angles, and the image processing system can use this information to calculate a transformation for each received image to stitch them together to provide a substantially seamless display of stitched images. The image processing system, also, can provide greater detail about the positions and/or orientations of the various cameras to the surgical visualization system. Even if the images are not stitched, the images can be arranged in a manner that is consistent with the arrangement and location of the cameras in the surgical field, e.g., on the retractor or their respective field-of-views.

The image processing system can be configured to combine images from a plurality of cameras to virtually enhance capabilities of the cameras in the surgical visualization system. For example, the image processing system can create an image of an area of interest having enhanced resolution by combining multiple images of the area of interest. As another example, the image processing system can create a virtual camera having an increased dynamic range by combining image data from cameras having differing gains.

In some embodiments, the image processing system can be configured to combine multiple substantially overlaid images to output a single image having a higher resolution than any of the multiple images. In certain implementations, enhancing the resolution in this manner results in an output image where the number of pixels per unit area imaged is greater for the output image than any of the multiple images. In certain implementations, the multiple substantially overlaid images are provided by multiple cameras having fields of view that substantially overlap. In some embodiments, images from cameras having different gain are aligned to provide an aggregate image having increased dynamic range.

The image processing system can be configured to provide electronic zoom and/or magnification using image data from a plurality of overlapping cameras. In some embodiments, cameras can be positioned at differing distances from an area or object of interest. As a result of these differing positions, differing views and/or magnifications of the area or object of interest are provided by the cameras. In some embodiments, electronic zoom may be used to normalize magnification levels. For example, images from cameras at different positions can have different magnifications and the image processing system can electronically adjust magnification levels when, e.g., stitching, tiling, and/or morphing the images prior to outputting the images. In some embodiments, the image processing system super-positions images to permit electronic magnification of objects to yield better quality and/or similar-sized images of an area of interest for display. In some embodiments, images that are overlapping can be electronically magnified such that the resulting magnified images provide adjacent views rather than overlapping views.

The image processing system can also utilize the differing magnifications resulting from cameras located at different distances to electronically zoom imagery of an area or object of interest. These varied levels of magnification can also be used by the image processing system when morphing images. Cameras that are closer to the area or object of interest present imagery having increased resolution of the area or object of interest which can be advantageous for electronically zooming. The image processing system can use this information to provide electronic zoom capabilities and magnification capabilities. In some embodiments, the image processing system uses superposition of images having differing levels of magnification to provide electronic zoom capabilities based at least in part on the different magnification levels. Accordingly, in some embodiments, the image processing system provides a zoom feature for magnification over an array of cameras having unequal or equalized image magnifications. In some embodiments, the image processing system rotates images to enable this variable magnification and zooming capability.

In some embodiments, the image processing system can use camera location information to create a distance guide (e.g., a look-up table) to magnify or de-magnify images corresponding to an area of interest. In some embodiments, the image processing system can use the location information to calculate a magnification of a camera and use this information when combining images from multiple cameras having differing magnifications. In some embodiments, the image processing system can be configured to present images from cameras with different levels of magnification to represent differing distances from an area or object of interest, for example when tiling or with picture-in-picture.

In some embodiments, cameras can include MEMS technology to provide zoom functionality by moving and/or positioning the camera optics. The zoom functionality can be used to alter magnification of the images acquired by a camera. The surgical visualization system can include modules and systems that provide feedback to the cameras such that the camera changes magnification levels by changing a focal length or zoom of the camera. For example, the tracking module can provide information about the position of the surgical tool to the image processing system and the image processing system can provide feedback to the camera to alter its magnification factor according to the surgical tool's distance from a targeted tissue site. Similarly, in some embodiments, cameras can include MEMS technology to provide focusing functionality by moving and/or positioning the camera optics. The focus functionality can be used to change a focal length of the camera optics to account for distance to a targeted site. For example, if the depth of focus of a camera on a surgical tool is not sufficient to maintain focus of targeted tissue when the position of the surgical tool changes, the MEMS system can change the focus of the camera. Thus, as described herein, the surgical visualization system can include methods of electronically zooming and methods of physically zooming cameras.

In some embodiments, the surgical visualization system can include cameras at different locations within a surgical site, and particularly at different depths within the surgical site. The image processing system can use the varying depths of field from the cameras at different depths to increase an output depth of field to provide focused imagery of a greater portion of the surgical site. For example, a retractor can have two or more cameras or camera pairs at two or more longitudinal distances along the length of the retractor (e.g. proximal and distal) and the cameras at each level can provide image data to the image processing system. For example, a retractor can have two or more rings or arrays of cameras (e.g. proximal and distal) located on the retractor so as to provide different distances to the same object in the surgical site. The proximal cameras may provide a main larger field of view of the area in the surgical site and the distal cameras may provide a closer-up view(s). The image processing system can combine overlapping image data to provide an output image having a greater depth of focus. An example of a system with cameras located at two depths or longitudinal positions along the length of the retractor is illustrated in FIG. 21. Locating cameras at varying distances in the surgical site may potentially provide for increased situational awareness. Locating cameras at varying distances and positions can provide for continuous viewing of a surgical site, and, in some embodiments, the continuous viewing can be provided without a need for repositioning cameras during surgery. For example, where tools or work obscures one or more cameras, imagery from non-obscured cameras can be utilized to provide a view of the surgical site.

In some embodiments, image processing can be used to track a position and/or orientation of a surgical tool. For tracking, the surgical tool can include distinguishable or identifiable coloration, patterns, markings, etc. such that the image processing system can identify the surgical tool, calculate its position within the surgical site, and/or calculate an orientation of the surgical tool.

In some embodiments, the image processing system receives imagery data from one or more cameras positioned on a retractor and processes this information to identify the surgical tool and prepares a video or image with a model of the surgical tool positioned and/or oriented within the image to represent the position and orientation of the surgical tool. For example, optical tracking of the surgical tool can be accomplished using cameras positioned on a frame of a retractor wherein the surgical tool includes, for example a pattern, e.g., a greycode possibly applied using laser marking with a known pattern around the tool axis. The image processing system can process the images from the cameras to identify the greycode on the surgical tool. Using this information and possibly additional information from one or more other tracking systems or stored data, the image processing system can identify a location and/or orientation of the surgical tool within the surgical site.

Accordingly, in some embodiments, a displayed image can be related to a position of the surgical tool. The image processing system can receive tracking information and/or it can extract position information from imagery and configure the output imagery (e.g., position or orient the image relative to a background image or other imagery being displayed) that corresponds to where the surgical tool is currently positioned. The image processing system can be configured to track movement of the surgical tool and integrate this information to smoothly track a position of the surgical tool on the display (e.g., by changing output imagery such that imagery of the surgical tool is presented, for example, as centered on the display system or has a changing location with respect to the background or wide field of view main view remains generally still). The image processing system can also change what images are displayed, for example, tiled, depending on the location of the surgical tool. The image processing system can establish, for example, a centroid of movement for the surgical tool and based on this centroid it can determine whether a movement can be ignored or followed. Such a decision can be based at least in part on dimensions of the surgical site and/or the retractor in use. In addition, the image processing system can be configured to ignore movements that are outliers compared to the centroid distribution, such as when the surgical tool is completely removed from the surgical site.

In some embodiments, the image processor can output imagery of the surgical site wherein the output imagery includes a rendering of the surgical tool positioned and oriented within the surgical site according to a measured position and/or orientation. In some embodiments, the rendering of the surgical tool can have a level of opacity that can vary from being completely transparent to being completely opaque and include varying levels of partial transparency/partial opacity therebetween, as described in more detail herein. In some embodiments, the surgical tool can be rendered, e.g., in a picture-in-picture, in a display, as described herein wherein the surgical tool can have a configurable level of transparency (e.g., the surgical tool can be presented as opaque or semi-transparent). By presenting the surgical tool with a level of transparency, a user can view underlying imagery of a surgical site. The transparent rendering described herein can help to overcome a problem in surgical visualization systems where a surgeon's view of the surgical site is obscured by the surgical tool. This functionality can be provided where multiple cameras acquire images of the surgical site from multiple viewpoints or using a single camera with the position of the surgical tool provided by a tracking system. To provide a rendering of the surgical tool, a computer model (e.g., a CAD model) of a surgical tool can be loaded into the surgical system during initialization or at some other point prior to surgery. In some embodiments, the user can select whether to display the rendering of the surgical tool. In some embodiments, an icon, graphic, or indicator can be provided on a graphical user interface that allows the user to control the rendering of the surgical tool, such as to choose a level of transparency and whether to display the rendering.

FIGS. 15 to 17 illustrate example display outputs of the image processing module, suitable for sending to a display system. In some embodiments, the image processing module can be configured to receive video from the plurality of cameras at different positions, process the received video, and output the processed video to the display. The output video can be stitched, tiled, superpositioned, or otherwise combined on the display. The arrangement and/or configuration of the output video can be automatically produced, manually configured, or both. In this way, the surgical visualization system can be configured to display video from multiple cameras for simultaneous viewing. In some embodiments, the display system can be configured to receive processed video from the image processing system and position the output video appropriately with respect to each other for display.

As illustrated in FIG. 15, the surgical visualization system can include one or more proximal cameras configured to provide a relatively wide field of view of a surgical site. This can provide a background or main view on a display showing the surgical site. The wide field perspective can provide to a surgeon a frame of reference for various areas or objects of interest to enhance a surgeon's situational awareness. In certain embodiments one camera or camera pair can be to provide the background or main view. In some embodiments, however, the image processing system can provide a wide field of view, for example, by stitching and/or morphing monocular wide field of view camera data, for example, from multiple, e.g., proximal cameras. In some embodiments, the surgical visualization system can include one or more, e.g., proximal (or distal), cameras configured to provide stereo imagery of at least a portion of the surgical site, wherein the cameras acquiring stereo imagery can have a field of view that is less than the field of view of the wide field of view cameras. The image processing system can provide stereo data from adjacent proximal (or distal) cameras or a two-dimensional sensor array with left and right portions dedicated for left and right eye (e.g., each with its own imaging optics) and can super-position the stereo data on the wide field of view or background view. Accordingly, in some embodiments, the display can include a central stereo image overlaid on a wide field of view background image providing peripheral vision information. In some embodiment the wide-field of view background or main view can be stereo and formed from images from proximal (or distal) cameras. Images from the stereo cameras can be displayed on separate displays (e.g. one for each eye) or on the same display (e.g., which is visible to the left and right eye at different times) to create a 3-D visual effect, as described in more detail herein.

As illustrated in FIG. 16, the surgical visualization system can include one or more distal cameras providing other, possibly smaller, fields of view of the surgical site, where the distal cameras are positioned further within the surgical site. In some embodiments, the distal cameras are configured to provide oblique or side video of the surgical site and can be displayed as tilted to help the surgeon visually interpret the video they provide, such as by providing depth clues to the surgeon. In some embodiments, the video received from the distal cameras can be stitched, tiled, tilted, or otherwise processed and displayed overlaying or overlaid with the video from the proximal wide field of view imagery and/or the proximal stereo imagery.

In some embodiments, a plurality of the distal (or proximal) cameras, if not all, are directed at substantially similar inclinations with respect to the surgical device (e.g., retractor) with which they are associated. In some embodiments, the distal (or proximal) cameras are directed normal to an axis of the surgical device. For example, the retractor may have the shape of a right circular cylindrical and have an axis through the center of the circular cross-section. The cameras may be directed toward each other and normal to this axis. Alternatively, the cameras may be directed downward into the surgical site not normal to this axis. The plurality of distal cameras, however, may have substantially similar inclinations or declinations with respect to the axis. In some embodiments, the inclination or declination with respect to the axis can be less than or equal to about 30 degrees, less than or equal to about 45 degrees, less than or equal to about 70 degrees, and/or less than or equal to about 110 degrees. In some embodiments, the inclination or declination with respect to the axis can be greater than or equal to about 0 degrees, greater than or equal to about 30 degrees, greater than or equal to about 45 degrees, and/or greater than or equal to about 70 degrees.

In some embodiments, a display of information from distal cameras can be activated according to criteria. For example, initially the proximal camera(s) may be activated and images produced by these proximal cameras displayed. When a tracked surgical tool is inserted into the patient and is at or near a proximal camera at a beginning of a procedure, monocular side views provided by the distal cameras can be displayed on either side of the central stereo view in the display, as illustrated in FIG. 16, to provide the surgeon with views of where the tool is to be placed. In some embodiments, the views provided by the distal cameras can be displayed as tiled images. Additionally as the surgeon or user proceeds deeper within the surgical site, the distal camera views can provide oblique views, and as appropriate, can be viewed in tiled or stitched form on either side of the central stereo view in the display. Cameras on the tool may also provide video that may be displayed. A central view of the display can comprise imagery from cameras on the tool or distal cameras and can be configured to switch between sources of imagery for the central view. In some embodiments, camera location information, camera calibration information, and/or area of interest distance and location can be sent to the image processing system. This information may be useful for unwrapping, purposefully distorting, electronically magnifying or de-magnifying a series of images. Such processing may enable a multi-camera viewing display to adjust various fixed camera magnifications and locations within an image. This processing may thereby assist in producing tiled or stitched images where the surgical site is substantially centrally located within a field of vision on the display. The processing may also provide an array of views from distal cameras adjacent to a stereo view from the proximal cameras.

Such processing may be employed as well when a user selects one or more camera views. For example, a plurality of thumbnails or windows presenting the video feed or icons representing the video feed from a plurality a cameras may be shown on the display, for example, off to the side of the screen. The user may select from these, for example, by clicking on the icon or thumbnail or enlarging the thumbnail or window. The user may also potentially move these more central video feeds and/or arrange these video feeds in some fashion such as in a manner consistent with the geometric arrangement of the camera or cameras with respect to each other and/or the retractor or surgical site. In some embodiments, when the user identifies a plurality of icons, thumbnails, and/or windows the processor automatically arranges the corresponding video feed in such a geometric arrangement. The user may select video feeds/images from a subset of the total number of cameras on the retractor and/or tool. One or more images may be used as a background over which other images are shown, e.g., as PIP or in a tiled arrangement. The user can for example identify one streaming video window, icon, or thumbnail to be used as the background image. This may be a wide field of view camera or a surgical microscope view (as discussed below). In some embodiments, multiple images are stitched together to obtain this background view. In various embodiments the background view is larger than the tiled or PIP image and may include substantially the entire view provided by the process such as at least 75%, 80%, 90%, 95% or 100% of the screen. In some embodiments, the processor selects which image to show as background. The user may for example identify a plurality of images (e.g., by selecting windows or thumbnails displayed on the display) and the processor may show as default one of those images as a background image.

In various embodiments, the display may show a first image or video stream or feed enlarged on the screen, for example, such as at least 75%, 80%, 90%, 95% or 100% of the screen. The user may select a second video from another camera by identifying a streaming video window, icon or thumbnail corresponding to the other camera. The user may enlarge the image from that other camera. The processor may automatically reduce the first image or remove the image altogether when the user enlarges the second image to a certain size. This threshold size may be for example least 75%, 80%, 90%, 95% or 100% of the screen. The user may set this threshold size and/or the processor may have a threshold size for this function. Similarly, the user could select a third video image by identify another camera and by enlarging the images beyond the threshold, the user could cause a window corresponding to the second image to close or be reduced to a thumbnail. The video stream window, icon, or thumbnail for that second image as well as for the first may be available for the user to identify (e.g., by clicking on or enlarging) and to enlarge as a background image. In some embodiments any of these images may be used as background for one or more other images, for example, that are each less than 75%, 80%, 90%, 95% or 100% of the screen. These smaller images may be shown PIP or tiled in front of the other image which is used as background. A wide variety of other capabilities may be integrated in the graphic user interface. In various embodiments, however, the user has the ability to select one or more cameras, represented by icons or thumbnails or windows which show video streams from the cameras, and enlarge and or reposition the images provided by those cameras. The user may, for example enlarge and/or position those images more prominently and/or more centrally on the display. The user may arrange the images if images from a plurality of cameras are selected. In some embodiments the processor may automatically (at least as a default) position and/or enlarge to a specific size images that are selected by a user. In some embodiments, a user can select a first video window on a first display and send the first video window to a second display. This can make the system swap the videos such that the video that was previously displayed on the second display is displayed on the first display and vice versa. In some embodiments, this functionality is configured to provide a quick-switching functionality to easily and quickly switch between video feeds. In some embodiments, a mode can be provided wherein by selecting the first video window on a first display, the first video window is sent to a second display; however, the video on the second display remains on the second display together with the first video. The user may select which mode by providing different input, for example, clicking versus double clicking, etc.

Figure 19:
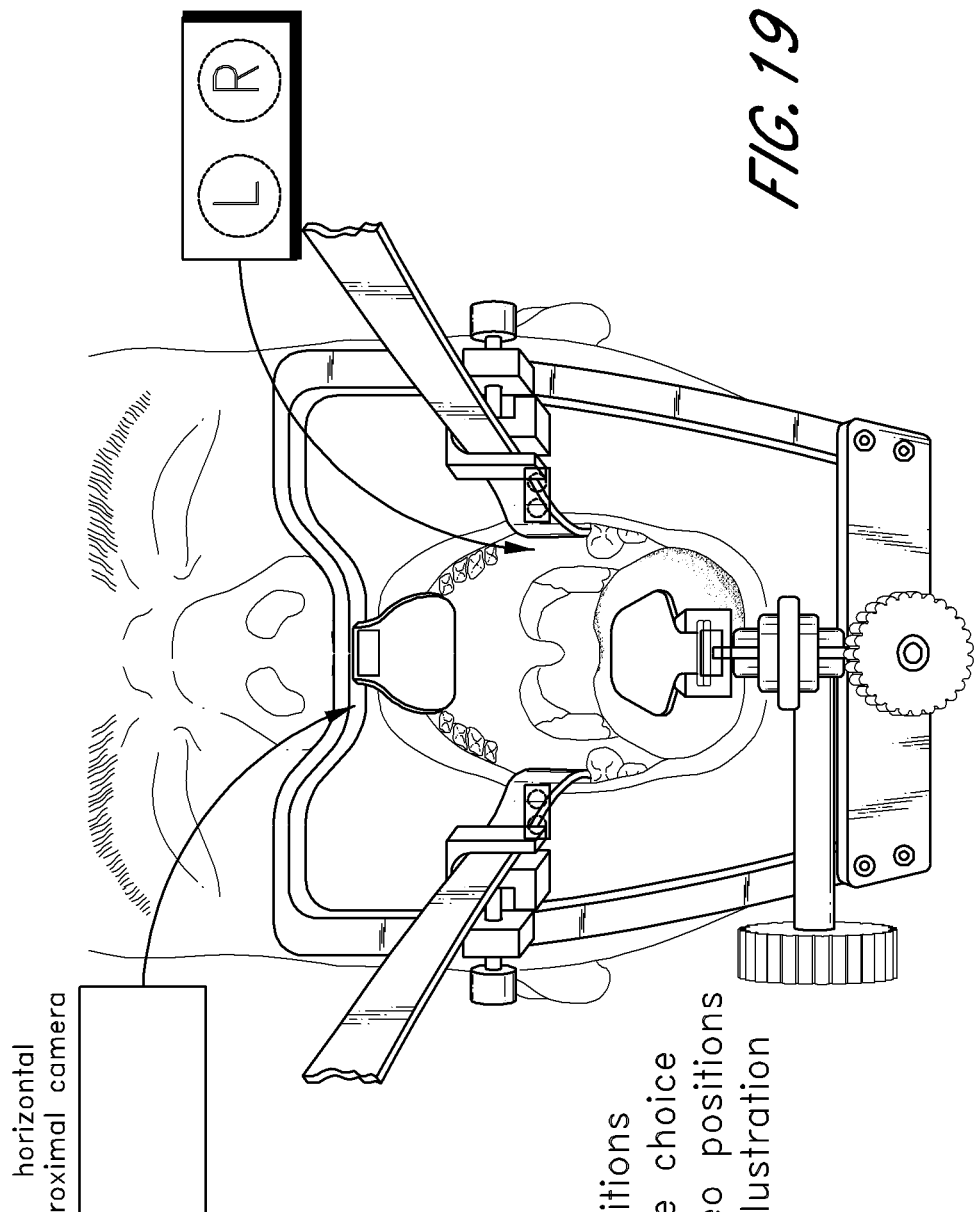
FIG. 19 shows an example configuration of proximal cameras that provide a wide field view and a stereo view.

FIG. 19 illustrates an example configuration of proximal cameras that provide a background or main view and a stereo view. FIG. 19 shows the camera views provided by the camera which may be disposed on the retractor and include a turning mirror such as provided by a prism (e.g., a right angle prism) or other optical element that redirected the image. Such an optical element may be a reflective surface angled, for example, at 45° or other angle with respect to the detector array of the camera. FIG. 4C shows an example of such an optical element configured to turn the optical path. Other types of optical elements such as prisms having multiple reflections can be used to redirect or turn the light. FIG. 21 also shows a tubular retractor having an optical design configured to turning the optical path downward into the surgical site and yet provide a low profile. In particular, using such an optical element such as a turning mirror or prism or other optical element configured to suitably redirect the optical path, may provide the desired camera view while reducing the profile of the camera that would otherwise potentially introduce obstruction and reduce access for surgical tools to the surgical site by the retractor.

The background or main view provided by the camera(s) shown in FIG. 19 can have a relatively larger field of view compared to the stereo field of view and imagery from the cameras, which can be displayed together (e.g., tiled, stitched, and/or via picture-in-picture). Any number of proximal wide field of view and/or stereo view cameras can be used to provide a desired image quality and display capabilities.

The image processing system can be configured to receive image data from proximal and distal cameras having various positions and/or orientations. The image processing module can tile these images for display wherein tiling can include outputting the images without stitching them together. The image processing system can tile the images based at least in part on a region being imaged, a field of view of the camera, camera position, a selection by a user, automated criteria, or any combination of these. A size and/or position of tiled images output to a display can be based at least in part on a field of view, a region being imaged by the camera, camera position, a relative importance of the imagery, a selection by a user, an automated placement, or some combination of these or other criteria. In some embodiments, the image processing system receives camera position and orientation information and uses this information to tile images according to regions the cameras are imaging. In some embodiments, the image processing system processes the imagery to magnify, de-magnify, distort, tilt, or otherwise transform the image prior to tiling the images for display. In some embodiments, the image processing system provides images to the display system which tiles the images on the display according to user selection and/or other criteria. In some embodiments the image processing system provides cues to the view so that the view can readily ascertain the orientation of the cameras. The images may, for example may be modified (e.g. distorted) or a symbol (e.g., an arrow) may be included to show the direction downward into the surgical site. In some embodiments, video data can be received from three or more cameras. A user can select at least two of these cameras for simultaneous viewing. The video from the selected cameras can be presented to the user and in some embodiments the image processing system can arrange and/or orient the video according to physical arrangement of the cameras, fields of view of the cameras, user configuration settings, or the like. The non-selected cameras can be configured to still provide video data to the system, and the video from the non-selected cameras can be obscured, hidden, dimmed, made transparent, or some similar effect or may be located non-centrally (e.g., placed moved off to the side or to another display) so that the video from the selected cameras is more prominent in the display.

The image processing system can be configured to output stereo image data using various methods. In some embodiments, images from one or more cameras designated as "left" cameras can be displayed on a "left" display or on a portion of the display system designated as a "left" portion, which are viewed by the left eye and not the right, for example, via the left ocular. Similarly, images from one or more cameras designated as "right" cameras can be displayed on a "right" display or on a portion of the display system designated as a "right" portion which are viewed by the right eye and not the left, for example, via the right ocular. Selective viewing of the left and right images by the left and right eye provides the three-dimensional effect. Accordingly, this method can provide stereo viewing on the display system for the surgeon. Similarly, as illustrated in FIG. 15, a divided sensor can be used to acquire stereo data. The appropriate imagery can be displayed on a left-eye display panel and a right-eye display panel. In this way, a right-eye and left-eye view is provided in real-time and the viewer fuses the images in their mind to create a 3-D effect. In some embodiments, the image processing system can process stereo data to output 3-D images to be displayed on a single monitor or display capable of presenting 3-D images. Such displays may, for example, modulate between the left and right image and selectively modulate the oculars through which the viewer sees the display, coordinating the passage of light through the left ocular and blocking of the right ocular at the same time that the display shows the left image. Likewise, the display may coordinate the passage of light through the right ocular and blocking of the left ocular at the same time that the display shows the right image.

In some embodiments, stereo data can be overlaid on a background or main view provided by a relatively wide field-of-view camera or cameras. The non-stereo images would be displayed at the same time by both left and right displays or/and at the same time through both left and right oculars. Accordingly, while the stereo portion of the images would be different for the left and right display or images, the non-stereo portions would be the same.

In some embodiments, the field of view of the stereo camera or cameras is less than total vision width (e.g., about 170 degrees horizontal and about 110 degrees vertical) and can be less than or equal to about 60 degrees, less than or equal to about 50 degrees, less than or equal to about 30 degrees, between about 30 degrees and about 60 degrees, and/or between about 50 degrees and about 55 degrees full width half maximum (FWHM). In some embodiments, the field of view of monocular cameras providing a wide field of view can be at least about 70 degrees and/or less than about 120 degrees, at least about 90 degrees and/or less than or equal to about 110 degrees, or at least about 70 degrees and/or less than or equal to about 90 degrees FWHM.

The image processing system can be configured to process images from a surgical tool and/or images of the surgical tool to provide output imagery that enhances or improves a surgeon's situational awareness. In some embodiments, cameras associated with a surgical tool can move during surgery and their position and/or their orientation can be transmitted to the image processing system to enable an output display of a close-up of tool-tissue interaction. This output display can be stitched with other imagery from other cameras or it can be provided as its own video stream or imagery such as picture-in-picture or via tiling. The output can be, for example, displayed as a picture-in-picture overlaid on a central scene such as the main or background view where the picture-in-picture display provides a magnified view of a targeted site. This picture-in-picture view can be enlarged or magnified to provide visual feedback to a surgeon to enhance the surgeon's ability to manipulate the surgical tool in a desired fashion. In certain implementations, an orientation of the picture-in-picture display can remain unchanged throughout the surgery, regardless of any change in orientation of the surgical tool. In such implementations, the image processor may reorient the image based on input from tracking sensors (e.g., IMUs) on the tool so that picture-in-picture image does not move as the tool is moved. In certain implementations, the orientation of the picture-in-picture display does change, for example, with rotation of the surgical tool.

In some embodiments, a portion of the surgical tool may be in view of cameras positioned on the retractor during surgery. To reduce or eliminate obscuration of the surgical site due at least in part to the surgical tool, the image processing system can process images from the cameras to output imagery of the surgical site having a variably transparent surgical tool displayed thereon rather than including imagery of the surgical tool itself. For example, a portion of the surgical tool within view of the cameras can be rendered based on CAD models of the tool and 6-degree of freedom tracking information. By providing this variably transparent tool representation, a trajectory of the surgical tool can be monitored on the display system while the tool is being manipulated. In some embodiments, the image of the tool as seen by cameras can be colored in a partially transparent manner when displayed over other views provided by other cameras. The transparency will permit the other camera views to show through and reduce the obscuration provided by the tool.

In some embodiments, a camera view from a side that is left (right) of the surgical tool, from the point of view of the surgeon, can be used to reduce or eliminate tool obscuration for right-handed (left-handed) surgeons. This can be done to reduce tool obscuration which can cause retinal rivalry where the surgeon is right-eye (left-eye) dominant. Accordingly, in some embodiments, the user can select a mode, in this example, right hand mode (or left hand mode) and the image processing modulate may select which images to display based on that mode selected without the user necessarily specifying the cameras and/or images.

FIG. 17 illustrates an example display incorporating image data from proximal and distal cameras, as in FIG. 16, along with a picture-in-picture view of imagery acquired by a camera associated with a surgical tool. The image information from cameras associated with the surgical tool can, for example, be displayed overlaid on the main or background image provided by proximal wide field of view cameras. The picture-in-picture presentation can be in stereo or it can be monocular. In some embodiments, the picture-in-picture display is presented with a different magnification or zoom than the background or main view. In some embodiments, the picture-in-picture display has a level of opacity that allows the surgeon to view image data displayed underneath the picture-in-picture.

As discussed above, the cameras can be arranged and positioned to produce an image of the surgical field having vertical and horizontal directions the same or substantially the same as the vertical and horizontal directions that the surgeon associates for the surgical field. If the cameras are not positioned correctly, the image of the surgical field may be rotated on the display such that vertical and horizontal directions on the display do not correspond to vertical and horizontal directions that the surgeon associates with the surgical field as oriented for the surgical procedure. Incorrect positioning or excessive rotation (e.g., greater than 30°) of the surgical field with respect to the vertical and horizontal directions on the display can decouple hand-eye coordination.

Figure 20A:
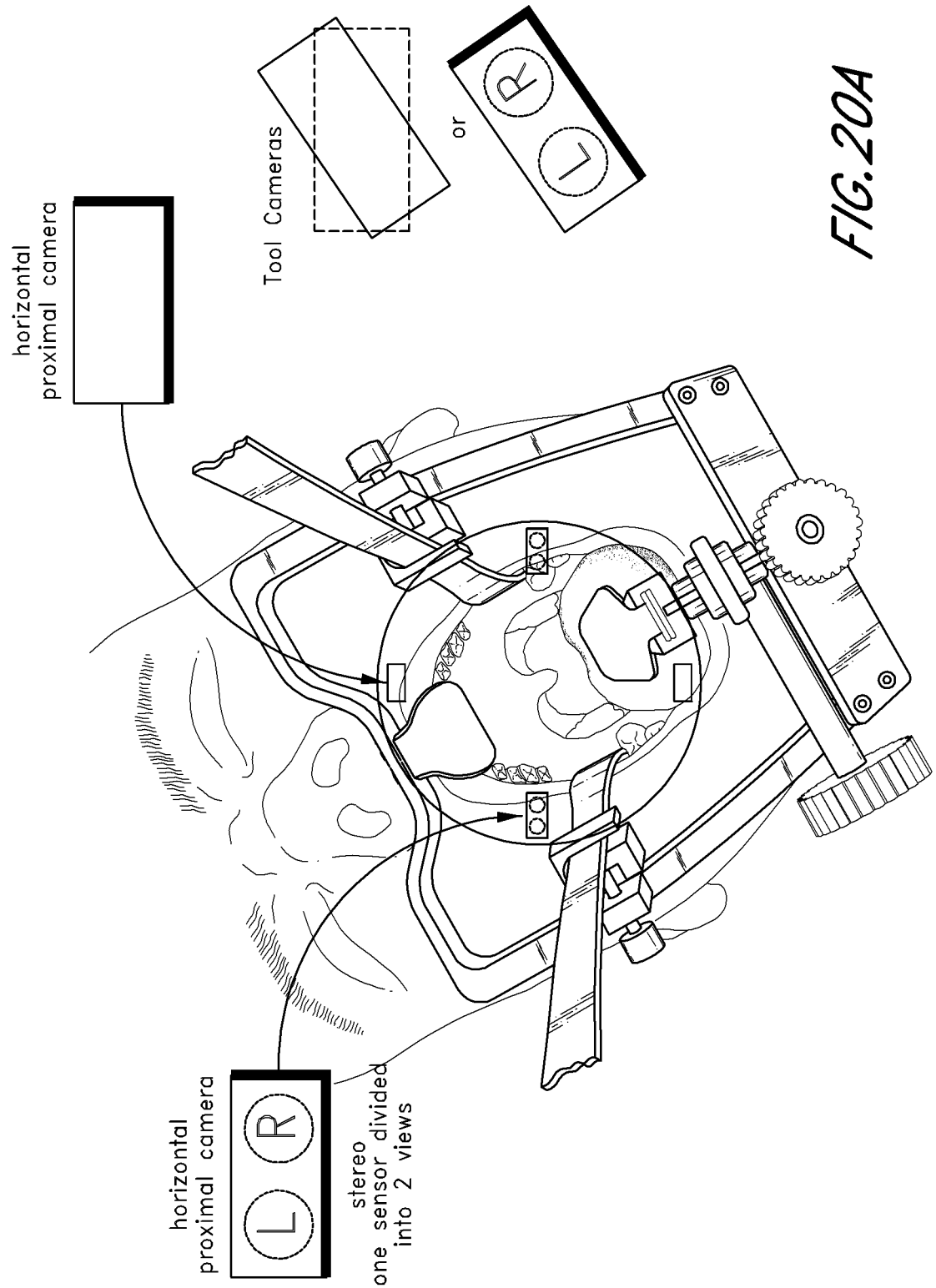
FIG. 20A shows an example configuration of proximal cameras that maintain a desired alignment relative to the gravity vector (a direction associated by the surgeon as opposite to the top of the surgical field as viewed from above the patient's body) as well as shows rotating or not rotating imagery from a camera associated with a surgical tool.

Accordingly, in various embodiments, the image processing system can display images such that the horizon of the displayed images from the cameras on the retractor remains substantially parallel to the horizon of the acquisition system. In some embodiments, the image processing system rotates and/or repositions acquired images such that the display horizon is parallel to the acquisition horizon which is typically perpendicular to the gravity vector, or in other words, the acquired images are displayed in an upright orientation relative to the horizon. As illustrated in FIG. 20A, in some embodiments, the surgical visualization system includes a horizon mechanism that rotates to maintain a substantially consistent orientation relative to gravity such that acquisition and display horizons remain substantially parallel with little or no image rotation performed by the image processing system. In some embodiments, the horizon mechanism can include a camera ring associated with the retractor that can be rotated while viewing a sterile alignment and/or white balancing target to address any alignment issues before performing surgery. In some embodiments, imagery from cameras associated with a surgical tool can be rotated when the tool is rotated or they can remain horizontal upon tool rotation, as illustrated in FIG. 20A.

Figure 20B:
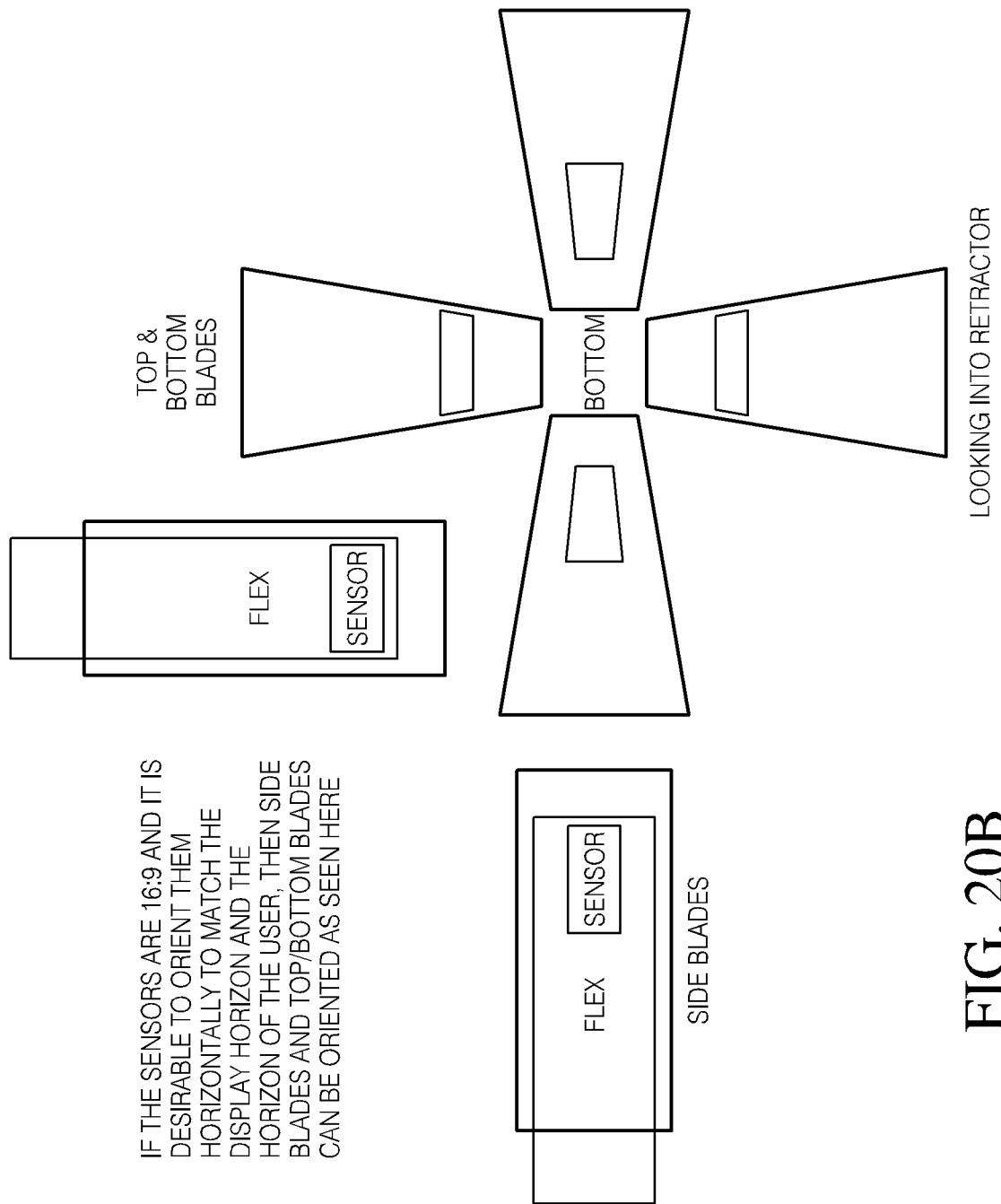
FIG. 20B shows an example configuration of optical sensors mounted on retractor blades to maintain a consistent horizon between a horizon of acquisition, a horizon of display, and a surgeon horizon.

In some embodiments, a visual axis line (the line that is perpendicular to both the visual axes of the surgeon's eyes) can be parallel to a stereo sensor line (the line perpendicular to both the optical axes of optical sensors providing stereo information). For example, if a z-axis is defined as an axis that generally runs along a spine of a standing surgeon (e.g., the z-axis is parallel to the gravity vector), the visual axis line and the stereo sensor line can be configured to be parallel lines when they are projected onto a plane perpendicular to the z-axis. This allows the visual axis line, the stereo sensor line, or both to rotate about the x-axis, the y-axis, or both (in a Cartesian coordinate system) while maintaining a desired parallel relationship. This parallel relationship can be useful to reduce disorientation of the surgeon when viewing imagery on a display where the imagery is displayed such that the z-axis of the surgeon and the z-axis of the displayed imagery are parallel. In some embodiments, as illustrated in FIG. 20B, the sensors can be oriented on retractor blades in a parallel fashion (in FIG. 20B, gravity would be a vector pointing into the page). The sensors on the top and bottom blades can be configured to provide monocular or stereo imagery, and the sensors on the side blades can be configured to provide monocular imagery. In some embodiments, the top and/or bottom blades as well as at least one of the side blades can be configured to provide stereo imagery. In various of these embodiments, the left and right camera apertures for the side blade(s) are arranged to provide consistent stereo perspective as provided by top and/or bottom blades. Accordingly, as shown in FIG. 20B, the pair of left and right camera apertures may be aligned in a different direction with respect to the length of the retractor blades for the side retractors as opposed to for the top and bottom retractors. Similarly, the left and right camera apertures are aligned in a different direction with respect to the central axis into the surgical site (into the figure) as defined by the retractor as compared to the orientation of the left and right camera apertures for the top and bottom retractors. In particular for the top, bottom and sides, the left and right camera apertures are arranged along the horizontal direction to provide a consistent stereo perspective for each of the retractors. The result, however, is that the cameras are oriented differently on the top and bottom retractor blades as compared to the side retractor blades.

This configuration for the top and bottom retractors can be advantageous when it is desirable to conserve space and provide more space for tools in the pathway to the surgical site provided by the retractor. Folded stereo top and bottom cameras, as shown in FIG. 20B, provide a relatively low profile. Stereo pairs on side cameras cannot typically be made small due at least in part to the horizontal axis being 90 degrees relative to the top and bottom configuration. In some embodiments, side cameras could be made relatively small, if there are no prisms for folding or deviating a line of sight, which can be useful in the 90 degree or opposing view configuration.

In various embodiments, the sensors can be oriented such that their optical axes are normal to gravity, parallel to gravity, or have another inclination or declination relative to gravity, as described herein. In some embodiments, the display system can be movable (e.g., using an articulating arm) to allow the surgeon to move relative to the patient, as described herein. The display system can be configured to have motion sensors such that this movement is detected and an alert or warning is provided indicating to the surgeon or other operator that the retractor should be repositioned to maintain a desirable parallel orientation between the surgeon, the display, and the cameras.

Figure 20C:
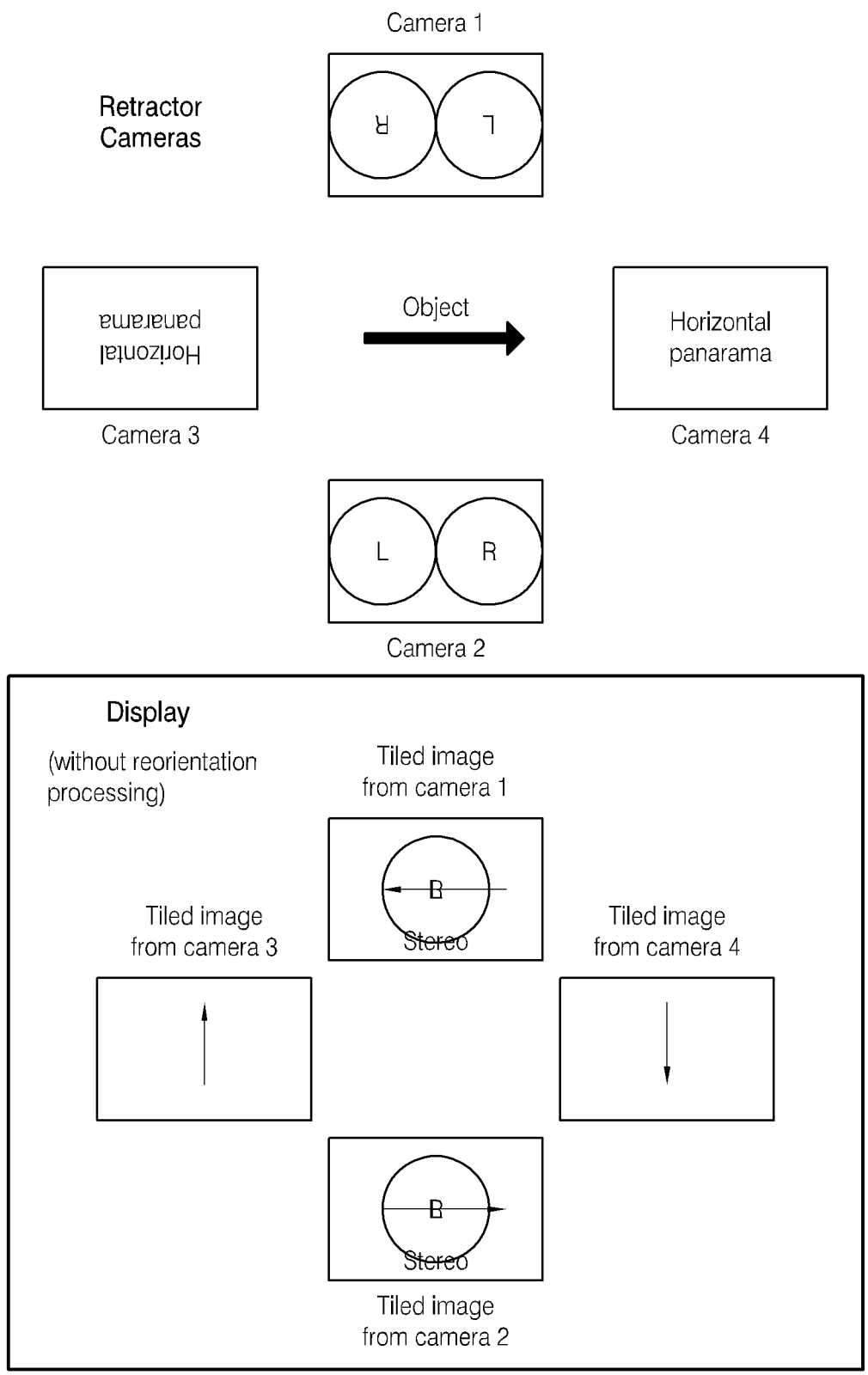
FIG. 20C illustrates a retractor camera configuration and display wherein the imagery from the retractor cameras is displayed as tiles on the display wherein their displayed location corresponds to their locations on the retractor and/or fields of view with respect to each other and/or the retractor.
Figure 20D:
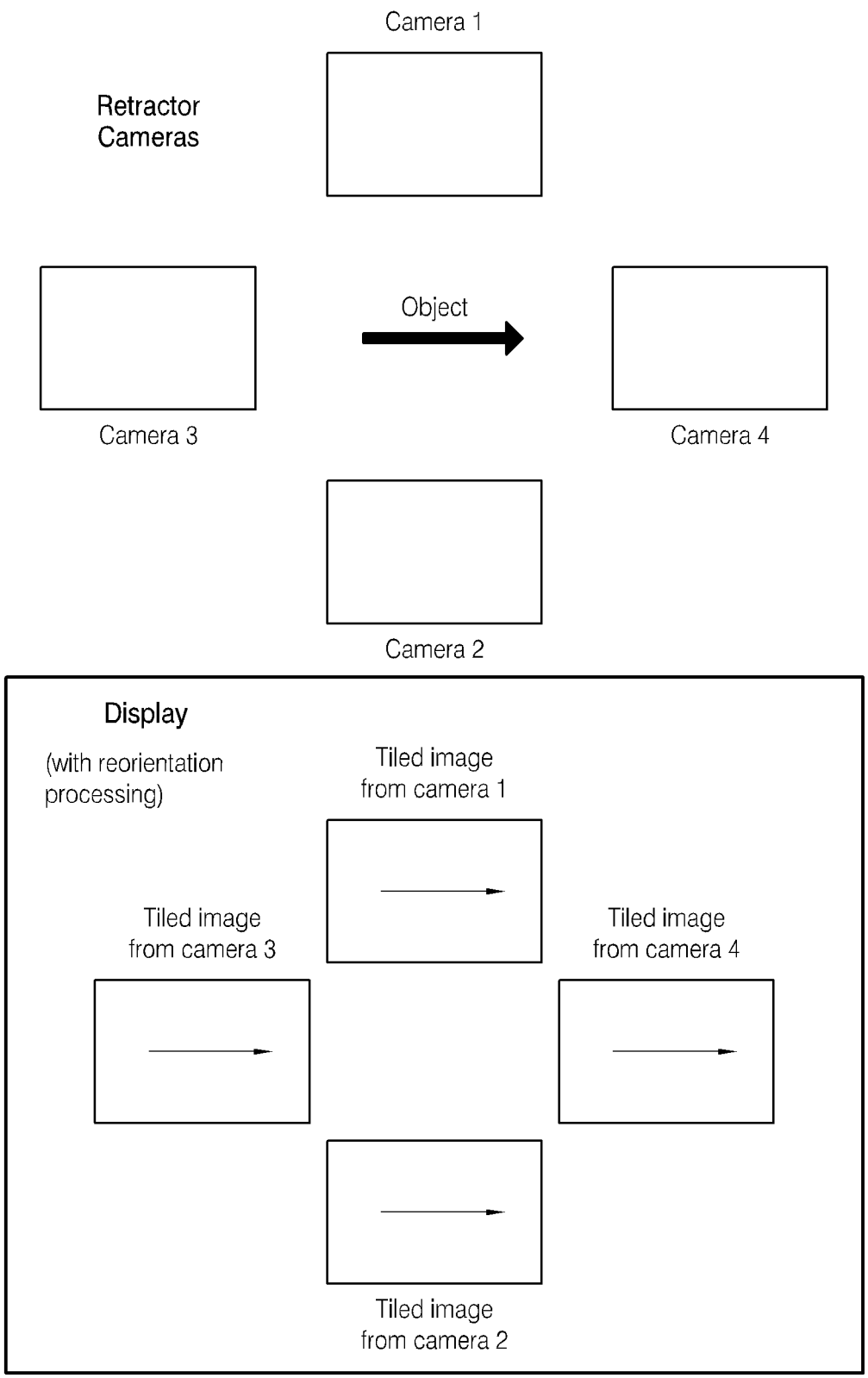
FIG. 20D illustrates a retractor camera configuration and display wherein the imagery from the retractor cameras is displayed as tiles on the display wherein their images are rotated via image processing to be more consistent.

In some embodiments, the image processing system can provide a default, predetermined, or appropriate image rotation and/or position based at least partly on a position and/or field of view of the camera that is providing imagery. Comparing FIGS. 20C and 20D, cameras 1-4 provide imagery of an object to a display system. In FIG. 20C, the image processing system tiles the images from the four cameras in locations on the display corresponding to their locations on the retractor or field of views. The locations on the display can be based at least partly on the positions or field of views of the cameras relative to the object, surgical field or site, to the surgeon, or to another reference frame that is automatically or manually selected. In some embodiments, cameras at opposing positions can be configured to provide stereo video data. For example, Camera 1 and Camera 2 can include cameras configured to acquire stereo data. Additionally, in some embodiments, Camera 1 and Camera 2 can be rotated relative to one another, for example, by 180 degrees. In some embodiments, Camera 3 and Camera 4 can be configured to provide panoramic and/or monocular video. Similar to Cameras 1 and 2, Cameras 3 and 4 can be rotated with respect to one another. In FIG. 20D, the image processing system positions the tiled images on the display as in FIG. 20C, but the image processing system also performs a rotation on the imagery (e.g. rotation of the separate images). The rotation can be configured to provide a uniform direction for the displayed object, as illustrated in FIG. 20D. For example, imagery from camera 1 can be rotated 180 degrees, imagery from camera 2 can be presented without rotation, camera 3 can be rotated 90 degrees, and camera 4 can be rotated 270 degrees. As a result, the object presented in the display will have the same relative orientation. This can facilitate the understanding of the observer as the object has the same orientation in the display even though it is viewed from different viewpoints. In other embodiments not all the images are reoriented. In various embodiments, for example, the images from the video images from camera 2 are rotated 180° with respect to camera 1, or vice versa while the images from camera 3 and 4 are not rotated. In other embodiments, the video images from camera 2 are rotated 180° with respect to camera 1, and the video images of camera 3 is rotated by 90° with respect to camera 4 or vice versa. Other variations are possible. Generally, maintaining camera 2 unrotated may increase the situational awareness or reduce confusion when using the surgical visualization system as camera 2's horizon may closely align with the horizon of the operator. In some embodiments, camera 2 can provide video data that is enlarged and displayed as a background image for the other three tiled videos from the other cameras. These concepts may apply to more or less number of tile camera views.

In some embodiments, the image processing system calculates the position and/or rotation for the displayed images based at least partly on tracking data, information provide with the camera such as memory (EEPROM) storing information regarding that camera, user selection, or a combinations thereof. In some embodiments, the image processing system can perform a default or predetermined rotation and/or positioning of the displayed image based on configuration settings or a configuration of the retractor cameras (e.g. positions and/or field-of-views). In some embodiments, the user can select the position and/or rotation of the tiled images using video windows, icons or thumbnails presented on a graphical user interface. The thumbnails can be rotated reduced-size images that correspond to the video being provided by the retractor cameras. The video windows, icons or thumbnails can remain unrotated, in some implementations, for example, to provide cues as to perspective of the cameras or can be rotated. The rotation of the video in this fashion, as illustrated in FIG. 20D, can be applied to monocular or stereo imagery. As described above, in various embodiments, the image processor can arrange the videos from the cameras selected by the user for example in an arrangement consistent with the geometrical arrangement of the cameras or their fields of view. The user can, for example, select images or video feeds from cameras by selecting video windows, icons or thumbnails. The processor can automatically enlarge and reposition the videos from these cameras, for example, to improve the ability of the surgeon to see the detail in the video. In some embodiments the processor moves the video to a more central position on the display or to a desired position on the display. In some embodiments, the user enlarges the video manually and/or repositions the video manually, for example, by enlarging the video window, thumbnail or icon and/or repositioning it. Again, the user may enlarge the video to improve ability to see detail in the video and may move the video in a more central position or may move the video to a desired location. In some embodiments, reduced size video windows, thumbnails or icons are on a first touch screen display used as a graphic user interface for the nurse or technician and possibly the surgeon, and the enlarge repositioned images are on a second display, such as the binocular display viewed extensively by the surgeon throughout the procedure. The video streams can thus switch from one display to another in various embodiments depending on the surgeon's interest in viewing the display while for example performing a detailed examination of the surgical site, performing tool manipulations in the surgical site, acting upon the surgical site, etc.

In some embodiments the group of videos can be rotated as one. For example, the processor provides that a plurality of videos such as those tiled videos shown in FIGS. 20C and 20D may be rotated as one. In some embodiments, the user initiates and/or controls the rotation of the videos as a group, although the processing system may do so as well. In some embodiments, the processing system automatically rotates one or more of the individual videos in the group of tiled videos when the group as a whole is rotated.

As shown in FIGS. 20C and 20D, the tiled videos can be configured to be displayed on a background video that is provided by another camera system, a mosaic of videos, auxiliary cameras, cameras on a surgical tool, a static image, or the like. In various embodiments, as shown in FIGS. 20C and 20D, tiled videos are spread out, for example, presented more toward the a periphery of the display or in a manner such that the a vacancy is provided in the center of plurality of images and/or of the display. This can allow, for example, for a presentation of an enlarged picture-in-picture video to be displayed (e.g., a tool image) and/or may be consistent with the concept of a retractor providing an open central pathway providing access to the surgical site. In some embodiments, the surgical tool image can be displayed with the tiled videos from retractor cameras and/or with video provided by an auxiliary camera that provides a surgical microscope view, as described herein. In some embodiments, the surgical tool videos can be displayed in a central region overlaid on the tile videos and can have a relatively fixed orientation or the orientation of the video can be adjusted with videos in the tool's orientation. For example, the surgical tool video can be presented on the display without undergoing any rotation with the image processing system. In some embodiments, the surgical tool camera may present the tool in a fixed position relative to the field of view of the surgical tool camera which will provide orientation cues.

Display

Embodiments described herein can provide a display having a form factor and articulated arm as well as binocularity that is familiar to surgical microscope users without the associated disadvantages. In contrast to the typical surgical microscope apparatus or endoscope, however, various embodiments described herein can avoid the need for operator control of the optical focus, positioning, distance to target, etc. Embodiments described herein can, for example, provide visualization that is generally always in focus, oriented, and provides a view of virtually the entire surgical field, emphasizing current task space as desired. Embodiments described herein may also avoid the glare/ambient light and view angle problems associated with looking at conventional endoscope flat panel, TV-like displays. Embodiments described herein may also provide a display that is near the surgical site and near the surgeon and oriented to be convenient for the surgeon to view the display while performing surgery, e.g., without having to turn substantially away from the surgical site to view the display. Embodiments described herein can also avoid the vertigo/nausea and weight/bulk on a user's head, problems which are typical with head-mounted displays.

Additionally, embodiments described herein can provide displays having advantages over current robotic-assisted surgery systems, such as the DaVinci. In contrast to the DaVinci approach, embodiments described herein provide a display at the patient, rather than at a remote location across the room. As noted above, embodiments described herein may provide a display that is similar to the operating microscope to which surgeons are familiar and comfortable but more compact and lighter. By providing a display at the patient site, the user is able to visualize body, wound, respiratory movement, endotracheal tube security, IV tubing, central lines, EKG leads, sterility/draping, and other relevant features easily throughout the surgical procedure. In contrast to an operating microscope where many optical elements are aligned from objective to ocular in a conventional manner, the display can be of a more compact form, allowing the surgeon to look under or over the display. Additionally, due to the electronic nature it can be folded in an advantageous manner to allow more working space for the operator's hands and tools.

The composite image described above can be displayed in a variety of ways. For example, a flat screen, curved (e.g. hemispherical) screen, or projection directly into a user's eyes or glasses may be used. In the case of a flat screen, the display can be, for example, two Ortus Technology, 4.8-inch color LCDs, arranged in landscape orientation with a resolution of 1920×1080, RGB 458 ppi, viewing angle of 160 degrees (horizontal/vertical), color depth of 16.77 million colors, NTSC 72% color gamut, with LED backlight. Different displays in respective left and right optical paths to the eyes can provide stereo and 3-D. A half-silvered mirror beam splitter or multiple mirrors or reflective surfaces (e.g. Wheatstone configuration) can be used to combine images from the displays or portions thereof and/or arrange them adjacent to each other for left and right eye viewing.

In some embodiments, an array of multiple, side-by-side emissive OLED displays in Wheatstone or over/under configuration may be used. In some embodiments, a LCoS pico projector array with rear screen or front screen projection may be used to achieve sufficient field of view ("FOV") and pixel density. Another option is to employ an array of OLEDs projecting on a 3M rear screen. OLED pico projectors have limited brightness, but in configurations in which the display is set up similar to a microscope as discussed below, where little or no ambient light is introduced, the limited brightness presents less of an obstacle. A wide variety of configurations are possible.

As referred to above, the display can be enclosed to eliminate stray light, for example in a manner similar to a standard microscope viewing platform. In particular, the use of a microscope-like display can avoid problems associated with insufficient brightness, as the oculars may block out ambient light.

Figure 21B:
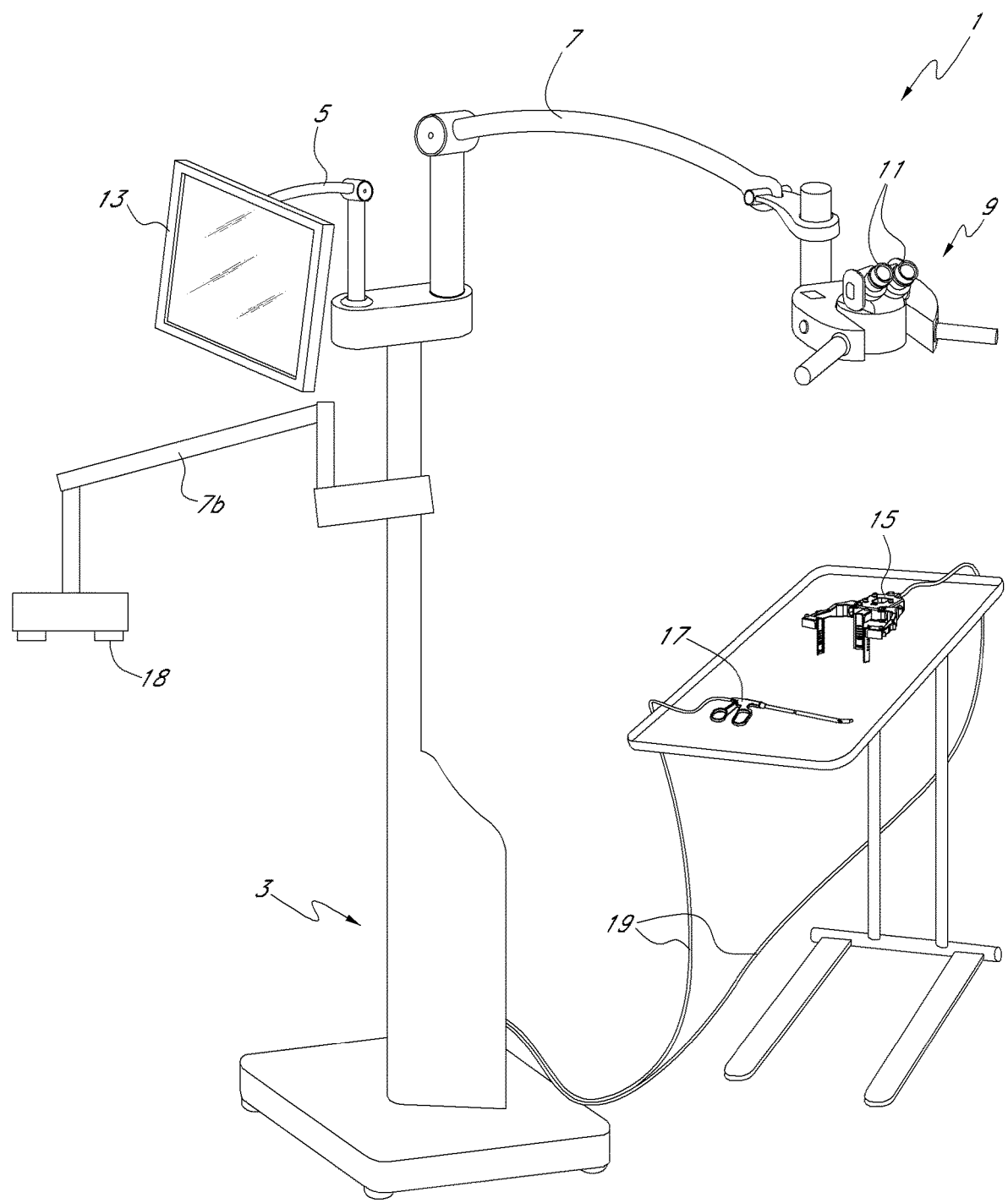
FIG. 21B illustrates an embodiment of the surgical visualization system having an articulating arm for an imaging system that can be configured to provide imagery similar to a direct-view surgery microscope.

As illustrated in FIGS. 1 and 21B, the surgical visualization system 1 can include a viewing platform 9 with oculars 11 for the surgeon to use to view a display of videos acquired with the various cameras in the surgical visualization system. FIG. 21B illustrates an embodiment of the surgical visualization system 1 having an articulating arm 7b for an imaging system 18 that can be configured to provide video similar to a direct-view surgery microscope. The imaging system 18 can be configured, then, to provide a surgical imaging system configured to provide an electronic microscope-like view that can comprise video of the work site or operational site from a position above the site (e.g., about 15-45 cm above the surgical site) or from another desired angle. By decoupling the imagers 18 from the display, the surgeon can manipulate the surgical imaging system to provide a desired or selected viewpoint without having to adjust the viewing oculars. This can advantageously provide an increased level of comfort, capability, and consistency to the surgeon compared to traditional direct-view operating microscope systems. In some embodiments, as described herein, the imagers 18 can be located on the viewing platform 9, on a dedicated articulating arm 7b, on a display arm 5, or detached from other systems. The imagers 18 can comprise a camera configured to be adjustable to provide varying levels of magnification, viewing angles, monocular or stereo imagery, convergence angles, working distance, or any combination of these.

The viewing platform 9 can be equipped with wide field-of-view oculars 11 that are adjustable for refractive error and presbyopia. In some embodiments, the oculars 11, or eyepieces, may additionally include polarizers in order to provide for stereoscopic vision. The display can be supported by an articulated arm 7 or 7b, such that it may be positioned for the user to comfortably view the display while in position to perform surgery.

In some embodiments, the image processing system and the display system are configured to display imagery placed roughly at infinity to reduce or eliminate accommodation and/or convergence when viewing the display. An optical display system comprising a pair of oculars, objectives, and a display resembling a binocular microscope can be employed. The display devices such as liquid crystal displays can be imaged with the objective and the pair of oculars and imaging optics within the display. The objective and the oculars and imaging optics within the display can be configured to produce an image of the displays at infinity. Such arrangements may potentially reduce the amount of accommodation by the surgeon. The oculars can also have adjustments (e.g., of focus or power) to address myopia or hyperopia of the surgeon. Accordingly, the surgeon or other users may view the displays through the oculars without wearing glasses even if ordinarily prescription glasses were worn for other activities.

Figure 21C:
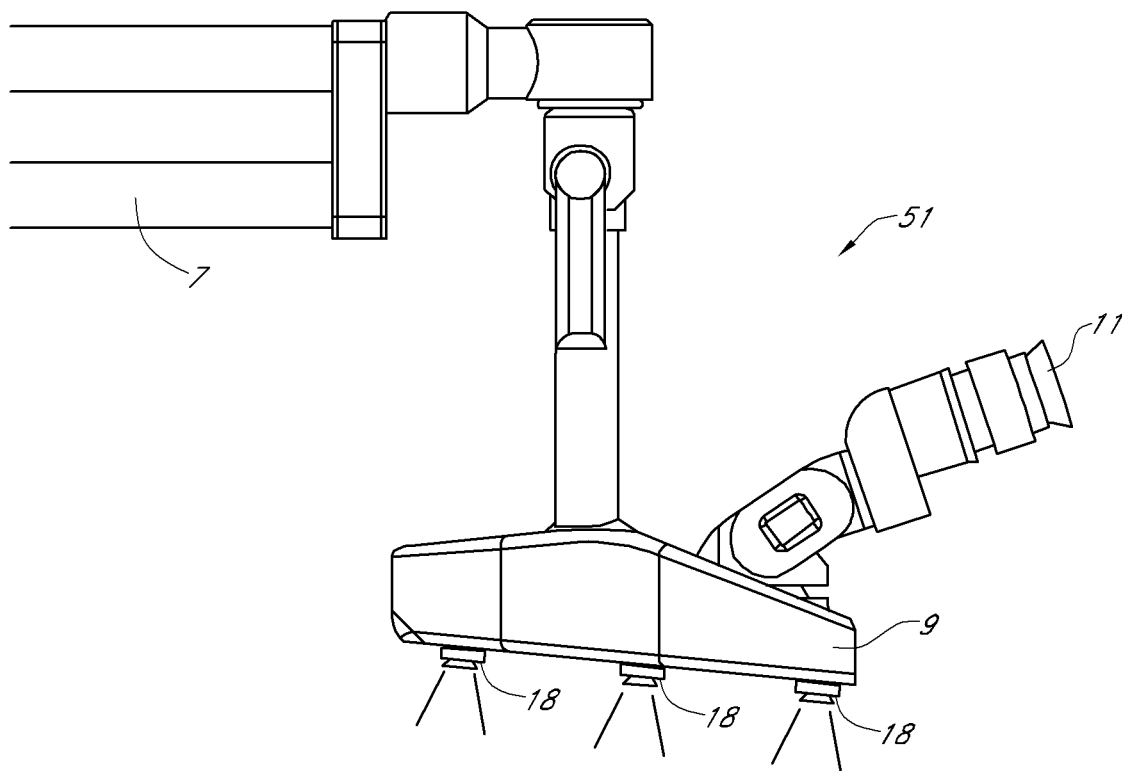
FIG. 21C illustrates an example surgical viewing system attached to an articulating arm, the system including one or more cameras mounted on a viewing platform.

In some embodiments, the viewing platform can include one or more imagers configured to provide electronic microscope-like imaging capabilities. FIG. 21C illustrates an example surgical imaging system 51 attached to an articulating arm 7, the system 51 including one or more cameras 18 mounted on a viewing platform 9. The cameras 18 can be configured to provide imagery of a worksite. The image data can be presented on a display that the user can view using oculars 11 mounted on the viewing platform 9. This design can be used to mimic other direct-view microscopes, but it can also be configured to provide additional capabilities. For example, the surgical imaging system 51 can be configured to have a variable working distance without adjusting the viewing platform 9 or the articulating arm 7. The surgical imaging system 51 can be configured to provide image processing capabilities such as electronic zooming and/or magnification, image rotation, image enhancement, stereoscopic imagery, and the like. Furthermore, the imagery from the cameras 18 can be combined with imagery from retractor cameras, from surgical tool cameras, and the like as described in greater detail herein.

In some embodiments, for example, the displays provide video windows, icons and/or thumbnails to identify cameras 18 that provide a surgical microscope view as well as cameras mounted on the retractor. The user may for example select to display either the surgical microscope view or one or more views from the retractor. The user interface may provide an easy way to switch back and forth that may be easier than moving video windows or icons. An icon, button, or other graphic may enable swift switching by the user back and forth between the two types of views. Such flipping back and forth may be useful at the early stage of the procedure when the incision is being made and the retractor is being introduces as well as when tools are being introduce into the surgical site. Flipping back and forth may similarly be useful at the end of the surgical procedure with extraction of items from the surgical site. However, switching back and forth may also be useful in the middle of the procedure.

In some embodiments, both the surgical microscope view as well as the retractor camera views may be simultaneously shown. For example, the surgical microscope view may be used as a large wide field of view background and one or more retractor camera views may be used as the foreground for example in PIP or tiled format.

Although the discussion and drawings such as FIGS. 1 and 21B consider images from retractors, numerous embodiments may involve at least one auxiliary camera 18 and one or more other cameras that are not disposed on retractors but are disposed on other medical devices. These medical devices may include devices introduced into the body such as endoscopes, laparoscopes, arthroscopes, etc. Accordingly, one or more displays such as the at least one display included in the viewing platform 9 may be used to provide a surgical microscope view using one or more cameras such as the auxiliary camera(s) 18 as well as to display views from one or more cameras located on such medical devices other than retractors. In some embodiments, cameras from a variety of sources, e.g., retractors, surgical tools, and other medical devices, in any combination, may be viewed on the display(s) on the surgical platform together with the surgical microscope view from the auxiliary cameras 18. As discussed above, various embodiments provide the ability to switch between the surgical microscope views and the views provided by cameras associated with other medical devices. Alternatively, the images from the auxiliary camera(s) 18 can be viewed simultaneously with camera view provided by cameras disposed on other medical devices. In some such embodiments, the surgical microscope view may be displayed as a wide field of view background view or main view with other views in the foreground or tiled thereon. As described herein, the displays may provide 3D thus any of the images and graphics may be provided in 3D.

In various embodiments a virtual touchscreen may be provided by the auxiliary cameras 18 or other virtual touchscreen cameras mounted to the viewing platform 9. Accordingly, in some embodiments a user may provide a gesture in the field of view of the auxiliary cameras and/or virtual touchscreen cameras and the processing module can be configured to recognize the gesture as an input. In some embodiments, this camera view can be simultaneously displayed in conjunction with icons, buttons, thumbnails, or other graphics for which gestures may be coordinated to permit the user to provide input. For example, the display(s) in the viewing platform 9 may provide an icon or thumbnail as well as views from the auxiliary camera 18 which show hand gestures or gestures made with a surgical tool held by a surgeon. The surgeon may for example identify a video window, thumbnail, or icon with a gesture of a surgical tool and activate the view of a particular camera such that the view of that camera is enlarged on the screen. In some embodiments, a graphic representation of the surgeon's hand is shown in the display when the surgeon's hand is in the field of view of the virtual touchscreen camera(s). In some embodiments, the virtual touchscreen can mimic a multi-touch display, allowing the surgeon to manipulate objects in the virtual environment with their hands and/or fingers. Although the virtual display has been described in the context of the auxiliary cameras 18, other cameras, e.g., virtual reality input cameras, possibly in addition to the auxiliary cameras 18 may be used. These cameras may be disposed on the viewing platform 9 or elsewhere, such as the additional articulated arm 7b shown in FIG. 21B. In some embodiments, a user may provide a voice command and the processing module can be configured to recognize the voice command as an input. Providing the virtual touch screen can help to create an immersive display experience for a user as it may not be necessary for the user to look away from the display to accomplish a majority of the tasks to be done during a surgical procedure.

As described herein the displays may provide 3D thus the virtual reality interface may appear in 3D. This may increase the immersive quality of the viewing experience, enhancing the detail and/or realistic presentation of video information on the display.

Figure 21D:
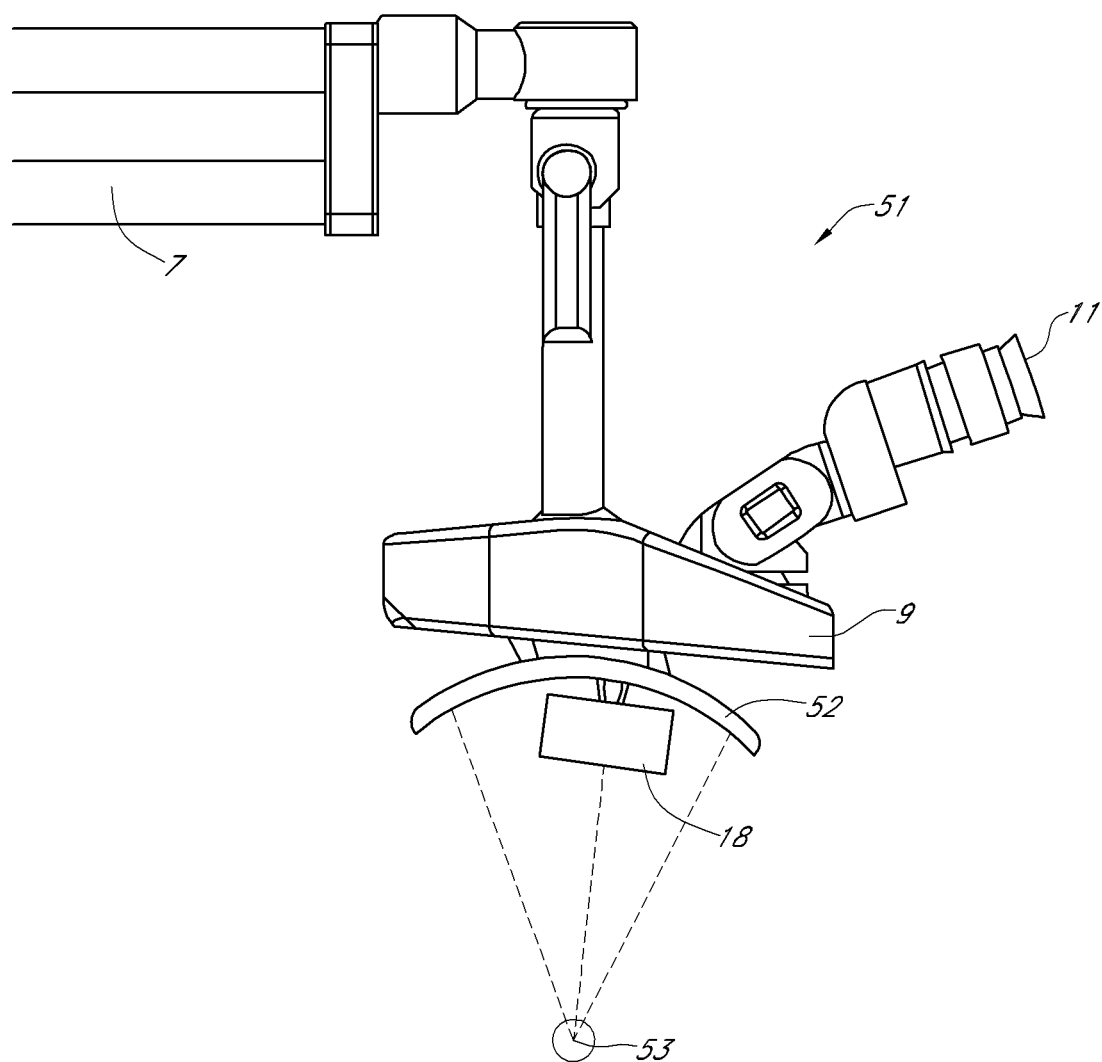

In some embodiments, as illustrated in FIG. 21D, the surgical imaging system 51 includes an isocenter positioning system 52 attached to the viewing platform 9. The isocenter positioning system 52 can include a single track or guide configured to move and orient the cameras 18 such that they are substantially pointed at a single point 53, the isocenter. In some embodiments, a second track or guide can be attached to the first guide in an orthogonal manner to provide movement along 2 dimensions while substantially maintaining the pointing angle towards the isocenter 53. Other configurations can be used to provide isocenter pointing capabilities, such as articulating arms, electro-mechanical elements, curved friction plates, etc. In some embodiments, as illustrated in FIG. 21D-2, the imaging system is configured to move in an isocenter manner. This can be used to enhance dexterity of the user of the system because hand-eye coordination is increased or maximized. Such enhanced dexterity can be vital for prolonged and/or difficult surgery. In the displayed embodiment, the horizons of the acquisition systems are configured to be horizontal to match the horizon of the display system and the user. As shown in FIG. 21D-2, in various embodiments, a stereo imaging system may be maintained in a horizontal configuration as it is moved across a range of locations to avoid confusion for the user viewing the video from the stereo camera. By maintaining a common relative horizon between the display and the acquisition system, the user can relatively easily translate hand motion to manipulation of objects in the display, which may not be the case where translation of the acquisition is accompanied by a relative rotation between the display and the acquisition system.

In the embodiments illustrated in FIGS. 21D and 21D-2, the isocenter assemblies can be a part of the display system or a separate, independent system. For example, the viewing platform 9 can be mounted on a separate articulated arm from the cameras 18. Thus, the display and the image acquisition of the surgical imaging system can be decoupled, similar to the embodiment illustrated in FIG. 21B. By decoupling the isocenter cameras 18 from the display ergonomic benefits are provided such as, for example, the surgeon does not need to be looking through binoculars for an extended period of time or at an uncomfortable position or angle. In various embodiments, a common relative horizon for both the display and the acquisition system is also employed to avoid confusion for the user viewing the video from the stereo camera as stated above.

In some embodiments, the distance between the surgical site of interest and the imagers, e.g., the working distance, can be at least about 20 cm and/or less than or equal to about 40 cm, at least about 10 cm and/or less than or equal to about 50 cm, or at least about 5 cm and/or less than or equal to about 1 m.

The user can interact with the surgical imaging system 51 to select a working distance, which can be fixed throughout the procedure or which can be adjusted at any point in time. Changing the working distance can be accomplished using elements on a user interface, such as the graphical user interface described herein with reference to FIGS. 24 and 24B, or using physical elements such as rotatable rings, knobs, pedals, levers, buttons, etc. In some embodiments, the working distance is selected by the system based at least in part on the cables and/or tubing being used in the surgical visualization system. For example, the cables and/or tubing can include an RFID chip or an EEPROM or other memory storage that is configured to communicate information to the surgical imaging system 51 about the kind of procedure to be performed. For an ENT/Head/Neck procedure, the typical working distance can be set to about 40 cm. In some embodiments, the user's past preferences are remembered and used, at least in part, to select a working distance.

In some embodiments, gross focus adjustment can be accomplished manually by positioning the cameras 18 and arm 7. The fine focus adjustment can be done using other physical elements, such as a fine focusing ring, or it can be accomplished electronically.

In some embodiments, the magnification of the surgical imaging system 51 can be selected by the user using physical or virtual user interface elements. The magnification can change and can range between about 1× and about 6×, between about 1× and about 4×, or between about 1× and about 2.5×. Embodiments may be able to change between any of these such as between 2.5× and 6× or between 2.5× and 6×. Values outside these ranges are also possible. For example, the system 51 can be configured to provide magnification and demagnification and image inversion, with a range from about −2× to about 10×, from about −2× to about 8×, from about −2× to about 4×, from about −0.5× to about 4×, or from about −0.5× to about 10×. The surgical imaging system 51 can be configured to decouple zoom features and focus adjustments, to overcome problems with traditional operating room microscopes. In some embodiments, the surgical visualization system 51 can be used to provide surgical microscope views. In some embodiments, the surgical imaging system 51 can decouple instrument myopia by providing an electronic display instead of a direct view of a scene. The electronic displays can be configured to be focused at varying levels of magnification allowing the user to view the displays without adjusting the oculars between magnification adjustments. Moreover, in various embodiments, the oculars can be configured to provide continuous views at infinity. In some embodiments, however, the principal user of the surgical imaging system may select an accommodation level for the oculars, rather than using a relaxed view provided by the electronic displays. The electronic displays, in various embodiments, however, can remain in focus and the ocular adjustments do not affect the focus of the various video acquisition systems. Thus, adjustments by the principal user do not affect the views of the other users of the system viewing, for example, other displays showing the video, as the cameras/acquisition systems can remain focused. In some embodiments, the surgical imaging system 51 can be focused at a relatively close working distance (e.g., a distance with a relatively narrow depth of field) such that the image remains focused when moving to larger working distances (e.g., distances with broader depth of field). Thus, the surgical imaging system 51 can be focused over an entire working range, reducing or eliminating the need to refocus the system after magnification or zoom adjustments are made.

Figure 21E:
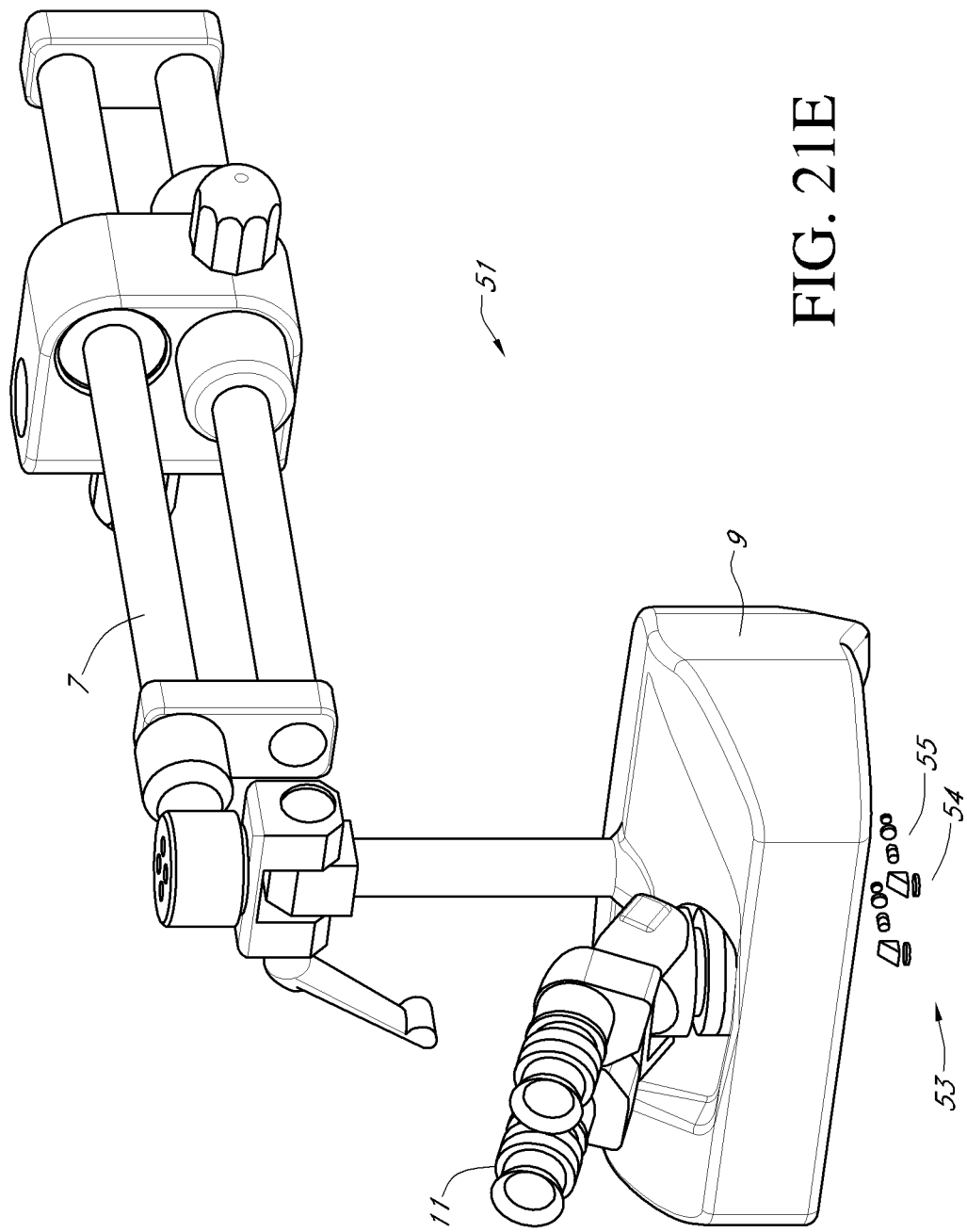
FIGS. 21E and 21F illustrate an embodiment of a surgical visualization system having an optical system mounted under the viewing platform.
Figure 21F:
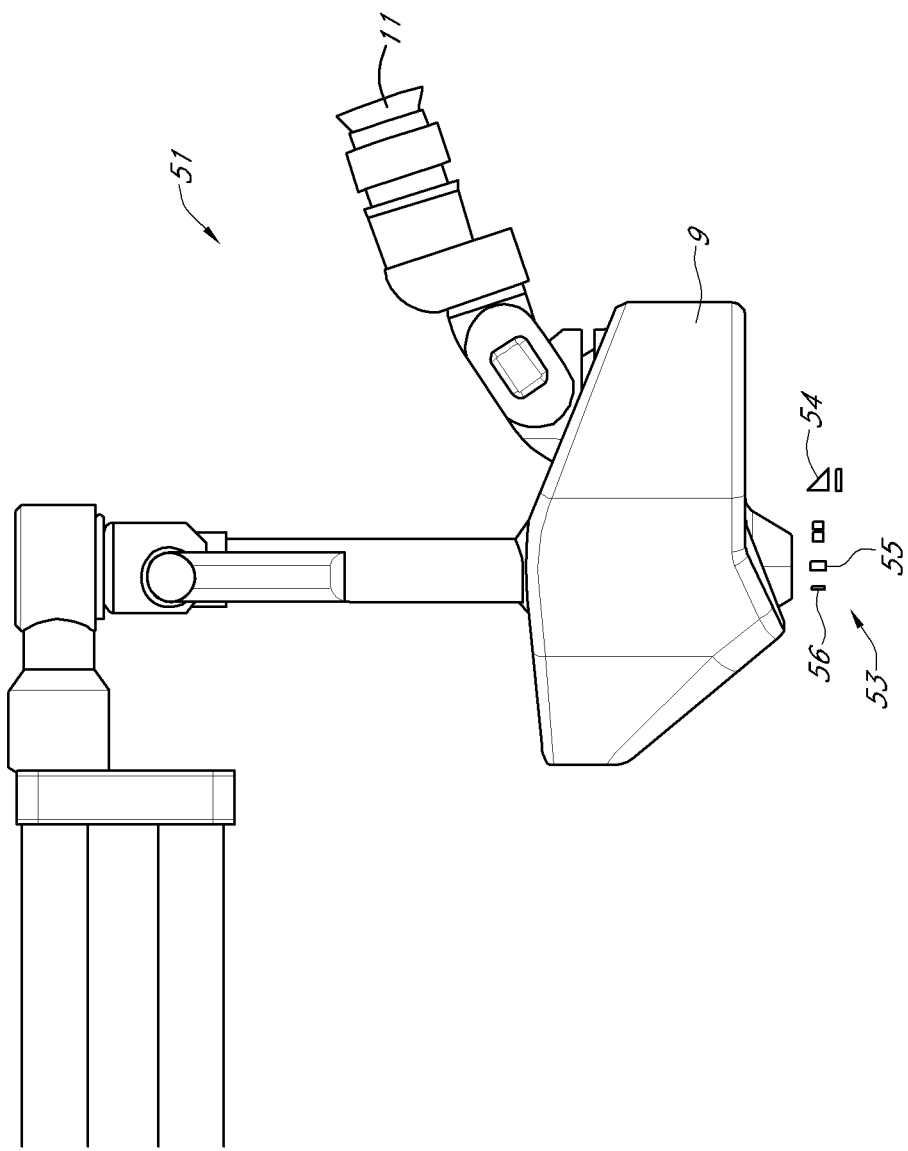

FIGS. 21E and 21F illustrate an embodiment of the surgical imaging system 51 having an optical system 53 mounted under the viewing platform 9. As illustrated, the optical components are shown as free-standing to show the structure of the components, but in practice the optical components 53 will be mounted within or on a structure attached to the viewing platform. In some embodiments, the optical system 53 and/or the cameras 18 (discussed above) can be modular and can be selected and swapped for use with the surgical imaging system 51.

The optical system 53 is configured to provide stereo image data to the imaging system 51. The optical system 53 includes a turning prism 54 to fold the optical path underneath the viewing platform 9 to decrease the physical extent (e.g., length) of the imaging system under the viewing platform 9.

In some embodiments, the optical system 53 comprises a Greenough-style system wherein the optical paths for each eye have separate optical components. In some embodiments, the optical system 53 comprises a Galilean-style system wherein the optical paths for each eye pass through a common objective. The Greenough-style system may be preferable where imaging sensors are being used to capture and convey the image data as compared to the Galilean-style system. The Galilean system can introduce aberrations into the imagery by virtue of the rays for each eye's optical path passing through a periphery of the objective lens. This does not happen in the Greenough-style system as each optical path has its own optics. In addition, the Galilean system can be more expensive as the objective used can be relatively expensive based at least in part on the desired optical quality of the lens and its size.

As shown in FIGS. 21E and 21F, the optical system 53 can include two right-angle prisms 54, two zoom systems 55, and two image sensors 56. This folding is different from a traditional operating room microscope because the optical path leads to image sensors rather than to a direct-view optical system.

In some embodiments, the optical system 53 can have a relatively constant F-number. This can be accomplished, for example, by varying the focal length and/or aperture of the system based on working distance and/or magnification. In one embodiment, as the focal length changes, the eye paths can move laterally apart (or together), the prisms 54 can rotate to provide an appropriate convergence angle, and the apertures can change their diameters to maintain the ratio of the focal length to the diameter a relatively constant value. This can produce a relatively constant brightness at the image sensor 56, which can result in a relatively constant brightness being displayed to the user. This can be advantageous in systems, such as the surgical visualization systems described herein, where multiple cameras are being used and changing an illumination to compensate for changes in focal length, magnification, working distance, and/or aperture can adversely affect imagery acquired with other cameras in the system. In some embodiments, the illumination can change to compensate for changes in the focal length and/or the aperture so as to provide a relatively constant brightness at the image sensors 56.

The optical assembly 53 can include a zoom system 55 configured to provide a variable focal distance and/or zoom capabilities. A Galilean-style stereoscopic system generally includes a common objective for the two eye paths. When this optical system is imaged with image sensors 56, it can create aberrations, wedge effects, etc. that can be difficult to compensate for. In some embodiments, the surgical imaging system 51 can include a Galilean-style optical system configured to re-center at least one of the stereo paths to a central location through the objective lens, which can be advantageous in some applications.

In some embodiments, the real-time visualization system utilizes a Greenough-style system. This can have separate optical components for each stereo path. The optical assembly 53 can be configured to provide variable magnification and/or afocal zoom and can be configured to operate in a magnification range from about 1× to about 6×, or from about 1× to about 4×, or from about 1× to about 2.5×.

The distal most portion of the Greenough assembly 53 can be similar in functionality to an objective lens of a typical, direct-view operating room microscope with the working distance set approximately to that of the focal length. The working distance, and in some implementations the focal length, can be between about 20 cm and about 40 cm, for example. In some embodiments the work distance may be adjustable from 15 cm to 40 cm or to 45 cm. Other values outside these ranges are also possible. In some embodiments, the surgical imaging system 51 includes an optomechanical focus element configured to vary the focal length of a part of the optical assembly 53 or the whole optical assembly 53.

Figure 21G:
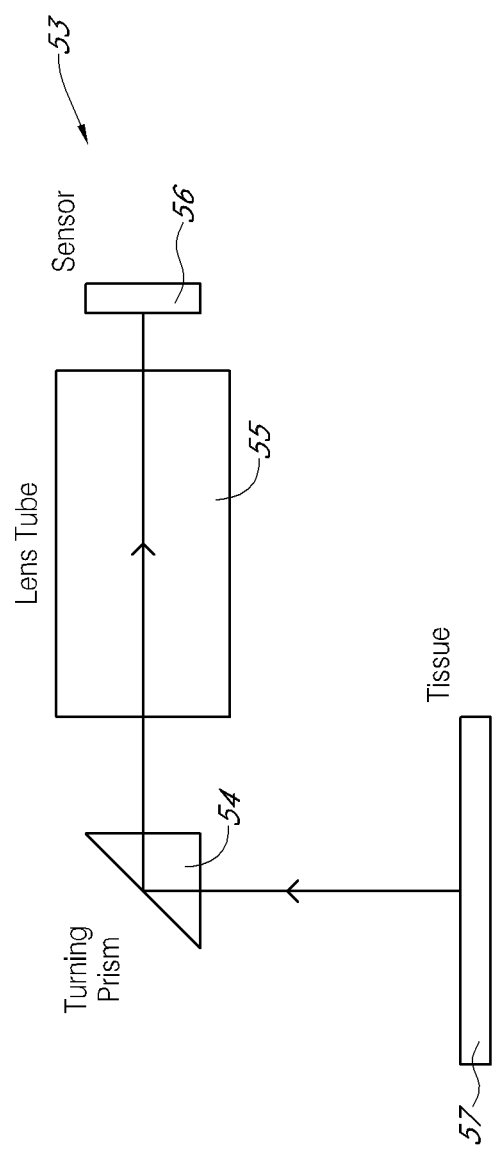
FIGS. 21G-21K illustrate embodiments of optical assemblies for use in a stereoscopic surgical viewing system, such as those illustrated in FIGS. 21E-F.

FIGS. 21G-21K illustrate embodiments of optical assemblies 53 for use in a stereoscopic surgical imaging system, such as those described herein with reference to FIGS. 21E-F. FIG. 21G illustrates a side view of an example optical assembly 53 configured to use a turning prism 54 to fold an optical path from a tissue 57 to a sensor 56 along a lens train 55 that is situated near or adjacent to a viewing platform 9. This can advantageously provide a relatively long optical path in a relatively compact distance.

Figure 21H:
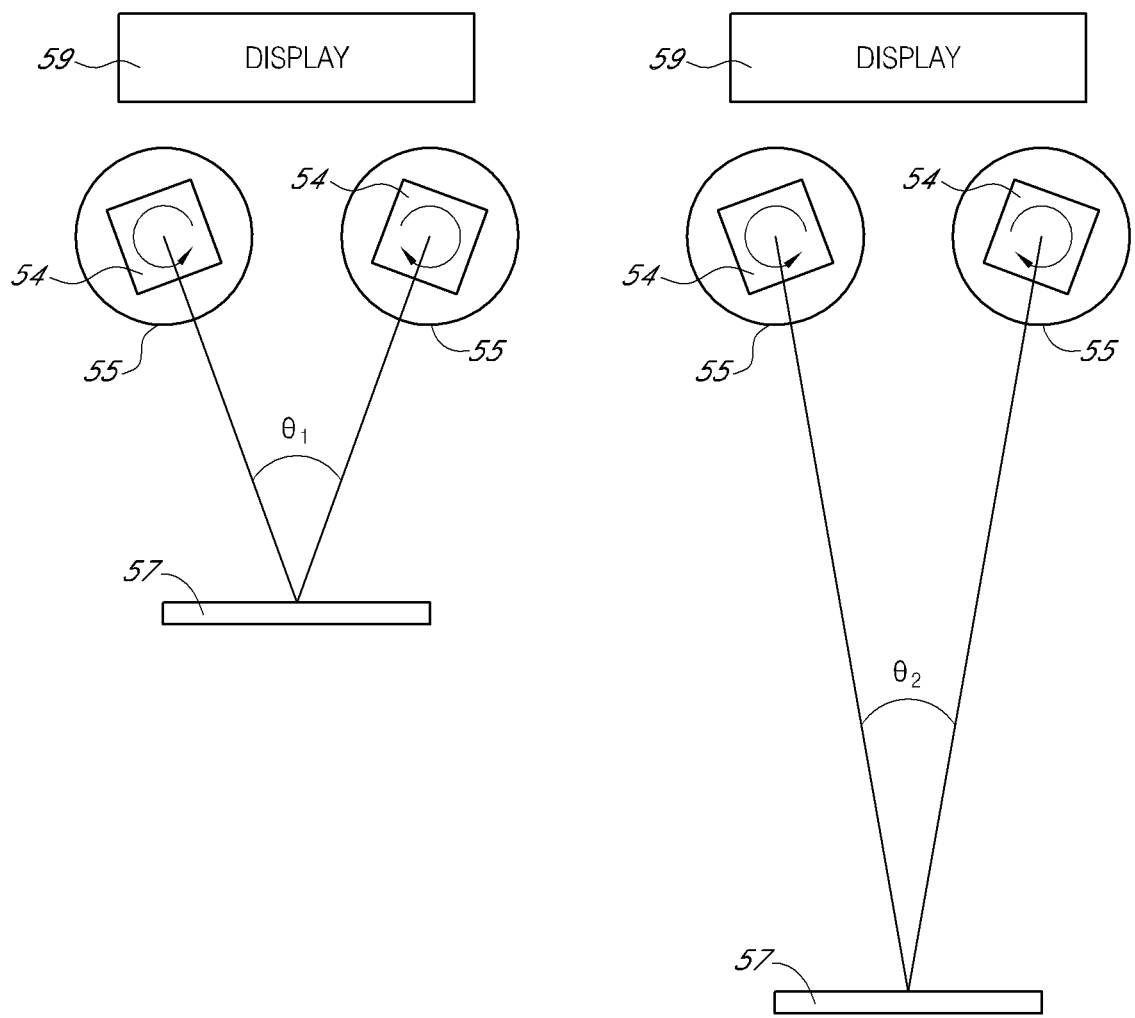

FIG. 21H illustrates a front view of an embodiment of an optical assembly configured to change a convergence angle in a stereoscopic imaging system. The prisms 54 can be the turning prism 54 illustrated in FIG. 21G. The prisms 54 can be configured to rotate to change a convergence angle, and as a result, a convergence point and/or a working distance. The working distance, which can be a distance from the prisms 54 to the target 57 (e.g., tissue), can be user-selectable or adjustable. In various embodiments, with increased working distance to the target 57, the convergence angle can decrease. Conversely, when the working distance gets smaller, the convergence angle can increase (e.g., θ1>θ2). This can be advantageous where the lens path 55 is fixed and the working distance is adjustable. The stereo imagery can then be viewed on the display 59 by a user.

Figure 21I:
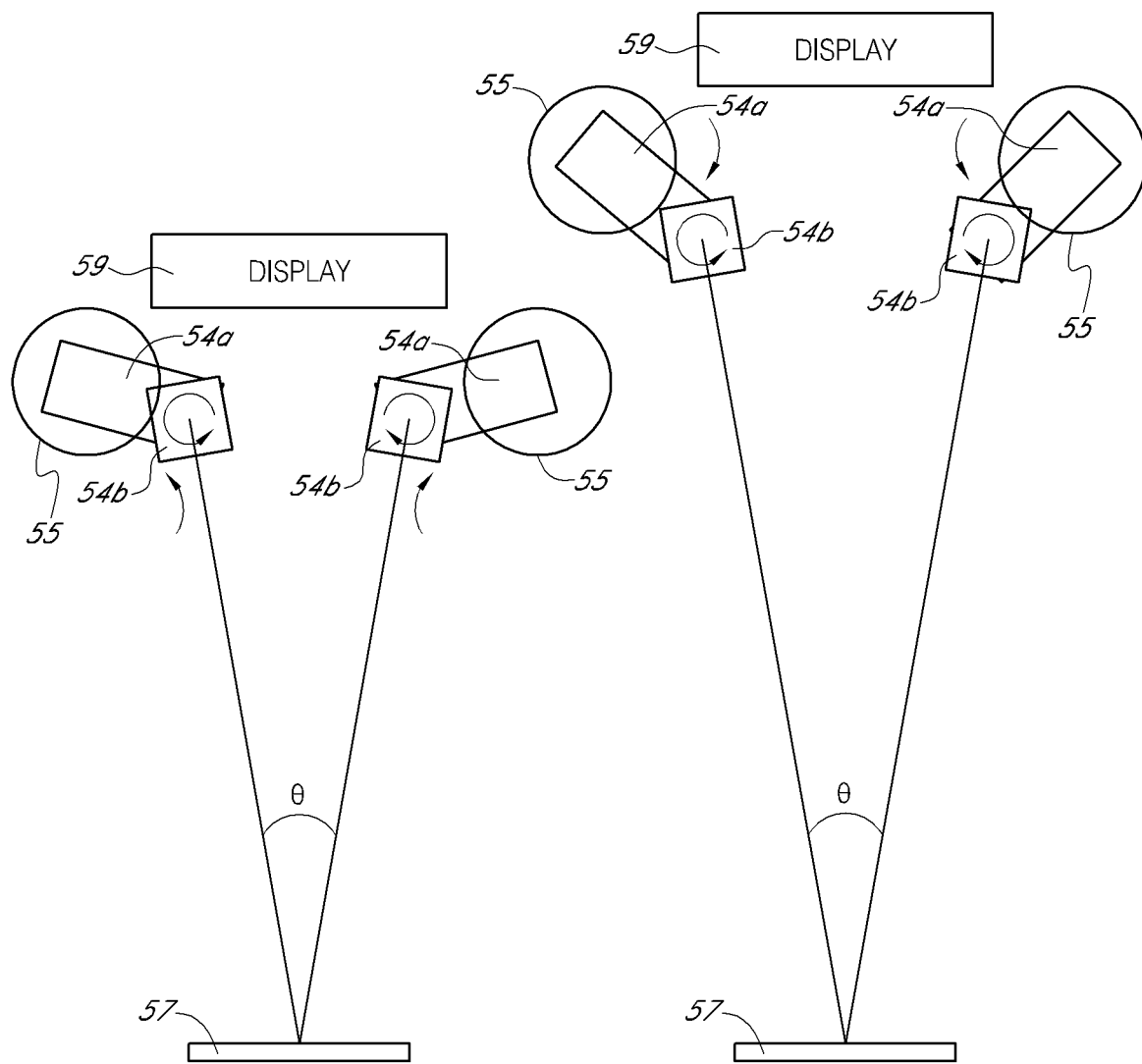

FIG. 21I illustrates a front view of an embodiment of an optical assembly 53 that is configured to maintain a substantially constant convergence angle. The optical assembly 53 can include two prisms 54a and 54b for each optical path, wherein the prisms 54a, 54b can move and/or rotate. For example, when the working distance decreases the first set of prisms 54a can rotate towards one another to decrease an effective distance between the second set of prisms 54b. The second set of prisms 54b can, in turn, rotate to compensate for the changed angle so as to converge on the common target. The second set of prisms 54b can direct the light to the first set of prisms 54a which can then direct the light down the fixed lens paths 55 (e.g., fixed in their position relative to the viewfinder). By providing a relatively fixed convergence angle, a change in working distance may not require refocusing for the user. Maintaining a constant convergence angle, especially a comfortable angle, may reduce the strain on the user such as a surgeon performing a prolonged, arduous procedure.

Figure 21J:
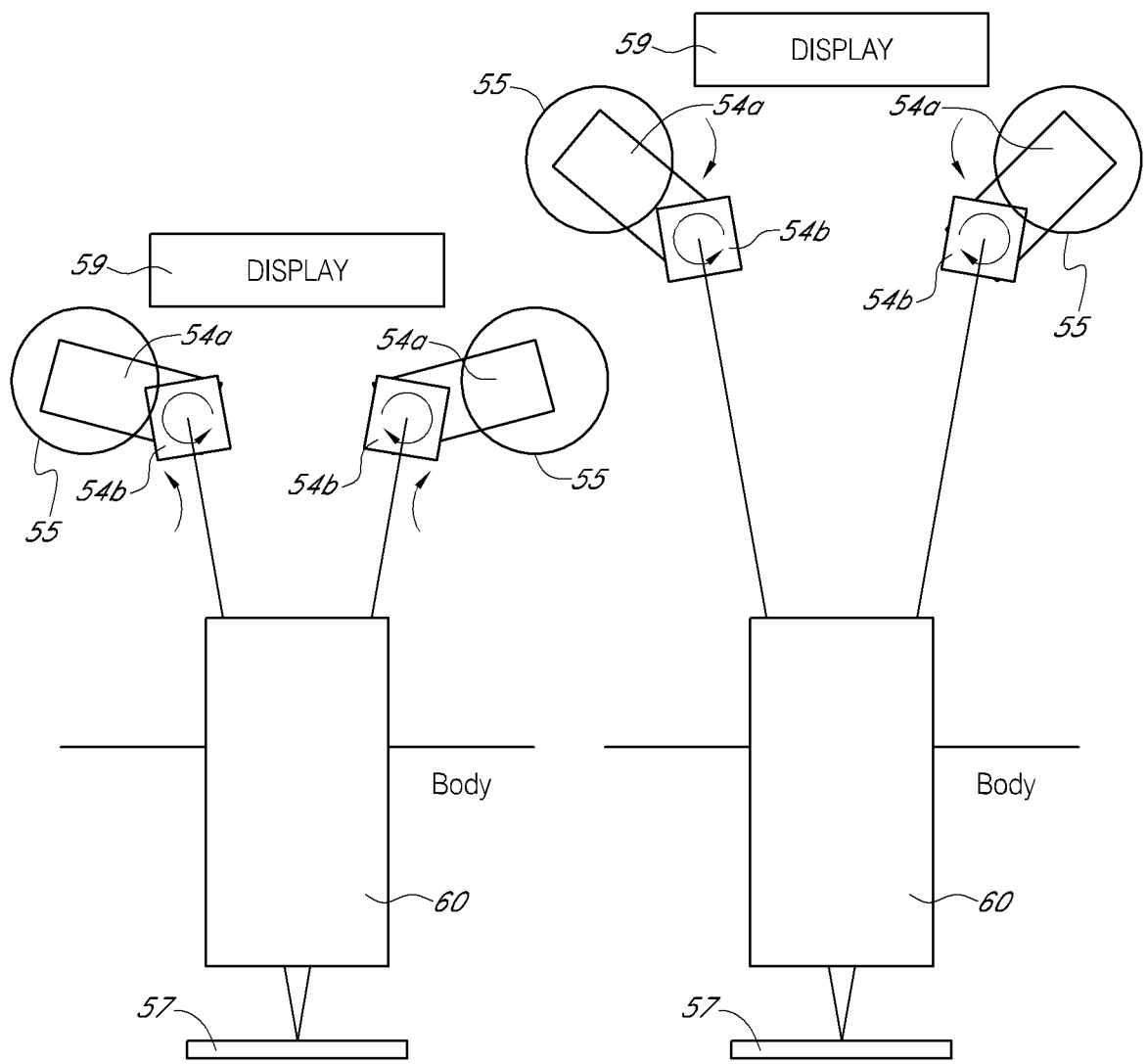

FIG. 21J illustrates a front view of an embodiment of an optical assembly 53 configured to provide a substantially narrow convergence angle to be able to view stereoscopic imagery through a narrow insertion tube 60 (e.g., a tube partially inserted into a body during a procedure). A similar assembly 53 can be used as described with reference to FIG. 21I, and the convergence angle can be maintained substantially constant or at least sufficiently narrow to view through the insertion tube 60.

Figure 21K:
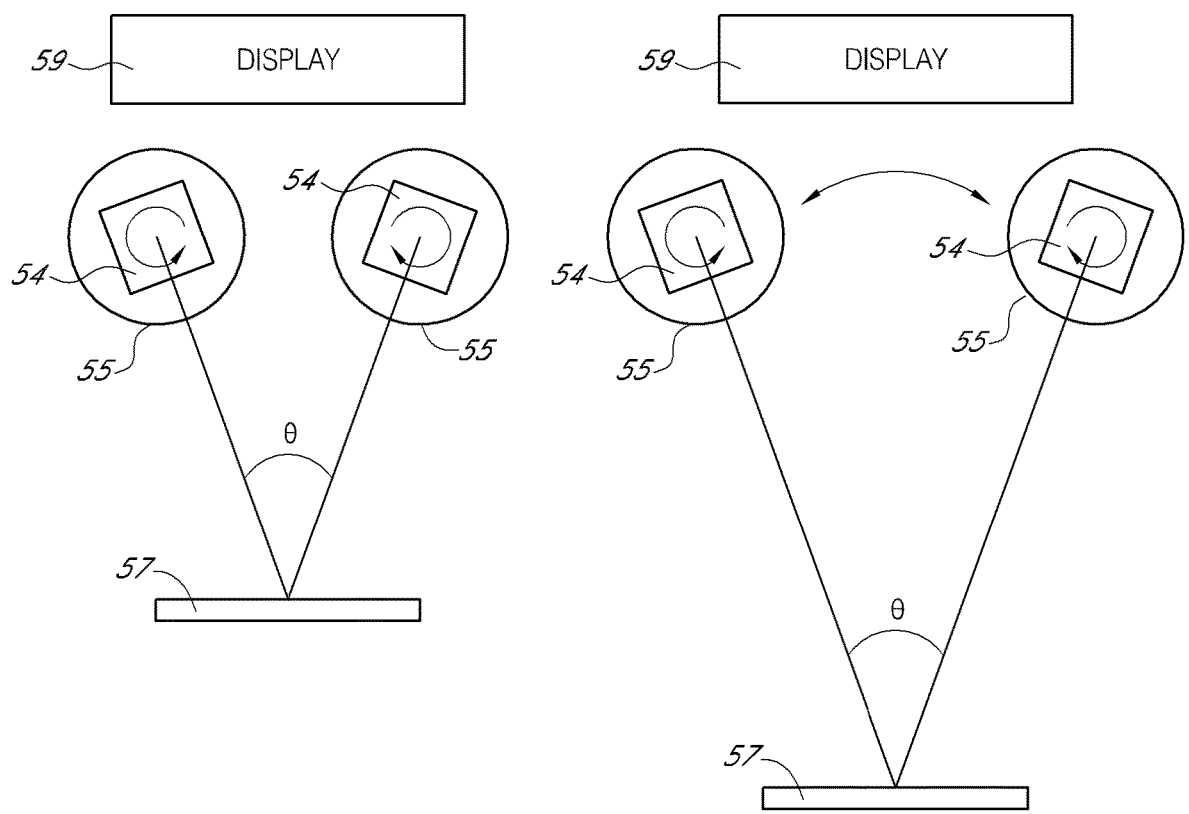

FIG. 21K illustrates a front view of an embodiment of an optical assembly 53 configured to provide a substantially constant convergence angle by moving the lens paths 55 laterally, e.g., toward or away from one another. The prisms 54 can be made to have a substantially constant orientation (e.g., no rotation for changing working distances) and compensation for changing working distance can be accomplished by translating the optical paths laterally to separate or join the optical paths. The translation of the optical paths can be accomplished using any suitable means including, for example, electro-mechanical actuators, slides, articulating arms, etc. This can simplify the optical assembly compared to the embodiments having two sets of prisms as only one set of prisms may be used when the lens paths are configured to move.

The embodiments of the optical assembly 53 which are configured to maintain a sufficiently narrow convergence angle can be advantageous as they allow stereo access to narrow surgical entries by allowing the angle to decrease and avoid clipping one of the stereo paths. For example, the left and right lens paths can move closer to one another and the prisms can adjust to the proper convergence angle for that distance. As another example, the left and right lens paths can remain fixed and there can be sets of prisms for each path configured to direct the light along the lens paths while maintaining a substantially constant convergence angle. In some embodiments, maintaining a constant convergence angle can be visually helpful to the user when zoom changes, e.g., because the changing depth cues do not confuse the user's eye and/or brain. In addition, constant convergence may induce less stress on the user.

In some embodiments, the surgical imaging systems 51 can include a fiber optic light guide (e.g. fiber optic bundle) that connects to the system 51 and that can provide illumination to the work site. In some embodiments, integrated into the body of the system 51 can be a mixing rod to reduce or eliminate imaging of the pixilated end of the fiber cable onto the surgical site. In some embodiments, the area illuminated by the system can be configured to match that of the imaging area.

In some embodiments, the optical assembly 53 can be sterilized by autoclave where the assembly can be made to detach from the viewing platform. In some embodiments, Hall effect switches or sensors can be used for focus and working distance adjustments.

The surgical imaging systems 51 can be configured to provide dual zooms, where a first zoom level is for working distance and a second zoom level is for magnification to match what a traditional operating room microscope provides. The dual zooms can be provided by the systems 51 where the optical assemblies 53 include, for example, a sensor, a camera block, a collimating block made up of a telephoto-like assembly of lenses (e.g., 5 or 6 lenses) with a zoom in front or an afocal changer (e.g., configured to adjust the magnification of each lens path's lenses), a second zoom or afocal assembly (e.g., configured to adjust the working distance), and a prism assembly that deviates the line of sight 90 degrees. Accordingly, various embodiments the surgical imaging system 51 includes one or more cameras that provide both variable work distance as well as a least partially independently variable magnification.

In some embodiments, the display can be a curved surface, for example either projection display or recent generation of flexible LCD or OLED displays having high-resolution (e.g., in excess of 300 ppi). A curved display may provide two advantages: the imaging optics for the display can be less complex than for flat panels, and the cone or numerical aperture of each picture element in the display can be directed towards the viewing optics and in the periphery of the display, thereby providing a brighter image less subject to vignetting.

In some embodiments, the display can be a volumetric display comprising two or more transmissive display panels having a single backlight wherein the transmissive display panels are stacked to provide different planes of focus for a surgeon. The transmissive displays can be active matrix liquid crystal displays ("AMLCD") or other types of transmissive displays. The backlight can be a fluorescent lamp, LEDs, or other suitable light source. By having displays positioned in different focal planes, image data from different focal planes may be presented to the surgeon with relatively less image processing and/or compression compared to a system which combines data from multiple focal planes into a single image. In some embodiments, a number of cameras can be positioned at varying depths or having varying focal distances such that the displays at different focal planes are configured to display image data from cameras positioned or focused at different depths to create a display that assists the surgeon in identifying positions of features within displayed images.

The display can show, as an overlay, pre-operative CT, MR, or other 3D image datasets from, for example, conventional surgical navigation systems (e.g., the Medtronic StealthStation or Treon, Stryker Surgical Navigation System, or Brainlab, among others). In various embodiments, in addition to images, the display can additionally provide numerical data and/or text. For example, in various embodiments, the display can overlay information such as distance or tool measurements, transparent tool renderings, camera identification information (e.g., the portion of the composite image attributable to a specific optical sensor may generate an identifying border around that portion), up/down orientation, elapsed time, and/or one or more still images captured from one or more optical sensors from a previous time in the operation The tracking system can provide 5-DOF (degrees of freedom) or 6-DOF position and orientation information to conventional surgical navigation systems. Other information, graphic, alpha numeric, or otherwise, can be provided.

The tool image can be magnified with respect to the wide-field view image, and change in image scaling will occur as the tool is moved in and out. In some embodiments, a visual metaphor for embodiments of the display is that of a hand-held magnifying glass for inspecting and doing work on a smaller region of a larger workpiece, while seeing the larger workpiece with lower magnification (if any) in more peripheral regions of the visual field to provide situational awareness. Tool images, for example, can be superimposed on the background image thereby blocking that portion of the background image. In various embodiments, the tool images may be stereo.

FIGS. 22A and 22B show examples of displaying a composite image 600 by stitching and tiling images 602a-c.

When tiled, the individual images 602a-c may each have a readily discernible border that is displayed against a background scene or color.

In the case in which the optical sensors 604a-c are pointed downwards or upwards within the surgical device, e.g., at an oblique angle, (for example, the sensors do not form an orthogonal ring of sensors whose chief lines of sight angles are parallel), the images may be rendered as trapezoids. For example, a keystone effect is shown in FIG. 22B when optical sensors 604a-c are pointed down with an angle, θ, relative to a surface of an object 606. The composite image, 600, can comprise trapezoidal images 602a-c tiled together without correction for the keystone effect. Trapezoids are powerful monocular clues for direction. The result may reveal the plurality of optical sensors is downwards or upwards, for example. In some embodiments, discontinuities in the tiled image 600 can provide visual cues to the operator to provide additional situational awareness. Other types of direction markings or indicators may be employed.

In some embodiments, it is possible for the user to reposition a single optical sensor or optical sensor pair from the array or a modular clip-on optical sensor in such an orientation that the image could not be stitched into the composite image. This image could, in some embodiments, be displayed as a picture-in-picture (PIP) overlaid in a peripheral portion of the composite image in the appropriate location. This PIP can be provided with a clear border so as to indicate that the image is not stitched into the composite image, but rather is a separate overlay.

Figure 23B:
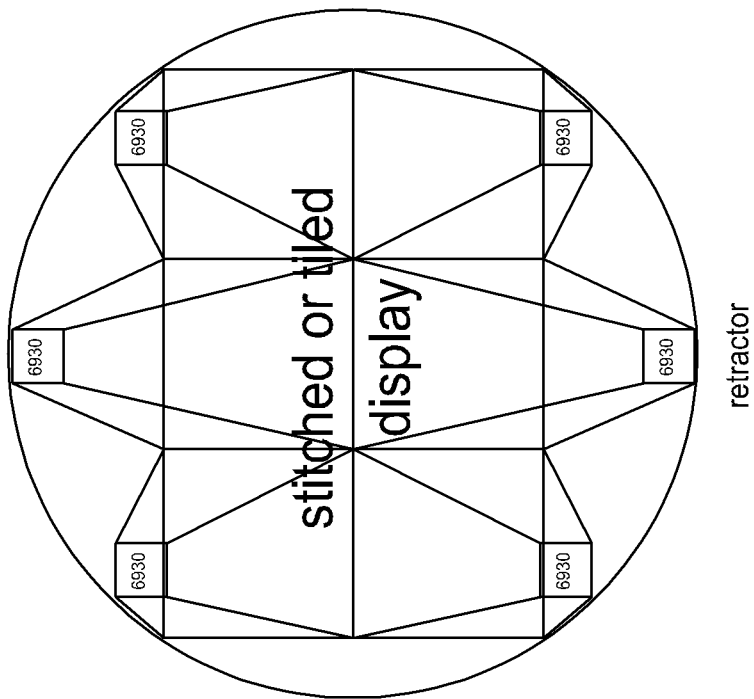
FIGS. 23A and 23B show example stitched or tiled displays incorporating image data from a plurality of cameras positioned on retractors.
Figure 23A:
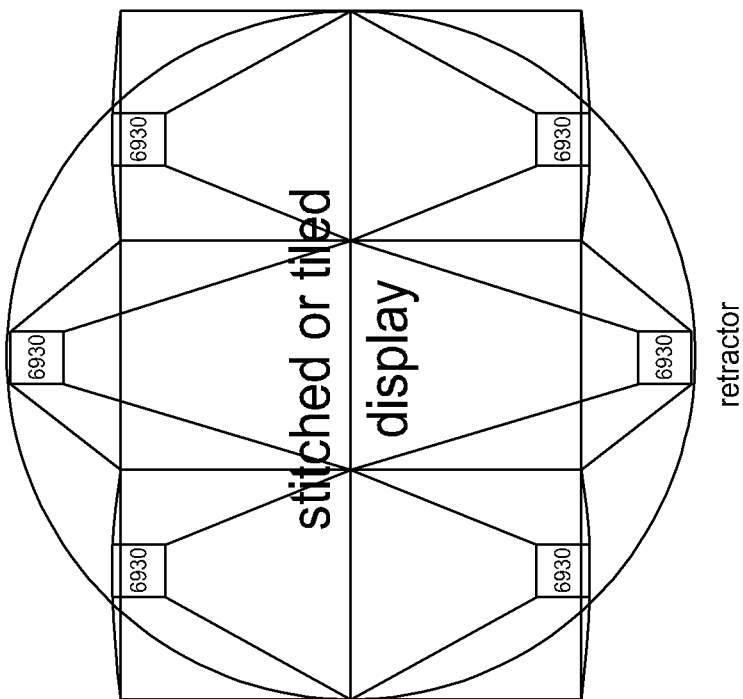

FIGS. 23A and 23B illustrate a display formed by stitching or tiled imagery from six cameras pointed inward into the surgical field between the surfaces of the retractor. In some embodiments, the cameras are positioned on retractors to image a surgical site such that there is little redundancy between sensors. The image processing module can be configured to stitch or tile imagery from the cameras to provide a relatively wide field of view of the surgical site. The differing positions of the cameras on the retractors in FIGS. 23A and 23B correspond to a retractor having an expanded size at a distal end and having the cameras positioned at a proximal end of the retractor (FIG. 23A) and a retractor having a cylindrical shape with cameras positioned at a proximal end (FIG. 23B). These cameras can be used to create the main or background view shown in FIGS. 15 to 17. FIG. 20 discussed below includes an example retractor that may yield such a distribution of field of views.

Visualization Display with Movable Arm

Figure 21M:
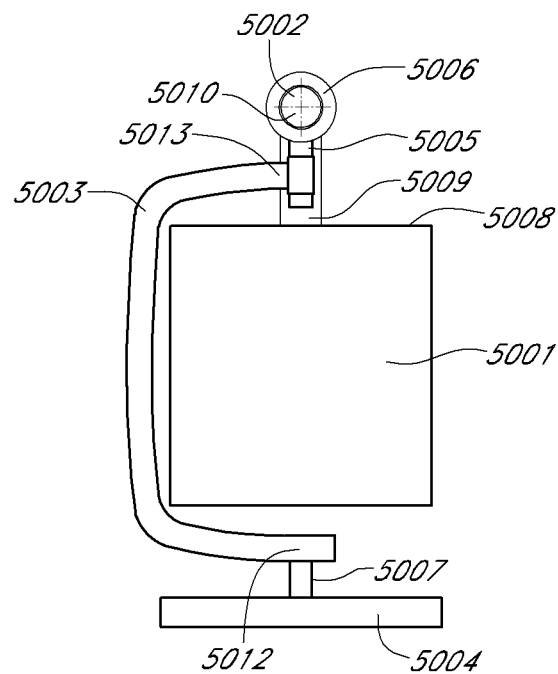
FIGS. 21L-21Q illustrate embodiments of a visualization display with viewing platform attached to a movable arm.
Figure 21L:
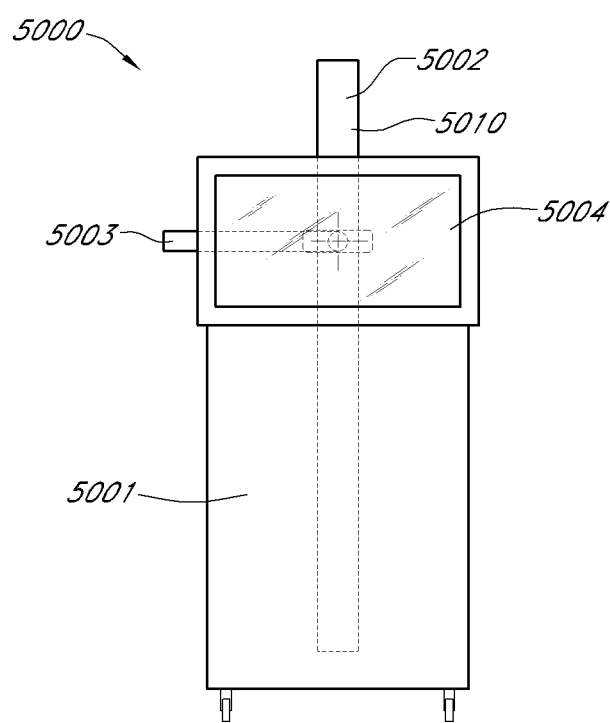

FIG. 21L illustrates a front view of an embodiment of a visualization display with a display support platform attached to a movable arm. The visualization display 5000 includes a housing 5001 and a support pole 5002 from which a movable arm 5003 extends. The movable arm 5003 can have a C-shaped configuration with a distal end 5012 and a proximal end 5013 as shown in FIG. 21M. The movable arm 5003 can have a display 5004 mounted to the distal end 5012 of the movable arm. The display 5004 can be mounted to the distal end 5012 of the movable arm 5003 through a tilt/rotate device 5007. The device 5007 can allow the display 5004 to be tipped, tilted, turned, and/or rotated to adjust the platform to achieve the required function and/or user preferences. In some embodiments the device 5007 can be a complex connection allowing for detailed movement, articulation, and positioning of the display. For example, the device 5007 can include one or more hinges, arms, and/or joints (e.g., ball and socket joints). In some embodiments, the movable arm 5003 at its proximal end 5013 can be attached to the support pole 5002. In some embodiments, the support pole 5002 can be attached to the back surface 5008 of the housing 5001. FIG. 21Q illustrates a perspective view of an embodiment of a visualization display 5000 with an L-shaped support pole 5002. In some embodiments, the support pole 5002 can be an L-shaped pole with a base 5009 and a stem 5010 as shown in FIG. 21Q. The base 5009 can attach to the back surface 5008 of the housing 5001 and can extent outward at an angle approximately perpendicular to the back surface 5008 of the housing 5001. The stem 5010 can extend vertically from the base 5009 at an angle approximately perpendicular to the base 5009.

In some embodiments, the movable arm 5003 can be attached to the support pole 5002 through an attachment mechanism. The attachment mechanism can include, for example, a pivot attachment 5005 and ring 5006. In some embodiments, the ring 5006 can surround the support pole 5002, preferably surrounding the stem 5010 of the support pole 5002. The ring 5006 can rotate about the support pole 5002, and can move vertically along the support pole 5002, preferably along the stem 5010. In some embodiments, a pivot attachment 5005 can be attached to the ring 5006 extending outward from the ring 5006 at an angle approximately perpendicular to the support pole 5002. In some embodiments, the movable arm 5003 can be attached to the pivot attachments 5005. In some embodiments, the proximal end 5013 of the movable arm 5003 can be attached to the pivot attachment 5005 at an approximately perpendicular angle to the movable arm 5003.

The ring 5006 can be moved vertically along the support pole 5002. Vertical movement of the ring 5006 can effectuate a vertical movement of the attached movable arm 5003 and the mounted display 5004. FIG. 21L illustrates a front view of the visualization display 5000 showing the movable arm 5003 and the display 5004 are positioned at a vertical position near the top of the stem 5010 of the support pole 5002. FIG. 21N illustrates a front view of the visualization display 5000 similar to that described in FIG. 21L except the movable arm 5003 and the display 5004 are positioned at a lower vertical position near the center of the support pole 5002. The vertical movement up and down the support pole 5002 of the movable arm 5003 and display 5004 can provide for the vertical position of the display 5004 to be adjusted to achieve the desired performance or user preferences. The vertical movement of the display 5004 can allow for accommodation of a surgeon in a seated or standing position. Additionally, the vertical movement of the display 5004 can accommodate the different heights of medical professionals. In some embodiments, the ring 5006 can slide along the support pole 5002. The ring 5006 can have a locking mechanism (not shown) to fix the ring 5006 to the support pole 5002 at the desired positioning. The locking mechanism can include, for example, a screw, a knob, a clip, clamp, pin, or any combination of these as well as any other method that can facilitate convenient locking or securing known in the art. In certain embodiments, friction between the ring 5006 and support pole 5002 can be adjusted. For example, the friction between the ring 5006 and support pole 5002 can be adjusted through use of surface features (e.g., roughness) and/or mechanical components (e.g., rubber pads or other material additions to effect a change in friction between the support pole 5002 and the ring 5006).

Figure 21O:
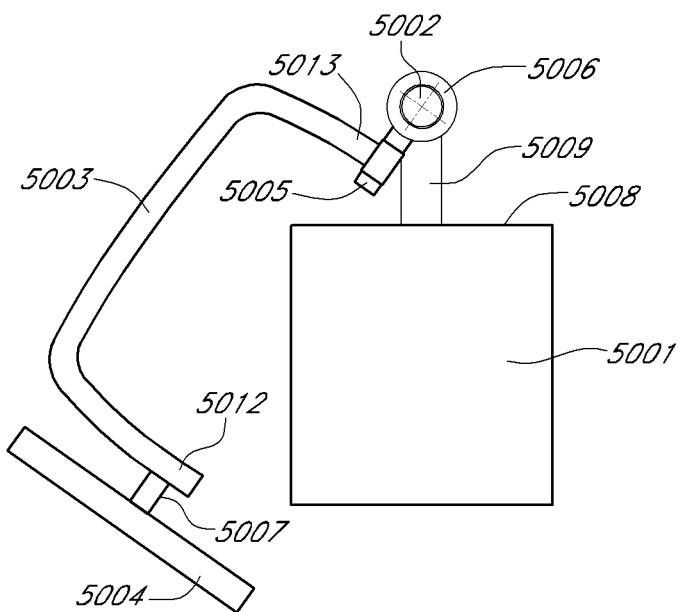
Figure 21N:
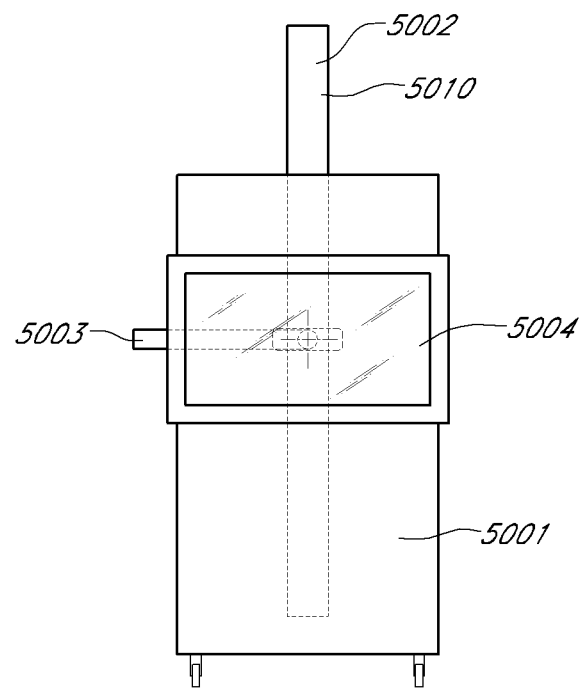

FIG. 21O illustrates a top view of an embodiment of a visualization display 5000 with the movable arm 5003 in a rotated position. The movable arm 5003 as illustrated in FIG. 21M shows the display 5004 in a first position directly in front of the housing 5001. FIG. 21O illustrates a top view of the visualization display 5000 similar to that described in FIG. 21M, but FIG. 21O shows the movable arm 5003 and the display 5004 rotated to a second position, outward from the housing 5001 and the display 5004 is positioned to the side of the housing 5001. The movable arm 5003 can rotate about the support pole 5002, preferably rotating around the stem 5010 of the support pole 5002. In some embodiments, the movable arm 5003 can rotate up to about 90 degrees clockwise and counterclockwise from its unrotated position or first position where the display 5004 is positioned directly in front of the housing 5001. In FIG. 21O, the movable arm 5003 is shown rotated about 45° degrees clockwise from its unrotated position with the display 5004 positioned directly in front of the housing 5001. In some embodiments, rotating the movable arm 5003 about the stem 5010 can provide the user with more convenient access to the display 5004. In some embodiments, the visualization display 5000 can contain an internal counter balance similar to surgical microscopes to allow for the rotation of the movable arm 5003 without having to compensate for the additional weight.

Figure 21P:
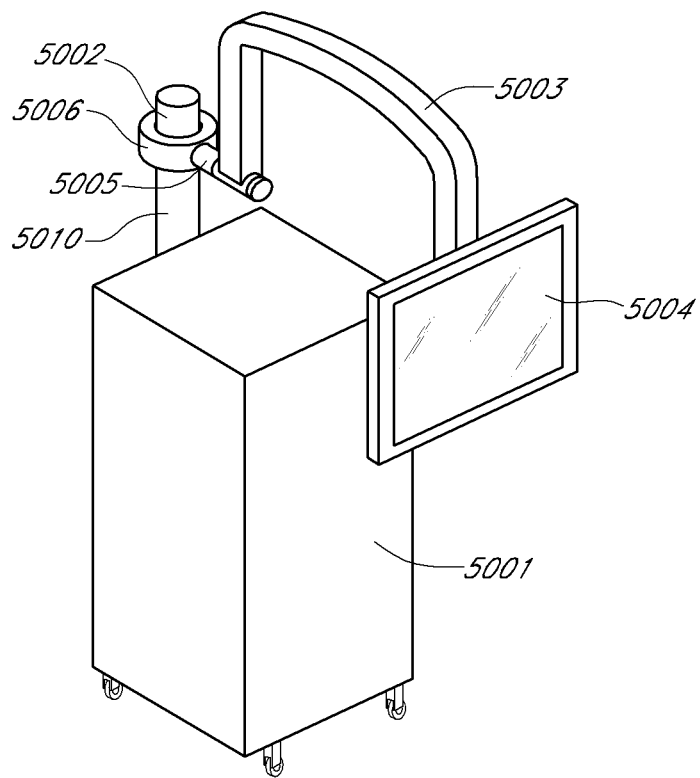
Figure 21Q:
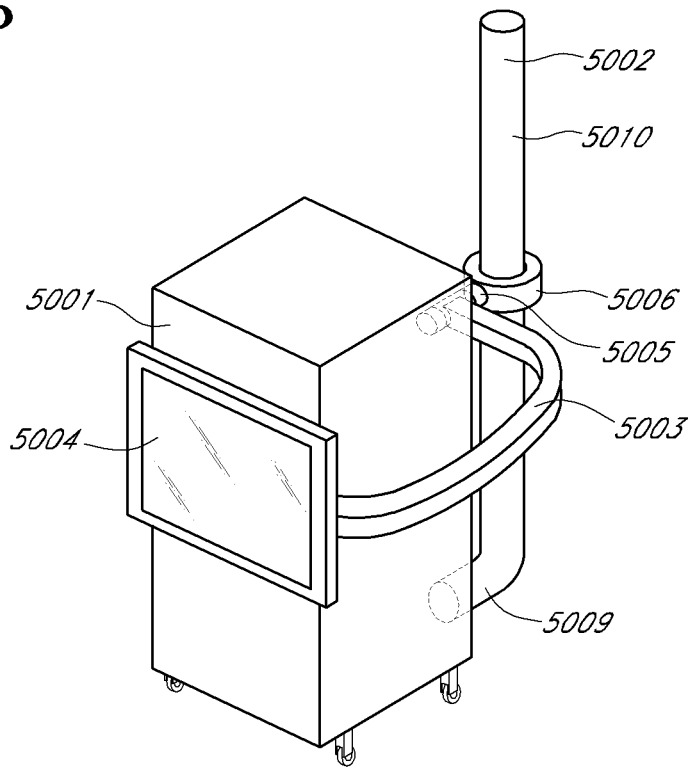

In some embodiments, the movable arm 5003 can rotate about the pivot attachment 5005, as illustrated in FIG. 21P. The rotation about the pivot attachment 5005 can allow for the movable arm 5003 and the display 5004 to rotate from one side of the housing 5001 to the opposite side. For example, FIG. 21L shows the movable arm 5003 positioned at a first position, the movable arm 5003 can then be pivoted about the pivot attachment 5005 and FIG. 21P shows the movable arm in a second position with the movable arm 5003 directly above the housing 5001. The movable arm 5003 can continue to pivot about the pivoting attachment 5005 until reaching a third position as shown in FIG. 21Q on the opposite side of the housing from the first position. In some embodiments, the movable arm 5003 can be locked in a particular position by a locking mechanism. The locking mechanism can include, for example, a screw, a knob, a clip, clamp, pin, or any combination of these as well as any other method that can facilitate convenient locking or securing known in the art. In some embodiments, the movable arm 5003 can be locked in a particular position by a self-locking mechanism in which the movable arm 5003 can be stabilized when placed at the appropriate position without the need for a locking mechanism. In some embodiments, the rotation of the movable arm 5003 about the pivoting attachment 5005 can facilitate rotation of the movable arm 5003 and display 5004 about the support pole 5002 between one side of the housing 5001 (e.g., the left side with reference to FIG. 21N) and another side of the housing 5001 (e.g., the right side with reference to FIG. 21N). Such rotation can permit left and right handed users to adjust the position of the display 5004 and can enhance versatility in set up of the display 5004. In some embodiments, the display 5004 can maintain the display orientation during the rotation of the movable arm 5003 about the pivoting attachment 5005. For example, in some embodiments, the display orientation can be maintained by turning the display 5004 about the device 5007 (e.g., see FIG. 21M). In some embodiments the display orientation can be maintained through image processing. In addition, for use with the surgical visualization system disclosed herein, the display 5064 can be, e.g., a computer or instrument display used in other applications more generally. In theory, the applications need not be even medical although medical applications such as disclosed are anticipated.

Graphical User Interface (GUI)

Figure 24:
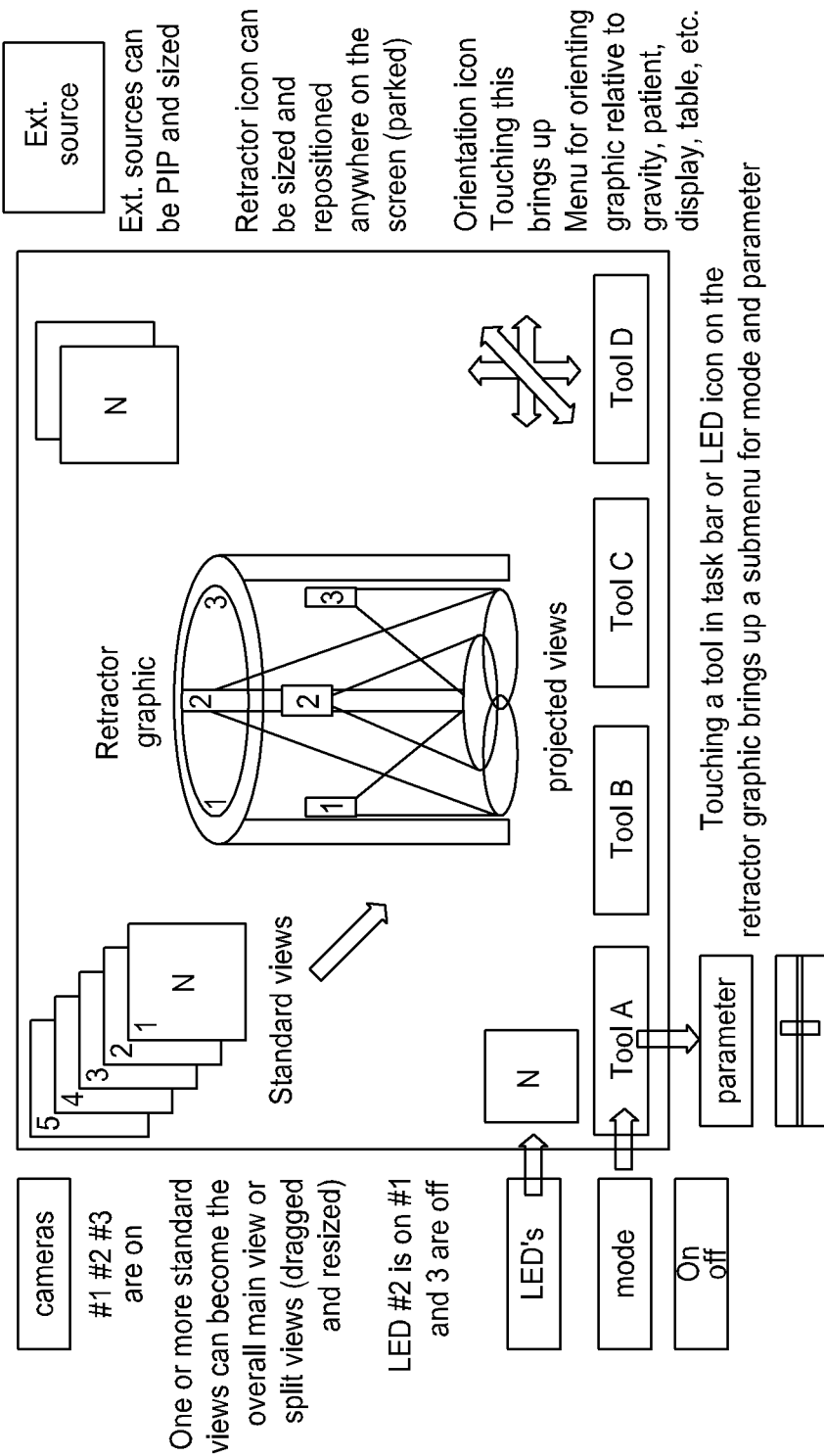
FIG. 24 shows an example graphical user interface that can be used in embodiments of surgical visualization systems.

FIG. 24 illustrates an example graphical user interface that can be used in embodiments of surgical visualization systems described herein. The graphical user interface (GUI) can be used to receive user input and to display operational information to the user. In some embodiments, the graphical user interface is displayed on a dedicated monitor system (such as shown, for example, in FIGS. 21M-21Q) separate from the display system used to display images from the cameras associated with the surgical visualization system. In some embodiments, the graphical user interface is incorporated into the same display system that displays image data from the cameras associated with the surgical visualization system (such as shown, for example, in FIGS. 21C, 21D, 21E and 21F), thereby providing a single display system that incorporates user interface elements and display output. In some implementations, both are used, for example to give the surgeon and a nurse or technician access to the control system.

The GUI can be implemented on a monitor having a sterile touch screen that is accessible to a surgeon, a surgical assistant, a scrub technician, or some other user or operator. The monitor with the GUI can include connectors that provide information to the GUI about the properties and characteristics of the surgical visualization system coupled thereto. The GUI can receive tracking, position, and/or orientation information associated with cameras and surgical devices to display these in correct relative positions and orientations, for example, on a schematic retractor graphic with a 3-D field of view cone being displayed extending into the surgical site. In some embodiments, a small, real-time video window from each camera can be displayed adjacent to a camera icon or included as the icon. The GUI can be used to select one or more cameras to operate and/or to be displayed. The GUI can be used to position and/or orient each camera image on the display system and to determine a size of the displayed image and/or a selected zoom of the image. In some embodiments, if a single camera is selected for viewing the default operation is to substantially fill the display with the selected image. In some embodiments, if two or more cameras are selected for viewing the default operation is to position and orient the displayed images in correct geometric arrangement relative one to another based on the relative locations of the camera or field of views etc. relative to a retractor frame coordinate system. In some embodiments, image data from cameras associated with a surgical tool can be displayed using picture-in-picture techniques, as described herein with reference to FIG. 17, and overlaid on a background or main image formed from one or more proximal wide field of view cameras. The picture-in-picture image can be a separate image or video stream from the other imagery. In some embodiments, the GUI can be used to select whether image data from the surgical tool will remain rotationally constant during use or whether it will rotate with tool rotation.

Accordingly, in various embodiments, the GUI can include camera selection elements, positioned on the GUI where the camera selection elements can provide a real-time video preview of the imagery acquired by the camera. The GUI can provide a retractor graphic to display relative positions of cameras in the retractor coordinate system. The GUI can provide control over LEDs using LED control element. The GUI can include an orientation icon to control whether the graphics are oriented relative to gravity (as described herein), the patient, the display, the table, etc. or to not orient the graphics (e.g., present imagery from cameras without any relative and/or absolute rotation). The GUI can include an external source control so that imagery from external sources can be incorporated into the display. The GUI can include tool control elements with functionality such as described in detail below. The GUI can provide a method of controlling views on the display through manipulation of graphics on the monitor. For example, windows or thumbnails, presenting real time video from the cameras on the retractor or icons representing such real time video feed, can be moved about such as moved more centrally, arranged with respect to each other, and changed in size, e.g., enlarged, as desired. The video windows or thumbnails themselves may be images from the camera or can be associated with images from the camera. The video windows or thumbnails can be larger in some embodiments. A video camera feed can form the background of the GUI as well. The GUI can provide information to the user about a status of various components such as cameras, LEDs, tools, orientation, and the like. The GUI can be used to select whether displayed imagery, such as the background or main image from a proximal camera, should change to track a position of the surgical tool. In some embodiments, the GUI incorporates information received from a trackball interface that a user can use to control view parameters. Also, the GUI can be split up into different screens that can be selected by the user in some embodiments.

The graphical user interface can be used to provide tool and fluidics control functions. In some embodiments, the GUI can be used to turn a drill on or off and to control a pressure associated with the drill. Similarly, the GUI can be used to operate a power Kerrison, a power aneurysm clip applier, power forceps, bipolar & tissue forceps, and/or power scissors controlling a state between on and off and controlling a fluid or air pressure associated with the tool. In some embodiments, the GUI can be used to operate optics pressure washing, changing a state between on, off, standby, or auto. The GUI can be used to control a frequency of washing and a pressure. The GUI can be used to control an air-dry functionality, changing a state between on and off and changing a pressure with which it operates.

In various embodiments, virtual display technology is employed for the GUI. For example, images of the user's hand or a surgical tool may be displayed with the display device interacting with other images, e.g., video windows or icons, displayed by the display device. Similarly, a motion detection system and/or gesture recognition system may be employed to capture and identify movement of the user's hand or a surgical tool and display the movement and/or gestures on the display device as well as associate those movements/gestures with input instruction. For example, using gesture control the surgeon can select cameras or imagery for viewing, zoom in on a video stream, and/or position video streams on the display.

In certain embodiments, for example, the viewing platform 9 shown in FIG. 21C with the cameras 18 mounted thereunder can employ one or more of the cameras to act as gesture recognitions cameras 18 to image the surgeon or user's hand located beneath the viewing platform. The surgeon/user can make gestures or otherwise move his or her hand, which will be imaged by the gesture recognition cameras. The gesture recognition cameras can send signals corresponding to the images of hand movement to the display device that is visible to the surgeon/user peering through the oculars. The image of the hand can be superimposed on images of graphics such as video windows, icons, buttons, etc. in the graphic user interface. The user can thus move his or her hand so that the image of his or her hand, or a representation of the user's hand, as seen through the ocular, overlaps and/or interacts with (e.g., presses, moves, grabs, etc.) graphics on the GUI presented by the display device as seen through the oculars. Additionally, image recognition and/or gesture recognition processes can be applied to the image of the moving hand to analyze the location, movement, gesture and any combination thereof to discern what instruction is being provided by the user/surgeon. In some embodiments, other types of sensors may be included to assist in identifying the location of the hand and/or the gesture being made. A wide range of configurations are possible. In some embodiments stereo or 3D views may be provided by the one or more cameras. Additionally, although the hand has been discussed as providing the recognizable gesture in this example, the system need not be so limited.

One advantage of a gesture recognition based GUI interface is that the surgeon's hands may have blood or other bio-materials thereon. The virtual type GUI interface reduces the amount of direct contact of the surgeon's contaminated hands with the visualization equipment and thereby reduces cleaning and/or sterilization requirements.

As discussed above, in some embodiments, unlike a conventional surgical microscope, the viewing platform 9 is not a direct view device where the surgeon or other user sees through the platform but is instead an indirect view device. The gesture recognition camera, however can also be used as a scene camera to view the patient and surgical site from above the patient, e.g., above the retractor by between 15-45 cm or more in some examples, as described herein with reference to FIGS. 21C-21K. The image of the patient and the surgical site can be displayed on the display device and seen through the oculars. Even in embodiments where the gesture recognition system is not employed, one or more cameras 18 beneath the viewing platform 9 can provide views of the patient and surgical site to the display device for viewing through the ocular. In some embodiments, stereo or 3D views may be provided by the one or more cameras.

Figure 24B:
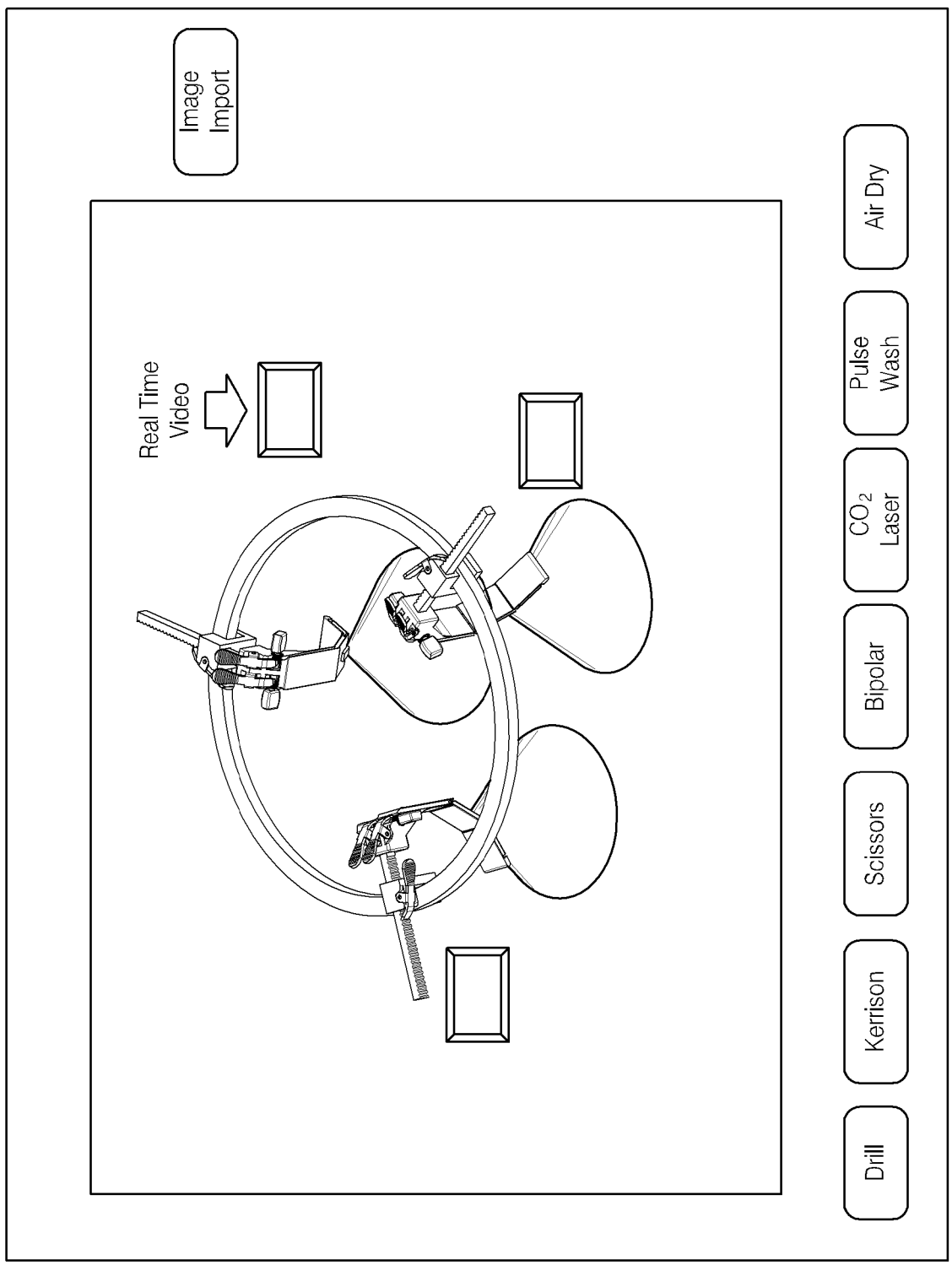
FIG. 24B shows another example graphical user interface that can be used in embodiments of surgical visualization systems.

FIG. 24B illustrates another example embodiment of a graphical user interface for use with the surgical visualization systems disclosed and described herein. The graphical user interface of FIG. 24B can be used to display a relative orientation of cameras on a retractor, showing the fields of view as cones on the display. A real-time video feed of the video coming from the respective cameras can be displayed next to or near the respective cameras or elsewhere on the GUI. In various embodiments, real-time video feeds are shown in windows having a reduced-size in comparison to the real-time video used by the surgeon to perform the tool manipulation and examine and interact with the surgical site. Accordingly, these reduced-sized windows may be sufficiently small such that the surgeon may desire to increase their size at a later time to glean sufficient detail from the video to assist in the surgical procedure. The user can manipulate the elements of the display to select cameras for viewing, for adjusting video streams on the display, identifying or verifying alignment of cameras on the retractor, import images or feeds for displaying, select and/or control surgical tools via a toolbar, and the like.

In various embodiments such as shown, the GUI includes a model or CAD image of each camera on a graphic, model or CAD depiction of the retractor frame with a conical field-of-view (FOV) for each camera, wherein the FOV depiction can be based on tracking information, such as EM tracking information. In some embodiments, the user can verify a placement and/or orientation of the retractor cameras using this GUI as the GUI shows the orientation and FOV. In some embodiments, the user can manually or remotely adjust the placement and/or orientation of the retractor cameras using this GUI or other associated user interface tools. In some embodiments, the FOV displayed for the cameras can be semi-opaque or at least partially transparent to allow a user to see other elements behind the cameras to give a better sense of their relative location and orientation.

The GUI includes real-time video feeds corresponding to the video data acquired with the various cameras on the retractor, the surgical tool, and/or auxiliary cameras. The real-time videos can be reduced-size presentations (e.g., reduced-size windows) of the acquired video which can be manipulated to select a video stream for viewing. For example, a user can select a video feed by selecting the appropriate reduced-size window or presentation and placing it on the surgeon's binocular display (e.g., if the reduced size window is on the separate touchscreen input and display device 13) and/or enlarging it on the surgeon's binocular display 13 (e.g. if the reduced size window and CAD depiction of the retractor frame with a conical FOV's are on the surgeon's binocular display).

The GUI includes a button or element that allows a user to import imaging data from other imaging modalities. For example, a user can import CT, MR, C-arm, O-arm, and/or ultrasound images as well as images from anatomic databases. These images can be sized and positioned on the screen, similar to the video feeds from the cameras of the surgical visualization system.

The GUI includes a positionable tool bar which enables control of optics washing, optics drying, LED cooling, choice and control of tools, and the like. The tools which can be controlled include, but are not limited to, drill, Kerrison, bipolar forceps, scissors, aneurysm clip applier, etc.

The GUI can be configured to respond to multi-touch input, allowing the user to virtually manipulate objects or video with their hands. The GUI can also be configured to respond to other methods of input including, for example, voice recognition, gesture recognition, and the like.

The use of the GUI can be illustrated by the following example. During the course of a procedure, a binocular surgical display can show one or more real-time video feeds from one or more cameras in a size sufficient for the surgeon to glean detail, which for the sake of this example is referred to as a primary surgical view. See, for example FIGS. 15, 16, 17, 20B, and 20D. If the user is interested in adjusting the views provided, the user can perform a designated input, via touch input, gesture, voice command, or the like to bring up the GUI illustrated in FIG. 24B and select a different camera for presentation. The GUI can then be presented on top of or instead of the primary surgical view (which for the sake of this example is referred to as a display configuration view). The user then manipulates the elements of the GUI of the display configuration to configure the display (e.g., by selecting cameras to view, sizing the camera views, arranging/orienting the camera views, etc.). Other functionality can be provided by the GUI, for example, the user can operate tools, import images, and the like. When finished, the display can revert to the primary surgical view which reflects the changes made by the user on the display configuration view. In some embodiments, actions taken on the display configuration can be configured to immediately trigger actions or results on the primary surgical view. For example, selecting a reduced size window showing a real-time video stream and resizing it about a threshold size can cause the display to show the primary surgical view with the selected camera view full size or enlarged on the surgical view. In this way, for example, the display can be configured to be immersive for the user due at least in part to the ability of the user to perform a majority of the desired functions without looking away from the display.

Transparent Rendering of Surgical Tools

In conjunction with the tracking information obtained as outlined above, the surgical tools can be rendered transparently or semi-transparently in the composite image. Electromagnetic tool trackers integrated with or fixed to surgical tools can provide position and orientation input to the image processor. This information can be used to enable rendering of tool images as a transparent or semi-transparent overlay on the continuous composite display. The tools can, for example, be rendered as wireframe objects, or can be shown having a ghost-like transparency. This can provide the dual benefits of both indicating the position of the tool and maintaining an unobstructed wide view of the surgical site. In some embodiments, the dimensions and shape of the various tools can be determined and catalogued prior to operation. The image processor may then associate the observed tool with the predetermined size and shape stored in a database or library of tools in order to render a wire-frame or semitransparent image of the tool.

Camera Cleaning

Positioned within the body, the surface of the cameras or optical elements, such as lenses, can become fogged or otherwise obstructed. To maintain visual clarity, the cameras can be cleansed while remaining in place within the surgical site. One approach to cleansing cameras is to provide pulses of fluid over the surface of the sensor or lens, thereby clearing any obstruction. Cleansing fluids may be, for example, distilled water, deionized water, or saline, among others. In some embodiments, these pulses may be brief, high-pressure, and low-volume. The pulse can be produced in a number of ways, for example by a diaphragm, actuated by a cam and motor in conjunction with a one-way valve. Fluid pressure can be supplied by air pressure in double spike IV bottle. A disposable diaphragm pump can be used to increase pulse pressure. In some embodiments, two pumps can be used to eliminate interruption in pulse pressure. In some embodiments, passive hydraulic amplifiers can be used to increase the fluid pressure. In some embodiments, solenoids, piezoelectric actuators, or other techniques may be used. A rolling edge diaphragm, Bourdon tube, or bellow can likewise be used to produce the pulse. In one embodiment, a reed valve can be configured to alternate between air and saline operating at the natural mechanical resonance frequency of the reed valve and associated fluid and air column dynamics. Pressure may then be maintained in the air and fluid circuits just below valve opening pressure, and an electrical signal may increase pressure until the reed valve opened, thus avoiding pulsating fluid tubing. In various embodiments, the fluid can be saline or other biocompatible liquid. In some embodiments, the lens elements are configured such that a stop is affixed to a first lens element wherein the stop covers a large fraction of the first lens element. Additionally, in some embodiments, the lens elements are configured such that a first element comprises a plano window. The stop can be located behind the plano window or more lens elements and can be relatively small. In such embodiments, the light collected by the stop is correspondingly small such that the area of the plano window that should remain clean is relatively small. This configuration can facilitate cleaning the lens system. In some embodiments, the plano window is secured to the lens system using a structure that does not extend over the top of the plano window so as to not interfere with mechanisms configured to clean the lens system. For example, the plano window can have a step edge or be retained by a support member (e.g., a metal ring or an edge of the lens system housing) that extends along a side portion of the plano window without extending beyond the distal face of the plano window through which light is collected for the sensor.

In some embodiments, a high-pressure fluid pulse can be followed by a high-pressure pulse of air or gas in order to dry the surface of the camera or lens and prevent salt deposits or image obscuration. Sources for the high-pressure air may be, for example, hospital compressed air nitrogen systems, or compressed air or nitrogen tanks. The air pulse can be actuated similar to the fluid pulse as described above. For example, a diaphragm actuated by a cam and motor in conjunction with a one way valve may be used. In some embodiments, a Venturi effect may be used to generate the post-wash air flow. The Venturi effect depends on the size and shape of the port through which the fluid flows. In general, when a fluid flows through a constricted section of pipe, the pressure is reduced. This low pressure can draw in additional outside air and can cause air flow following the fluid pulse. As discussed in more detail below, a proportional foot pedal can control actuation of the fluid and/or air pulses.

In some embodiments, the flex cable may include fluidic channels to convey the air, gas, or liquid to the camera optics to provide for cleaning. Fluidic channels can also transport other fluids such as pharmaceuticals, saline for irrigation, fluorescent dyes, etc. to the surgical site. Fluidic channels can also be provided for aspiration, to provide egress of gases or liquids from the surgical site. The fluidic channel containing flex cable may be an overlay or surrounding member affixed over the electronic flex cable, thereby allowing the fluid-carrying component to be disposable, whereas the electronic flex cable with integrated optics module may be sterilizable and reusable. The distal end of the fluidic flex cable can contain an outer housing that is secured over the imaging module. In some embodiments, it is the annular space and shape of the inner surface of said outer housing that directs the fluid and or fluid air pulse over the most distal surface of the optics for cleaning.

FIGS. 25A-C show an embodiment wherein an irrigation pathway 403 is provided by an outer sheath 401 comprising a flex cable 405 including fluidic channel containing flex cable and a portion that covers the sensor and imaging optics 409. The portion 402 of the sheath 401 that covers the sensor and imaging optics 409 can be shaped to provide conformal fitting yet leave a space 411 between the sheath 401 and the sensor and imaging optics 409 for air flow. A section 410 of the outer sheath 401 forward of the imaging optics can be shaped to direct the fluid across the distal surface of the lens. In some embodiments, the outer sheath 401 that delivers the fluid can be a separable assembly that can be added to or attached to the optical stack 409. In some embodiments, the fluid is delivered in the flex cable 405 that forms part of this sheath 401. This flex cable 405 is separate from the flex cable 407 that includes electrical connection for powering and receiving signal from the camera. In some embodiments, when the separable assembly is attached to the optical stack 409 and electric flex cable 407, the fluidic flex cable 405 assembly sits on top of the electrical flex cable 407 and above the optical stack 409. In some embodiments, the outer sheath 401 can be designed to snap onto the optical portion creating a seal around the optical stack 409 and then later detached. In various embodiments, the detachable sheath 401 is disposable while the imaging optics 409, sensor, and flex wire 407 connected thereto are sterilizable. In other embodiments, a fluid nozzle can be positioned on one side of the imaging optics, with an air nozzle on the other side with no sheath.

In some embodiments, the outer sheath 401 at the location of the camera and imaging optics 409 includes an inner wall 412 in addition to an outer wall 414, both shaped as concentric right circular cylinders, one inside the other. In some embodiments, the inner wall 412 which is closest to the imaging optical 409 surrounds the optical stack so as to leave a gap 411 of air between the optical stack 409 and the cylindrical inner wall 412. This gap 411 advantageously facilitates air flow between the optical elements (e.g., lenses) in the optical stack and thereby reduce the risk of condensation forming on the optical elements. In various embodiments, the outer sheath 401 is configured so as to allow fluid to enter the outer sheath 401 and be directed over the front most surface of the imaging optics 409. As described above, the delivered fluid can be liquid, or gas, or a combination of both. In some embodiments, the irrigation pathway 403 can also be used to deliver other fluids such as pharmaceutical and fluorescent dies. In some embodiments, the irrigation pathway 403 can be used for aspiration and fluid egress.

Other configurations are possible. For example, in some embodiments, the fluid can be delivered by separate fluidic channels of the same flex cable that includes the electrical power and signal lines.

Figure 26:
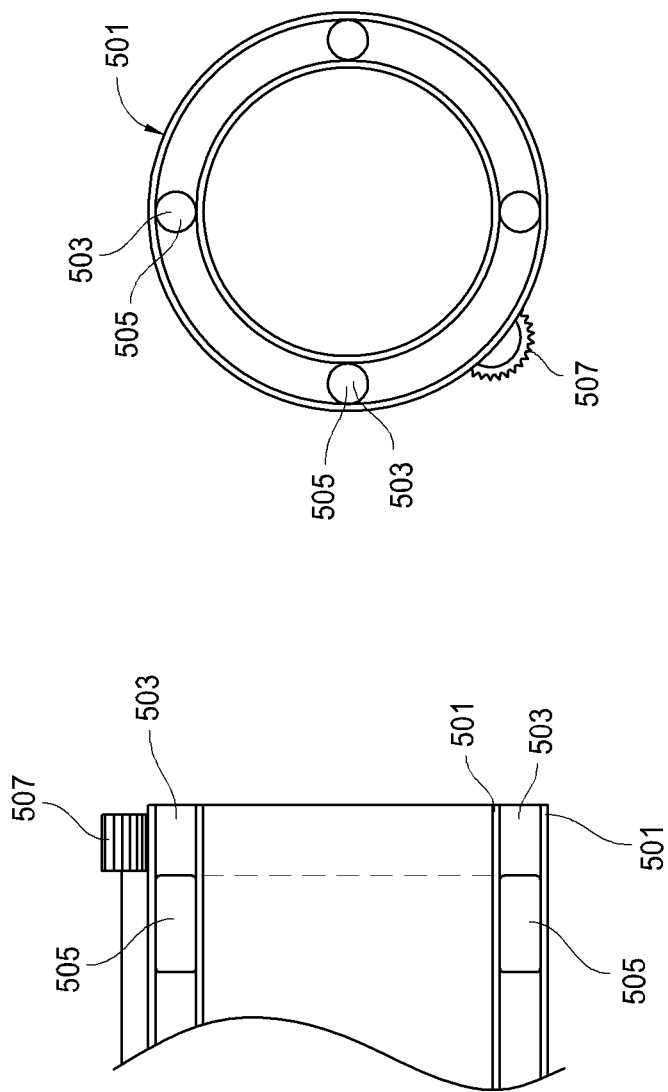
FIG. 26 shows a fenestrated ring configured to cleanse optical sensors.

An additional approach to cleansing optical sensors and/or lenses is to mechanically 'squeegee' the surface. In one embodiment, as illustrated in FIG. 26, a fenestrated, rotary ring 501 with silicone rubber surface that can be arranged such that it is normally positioned with holes 503 in front of the cameras 505. This approach may be particularly useful in embodiments in which the surgical device is a tubular retractor, for example those used in minimally invasive spinal surgery. The cameras 505 can be arranged along the annulus of the retractor. The rotary ring 501 disposed over the cameras 505 may then be rotated such that silicone sweeps across the surface of the cameras 505 or lenses to clean them as a squeegee. The ring 501 may be rotated by a number of mechanisms. In the illustrated embodiment, a gear assembly 507 is disposed at the periphery of the ring 501. In another embodiment, MEMS or pneumatically actuated individual blades may be arranged adjacent the front surface of a camera module. The blade can be actuated to sweep across the front surface in a windshield-wiper fashion or otherwise, thereby cleansing the camera.

Temperature Control

In various embodiments it may be advantageous to control the temperature of certain components of the system. For example, heating the cameras to approximately body temperature can reduce fogging effects during surgery. In some embodiments, the flexible cable and/or retractor blades can include a heater to heat the cameras. However, excessive heat—such as from LEDs or from an over-heated cameras—can damage surrounding tissue during use. Accordingly, in some embodiments a thermocouple may be included in the device. For example, a thermocouple may be disposed near the cameras and/or LEDS. In some embodiments, a thermocouple sensor can be used to provide temperature measurement and control of the heated camera or flexible cable. The thermocouple may be configured to provide feedback such that the system provides heating or cooling as appropriate.

Heating can be provided in a number of ways. For example, small resistive heaters may be disposed within or near the cameras and/or LEDs. In some embodiments, a metallization disposed within the retractor can provide the heating element. In some embodiments, the metallization can be a part of the flexible cable described above. Similarly, cooling can be provided in a number of different ways. For example, the fluid pulses described above with respect to cleansing of the cameras may also provide cooling effects. Accordingly, should a camera or LED become dangerously hot, a brief, high-pressure pulse of fluid may be dispensed to decrease the temperature.

Foot Pedal with Feedback

A foot pedal may be used by the operator to actuate surgical tools and/or to actuate cleansing of the cameras. For example, an operator may depress a foot pedal to initiate the pulsing of liquid followed by the pulsing of air over the surface of the cameras. In some embodiments, the liquid pulse and the air pulse may be controlled by separate foot pedals. With respect to surgical tools, a foot pedal may similarly be used for actuation. For example, a cutting tool such as scissors may be moved from an open to a closed position by depressing the foot pedal. A plurality of foot pedals may be provided, each associated with a different surgical tool. In some embodiments, a left foot pedal can provide control of a surgical tool that would manually be controlled by the operator's left hand, and a right foot pedal can provide control of a surgical tool that would manually be controlled by the operator's right hand.

In some embodiments, the foot pedal may actuate the device proportionally. For example, the degree to which the foot pedal is depressed can control the amount of force applied to the closing of scissors blades or forceps moving elements of an associated surgical tool. In some embodiments, the foot pedal may provide sensory feedback with respect to the actuation of surgical tools. For example, the resistance to the closing of scissor blades can be measured and communicated to the operator by increased resistance to the depression of the foot pedal. Such feedback can provide the operator with a sense of the resistance to cutting, despite the fact that the tool is actuated indirectly via the foot pedal. The position of the foot pedal can be measured in a number of ways, for example by the use of an angular optical encoder and/or a force-sensing resistor.

Switching Illumination On and Off

As noted above, in some embodiments one or more of the cameras may have associated illumination sources integrated nearby. For example, in some embodiments, each camera can include two adjacent LEDs, each on opposite sides, so that the LEDs illuminate the field of view of the camera. This illumination, however, can be problematic in instances in which one or more of the cameras are oriented so as to at least partially face another camera. For example, if a first camera faces a second camera, adjacent LEDs on the second camera may effectively blind the first camera. The same principle applies to configurations in which the illumination sources are not associated with particular cameras. In any arrangement in which a camera directly images an illumination source, there is a risk of blinding the camera, or at least degrading the quality of the image.

To address this shortcoming, the illumination sources and the cameras can be carefully timed or synched to avoid a camera directly imaging an active illumination source. For example, an illumination source that is in the field of view of a camera can be controlled such that it is off or blocked while the camera is on, and conversely the illumination system can be on while the camera is off or blocked. This arrangement can be toggled rapidly, effectively strobing both the camera and the illumination source so as to reduce or eliminate the time during which the camera directly images an active illumination source. The camera and illumination source can be electronically controlled to allow for automatic and rapid strobing. At a sufficiently high strobing frequency, the effect can be undetectable by an observer. The composite image generated by stitching the views of the plurality of cameras can avoid any particular camera being blinded by the presence of an active illumination source in its field of view.

As noted above, in some embodiments described herein there may be many cameras, and additionally there may be many illumination sources. The strobing principle noted above can be applied to such configurations in a similar fashion. For example, by appropriately timing each of the illumination sources and each of the cameras, images can be captured in which the active unblocked illumination sources are imaged less often, or in some embodiments not at all. Such timing can be realized in a number of different approaches. For example, in one embodiment, each camera and its associated illumination source(s) can be turned on while all other cameras and illumination sources are turned off. When one camera and its illumination source(s) are then turned off, a next camera and its illumination source(s) can then be turned on. This can continue at a rapid pace such that each camera is active for a brief time in a given cycle. The cycle can be repeated continuously so that the composite image can effectively provide continuous wide field-of-view visualization.

In other embodiments, the strobing can be applied only to those cameras which directly image or have an illumination source in the field-of-view of the camera. In some embodiments, optical recognition, positional tracking, or other techniques can be used to determine when a camera is positioned to image an illumination source. In some embodiments, once this condition has been determined, that camera may be modulated, synched, or strobed (e.g., switched on and off or blocked during intervals of time and unblock during other intervals) in coordination with the associated illumination source, which also may be modulated or strobed (e.g., switched on and off or blocked for certain intervals of time and unblocked during other intervals). This approach can be applied to configurations containing many cameras and many illumination sources. As noted above, the strobing may be affected continuously and rapidly, such that an observer is unable to detect the strobing, however, in other embodiments the rate of modulation or strobing need not be so fast as to be undetectable by the eye. In some embodiments, the rates of modulation, for example, may be below the absolute threshold of seeing, or below a difference threshold, where the measure or sensation of 2 or more individual image modulations are not detected by the user. Moreover, brief flashes of the light sources and/or short activation periods for the sensors need not be used. Yet, in such embodiments, the illumination may be alternated in synchrony with the operation of image sensors that are in the field-of-view of the light sources and vice versa.

In addition to direct blinding of a camera by an illumination source, specular reflections from instruments in the field of view of one or more cameras may reduce image quality. For example, a particular sensor may receive an unwanted specular reflection from a particular tool originating at a particular illumination element. In various embodiments, there are at least two possible responses: strobing and synching of the offending illumination source and sensor, and/or an area-of-interest calculation to reduce blooming or oversaturation in a portion of a sensor's image, in particular a CMOS sensor. As the tools, sensors, and illumination sources can be known through tracking, in various embodiments a global response to blooming may take the form of a look up table or global ray tracing algorithm to minimize over-saturated areas within an image or array of images as the tools are used within the illuminated scene.

White Balancing

As discussed elsewhere herein, a composite image can be formed by stitching together multiple, separate images from a plurality of cameras. The images obtained from the separate cameras may, however, have different optical properties depending on a variety of factors. For example, the images obtained may vary in saturation, brightness, contrast, etc. depending on the camera and the configuration thereof and the conditions under which the images are recorded. Stitching together images of varying optical properties can create a patchwork effect in which the composite image can be degraded by the stark contrast in optical properties from a region captured by one camera to the next.

In order to counterbalance such effects, the images recorded from the separate cameras can be balanced or normalized. One such approach involves white balancing of the images from the cameras. For example, a white or neutral colored object, such as a cylindrical fixture, can be inserted into the surgical space observable by some or all of the cameras. The color of this object can be used to normalize the optical properties (color gamut and gain) of the sensors and the different images, thereby allowing for a more seamless composite image generated by stitching or tiling. In some embodiments, a multiple camera array can color balance composite images, wherein color balancing can include a global adjustment on one or more primary colors, red for example. Much of the surgical scene is dominated by red and its corresponding channel may be adjusted for continuity.

In some embodiments, the cameras could white balance on the mechanism, that holds the array of cameras inside a tubular retractor where one camera image intersects another. Various other approaches can be used to normalize the images obtained from the plurality of cameras. The resulting composite image can therefore appear seamlessly stitched, such that the user is unable to readily determine the borders between one image and the next. Note that in some embodiments, the images may be tiles such that discontinuities and/or gaps may exist in the composite image as a result of regions of the surgical site not imaged by the cameras.

In some embodiments, the item or mechanism used for color- or white-balancing can include a target to assist in aligning images from various cameras. In some embodiments, the target can be a mechanism that is used prior to inserting the retractor into the surgical site. For example, the mechanism can include a cylindrical or conical element with a substantially uniform color (e.g., white) and an asymmetric pattern. The retractor having a plurality of cameras can be positioned on the mechanism such that the cameras image the mechanism. The image processing module can calibrate the cameras based at least in part on the imagery of the mechanism where calibration information can include white balancing and/or alignment information. The white balance can be based at least in part on differences in color of the images of the mechanism between the cameras. Alignment information can be based at least in part on aligning the asymmetric pattern of adjacent images. For example, the white-balancing/alignment mechanism can be a uniformly white cylinder having asymmetric horizontal and/or vertical lines. The image processing system can use these features to align the images received from the various cameras by aligning the features within the composite image. Such a system can be used in association with a surgical tool as well. For example, the surgical tool can have a known color and/or pattern and the image processing system can process images of the surgical tool to calculate a position and/or orientation of the surgical tool as well as use the features of the surgical tool to align images from multiple cameras and/or color- or white-balance the images.

Example Embodiments of Imaging Modules

Figure 27A:
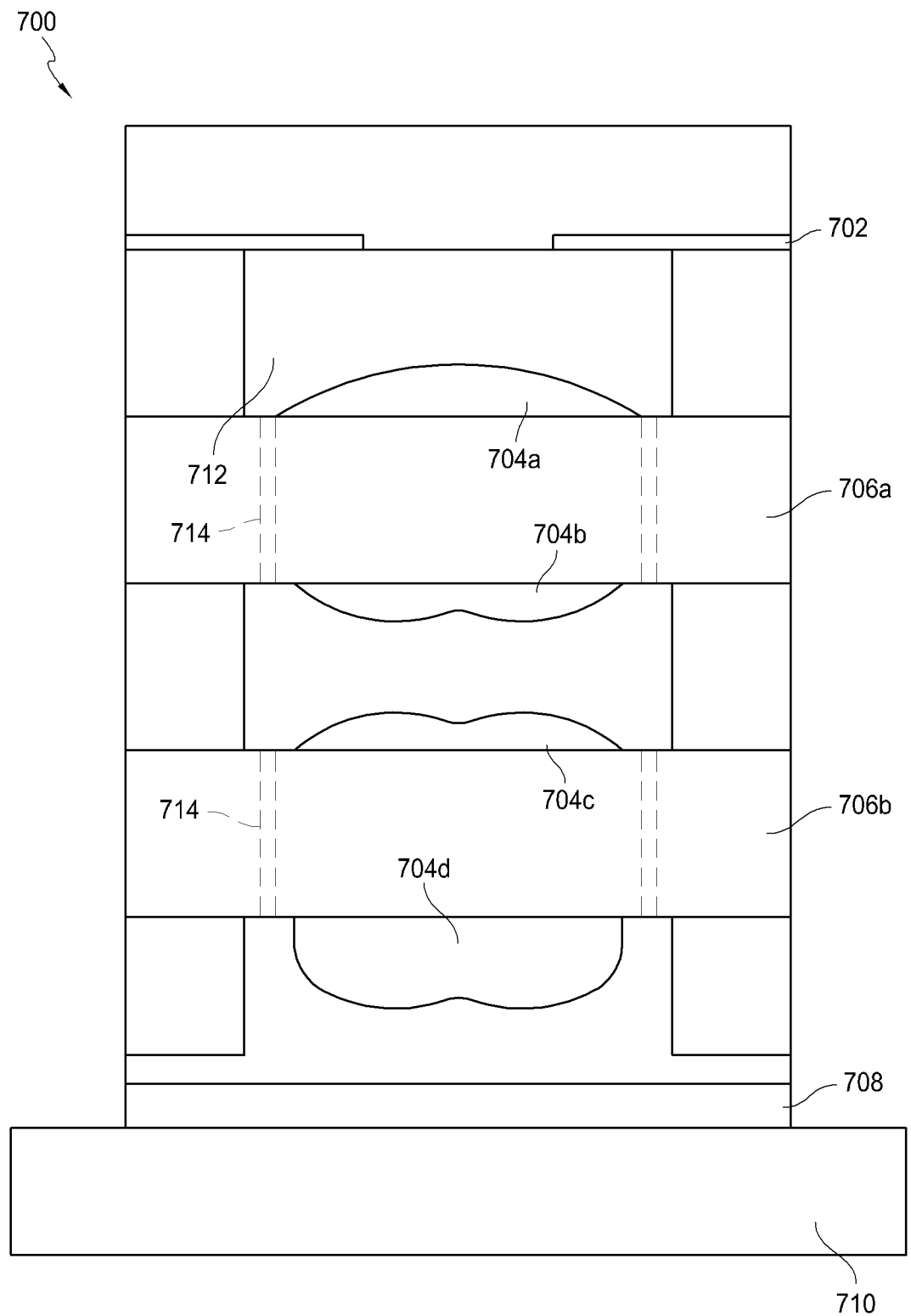
FIG. 27A shows some embodiments of wafer-scale optics for use with a surgical device.

FIG. 27A shows some embodiments of an imaging module 700 comprising wafer-scale optics (or wafer level optics) for use with a surgical device. The imaging module 700 can include a stop 702 at a distal end of the module. In some embodiments, the stop 702 provides an f-number for the imaging module 700 having a value at least about 2.8 and/or less than or equal to about 3.3. The imaging module 700 can include one or more regions of material 704a-d configured to act as optical elements, such as lenses. The elements 704a-d can be configured to direct light and/or control distortion in the imaging module 700. In some embodiments, the elements 704a-d may comprise optically transparent material such as but not limited to plastic or glass (e.g., molded glass). The elements may comprise, for example, monomers, polymers, or other compositions. In some embodiments, the elements 704a-d comprise resin. In some embodiments, the elements 704a-d comprise acrylic, benzyl (meth)acrylate, (meth)acrylic acid copolymers or multicomponent copolymers comprising benzyl (meth)acrylate, (meth)acrylic acid or other materials. The elements may also comprise a wide range of other materials instead. As an example, and without limitation, elements 704a-d can have a refractive index that is at least about 1.5 and/or less than or equal to about 1.7, or at least about 1.52 and/or less than or equal to about 1.65. As an example, some elements 704a-d can have a relatively high dispersion and can have an Abbe number that is, without limitation, at least about 50, at least about 55, or at least about 60. Some elements 704a-d can have a relatively low dispersion and can have an Abbe number that is, without limitation, less than or equal to about 30, less than or equal to about 25, or less than or equal to about 20. For some examples of wafer-scale optics (or wafer level optics), see U.S. Patent Pub. Nos. 2011/0063734 to Sakaki and 2012/0134028 to Maruyama.

The imaging module 700 can include structural elements 706a and 706b configured to separate optical elements, provide mechanical durability, provide support to optical elements, maintain one or more gaps 712 in the imaging or sensor module, or any combination of these. In some embodiments, the structural elements 706a and 706b can comprise a material that has a relatively low index of refraction, that has a low coefficient of thermal expansion, that is relatively impervious, or any combination of these properties. The structural elements 706a and 706b can be borosilicate glass, low-iron crown glass, or other similar material. For example, the structural elements 706a and 706b can be SCHOTT MEMpax®, BOROFLOAT® 33 borosilicate glass, D 263 T® eco borosilicate glass, AF 32® eco aluminoborosilicate glass, or B 270® low-iron crown glass supplied by Schott North America, Inc. or Duryea, Pa. Other materials, however, may also be used.

As an example, and without limitation, typical values for coefficients of thermal expansion for structural elements 706a and 706b can be between about $2 \times 10^{-6}$ $K^{-1}$ and $9.9 \times 10^{-6}$ $K^{-1}$. As an example, and without limitation, typical values for refractive indices for structural elements 706a and 706b can be between about 1.4 and 1.6 As an example, and without limitation, typical values for Abbe numbers for structural elements 706a and 706b can be between about 50 and 70. Value outside these ranges, however, are possible.

The imaging module 700 can include an image sensor 708, as described more fully herein. The imaging module 700 can be electrically and/or physically coupled to cable 710. In some embodiments, cable 710 is a flex cable, as described more fully herein. In some embodiments, the module 700 has a field of view that is about 70 degrees.

In some embodiments, the imaging module 700 includes a moving element configured to adjust a position and/or orientation of one or more lens elements. For example, the moving element can include a piezo, motor, or other transducer or actuator configured to translate one or more lens elements in one or more directions.

The imaging module 700 comprising wafer-scale optics can be manufactured using processes utilized in semiconductor wafer manufacturing. In some embodiments optically transparent material is deposited on a surface of a substrate or structural support element (706a, 706b) such as a circular wafer like the wafers used for semiconductor device fabrication and is shaped to form a lens (704a-704d). The optically transparent material may be shaped, for example, by imprinting, embossing, or molding using a master. The master may be formed, in part by ion etching in certain embodiments. In some embodiments, material is added to the optically transparent material disposed on the substrate, material is removed from the optically transparent material disposed on the substrate, or as mentioned above, the optically transparent material disposed on the substrate is shaped. In some embodiments, ion milling may be employed. In some embodiments, multiple layers maybe be formed and joined during manufacturing. For example, multiple substrates or structural support elements 706a, 706b may be provided, and lenses (704a-704d) formed thereon. The substrate or structural support elements 706a, 706b can be stacked. In some embodiments, lenses 704a are formed on a wafer which is cut to create separate support elements 706a having lenses disposed thereon. Similarly, lenses 704b are formed on a different wafer which is cut to produce separate support elements 706b having lenses thereon. Support elements 706a having lenses 704a thereon can be stacked on support elements 706b also having lenses 704b thereon. Additional layers may be added as well.

Likewise, the wafer scale optics shown in FIG. 27A comprises a plurality of substrates stacked on top of each other with spaces therebetween. Lenses having one planar surfaces adjacent to the planar surface of the substrate and one curved surface can, for example, refract and bend light. As shown, such lenses having one planar surface formed on a substrate and one curved surface can be formed on both sides of a substrate (which as shown has two planar surfaces). Accordingly, in some embodiments, two curved surface are provide for a given substrate.

For example, as illustrated in FIG. 27B, a first layer 740 can be formed having a first thickness, $d_1$, and interlocking features 742. The first layer 740 may comprise the structural support element 706a having layer of material formed thereon and patterned to produce the interlocking features 742. A second layer 744 can be formed having a second thickness, $d_2$, and interlocking features 746 that are complementary to the first layer interlocking features 742. The second layer 744 may comprise the structural support element 706b having a layer of material formed thereon and patterned to produce the interlocking features 746. The layer of material that is deposited may comprise monomer, polymer, glass or other material. The first and second layers 740, 744 can be stacked and interlocked to produce a portion of a wafer-scale optics or wafer level optics element. The first thickness, $d_1$, and the second thickness, $d_2$, can be different. The height of the interlocking features 742 and 746 can also be different. In some embodiments, multiple layers (e.g., two, three, four, five or more layers) are stacked to form the imaging module 700.

In some embodiments, wafers 750 such as illustrated in FIG. 27C are diced up to form the structural support elements 706a, 706b after having the elements 704a, 704b formed thereon thereby producing the separate multiple wafer-scale optics elements 752 that are stackable. To align the wafer-scale optics elements 752, fiducials features 754 can be included. In some embodiments, these fiducial features comprise the interlocking features 742, 746 discussed above. Accordingly, fiducials 754 on a proximal surface of a first wafer can be configured to mate with complementary fiducials 754 on a distal surface of a second wafer such that the wafers interlock when aligned. In some embodiments, adhesives are included when stacking the layers. The adhesives can be UV-cured adhesives, thermal-cured adhesives, or other types of adhesives. The plurality of the wafer-scale optics elements 752 can be aligned and locked together as described. In some embodiments, wafers 750 such as illustrated in FIG. 27C are diced and then stacked. Alternatively, the wafers 750 can be stacked and then diced. Combinations of these approaches may also be used.

In certain embodiments, the fiducials 754 can provide stress relief to the imaging module 700 thus formed. The structural support elements 706a, 706b, having lenses 704a, 704b formed thereon may be subject to stress that causes the structural support element 706a, 706b to bow or otherwise misshapen. This stress may be caused at least in part, for example, by differing coefficients of thermal expansion of various components of the wafer-scale optics elements 752 such as of the structural support element 704 and the lens 706. In various embodiments, the fiducials 754 can be used to apply forces on proximal and distal surfaces of the wafers and structural support element 706a, 706b thus assisting the structural support element 704 and the lens 706 thereon to substantially to retain its shape. In some embodiments, the fiducials 754 comprise monomers, polymers, glass, or other material deposited on proximal and/or distal surfaces of a wafer 750. The fiducials 754 can be configured to reduce or eliminate stress-induced warping due at least in part to differing coefficients of thermal expansion of various elements on the wafer and/or in the imaging module 700. In various embodiments, the stress contributed by the fiducial layers 754 on opposite sides of the structural support element 704 largely offset each other to reduce the amount of bowing. In some embodiments, the amount of material forming the fiducial 754 may exceed the amount of material forming the lens such that the stress induced by the fiducial on both proximal and distal sides of the structural support element exceeds and overwhelms the stress induced by the lens. In some embodiments, the stress induced by the lens 704 and the fiducials on the same side of the support element 706 is substantially similar to the stress induced by the fiducial layer on the opposite side of the support element 706.

In certain embodiments, the structural elements 706a, 706b (referring to FIG. 27A) in the imaging module 700 comprise substrates having one or more holes 714 extending from a proximal surface to a distal surface of the substrate. The holes 714 in the substrate can allow fluids to communicate between regions or gaps 712 between the structural elements 706a and 706b. The holes 714 can be formed by drilling through the substrate or using a chemical machining process during manufacture or may be formed using other techniques. With reference to FIG. 27C, the holes 714 can be cut in the plurality of wafers 750. As described above, the wafers 750 can be cut and the substrates 706 formed therefrom can be stacked and interlocked, creating compartments 712 between the substrates 706 that otherwise would provide a barrier preventing fluidic communication between compartments. The holes 714, however, thus can provide for fluidic communication between these compartments. Fluidic communication can reduce or eliminate condensation on optical elements in the imaging module 700, e.g., on the lenses 704 during use or procedures where elements are exposed to fluids and/or changes in temperature that facilitate or promote the formation of condensation.

Figure 28:
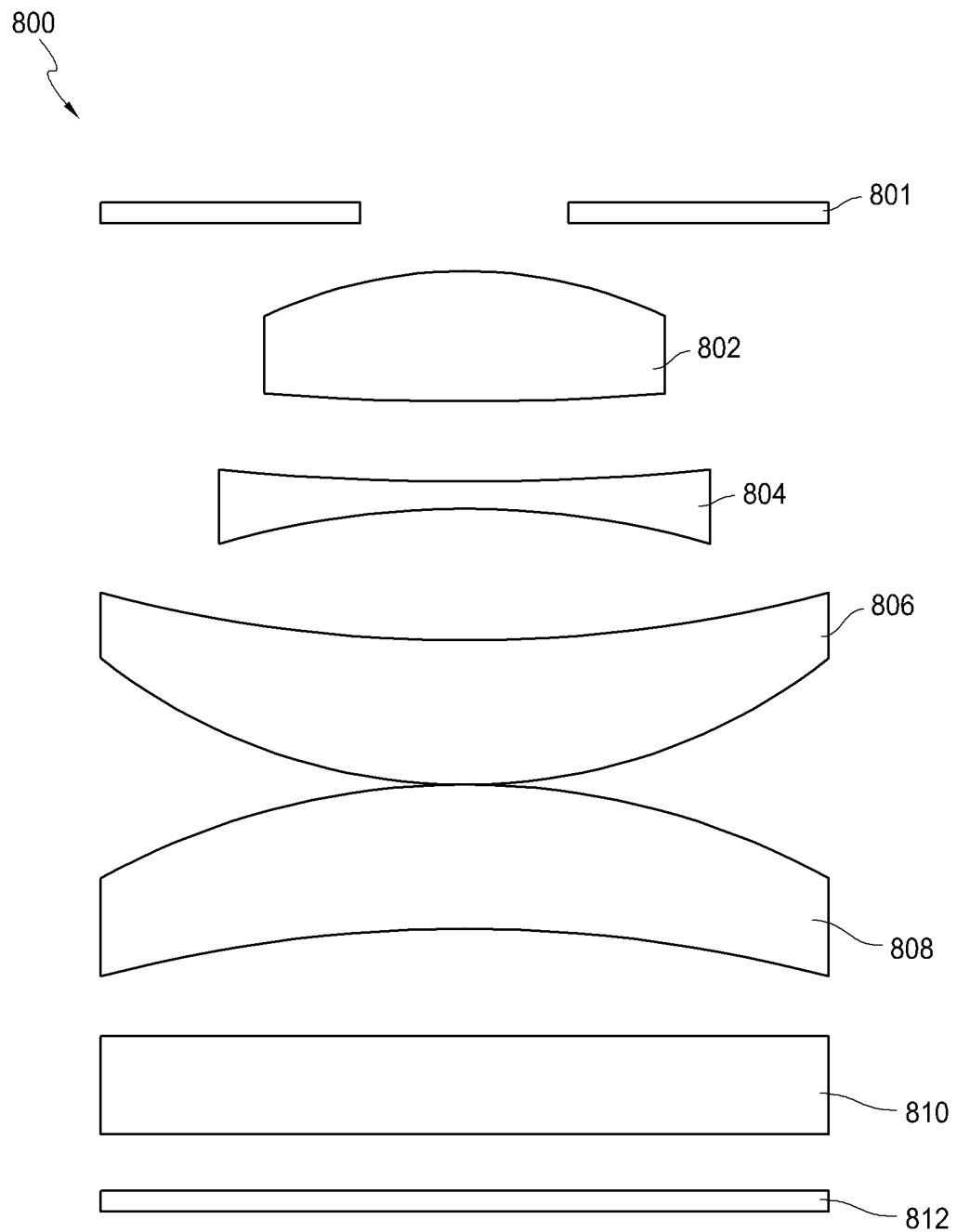
FIG. 28 shows an embodiment of an optical prescription for an imaging module having a field of view less than or equal to about 70 degrees.

FIG. 28 shows some embodiments of an optical prescription for an imaging module 800 having a field of view less than or equal to about 70 degrees. The imaging module 800 can include a stop 801 on a distal portion of the imaging module in combination with four or more lenses. In some embodiments, the imaging module 800 includes the stop 801, a positive lens, a negative lens, and a plurality of positive lenses. The imaging module 800 can be relatively compact while providing a moderate field of view and resulting in relatively low distortion (e.g., less than about 10% distortion). In some embodiments, the first element 802 is a positive lens having a relatively high index of refraction and relatively moderate dispersion. The first element 802 can be combined with a lens having a relatively high index of refraction and relatively high dispersion. Lens elements 806 and 808 can be positive lenses and configured to shorten an optical path and correct for distortions introduced by previous lens elements. The imaging module 800 can comprise wafer-scale optics. The imaging module 800 can be used with a surgical device.

As shown in FIG. 28, the imaging module 800 comprises lens elements 802, 804, 806, 808, 810, and can be configured to form an image at 812. The respective lens elements can have properties, such as distal and proximal radii, thickness, distance to the next element, index of refraction (n), Abbe number (V), and the like. Table 1 lists example values for various properties of the optical elements 802 through 810. For reference, a distal surface of a lens element is the surface furthest from the image 812, and a proximal surface of the lens elements is the surface closest to the image 812. Furthermore, a thickness is the distance from the distal surface to the proximal surface in a particular lens element. Finally, the column labeled distance in the table refers to the distance from the proximal surface of the element in that row to the next element (i.e., the element in the next row). In the example shown in FIG. 28 and Table 1, the stop is at the first surface and has an aperture of 0.125. The values in the table are normalized to produce an effective focal length of 1. Note that in this design, the aperture stop is in front and the lens, in order, from front to back are positive, negative, positive, and positive. This design may be suitable for providing fields-of-view less than 70 degrees, e.g., between 50-70 degrees.

TABLE 1

| Lens Element | Distal R | Proximal R | Thickness | Distance | n | V |
|---|---|---|---|---|---|---|
| Element 802 | 0.823 | −3.216 | 0.235 | 0.089 | 1.79 | 47.5 |
| Element 804 | −1.04 | 1.04 | 0.07 | 0.13 | 1.76 | 26.5 |
| Element 806 | −2.94 | −0.8 | 0.255 | 0.012 | 1.79 | 50.0 |
| Element 808 | 1.3 | 6.055 | 0.44 | 0.341 | 1.79 | 50.0 |
| Element 810 | infinity | n/a | 0.25 | 0.04 | 1.52 | 58.6 |

In certain embodiments, the imaging module 800 includes a lens group comprising two or more lenses (806, 808) at a proximal end that concentrate or focus light, similar to a condenser lens group. In some embodiments, this group comprises two positive power lenses. In some embodiments, these lenses may comprise positive power lens 806 having a concave distal surface and a convex proximal surface and a positive power lens 808 having a convex distal surface and a concave proximal surface as shown. Accordingly, the vertices of these lenses 806, 808 may face each other and be in close proximity or even be in contact with each other. Although the stop is shown forward the first lens 802, in certain embodiments, the stop 702 can be located between lens elements.

FIG. 29A shows some embodiments of a wide field-of-view imaging module 900 with a buried stop 904 for use with a surgical device. Advantageously, some embodiments include the buried stop 904 allowing for a relatively wider field of view. In some embodiments, aspheres and/or more elements are included in the imaging module 900 to correct for distortion. In various embodiments, the imaging module 900 may include imaging optics comprising a negative distal lens group 902 having one or more lenses that produce a total optical power for that group that is negative and a positive proximal lens group 906 having one or more lenses that produce a total optical power for the group that is positive. The negative distal lens group 902 can be relatively strongly curved. A plano-concave lens can be used to facilitate fabrication, alignment, and/or cleaning, among other advantageous features. In some embodiments, the negative distal lens group 902 can include a plano-concave lens that has a relatively large negative optical power, a relatively high index of refraction, and a relatively moderate dispersion. In certain embodiments, the negative distal lens group 902 has a relatively high index of refraction and a relatively high dispersion. Some examples of lens elements suitable for use in the negative distal lens group 902 are SF10, SF14, SF57, supplied by Schott North America, Inc. of Duryea, Pa., and LAH58, LAF-21, LAFN31, LASF41, and LASF44 supplied by Ohara of Rancho Santa Margarita, Calif. In some embodiments, the negative distal lens group 904 includes lens elements configured to correct for distortion introduced by lens elements having a relatively strong curvatures or a relatively high negative optical power. In certain embodiments, the positive proximal lens group 906 is configured to correct for distortions introduced by the negative distal lens group 904. The imaging module 900 can include a stop 904 wherein the negative distal lens group 902 is on a distal side of the stop 904 and the positive proximal lens group 906 is on a proximal side of the stop 904. In some embodiments, the stop 904 can have an f-stop value that is, for example, at least about 3 and less than or equal to about 10 and may be at least about 4 and less than or equal to about 8. In some embodiments, the imaging module 900 can include one or more afocal lens groups but may be non-afocal as well. The imaging module 900 can include a camera 908, as described more fully herein. The imaging module 900 can be configured to have a wide field-of-view. For example, the imaging module 900 can be configured to have a field-of-view that is at least about 90 degrees and/or less than or equal to about 120 degrees.

In some embodiments, the wide field-of-view imaging module 900 comprises non-wafer-scale optics combined with wafer-scale optics on a distal side of the stop 904. The wide-field of view imaging module 900 can include additional optics on a proximal side of the stop 904. In certain embodiments, the negative distal lens group 902 comprises non-wafer-scale optics and the positive proximal lens group 906 comprises wafer-scale optics. In some embodiments, the negative distal lens group 902 comprises wafer-scale optics having a stack of negative lens elements on a distal side of the stop 904. The wide field-of-view imaging module 900 can include optics on a proximal side of the stop 904 comprising wafer-scale optics or non-wafer-scale optics.

FIG. 29B shows an example embodiment of an optical assembly 950 comprising an afocal module 955 coupled to an optical imaging module 960 for use with a surgical device. The afocal module 955 can be added to an existing optical imaging module 960 to create a combined optical assembly 950 configured to achieve desired optical properties. The previously existing optical imaging module 960 may comprise, for example, a wide field-of-view, imaging module that otherwise would form an image on the sensor 975 In some embodiments, the optical assembly 950 has a different field of view than the optical imaging module 960 due at least in part to the afocal module 955. For example, when compared to the optical module 960, the combination of the afocal module 955 and the optical module 960 can have a broader or narrower field of view as determined, at least in part, to the optical properties of the afocal assembly 955. In some embodiments, the optical assembly 950 includes an optical filter. The optical filter can be included between the afocal module 955 and the optical module 960, the optical filter can be part of the afocal module 955, or the optical filter can be a part of the optical module 960. The optical assembly 950 has a stop 970 located in the optical module 960. In some embodiments, the stop 970 can be located in the afocal assembly 955 or between the afocal assembly 955 and the optical module 960.

The afocal assembly 955 includes optical elements 957a, 957b. A first optical element 957a can have a negative optical power. A second optical element 957b can include optical elements that, when combined with the first optical element 957a, form an afocal module 955. The optical elements 957a, 957b can be wafer-scale optics, non-wafer-scale optics, or a combination of these. The second optical element 957b of the afocal assembly 955 includes a lens element 965 having a configuration wherein a central circular portion 966 has a negative optical power and an annular peripheral portion 968 has a positive optical power. The lens element 965 can be configured to alter a direction of propagation of peripheral rays more than of central rays. The lens element 965 can be used to correct for distortions introduced by the first optical element 957a. The lens element 965 can be positioned to increase or maximize corrections to distortions. For example, the lens element 965 can be positioned near the image plane 975 or near the first optical element 957a. The lens element 965 can be positioned before the stop 970.

As shown, the optical element 957b includes lens on the proximal and distal sides thereof. The lens shown on the distal side may comprise a positive power lens in some embodiments. Other configurations, however, are possible.

The optical elements 957a, 957b can be aspherical, spherical, or have another shape. The optical module 960 can include one or more optical elements 962 wherein the optical elements comprise wafer-scale optics, non-wafer-scale optics elements such as glass, or a combination of these. In some embodiments, the afocal module 955 comprises non-wafer-scale optics optical elements made of glass. In some embodiments, the optical module 960 comprises wafer-scale optics. The optical assembly 950 can thus be configured as a combination of non-wafer-scale optics optical elements and wafer-scale optics. The afocal module 955 can include spherical lens elements. The lens elements of the afocal module 955 can comprise materials having a relatively high index of refraction (e.g., without limiting the indices of refraction, typical values can be between about 1.55 and about 1.7) and relatively high dispersion (e.g., without limiting the Abbe number, typical values can be at least about 50, 55, or 60) or materials having a relatively low index of refraction (e.g., without limiting the indices of refraction, typical values can be between about 1.3 and about 1.6) and relatively low dispersion (e.g., without limiting the Abbe number, typical values can be less than or equal to about 30, 25, or 20). In some embodiments, the optical assembly 950 can have a relatively low f-number compared to other wafer-scale optical assemblies wherein the f-number is set to provide a relatively greater depth of field compared to wafer-scale optics suitable for use where the subject is relatively far from the image sensor. In some embodiments, adding the afocal module 955 to the optical module 960 reduces the focal length, thereby increasing the field of view. Although module 955 has been described as an afocal module 955, this module need not be afocal.

As described above, the module 955 may advantageously be added to a pre-existing optical imaging module 960. In this manner, the field-of-view may be altered. For example, the pre-existing optical imaging module 960 may have a modest field-of-view, e.g. of between 50°-70°. However, addition of the add-on module 955 may increase the field-of-view to beyond 70° such as to 90°-120°.

FIG. 29C shows an imaging module 980 comprising optical elements 982a and 982b configured to change properties of the imaging module 980. For example, a first interchangeable optical element 982a can comprise a plano-plano block having an optical path length of d. This block provides for a substantially straight linear optical path as shown. A second interchangeable optical element 982b can comprise a block having features 983 that change the direction of the optical path within the interchangeable optical element 982b. These features 983 may comprise, for example, refractive surfaces that redirect light towards a side of the optical element 982b. These refractive index surfaces comprise interfaces between different section (three shown) of the prism 982b optical elements. Although three are shown, more or less may be included. The second interchangeable optical element 982b can have an optical path length of d, same as the first interchangeable optical element 982a. By switching between interchangeable optical elements 982a and 982b (e.g., at the manufacturing stage), a viewing angle of the imaging module 980 can be changed. Having similar optical path lengths reduces the design implications of the change. The imaging module 980 can include a first negative lens or lens group 984 that can be moved or reoriented when changing between interchangeable elements 982a, 982b. In some embodiments, the negative lens or lens group 984 can be a part of the interchangeable optical element 982a, 982b. The imaging module 980 includes a proximal positive lens group 986. The lens group 986 can have a total power that is positive or negative and may comprise wafer-scale optics.

Figure 29D:
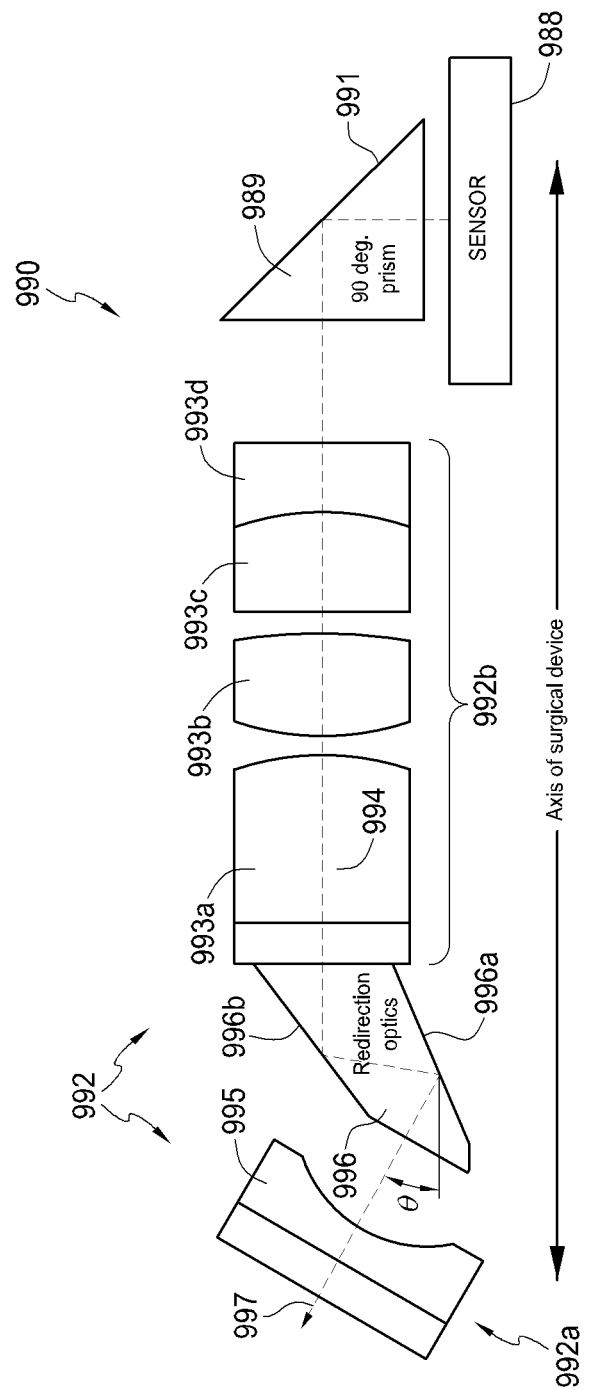
FIG. 29D shows an example imaging module with optics providing a viewing angle relative to a surgical tool axis.

FIG. 29D shows an example imaging module 990 with optics providing a viewing angle relative to a surgical tool axis. The example imaging module 990 can be used with a stereo optical sensor 988 to provide a narrow profile along a surgical device (e.g., a retractor blade) while providing a viewing angle, θ, that is not parallel to the axis of the surgical device nor parallel to the surgical device. This can allow for the use of a relatively large image sensor 988 with little or minimal obstruction of a surgical site due to an imaging module protruding from a surgical device such as a retractor. In particular, the imaging sensor 988 can be disposed such that the widest and longest dimensions (and the input face of the sensor that received the light for conversion into an electrical signal) are more parallel to (and less normal to), for example, the surface of the retractor blade, or surface of the tubular retractor so as not to obstruct access to the surgical site. The imaging module 990 can include a sensor 988, wherein the sensor can be configured for monocular imaging or the sensor can be a divided sensor configured to provide stereo imagery. The imaging module can include first redirection optics, for example, comprising a prism 991 configured to direct light to the sensor where the incoming optical axis is substantially parallel to an axis of the surgical device. In the embodiment shown in FIG. 29D, the prism is a 90 degree prism having a reflective surface 991 oriented to provide a 90° turn of the optical path propagating therethrough. The imaging module 990 can include imaging optics 992 configured to focus light from the surgical site onto the sensor 988 and form an image of the surgical site thereon. The imaging optics may include a negative power section 992a comprising a negative power lens 995 as well as a positive power lens group 992b. The positive power lens group 992b includes but is not limited to a first positive lens 993a, a second positive lens 993b, a third positive lens 993c, and a fourth negative lens 993d. In some embodiments, this second lens 992b group may have total positive power.

The imaging module 990 can include second redirection optics 996 configured to direct light from a region of interest to the first redirection optics, e.g., the prism 989, such that light comes generally from an angle, θ, relative to the axis of the surgical device and forms an image of the surgical sight on the sensor. The second redirection optics 996 may comprise for example a prism having first and second reflective surfaces 996a, 996b through which light from the surgical sight is reflected and directed into the second group of lenses 992b. The second redirection optics, however, may be configured to reorient the optical path, for example, such that the imaging optics 990 has a line of sight 997 that is directed inward toward into the surgical sight. For example, the imaging module 990 can provide a viewing angle, θ, that is at least about 30 degrees, at least about 45 degrees, at least about 70 degrees relative to the axis of the surgical device and for example up to 90 degrees. FIG. 29D shows the line-of-sight 997 of the imaging module 990 at the angle θ, with respect to the axis of the surgical device.

FIG. 29D additionally shows an optical axis 994 through the imaging optics 992 and through the second lens group 992b. The optical axis 994 is shown in FIG. 29D as coinciding with the line-of-sight 997 of the imaging module and imaging optics. In the embodiment shown, the line-of-sight 997 of the imaging optics is at an oblique angle with respect to the axis of the surgical device and the optical axis of the second group of lenses 992b which extends lengthwise along the axis of the surgical device. In various embodiments, the imaging module is mounted on a surface of a surgical device that also extends longitudinally along the length of the imaging module. For example, the second group of lenses extends longitudinally along a line parallel to the surface on which the imaging module is mounted. Similarly, the optical axis of the second group of lenses is substantially parallel to the surface on which the imaging module is mounted. In the embodiment shown by FIG. 29D, the sensor also has a front surface for receiving light on which an image of the surgical site is formed by the imaging optics 992. This front surface is also parallel to the surface on which the imaging module 990 is mounted and parallel to the optical axis of the second group of lenses 992b. Such a configuration allows for a compact design wherein the imaging module (e.g., the sensor and imaging optics) maintains a low profile that does not unduly obstruct the surgeon's access to the surgical sight.

In the embodiment shown in FIG. 29D, the imaging optics 992 comprise a negative lens 995 that forms the first lens group 992a. The second redirection optics 996 is disposed in the optical path between the first lens group 992a and the second lens group 992b. The first redirection optics 989 is disposed in the optical path between the second lens group 992b and the optical sensor 988. In some embodiments, an auto focus mechanism can be added between the sensor and the prism which can allow a user to control a focus of the imaging module and/or a faster f-number.

In various embodiments other types of prism elements may be used instead of the prism element 982b shown in FIG. 29C. For example, the prism element may be formed by cementing together smaller prism sections to create a "compound" or "compact" prism or alternatively the prism element may comprise a deviating prism that is a single homogenous piece of transparent material having outer surface shaped to obtain the desired beam direction. This material may be glass in various embodiments. An optical element that redirects light using multiple and in some embodiments an even number of reflections, e.g., 2, reflections can offer benefits with respect to parity or inverting and/or re-orienting an image upright.

Such interchangeable optical elements 982a, 982b can be used for cameras on surgical tools to change the view of the camera from directly in front of the camera, for example, directly forward the distal end of the tool. Instead, a view angle towards the side of the tool can be provided by interchanging the optical element 982a, 982b.

Figure 30A:
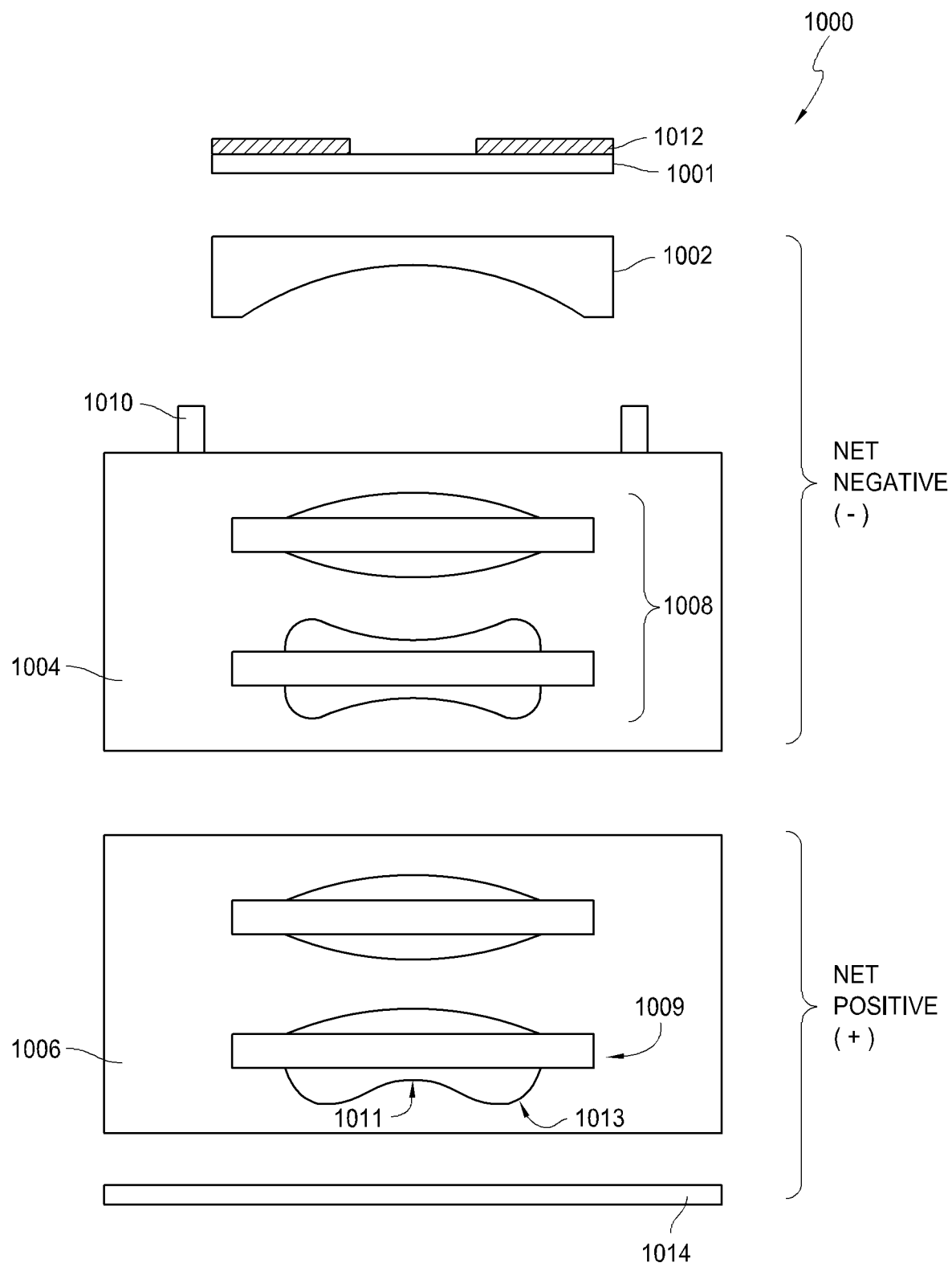
FIG. 30A shows an embodiment of an imaging stack comprising non-wafer-scale optics in combination with wafer-scale optics.

FIG. 30A shows some embodiments of an imaging stack 1000 comprising non-wafer-scale optics 1002 in combination with wafer-scale optics 1004 and 1006 for use with a surgical device. The imaging stack 1000 includes a cover glass 1001. The cover glass 1001 can be made of a material having desirable optical and/or mechanical properties, such as sapphire. The cover glass 1001 can be a plano-plano optical element having a stop 1012 bonded thereto or formed thereon. The combination of the cover glass 1001 and stop 1012 can provide for a relatively small area of the cover glass 1001 to be exposed, thereby facilitating cleaning. In some embodiments, the non-wafer-scale optics 1002 include one or more components made of glass, polycarbonate, sapphire, or other material having desired optical properties. In some embodiments, the non-wafer-scale optics 1002 have one or more lenses that produce a total optical power that is negative. For example, the non-wafer-scale optics 1002 can include a lens with a negative optical power having a relatively strong curvature typically not produced for wafer-scale optics. The imaging stack 1000 can include a first wafer-scale optical element 1004. The first wafer-scale optical element 1004 can include one or more components 1008 configured to provide optical correction, provide a desired focal length, provide an afocal system, or the like. In some embodiments, the one or more components 1008 are configured to compensate for distortion in a wide field-of-view system. The first wafer-scale optical element 1004 can include registration marks, structures, fiducials, or features 1010 configured to aid in subsequent image processing or mounting/registering non-wafer-scale optics 1002 with minimal or reduced active optical alignment and increased alignment precision. In some embodiments, the combination of non-wafer-scale optics 1002 and first wafer-scale optical element 1004 provides a total optical power that is negative. The imaging stack 1000 can include a positive proximal wafer-scale optical group 1006 having one or more optical elements that produce a total optical power for the group that is positive.

Figure 30B:
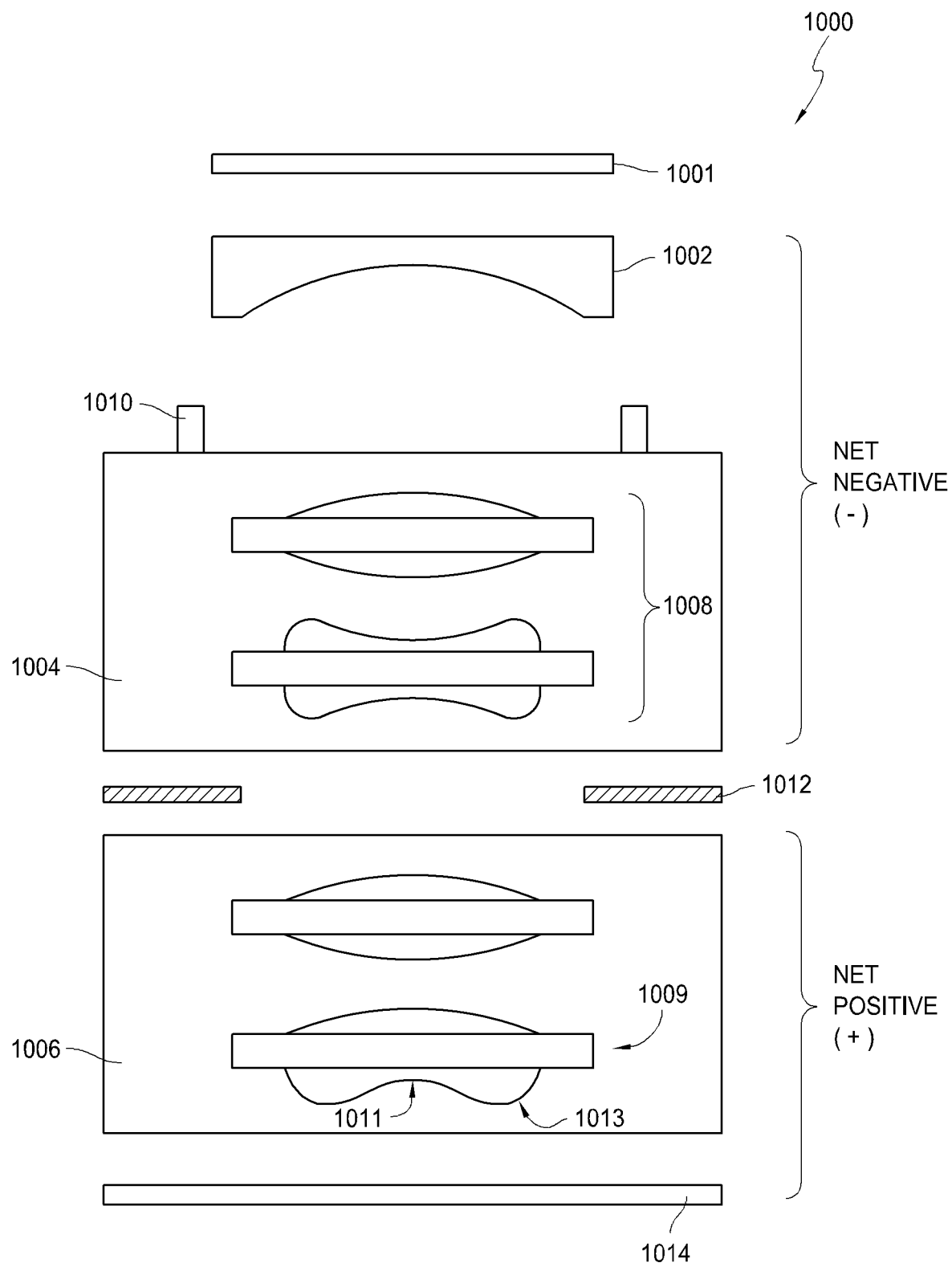
FIG. 30B shows an example embodiment of an imaging stack comprising a stop between a negative lens group and a positive lens group, wherein the positive lens group has a distortion-correcting lens element.

FIG. 30B shows some embodiments of an imaging stack 1000 comprising non-wafer-scale optics 1002 in combination with wafer-scale optics 1004 and 1006 for use with a surgical device. In some embodiments, the imaging stack 1000 includes a stop 1012 positioned between the first wafer-scale optical element 1004 and the positive proximal wafer-scale optical group 1006. The positive proximal wafer-scale optical group 1006 can include an optical element 1009 wherein a radial central portion 1011 of the optical element 1009 has a negative optical power and a radial peripheral portion 1013 of the optical element 1009 has a positive optical power. In some embodiments, the optical element 1009 can be configured to alter a direction of propagation of peripheral rays more than of central rays. The optical element 1009 can be used to correct for distortions introduced by optical elements in the non-wafer-scale optics 1002, the first wafer-scale optics, and/or the positive proximal wafer-scale optical group 1006. The optical element 1009 can be positioned to increase or maximize corrections to distortion. The imaging stack 1000 includes an image plane 1014.

In some embodiments, wafer scale optics (or wafer level optics) may include an aperture therein provided, for example, by the manufacturer. Nevertheless, in various embodiments, another aperture that can be used as the stop can be placed between a non-wafer scale optical element and the wafer scale optics having the aperture therein. For example, a stop may be included between a negative power distal lens group comprising one or more non-wafer scale optical element and a proximal lens group comprising wafer scale optics.

In some embodiments, the cameras and/or optical systems described herein can include MEMS configured to change optical properties of the optical system, such as, for example, a focal length, a magnification, a pointing angle, a field of view, or any combination of these. In some embodiments, an actuator can be used to drive a low power optical element substantially along the optical axis. The optical element can be driven at a rate such that the full sinusoidal cycle of focus is completed at a greater rate than the human critical flicker fusion rate (e.g., about 60 Hz). This can increase a depth of field of the camera or optical system. The actuator can include, for example, a voice coil, a moving magnet, a piezo, or other such actuators. In some embodiments, increasing the depth of field in this manner can be accomplished using COTS MEMS auto-focus modules driven by a sine wave having a frequency that is greater than or equal to about 60 Hz. In some embodiments, the auto-focus actuator can be driven such that the focal plane or median of increased depth of focus volume tracks a desired portion of a surgical tool, such as a tip of the surgical tool, where a position of the surgical tool is acquired using any of the tracking methods described herein, such as EM tracking.

In some embodiments, cameras can be positioned at different depths within the surgical site along a retractor. The image processing system can use the varying depths of field from the cameras at different depths to increase an output depth of field to provide focused imagery of a greater portion of the surgical site. For example, a retractor can have two or more rings of cameras and the cameras at each level can provide image data to the image processing system. The image processing system can combine overlapping image data (e.g., by tiling and/or stitching images) to provide an output image having a greater depth of focus. An example of a system with cameras at two depths is illustrated in FIG. 21.

In some embodiments, surgical devices, such as surgical tools or retractors, can include right-angle prisms to direct light from a scene onto an optical sensor. This can be used so that the optical sensor and associated optics can be housed within the surgical device or other protective housing thereby providing increase working room for the surgeon that is not obstructed by cameras and to reducing possible damage to cameras from use.

In some embodiments, LEDs associated with cameras can produce a light cone that is substantially similar to the field of view of the associated camera. Such a light beam may be used in set-up to position and/or orient the cameras. This process may be employed when the cameras are in the initialization platform.

FIGS. 31A and 31B respectively show top and side views of some embodiments of an imaging module 1100 comprising an imaging stack 1106, sensor layer 1114, via layer 1104, and flex layer 1110. The via layer 1104 can include vias configured to permit liquid or electrical cables to pass through. The via layer 1104 can be coupled to the flex layer 1110, which can comprise a flex cable according to some embodiments described herein. The flex layer 1110 can include a plurality of channels 1112 configured to transmit liquid or house electrical cable. The imaging module 1100 can include an image stack 1106, such as imaging stacks described herein with specific reference to FIGS. 27A-30B. The imaging module 1100 can include a sensor layer 1114 configured to house an image sensor, as described more fully herein. The vias 1102 in the via layer 1104 can be configured to transmit liquid to or from the flex layer 1110. In some embodiments, the vias 1102 are coupled to or combined with cleaning systems as described herein. The vias 1108 can be configured to pass electrical cables from the flex layer 1110 to the sensor layer 1114. In some embodiments, the flex layer 1110 comprises more than one flex cable with at least one flex cable configured to house electrical cables and at least one flex cable configured to transmit fluid to and from the imaging module 1100.

As noted above, in some embodiments, illumination sources such as LEDs may be positioned near the optical sensors. For example, in the case of a retractor, in some embodiments optical sensors positioned on the retractor blades may each have one or more corresponding LEDs positioned adjacently. However, in other embodiments, the LEDs need not be positioned adjacent the optical sensors. For example, the LED or other illumination source may be positioned at some distance from the optical sensors, but light may be directed from the LED to an area near the optical sensor using a one or more light guides or mixers.

Figure 32A:
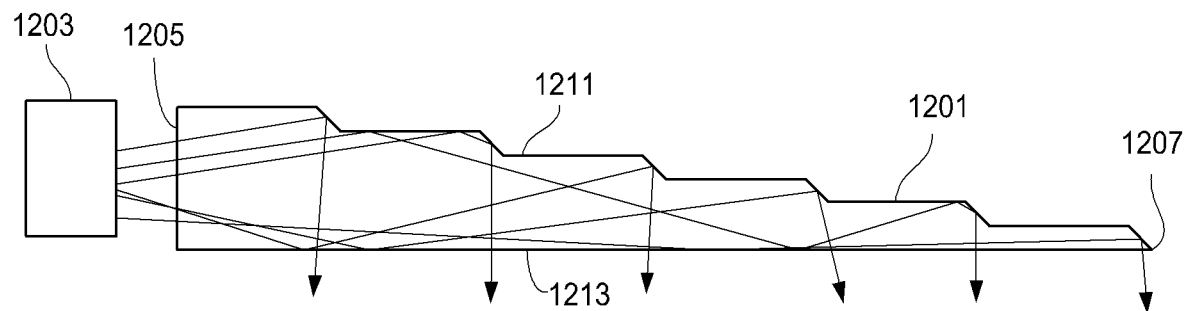
FIGS. 32A and 32B illustrate two embodiments of light guides for use with imaging modules to provide illumination.
Figure 32B:
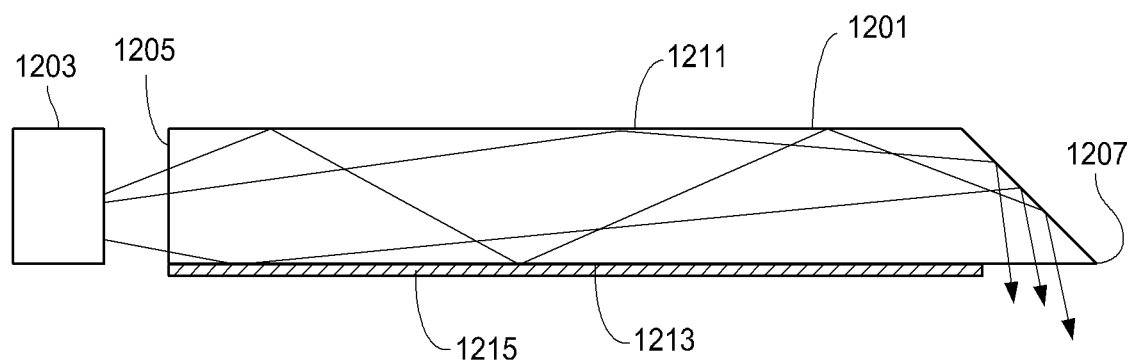

FIGS. 32A and 32B illustrate two embodiments of light guides/mixers for use with imaging modules. As shown in FIG. 32A, a light guide 1201 has an illumination source 1203 disposed adjacent the first end 1205 of the light guide 1201. In various embodiments, the light guide 1201 can be made of resin, glass, plastic, or any other transparent material suitable for propagation of light therein. The thickness of the light guide 1201 can decrease from the first end 1205 to the second end 1207, creating a tapered profile. In various embodiments, light entering the light guide 1201 at the first end 1205 propagates through the body of the light guide 1201 by total internal reflection. In implementations in which the light guide 1201 is tapered, light guided in the light guide 1201 will propagate by total internal reflection until it is ejected by the light guide 1201 at an oblique angle relative the light guide 1201. In some implementations, the rearward surface 1211 of the light guide 1201 can have a reflective surface so as to reflect light emitted from the light guide plate 1201 such that the light is turned and output from through light guide 1201 and emitted from the forward surface 1213. In various embodiments, the reflective surface can be metallic. In some embodiments, a film having a lower index of refraction than that of the light guide 1201 may be positioned over the rearward surface 1211 to support the propagation of light therein.

As shown in FIG. 32A, light can be emitted from the forward surface 1213 of the light guide 1201 along the length of the light guide 1201. In various embodiments, the light emitted from the forward surface 1213 can be substantially uniform across the entire length of the light guide 1201. In some embodiments, the light emitted from the forward surface 1213 can be emitted across substantially the entire forward surface 1213. In some embodiments, the emitted light may exhibit directionality. In other embodiments, the emitted light may be dispersed substantially uniformly.

FIG. 32B shows a light guide 1201 and illumination source 1203 similar to that of FIG. 32A. However, as shown in FIG. 32B, the light guide 1201 has a substantially rectangular profile along part of its length, with a tapered profile near the second end 1207. Additionally, a reflective layer 1215 is disposed over a portion of the forward surface 1213 of the light guide 1201. The reflective layer 1215 can be, for example, a metallic layer. In other embodiments, the reflective layer 1215 can be replaced with a dielectric film that is substantially non-transmissive. In various embodiments, a reflective opaque layer is used for the layer 1215. As a result of the reflective layer 1215, light propagating within the light guide 1201 that would otherwise be emitted from the forward surface 1213 is reflected by the reflective layer 1215 and continues to propagate within the light guide 1201. As illustrated, the reflective layer 1215 does not extend along the full length of the light guide 1201. The portion of the forward surface 1213 nearest the second end 1207 of the light guide 1201 is not covered by a reflective layer 1215. As a result, light propagating within the light guide plate 1201 can be emitted from the forward surface 1213 in the region not covered by the reflective layer 1215. In other embodiments, the light guide 1201 may be tapered along part of its length such that the thickness increases from the first end 1205 towards the second end 1207, until it the portion nearest 1207, at which point the thickness decreases as with the illustrated embodiment.

In contrast to FIG. 32A, the light guide of FIG. 32B emits light from the forward surface 1213 only in one region of the light guide 1201. Accordingly, the emitted light can be directed to a specific region, resulting in a spotlight effect depending on the directionality of the emitted light. As noted above, the configuration illustrated in FIG. 32A can provide substantially uniform emission across the entire forward surface 1213 of the light guide, resulting in a wider floodlight effect.

In either of the illustrated embodiments, the illumination source 1203 may include one or more light emitters such as light emitting diodes. In some embodiments, the illumination source 1203 can include multiple LEDs of different colors. For example, in various embodiments the illumination source 1203 can include red, green, and blue LEDs. Light from each of the different colored LEDs propagates through the light guide 1201 and in the process the light is mixed. As a result, light emitted from the forward surface 1213 can be mixed, for example such that the red, green, and blue light produces an emitted white light from the forward surface 1213 of the light guide 1201. In various embodiments, additional colors, such amber, near infrared, or other colors can be added. The inclusion of amber light may provide additional color between green and red where the LED spectrum from phosphor whites or discreet RGB modules may have a gap.

In some embodiments, an optical film may be positioned over the forward surface 1213 of the light guide 1201. For example, a diffusing film can be positioned to aid in color mixing and/or to provide a more uniform emission profile. In some embodiments, the optical film can have other properties, for example the optical film can operate to focus the direction of the emitted light over a narrower range. In various embodiments, an optical film comprising a color filter can be positioned over the forward surface of the light guide. As with the reflective layer 1215 illustrated in FIG. 32B, in various embodiments any additional optical film may not necessarily extend across the entire forward surface of the light guide. In various embodiments, the film could have a diffractive or other pattern for improving or modifying the output distribution.

Although the illustrated embodiments show a tapered light guide, in various embodiments the light guide may assume other profiles. For example, in some embodiments the light guide can be substantially rectangular in profile, and may include light-turning features on one or more surfaces to redirect light propagating within the light guide such that the light is emitted out the forward surface. Such light-turning features may be prismatic (e.g. facets) or diffractive (e.g., a holographic film), and may be formed integrally with the light guide or may be included in a separate optical film placed over one or more surfaces of the light guide. In various embodiments, the light guide 1201 can include prismatic light-turning features to redirect light out of the light guide 1201, rather than relying solely on the tapered profile.

Figure 33A:
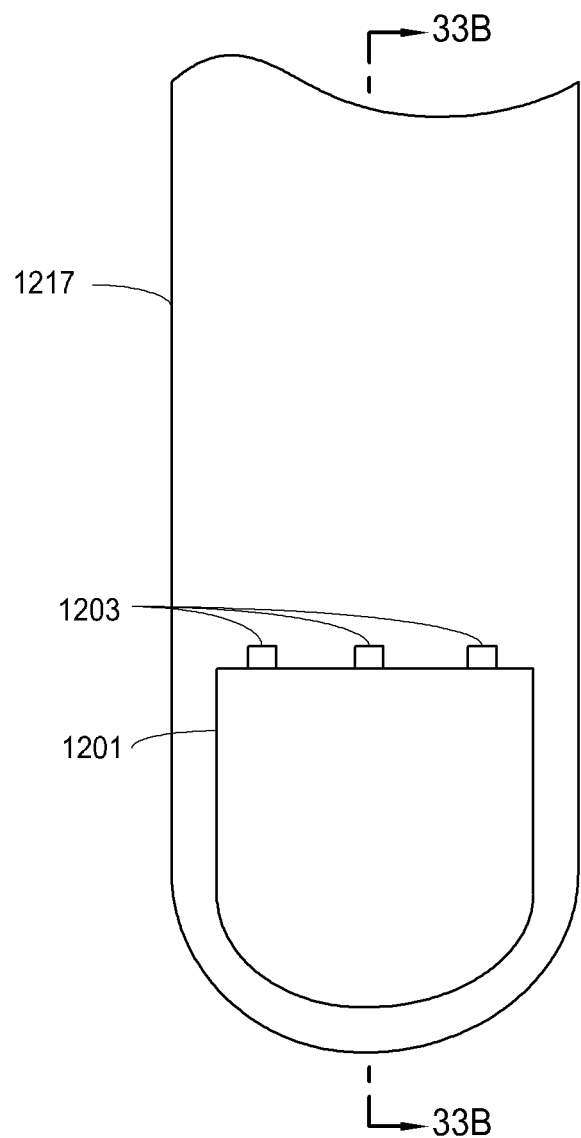
FIGS. 33A and 33B illustrate top and side cross-section views, respectively, of a retractor blade with a light guide and illumination source integrated therein.
Figure 33B:
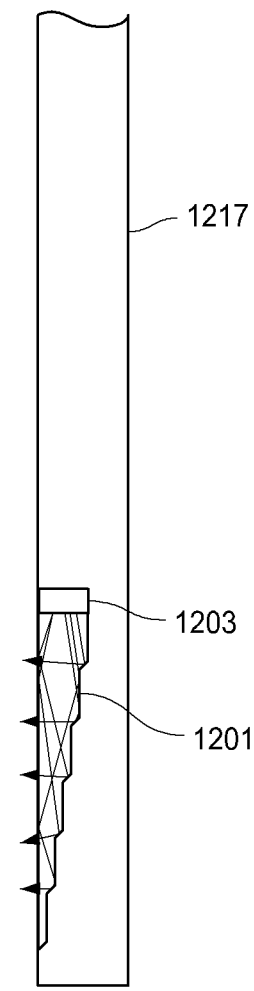

FIGS. 33A and 33B illustrate top and side cross-section views, respectively, of a retractor blade with a light guide and illumination source integrated therein. As shown, the distal portion of one retractor blade 1217 can have positioned thereon a light guide 1201 with an illumination source 1203 positioned adjacently. In the illustrated embodiment, the illumination source 1203 comprises three separate LEDs. As noted above, in various embodiments, different color LEDs such as red, green, and blue LEDs may be used to inject light into the light guide 1201, where it is then mixed and ejected as white light. In some embodiments, red, green, and blue LEDs may be used in conjunction with an amber LED. Such combination may provide a desirable look for red tissue that is viewed by the cameras. In some embodiments, white LEDs may be used. Light sources other than LEDs may also be used. As described above, light from the illumination source 1203 propagates in the light guide 1201 until emitted from the forward surface of the light guide 1201.

The retractor blade 1217 may be used in conjunction with multiple other retractor blades, each similarly equipped with an illumination source 1203 coupled to a light guide 1201. Each retractor blade may include one or more optical sensors (not shown). Each light guide 1201 on a retractor blade 1217 can provide illumination for a certain area, depending on the orientation of the retractor blade and the properties of the light guide and illumination source. The light guide 1201 may be imbedded within or incorporated as part of the retractor blade or may be removably attached thereto. For example, the light guide may be included with a support component such as a slide or finger that is removably attached to the retractor blade 1217. Although the embodiment illustrated in FIGS. 33A and 33B is a retractor blade, the illumination system can be used in conjunction with any number of surgical devices.

Positioning the LEDs at a distance from the optical sensors and using light guides to direct light from the illumination sources can provide several advantages. For example, illumination sources such as LEDs are subject to rising temperature during operation. Positioning such illumination sources in portions of the surgical device, which will be introduced into a patient's body, presents the danger of increased temperature damaging nearby tissue. Fluids also coming in contact with the LEDs may become heated. In such a configuration, an illumination source providing a broad flat light (i.e. having a relatively low level of illumination per area) may produce similar illumination levels at the surgical site that a plurality of smaller, hotter illumination sources would. Additionally, heat management devices, such as external heat sinks, can disadvantageously add bulk to the illumination source, thereby reducing the working area available to the user. Additionally, as noted above, the use of light guides can allow for mixing of light from the illumination source prior to emission from the light guide. For example, in various embodiments the illumination source can comprise multiple LEDs of different colors. In some embodiments, for example, red, green, blue and possibly amber light emitted from LEDs can propagate through the light guide and be mixed therein, such that substantially white light is emitted from the light guide and directed towards the surgical site. By adjusting the properties of the light guide and the number, intensity, and/or color of the LEDs, the properties of emitted light from the light guide towards the surgical site can be controlled.

Embodiments of Hydraulic Actuator Circuits

Hydraulic actuator circuits can be used in combination with surgical tools and corresponding imaging systems to perform various functions within the surgical systems. For example, without limitation, the hydraulic actuator circuits can power the surgical tools, provide cooling to components within the imaging systems, and/or clean components within the system. In some embodiments, using hydraulic actuator circuits and subcomponents thereof to power the surgical tools can create reduced or minimal electromagnetic interference with tracking tools. For example, electromagnetic fields that may otherwise interfere with electromagnetic tracking need not be inserted into the body proximal to the retractor blade and surgical access site and the tracking elements associated with cameras on the retractor blades and/or tracking elements on the surgical tools. Although in some embodiments electrical motors and devices may be employed to drive hydraulic components, such electrical motors and devices can be located a distance from the tracking devices included on the retractor and/or the surgical tools so as to reduce or eliminate electromagnetic interference. In various embodiments, the tracking devices and/or the optical sensors may include shielding such as a casing or shield comprising metal or Mu-metal.

In some embodiments, the components of the hydraulic circuit (e.g., pumps, valves, surgical tools, manifolds) can be made or at least partially constructed from non-metal materials (e.g., polymers) and/or non-ferrous materials. Hydraulic actuator circuits can include many inexpensive and/or disposable components (e.g., molded components and/or subcomponents). In some configurations, hydraulic actuator circuits can operate at low noise volumes compared to pneumatic drills, reducing or minimizing irritation and potential ear damage for the surgeons and medical staff. The components of the hydraulic actuation circuits can be constructed from a combination of computer numerical control (CNC) parts and molded parts.

Figure 34:
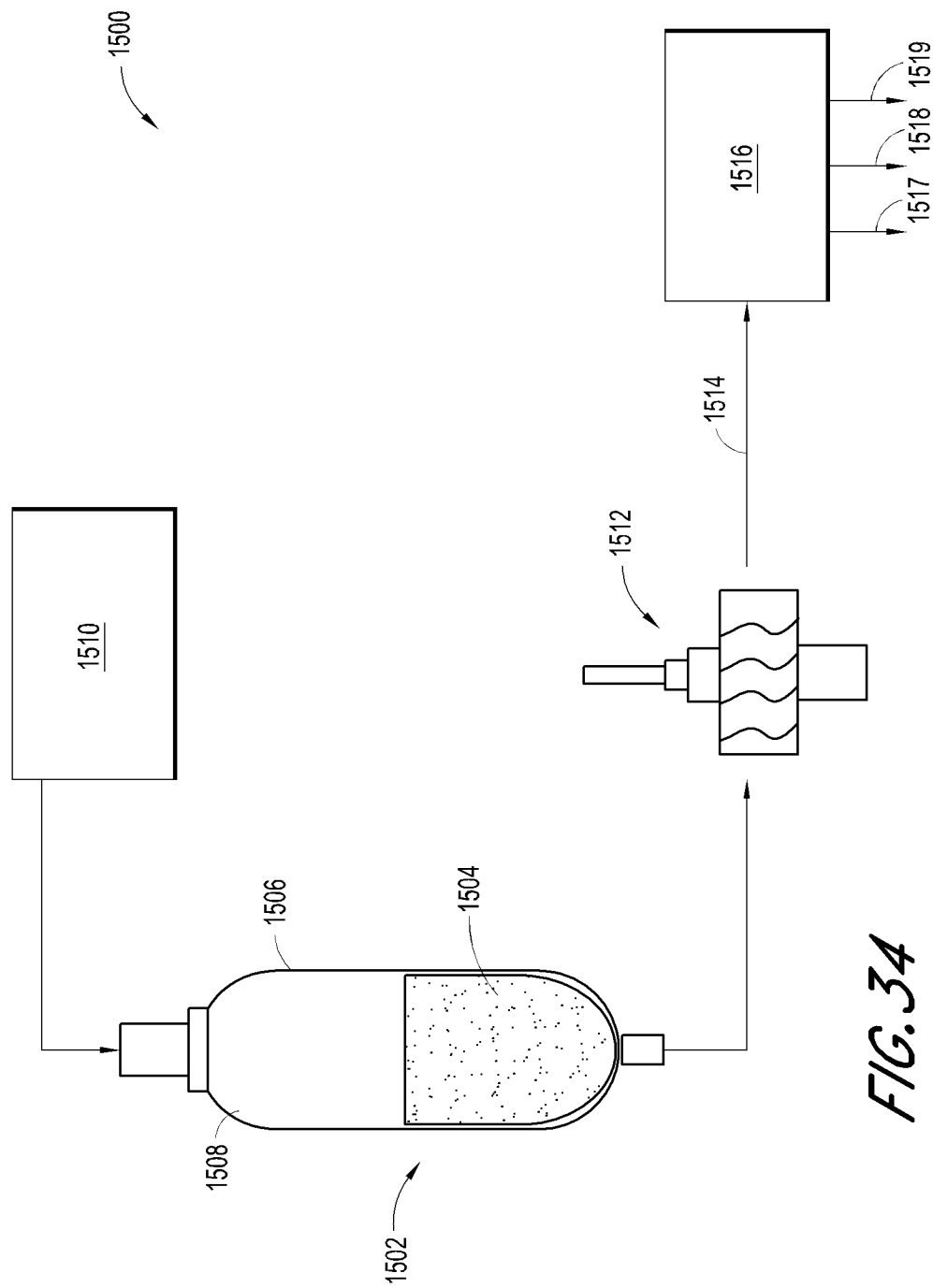
FIG. 34 is a schematic illustration of one embodiment of a hydraulic actuation system.

FIG. 34 illustrates an embodiment of a hydraulic actuator circuit 1500. The circuit 1500 preferably includes a hydraulic pressure source. In some embodiments, the hydraulic pressure source is a fluid interface chamber 1502. Portions of or the entire fluid interface chamber 1502 can be disposable and/or non-autoclavable. The fluid interface chamber 1502 can be pre-loaded with a hydraulic fluid 1504 (e.g., saline). As discussed in the present disclosure, the term "hydraulic fluid" can refer to saline (e.g., a physiological saline) and/or to any other physiologically compatible fluid (e.g., fluid suited to interaction with the interior of the body of a patient). A pneumatic fluid source 1510 (e.g., a hospital nitrogen system, a nitrogen tank, etc.) can be actuated to exert pressure on the hydraulic fluid 1504 within a cavity 1508 of the housing 1506, thereby pressurizing the fluid 1504. The pneumatic fluid source 1510 can be controlled via user input (e.g., a treadle, button, dial, etc.) and/or via automatic control (e.g., a pre-programmed computer).

The fluid interface chamber 1502 can output hydraulic fluid 1504 (e.g., saline) to a tool-powering apparatus. For example, the fluid interface chamber 1502 can output saline to a saline turbine 1512 configured to power a hydraulic drill or other tool, as further discussed below. In one embodiment, the fluid interface chamber 1502 can output saline in a pulsed manner to cause rotation of the saline turbine 1512 (e.g., via the impingement of the fluid flow stream with one or more vanes of the saline turbine 1512). In some embodiments, the saline turbine 1512 and/or powered drill/tool are disposable and/or non-autoclavable. The saline input into the turbine 1512 can cool the turbine 1512. The turbine 1512 can include a hydrostatic bearing. In some embodiments, leakage of saline from the turbine 1512 via the hydrostatic bearing or otherwise can irrigate the surgical field. In some embodiments, the saline turbine 1512 can operate at low noise volumes (e.g., compared to pneumatic drills) at high operation speeds (e.g., speeds exceeding 40,000 rpm). However, the turbine 1512 can operate at other speeds. The saline turbine 1512 can be lightweight, can have a high torque to mass ratio, and can operate without producing $I^2R$ losses, thus reducing heating within the hydraulic actuator circuit 1500. Preferably, the saline turbine 1512 can be an impulse turbine. In some embodiments, the saline turbine 1512 is a vane motor, or a Tesla turbine.

In the preferred embodiment, the exhaust fluid 1514 can be output from the turbine 1512 to a hydraulic manifold 1516. The manifold 1516 can distribute the exhaust fluid 1514 amongst one or more manifold outputs. For example, a portion of the exhaust fluid 1514 can be directed through a first manifold outlet 1517 to be used to wash optics such as imaging optics included in cameras on the retractor blades or surgical tools, for example, as discussed above. The manifold 1516 can include one or more pumps and/or valves. For example, fluid directed toward the first manifold outlet 1517 can be manipulated by a linear actuator compressing an elastomeric valve or a multi-lobed cam on a brushless DC motor or a proportional solenoid array to produce tube compression and/or compression of blisters on the manifold 1516 to produce optics washing pulses. In some embodiments, air or other gases can be input into the manifold 1516 to dry the optics after washing. The optics can be sterilized before, after, or during washing. A portion of the fluid 1514 can be directed through a second manifold outlet 1518 to cool LEDs used to provide illumination to the surgical site to facilitate imaging by cameras on the retractor and or surgical tools and viewing by the surgeon and a portion of the fluid 1514 can be directed through a third manifold outlet 1519 toward hydraulics for a power Kerrison or rongeur. The manifold 1516 can include more than or less than three manifold outlets depending on the specific application of the hydraulic circuit 1500. In one embodiment, the manifold 1516 can include one or more valves (not shown) that can be selectively actuated to direct exhaust fluid 1514 to one or more manifold outlets, while not directing exhaust fluid to other manifold outlets. For example, the valves can be selectively actuated (e.g., via a controller based on user inputs or based on an automatic control algorithm implemented by the controller) so that exhaust flow is directed to the first and second manifold outlets 1517, 1518, but not the third manifold outlet 1519, or so that exhaust flow is directed to the third manifold outlet 1519, but not the first and second manifold outlets 1517, 1518. The manifold may comprise flexible plastic and may be ultrasonically welded or adhesive bonded to make channels with edge connectors for tubing in some embodiments.

Figure 35A:
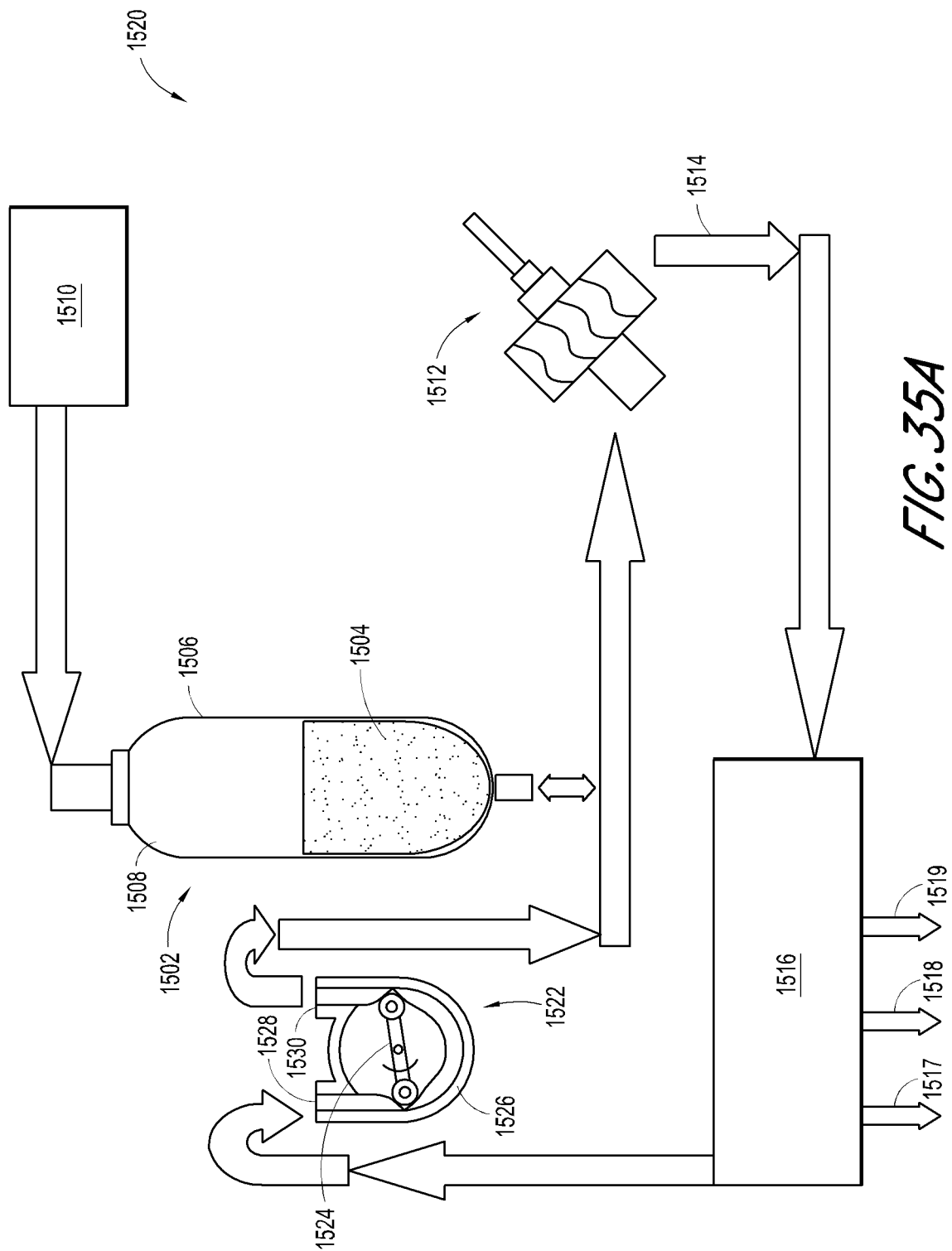
FIGS. 35A-35C are schematic illustrations other embodiments of a hydraulic actuation system.

FIG. 35A illustrates an embodiment of a hydraulic circuit 1520 which includes a pump 1522. The pump 1522 can be a roller pump configured to pressurize exhaust fluid 1514 from the turbine 1512. In some embodiments, a roller pump can reduce the overall envelope size of the system. The pump 1522 can include a roller 1524 configured to compress a flexible tube 1526 in a rotational manner such that fluid entering the pump 1522 via the pump inlet 1528 is compressed and/or accelerated through the flexible tube 1526 to the pump outlet 1530 as the roller 1524 rotates. The flexible tube 1526 and/or other components of the pump 1522 can be disposable. Pressurized fluid exiting the pump outlet 1530 can be directed to the fluid interface chamber 1502 and/or to the turbine 1512. In some embodiments, a bi-directional valve is located between the pump outlet 1530 and the fluid interface chamber 1502 and turbine 1512. Such a valve can be manually or automatically controlled (e.g., via a computer controller) to direct flow to the fluid interface chamber 1502 and/or to the turbine 1512. In some embodiments, the hydraulic circuit 1520 or portions thereof can be configured to be releasably installed within a cassette assembly. The cassette assembly can be disposable and can provide a condensed volume of portions of or the entire hydraulic circuit 1520. Similar or identical cassette assemblies can be used in conjunction with the hydraulic circuits described herein.

Figure 35B:
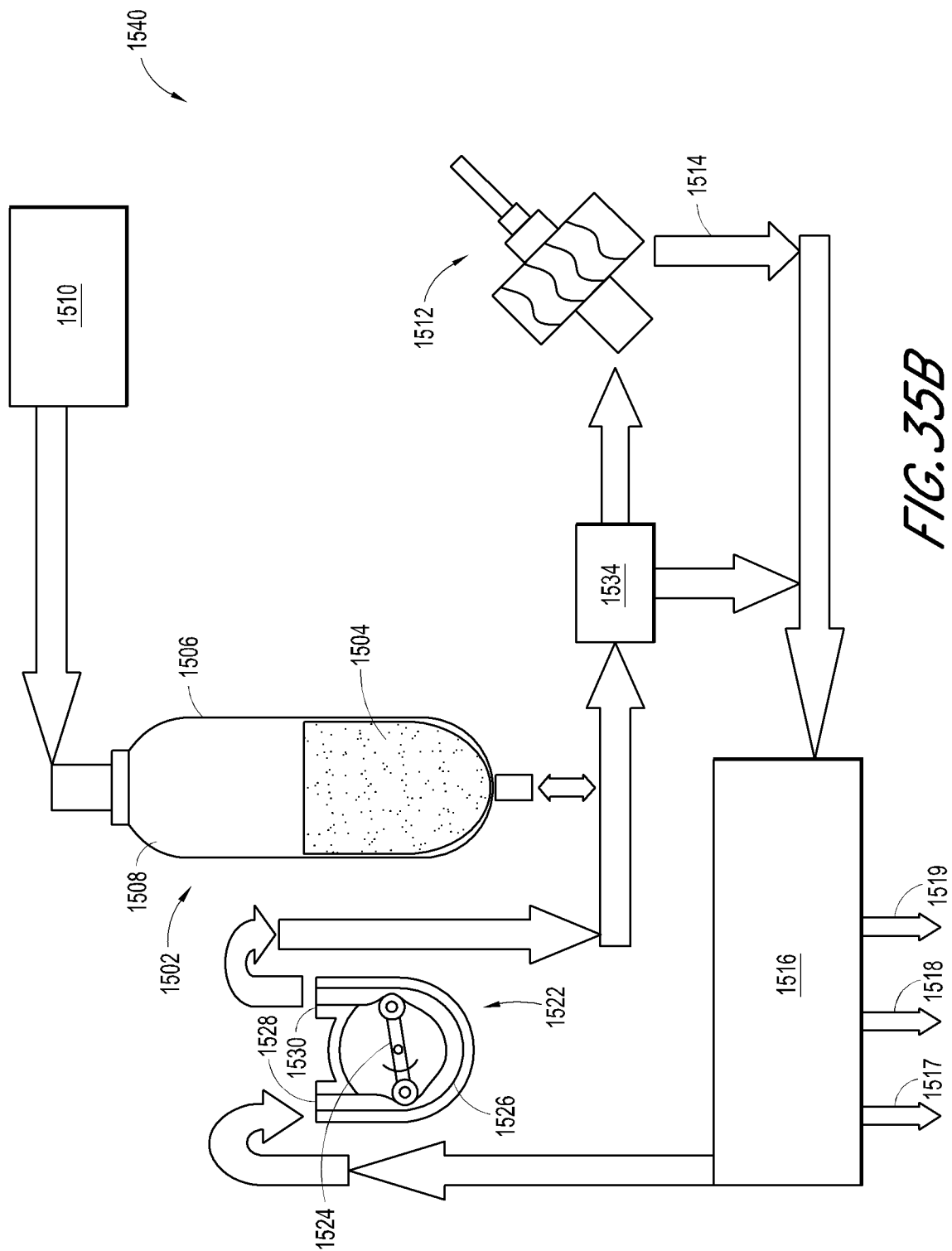

According to some variants, as illustrated in FIG. 35B, a hydraulic circuit 1540 can include a proportioning valve 1534 configured to automatically direct a desired proportion of the hydraulic fluid output by the fluid interface chamber 1502 directly to one or both of the turbine 1512 and the hydraulic manifold 1516. The proportional valve 1534 can be inexpensive and/or disposable. In some embodiments, the proportional valve 1534 is non-autoclavable. The proportioning valve 1534 can be driven by a proportional solenoid or non-commutated linear motor (e.g., with either moving a coil or moving magnet).

Figure 35C:
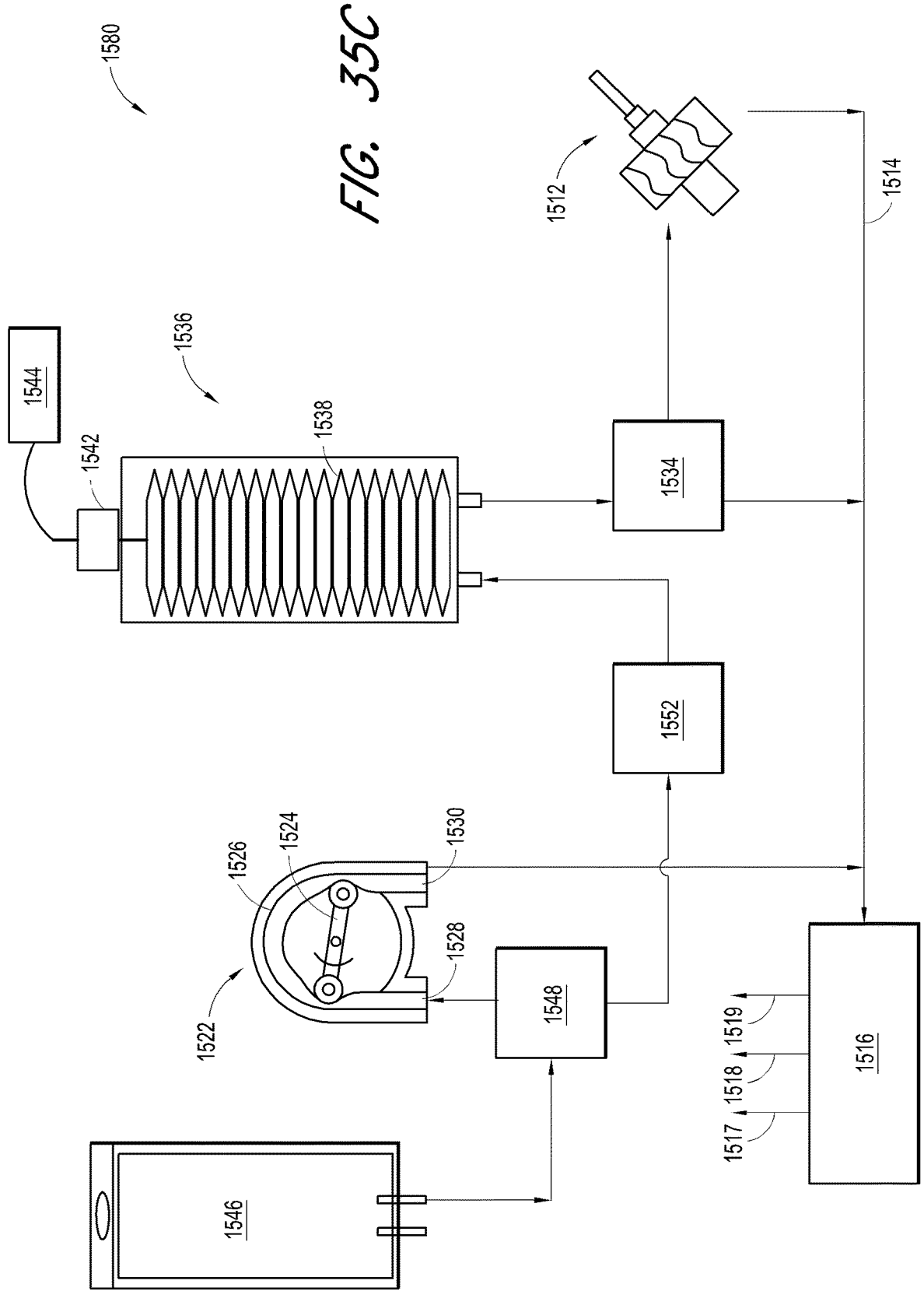

FIG. 35C illustrates a hydraulic circuit 1580 that includes a bellows actuator 1536 for use as a hydraulic pressure source. The bellows actuator 1536 can include a bellows (e.g., a metal bellows) actuated at least in part by a linear actuator 1542. The linear actuator 1542 can be controlled by a motor 1544 (e.g., a brushless motor) or other controller device. The bellows actuator 1536 can perform many or all of the functions previously described with respect to the fluid interface chamber 1502. For example, the bellows actuator 1536 can provide pressurized hydraulic fluid (e.g., saline) to the proportioning valve 1534 and/or turbine 1512. The bellows actuator 1536 can include a return spring that biases the bellows 1536 to an expanded position. In one embodiment, a controller (e.g., a computer controller) can control the operation of the motor 1544 (e.g., based on user input, such actuation of a foot pedal, push button, lever, voice command, etc.), thereby controlling the operation of the bellows actuator 1536 to provide a desired fluid flow and/or pressure to the proportioning valve 1534.

The hydraulic circuit 1580 can include a second hydraulic pressure source. For example, the circuit 1580 can include an IV bag pressurized fluid source 1546. The IV bag source 1546 can output fluid to a directional valve 1548. The directional valve 1548 can be constructed inexpensively and/or can be disposable. The directional valve 1548 directs the output fluid from the IV bag source to a pump 1522 and/or to a check valve 1552. The check valve 1552 can be configured to permit fluid flow from the directional valve 1548 to the bellows actuator 1536 while preventing fluid flow through the check valve 1552 from the bellow actuator 1536 to the directional valve 1548. Fluid directed to the pump 1522 can be pressurized within the pump 1522 and output to the hydraulic manifold 1516. In some embodiments, the bellows actuator 1536 and fluid interface chamber 1502 are interchangeable structurally and/or functionally within the hydraulic circuits 1500, 1520, 1540, 1580.

Figure 36A:
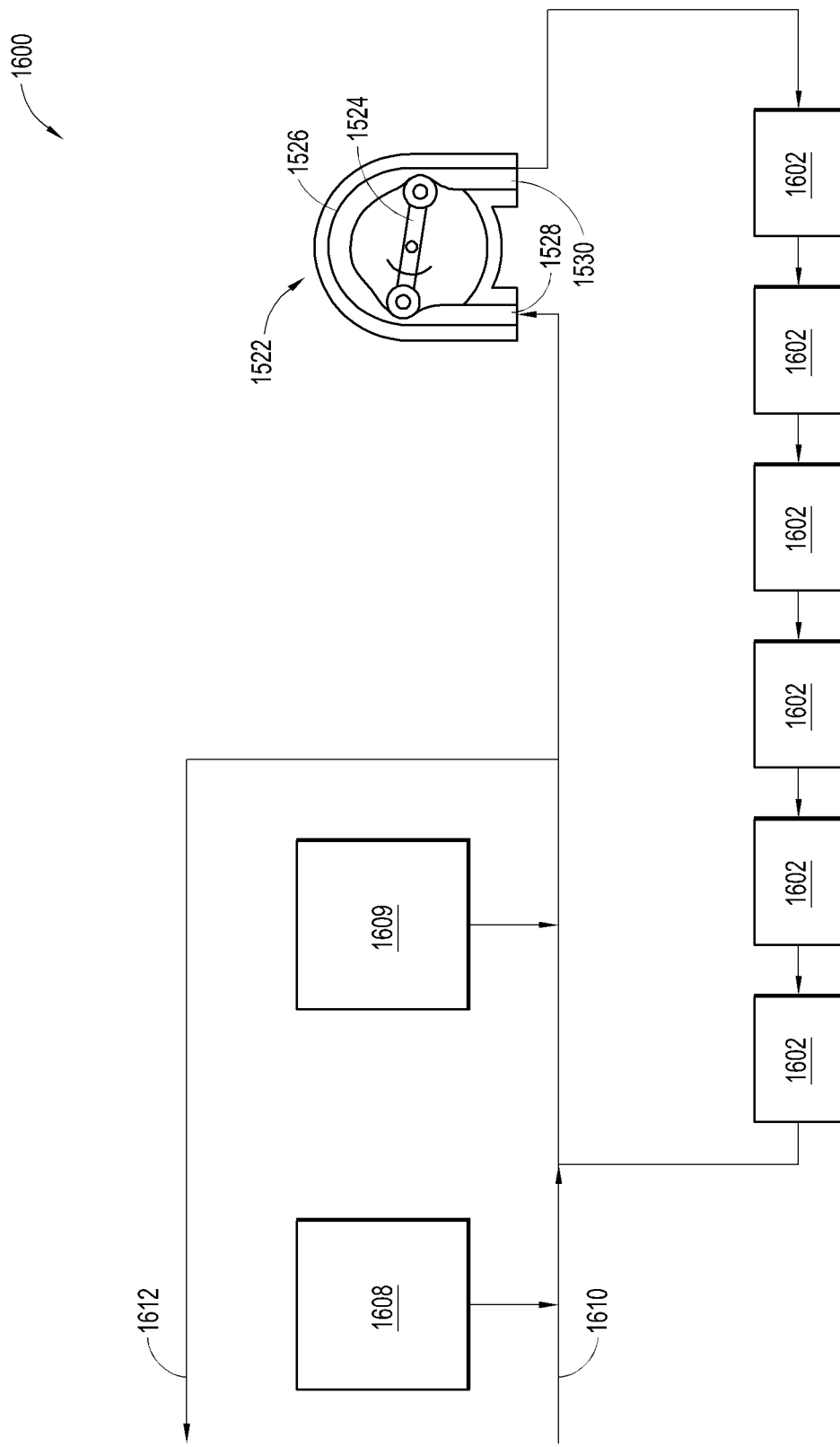
FIG. 36A is a schematic illustration of a portion of another embodiment of a hydraulic flow circuit.

FIG. 36A illustrates an embodiment of an LED cooling system 1600. The cooling system 1600 can include a pump 1522 that is similar or identical to the pump 1522 described above. The system 1600 can include a fluid input 1610 via a vent line for saline priming. A pinch valve 1608 (e.g., a solenoid pinch valve) or other valve can be positioned at or near the fluid input 1610. The pinch valve 1608 can be configured to selectively inhibit fluid flow into the LED cooling system 1600. The pinch valve 1608 can be manually and/or automatically controlled (e.g., via an electronic or computer controller).

The cooling system 1600 can be used to cool one or more LEDs 1602 used to provide illumination to the surgical site to facilitate imaging by cameras on the retractor and or surgical tools and viewing by the surgeon. In this example, 6 LEDs 1602 are shown. Fewer or more LEDs 1602 are possible. The fluid (e.g., saline) received into the system 1600 via the input 1610 (e.g., received via the manifold described above) can be passed through, over, and/or past the LEDs 1602 to cool the LEDs 1602. The pump 1522 can be used to pump the fluid past the LEDs 1602. In some embodiments, the pump 1522 pumps the fluid back to the hydraulic actuator circuits and/or to an optics washing circuit via a cooling system outlet 1612. A second pinch valve 1609 can be positioned within the cooling system 1600 to selectively inhibit the fluid output from the first pinch valve 1608 from accessing the pump 1522 without passing by/through the LEDs 1602. Accordingly, the cooling of the LED provided by the hydraulic system can be switched on or off. The pinch valves 1608, 1609 can be configured in some embodiments, so that a portion of the fluid that flows into the LED cooling system 1600 can exit the system 1600 via the cooling system outlet 1612 without passing through the pump 1522 or past the LEDs 1602.

Figure 36B:
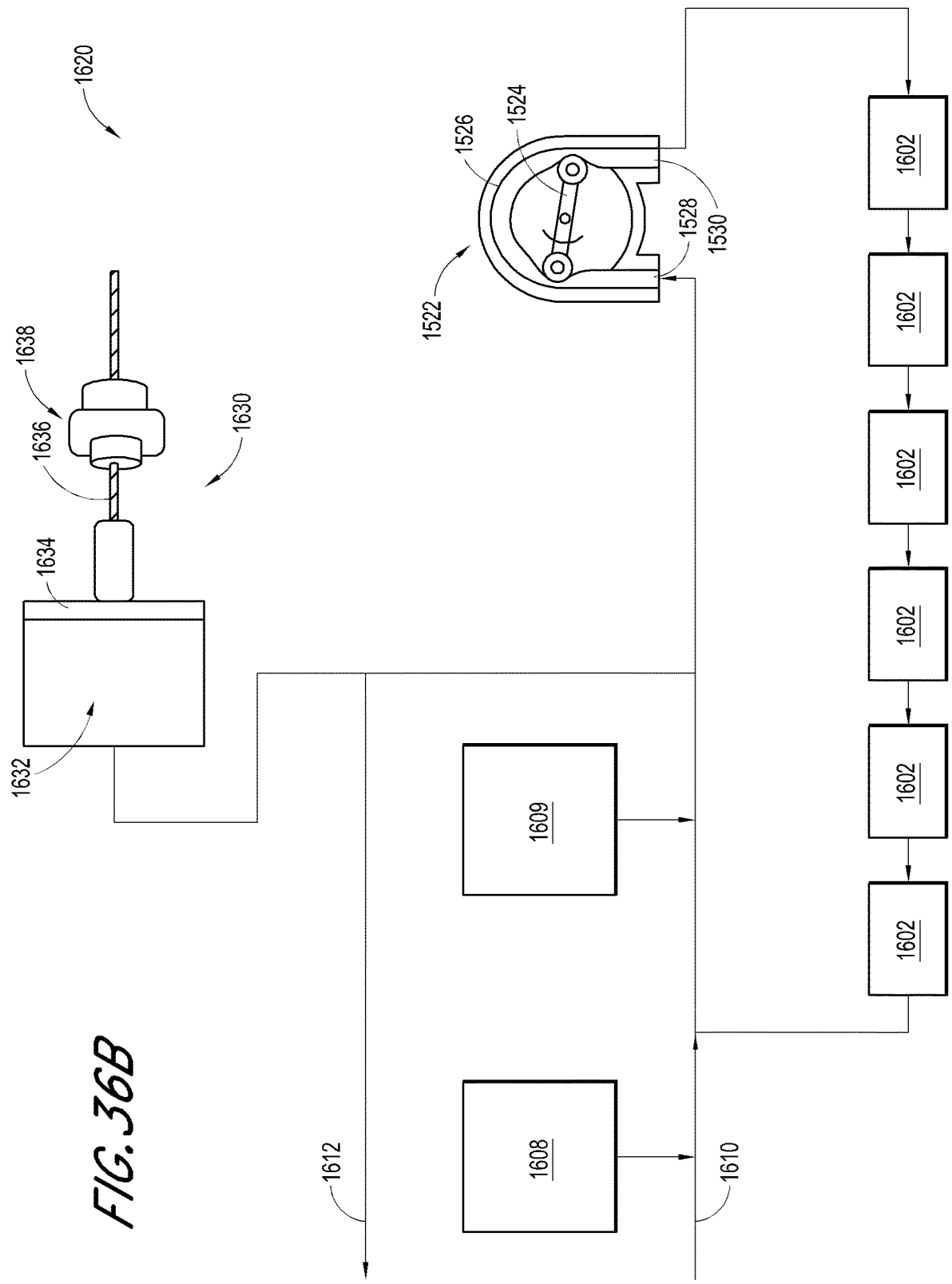
FIG. 36B is a schematic illustration of a portion of another embodiment of a hydraulic flow circuit.

In some embodiments, as illustrated in FIG. 36B, the cooling system 1600 includes a hydraulic pressure source. The hydraulic pressure source can be, for example, a saline piston system 1630. The piston system 1630 can include a piston chamber 1632 pre-charged with hydraulic fluid (e.g., saline) and disposed in a housing, for example via fluid flow from fluid input 1610. The piston system 1630 can have a driven piston element 1634 (e.g., a plate, piston) configured to move within the piston chamber 1632. The piston element 1634 can be driven by a motor or other actuator (e.g., other electrical, mechanical or pneumatic actuator). For example, the actuator can be a motor 1638 configured to drive an Acme or preferably ball screw 1636. The screw 1636 can couple with the piston element 1634 and can move the piston element 1634 back and forth within the piston chamber 1632 upon input from the motor 1638. The piston system 1630 or other hydraulic pressure source can provide pressurized hydraulic fluid to the cooling system 1600. In some embodiments, a portion of the fluid output from the piston system 1630 is directed to the hydraulic actuator circuits and/or to an optics washing circuit via the cooling system outlet 1612. The pinch valve 1608, 1609 can be configured to selectively inhibit access to the fluid input 1610 by the fluid output from the piston system 1630.

In some embodiments, the hydraulic pressure source of the hydraulic pressure circuits and/or LED cooling systems can be a rolling edge diaphragm, a syringe (e.g., a disposable syringe) or any other suitable hydraulic pressure source or combination or pressure sources (e.g., a syringe in combination with bellows). The hydraulic pressure source(s) can be free from valves.

Figure 37:
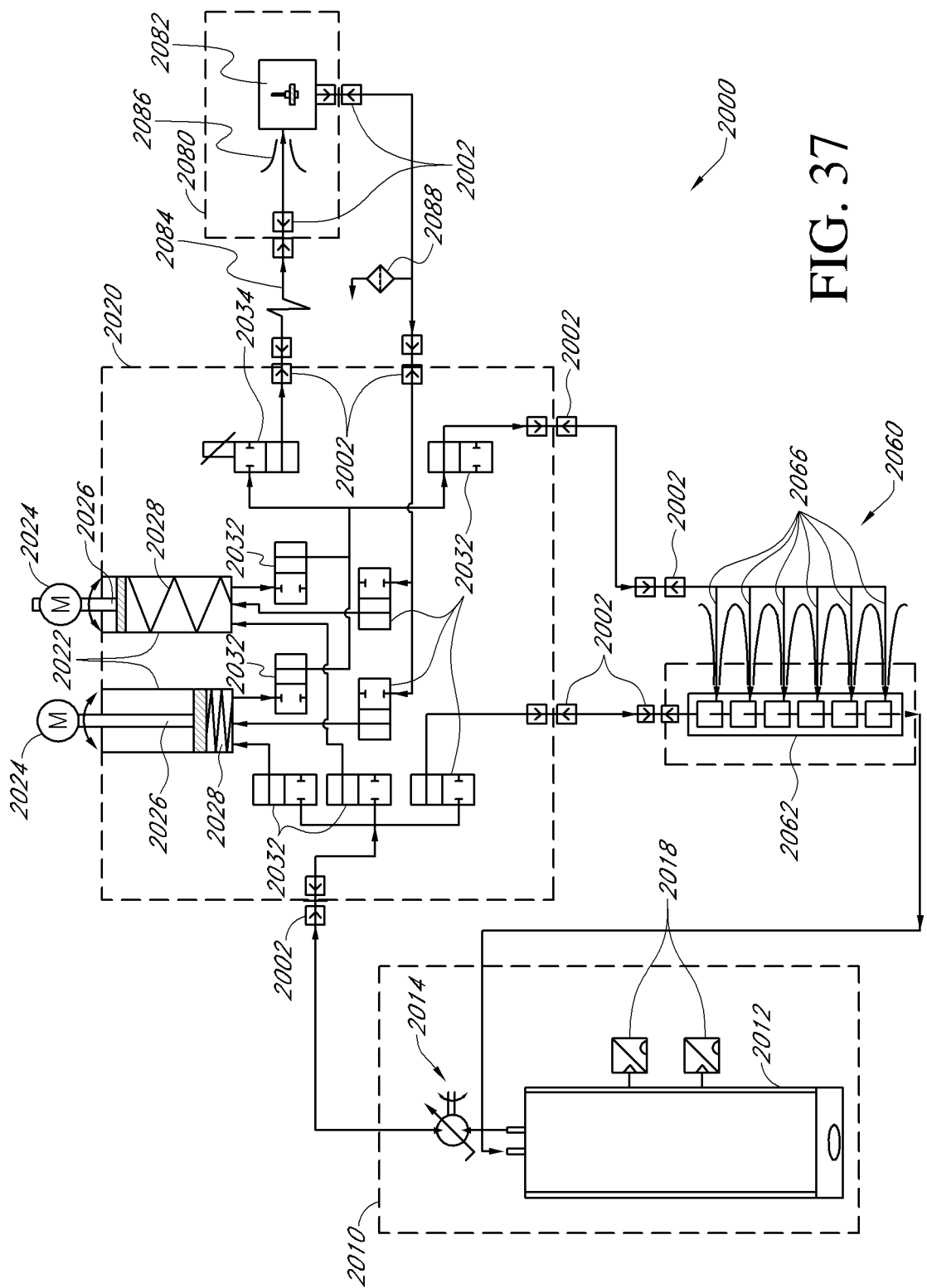
FIGS. 37-42 are schematic illustrations various embodiments of a hydraulic pressure circuit.

As illustrated in FIG. 37, a hydraulic pressure circuit 2000 for use with surgical tools or otherwise can include a fluid source 2010. The fluid source 2010 can include a fluid reservoir 2012 (e.g., an IV bag or other fluid container). The fluid source 2010 can be gravity-driven. In some embodiments, the hydraulic pressure circuit 2000 includes a fluid source actuator configured to force fluid from the fluid source 2010. In some embodiments, the fluid source 2010 includes a hydraulic pump 2014 (e.g. a roller (peristaltic) pump, a linear actuator pump, a gear pump, a radial piston pump, a screw pump, and/or an axial piston pump) fluidly connected to the reservoir 2012. The hydraulic pump 2014 can be configured to force fluid out of and/or into the fluid reservoir 2012. One or more feedback sensors (e.g., pressure transducers 2018) can be connected to the fluid reservoir 2012 to monitor the fluid pressure within the fluid reservoir 2012 and/or within the fluid lines connected to the reservoir 2012.

The hydraulic pressure circuit 2000 can include a hydraulic manifold 2020. In some embodiments, the hydraulic manifold 2020 is housed at least partially within a cassette assembly, an example of which will be discussed below. The hydraulic manifold 2020 can include one or more external connectors 2002. The external connectors 2002 can be configured to facilitate fluid communication between the hydraulic manifold 2020 and other components of the hydraulic circuit 2000. For example, an external connector 2002 can provide a fluid interface between the hydraulic manifold 2020 and one or more fluid lines of the fluid source 2010.

In some embodiments, the external connectors 2002 define one or more fluid inlets and/or fluid outlets into and out of the hydraulic manifold 2020. For example, the external connector 2002 configured to connect to the fluid source 2010 can define a fluid inlet into the hydraulic manifold 2020. The hydraulic manifold 2020 can include one or more external connectors 2002 configured to facilitate fluid connection between the hydraulic manifold 2020 and a tool assembly 2080. For example, the hydraulic manifold 2020 can include a tool fluid outlet and a tool fluid inlet to facilitate fluid transfer to and from the tool assembly 2080. In some cases, a long flexible tube 2084 (e.g., a seven foot flexible tube) can be used to fluidly connect the hydraulic manifold 2020 to the tool assembly 2080. In some embodiments, the hydraulic manifold 2020 includes external connectors 2002 configured to form one or more LED fluid inlets and one or more LED fluid outlets to facilitate fluid transfer between the hydraulic manifold 2020 and an LED assembly 2060. In some embodiments, the LED assembly 2060 can be fluidly connected to the fluid source 2010, with or without the use of external connectors on the LED assembly 2060 and the fluid source 2010.

The external connectors 2002 can be configured to reduce the time and effort associated with fluidly connecting and/or disconnecting the components of the hydraulic pressure circuit 2000 (e.g., the fluid source 2010, the hydraulic manifold 2020, the LED assembly 2060, and/or the tool assembly 2080) to each other. For example, the connectors 2002 can comprise tapered connectors onto which tubing (e.g., flexible plastic tubing) can be pressure-fit. In some embodiments, the connectors 2002 can comprise male and/or female luer connectors (e.g., ANSI-compliant connector interfaces) configured to connect with a corresponding connector on a fluid conduit. In some embodiments, the connectors 2002 include internal and/or external threading configured to releasably engage with external and/or internal threading on a fluid conduit.

According to some variants, one or more valves 2032 can be positioned on or within the hydraulic manifold 2020 to control and/or limit the fluid flow through one or more fluid conduits within the hydraulic manifold 2020. The one or more valves 2032 can be, for example, two-way two position valves 2032 (e.g., pinch valves). In some embodiments, the hydraulic manifold 2020 can include one or more proportioning valves 2034 (e.g., proportional two-way two position valves, diaphragm-type valves, and/or spindle valves) configured to control and/or limit fluid flow through one or more fluid conduits within the hydraulic manifold 2020. In certain cases, a valve 2032, 2034 is positioned on each fluid channel within the hydraulic manifold 2020 (e.g., FIG. 37). The valve 2032, 2034 can act as on/off valves to provide pulsed flow through one or more of the fluid conduits in the hydraulic manifold 2020.

In some embodiments, the hydraulic manifold 2020 includes one or more fluid actuators. For example, the hydraulic manifold 2020 can include one or more bellows actuators 2022. Other types of fluid actuators such as master-slave balloon pumps, axial pistons, and peristaltic pumps can also be used in addition to or instead of the bellows actuators 2022 to pressurize hydraulic fluid within the hydraulic pressure circuit 2000. Although the following discussion will refer to bellows actuators 2022 as the fluid actuator, the concepts disclosed herein could also apply to other types of fluid actuators disclosed above. The bellows actuators 2022 can be configured to increase fluid pressure within the fluid conduits of the hydraulic manifold 2020. The bellows actuators 2022 can include a bellows 2028. One or more linear actuators 2026 can be configured to compress and decompress the bellows 2028. The one or more linear actuators 2026 can be manipulated by one or more motors 2024 (e.g., brushless motors, stepper motors).

Fluid can be provided to the bellows actuators 2022 from the fluid source 2010. One or more valves 2032, 2034 can be positioned in the fluid paths between the fluid source 2010 and the bellows actuators 2022. The bellows actuators 2022 can output high pressure fluid to the tool assembly 2080 and/or to the LED assembly 2060. In some embodiments, the hydraulic manifold 2020 includes two or more bellows actuators 2022. In some cases, the use of two or more bellows actuators 2022 can provide continual pressurization of fluid travelling from the bellows actuators 2022 to the tool assembly 2080 and/or to the LED assembly 2060. For example, the compression strokes of the linear actuator 2026 of the bellows actuators 2022 can be timed such that, at a given moment in the operation of the hydraulic pressure circuit 2000, at least one of the linear actuators 2026 is operating in a compression stroke.

Pressurized fluid output from the bellows actuators 2022 to the tool assembly 2080 can pass through a proportioning valve 2034. The proportioning valve 2034 can control the amount of fluid and/or the pressure of the fluid that passes from the bellows actuators 2022 to the tool assembly 2080. In some cases, the proportioning valve 2034 can control the operating speed and/or operating power of the tool assembly 2080. As will be explained in more detail below, pressurized fluid from the bellows actuators 2022 can be passed through a nozzle 2086 and impeded upon a turbine or other drive source for a tool 2082 (e.g., a hydraulic drill or other surgical tool). In some embodiments, the nozzle 2086 intensifies the velocity of the pressurized fluid. At least a portion of the fluid used to drive the tool 2082 can be collected and/or redirected back to the bellows actuators 2022 in order to reenergize the fluid. In some embodiments, a hydrophobic filter 2088 can be positioned in a branch of the fluid channel through which fluid returning from the tool assembly 2080 to the bellow actuators 2022 flows. The hydrophobic filter 2088 can allow air or other gases from the fluid channel to exit the hydraulic pressure circuit 2000 while preventing the hydraulic fluid (e.g., the water, saline, and/or oil) from exiting the hydraulic pressure circuit 2000. In some embodiments, a one-way valve can be positioned in the return fluid channel between the tool assembly 2080 and the bellow actuators 2022 to inhibit air or other gases from entering the hydraulic pressure circuit 2000 through the hydrophobic filter 2088.

In some embodiments, a portion of the fluid exiting the fluid source 2010 can be directed to the LED assembly 2060. This portion of fluid can be directed through the hydraulic manifold 2020 before it reaches the LED assembly 2060. This portion of fluid can bathe the LEDs 2062 and can provide conductive and/or convective cooling for the LEDs 2062. In some embodiments, the LED assembly 2060 includes a roller pump or other source of fluid pressurization that pulls fluid onto and around the LEDs 2062 from the hydraulic manifold 2020 and/or from the fluid source 2010. After passing over/around the LEDs 2062, the cooling fluid can be directed via a fluid conduit back to the fluid source 2010, as illustrated in FIG. 37.

In some embodiments, a portion of the fluid exiting the bellows actuators 2022 is directed to one or more nozzles 2066 in or on the LED assembly 2060. An on/off valve can be positioned on or around the fluid conduit between the bellows actuators 2022 and the LED assembly 2060. The on/off valve can be configured to provide a pulsed pressure for washing the LEDs 2062. The fluid used to wash the LEDs 2062 can be redirected to the fluid source 2010.

In some embodiments, the pressure and pulse rate of the fluid washing and air drying of the LEDs 2062 can be further controlled through the addition of a check valve near the nozzles 2066. In some embodiments, when a pressure differential across the check valve (e.g., the ratio of the upstream fluid pressure to the downstream fluid pressure) reaches a predetermined level, the check valve can open to release a stronger pulse and higher pressure of fluid for washing the LEDs than would be achieved with the pulsing regulated by valves at the cassette. The check valve can be a duck billed valve, a diaphragm check valve, lift check valve, or any other check valve known in the art. In some embodiments, a T connector can be used near the nozzle connecting the air line and the saline line to the nozzle, thereby allowing for the air and saline to share the same nozzle. Additionally, in some embodiments, the two saline lines from the fluid source and/or pistons can be connected by a T connector to connect the two fluid lines to the nozzle. A check valve can be positioned near the nozzle to facilitate a pressure buildup on the upstream side of the check valve. In some embodiments, such a buildup of pressure can release a high pressure pulse of fluid for washing the LEDs. Alternatively, in some embodiments, a T connector can be used to connect a fluid line, from the fluid source and/or the pistons, and an air line. The air line can contain a high pressure and low pressure air source. The low pressure combined with the fluid line can exert a force to open the check valve near the nozzle. In some embodiments, a subsequent higher pressure blows air through the nozzle to allow for drying of the LEDs through the same nozzle as washing. In some embodiments, the pulse of fluid for washing the LEDs can have a pressure ranging from about 60 psi to about 125 psi.

Additionally, in some embodiments, the LED assembly 2060 can be cooled by a refrigeration system. In some embodiments, the refrigeration system can comprise a micro miniature refrigerator (Joule Thomson effect) cooler to circulating saline and cool the LEDs 2062. The temperature change in the compressed gas system when the gas or fluid is forced through a valve can allow for the cooling of the gases or fluids if kept insulated so that no heat is exchanged with the environment.

Figure 38:
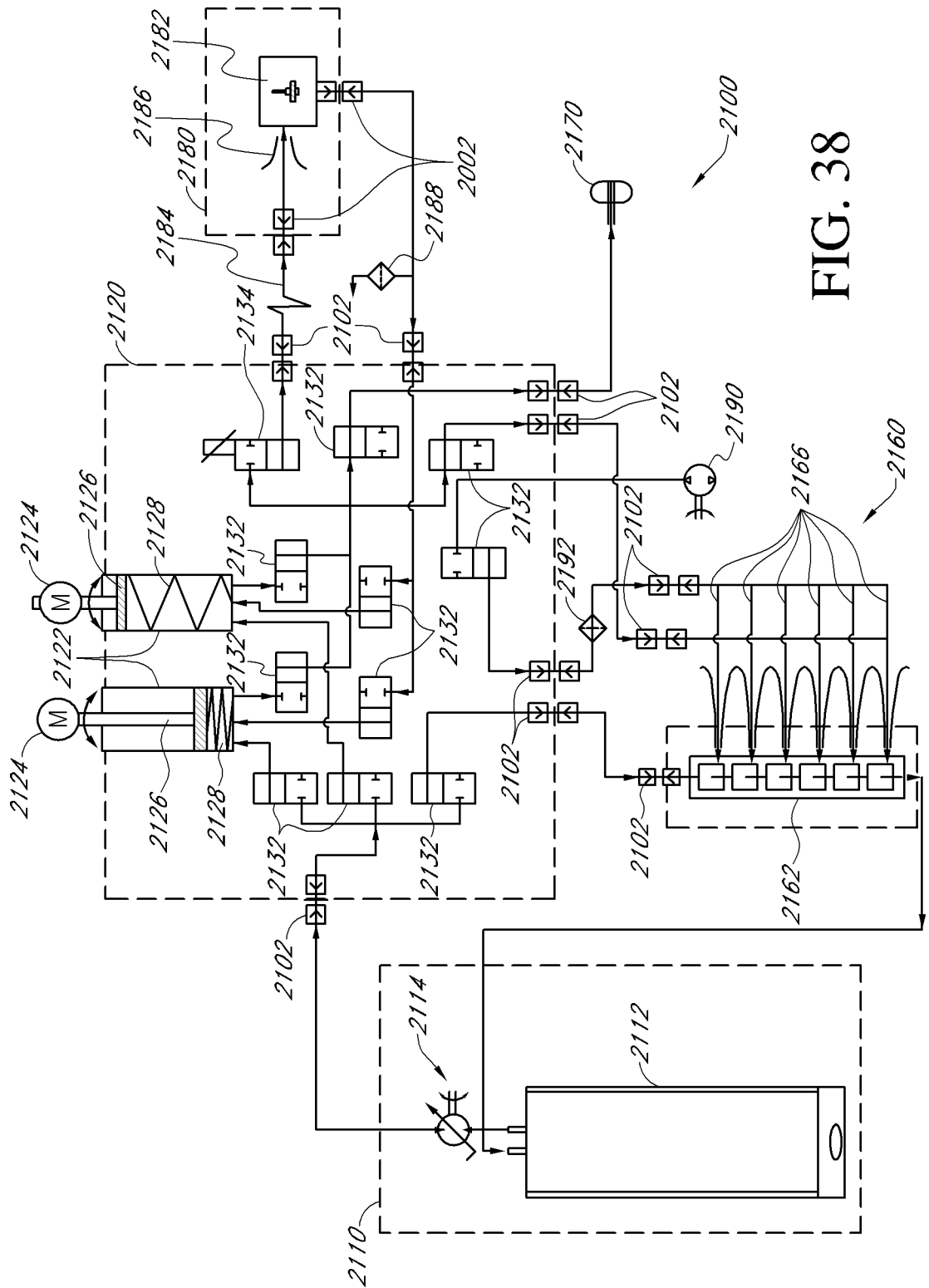

FIG. 38 illustrates an embodiment of a hydraulic pressure circuit 2100. Some numerical references to components in FIG. 38 are the same as or similar to those previously described for the hydraulic pressure circuit 2000 (e.g. hydraulic manifold 2120 v. hydraulic manifold 2020). It is to be understood that the components can be the same in function or are similar in function to previously-described components. The hydraulic pressure circuit 2100 of FIG. 38 shows certain variations to the hydraulic pressure circuit 2000 of FIG. 37.

In some embodiments, the hydraulic pressure circuit 2100 includes an air pump 2190. The air pump 2190 can be configured to provide pressurized air, via a fluid conduit, to the nozzles 2166 of the LED assembly 2160. In some embodiments, the pressurized air can be used to dry the LEDs 2162 before or after washing the LEDs. A filter 2192 (e.g., a hydrophobic and/or antimicrobial filter) can be positioned between the air pump 2190 and the nozzles 2166.

The hydraulic pressure circuit 2100 can include a balloon 2170. The balloon 2170 can be used as a slave actuator to power a tool (e.g., a Kerrison). For example, the balloon 2170 can be used to power tools that require high pressure (e.g., 100-150 psi) actuators. In some embodiments, as discussed below, one or more tools are actuated via pneumatic actuators.

Figure 39:
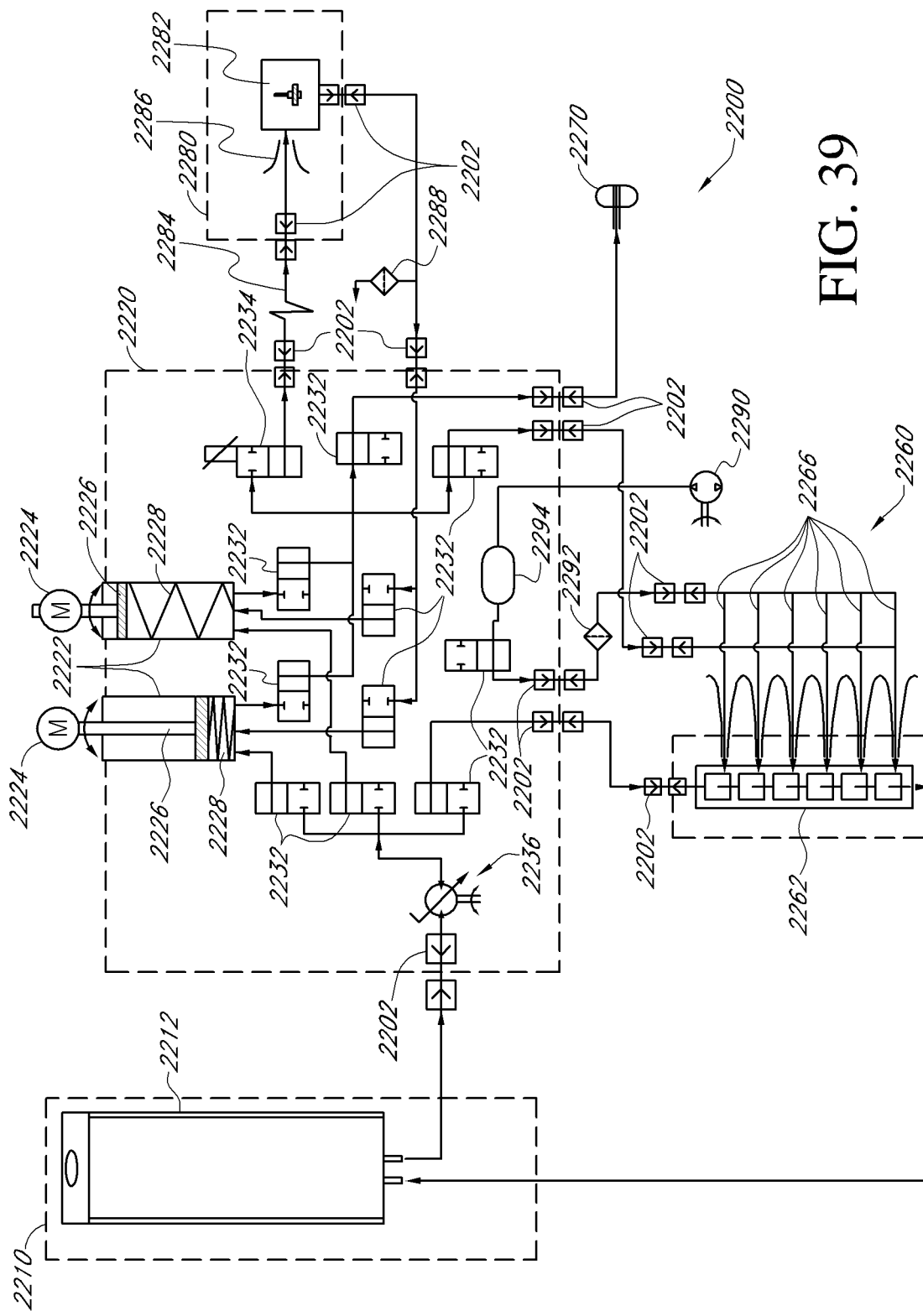

FIG. 39 illustrates an embodiment of a hydraulic pressure circuit 2200. Some numerical references to components in FIG. 39 are the same as or similar to those previously described for the hydraulic pressure circuit 2100 (e.g. hydraulic manifold 2220 v. hydraulic manifold 2120). It is to be understood that the components can be the same in function or are similar in function to previously-described components. The hydraulic pressure circuit 2200 of FIG. 39 shows certain variations to the hydraulic pressure circuit 2100 of FIG. 38.

In some cases, the hydraulic pressure circuit 2200 can include an air accumulator 2294 located between the air pump 2290 and the nozzles 2066 of the LED assembly 2060. The air accumulator 2294 can provide a pre-loaded source of air for use in drying the LEDs 2266 and can help reduce lag between the operation of the air pump 2290 and the delivery of air to the nozzles 2066.

A hydraulic pump 2236 (e.g. a roller (peristaltic) pump, a linear actuator pump, a gear pump, a radial piston pump, a screw pump, and/or an axial piston pump) can be positioned within the hydraulic manifold 2220. The hydraulic pump 2236 can be positioned and configured to increase the fluid pressure and/or fluid velocity of fluid output from the fluid source 2210. In some embodiments, the hydraulic pump 2236 pulls fluid from the fluid source 2210. Fluid from the hydraulic pump 2236 can be directed toward the bellows actuators 2222 and/or toward the LED assembly 2260. In some embodiments, positioning the hydraulic pump 2236 within the hydraulic manifold 2220 can eliminate the need for a nurse or other practitioner to handle the hydraulic pump 2236 during assembly and/or disassembly of the hydraulic pressure circuit 2200.

Figure 40:
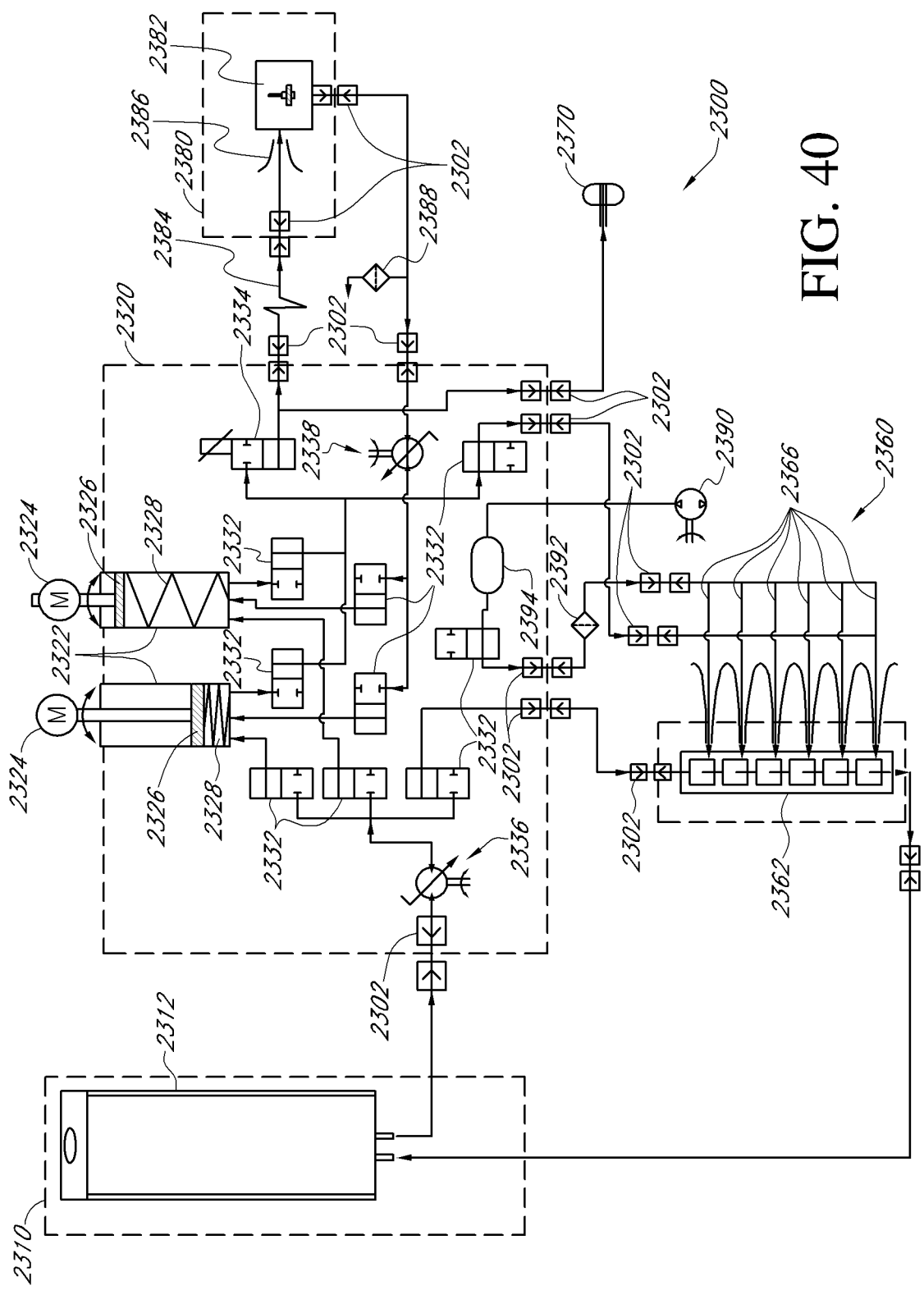

FIG. 40 illustrates an embodiment of a hydraulic pressure circuit 2300. Some numerical references to components in FIG. 40 are the same as or similar to those previously described for the hydraulic pressure circuit 2200 (e.g. hydraulic manifold 2320 v. hydraulic manifold 2220). It is to be understood that the components can be the same in function or are similar in function to previously-described components. The hydraulic pressure circuit 2300 of FIG. 40 shows certain variations to the hydraulic pressure circuit 2200 of FIG. 39.

The hydraulic pressure circuit 2300 can include a second hydraulic pump 2338 (e.g. a roller (peristaltic) pump, a linear actuator pump, a gear pump, a radial piston pump, a screw pump, and/or an axial piston pump). The second hydraulic pump 2338 can be positioned on or within the hydraulic manifold 2320. In some embodiments, the second hydraulic pump 2338 is positioned on the fluid path through which the fluid exiting the tool assembly 2380 is directed as the exiting fluid is redirected to the bellows actuators 2322. The second hydraulic pump 2338 can be configured to increase the pressure and/or velocity of said exiting fluid. In some embodiments, the second hydraulic pump 2338 pulls fluid from the tool assembly 2380 after the fluid has been used to power the turbine or other power source for the tool 2382.

Figure 41:
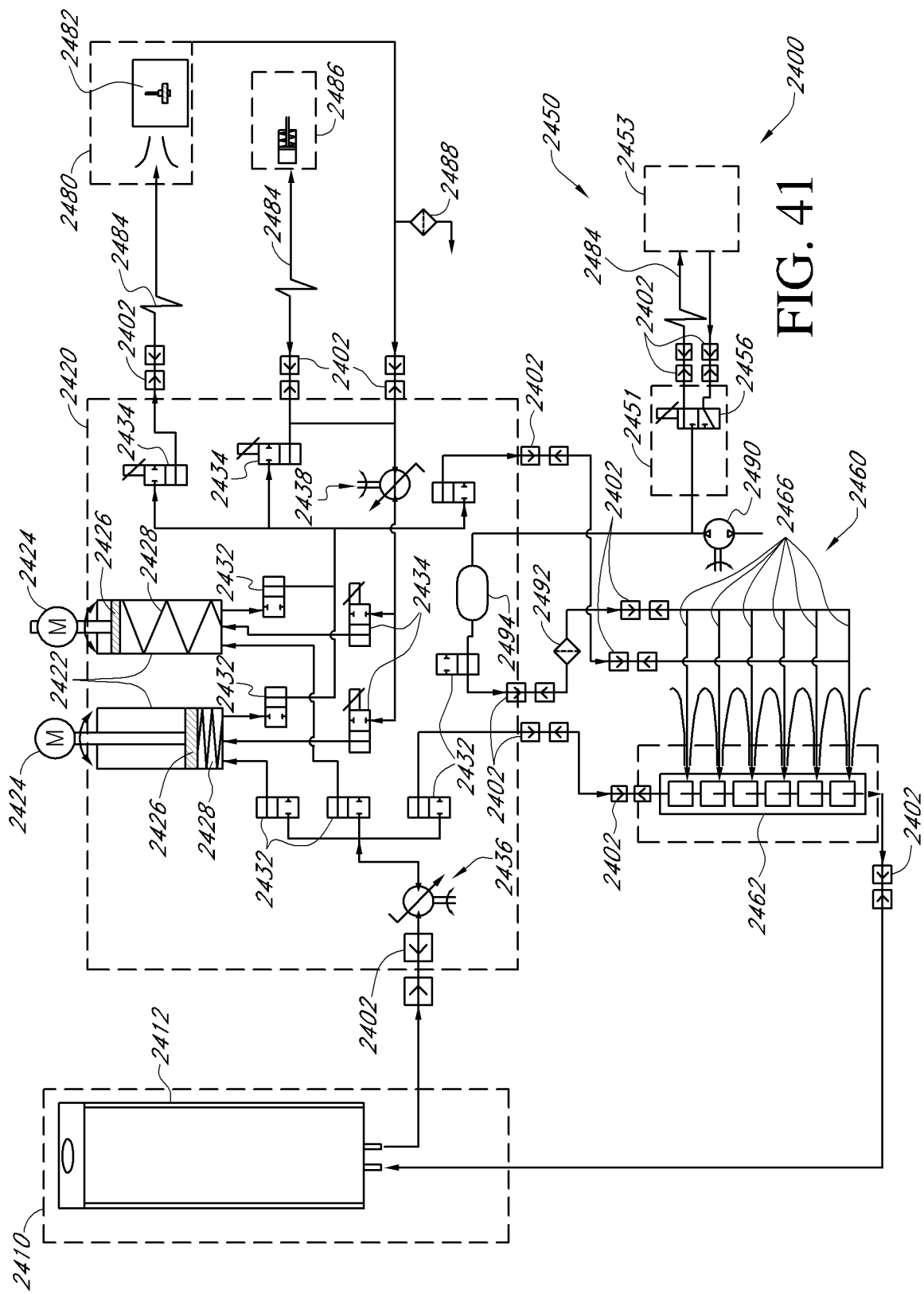

FIG. 41 illustrates an embodiment of a hydraulic pressure circuit 2400. Some numerical references to components in FIG. 41 are the same as or similar to those previously described for the hydraulic pressure circuit 2300 (e.g. hydraulic manifold 2420 v. hydraulic manifold 2320). It is to be understood that the components can be the same in function or are similar in function to previously-described components. The hydraulic pressure circuit 2400 of FIG. 41 shows certain variations to the hydraulic pressure circuit 2300 of FIG. 40.

In some embodiments, the hydraulic pressure circuit 2400 includes a second tool 2486. The second tool 2486 can be, for example, a hydraulically-driven Kerrison. In some embodiments, the second tool 2486 is driven by fluid by a bellows actuators 2422. The hydraulic manifold 2420 can include a proportioning valve 2434 positioned on the fluid path between the bellows actuators 2422 and the second tool 2486. This proportioning valve 2434 can control the amount of fluid and/or the pressure of the fluid that passes from the bellows actuators 2422 to the second tool 2486. In some cases, the proportioning valve 2434 can control the operating speed and/or operating power of the second tool 2486. Additional proportioning valves 2434 can be positioned on the fluid paths of the fluid returning from the tool 2482 to the bellows actuators 2422. These proportioning valves 2434 can be configured to control the rate at which fluid is returned to the bellows actuators 2422 from the tool 2484. In some embodiments, one or more of the valves 2432 in the hydraulic manifold 2420 can be interchangeable with a proportioning valve 2434.

In some embodiments, the hydraulic pressure circuit 2400 includes a pneumatic tool assembly 2450. The pneumatic tool assembly 2450 can include a pneumatic tool 2453 (e.g., micro-scissors, micro-forceps). The pneumatic tool 2453 can be powered by the air pump 2490. In some embodiments, the pneumatic tool assembly 2450 includes a pneumatic module 2451 which can include a three-way valve 2456 (e.g., a three-way, two position valve) positioned between the air pump 2490 and the pneumatic tool 2453. The three-way valve 2456 can be configured to selectively direct air or other gases from the air pump 2490 to the pneumatic tool 2453. In some embodiments, the pneumatic tool assembly 2453 includes a fluid conduit extending between the pneumatic tool 2453 and the three-way valve 2456 and configured to facilitate passage of air or other gases from the pneumatic tool 2453 to the three-way valve 2456.

Figure 42:
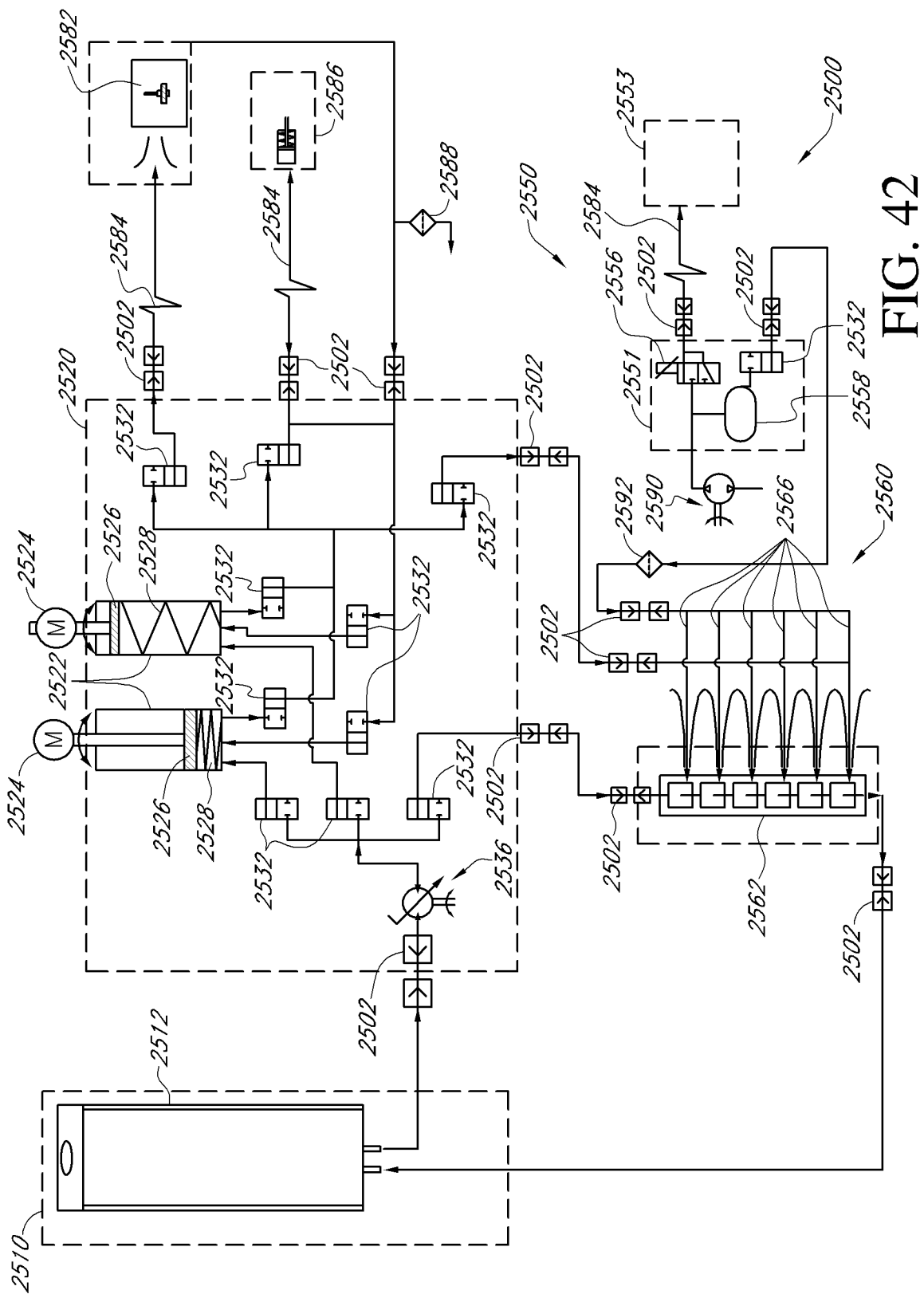

FIG. 42 illustrates an embodiment of a hydraulic pressure circuit 2500. Some numerical references to components in FIG. 42 are the same as or similar to those previously described for the hydraulic pressure circuit 2400 (e.g. hydraulic manifold 2520 v. hydraulic manifold 2420). It is to be understood that the components can be the same in function or are similar in function to previously-described components. The hydraulic pressure circuit 2500 of FIG. 42 shows certain variations to the hydraulic pressure circuit 2400 of FIG. 41.

In some embodiments, the pneumatic module 2551 can include an air accumulator 2558. The air accumulator 2558 can be positioned along the fluid path between the air pump 2590 and the nozzles 2566 of the LED assembly 2560. The air accumulator 2558 can be configured to reduce lag between the production of pressurized gas by the air pump 2590 and delivery of said pressurized gas to the nozzles 2566. Positioning the air accumulator 2558 outside the hydraulic manifold 2520 can simplify the structure and design of the hydraulic manifold 2520 unit (e.g., the cassette in which the hydraulic manifold 2520 may be housed).

Figure 43:
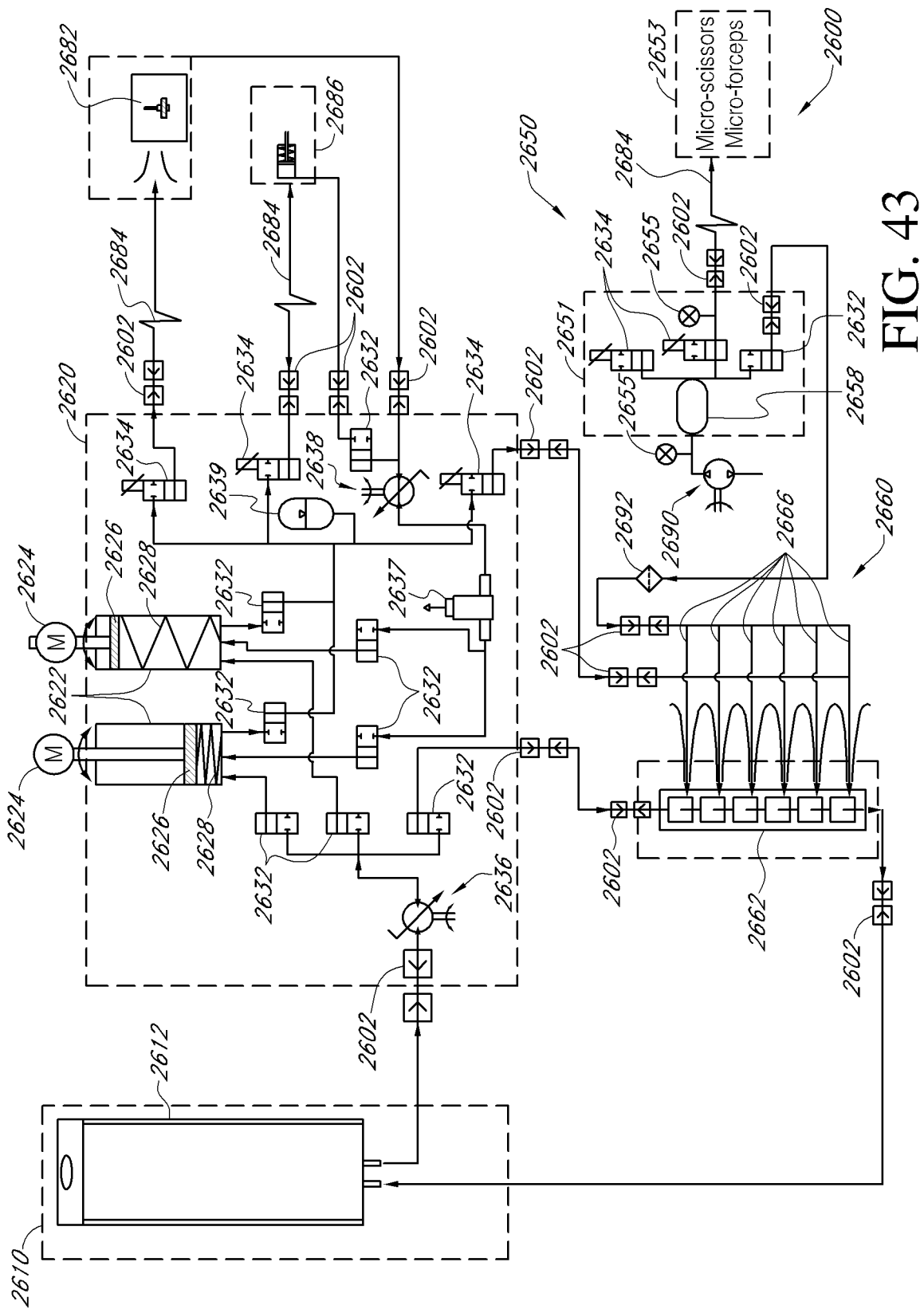
FIGS. 43-43D are schematic illustrations of additional embodiments of a hydraulic pressure circuit.

FIG. 43 illustrates an embodiment of a hydraulic pressure circuit 2600. Some numerical references to components in FIG. 43 are the same as or similar to those previously described for the hydraulic pressure circuit 2500 (e.g. hydraulic manifold 2620 v. hydraulic manifold 2520). It is to be understood that the components can be the same in function or are similar in function to previously-described components. The hydraulic pressure circuit 2600 of FIG. 43 shows certain variations to the hydraulic pressure circuit 2500 of FIG. 42.

In some embodiments, the air accumulator 2658 can be positioned on or in the fluid path between the air pump 2690 and the pneumatic tool 2653. The air accumulator 2690 can reduce the lag between the production of pressurized gas from the air pump 2658 and the delivery of said pressurized gas to the pneumatic tool 2653 and/or to the nozzles 2666 of the LED assembly 2660. Various pneumatic indicators 2655 can be positioned around and/or within the pneumatic assembly 2650 to provide visual indication of the status of various pneumatic components within the pneumatic assembly 2650.

In some cases, the second tool 2686 can be configured to redirect at least a portion of the fluid used to power the second tool 2686 back to the hydraulic manifold 2620. For example, a fluid line can extend from the second tool 2686 to the hydraulic manifold 2620 such that fluid exhausted from the second tool 2686 can be directed to the bellows actuators 2622 to reenergize said exhausted fluid.

The hydraulic manifold 2620 can include a fluid-air separator 2637. The air separator 2637 can be configured to remove air and other gases from the fluid line onto which the air separator 2637 is installed. For example, the fluid-air separator 2637 can be positioned and configured to remove air and other gases from the fluid that is directed toward the bellows actuators 2622 from the tool 2682 and/or from the second tool 2686. Such air-gas mixtures can result from actively scavenging low velocity hydraulic fluid and air from the tool 2682 and/or second tool 2686 via annular vents around the turbines of the tools or otherwise after the hydraulic fluid is used to power the tool 2682 and/or second tool. Removal of gases from the fluid lines of the hydraulic manifold 2620 can improve the performance of the hydraulic components of the hydraulic pressure system 2600 (e.g., the tools 2682, 2686). In some embodiments, the hydraulic manifold 2620 includes a pressure compensation source 2639 (e.g., a master-slave balloon) configured to regulate the pressure in one or more of the fluid lines of the hydraulic manifold 2620.

In some embodiments, one or more of the valves within the hydraulic pressure circuits described above can be a consumable valve (e.g., the valve can be one-time use and/or disposable). For example, one or more of the valves within the hydraulic manifolds can be a consumable check valve configured to be discarded after use. Use of disposable valve can reduce the part and maintenance costs associated with the hydraulic pressure circuits. For example, the reusable valves or other reusable components of the hydraulic manifold (e.g., valves, housings, fluid lines, pumps) could be constructed from polymers, elastomers, and/or other low-cost materials.

Figure 43A:
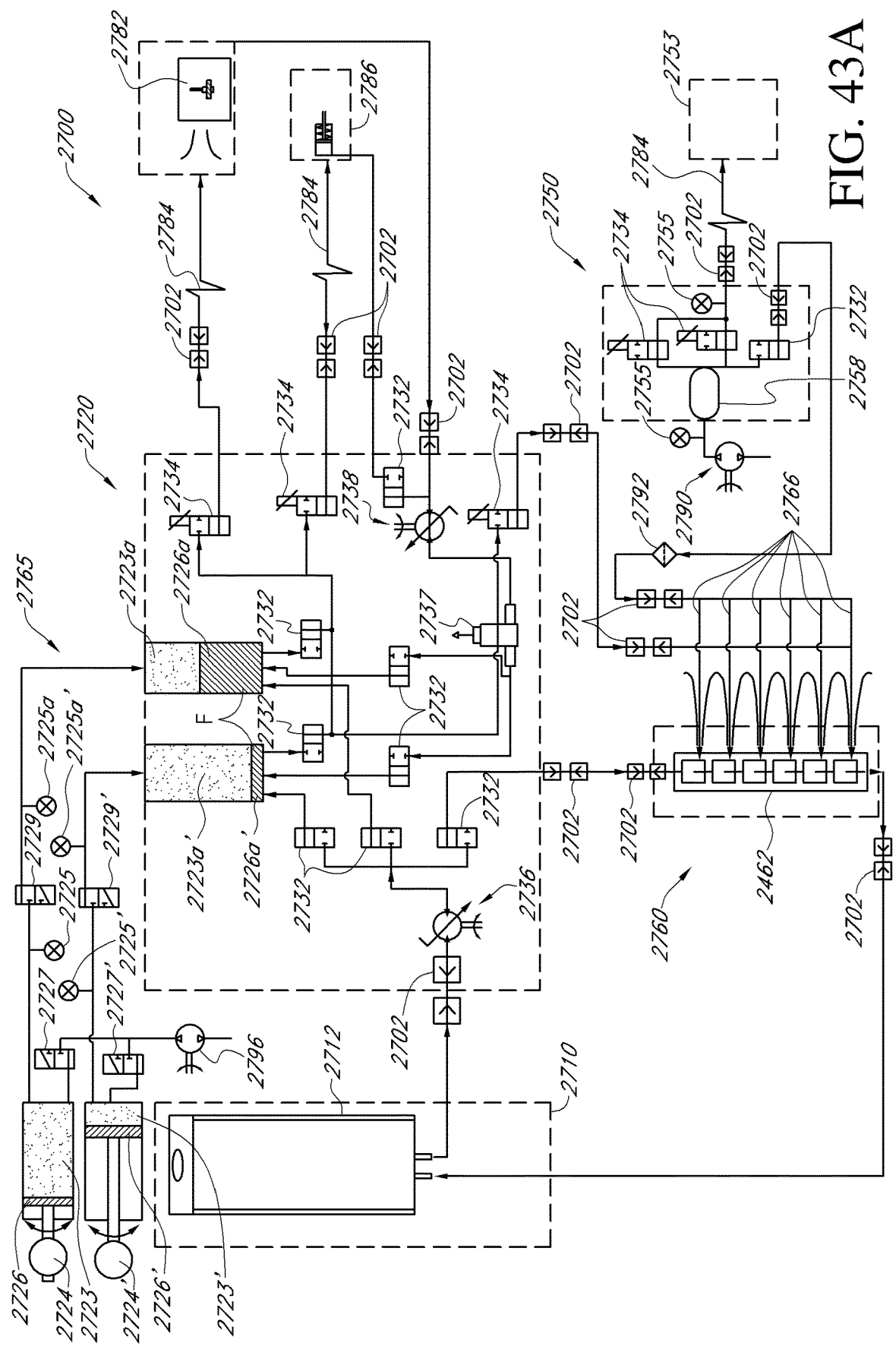

FIG. 43A illustrates an embodiment of a hydraulic pressure circuit 2700. Some numerical references to components in FIG. 43A are the same as or similar to those previously described for the hydraulic pressure circuit 2600 (e.g. hydraulic manifold 2720 v. hydraulic manifold 2620). It is to be understood that the components can be the same in function or are similar in function to previously-described components. The hydraulic pressure circuit 2700 of FIG. 43A shows certain variations to the hydraulic pressure circuit 2600 of FIG. 43.

In some embodiments, the hydraulic pressure circuit 2700 can include a pneumatic pressure assembly 2765. The pneumatic pressure assembly 2765 can function as a pressure source for the hydraulic fluid of the hydraulic pressure circuit 2700. In some embodiments, the pneumatic pressure assembly 2765 is used in combination with mechanical actuators (e.g., bellows similar to or the same as bellows 2628) to pressurize the hydraulic fluid within the hydraulic pressure circuit 2700. In some embodiments, the pneumatic pressure assembly 2765 is used instead of such mechanical actuators to pressurize the hydraulic fluid within the hydraulic pressure circuit 2700.

The pneumatic pressure assembly 2765 can include one or more pneumatic actuators. The pneumatic actuators can be configured to pressurize air or other gases within the pneumatic pressure assembly 2765. For example, the pneumatic pressure assembly 2765 could include one or more linear actuators 2726, 2726' driven by one or more motors 2724, 2724'. The linear actuators 2726, 2726' can be used to increase and decrease the pressure of a pneumatic fluid within a pneumatic actuator chamber 2723, 2723'. For example, the linear actuators 2726, 2726' can be used to increase and decrease the size (e.g., the volume) of the pneumatic actuator chambers 2723, 2723' to effect changes in pressure for the pneumatic fluid within the actuator chambers 2723, 2723'.

In some embodiments, the pneumatic pressure assembly 2765 includes one or more pneumatic pressure sources. The one or more pneumatic pressure sources can be in fluid communication with the actuator chambers 2723, 2723'. For example, the pneumatic pressure assembly 2765 can include a pump 2796. The pump 2796 can be configured to provide pressurized pneumatic fluid (e.g., air and/or other gases) to the actuator volumes 2723, 2723'. The pump 2796 can be configured to pressurize the pneumatic fluid to pressures above atmospheric (e.g., 60 psi). In some configurations, one or more valves 2727, 2727' can be positioned in the fluid path(s) between the pump 2796 and the chambers 2723, 2723'. In some embodiments, the use of the pump 2796 can reduce or eliminate a need to connect the pneumatic pressure assembly 2765 and/or hydraulic pressure system 2700 to a hospital compressed air system. The valves 2727, 2727' can be configured to selectively allow and/or constrict fluid communication between the pump 2796 and the chambers 2723, 2723'. In some embodiments, the valve 2727, 2727' are three way, two position valves. Many different types of valves are possible (e.g., one-way check valves, pincher valves, solenoid valves, etc.).

The pneumatic actuator chambers 2723, 2723' can be in fluid communication with secondary pneumatic actuator chambers 2723a, 2723a'. In some embodiments, one or more valves 2729, 2729' can be positioned in the fluid path(s) between the actuator chambers 2723, 2723' and the secondary pneumatic actuator chambers 2723a, 2723a'. The valves 2729, 2729' can be configured to selectively allow and/or constrict fluid communication between the actuator chambers 2723, 2723' and the secondary pneumatic actuator chambers 2723a, 2723a. In some embodiments, the valve 2729, 2729' are three way, two position valves. Many different types of valves are possible (e.g., one-way check valves, pincher valves, solenoid valves, etc.).

The secondary pneumatic actuator chambers 2723a, 2723a' can be positioned at least partially within the hydraulic manifold 2720. Pressure within chambers 2723a, 2723a' can exert force upon floating piston heads 2726a, 2726a'. In some embodiments, the secondary chambers 2723a, 2723a' do not include floating piston heads and the pressurized pneumatic fluid interacts directly with the hydraulic fluid in the chambers 2723a, 2723a'. The floating piston heads 2726a, 2726a' can define an interface between the pneumatic fluid of the pneumatic pressure assembly 2765 and the hydraulic fluid F of the hydraulic manifold 2720 and hydraulic pressure circuit 2700. Exertion of force upon the floating piston heads 2726a, 2726a' by the pneumatic fluid within the chambers 2723a, 2723a' can cause the floating piston heads 2726a, 2726a' to increase the pressure of the hydraulic fluid F on the side of the floating piston heads 2726a, 2726a' opposite the chambers 2723a, 2723a'. In embodiments without piston heads, introduction of pressurized pneumatic fluid into the chambers 2723a, 2723a' can increase the pressure of the hydraulic fluid F within the chambers 2723a, 2723a'. In some embodiments, the floating piston heads 2726a, 2726a' in combination the pressurized pneumatic fluid within the secondary pneumatic actuator chambers 2723a, 2723a' can perform the same or a similar function as performed by the bellows actuators described above and below. In some embodiments without floating piston heads, the pressurized pneumatic fluid acting directly on the hydraulic fluid within the chambers 2723a, 2723a' can perform the same or a similar function as performed by the bellows actuators described above and below.

In some embodiments, the pneumatic pressure assembly 2765 includes one or more pneumatic indicators 2725, 2725', 2725a, 2725a'. In some embodiments, pneumatic indicators 2725a, 2725a' are redundant backup indicators in the case of malfunction and/or failure of the indicators 2725, 2725'. The indicators can be configured to monitor the pressure within the fluid lines connecting the pneumatic actuator chambers 2723, 2723' with the secondary pneumatic actuator chambers 2723a, 2723a'. The indicators can be operably coupled (e.g., electrically connected via wired and/or wireless connections) with the motors 2724, 2724' and/or with the linear actuators 2726, 2726'. In some embodiments, the indicators 2725, 2725', 2725a, 2725a' are operably coupled with the pump 2796 and/or other pneumatic pressure source.

According to some configurations, the pneumatic pressure assembly 2765 can operate in the following manner. During a compression stroke, the linear actuator 2726 can be configured to compress the pneumatic fluid within the chamber 2723 (e.g., in response to input from the motor 2724) to maintain a predetermined pressure (e.g., 120 psi) within the fluid line connecting the chamber 2723 with the secondary chamber 2723a. The indicator 2725 can monitor the pressure within the fluid line and can communicate (e.g., via an operable connection such as a wired or wireless electrical connection) with the motor 2724 to ensure that the pressure within the fluid line remains at or above a minimum acceptable pressure.

The valve 2729 can be configured to permit fluid communication between the chamber 2723 and the secondary chamber 2723a during the compression stroke of the linear actuator 2726. Compression of the pneumatic fluid within the chamber 2723 during the compression stroke can cause an increase in pressure within the secondary chamber 2723a. Increase in pressure of the pneumatic fluid in the secondary chamber 2723a can force the floating piston 2726a to (or can directly, in the case of a piston-less embodiment) compress the hydraulic fluid F, thus pressuring the fluid F for use in the hydraulic pressure circuit.

Upon completion of the compression stroke of the linear actuator 2726, the valve 2729 can cut off fluid communication between the chamber 2723 and the secondary chamber 2723a and allow the secondary chamber 2723a to vent to ambient. At this point, the pneumatic fluid within the secondary chamber 2723a can vent to atmosphere and the hydraulic fluid F provided by the return lines from the tool 2782 and/or second tool 2786 and/or from the fluid reservoir 2712 can increase the pressure on the hydraulic side of the floating piston 2726a. Such an increase in pressure can cause the piston 2726a to move and reduce the volume of the secondary chamber 2723a. In embodiments without piston heads in the chambers 2723a, 2723a', the introduction of hydraulic fluid F from the return lines from the tool 2782 and/or second tool 2786 and/or from the fluid reservoir 2712 can force the pneumatic fluid out from the chambers 2723a, 2723a'.

Concurrent with the venting of the secondary chamber 2723a, the valve 2727 can be opened to permit fluid communication between the pump 2796 and the chamber 2723. The pump 2796 can provide pneumatic fluid (e.g., air and/or other gases) at a pressure above ambient (e.g., 60 psi) to help facilitate retraction of the linear actuator 2726. In some embodiments, the motor 2724 can act in combination with or instead of the pump 2796 to quickly retract the linear actuator 2726. Upon refilling of the chamber 2723 with pneumatic fluid (e.g., upon completion of the expansion stroke of the linear actuator 2726), the valve 2727 can cut off fluid communication between the pump 2796 and the chamber 2723. In some embodiments, the valve 2727 can be configured to facilitate venting of the pressurized fluid from the pump 2796 to ambient. Although the operation of the pneumatic circuit 2765 has been described in the context of one linear actuator 2726, all or at least most of the functions described with regard to linear actuator 2726 and its corresponding valves and chambers equally describe the functioning of linear actuator 2726' and its corresponding valves and chambers (e.g., chambers 2723' and 2723a', valves 2727' and 2729', piston 2726a'). In some embodiments, the use of more than one linear actuator 2726 and corresponding valves and chambers can facilitate substantially continual pressurization of the hydraulic fluid F in the hydraulic pressure circuit 2700. For example, while the linear actuator 2726 is in the compression stroke, the linear actuator 2726' can be configured to operate in the expansion stroke such that, upon completion of the compression stroke of the linear actuator 2726, the compression stroke of the linear actuator 2726' can begin.

Figure 43B:
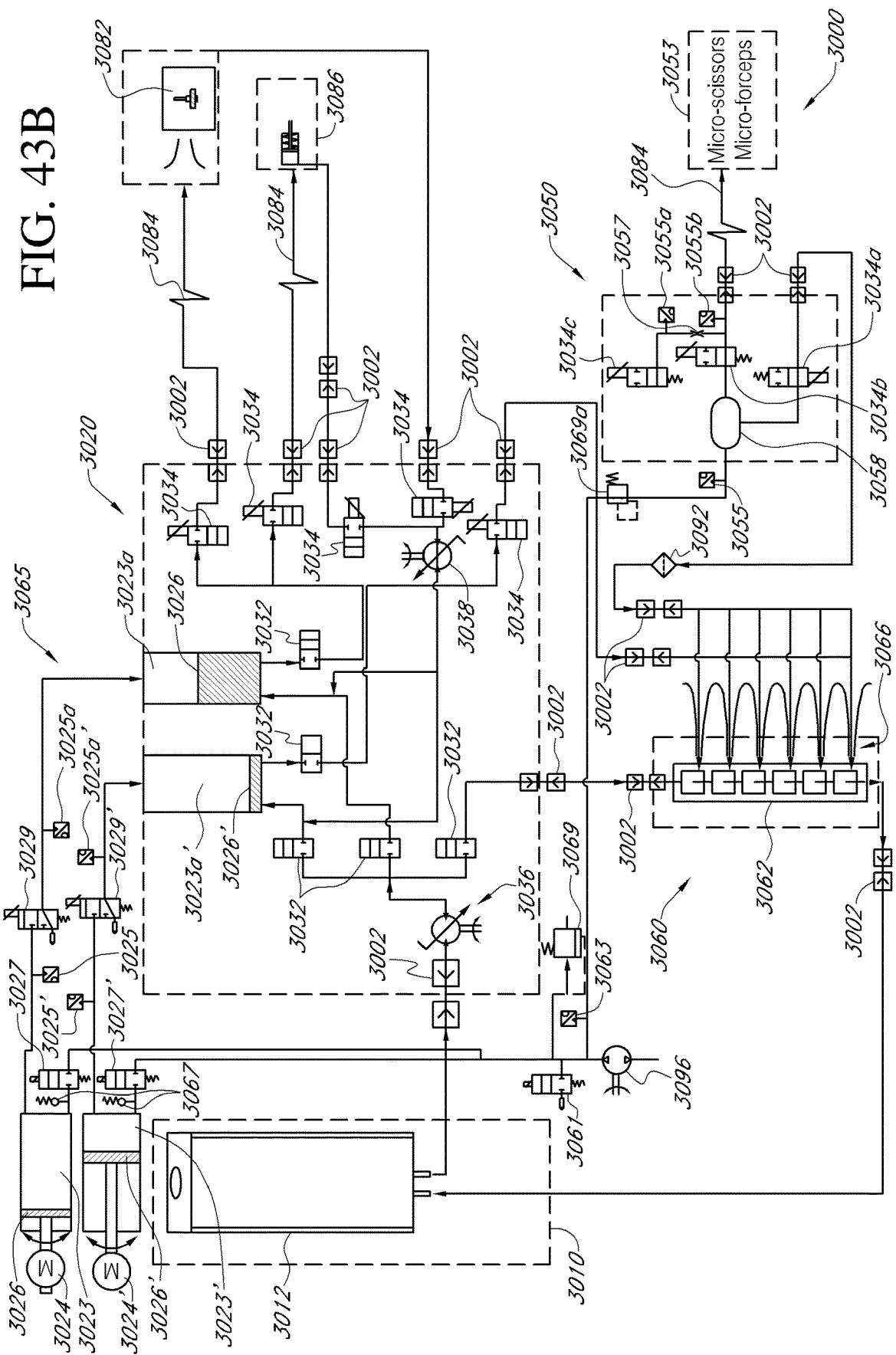

FIG. 43B illustrates an embodiment of a hydraulic pressure circuit 3000. Some numerical references to components in FIG. 43B are the same as or similar to those previously described for the hydraulic pressure circuit 2700 (e.g. hydraulic manifold 3020 v. hydraulic manifold 2720). It is to be understood that the components can be the same in function or are similar in function to previously-described components. The hydraulic pressure circuit 3000 of FIG. 43B shows certain variations to the hydraulic pressure circuit 2700 of FIG. 43A.

In some embodiments, the fluid lines connecting the various components of the pneumatic pressure assembly 3065 can include one or more release valves 3067 configured to open if the pressure within a given fluid line rises above a predetermined maximum (e.g., 150 psi). The release valves 3067 can be positioned on the fluid lines between the valves 3027, 3027' and the chambers 3023, 3023'. In some embodiments, the fluid line connecting the pump 3096 with the chambers 3023, 3023' can include a venting valve 3061 configured to selectively vent to atmosphere. Such a venting valve 3061 can improve the safe operation of the pneumatic pressure assembly 3065 and can allow the pump 3096 to continue safely running throughout the use of the pneumatic pressure assembly 3065. In some embodiments, the fluid line connecting the pump 3096 with the chambers 2723, 2723' can include a venting valve and/or pressure relief valve 3069 configured to open and vent to atmosphere upon detection of a predetermined maximum pressure (e.g., 70 psi).

In certain configurations, the pump 3096 can be in fluid communication with and supply pressurized pneumatic fluid to the air accumulator 3058 of the pneumatic assembly 3050. A pressure regulator 3069a can be positioned on the fluid line between the pump 3096 and the accumulator 3058 to regulate the pressure within the line. In some embodiments, one or more pneumatic indicators 3055, 3063 can be positioned on the fluid line between the pump 3096 and the air accumulator 3058. In some embodiments, such an arrangement can eliminate the need for a second pump 2790 and can simplify the overall design of the hydraulic pressure circuit 3000. The pneumatic assembly 3050 can include one or more vent valves 3034c (e.g., valves configured to vent to atmosphere) configured to reduce the risk of over-pressurizing the pneumatic assembly 3050. In some embodiments, a pair of pneumatic indicators (e.g., pressure sensors) 3055a, 3055b are positioned on the fluid lines between the air accumulator 3058 and the vent valve 3034c and between the air accumulator 3058 and the pneumatic tool 3053. A restriction 3057 (e.g., an orifice) between the two pneumatic indicators 3055a, 3055b can help to detect an open pneumatic line. In some embodiments, a restriction 3057 can help prevent sudden reaction in the pneumatic tool 3053 when the vent valve 3034c is opened to vent the pneumatic assembly 3050.

One or more of the valves (e.g., valves 3027, 3027', 3029, 3029', 3034a, 3034b, 3034c) in the pneumatic pressure assembly 3065 and/or in the pneumatic assembly 3050 can be spring-driven. For example, the valves can be biased to the open/venting configuration in the default position. In some embodiments, such a configuration can help reduce the risk of over-pressurization of the pneumatic pressure assembly 3065 and/or of the pneumatic assembly 3050 and can ensure venting of the assemblies 3065, 3050 upon shut down of the assemblies 3065, 3050.

One or more of the valves 3034 on the cassette 3020 can be diaphragm valves formed by an elastomeric element. The valves 3034 can be used to control the first tool 3082 and/or second tool 3086 (e.g., a Kerrison and/or drill). The valves 3034 can be actuated by non-disposable linear electromagnetic actuators.

Figure 43C:
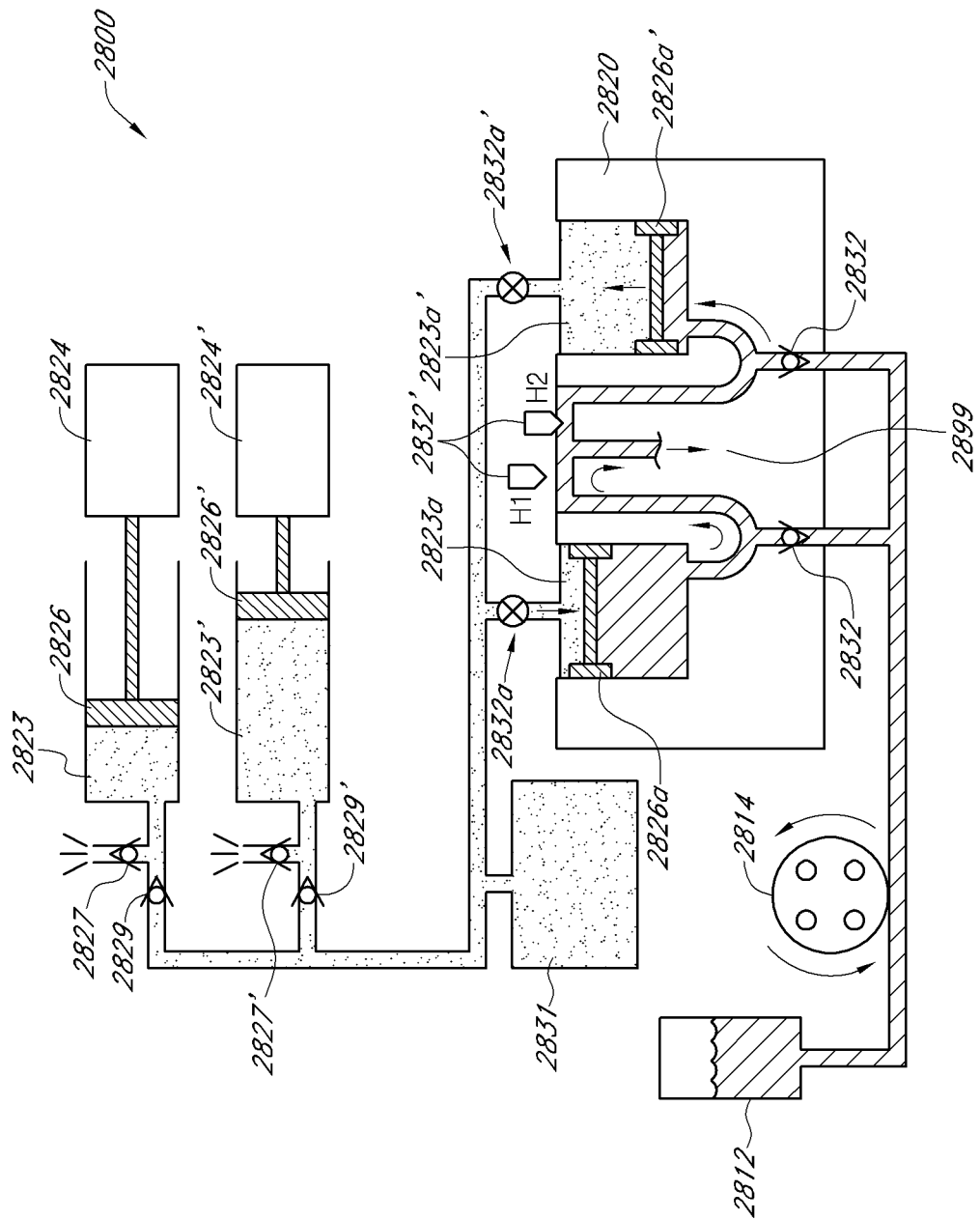

FIG. 43C illustrates an embodiment of a hydraulic pressure circuit 2800. Some numerical references to components in FIG. 43C are the same as or similar to those previously described for the hydraulic pressure circuit 3000 (e.g. linear actuators 2824, 2824' v. linear actuators 3024, 3024'). It is to be understood that the components can be the same in function or are similar in function to previously-described components. The hydraulic pressure circuit 2800 of FIG. 43C shows certain variations to the hydraulic pressure circuit 3000 of FIG. 43B.

For example, the hydraulic pressure circuit 2800 can include a hydraulic pump 2814 (e.g., a peristaltic pump) or other fluid pressurizing component to inhibit fluid backflow into the fluid source 2812 from the secondary chambers 2823a, 2823a'. One way valves 2832 can be positioned in the fluid paths between the fluid source 2812 and the secondary chambers 2823a, 2823a' to selectively permit refilling of one or more of the secondary chambers 2823a, 2823a' from the fluid source 2812.

The pneumatic pressure assembly 2865 can include two or more linear actuators 2824, 2824' configured to translate within two or more chambers 2823, 2823'. The fluid lines between the chambers 2823, 2823' and the secondary chambers 2823a, 2823a' can include air inlet valves 2827, 2827'. In some embodiments, the inlets to the secondary chambers 2823a, 2823a' include three-way solenoid valves 2832a, 2832a' configured to selectively allow fluid ingress/egress two and from the secondary chambers 2823a, 2823a'. The three-way solenoid valves 2832a, 2832a' can be configured to vent the fluid lines between the chambers 2823, 2823' and the secondary chambers 2823a, 2823a'. Pinch valves 2832' or other valves can be used to selectively permit passage of pressurized hydraulic fluid from the secondary chambers 2823a, 2823a' to the remaining hydraulic circuit (e.g., via fluid path 2899).

Figure 43D:
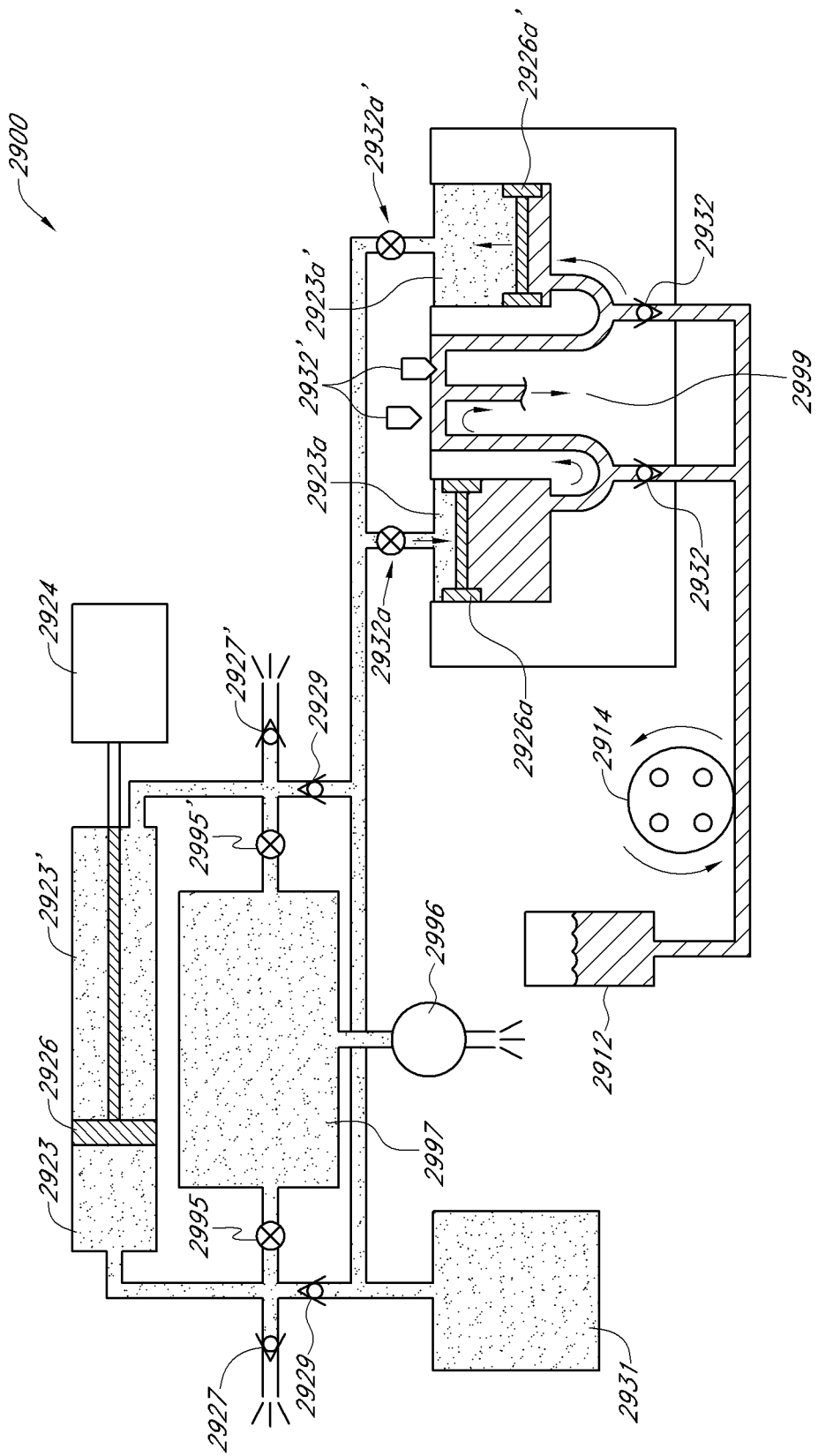

FIG. 43D illustrates an embodiment of a hydraulic pressure circuit 2900. Some numerical references to components in FIG. 43D are the same as or similar to those previously described for the hydraulic pressure circuit 2800 (e.g. secondary chambers 2923a, 2923a' v. secondary chambers 2823a, 2823a'). It is to be understood that the components can be the same in function or are similar in function to previously-described components. The hydraulic pressure circuit 2900 of FIG. 43D shows certain variations to the hydraulic pressure circuit 2800 of FIG. 43C.

For example, the pneumatic pressure assembly 2965 can include a single pneumatic actuator chamber split into a first pneumatic actuator chamber 2923 and a second pneumatic chamber 2923'. A single linear actuator 2924 can be transitioned back and forth (e.g., right and left in FIG. 43D) to alternately compress and expand the first and second chambers 2923, 2923'. A pump 2996 can be used to provide compressed pneumatic fluid to the chambers 2923, 2923' during their respective expansion strokes via valves 2995, 2995' (e.g., solenoid valves). In some embodiments, the pneumatic circuit 2965 includes a pressure chamber 2997 configured to store pre-compressed pneumatic fluid for distribution to the chambers 2923, 2923'.

Figure 44A:
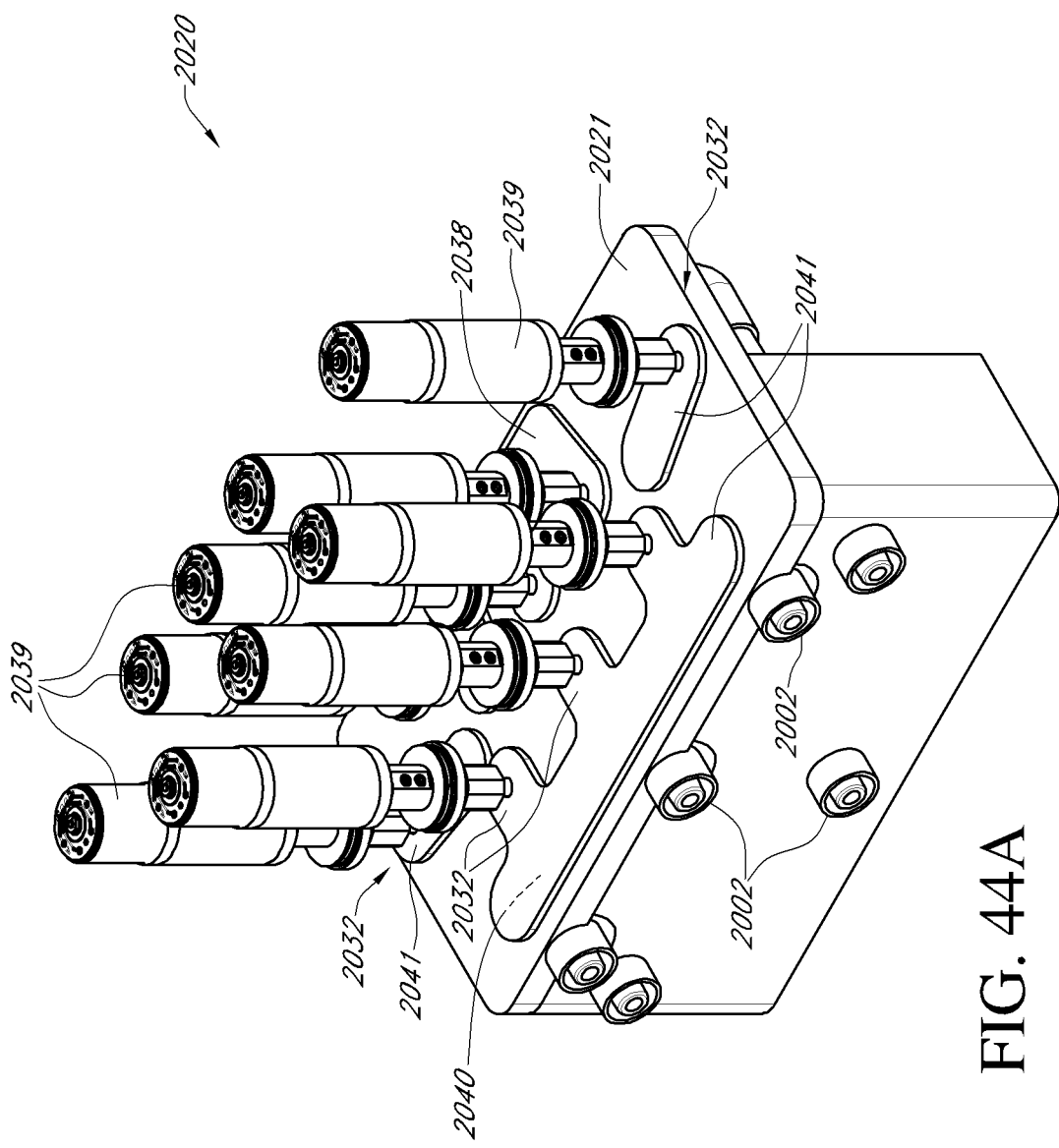
FIG. 44A shows a perspective view of one embodiment of a hydraulic manifold.

As explained above, portions of or the entire hydraulic manifold 2020, 2120, 2220, 2320, 2420, 2520, 2620 (2020 hereinafter for simplicity) can be housed within a cassette containment apparatus. For example, as illustrated in FIG. 44A, a cassette housing 2021 can include a number of external connectors 2002. One or more valves 2032 (e.g., pinch valves, diaphragm valves, elastomeric valves) can be attached to the cassette housing 2021. In some embodiments, the valve assembly 2032 on the cassette housing 2021 can have a flexible pad 2041, a cavity 2040, a valve opening 2038, and a pincher or valve stem actuator 2039. The valve stem actuators 2039 can be fixed to a console into or onto which the cassette is connected. In some embodiments, the valve stem 2039 can exert a downward force on the flexible pad 2041 thereby compressing the flexible pad 2041 into the cavity 2040 of the cassette housing 2021 above the valve opening 2038 and toward the valve opening 2038. The valve opening 2038 can be fully obstructed, partially obstructed, or fully open at varying amounts depending on the compression of the flexible pad 2041 by the valve stem 2039. The degree of obstruction of the valve opening 2038 by the flexible pad 2041 can regulate, direct, or control the flow of fluid into the valve. For example, the valve stem 2039 can be used to pulse the flow of fluid through a valve opening 2038. In some embodiments, the valve stem 2039 can be used to accelerate fluid flow through a valve opening 2038 (e.g., the valve stem 2039 can constrict the valve opening 2038 and act as a nozzle).

In some embodiments, the valve opening 2038 can be obstructed by the flexible pad 2041 and can allow for precise control of the degree and period of obstruction by the valve stems 2039 depression onto to the flexible pad. The flexible valve opening can allow for the flow of fluid through the valve to be obstructed at such varying degrees or with a pulsing flow thereby allowing for a fluid flow through the valve to be sustained at a wide range of desired flow rates by controlling the frequency and distance of depression of the flexible pad 2041 by the valve stem 2039. For example, the valves 2032 in and on the cassette housing 2021 can act as diaphragm valves to flex flexible pads on the top of the cassette housing 2021 and throttle the substantially constant high pressure hydraulic fluid supplied from the bellows or other hydraulic pressure source. In some embodiments, the valve stem 2039 can be depressed into the flexible pad 2041 by mechanical or hydraulically driven forces, or other forces known in the art or described herein. In some such configurations, pressurized hydraulic fluid can be proportionally directed to the various subsystems and fluid pathways of the hydraulic pressure circuit (e.g., the hydraulic tools, LED arrays). In some configurations, the cassette housing 2021 is a substantially closed container. In some embodiments, the cassette housing 2021 has one or more opened portions.

Figure 44B:
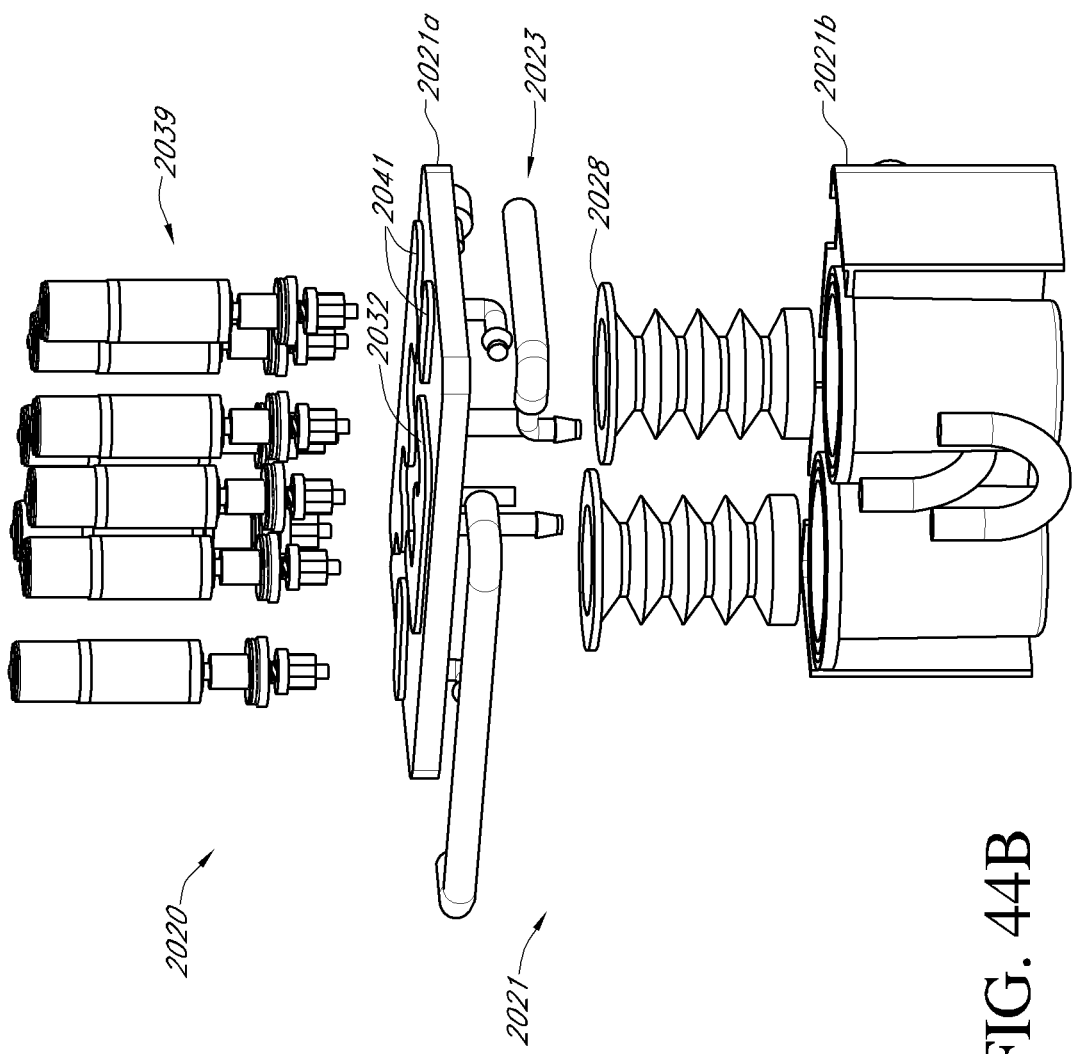
FIG. 44B shows an exploded view of the hydraulic manifold of FIG. 44A.
Figure 44C:
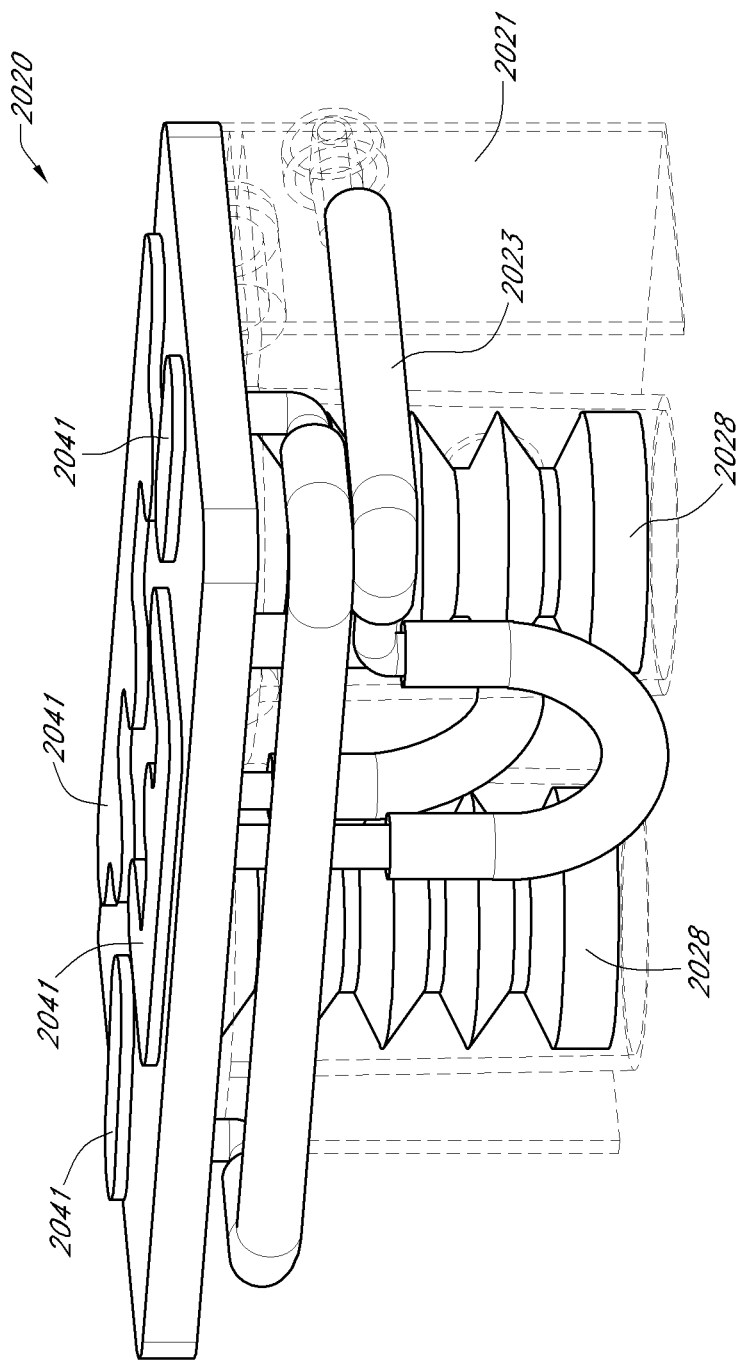
FIG. 44C shows a rear view of the hydraulic manifold of FIG. 44A.

As illustrated in FIGS. 44B and 44C, the cassette assembly 2021 can include a cassette cap portion 2021a and a cassette body 2021b. The cassette cap portion 2021a can include one or more flexible pads 2041, one or more valves 2032, and one or more cavities 2040. Additionally, the pinchers or valve stem actuators 2039 can be included in the cassette assembly 2021. The cassette body 2021b can include one or more cylindrical containers configured to house the bellows 2028 of the bellows actuators 2022. In some embodiments, the cassette assembly 2021 includes a plurality of tubing sections 2023 configured to connect various components and external connectors 2002 to one another. One or more of the components of the cassette assembly 2021 and/or of the hydraulic manifold 2020 can be consumable. For example, as explained above, the valves, fluid lines, body, cap portion, bellows, and/or ports of the cassette assembly 2021 can be consumable. The use of consumable parts can reduce the amount of assembly required for the hydraulic manifold 2020 and can reduce the likelihood of introducing contaminants to the hydraulic pressure circuit 2000 and can reduce or eliminate the cleanup process required for the hydraulic pressure circuit 2000 after use.

Figure 44D:
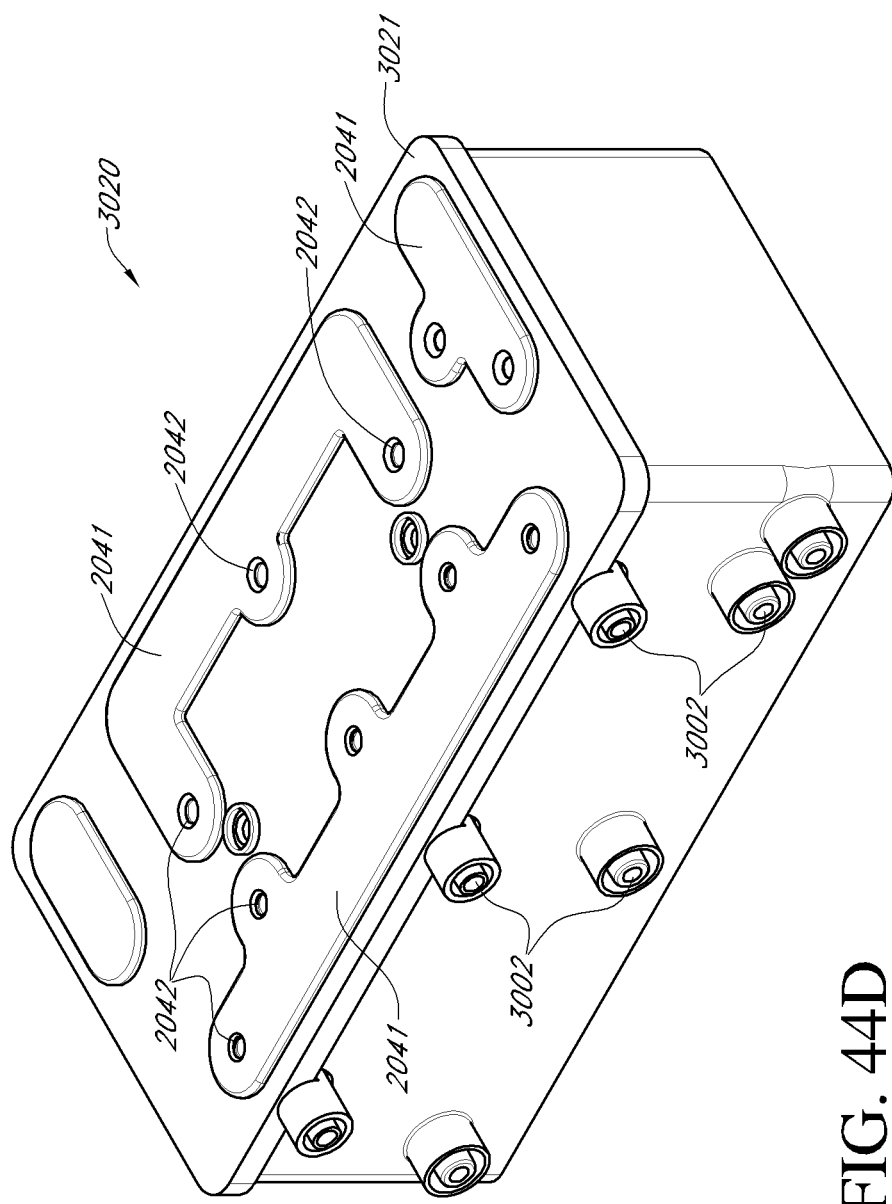
FIG. 44D shows a perspective view of one embodiment of a hydraulic manifold.
Figure 44E:
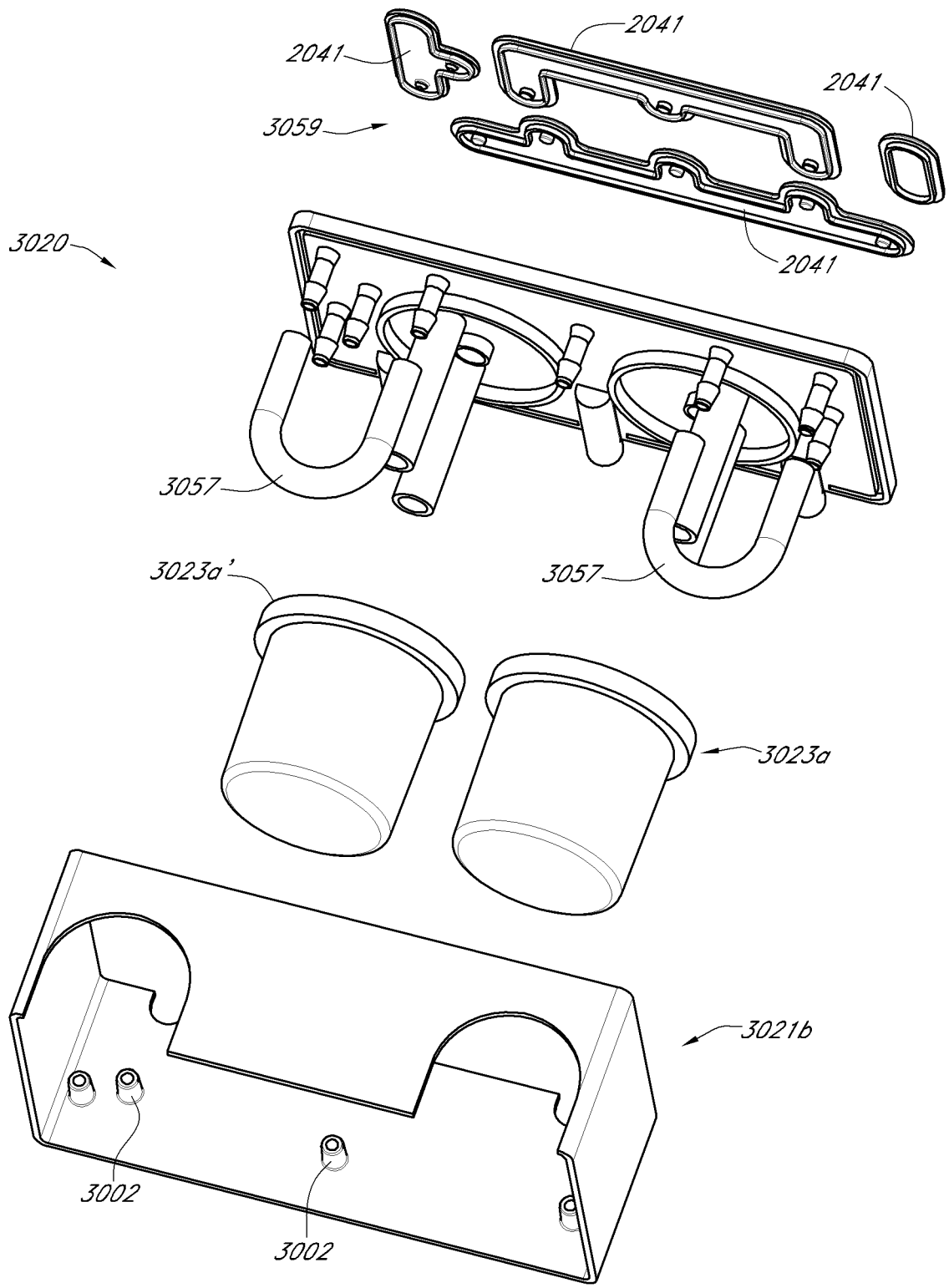
FIG. 44E shows an exploded view of the hydraulic manifold of FIG. 44D.
Figure 44F:
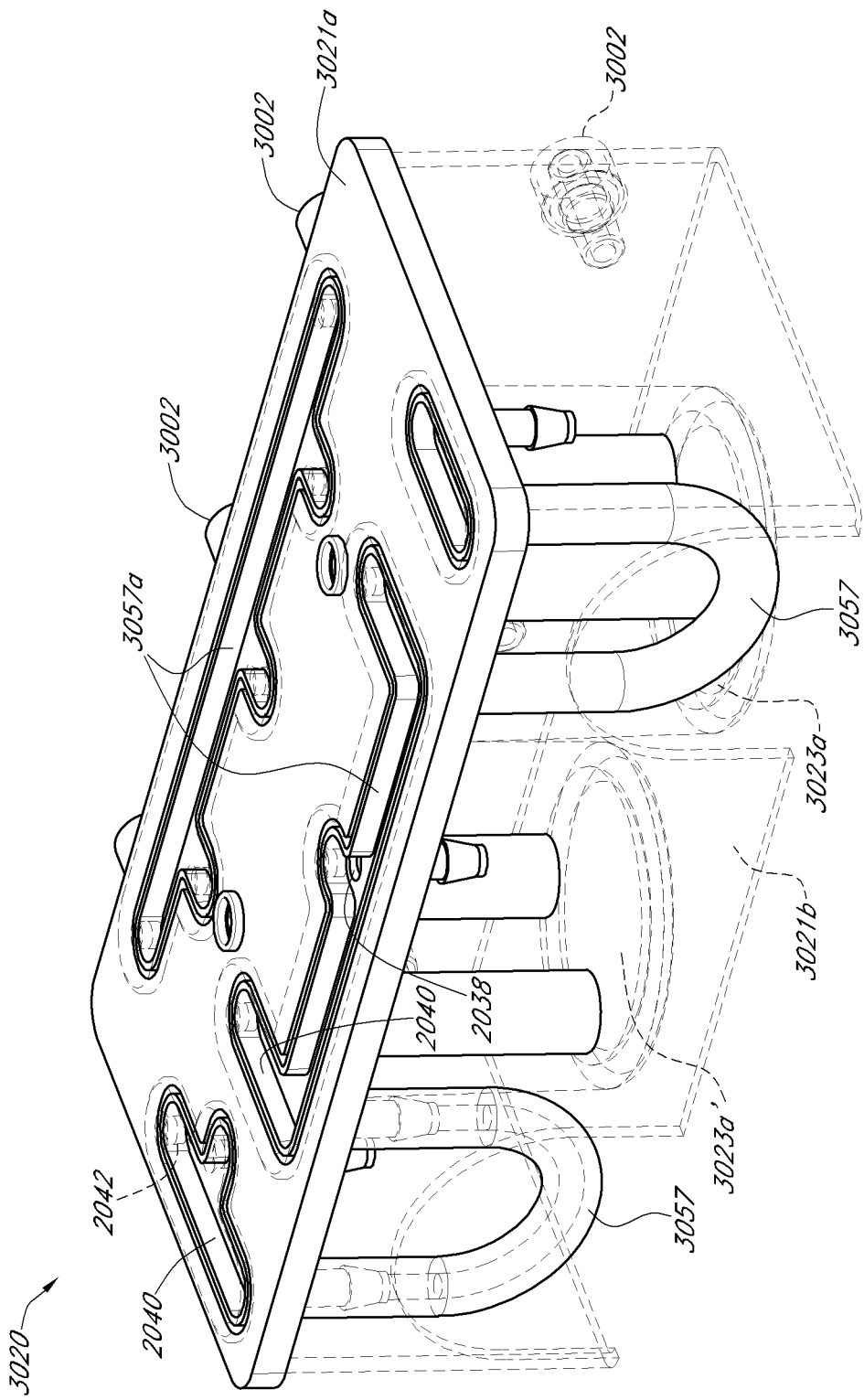
FIG. 44F shows a rear view of the hydraulic manifold of FIG. 44D.

FIGS. 44D-44F illustrate an embodiment of a cassette assembly configured to contain the at least a portion of the hydraulic manifold 2720, 3020. The cassette housing 3021 can include one or more connector interfaces 3002. The cassette housing 3021 can be a substantially closed container. In some embodiments, the cassette 3021 is at least partially open on one or more side.

In some embodiments, the cassette housing 3021 includes a cassette cap portion 3021a and a cassette body 3021b. The cassette cap portion 3021a can define one or more cap fluid channels 3057a configured to provide fluid communication between fluid lines and connectors/ports in and on the cassette 3021. In some embodiments, the fluid channels can comprise the cavity 2040 in which the flexible pads 2041 are depressed into by the valve stem 2039 as described herein. Fluid channel caps 3059 can be positioned on top of the cap fluid channels 3057a to inhibit fluid from leaking from the channels 3057a. In some embodiments, the fluid channel caps can be a flexible pad 2041 used for the valve assembly as described herein. The fluid channel caps 3059 can be constructed from a flexible or semi-flexible material (e.g., elastomers, polymers, etc.). Valves stems 2039 can be used to flex the caps 3059. The valves stems 2039 can be used to close off or open the connectors/ports in the cassette 3021. In some embodiments, the valve stems 2039 act as diaphragm valves and restrict the flow paths in the fluid channels 3057a without completely closing off the connectors/ports. In some such configurations, the valves stems 2039 act as proportional valves to selectively distribute hydraulic fluid flow between the various components and subsystems of the hydraulic pressure circuit 3000 (e.g., the hydraulic tools, the LED array, etc.). One or more flexible and/or rigid tubing sections 3057 can be used to connect fluid connectors/ports (e.g., connectors interfaces 3002) within the cassette 3021. The secondary chambers 3023a, 3023a' can, in some embodiments, be housed at least partially within the cassette 3021.

Figure 45A:
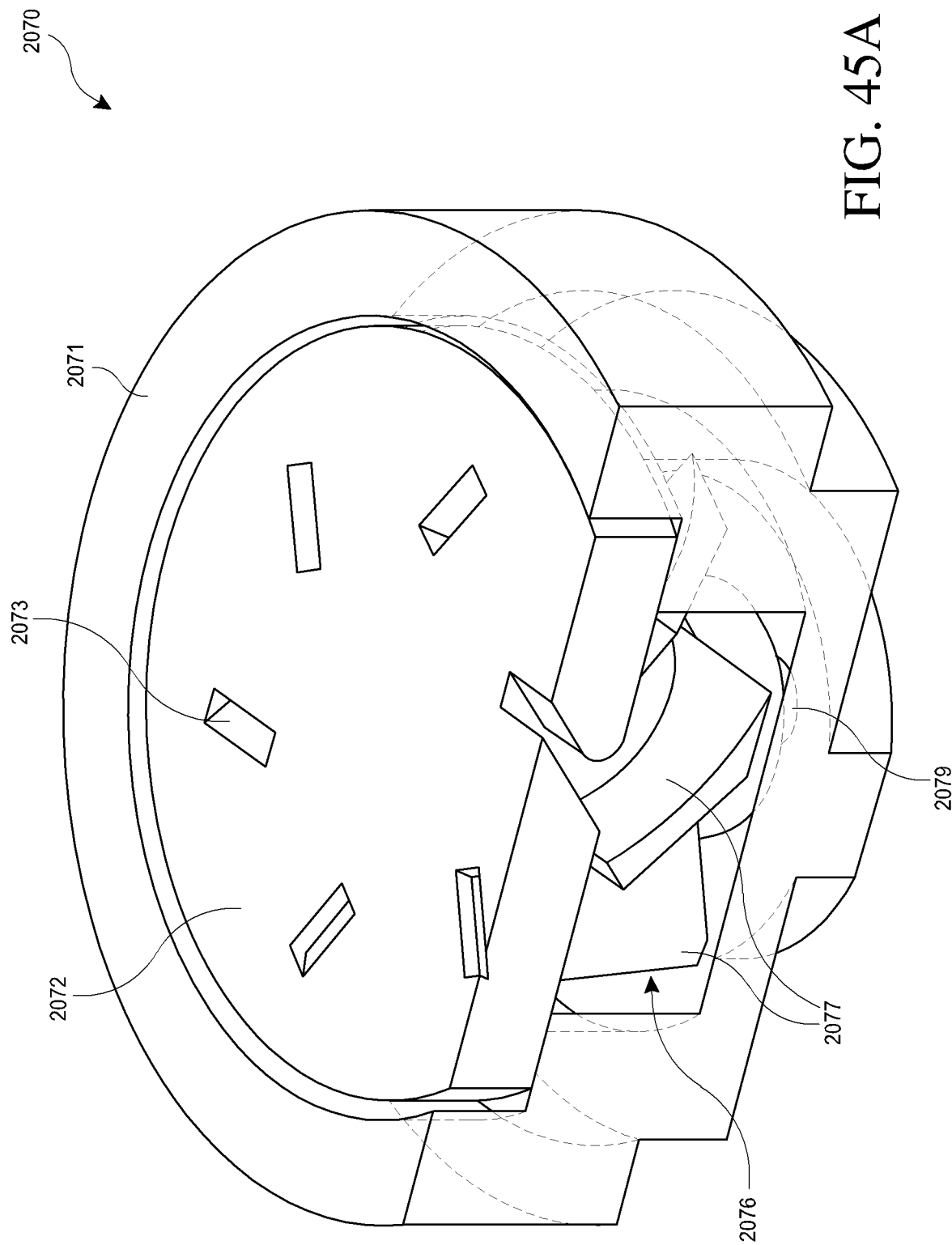
FIG. 45A shows a perspective cross-section of a hydraulic turbine.
Figure 45B:
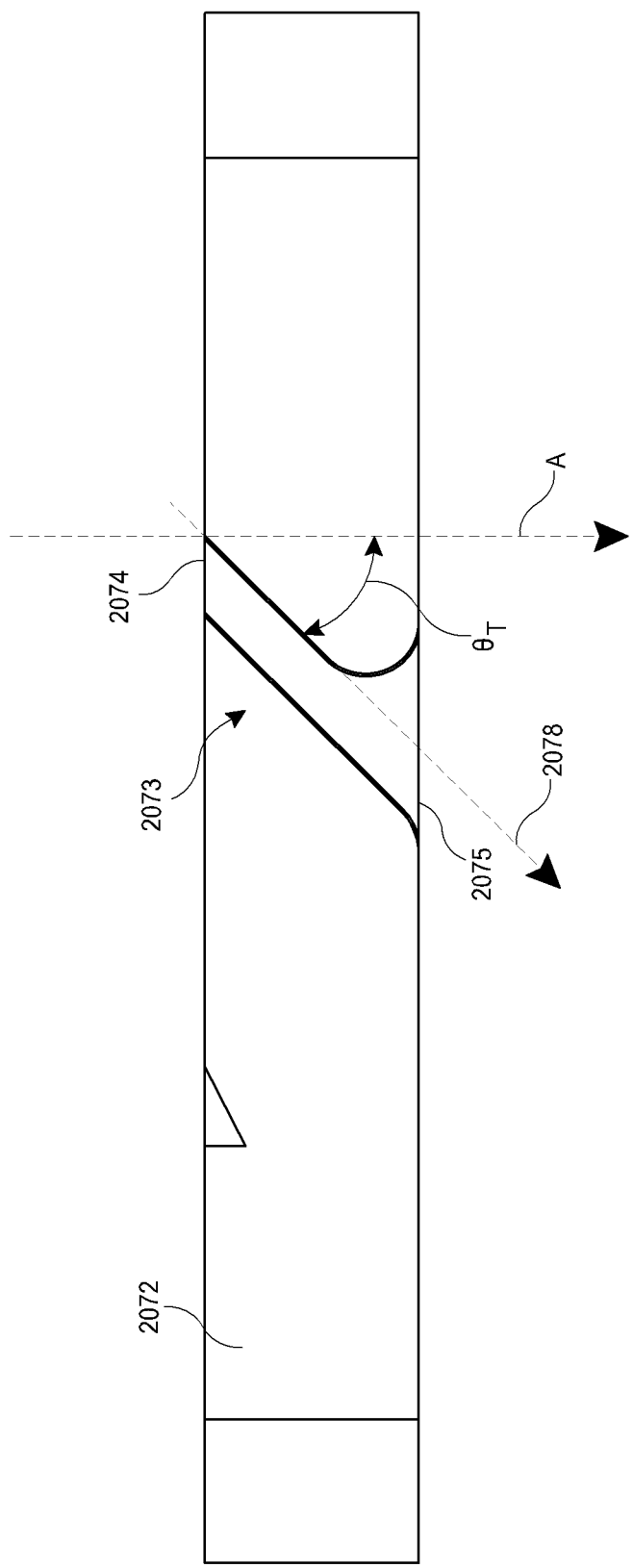
FIG. 45B shows a cross-section of a portion of the hydraulic turbine of FIG. 45A.

As explained above, the tool 2082, 2182, 2282, 2382, 2482, 2582, 2682 (hereinafter 2082 for simplicity) can be driven by a hydraulic turbine. In some embodiments, as illustrated in FIGS. 45A and 45B, a hydraulic turbine 2070 includes a turbine housing 2071. In some cases, at least a portion of a nozzle frame 2072 is housed within the turbine housing 2071. In some embodiments, stator vanes can be used in conjunction with and/or in place of the nozzle frame 2072. The nozzle frame 2072 can include one or more turbine nozzles 2073. In some embodiments, the turbine nozzles 2073 are positioned in a circumferential array, as illustrated in FIG. 45A. Each of the turbine nozzles 2073 can have a nozzle inlet 2074 and a nozzle outlet 2075. In some embodiments, the nozzles 2073 have substantially constant cross-sectional areas from nozzle inlet 2074 to nozzle outlet 2075 (e.g., drill hole-type nozzles). For example, circular nozzles can be used.

The relative areas of the nozzle inlet 2074 and the nozzle outlet 2075 can vary. For example, the nozzle outlet 2075 can have an area that is greater than or equal to approximately 125% of the area of the nozzle inlet 2074 and/or less than or equal to about 600% of the area of the nozzle inlet 2074. In some embodiments, the area of the nozzle outlet 2075 is approximately 300% of the area of the nozzle inlet 2074.

As illustrated in FIG. 45B, the profile of the nozzle 2073 can widen between the nozzle inlet 2074 and the nozzle outlet 2075. The rate at which the turbine nozzle 2073 widens between the nozzle inlet 2074 and the nozzle outlet 2075 can vary. For example, the nozzle 2073 can flare out in the direction of the nozzle outlet 2075. In some embodiments, the profile of the nozzle 2073 narrows between the nozzle inlet 2074 and the nozzle outlet 2075. In some embodiments, the nozzles 2073 have substantially constant cross-sectional areas from nozzle inlet 2074 to nozzle outlet 2075 (e.g., drill hole-type nozzles). In some embodiments, the nozzle inlet 2074 can be tapered or flared in such that an opening into the nozzle inlets 2074 is wider or larger than a midsection of the nozzles 2073.

In some embodiments, hydraulic fluid is directed through the nozzle frame 2072 toward an impeller 2076. The impeller 2076 can include a plurality of impeller blades 2077 around the outer periphery of the hub of the impeller 2076. The impeller blades 2077 can rotate within a blade cavity 2077a. (See FIG. 45C.) The impeller 2076 can be integral with or otherwise rotationally coupled with an output shaft 2079 for driving the tool 2082, which can be a drill or other rotational tool. The outer diameter of the hub of the impeller 2076 can be smaller than the outside diameter of the array of hydraulic nozzles 2073. For example, the outer diameter of the hub of the impeller 2076 can be greater than or equal to approximately 15% of the outer diameter of the hydraulic nozzles 2073 and/or less than or equal to approximately 75% of the outer diameter of the hydraulic nozzles 2073. In some cases, the outer diameter of the impeller 2076 can be greater than or equal to 0.5 inches and/or less than or equal to approximately 1.5 inches. Many variations sizes and relative sizes of the components of the hydraulic turbine 2070 and its subcomponents are possible.

In some cases, the impeller blades 2077 are oriented at an angle offset from the central axis of the impeller 2077. The hydraulic nozzles 2073 can be configured to turn the flow of hydraulic fluid from an axial direction A to nozzle direction 2078 as the flow is passed through the nozzle frame 2072 toward the impeller 2076. The nozzle direction 2078 can be selected to be at an angle $\theta_T$ offset from axial A such that the nozzle direction 2078 is substantially perpendicular to the faces of the impeller blades 2077. The closer nozzle outlets are to the plane of the impeller blades 2077 and the more radially-directed the flow from the nozzles, the more torque can be imparted upon the impeller blades 2077. For example, the nozzle outlets can be positioned close to the impeller blades 2077 in the axial direction and can direct hydraulic fluid at a highly-radial angle toward impeller blades 2077 whose surfaces are close to parallel to the rotation of axis of the impeller 2076.

In some cases, utilizing a plurality of circumferentially-distributed turbine nozzles 2073 to drive a plurality of impeller blades 2077 can increase the torque output of impeller 2076 as compared to a configuration wherein only one turbine nozzle 2073 is utilized. In some such configurations, the outer diameters of the nozzle frame 2072 and impeller 2076 can smaller than a single-nozzle configuration of equal output torque.

In some embodiments, the hydraulic turbine 2070 can be configured to operate at rotational speeds of 40,000 rpm to 60,000 rpm, though higher and lower rpm values may be possible. The hydraulic turbine 2070 can be configured to operate at operating pressures between 70 psi and 190 psi, though greater and lesser operating pressures are possible. In some embodiments, the operating pressure of the hydraulic turbine 2070 is designed to be approximately 120 psi.

Figure 46:
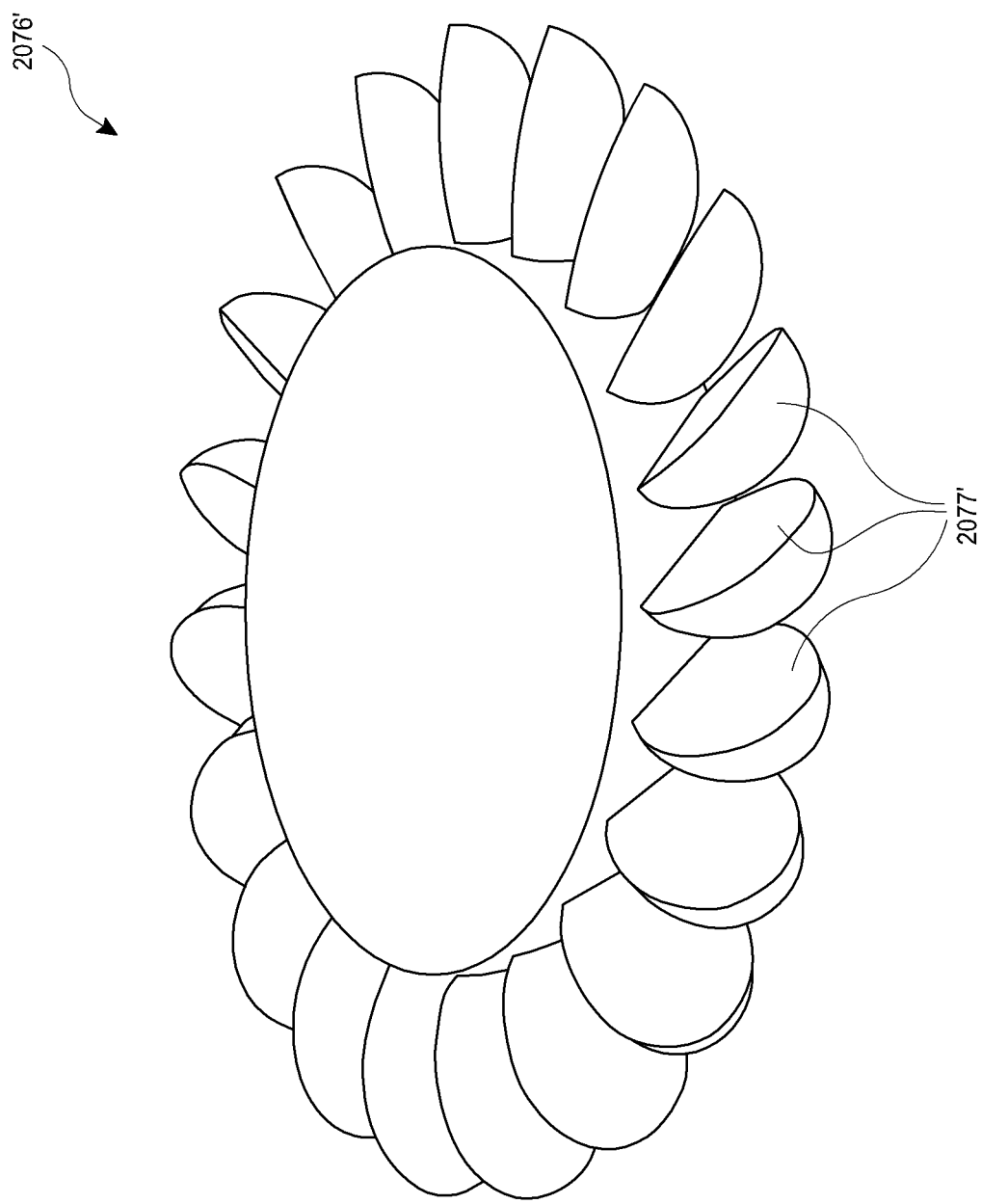
FIG. 46 shows one embodiment of an impeller.

As illustrated in FIG. 46, an impeller 2076' can be designed to have bucket-shaped impeller blades 2076'. The bucket-shaped impeller blades 2077' can be oriented at an angle of approximately 45° from the axial direction A. Many variations of the impeller blade 2077' angles are possible. Additionally, many different shapes of blades 2077 are possible, such as Pelton or Turgo shaped blades.

Figure 45C:
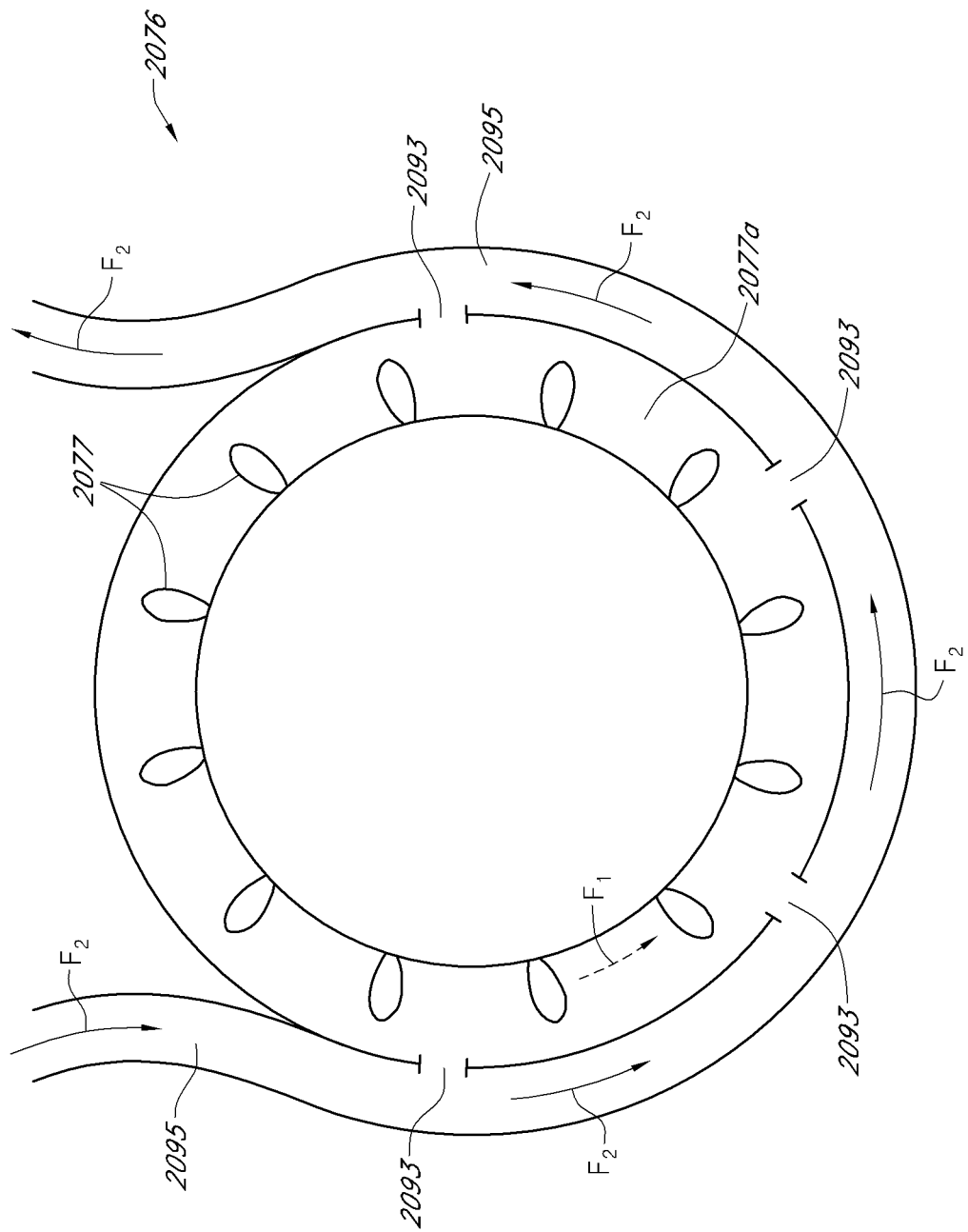
FIG. 45C shows a cross-section of a portion of the hydraulic turbine of FIG. 45A and a diverted fluid flow path.

As illustrated in FIG. 45C, the hydraulic turbine 2070 can be designed to collect the hydraulic fluid that has already impacted the impeller blades 2077, 2077' (hereinafter 2077 for simplicity). For example, an exhaust angle can be calculated to represent the angle at which hydraulic fluid reflects off of the impeller blades 2077 after impact with the impeller blades 2077. One or more vacuum ports 2093 can be positioned on or in the turbine housing 2071 to extract the fluid F1 that is reflected off of the impeller blades 2077 and redirect the fluid F1 into a bypass channel 2095. In some embodiments, the vacuum source can be an external pump (e.g., a peristaltic pump) or the vacuum can be the result of a Venturi effect created by the diversion of fluid. For example, in some embodiments, the vacuum source can be provided by diverted, high velocity fluid F2 directed to bypass the impeller 2076. In some embodiments, one or more ports 2093 in the hydraulic turbine housing 2071 (e.g., on the side of the housing closer to the impeller 2076 than to the nozzle frame 2072) can create fluid communication between the reflected fluid F1 in the blade cavity 2077A and the diverted high velocity fluid F2 in the bypass channel 2095. The pressure differential between the two fluid bodies (e.g., lower pressure in fluid F2 and higher pressure in fluid F1) will pull the reflected fluid F1 out of the housing 2071 and into the diverted fluid path 2095. Removal of the reflected fluid from the housing 2071 can increase the performance of the turbine 2070 by reducing the viscous drag on the impeller from undiverted fluid F1. For example, the viscous frictional losses that would be otherwise incurred from interaction between the reflected fluid F1 and the impeller 2076 and/or output shaft 2079 can be reduced. The diverted high velocity fluid F2 and scavenged reflected fluid F1 can be diverted back to the cassette 2020 for re-pressurization. In some embodiments, scavenging reflected fluid F1 and diverting it back to the cassette 2020 can reduce the amount of hydraulic fluid (e.g., saline) required to operate the tools and/or other components of the system.

In some embodiments, multiple impellers 2076 (e.g., multiple turbine wheels) can be utilized in the same turbine housing 2071. In some such embodiments, the overall diameter of the turbine 2070 and/or some of its components can be reduced relative to a single-impeller turbine 2070 without sacrificing output torque.

Some instruments such as surgical tools use torque or mechanical force to translate manual input into tool actuation. For example, a Kerrison for bone removal generally includes a handle mechanically coupled to a head including a stationary portion and a movable portion. When a user squeezes the handle, the movable portion moves closer to the stationary portion in a cutting manner (e.g., in a shearing manner), for example to remove bone by trapping the removed bone between the stationary portion and the movable portion (e.g., within a channel between the stationary portion and the movable portion). Other examples of tools include an aneurysm clipper, a rongeur, forceps, scissors, and the like, although many other hand-operated tools are known to those skilled in the art. Referring again to the Kerrison, the pace and force of the squeezing translates to the pace and force of the cutting, and this phenomenon is also applicable to other hand-operated tools. This translation can be disadvantageous, for example varying based on each user, being too slow or too fast or having variable speed, lacking force or imparting too much force or having variable force, etc. Additionally, periodic use of such manually operated tools (e.g., during a lengthy operation or procedure) can lead to hand fatigue of the surgeon or user. Manual actuation leads to inadvertent movement of the tool tip.

Figure 47A:
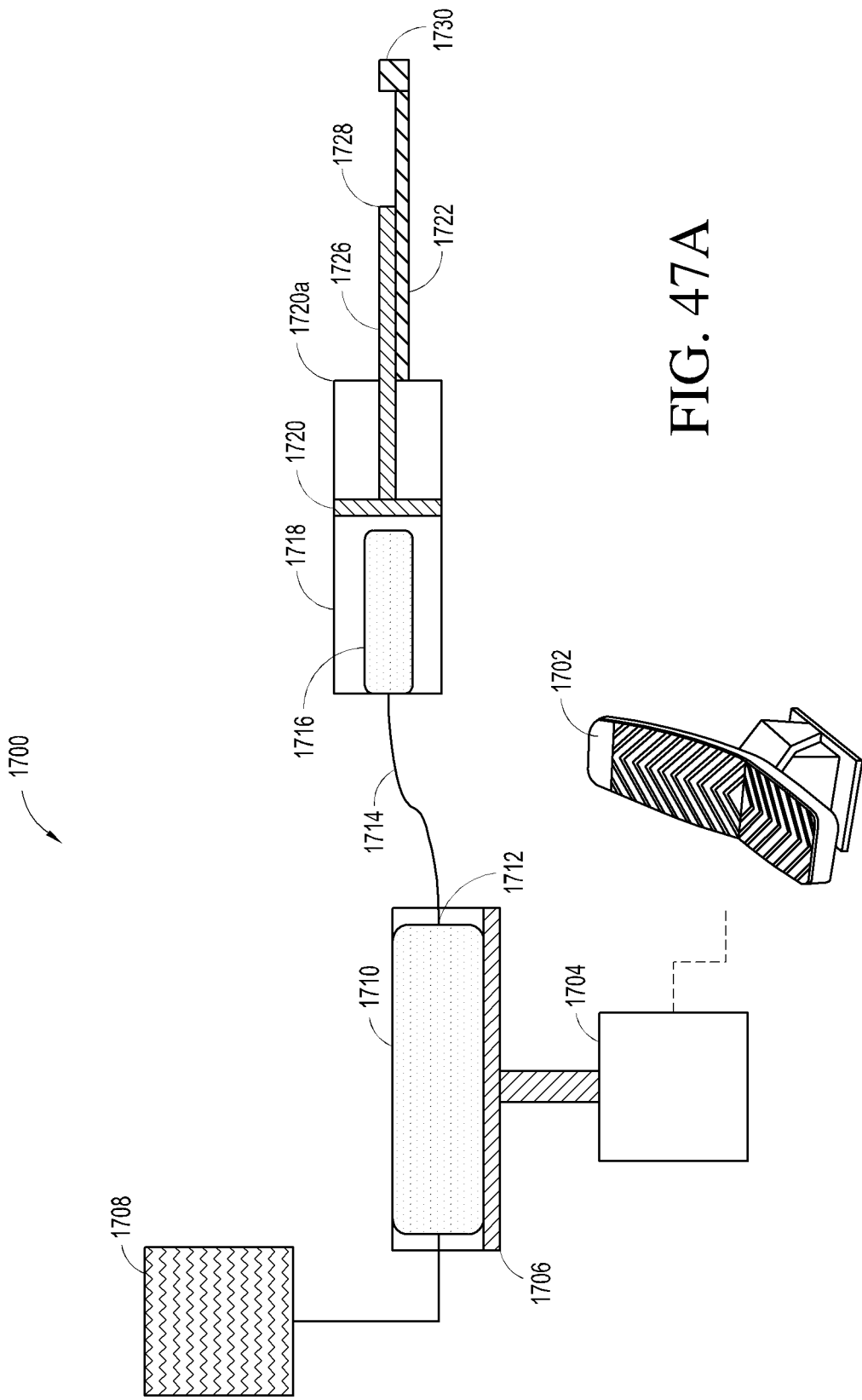
FIG. 47A is a schematic illustration of another embodiment of a hydraulic actuation system coupled to a hydraulically actuated surgical device, where the hydraulic actuation system is in a first operating state.
Figure 47B:
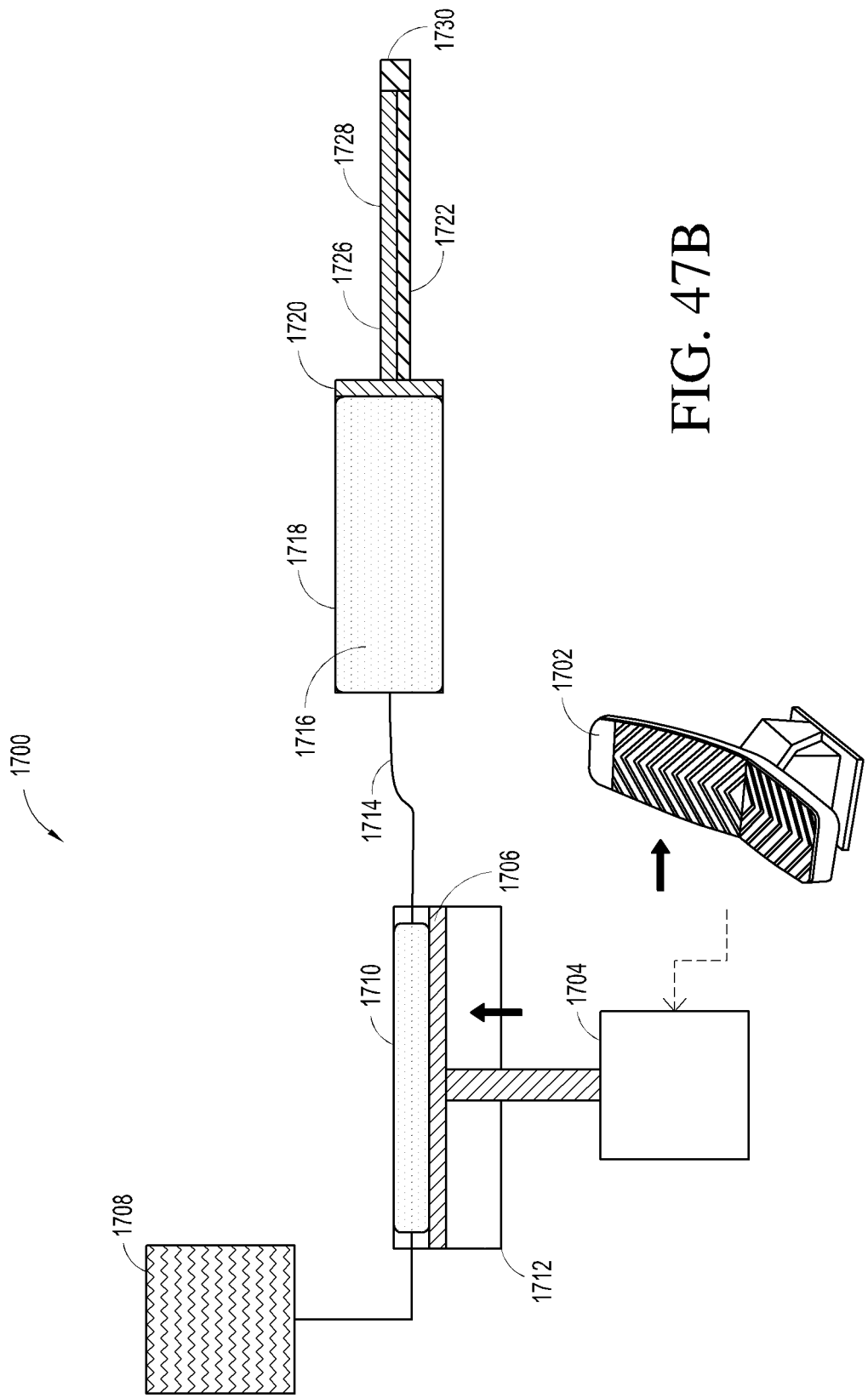
FIG. 47B is a schematic illustration of the hydraulic actuation system of FIG. 47A, where the hydraulic actuation system is in a second operating state.

FIGS. 47A and 47B schematically illustrate an example embodiment of a system 1700 for hydraulically actuating instruments. The system 1700 includes a user interface 1702, a drive system 1704, a pusher member 1706 (e.g., piston, plunger), a fluid reservoir 1708, a first inflatable element 1710, a housing 1712, a fluid conduit 1714, a second inflatable element 1716, a chamber or housing 1718, a piston 1720, and an instrument 1722. In some embodiments, a shaft 1726 can extend away from the piston 1720 to actuate any number of tools, such as a Kerrison, standard forceps, micro forceps, bipolar forceps, rongeur, clip appliers, scissors, or any other desired tool, as will be described in greater detail below. The system 1700 allows the user to actuate the instrument 1722 by operation of the user interface 1702. The user interface 1702 is not mechanically coupled to the instrument 1722, so the forces on the user interface 1702 are not necessarily directly translated to the forces on the instrument 1722.

Any of the tool embodiments disclosed herein, including any of the Kerrison, standard forceps, micro forceps, bipolar forceps, rongeur, clip appliers, or scissors embodiments disclosed herein, can be configured to be anatomically designed to fit snugly in a particular orientation relative to a user's hand. Configuring the tools for a predetermined orientation in a user's hand can dictate the orientation (rotational orientation or otherwise) of the tool relative to a reference point or surface, such as a ground surface. In this configuration, a CMOS sensor supported by the tool will always be oriented right side up (i.e., in the proper orientation), thereby eliminating the need for PIP image rotation. PIP computation will then be translational and scaling only.

Operation of the user interface 1702 sends a signal to the drive system 1704. The user interface 1702 may include a proportional foot pedal, a push button, lever and the like. In some embodiments, the user interface 1702 is analog, where different levels of operation of the user interface 1702 cause different responses by the drive system 1704. In some embodiments, the user interface 1702 is digital, where the drive system 1704 responds the same regardless of the level of input on the user interface 1702. In some embodiments, the user interface 1702 includes a single direction, for example a pedal that may be operated only forward. In some embodiments, the user interface 1702 includes a plurality of directions, for example a pedal that may be operated forward or backward. The user interface 1702 may be biased (e.g., by a resilient force such as a spring) to a particular orientation, for example to a resting point opposite the single direction or to a point between a plurality of directions.

In response to the signal sent from the user interface 1702, the drive system 1704, which may for example comprise a linear actuator, drives a pushing member or plunger 1706 by way of a proportional solenoid, Acem or ball screw, and the like. In some embodiments, the drive system 1704 converts random forces on the user interface 1702 into uniform, known, and/or predictable forces on the pushing member 1706. The drive system 1704 may increase accuracy of the instrument 1722. In some embodiments, rather than a user attempting fine control by different forces squeezing on a handle, the drive system may respond to operation of the user interface in fine increments. For example, each operation of the user interface 1702 may cause a partial actuation of the instrument 1722 (e.g., advancing a movable portion of a Kerrison 1 mm for each interaction with the user interface 1702).

The fluid reservoir 1708 is fluidly coupled to the first or master inflatable element 1710. The fluid reservoir 1708 may comprise a mass of fluid such as saline, deionized water, etc., for example, contained in an intravenous bag positioned higher than the first inflatable element 1710 such that gravity causes fluid to flow from the fluid reservoir 1708 into the first inflatable element 1710, or may comprise a pressurized canister and the like. After inflating or priming the first inflatable element 1710, the fluid reservoir 1708 may be disconnected from the first inflatable element 1710 (e.g., physically disconnected from the first inflatable element 1710 or fluidly disconnected by closing a valve between the fluid reservoir 1708 and the first inflatable element 1710). The first inflatable element 1710 includes a defined volume to contain an amount of fluid in an inflated state. In some embodiments, the first inflatable element 1710 includes an inflatable balloon similar to those used for percutaneous transluminal angioplasty or kyphoplasty. Certain such balloons are generally inexpensive, disposable, sterile, and/or are not susceptible to overinflation. The pusher member 1706 and the first inflatable element 1710 may be at least partially contained by a housing 1712. The housing 1712 may include apertures for connection to the fluid reservoir 1708 and the fluid conduit 1714, and for the shaft of the pusher member 1706 and/or to allow air and/or fluid to enter and exit the chamber as the air and/or fluid is displaced by inflation or deflation of the first inflatable element 1710. The fluid conduit 1714 is in fluid communication with the first inflatable element 1710 and the second or slave inflatable element 1716.

As illustrated in FIG. 47B, with the first inflatable element 1710 at least partially inflated by a fluid such as saline, for example after being primed by the fluid reservoir 1708, the user interface 1702 is actuated, which causes the drive system 1704 to move the pusher member 1706 to compress the first inflatable element 1710 within the housing 1712, for example against a platen. Although illustrated as compressing the first inflatable element 1710 radially inwardly (e.g., widthwise), longitudinal compression is also possible. Although illustrated as compressing the first inflatable element 1710 in a single direction, a plurality of plungers or other compression mechanisms are also possible. For example, drive system 1704 may cause longitudinal compression of the first inflatable element 1710 from each end. For another example, drive system 1704 may cause inflation of a toroidal element around the first inflatable element 1710. Fluid flows out of the first inflatable element 1710 through the fluid conduit 1714 and into the second inflatable element 1716. As the fluid enters the second inflatable element 1716, the second inflatable element 1716 inflates within the chamber 1718. The chamber 1718 may restrict inflation of the second inflatable element 1716 to be substantially linear or substantially in a single direction (e.g., towards the piston 1720). During inflation of the second inflatable element 1716, the second inflatable element 1716 pushes the piston 1720. The piston 1720 is coupled to the instrument 1722 or may even be part of the instrument 1722. As illustrated in FIGS. 47A and 47B, the instrument 1722 is coupled to the chamber 1718. In some embodiments, the instrument 1722 is spaced from and/or separate from the chamber 1718. The chamber 1718 may include apertures for connection to the fluid conduit 1714, and for the shaft of the piston 1720 and/or to allow air and/or fluid to enter and exit the chamber as the air and/or fluid is displaced by inflation or deflation of the second inflatable element 1716.

The instrument 1722 may comprise any instrument actuatable by motion of the piston 1720 caused by the second inflatable element 1716. For example, the instrument 1722 may comprise a Kerrison, an aneurysm clip applier, a rongeur, a tissue cutter, scissors, forceps, and other surgical instruments. The instrument 1722 may be a non-surgical instrument, for example used for machinery, plumbing, electrical, and the like. As described herein, hydraulic power can inhibit or eliminate interference with electromagnetic tracking, so the instrument 1722 may comprise any instrument used in a setting in which reduction of interference with electrical devices may be advantageous. In embodiments in which the instrument 1722 comprises a Kerrison, the Kerrison may include a D-shaped cutting surface, for example to cut bone without a twisting motion. In some embodiments, the cut bone fragments can accumulate in a Kerrison lumen proximal to the cutting surface (e.g., for later extrusion for removal such as by a screw auger), and the like.

The second inflatable element 1716, the chamber 1718, and the piston 1720 may provide certain advantages over other systems. For example, if the system 1700 did not include the second inflatable element 1716 such that fluid flowed from the fluid conduit 1714 directly into the chamber 1718, the chamber 1718, including interaction between the chamber 1718 and the piston 1720, would need to be fluid-tight, but such systems are prone to leakage, especially at high pressure. A fluid-tight piston 1720 may also cause stiction issues, leading to the use of higher pressure, which can disadvantageously lead to leakage. Lubricants that may reduce these disadvantages are generally not biocompatible. Stiction may also lead to difficulty in precise movement of the piston 1720. By contrast, a system 1700 comprising a second inflatable element 1716 can allow the piston 1720 to generally fit in the chamber 1718, but does not require a fluid-tight fit. This can reduce or eliminate issues with stiction. Because the fluid is contained within the second inflatable element 1716, issues with leakage of the chamber 1718 may be reduced or eliminated. Distal mechanisms such as diaphragms and bellows may also have issues. For example, a diaphragm generally has less range of motion than an inflatable element 1716. For another example, bellows are generally expensive and therefore are possibly not disposable. By contrast, inflatable elements 1716 such as balloons may have a high range of motion and/or be readily disposable.

In some embodiments, the second inflatable element 1716 comprises an expandable elastomer (e.g., comprising flexible polyvinyl chloride (PVC), cross-linked polyethylene, polyurethane, polyethylene terephthalate (PET), nylon, and/or other polymers). Nylon may be weaker and less compliant than PET, but may be softer and still thin and strong compared to other materials. Advantages provided by PET over other materials can include tensile strength and/or maximum pressure rating. In some embodiments, the second inflatable element 1716 includes an inflatable balloon such as those used for percutaneous transluminal angioplasty or kyphoplasty. In some embodiments, the second inflatable element 1716 is the same or substantially the same as or includes at least one property (e.g., volume, radius, and/or length in an inflated state, type of material, etc.) as the first inflatable element 1710. In embodiments in which the second inflatable element 1716 is the same or substantially the same as the first inflatable element 1710, actions on the first inflatable element 1710 by the drive system 1704 may cause an equal but opposite effect on the second inflatable element 1716. This may be useful, for example, to visualize on the first inflatable element 1710 what is happening to a non-viewable second inflatable element 1716. The use of a first inflatable element 1710 can provide a defined volume, for example to inhibit or prevent overinflation of the second inflatable element 1716. In some embodiments, at least one of the first inflatable element 1710, the second inflatable element 1716, the housing 1712, and the chamber 1718 comprises a lubricious coating, for example to reduce friction between the first inflatable element 1710 and the housing 1712 and/or between the second inflatable element 1716 and the chamber 1718. In some embodiments, at least one of the first inflatable element 1710 and the second inflatable element 1716 comprises an abrasion and puncture-resistant coating, for example to increase reliability.

Although illustrated in FIGS. 47A and 47B as having both ends as square ends, either or both of the ends of the first inflatable element 1710 and/or the second inflatable element 1716 may be any appropriate shape including, for example, conical sharp corner, conical radius corner, spherical end, and/or offset neck. For example, the first inflatable member 1710 may include two offset necks (e.g., as in offset or directional balloons) such that the connections to the fluid reservoir 1708 and the fluid conduit 1714 do not move during inflation and deflation of the first inflatable element 1710. Although illustrated in FIGS. 47A and 47B as having a uniform longitudinal profile, the first inflatable element 1710 and/or the second inflatable element 1716 may include longitudinal tapers, steps, combinations thereof, and the like. Although the first inflatable element 1710 is illustrated in FIGS. 47A and 47B as inflating and deflating only radially and the second inflatable element 1716 is illustrated in FIGS. 47A and 47B as inflating and deflating in all directions, the first inflatable element 1710 and/or the second inflatable element 1716 may be designed to inflate and/or deflate in a single dimension or direction (e.g., a single longitudinal direction, radially, etc.) or in all dimensions.

In some embodiments, the system 1700 optionally does not include the first inflatable element 1710. For example, upon receiving a signal from the user interface 1702, the drive system 1704 may cause fluid to flow into the second inflatable element 1716 by operating a valve, advancing a piston within a cylinder (e.g., advancing the pusher member 1706 within a fluid-tight housing 1712 in fluid communication with the fluid conduit 1710), or otherwise causing fluid to flow through the fluid conduit 1714.

In some embodiments, a biasing element such as a metal spring or a resilient elastomeric member can be positioned between the pusher member 1706 and the housing 1712 and/or between the piston 1720 and the chamber 1718. Such biasing element(s) can cause the system 1700 to be in a default state when a user is not interacting with the user interface 1702. For example, the pusher member 1706 can be biased away from the first inflatable element 1710 (e.g., the pusher member 1706 being between a negative biasing element and the first inflatable element 1710), and the force of the biasing element on the pusher member 1706 provides available volume for at least partial inflation of the first inflatable element 1716. For another example, the piston 1720 can be biased towards the second inflatable element 1716 (e.g., the piston 1720 being between a positive biasing element and the second inflatable element 1716), and if the force of the biasing element on the piston 1720 is sufficient to cause at least partial deflation of the second inflatable element 1716, the second inflatable element 1716 can be biased to a deflated state and the instrument 1722 can be biased to a first state or open state in which inflation of the second inflatable element 1716 is not providing force to the piston 1720.

Figure 47C:
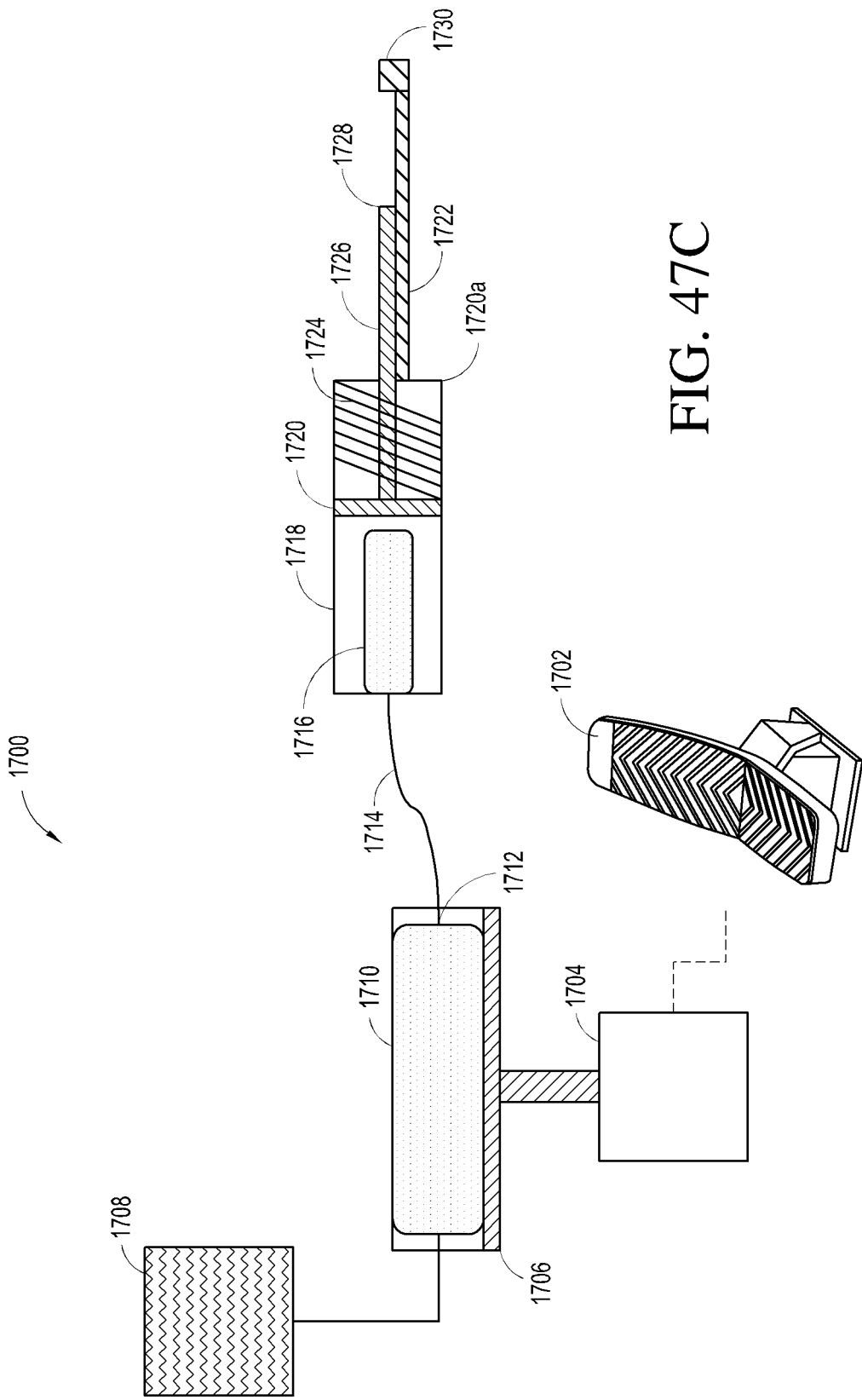
FIG. 47C is a schematic illustration of another embodiment of a hydraulic actuation system coupled to a hydraulically actuated surgical device, where the hydraulic actuation system is in a first operating state.

In some embodiments, as illustrated in FIG. 47C, a spring member 1724 (which can be a metal spring member, an elastomeric spring member, or any other suitable axially resilient member) can be positioned between the piston 1720 and the chamber 1718 to cause the piston 1720 to return to the default or initial position of the piston. In this arrangement, when the piston 1720 is in the default position (i.e., where the spring member 1724 is substantially fully expanded), a cutting head 1728 of the Kerrison attached to the shaft 1726 will be in an open or retracted position so as to be spaced apart from the fixed cutting surface 1730 of the Kerrison. As the second inflatable element 1716 is expanded, the piston 1720 will be forced toward a first end 1720a of the housing 1718 against the bias of the spring member 1724, causing the cutting head 1728 of the Kerrison to move toward the fixed surface 1730 of the Kerrison, to effect the cutting of the bone or other tissue to be cut with the Kerrison.

Additionally, with reference to FIGS. 47D-47G, the Kerrison can have a variety of cutting head configurations. For example, with reference to FIGS. 47E-47G, in any of the embodiments disclosed herein, the cutting head 1728 can have a circular shaped cross-section (as in FIG. 47E), the cutting head 1728 can have a C shaped cross-section (as in FIG. 47F) or a closed D shaped cross-section (as in FIG. 47G). Other shapes and designs are possible.

Additionally, in any of the Kerrison embodiments described herein, the fixed cutting surface 1730 can be generally vertically oriented. As shown in FIG. 47D, the fixed cutting surface 1730 can also be angulated (for example, angled at approximately 45 degrees, or from approximately 35 degrees or less to 55 degrees or more).

In any of the tool embodiments disclosed herein, including without limitation the Kerrison, the housing supporting or comprising the tool can be configured to have a port or lumen therein arranged to facilitate the removal of tissue and bone extracted from the surgical site. For example, the Kerrison can have a side port or opening located proximal of the cutting head 1728, though which cut tissue can be removed (e.g., pushed through port or opening as cutter withdraws and Kerrison returns to the default position). In some embodiments, a source of suction, or a source of saline and suction, can be supplied to the port. Additionally, the removal port or lumen of the housing can also support a mechanical removal mechanism, such as but not limited to a screw type auger (which can be hydraulically actuated, via for example a gear motor, gerotor, or vane motor 1512 discussed above), to facilitate removal of bone debris and extracted tissue from the surgical site. In some embodiments, the removed tissue can be extracted to a waste reservoir supported by or tethered to the housing of the tool. In another embodiment, the movable cutting head of the Kerrison can be a generally cylindrical tube that can be actuated (in the matter described above) to slidably move against the fixed cutting surface 1730. For example, said cylindrical tube can be slidable within an outer housing of the Kerrison when a force is exerted thereon via the expansion of the second inflatable element 1716, as discussed above.

Additionally, in any of the tool embodiments disclosed herein, including without limitation the Kerrison, the housing supporting or comprising the tool can be configured to have a suction port and a source of saline so that the tool and/or the surgical site can be flushed with saline and the saline and debris can removed via the suction line simultaneously or sequentially with the flushing. In some embodiments, the saline can be provided through the conduit used to provide saline to the second inflatable element, through the same or a different lumen of such conduit.

Additionally, the saline source or conduit and/or the suction source or conduit can be separate from the tool so that it can be independently positioned. In some embodiments, the saline source or conduit and/or the suction source or conduit can be tethered to the tool.

Any of the hydraulic system embodiments disclosed herein can be configured to incorporate or use any suitable surgical tools, including without limitation scissors, micro-scissors, forceps, micro-forceps, bipolar forceps, clip appliers including aneurysm clip appliers, rongeur, and, as described, Kerrison tools.

Figure 48A:
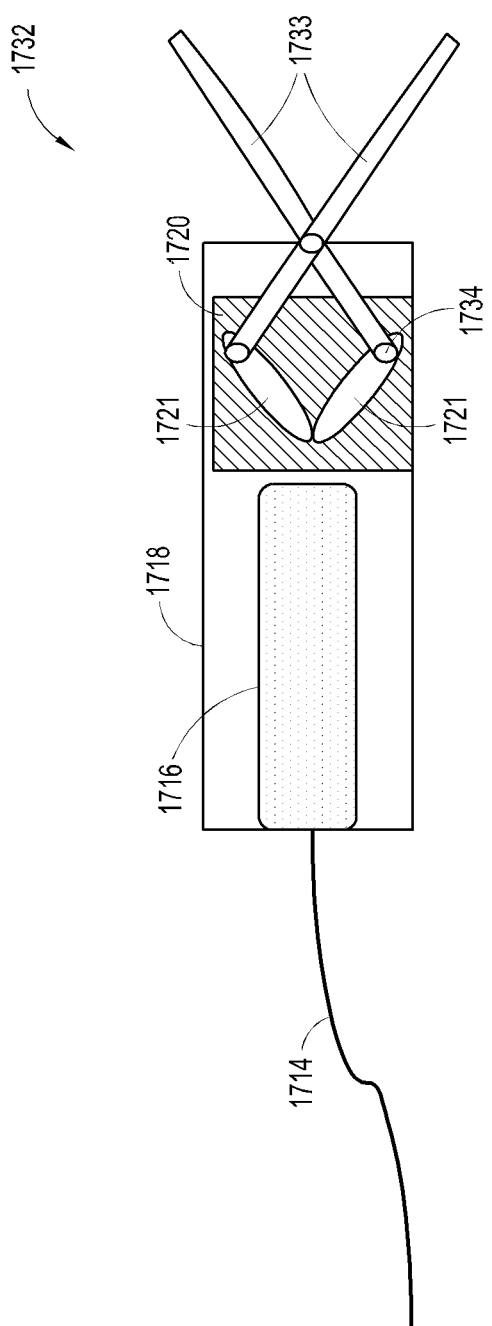
FIG. 48A is a schematic illustration of another embodiment of a hydraulically actuated surgical device in a first position.
Figure 48B:
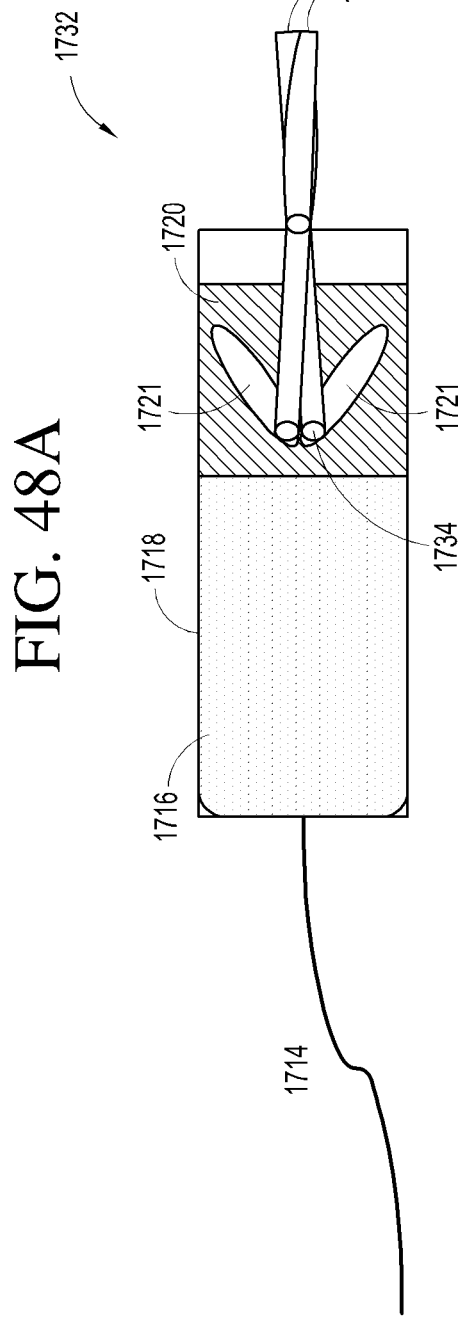
FIG. 48B is a schematic illustration of the embodiment of the hydraulically actuated surgical device of FIG. 48A in a second position.

For example, FIGS. 48A and 48B show an embodiment of a hydraulic scissors tool 1732 that can be used with any of the hydraulic system embodiments disclosed herein, including system 1700. (See, e.g., FIG. 47A-47C.) The scissors tool can have other configurations than shown in FIGS. 48A and 48B, and can but is not required to have an adapted version of or some similar components as a commercially available non-hydraulically operated scissors tool.

In use, the second inflatable element 1716 can be actuated, as described above, to move the hydraulic micro-scissor tool 1732 from a first, open position, as shown in FIG. 48A, to a second, closed position, as shown in FIG. 48B. In particular, in some embodiments, the second inflatable element 1716 can be inflated to advance the piston 1720 toward the second end of the housing 1718. The piston can have one or more channels 1721 formed therein. Each blade 1733 of the scissors can have a pin, dowel, tab, or other protrusion 1734 supported at an end thereof, the pins 1734 each being configured to translate along the length of the channels 1721. In this arrangement, as the piston 1720 is advanced toward the scissors 1732, the pins 1734 will move along the length of the channels 1721 and move inwardly, causing the blades 1733 of the scissors 1732 to come together, as illustrated in FIG. 48B. The scissors can be in a fixed axial position relative to the piston 1720 to effect the relative motion between the piston 1720 and scissors 1732 that operates the scissors. A spring or other biasing mechanism (for example, between the end of the housing and the piston) can be used to return the piston back to the retracted position to return the scissors to an open arrangement or state.

Figure 49A:
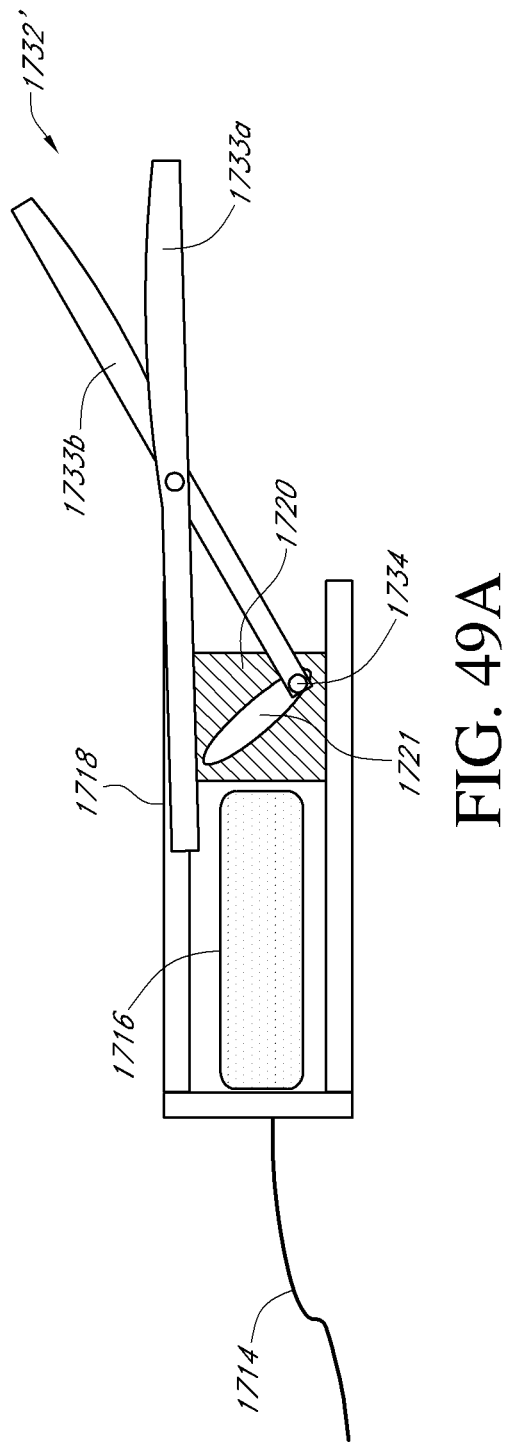
FIG. 49A is a schematic illustration of another embodiment of a hydraulically actuated surgical device in a first position.
Figure 49B:
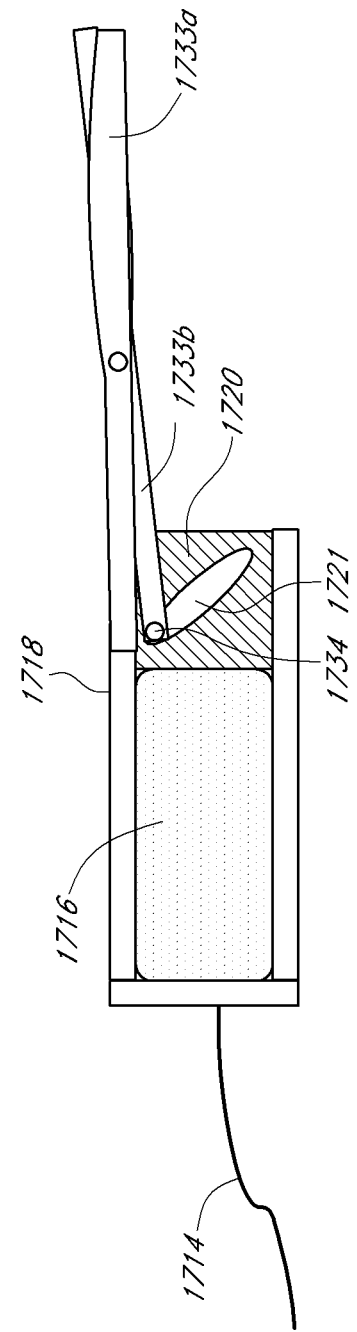
FIG. 49B is a schematic illustration of the embodiment of the hydraulically actuated surgical device of FIG. 49A in a second position.

FIGS. 49A and 49B show another embodiment of a hydraulic scissors tool 1732' that can be used with any of the hydraulic system embodiments disclosed herein, including system 1700. The scissors tool can have other configurations than shown in FIGS. 49A and 49B, and can, but are not required to, have an adapted version of or some similar components as a commercially available non-hydraulically operated scissors tool. With reference to FIGS. 49A and 49B a first scissors blade 1733a can be fixed or otherwise attached to the housing 1718, and the second scissors blade 1733b can be caused to move relative to the first scissors blade 1733a by moving the piston 1720 relative to the end of the housing, thereby causing a pin or other protrusion 1734 in the end of the handle 1733b to translate within the channel 1721, as described above with reference to FIGS. 48A and 48B. A spring or other biasing mechanism (for example, between the end of the housing and the piston) can be used to return the piston back to the retracted position to return the scissors to an open arrangement or state.

Figure 50A:
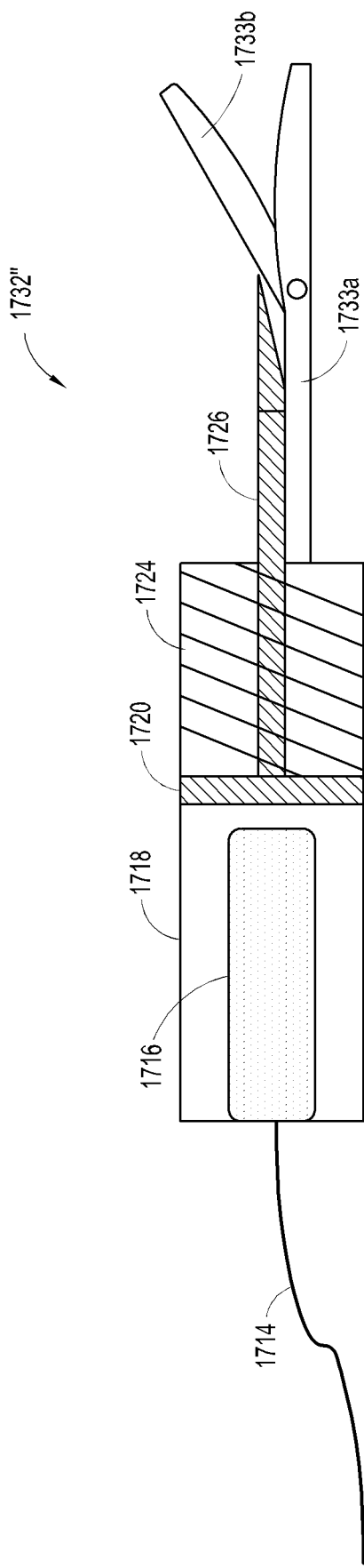
FIG. 50A is a schematic illustration of another embodiment of a hydraulically actuated surgical device in a first position.
Figure 50B:
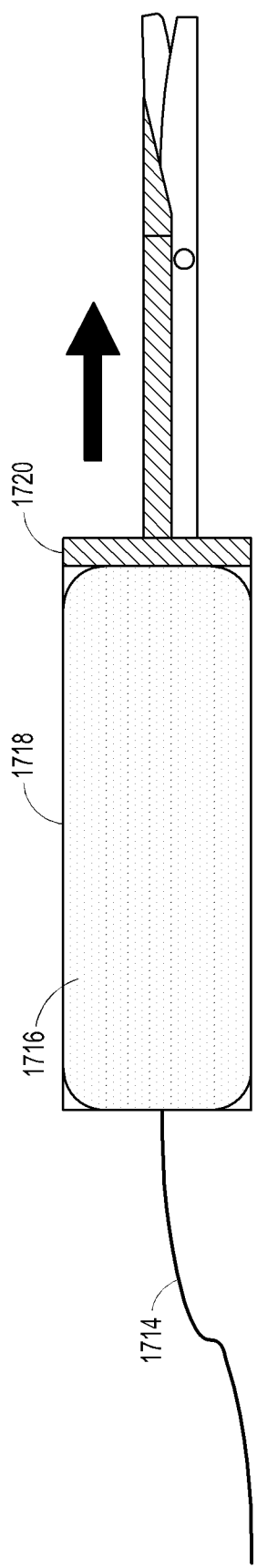
FIG. 50B is a schematic illustration of the embodiment of the hydraulically actuated surgical device of FIG. 50A in a second position.
Figure 52:
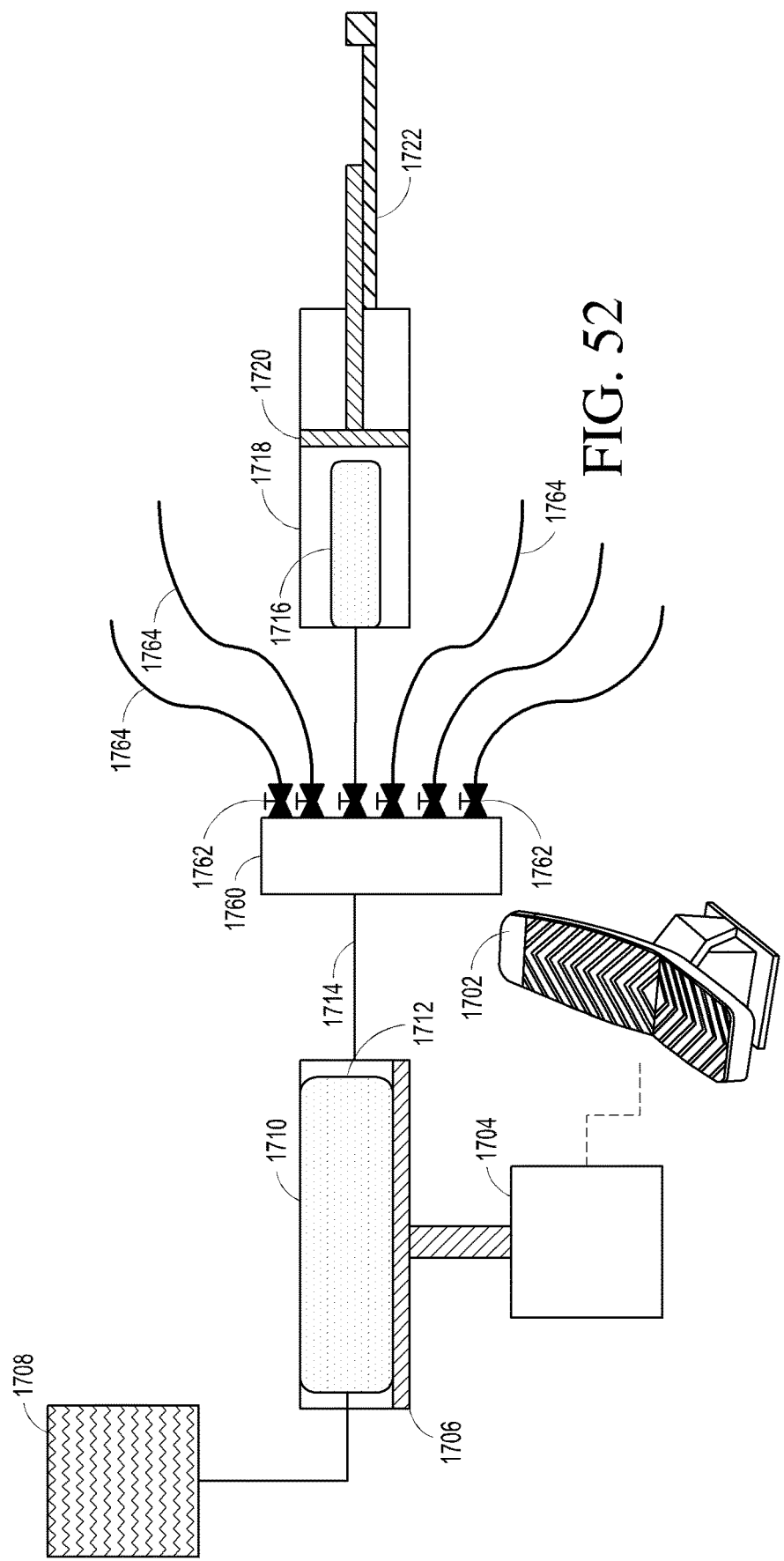
FIG. 52 is a schematic illustration of another embodiment of a hydraulic actuation system coupled to one or more hydraulically actuated surgical devices.

FIGS. 50A and 50B show another embodiment of a hydraulic scissors tool 1732" that can be used with any of the hydraulic system embodiments disclosed herein, including system 1700. The scissors tool can have other configurations than shown in FIGS. 50A and 50B, and can, but is not required, to have an adapted version of or some similar components as a commercially available non-hydraulically operated scissors tool. With reference to FIGS. 50A and 50B, a first scissors blade 1733a can be fixed or otherwise attached to the housing 1718, and the second scissors blade 1733b can be caused to move relative to the first scissors blade 1733a by moving the piston 1720 and shaft 1726 relative to the end of the housing. The end of the shaft 1726 can have a slanted, curved, or angulated shape or surface that, when translated relative to the second blade 1733b, can cause the second blade 1733b to rotate relative to the first blade 1733a, causing the cutting action. As with the other embodiments disclosed above, in some embodiments, a spring member or other biasing mechanism 1724 can be positioned between the end of the housing 1718 and the piston 1720 to bias the piston 1720 to the first, retracted position, thereby biasing the scissors to an open position.

Any other desired tool, such as a micro-scissors, forceps, micro-forceps, bipolar forceps, clip appliers including aneurysm clip appliers, rongeurs, and, as described, Kerrison tools, can be configured to work with any embodiments of the hydraulic system disclosed herein. Further as described above, any of the tools and configurations that provide actuation may be configured differently.

Additionally, the chamber or housing 1718 and shaft 1726 can be configured and adapted to work with and/or interchangeably support any suitable tool, including without limitation scissors, micro-scissors, forceps, micro-forceps, bipolar forceps, clip appliers including aneurysm clip appliers, rongeurs, and, as described, Kerrison tools. For example, with reference to FIGS. 51A-51B, the system 1700 can be configured such that any of the aforementioned tools, or other suitable tools (represented schematically by the box 1740 can be removably attached to an end portion 1718a of the chamber 1718. In some embodiments, the tool 1740 can have an attachment element 1742 that can be removably coupled with an end portion 1718a of the chamber 1718. Any of the tools used in this configuration can be modified from their standard form, as necessary, to be actuated with the linear moving shaft 1726 or with a configuration similar to any other embodiment disclosed herein, such as without limitation the embodiments shown in FIGS. 48A-50B.

In some embodiments, the attachment element 1742 for each of the tools can be threadedly secured, or otherwise removably coupled, to the end portion 1718a of the chamber 1718. However, the system 1700 can be configured such that the tool is integrally formed or otherwise non-removably secured to the chamber 1718. Any desired tools, including without limitation scissors, micro-scissors, forceps, micro-forceps, bipolar forceps, clip appliers including aneurysm clip appliers, rongeurs, and, as described, Kerrison tools, can be similarly adapted to be removably or non-removably coupled with the chamber 1718. Though in some embodiments, the surgical devices or tools can be modularly coupled to the hydraulic actuation system, in other embodiments the surgical devices or tools can at least partially incorporate one or more components (e.g., chamber 1718, second inflatable element 1716), so that the tool and such components are part of a single piece.

In some embodiments, the chamber 1718 can be contoured and shaped to fit comfortably within the hand of a surgeon, so that the surgeon can accurately control the positioning and orientation of the tool. This chamber or housing 1718 is not required to be cylindrical, but can have any suitable shape. For example, in some embodiments, the housing 1718 can have an ovular cross-sectional shape or any anatomically or aesthetically desirable shape. Additionally, the size of the housing 1718 can be varied depending on the size requirements of the second expansion element 1716, the amount of force required to be exerted on the tool by the second expansion element and piston 1720, and other factors such as gripability and comfort for the user of the device.

Further to the description above, the operation of the tool attached to the housing 1718 can be controlled by the positioning and orientation of the tool and by operation of the user interface, such as the user interface 1702 discussed above. In some embodiments, the user interface can define a variety of different positions to enable the surgeon to accurately control the amount of extension of the shaft 1726 and, hence, the state of the tool. Additionally, a spring mechanism or member can be positioned within the chamber of any tool disclosed herein to bias the piston 1720 and shaft 1726 toward a first or retracted position. In this configuration, when the linear actuator is moved toward the relaxed state, by operation of the user interface and the drive system 1704, the spring mechanism can cause the piston to compress the second inflatable element of any tool disclosed herein to force the fluid within the second inflatable element through the conduit 1714 and back into the first inflatable element.

Some embodiments of the system 1700 can have a manifold 1760 in fluid communication with the conduit 1714, the manifold being configured to divert the fluid supplied through the conduit 1714 through any desired number of sub conduits. For example, with reference to FIG. 52, six or more sub-conduits 1764 can be in coupled with the manifold 1760. Each of the different sub-conduits 1764 can be used to provide fluid to any desired number of tools connected to the sub-conduits, each sub-conduit 1764 being configured to couple with one tool. For example, a first sub-conduit 1764 can be coupled with a Kerrison, a second sub-conduit 1764 can be coupled with a rongeur, a third sub-conduit 1764 can be coupled with micro-scissors, a fourth sub-conduit 1764 can be coupled with micro-forceps, and so on. In some embodiments, a first pneumatic port is directed toward powering scissors and forceps, a first hydraulic port is used to power a drill, and a second hydraulic port is used to power a Kerrison, with individual tubing for each flow path. In some such embodiments, individual tools can be replaced without replacing other tools or tubing associated with other tools.

Each of the variety of tools connected to the conduits can have a secondary inflation element, a chamber, a piston, and any other components used to independently operate such tool, similar to that described in the embodiments above.

Additionally, though not required, each of the different sub-conduits 1764 can have a flow valve 1762 associated therewith to independently control the flow of fluid through such sub-conduits 1764. A user interface can be used to independently control the operation of the plurality of flow valves 1762 (e.g., via a controller, such as a computer controller) such that a surgeon or other user can electronically control the flow of fluid through the sub-conduits 1764 using a control panel or other user interface. In this configuration, the surgeon or user can control the flow of fluid into and out of the sub-conduits 1764 and, hence, into and out of the second inflation elements 1716, of the respective tools, to exchange fluid between the primary or first inflation element 1710 of the system and the second inflatable elements 1716.

For example, in use, a user may wish to perform an operation with a Kerrison coupled with a first sub-conduit 1764, but not a rongeur (e.g., a second Kerrison) coupled with a second sub-conduit 1764. Even though both such tools may be attached to the system, the user can essentially restrict the flow of fluid from the first inflatable element to the rongeur by closing the valve associated with the sub-conduit connected to the rongeur. The valve associated with the first sub-conduit can be opened such that any fluid advanced into the manifold from the first inflation element can fill the second inflation element of the Kerrison to operate the Kerrison.

In some embodiments, the system can be coupled with a source of saline at the hospital or other facility to prime or prefill the first inflatable element. Alternatively, the system can be prefilled with saline such that the first inflatable element has enough saline or other desired fluid therein to completely fill all of the second inflatable elements in communication therewith. Though several embodiments of hydraulically actuated surgical devices or tools are described above, one of skill in the art will recognize that the hydraulic actuation systems described herein (e.g., master-slave balloon hydraulic system, vane motor hydraulic system) can be used to actuate a variety of surgical tools by using a hydraulically generated force or torque to turn, pivot, or otherwise move one mechanical component relative to another to perform a desired surgical procedure (e.g., cut, hold, press).

Figure 53:
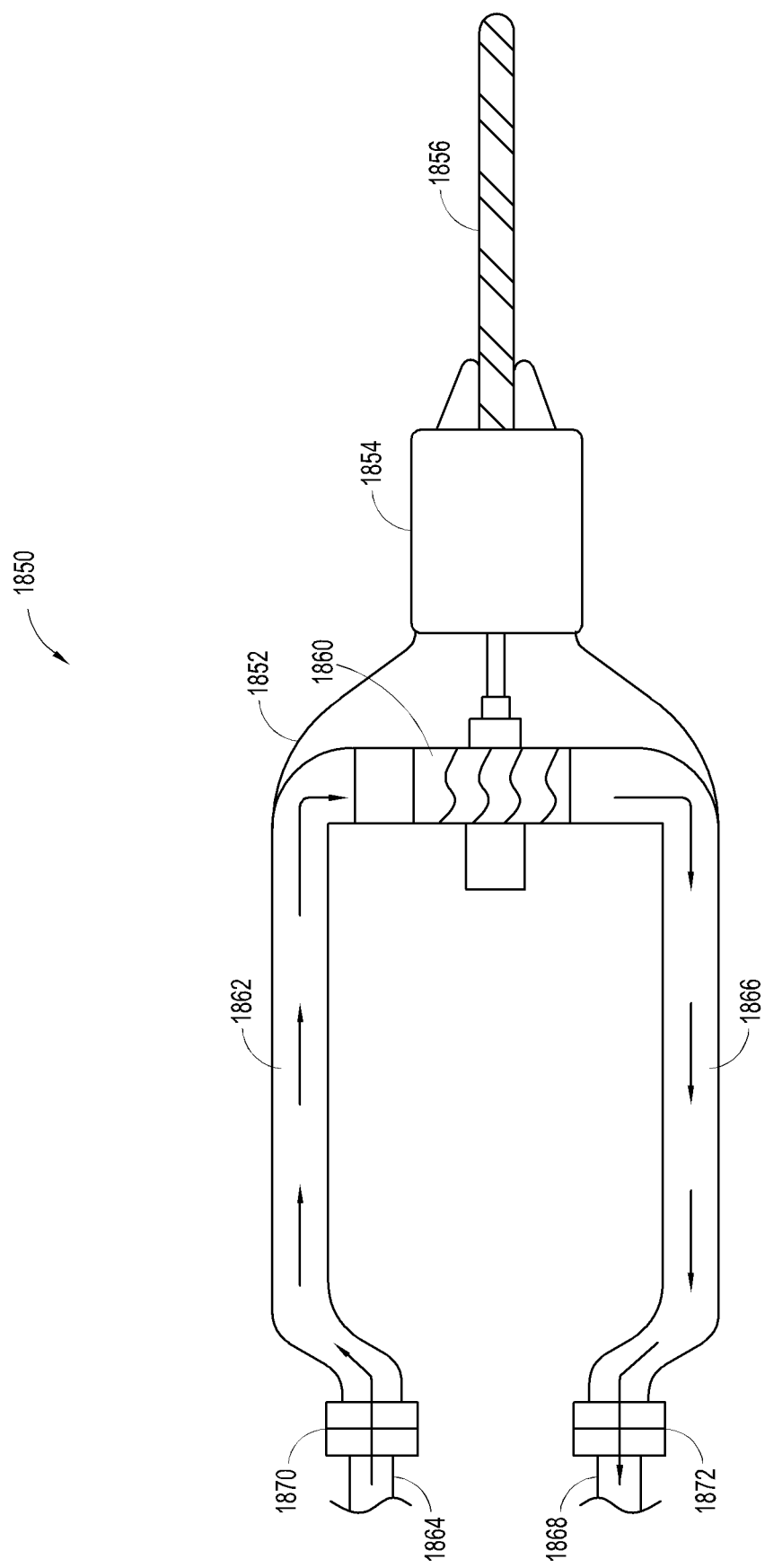
FIG. 53 is a schematic illustration of another embodiment of a hydraulically actuated surgical device.

In some embodiments, a hydraulically powered or actuated drill can be adapted to be used with any of the pressurized hydraulic systems disclosed herein, including without limitation any of the saline systems pre-charged by a bag compressor and/or roller pump, or otherwise, as discussed above. With reference to FIG. 53, some embodiments of the drill 1850 can have a housing 1852, a drill chuck or other suitable connector 1854 for receiving and supporting a drill bit or other desired rotary bit 1856 therein, a turbine 1860 rotationally coupled with the chuck 1854. A first inlet fluid flow path or conduit 1862 connectable to a first or inlet conduit 1864 can direct a fluid, such as saline, toward the turbine 1860 with a level of fluid flow velocity sufficient to rotate the turbine and, hence the chuck and rotary bit 1856 at the desired velocity. In some embodiments, the drill can have a hydrostatic bearing coupled with the turbine. In some embodiments, the drill can have an air bearing coupled with the turbine. The air bearing and/or hydrostatic bearing can function as a thrust bearing. In some embodiments, the turbine used for the drill or any desired rotational tool can be arranged similarly as compared to the impeller 2076 and nozzle frame 2072 described above, which can reduce the diameter or size of the turbine or impeller and the rotational tool. In this case, the output shaft 2079 can be coupled with a drill chuck or with a drill bit or other rotational tool.

A controller attached to a flow valve in the inlet line or conduit 1862 or 1864 can be used to adjust the velocity of the flow against the turbine 1860. In some embodiments, a valve and valve controller (not illustrated) can be supported by or within the housing 1852 such that a surgeon can quickly and easily change the velocity of the drill by adjusting the valve in communication with the inlet flow conduit 1862. A flow meter can be used to measure a flow velocity within the fluid flow path.

In some embodiments, the outlet channel and conduit 1866, 1868 can have the same cross-sectional size as the inlet conduit and channel, respectively. In some embodiments, the outlet channel and conduit 1866, 1868 can have a larger cross-sectional size as compared to the inlet conduit and channel, respectively, to reduce pressure buildup in the outflow portion of the flow pathway.

The inlet and outlet lines can each have a one-way flow valve and quick connector thereon to permit the drill to be removed from the hydraulic lines or system without the substantial loss of hydraulic fluid. Couplings 1870, 1872 can be positioned at the rear end of the housing 1852 to removably couple the inlet and outlet conduits with the housing 1852.

A saline or hydraulically powered tool, such as any of the tools described herein, can have several advantages. First, they can be configured to work with EM tracking without interference to the EM tracking, which electric powered drills and other tools will not. Accordingly, the surgical tool, such as a disposable or non-disposable hydraulic drill or Kerrison could include or have attached thereto (e.g., via clip-on connector) an electromagnetic tracker sensor. Accordingly, the surgical tool, such as a disposable or non-disposable hydraulic drill or Kerrison could include or have attached thereto (e.g., via clip-on connector) an optical sensor such as a CCD or CMOS camera sensor or detector array. Additionally, such saline or hydraulically powered tools are lightweight, generate very little or no heat, use hydrostatic bearings, and produce little noise during use.

The hydraulic system may also be used for other purpose such as cleaning optics and/or cooling light emitters for illuminating a surgical site.

Figure 53A:
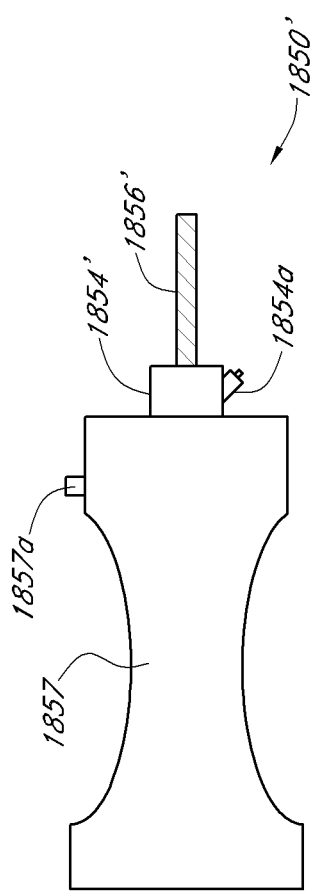
FIG. 53A is a schematic illustration of an embodiment of a powered drill.

As illustrated in FIG. 53A, a powered drill 1850' (e.g., a hydraulically or electrically powered drill) can include a camera 1854a. The camera 1854a can be positioned on the chuck 1854' and/or on the handle 1857 of the drill 1850'. The camera 1854a can be fixed in position rotationally (e.g., with respect to the axis of the rotary bit 1856'). The handle 1857 can include a waist portion to inhibit axial movement of the hand of a surgeon or other practitioner during use of the drill 1850'. In some embodiments the drill 1850' include a tactile feature 1857a (e.g., a faceted ring, a nub, a protrusion, a roughened portion) fixed in a rotational position on the handle 1857. The tactile feature 1857a can provide the practitioner with a tactile indication of the orientation of the camera 1854a.

Figure 53B:
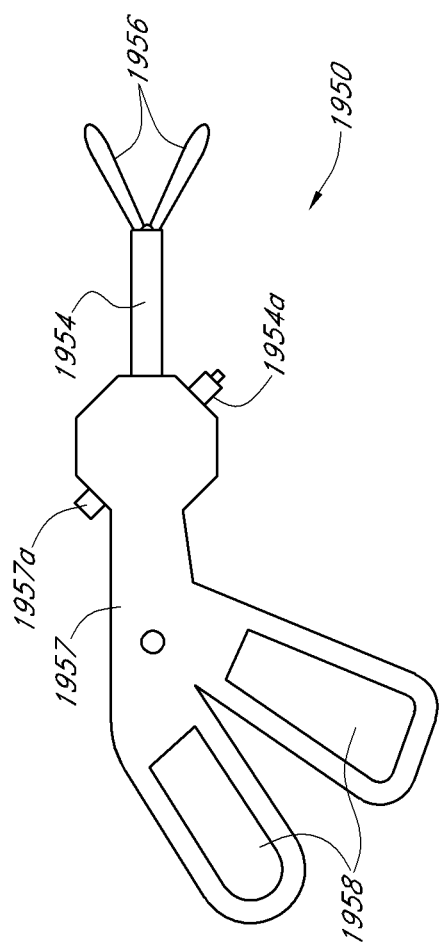
FIG. 53B is a schematic illustration of an embodiment of powered scissors.

In some embodiments, as illustrated in FIG. 53B, a set of powered (e.g., hydraulically, pneumatically, and/or electrically powered) scissors 1950 comprises handles 1958 and a body 1957. A blade coupler 1954 can be coupled with the body 1957 and can provide mechanical coupling between the body 1957 and a set of blades 1956. In some embodiments, the powered scissors 1950 include a camera 1954a mounted in a fixed rotational position (e.g., with respect to an axis of the blade coupler 1954). In some embodiments, the coupler 1554' can be rotated (e.g., using a gnarled ring fixed thereto) to rotate the orientation of the blades 1956 with respect to the handles 1958. In various embodiments, the orientation of the camera with respect to the handles 1958 remains intact. The powered scissors 1950 can also include a tactile feature 1957 configured to provide the user of the scissors with tactile confirmation of the alignment of the camera 1954a. This tactile feature may, include but is not limited to a facet, dimple or other surface.

A wide range of embodiments are therefore possible. Various embodiments may comprise, for example, a retractor having a plurality of cameras that form images and an image processing module and display configured such that the user selects which images formed by the cameras are displayed. These images may be video streams. In some embodiments, the user may enlarge one or more of the images and/or display the one or more images more centrally. For example, the user may select icons that represent the images and enlarge and place the image more central or at a desired location. These icons may actually show the images, which as stated above may comprise a video stream. The images or video stream may be real time.

Various embodiments may comprise, for example, a retractor having plurality of cameras having respective field-of-views and that are configured to obtain images as well as an image processing module and display configured to display the images tiled in a geometric arrangement that is consistent with the field-of-views and/or positions of the cameras. As described above, these images may be video streams. The geometric arrangement may include position and/or orientation of the images.

Various embodiments may comprise, for example, a retractor and plurality of cameras, wherein the retractor is configured to hold open a surgical site and the plurality of cameras are inwardly facing toward the surgical site. The retractor may, for example, comprise a plurality of blades having the cameras disposed thereon wherein the blades hold back tissue to hold open the surgical site. In some embodiments, the cameras face downward and inward into the surgical site. In some embodiments, the retractor includes proximal and distal cameras.

Various embodiments may comprise, for example, a surgical device such as a retractor and plurality of cameras comprising at least one distal camera and at least one proximal camera. In some embodiments, the plurality of cameras comprise a plurality of distal cameras and/or a plurality of proximal cameras. In some embodiments, the proximal cameras can be disposed more toward the end of a retractor blade and the distal cameras can be disposed more toward the distal end of the retractor. In some embodiments, the cameras face inward and possible downward into the surgical site held open by the retractor.

Various embodiments may comprise, for example, a surgical devices such as a retractor, a plurality of cameras, and a tracking system, wherein the plurality of cameras comprises a first and a second camera and the tracking system is configured to track a first movement of the first camera and a second movement of the second cameral wherein the movements are different. For example, the movements may be in different directions and/or to different extents.

Various embodiments may comprise, for example, a surgical device such as a retractor having a plurality of cameras that form images and an image processing module and display configured to display at least one of the images and a tool rendered as partially transparent.

Various embodiments may comprise, for example, a surgical device such as a retractor having a plurality of cameras that form images, and an image processing module and a display configured to display an image morphed from at least two of the images.

Various embodiments may comprise, for example, a surgical devices such as a retractor having a plurality of cameras that form images, and an image processing module and a display configured to display at least two of the images, wherein the at least two images are from cameras disposed on opposite sides of the surgical device (e.g. retractor) and wherein the imaging processing module flips one of the two images.

Various embodiments may comprise, for example, a surgical device having a plurality of cameras that form images, and a binocular display with at least one internal display device coupled to the cameras to display images from the cameras. In some embodiments, the binocular display is disposed on an articulated arm. In some embodiments, the binocular display comprises a pair of oculars attached to a housing containing the internal display device. In some embodiments, the binocular display comprises a non-direct view microscope comprising at least one camera coupled to the binocular display (e.g., disposed at the bottom of the housing) to provide images of the region below the binocular display. The images of the region below the binocular display may be displayed on the at least one internal display device. The non-direct view microscope may further comprise a variable zoom to alter the work distance of the non-direct view microscope. The variable zoom may comprise a two stage zoom providing one control for changing the work distance and one control for changing the magnification. In some embodiments, virtual reality gesture recognition may be provided to receive input from gestures made below the binocular display. In some embodiments, the camera below the binocular display may be used for such gesture recognition. In some embodiments, the camera further comprises an additional sensor (e.g. below the housing) for providing the gesture recognition.

Accordingly, various embodiments may comprise, for example, a surgical device having a plurality of cameras that form images, and a display with at least one internal display device coupled to the cameras to display images from the cameras and at least one sensor underneath to provide a virtual reality graphic user interface. In some embodiments the sensor comprises an optical detector array for imaging. In some embodiments, the sensor comprises a distance measuring device.

Various embodiments may comprise, for example, a retractor having plurality of cameras that form images and an image processing module and display configured to provide a main wide field of view image with plurality of narrow field of view tiled images superimposed thereon. The user may select which images formed by the cameras are displayed. These images may be video streams. The images or video stream may be real time.

Various embodiments may comprise, for example, a retractor having plurality of cameras that form images and an image processing module and display configured to provide a composite main wide field of view image produced from plurality of images (e.g., stitched or tiled) with an image (e.g., picture-in-picture image) superimposed thereon. The user may select which images formed by the cameras are displayed. These images may be video streams. The images or video stream may be real time.

Various embodiments may comprise, for example, a retractor having plurality of cameras that form images and an image processing module and display configured to provide a main wide field of view image from the retractor camera with an image superimposed thereon from a camera disposed on a surgical tool. The user may select which images formed by the cameras are displayed. These images may be video streams. The images or video stream may be real time.

Various embodiments may comprise, for example, a retractor having a plurality of cameras that form images and an image processing module and display configured to provide multiple images from cameras on the retractor as icons showing images that can be enlarged and/or arranged by a user. These images may be video streams. The images or video stream may be real time.

Various embodiments may comprise, for example, a retractor having a plurality of cameras that form images, a surgical tool, and an image processing module and display configured to display camera images, wherein movement of the tool triggers selection of different sets of camera images. For example, the movement may comprise movement of the tool to different locations, e.g., to different depths within the surgical site. These images may be video streams. The images or video stream may be real time.

Various embodiments may comprise, for example, a retractor having a plurality of cameras and a surgical tool having at least one camera that form images.

As disclosed elsewhere herein, in various embodiments, the camera(s) and/or other features can be included without the retractor, and may, for example, be configured for use with a retractor or other surgical device such as a surgical tool. Additionally, the camera(s) and/or other features may be configured for use and/or used with medical devices other than retractors. Moreover, any combination of the various features of any of the embodiments disclosed herein may be combined with any other features from other embodiments.

Various embodiments may comprise, for example, a multiple pump hydraulic system for driving surgical tools, wherein the multiple pumps provide substantially constant pressure to the system. The tools may be used in conjunction with a surgical device such as a retractor having cameras and a possible tracking system for tracking the cameras and/or tool. Proportional valves may be used to portion out pressurized fluid from the multiple pumps to the hydraulic tools. The multiple pumps may combine pneumatics and hydraulics. The multiple pumps may be included in a disposable cassette.

Various embodiments may comprise a retractor, use a retractor, or are configured to be used with a retractor and not an endoscope, laparoscope, or arthroscope. Similarly, many embodiments comprise retractors or use retractors or are configured to be used with retractors wherein cameras are disposed on the retractors, not endoscope, laparoscope, or arthroscope.

In various embodiments the retractor fits in an opening in a manner to provide ample room for the surgeon to operate but does not provide a gas seal for pumping up a cavity as may a laparoscope. Similarly, in many embodiments the retractor does not maintain alignment of the layers of tissue that are cut through to form the incision.

In various embodiments, the retractor is not employed as a fulcrum for surgical tools.

In various embodiments the camera(s) can be positioned on top of the retractor near and above the body surface or on the retractor at a depth within the surgical site (e.g., at the far distal end of the retractor into the deepest portion of the surgical site, or elsewhere on the retractor such as more proximal).

Many embodiments are employed for spine surgery, neurosurgery, head and/or neck surgery, and ear nose and throat surgery and many embodiments involve the cutting and extraction of bone, for example, through the pathway provided by the retractor.

Various embodiments, however, may be used with devices other than retractors.

Many other embodiments are possible, including numerous combinations of the above recited features.

CONCLUSION

Unless otherwise indicated, the functions described herein may be performed by software (e.g., including modules) including executable code and instructions running on one or more systems including one or more computers. The software may be stored in computer readable media (e.g., some or all of the following: optical media (e.g., CD-ROM, DVD, Blu-ray, etc.), magnetic media (e.g., fixed or removable magnetic media), semiconductor memory (e.g., RAM, ROM, Flash memory, EPROM, etc.), and/or other types of computer readable media.

The one or more computers can include one or more central processing units (CPUs) that execute program code and process data, non-transitory, tangible memory, including, for example, one or more of volatile memory, such as random access memory (RAM) for temporarily storing data and data structures during program execution, non-volatile memory, such as a hard disc drive, optical drive, or FLASH drive, for storing programs and data, including databases, a wired and/or wireless network interface for accessing an intranet and/or Internet, and/or other interfaces.

In addition, the computers can include a display for displaying user interfaces, data, and the like, and one or more user input devices, such as a keyboard, mouse, pointing device, touch screen, microphone and/or the like, used to navigate, provide commands, enter information, provide search queries, and/or the like. The systems described herein can also be implemented using general-purpose computers, special purpose computers, terminals, state machines, and/or hardwired electronic circuits.

Various embodiments provide for communications between one or more systems and one or more users. These user communications may be provided to a user terminal (e.g., an interactive television, a phone, a laptop/desktop computer, a device providing Internet access, or other networked device). For example, communications may be provided via Webpages, downloaded documents, email, SMS (short messaging service) message, MMS (multimedia messaging service) message, terminal vibrations, other forms of electronic communication, text-to-speech message, or otherwise.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be described as occurring in a particular order, this should not be understood as requiring that such operations be performed in the particular order described or in sequential order, or that all described operations be performed, to achieve desirable results. Further, other operations that are not disclosed can be incorporated in the processes that are described herein. For example, one or more additional operations can be performed before, after, simultaneously, or between any of the disclosed operations. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single product or packaged into multiple products. Additionally, other embodiments are within the scope of the following claims. In some cases, the actions recited in the claims can be performed in a different order and still achieve desirable results.

What is claimed is:

1. A surgical visualization system comprising:
an endoscope camera configured to acquire video images of a surgical site;
an auxiliary camera having a field of view that can be configured to include the surgical site, wherein the auxiliary camera is configured to provide a surgical microscope view of the surgical site;
a viewing assembly comprising a housing and configured to provide views of at least one display disposed in the housing;
a viewing articulating arm, the viewing assembly disposed on the viewing articulating arm, the viewing articulating arm configured to adjust a position of the viewing assembly;
a support, the viewing articulating arm attached to the support such that the viewing articulating arm can move relative to the support;
a second articulating arm, the auxiliary camera disposed on the second articulating arm so that the auxiliary camera can be positioned independently of the viewing assembly, the second articulating arm configured to provide isocenter positioning of the auxiliary camera, the second articulating arm configured to move in an isocenter manner such that at a plurality of locations, said auxiliary camera remains a fixed distance away from a common point; and an image processing system in communication with the endoscope camera, the auxiliary camera, and the at least one display, the image processing system comprising at least one physical processor, wherein the image processing system is configured to:
receive video images acquired by the endoscope camera,
receive video images acquired by the auxiliary camera,
provide output video images based on the received video images,
present the output video images on the at least one display so that the output video images are viewable in said viewing assembly, and
switch between displaying the output video images comprising at least one output video image from the auxiliary camera and at least one output video image from the endoscope camera,
wherein the viewing assembly does not provide a view of the surgical site via an optical pathway that passes through the housing.

2. The surgical visualization system of claim 1, wherein the auxiliary camera comprises a 3-D camera and the at least one display is configured to provide 3-D viewing of images from the 3-D camera.

3. The surgical visualization system of claim 1, wherein the auxiliary camera comprises an optical assembly having an adjustable working distance of between about 15 cm and about 45 cm.

4. The surgical visualization system of claim 3, wherein the optical assembly has a variable magnification of between about −0.5× and about 10×.

5. The surgical visualization system of claim 1, wherein the viewing assembly further comprises a plurality of oculars configured to provide the views of the at least one display disposed in the housing.

6. A surgical visualization system comprising:
an endoscope camera configured to acquire video images of a surgical site;
an auxiliary camera having a field of view that can be configured to include the surgical site, wherein the auxiliary camera is configured to provide a surgical microscope view of the surgical site;
a viewing assembly comprising a housing and configured to provide views of at least one display disposed in the housing;
a viewing articulating arm, the viewing assembly disposed on the viewing articulating arm, the viewing articulating arm configured to adjust a position of the viewing assembly;
a support, the viewing articulating arm attached to the support such that the viewing articulating arm can move relative to the support; and
a second articulating arm, the auxiliary camera disposed on the second articulating arm so that the auxiliary camera can be positioned independently of the viewing assembly, the second articulating arm configured to provide isocenter positioning of the auxiliary camera, the second articulating arm configured to move in an isocenter manner such that at a plurality of locations, said auxiliary camera remains a fixed distance away from a common point;
wherein the viewing assembly does not provide a view of the surgical site via an optical pathway that passes through the housing.

7. The surgical visualization system of claim 6, wherein the auxiliary camera comprises a 3-D camera and the at least one display is configured to provide 3-D viewing of images from the 3-D camera.

8. The surgical visualization system of claim 6, wherein the auxiliary camera comprises an optical assembly having an adjustable working distance of between about 15 cm and about 45 cm.

9. The surgical visualization system of claim 8, wherein the optical assembly has a variable magnification of between about −0.5× and about 10×.

10. The surgical visualization system of claim 6, wherein the viewing assembly further comprises a plurality of oculars configured to provide the views of the at least one display disposed in the housing.

* * * * *